US008492582B2

(12) United States Patent
Yokotani et al.

(10) Patent No.: US 8,492,582 B2
(45) Date of Patent: Jul. 23, 2013

(54) N-ACYL ANTHRANILIC ACID DERIVATIVE OR SALT THEREOF

(75) Inventors: Junichi Yokotani, Toyama (JP); Arihiro Takatori, Toyama (JP); Yukie Tada, Toyama (JP); Minori Yanai, Toyama (JP); Hiroshi Kato, Toyama (JP); Yoichi Taniguchi, Toyama (JP); Chiharu Tanabe, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/145,813

(22) PCT Filed: Jan. 29, 2010

(86) PCT No.: PCT/JP2010/051209
§ 371 (c)(1),
(2), (4) Date: Jul. 22, 2011

(87) PCT Pub. No.: WO2010/087430
PCT Pub. Date: Aug. 5, 2010

(65) Prior Publication Data
US 2011/0275797 A1  Nov. 10, 2011

(30) Foreign Application Priority Data

Jan. 30, 2009  (JP) ................ 2009-020274
Jan. 30, 2009  (JP) ................ 2009-020424
Jan. 30, 2009  (JP) ................ 2009-020462
Oct. 16, 2009  (JP) ................ 2009-239188

(51) Int. Cl.
*C07C 229/56* (2006.01)
(52) U.S. Cl.
USPC ........................... 562/433; 562/455

(58) Field of Classification Search
USPC ................. 562/455, 433; 514/561, 563
See application file for complete search history.

(56) References Cited

U.S. PATENT DOCUMENTS

| 7,999,132 B2 | 8/2011 | Yokotani et al. |
| 2003/0073862 A1 | 4/2003 | Gustavsson et al. |
| 2006/0106048 A1 | 5/2006 | Inoue et al. |
| 2007/0135392 A1 | 6/2007 | Wendt et al. |
| 2009/0105474 A1 | 4/2009 | Yokotani et al. |
| 2009/0240052 A1 | 9/2009 | Yokotani et al. |

FOREIGN PATENT DOCUMENTS

| JP | 2001 89412 | | 4/2001 |
| JP | 2004 67690 | | 3/2004 |
| JP | 2009 501157 | | 1/2009 |
| WO | 03 004458 | | 1/2003 |
| WO | 2006 062093 | | 6/2006 |
| WO | 2006 098308 | | 9/2006 |
| WO | WO2009/030887 | * | 9/2008 |

OTHER PUBLICATIONS

Patani, 1996, Chem. Rev., vol. 96, p. 3147-3176.*
Kisseleva, T. et al., "Mechanisms of Fibrogenesis", Experimental Biology and Medicine, vol. 233, pp. 109-122, (2008).
Wynn. T., "Cellular and Molecular Mechanisms of Fibrosis", Journal of Pathology, vol. 214, pp. 199-210, (2008).
Pirespa 200 mg Package Insert, vol. 1, Shionogi & Co., Ltd., Prepared on Oct. 2008.
International Search Report Issued Mar. 16, 2010 in PCT/JP10/051209 filed Jan. 29, 2010.

* cited by examiner

*Primary Examiner* — Wu-Cheng Winston Shen
*Assistant Examiner* — Karen Cheng
(74) *Attorney, Agent, or Firm* — Oblon, Spivak, McClelland, Maier & Neustadt, L.L.P.

(57) ABSTRACT

The invention relates to an N-acyl anthranilic acid derivative or it's salt having collagen production inhibitory action.

19 Claims, No Drawings

N-ACYL ANTHRANILIC ACID DERIVATIVE OR SALT THEREOF

This application is a National Stage of PCT/JP10/051,209 fled Jan. 29, 2010 and claims the benefit of JP 2009-020274 filed Jan. 30, 2009, JP 2009-020424 filed Jan. 30, 2009, JP 2009-020462 filed Jan. 30, 2009, and JP 2009-239188 filed Oct. 16, 2009.

TECHNICAL FIELD

The present invention relates to an N-acyl anthranilic acid derivative having collagen production inhibitory action or a salt thereof.

BACKGROUND ART

Fibrogenesis, which produces extracellular matrixes including collagen as a typical example, is a mechanism of wound healing. However, if injury is prolonged, it deviates from a usual process, and the extracellular matrix is excessively deposited over a wide range, resulting in the development of fibrosis. Fibrosis is observed in various organs, but the origins of extracellular matrix-producing cells are considered to be the same. Such origins are considered to be endogenous fibroblasts, epithelial cells that have undergone epithelial-mesenchymal transition, and fibrocytes (Non Patent Document 1). Fibrosis is a disease in which functional disorder occurs as a result of the damage of a tissue itself due to a causal disease and the subsequent fiber forming, resulting in organ failure. This disease has poor prognosis.

To date, suppression of inflammatory response has been attempted to treat fibrosis, but sufficient effects could not be obtained from such treatment. Studies have been conducted to develop an antifibrotic agent that targets fibrosis regulatory factors, such as TGF (Transforming Growth Factor)-β1, VEGF (Vascular Endothelial Growth Factor), PDGF (Platelet-Derived Growth Factor) and angiotensin H (Non Patent Document 2).

Pirfenidone has been applied as only such an antifibrotic agent to idiopathic pulmonary fibrosis. The effectiveness of pirfenidone recognized in clinical tests has been only suppression of a decrease in vital capacity. In addition, pirfenidone has had side effects such as photosensitivity in 87.9% of subjects (Non Patent Document 3). Hence, application of pirfenidone is not a sufficient therapeutic method in terms of both effectiveness and safety.

A main ingredient of an extracellular matrix that is excessively deposited in fibrosis is collagen. Among others, the most abundant collagen is type I collagen. Accordingly, a substance that inhibits production of collagen is useful for the prevention or treatment of diseases attended with fibrosis lesion.

To date, it has been reported that an anthranilic acid derivative has action to inhibit production of matrix metalloprotease-13 (Patent Document 1). However, it has been completely unknown that the anthralinic acid derivative has action to suppress production of collagen.

CITATION LIST

Patent Document

Patent Document 1: International Publication WO2006/062093, pamphlet

Non Patent Document

Non Patent Document 1: Experimental Biology and Medicine, Vol. 233, pp. 109-122, 2008
Non Patent Document 2: Journal of Pathology, Vol. 214, pp. 199-210, 2008
Non Patent Document 3: Pirespa 200 mg Package Insert, Vol. 1, Shionogi & Co., Ltd., prepared on October, 2008

SUMMARY OF INVENTION

Technical Problem

It has been desired to develop an agent, which has collagen production inhibitory action and is used for the prevention, treatment and the like of diseases associated with excessive production of collagen.

Solution to Problem

Under the aforementioned circumstances, the present inventors have conducted intensive studies. As a result, the inventors have found that an N-acyl anthranilic acid derivative represented by the following general formula [1] or a salt thereof:

[Formula 1]

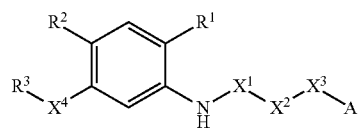

wherein
$R^1$ represents an optionally protected carboxyl group or an optionally protected 1H-tetrazol-5-yl group;
$R^2$ represents a hydrogen atom, a halogen atom, a cyano group, a nitro group, an optionally protected hydroxyl group, an optionally protected amino group, an optionally protected or substituted alkylamino group, an optionally substituted dialkylamino group, an optionally substituted alkyl group or an optionally substituted alkoxy group;
$R^3$ represents an optionally substituted cycloalkyl group, an optionally substituted cycloalkenyl group, an optionally substituted aryl group or an optionally substituted heterocyclic group;
$X^1$ represents a carbonyl group;
$X^2$ represents an optionally substituted alkylene group, an optionally substituted alkenylene group, an optionally substituted alkynylene group or a bond;
$X^3$ represents an oxygen atom, a sulfur atom or a bond;
$X^4$ represents a group represented by a general formula —$X^5$—$X^6$— or —$X^6$—$X^5$— (provided that the bond on the left side of each general formula binds to $R^3$), wherein
$X^5$ represents an oxygen atom, a sulfur atom, an optionally protected imino group, a sulfinyl group, a sulfonyl group or a bond; and
$X^6$ represents an optionally substituted alkylene group, an optionally substituted alkenylene group, an optionally substituted alkynylene group or a bond; and
A represents an optionally substituted phenyl group, an optionally substituted cycloalkyl group or an optionally substituted heterocyclic group, has collagen production inhibitory action, and it is useful for the prevention, treatment and the like of diseases associated with excessive production of collagen.

Moreover, the present inventors have also found that a novel N-acyl anthranilic acid derivative represented by the following general formula [1] or a salt thereof:

[Formula 2]

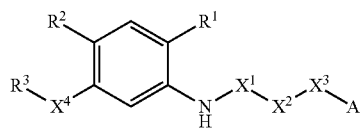

[1]

wherein
$R^1$ represents an optionally protected carboxyl group or an optionally protected 1H-tetrazol-5-yl group;
$R^2$ represents a hydrogen atom, a halogen atom, a cyano group, a nitro group, an optionally protected hydroxyl group, an optionally protected amino group, an optionally protected or substituted alkylamino group, an optionally substituted dialkylamino group, an optionally substituted alkyl group or an optionally substituted alkoxy group;
$R^3$ represents an optionally substituted aryl group or an optionally substituted heterocyclic group;
$X^1$ represents a carbonyl group;
$X^2$ represents a bond;
$X^3$ represents a bond;
$X^4$ represents an oxygen atom, an optionally protected imino group, an optionally substituted alkylene group or a bond; and
A represents a group represented by the following general formula:

[Formula 3]

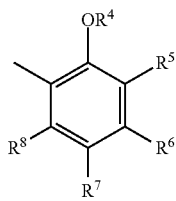

wherein
$R^4$ represents a hydrogen atom or a phenolic hydroxyl protecting group; one of $R^5$, $R^6$, $R^7$ and $R^8$ represents a group represented by a general formula —Y—$R^9$:
wherein
$R^9$ represents a halogen atom, a cyano group, a nitro group, an optionally protected hydroxyl group, an optionally protected amino group, an optionally protected or substituted alkylamino group, an optionally substituted dialkylamino group, an optionally substituted alkyl group, an optionally substituted alkoxy group, an optionally substituted aryl group, an optionally substituted aryloxy group, an optionally substituted heterocyclic group, an optionally substituted heterocyclic oxy group, an optionally substituted acyl group or an optionally substituted acyloxy group;
Y represents an optionally substituted alkylene group, an optionally substituted alkenylene group, an optionally substituted alkynylene group, a bond, a group represented by a general formula —$(CH_2)_m$—O—$(CH_2)_n$—:
wherein m represents an integer of 0 to 4; and n represents an integer of 1 to 4, or a general formula —$(CH_2)_m$—$NR^{10}$—$(CH_2)_n$—:
wherein $R^{10}$ represents a hydrogen atom, an optionally substituted lower alkyl group or an imino protecting group; and m and n have the same meanings as above, and
the remaining others identically or differently each represent a hydrogen atom, a halogen atom, an optionally protected hydroxyl group, an optionally protected amino group, an optionally protected or substituted alkylamino group or an optionally substituted dialkylamino group; or
$R^5$ and $R^8$ identically or differently each represent a hydrogen atom, a halogen atom, an optionally protected hydroxyl group or an optionally protected amino group, and
$R^6$ and $R^7$ each represent, together with carbon atoms to which they bind, an optionally substituted 5- to 7-membered heterocyclic group, or
a group represented by the following general formula:

[Formula 4]

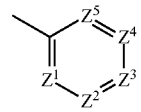

wherein
one of $Z^1$, $Z^2$, $Z^3$, $Z^4$ and $Z^5$ represents a nitrogen atom,
One of the remaining four represents a group represented by a general formula C—$R^{11}$:
wherein $R^{11}$ represents an optionally substituted aryl group, an optionally substituted nitrogen-containing 6-membered aromatic heterocyclic group, an optionally substituted oxygen-containing 5-membered aromatic heterocyclic group, an optionally substituted nitrogen-containing oxygen-containing 5-membered aromatic heterocyclic group or an optionally substituted nitrogen-containing sulfur-containing 5-membered aromatic heterocyclic group, the remaining three identically or differently each represent a group represented by a general formula C—$R^{12}$:
wherein $R^{12}$ represents a hydrogen atom or a halogen atom, has collagen production inhibitory action, and it is useful for the prevention, treatment and the like of diseases associated with excessive production of collagen, and is excellent in terms of safety and kinetics, thereby completing the present invention.

Advantageous Effects of Invention

Since the N-acyl anthranilic acid derivative of the present invention or a salt thereof has collagen production inhibitory action and is excellent in terms of safety and kinetics, it is useful for the prevention, treatment, and the like of diseases associated with excessive production of collagen, such as pulmonary fibrosis, scleroderma, nephrosclerosis and hepatocirrhosis.

DESCRIPTION OF EMBODIMENTS

The compound of the present invention will be described in detail below.

In the present specification, each term has the following meanings, unless otherwise specified.

The halogen atom means a fluorine atom, a chlorine atom, a bromine atom or an iodine atom.

The alkyl group means a linear or branched $C_{1-12}$ alkyl group such as methyl, ethyl, propyl, isopropyl, butyl, sec-butyl, isobutyl, tert-butyl, pentyl, isopentyl, hexyl, heptyl and octyl.

The lower alkyl group means a linear or branched $C_{1-6}$ alkyl group such as methyl, ethyl, propyl, isopropyl, butyl, sec-butyl, isobutyl, tert-butyl, pentyl and isopentyl.

The alkenyl group means a linear or branched $C_{2-12}$ alkenyl group such as vinyl, allyl, propenyl, isopropenyl, butenyl, isobutenyl, pentenyl, hexenyl, heptenyl and octenyl.

The alkynyl group means a linear or branched $C_{2-12}$ alkynyl group such as ethynyl, 2-propynyl and 2-butynyl.

The cycloalkyl group means a $C_{3-8}$ cycloalkyl group such as cyclopropyl, cyclobutyl, cyclopentyl and cyclohexyl.

The aryl group means a group such as phenyl or naphthyl.

The aralkyl group means an ar-$C_{1-6}$ alkyl group such as benzyl, diphenylmethyl, trityl, phenethyl and naphthylmethyl.

The alkylene group means a linear or branched $C_{1-6}$ alkylene group such as methylene, ethylene, propylene, butylenes and hexylene.

The alkenylene group means a linear or branched $C_{2-6}$ alkenylene group such as vinylene, propenylene, 1-butenylene and 2-butenylene.

The alkynylene group means a linear or branched $C_{2-6}$ alkynylene group such as ethynylene, propynylene, 1-butynylene and 2-butynylene.

The alkoxy group means a linear or branched $C_{1-6}$ alkyloxy group such as methoxy, ethoxy, propoxy, isopropoxy, butoxy, isobutoxy, sec-butoxy, tert-butoxy, pentyloxy and isopentyloxy.

The aryloxy group means a group such as phenoxy or naphthoxy.

The alkoxyalkyl group means a $C_{1-6}$ alkyloxy $C_{1-6}$ alkyl group such as methoxymethyl and 1-ethoxyethyl.

The aralkyloxyalkyl group means an ar-$C_{1-6}$ alkyloxy $C_{1-6}$ alkyl group such as benzyloxymethyl and phenethyloxymethyl.

The acyl group means, for example, a formyl group, a linear or branched $C_{2-12}$ alkanoyl group such as acetyl, propionyl and isovaleryl, an ar-$C_{1-6}$ alkylcarbonyl group such as benzylcarbonyl, a cyclic hydrocarbon-carbonyl group such as benzoyl and naphthoyl, a heterocyclic carbonyl group such as nicotinoyl, thenoyl, pyrrolidinocarbonyl and furoyl, a succinyl group, a glutaryl group, a maleoyl group, a phthaloyl group, or a linear or branched α-aminoalkanoyl group having an optionally protected N-terminus, which is derived from an amino acid (wherein examples of the amino acid include glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline and hydroxyproline).

The acylalkyl group means a group such as acetylmethyl, benzoylmethyl, p-nitrobenzoylmethyl, p-bromobenzoylmethyl, p-methoxybenzoylmethyl or 1-benzoylethyl.

The acyloxy group means a linear or branched $C_{2-6}$ alkanoyloxy group such as acetyloxy and propionyloxy, or an aryloxy group such as benzoyloxy.

The acyloxyalkyl group means a group such as acetoxymethyl, propionyloxymethyl or pivaloyloxymethyl.

The alkyloxycarbonyl group means a linear or branched $C_{1-12}$ alkyloxycarbonyl group such as methoxycarbonyl, ethoxycarbonyl, 1,1-dimethylpropoxycarbonyl, isopropoxycarbonyl, 2-ethylhexyloxycarbonyl, tert-butoxycarbonyl and tert-pentyloxycarbonyl.

The aralkyloxycarbonyl group means an ar-$C_{1-6}$ alkyloxycarbonyl group such as benzyloxycarbonyl and phenethyloxycarbonyl.

The aryloxycarbonyl group means a group such as phenyloxycarbonyl.

The alkylamino group means a mono($C_{1-6}$ alkyl)amino group such as methylamino, ethylamino, propylamino, isopropylamino, butylamino, tert-butylamino and pentylamino.

The dialkylamino group means a di($C_{1-6}$ alkyl)amino group such as dimethylamino, diethylamino, dipropylamino, dibutylamino, (ethyl)(methyl)amino, (methyl)(propyl)amino, (butyl)(methyl)amino and (methyl)(pentyl)amino.

The alkylthioalkyl group means a $C_{1-6}$ alkylthio $C_{1-6}$ alkyl group such as methylthiomethyl, ethylthiomethyl and propylthiomethyl.

The arylthio group means a group such as phenylthio.

The arylthioalkyl group means a group such as phenylsulfanylmethyl or 2-(p-nitrophenyl sulfenyl)ethyl.

The alkylsulfonyl group means a $C_{1-6}$ alkylsulfonyl group such as methylsulfonyl, ethylsulfonyl and propyl sulfonyl.

The arylsulfonyl group means a group such as benzenesulfonyl, p-toluenesulfonyl or naphthalenesulfonyl.

The arylsulfonylalkyl group means a group such as p-toluenesulfonylethyl.

The alkylsulfonyloxy group means a $C_{1-6}$ alkylsulfonyloxy group such as methylsulfonyloxy and ethylsulfonyloxy.

The arylsulfonyloxy group means a group such as benzenesulfonyloxy or p-toluenesulfonyloxy.

The alkylsulfonylamino group means a $C_{1-6}$ alkylsulfonylamino group such as methylsulfonylamino and ethylsulfonylamino.

The substituted silyl group means a group such as trimethylsilyl, triethylsilyl or tributylsilyl.

The alkylsilylalkyl group means a group such as 2-(trimethylsilyl)ethyl.

The nitrogen-containing 6-membered aromatic heterocyclic group means a pyridyl, pyrazinyl, pyrimidinyl or pyridazinyl group, etc.

The oxygen-containing 5-membered aromatic heterocyclic group means a furanyl group, etc.

The nitrogen-containing oxygen-containing 5-membered aromatic heterocyclic group means an oxazolyl, oxadiazolyl or isoxazolyl group, etc.

The nitrogen-containing sulfur-containing 5-membered aromatic heterocyclic group means a thiazolyl, thiadiazolyl or isothiazolyl group, etc.

The oxygen-containing heterocyclic group means a group such as 2-tetrahydropyranyl or 2-tetrahydrofuranyl The sulfur-containing heterocyclic group means a group such as tetrahydrothiopyranyl.

The heterocyclic oxycarbonyl group means a group such as 2-furfuryloxycarbonyl or 8-quinolyloxycarbonyl.

The nitrogen-containing heterocyclic alkyl group means a group such as phthalimidomethyl or succinimidomethyl.

The monocyclic heterocyclic group means: a monocyclic nitrogen-containing heterocyclic group, which comprises only a nitrogen atom as a heteroatom to form the ring, such as azetidinyl, pyrrolyl, pyrrolinyl, pyrrolidinyl, piperidyl, piperazinyl, homopiperazinyl, azepanyl, diazepanyl, octahydroazocinyl, imidazolyl, pyrazolyl, pyridyl, tetrahydropyridyl, pyridazinyl, pyrazinyl, pyrimidinyl, tetrazolyl, imidazolinyl, imidazolidinyl, pyrazolinyl and pyrazolidinyl groups; a monocyclic oxygen-containing heterocyclic group, which comprises only an oxygen atom as a heteroatom to form the ring, such as tetrahydrofuranyl, furanyl and pyranyl groups; a monocyclic sulfur-containing heterocyclic group, which comprises only a sulfur atom as a hetero atom to form the ring, such as a thienyl group; a monocyclic nitrogen- and oxygen-containing heterocyclic group, which comprises only a nitrogen atom and an oxygen atom as heteroatoms to form the ring, such as oxazolyl, oxadiazolyl, isoxazolyl and morpholinyl groups; a monocyclic nitrogen- and sulfur-containing heterocyclic group, which comprises only a nitrogen atom and a sulfur atom as heteroatoms to form the ring, such as thiazolyl, isothiazolyl, thiadiazolyl, thiomorpholinyl, 1-oxidothiomorpholinyl and 1,1-dioxidothiomorpholinyl groups; a monocyclic oxygen- and sulfur-containing heterocyclic group, which comprises only an oxygen atom and a sulfur atom as heteroatoms to form the ring, such as a thioxanyl group; or the like.

The bicyclic heterocyclic group means: a bicyclic nitrogen-containing heterocyclic group shown with a condensed ring or a crosslinked ring, which comprises only a nitrogen atom as a heteroatom to form the ring, such as indolyl, indolinyl, 2-oxoindolinyl, isoindolyl, indolizinyl, benzimidazolyl, benzotriazolyl, indazolyl, quinolyl, tetrahydroquinolinyl, tetrahydroisoquinolinyl, quinolizinyl, isoquinolyl, phthalazinyl, naphthylidinyl, quinoxalinyl, dihydroquinoxalinyl, quinazolinyl, cinnolinyl, quinuclidinyl and 2,3-dihydrobenzopyrrolyl groups; a bicyclic oxygen-containing heterocyclic group shown with a condensed ring or crosslinked ring, which comprises only an oxygen atom as a heteroatom to form the ring, such as benzofuranyl, isobenzofuranyl, chromenyl, chromanyl, isochromanyl, benzo-1,3-dioxolyl, benzo-1,4-dioxanyl and 2,3-dihydrobenzofuranyl groups; a bicyclic sulfur-containing heterocyclic group shown with a condensed ring or a crosslinked ring, which comprises only a sulfur atom as a heteroatom to form the ring, such as benzothienyl and 2,3-dihydrobenzothienyl groups; a bicyclic nitrogen- and oxygen-containing heterocyclic group shown with a condensed ring or a crosslinked ring, which forms the ring with 10 or more atoms and which comprises a nitrogen atom and an oxygen atom as heteroatom, such as benzomorpholinyl and benzomorpholonyl groups; or a bicyclic nitrogen- and sulfur-containing heterocyclic group shown with a condensed ring or a crosslinked ring, which comprises a nitrogen atom and a sulfur atom as heteroatoms to form the ring, such as benzothiazolyl and benzothiadiazolyl groups.

The heterocyclic group means: a monocyclic heterocyclic group; a bicyclic heterocyclic group; or a tricyclic heterocyclic group such as thiantholenyl, xanthenyl, phenoxathiinyl, carbazolyl, β-carbolinyl, phenanthridinyl, acridinyl, perimidinyl, phenanthrolinyl, phenazinyl, phenothiazinyl and phenoxazinyl.

The 5- to 7-membered heterocyclic group means a group such as imidazolyl, triazolyl, pyrrolyl, furanyl, dioxolyl, dioxanyl, thienyl, morpholinyl, morpholonyl or thiazolyl.

The heterocyclic oxy group means a group such as pyrrolidinyloxy, piperidinyloxy, piperazinyloxy, morpholinyloxy, thiomorpholinyloxy, tetrahydrofuranyloxy, tetrahydropyranyloxy, tetrahydrothiopyranyloxy, pyridyloxy or pyrimidinyloxy.

The cyclic amino group may be either a saturated or unsaturated cyclic amino group. In addition, it may further comprise, in the ring thereof, one or more heteroatoms such as a nitrogen atom, an oxygen atom or a sulfur atom, and a carbonyl carbon. Moreover, it may be a monocyclic, bicyclic or tricyclic group. More specifically, the cyclic amino group means: a saturated or unsaturated monocyclic 3- to 7-membered cyclic amino group having one nitrogen atom, such as aziridin-1-yl, azetidin-1-yl, pyrrolidin-1-yl, pyrrolin-1-yl, pyrrol-1-yl, dihydropyridin-1-yl, tetrahydropyridin-1-yl, piperidin-1-yl, dihydroazepin-1-yl and perhydroazepin-1-yl; a saturated or unsaturated monocyclic 3- to 7-membered cyclic amino group having two nitrogen atoms, such as imidazol-1-yl, imidazolidin-1-yl, imidazolin-1-yl, pyrazolidin-1-yl, piperazin-1-yl, 1,4-dihydropyrazin-1-yl, 1,2-dihydropyrimidin-1-yl, perhydropyrazin-1-yl and homopiperazin-1-yl; a saturated or unsaturated monocyclic 3- to 7-membered cyclic amino group having three or more nitrogen atoms, such as 1,2,4-triazol-1-yl, 1,2,3-triazol-1-yl, 1,2-dihydro-1,2,4-triazin-1-yl and perhydro-5-triazin-1-yl; a saturated or unsaturated monocyclic 3- to 7-membered cyclic amino group having 1 to 4 heteroatoms selected from an oxygen atom and a sulfur atom, as well as a nitrogen atom, such as oxazolidin-3-yl, isoxazolidin-2-yl, morpholin-4-yl, thiazolidin-3-yl, isothiazolidin-2-yl, thiomorpholin-4-yl, homothiomorpholin-4-yl and 1,2,4-thiadiazolin-2-yl; a saturated or unsaturated bicyclic or tricyclic cyclic amino group, such as isoindolin-2-yl, indolin-1-yl, 1H-indazol-1-yl, 1H-indol-1-yl, 1H-benzimidazol-1-yl, purin-7-yl, tetrahydroquinolin-1-yl and tetrahydroisoquinolin-2-yl; or a spiro-type or crosslinked saturated or unsaturated 5- to 12-membered cyclic amino group, such as 5-azaspiro[2.4]heptan-5-yl, 2,8-diazabicyclo[4.3.0]nonan-8-yl, 3-azabicyclo[3.1.0]hexan-3-yl, 2-oxa-5,8-diazabicyclo[4.3.0]nonan-8-yl, 2,8-diazaspiro[4.4]nonan-2-yl and 7-azabicyclo[2.2.1]heptan-7-yl.

The amino protecting group includes all groups that can be used as common amino protecting groups. Examples of such an amino protecting group include those described in W. Greene et al., Protective Groups in Organic Synthesis, 4$^{th}$ edition, pp. 696-868, 2007, John Wiley & Sons, INC. Specific examples include an acyl group, an alkyloxycarbonyl group, an aralkyloxycarbonyl group, an aryloxycarbonyl group, an aralkyl group, an alkoxyalkyl group, an aralkyloxyalkyl group, an arylthio group, an alkylsulfonyl group, an arylsulfonyl group and a substituted silyl group.

The imino protecting group includes all groups that can be used as common imino protecting groups. Examples of such an imino protecting group include those described in W. Greene et al., Protective Groups in Organic Synthesis, 4$^{th}$ edition, pp. 696-868, 2007, John Wiley & Sons, INC. Specific examples include an acyl group, an alkyloxycarbonyl group, an aralkyloxycarbonyl group, an aryloxycarbonyl group, an aralkyl group, an alkoxyalkyl group, an arylthio group, an alkylsulfonyl group, an arylsulfonyl group and a substituted silyl group.

The hydroxyl protecting group includes all groups that can be used as common hydroxyl protecting groups. Examples of such a hydroxyl protecting group include those described in W. Greene et al., Protective Groups in Organic Synthesis, 4$^{th}$ edition, pp. 16-299, 2007, John Wiley & Sons, INC. Specific examples include an acyl group, an alkyloxycarbonyl group, an aralkyloxycarbonyl group, a heterocyclic oxycarbonyl group, an alkyl group, an alkenyl group, an aralkyl group, an oxygen-containing heterocyclic group, a sulfur-containing heterocyclic group, an alkoxyalkyl group, an aralkyloxyalkyl group, an alkylsulfonyl group, an arylsulfonyl group and a substituted silyl group.

The carboxyl protecting group includes all groups that can be used as common carboxyl protecting groups. Examples of such a carboxyl protecting group include those described in W. Greene et al., Protective Groups in Organic Synthesis, 4$^{th}$ edition, pp. 533-643, 2007, John Wiley & Sons, INC. Specific examples include an alkyl group, an aryl group, an aralkyl group, an acylalkyl group, an arylthioalkyl group, an arylsulfonylalkyl group, an oxygen-containing heterocyclic group, an alkylsilylalkyl group, an acyloxy alkyl group, a nitrogen-containing heterocyclic alkyl group, a cycloalkyl group, an alkoxyalkyl group, an aralkyloxyalkyl group, an alkylthioalkyl group, an alkenyl group and a substituted silyl group.

The phenolic hydroxyl protecting group includes all groups that can be used as common phenolic hydroxyl protecting groups. Examples of such a phenolic hydroxyl protecting group include those described in W. Greene et al., Protective Groups in Organic Synthesis, $4^{th}$ edition, pp. 370-424, 2007, John Wiley & Sons, INC. Specific examples include an acyl group, an alkyl group, an alkenyl group, an aralkyl group, an oxygen-containing heterocyclic group, a sulfur-containing heterocyclic group, an alkoxyalkyl group, an alkylsulfonyl group, an arylsulfonyl group and a substituted silyl group.

The tetrazole protecting group includes all groups that can be used as common tetrazole protecting groups. Examples of such a tetrazole protecting group include those described in W. Greene et al., Protective Groups in Organic Synthesis, $4^{th}$ edition, pp. 872-894, 2007, John Wiley & Sons, INC. Specific examples include an acyl group, an alkyloxycarbonyl group, an aralkyloxycarbonyl group, an aryloxycarbonyl group, an aralkyl group, an acylalkyl group, an alkoxyalkyl group, an arylsulfonyl group and a substituted silyl group.

Examples of the leaving group include a halogen atom, an alkylsulfonyloxy group and an arylsulfonyloxy group.

Examples of the aliphatic hydrocarbon include pentane, hexane and cyclohexane.

Examples of the halogenated hydrocarbon include methylene chloride, chloroform and dichloroethane.

Examples of the alcohol include methanol, ethanol, propanol, 2-propanol, butanol and 2-methyl-2-propanol.

Examples of the ether include diethyl ether, diisopropyl ether, dioxane, tetrahydrofuran, anisole, ethylene glycol dimethyl ether, diethylene glycol dimethyl ether and diethylene glycol diethyl ether.

Examples of the ketone include acetone, 2-butanone and 4-methyl-2-pentanone.

Examples of the ester include methyl acetate, ethyl acetate, propyl acetate and butyl acetate.

Examples of the amide include N,N-dimethylformamide, N,N-dimethylacetamide and 1-methyl-2-pyrrolidone.

Examples of the aromatic hydrocarbon include benzene, toluene and xylene.

Examples of the salt of the compound of the general formula [1] include: the salts of basic groups such as a generally known amino group; or the salts of acidic groups such as a phenolic hydroxyl group or carboxyl group.

Examples of the salts of basic groups include: salts with mineral acids such as hydrochloric acid, hydrogen bromide and sulfuric acid; salts with organic carboxylic acids such as tartaric acid, formic acid, acetic acid, citric acid, trichloroacetic acid and trifluoroacetic acid; and salts with sulfonic acids such as methanesulfonic acid, benzenesulfonic acid, p-toluenesulfonic acid, mesitylenesulfonic acid and naphthalenesulfonic acid.

Examples of the salts of acidic groups include: salts with alkaline metals such as sodium and potassium; salts with alkaline-earth metals such as calcium and magnesium; ammonium salts; and salts with nitrogen-containing organic bases such as trimethylamine, triethylamine, tributylamine, pyridine, N,N-dimethylaniline, N-methyl piperidine, N-methyl morpholine, diethylamine, dicyclohexylamine, procaine, dibenzylamine, N-benzyl-β-phenethylamine and N,N'-dibenzylethylenediamine.

Moreover, among the aforementioned salts, preferred salts of the compound represented by a general formula [1] include pharmacologically acceptable salts.

The alkylamino group as $R^2$ and the dialkylamino group as $R^2$ may be optionally substituted with one or more groups selected from among an amino group, a hydroxyl group, a carboxyl group and an alkoxy group.

The alkyl group as $R^2$ and the alkoxy group as $R^2$ may be optionally substituted with one or more groups selected from among a halogen atom, a cyano group, a hydroxyl group, a carboxyl group and an alkoxy group.

The cycloalkyl group as $R^3$, the cycloalkenyl group as $R^3$, the aryl group as $R^3$, the monocyclic heterocyclic group as $R^3$, the bicyclic heterocyclic group as $R^3$, and the heterocyclic group as $R^3$ may be optionally substituted with one or more groups selected from among a halogen atom, a cyano group, a nitro group, an acyl group, an acyloxy group, a sulfo group, a phosphoryl group, an alkylsulfonyl group, an alkylsulfonylamide group, an acetamide group, a carbamoyl group, an oxo group, optionally protected carboxyl, amino, alkylamino and hydroxyl groups, and optionally substituted alkyl, alkenyl, alkynyl, alkoxy, aryl, alkylamino, dialkylamino, cyclic amino, aralkyl and heterocyclic groups.

The alkylamino groups as $R^5$, $R^6$, $R^7$ and $R^8$ and the dialkylamino groups as $R^5$, $R^6$, $R^7$ and $R^8$ may be optionally substituted with one or more groups selected from among an amino group, a hydroxyl group and an alkoxy group.

The 5- to 7-membered heterocyclic group formed by $R^6$ and $R^7$ together with carbon atoms, to which they bind, may be optionally substituted with one or more groups selected from among a halogen atom, a cyano group, a nitro group, an acyl group, an acyloxy group, a sulfo group, a phosphoryl group, an alkylsulfonyl group, an alkylsulfonylamino group, an acetamide group, a carbamoyl group, an oxo group, optionally protected carboxyl, amino, alkylamino and hydroxyl groups, and optionally substituted alkyl, alkenyl, alkynyl, alkoxy, aryl, alkylamino, dialkylamino, cyclic amino, aralkyl and heterocyclic groups.

The alkylamino groups as $R^9$ and $R^{9a}$ and the dialkylamino groups as $R^9$ and $R^{9a}$ may be optionally substituted with one or more groups selected from among a hydroxyl group, optionally protected carboxyl, amino and alkylamino groups, and optionally substituted alkyl, alkenyl, alkynyl, alkoxy, aryl, alkylamino, dialkylamino, cyclic amino, aralkyl and heterocyclic groups.

The alkyl groups as $R^9$ and $R^{9a}$ and the alkoxy groups as $R^9$ and $R^{9a}$ may be optionally substituted with one or more groups selected from among a halogen atom, a cyano group, a hydroxyl group and an alkoxy group.

The aryl groups as $R^9$ and $R^{9a}$, the aryloxy group as $R^9$ and $R^{9a}$, the heterocyclic groups as $R^9$, $R^{9a}$ and $R^{9b}$, and the heterocyclic oxy groups as $R^9$ and $R^{9a}$ may be optionally substituted with one or more groups selected from among a halogen atom, a cyano group, a nitro group, an acyl group, an acyloxy group, a sulfo group, a phosphoryl group, an alkylsulfonyl group, an alkylsulfonylamino group, an acetamide group, a carbamoyl group, an oxo group, optionally protected carboxyl, amino, alkylamino and hydroxyl groups, and optionally substituted alkyl, alkenyl, alkynyl, alkoxy, aryl, alkylamino, dialkylamino, cyclic amino, aralkyl and heterocyclic groups.

The acyl groups as $R^9$ and $R^{9a}$ and the acyloxy groups as $R^9$ and $R^{9a}$ may be optionally substituted with one or more groups selected from among a halogen atom, a cyano group, a hydroxyl group and an alkoxy group.

The lower alkyl group as $R^{10}$ may be optionally substituted with one or more groups selected from among a hydroxyl group, optionally protected carboxyl, amino and alkylamino groups, and optionally substituted alkyl, alkenyl, alkynyl, alkoxy, aryl, alkylamino, dialkylamino, cyclic amino, aralkyl and heterocyclic groups.

The aryl groups as $R^{11}$ and $R^{11a}$, the nitrogen-containing 6-membered aromatic heterocyclic groups as $R^{11}$ and $R^{11a}$, the oxygen-containing 5-membered aromatic heterocyclic groups as $R^{11}$ and $R^{11a}$, the nitrogen-containing oxygen-containing 5-membered aromatic heterocyclic group as $R^{11}$, and the nitrogen-containing sulfur-containing 5-membered aromatic heterocyclic group as $R^{11}$ may be optionally substituted with one or more groups selected from among a halogen atom, a cyano group, a nitro group, an acyl group, an acyloxy group, a sulfo group, a phosphoryl group, an alkylsulfonyl group, an alkylsulfonylamino group, an acetamide group, a carbamoyl group, an oxo group, optionally protected carboxyl, amino, alkylamino and hydroxyl groups, and optionally substituted alkyl, alkenyl, alkynyl, alkoxy, aryl, alkylamino, dialkylamino, cyclic amino, aralkyl and heterocyclic groups.

The alkylene groups as $X^2$ and $X^6$, the alkenylene groups as $X^2$ and $X^6$, and the alkynylene groups as $X^2$ and $X^6$, may be optionally substituted with one or more groups selected from among a halogen atom, and optionally substituted alkyl, phenyl, cyclic amino and heterocyclic groups.

The alkylene group as $X^4$ may be optionally substituted with one or more groups selected from among a halogen atom, a cyano group, a hydroxyl group and an alkoxy group.

The alkylene groups as Y and $Y^a$, the alkenylene group as Y, and the alkynylene group as Y may be optionally substituted with one or more groups selected from among a hydroxyl group and an alkoxy group.

The phenyl group as A, the cycloalkyl group as A, and the heterocyclic group as A may be optionally substituted with one or more groups selected from among a halogen atom, a cyano group, a nitro group, an acetamide group, a carbamoyl group, optionally protected carboxyl, amino and hydroxyl groups, and optionally substituted alkyl, alkoxy, phenyl, cyclic amino and heterocyclic groups.

Examples of a substituent for the above described, optionally substituted alkyl, alkenyl, alkynyl, alkoxy, aryl, alkylamino, dialkylamino, cyclic amino, aralkyl and heterocyclic groups include a halogen atom, a cyano group, a nitro group, an acyl group, a sulfo group, a phosphoryl group, a cyclic amino group, an alkylsulfonyl group, an alkylsulfonylamino group, an acetamide group, an aralkyl group, a carbamoyl group, an alkyl group, an alkenyl group, an alkynyl group, an alkoxy group, an aryl group, a heterocyclic group, and optionally protected carboxyl, amino and hydroxyl groups.

The compound represented by a general formula [1] of the present invention preferably includes the following compounds.

A compound, wherein $R^1$ is an optionally protected carboxyl group, is preferable.

A compound, wherein $R^2$ is a hydrogen atom or a halogen atom, is preferable, and a compound, wherein $R^2$ is a hydrogen atom, is more preferable.

A compound, wherein $R^3$ is an optionally substituted phenyl group, an optionally substituted furanyl group, or an optionally substituted thienyl group, is preferable, and a compound, wherein $R^3$ is an optionally substituted phenyl group or an optionally substituted furanyl group, is more preferable.

A compound, wherein $R^3$ is an optionally substituted cycloalkyl group, an optionally substituted cycloalkenyl group, an optionally substituted phenyl group, an optionally substituted monocyclic heterocyclic group, or an optionally substituted bicyclic heterocyclic group, is preferable; a compound, wherein $R^3$ is an optionally substituted phenyl group or an optionally substituted bicyclic heterocyclic group, is more preferable; and a compound, wherein $R^3$ is an optionally substituted phenyl group, is further preferable.

A compound, wherein $R^4$ is a hydrogen atom, is preferable.

A compound, wherein one of $R^5$, $R^6$, $R^7$ and $R^8$ represents a group represented by a general formula —Y—$R^{9a}$ [wherein $R^{9a}$ represents a halogen atom, a nitro group, an optionally protected hydroxyl group, an optionally protected amino group, an optionally protected or substituted alkylamino group, an optionally substituted dialkylamino group, an optionally substituted alkyl group, an optionally substituted alkoxy group, an optionally substituted aryl group, an optionally substituted aryloxy group, an optionally substituted heterocyclic group, an optionally substituted heterocyclic oxy group, an optionally substituted acyl group or an optionally substituted acyloxy group;

$Y^a$ represents an optionally substituted alkylene group, a bond, a group represented by a general formula —O—$(CH_2)_n$— [wherein n represents an integer of 1 to 4], or a group represented by a general formula —$NR^{10a}$—$(CH_2)_n$— [wherein $R^{10a}$ represents a lower alkyl group; and n has the same meanings as above]], and the remaining others each represent a hydrogen atom, is preferable. A compound, wherein $R^5$, $R^6$ and $R^8$ each represent a hydrogen atom, and $R^7$ represents a group represented by a general formula —$Y^b$—$R^{9b}$ [wherein $R^{9b}$ represents an optionally substituted heterocyclic group; and $Y^b$ represents an alkylene group, a bond, or a group represented by a general formula —O—$(CH_2)_n$— [wherein n represents an integer of 1 to 4]], is more preferable. A compound, wherein $R^5$, $R^6$ and $R^8$ each represent a hydrogen atom, and $R^7$ represents a group represented by a general formula —$Y^c$—$R^{9c}$ [wherein $R^{9c}$ represents a heterocyclic group that may be optionally substituted with a lower alkyl group; and $Y^c$ represents a methylene group, a bond, or a group represented by a general formula —O—$(CH_2)_2$—], is further preferable.

A compound, wherein $X^2$ is an optionally substituted alkylene group, an optionally substituted alkenylene group, or a bond, is preferable, and a compound, wherein $X^2$ is a bond, is more preferable.

A compound, wherein $X^3$ is a bond, is preferable.

A compound, wherein $X^4$ is an oxygen atom, an optionally protected imino group, or a bond, is preferable, and a compound, wherein $X^4$ is a bond, is more preferable.

A compound, wherein $X^4$ is an oxygen atom, an alkylene group, an alkenylene group, or a bond, is preferable, and a compound, wherein $X^4$ is a bond, is more preferable.

A compound, wherein $Z^1$ represents CH, $Z^2$ represents a nitrogen atom, $Z^3$ represents CH, $Z^4$ represents a group represented by a general formula C—$R^{11a}$ [wherein $R^{11a}$ represents an optionally substituted aryl group, an optionally substituted nitrogen-containing 6-membered aromatic heterocyclic group, or an optionally substituted oxygen-containing 5-membered aromatic heterocyclic group], and $Z^5$ represents CH, is preferable. A compound, wherein $Z^1$ represents CH, $Z^2$ represents a nitrogen atom, $Z^3$ represents CH, $Z^4$ represents C—$C_6H_5$, and $Z^5$ represents CH, is more preferable.

A compound, wherein A is an optionally substituted phenyl group or an optionally substituted heterocyclic group, is preferable, and a compound, wherein A is an optionally substituted phenyl group or an optionally substituted pyridyl group, is more preferable.

Examples of the diseases associated with excessive production of collagen include pulmonary fibrosis, scleroderma, nephrosclerosis and hepatocirrhosis. Of these, a preferred disease is pulmonary fibrosis.

Preferred examples of the compound represented by a general formula [1] of the present invention include the following compounds:

2-(2-hydroxy-5-(pyridin-4-yl)benzamido)-4-phenylbenzoic acid,
2-(2-hydroxy-5-(pyridin-3-yl)benzamido)-4-phenylbenzoic acid,
2-(2-hydroxy-5-(pyrimidin-2-yl)benzamido)-4-phenylbenzoic acid,
2-(2-hydroxy-5-(piperidin-1-yl)benzamido)-4-phenylbenzoic acid,
2-(2-hydroxy-5-(1-methylpiperidin-4-yl)benzamido)-4-phenylbenzoic acid,
2-(5-(1-ethylpiperidin-4-yl)-2-hydroxybenzamido)-4-phenylbenzoic acid,
2-(2-hydroxy-5-(piperidin-1-yl)benzamido)-4-(3-methylphenyl)benzoic acid,
2-(2-hydroxy-5-(morpholin-4-yl)benzamido)-4-phenylbenzoic acid,
4-(3-fluorophenyl)-2-(2-hydroxy-5-(morpholin-4-yl)benzamido)benzoic acid,
2-(2-hydroxy-5-(morpholin-4-yl)benzamido)-4-(3-methoxyphenyl)benzoic acid,
2-(2-hydroxy-5-(morpholin-4-yl)benzamido)-4-(3-methylphenyl)benzoic acid,
2-(2-hydroxy-5-(methyl(2-(pyrrolidin-1-yl)ethyl)amino)benzamido)-4-phenylbenzoic acid,
2-(2-hydroxy-5-(2-(4-methylpiperazin-1-yl)ethyl)benzamido)-4-phenylbenzoic acid,
2-(2-hydroxy-5-((4-methylpiperazin-1-yl)methyl)benzamido)-4-phenylbenzoic acid,
2-(5-(2-(4-ethylpiperazin-1-yl)ethoxy)-2-hydroxybenzamido)-4-phenylbenzoic acid,
2-(2-hydroxy-5-(2-(1-methylpiperidin-4-yl)ethoxy)benzamido)-4-phenylbenzoic acid,
4-(2-(methylamino)phenyl)-2-(5-phenylpyridin-3-carboxamido)benzoic acid,
4-(2-(ethylamino)phenyl)-2-(5-phenylpyridin-3-carboxamido)benzoic acid, and
4-(furan-2-yl)-2-(5-phenylpyridin-3-carboxamido)benzoic acid.

Representative examples of the compound of the present invention include the compounds shown in Tables 1a, 1b, 1c, 2a and 2b. These are novel compounds. These compounds have collagen production inhibitory action and are useful for the prevention, treatment and the like of diseases associated with excessive production of collagen.

TABLE 1a

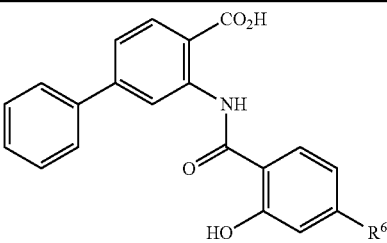

| $R^6$ |
|---|
| Cl |
| Methyl |
| Methoxy |
| Dimethylamino |
| Phenyl |
| Pyridin-2-yl |
| Pyridin-3-yl |
| Pyridin-4-yl |
| Pyrimidin-2-yl |
| Pyrimidin-5-yl |

TABLE 1a-continued

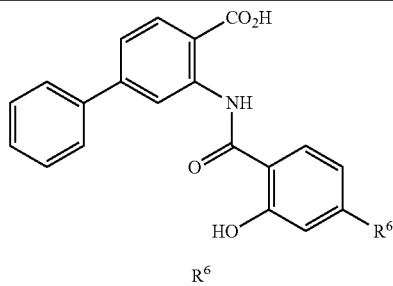

| $R^6$ |
|---|
| Furan-3-yl |
| 1H-Pyrazol-1-yl |
| 1H-Imidazol-1-yl |
| Piperidin-1-yl |
| 1-Methylpiperidin-4-yl |
| Morpholin-4-yl |
| (2-(Dimethylamino)ethyl)(methyl)amino |
| 2-(Morpholin-4-yl)ethoxy |
| 2-(4-Methylpiperazin-1-yl)ethoxy |

TABLE 1b

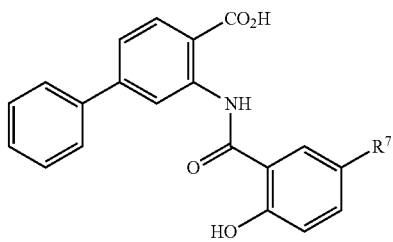

| $R^7$ |
|---|
| Cl |
| Br |
| Acetyl |
| Methyl |
| Methoxy |
| Ethoxy |
| Propoxy |
| Isopropoxy |
| Dimethylamino |
| Diethylamino |
| Phenyl |
| Phenoxy |
| Piperidin-1-yl |
| Piperidin-2-yl |
| Piperidin-3-yl |
| 1-Methylpiperidin-2-yl |
| 1-Methylpiperidin-4-yl |
| 2-Methylpiperidin-1-yl |
| 3-Methylpiperidin-1-yl |
| 4-Methylpiperidin-1-yl |
| 1-Ethylpiperidin-4-yl |
| 1-Propylpiperidin-4-yl |
| 1-(2-Hydroxyethyl)piperidin-4-yl |
| 3-Hydroxypiperidin-1-yl |
| 4-(Hydroxymethyl)piperidin-1-yl |
| 4-(Diethylamino)piperidin-1-yl |
| Azetidin-1-yl |
| Thiomorpholin-4-yl |
| Morpholin-4-yl |
| 4-Methylpiperazin-1-yl |
| 4-Ethylpiperazin-1-yl |
| Pyridin-2-yl |
| Pyridin-3-yl |
| Pyridin-4-yl |
| Pyrimidin-2-yl |
| Pyrimidin-5-yl |
| 6-Aminopyridin-2-yl |
| Furan-2-yl |

TABLE 1b-continued

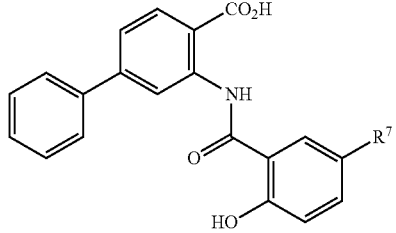

R⁷

Furan-3-yl
Tetrahydrofuran-3-yl
1H-Pyrazol-1-yl
1H-Imidazol-1-yl
Oxazol-5-yl
1,4-Oxazepan-4-yl
4-Methyl-3-oxopiperazin-1-yl
4-Ethyl-3-oxopiperazin-1-yl
Methyl(2-(pyrrolidin-1-yl)ethyl)amino
Methyl(2-(piperidin-1-yl)ethyl)amino
Methyl(2-(morpholin-4-yl)ethyl)amino
(2-(Dimethylamino)ethyl)(methyl)amino
(2-(Diethylamino)ethyl)(methyl)amino
(3-(Dimethylamino)propyl)(methyl)amino
(2-(Dimethylamino)ethyl)(ethyl)amino
(4-Methylpiperazin-1-yl)methyl
(4-Ethylpiperazin-1-yl)methyl
(4-Propylpiperazin-1-yl)methyl
(4-Isopropylpiperazin-1-yl)methyl
(Piperidin-1-yl)methyl
(Piperazin-1-yl)methyl
(Morpholin-4-yl)methyl
(4-Methylhomopiperazin-1-yl)methyl
(4-Aminopiperidin-1-yl)methyl
(4-(Methylamino)piperidin-1-yl)methyl
(4-(Dimethylamino)piperidin-1-yl)methyl
((2-Dimethylamino)ethyl)(methyl)amino)methyl
2-(Piperazin-1-yl)ethyl
2-(4-Methylpiperazin-1-yl)ethyl
2-(4-Ethylpiperazin-1-yl)ethyl
1-Methylpiperidin-4-yloxy
2-(Dimethylamino)ethoxy
2-(Diethylamino)ethoxy
2-(Morpholin-4-yl)ethoxy
2-(Pyrrolidin-1-yl)ethoxy
2-(Piperazin-1-yl)ethoxy
2-(Thiomorpholin-4-yl)ethoxy
2-(Azetidin-1-yl)ethoxy
2-(4-Hydroxypiperidin-1-yl)ethoxy
2-(4-(Hydroxymethyl)piperidin-1-yl)ethoxy
2-(4-(2-Hydroxyethyl)piperidin-1-yl)ethoxy
2-(4-Methylpiperazin-1-yl)ethoxy
2-(4-Ethylpiperazin-1-yl)ethoxy
3-(4-Methylpiperazin-1-yl)propoxy
2-(4-(2-Hydroxyethyl)piperazin-1-yl)ethoxy
2-(4-(3-Hydroxypropyl)piperazin-1-yl)ethoxy
(1-Methylpiperidin-4-yl)methoxy
2-(1-Methylpiperidin-4-yl)ethoxy

TABLE 1c

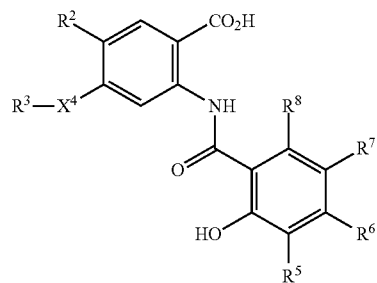

| R² | R³—X¹ | R⁵ | R⁶ | R⁷ | R⁸ |
|---|---|---|---|---|---|
| H | Phenyl | Cl | H | H | H |
| H | Phenyl | Methoxy | H | H | H |
| H | Phenyl | Methyl | H | H | H |
| H | Phenyl | H | H | H | Methoxy |
| H | Phenyl | Pyridin-3-yl | H | H | H |
| H | Phenyl | Pyridin-4-yl | H | H | H |
| H | 2-Methoxyphenyl | H | H | Methoxy | H |
| H | 2-Methoxyphenyl | H | H | Pyridin-2-yl | H |
| H | 2-Methoxyphenyl | H | H | Pyridin-3-yl | H |
| H | 2-Methoxyphenyl | H | H | Pyridin-4-yl | H |
| H | 2-Methoxyphenyl | H | H | Piperidin-1-yl | H |
| H | 3-Methoxyphenyl | H | H | Piperidin-1-yl | H |
| H | 4-Methoxyphenyl | H | H | Piperidin-1-yl | H |
| H | 2-Methylphenyl | H | H | Piperidin-1-yl | H |
| H | 3-Methylphenyl | H | H | Piperidin-1-yl | H |
| H | 4-Methylphenyl | H | H | Piperidin-1-yl | H |
| H | 2-Fluorophenyl | H | H | Piperidin-1-yl | H |
| H | 3-Fluorophenyl | H | H | Piperidin-1-yl | H |
| H | 4-Fluorophenyl | H | H | Piperidin-1-yl | H |
| F | Phenyl | H | H | Piperidin-1-yl | H |
| Methoxy | Phenyl | H | H | Piperidin-1-yl | H |
| H | Phenoxy | H | H | Piperidin-1-yl | H |
| H | Phenethyl | H | H | Piperidin-1-yl | H |
| H | Furan-2-yl | H | H | Methoxy | H |
| H | Furan-2-yl | H | H | Pyridin-3-yl | H |
| H | Furan-2-yl | H | H | Piperidin-1-yl | H |
| H | Furan-3-yl | H | H | Pyridin-3-yl | H |
| H | Thiophen-2-yl | H | H | Piperidin-1-yl | H |
| H | 1H-Pyrrol-2-yl | H | H | Piperidin-1-yl | H |
| H | 2-(Methyl-amino)phenyl | H | H | Methoxy | H |
| H | 2-(Methyl-amino)phenyl | H | H | Pyridin-3-yl | H |
| H | 2-(Ethyl-amino)phenyl | H | H | Pyridin-3-yl | H |
| H | 2-Fluorophenyl | H | H | Morpholin-4-yl | H |
| H | 3-Fluorophenyl | H | H | Morpholin-4-yl | H |
| H | 4-Fluorophenyl | H | H | Morpholin-4-yl | H |
| H | 2-Methylphenyl | H | H | Morpholin-4-yl | H |
| H | 3-Methylphenyl | H | H | Morpholin-4-yl | H |
| H | 4-Methylphenyl | H | H | Morpholin-4-yl | H |
| H | 2-Methoxyphenyl | H | H | Morpholin-4-yl | H |
| H | 3-Methoxyphenyl | H | H | Morpholin-4-yl | H |
| H | 4-Methoxyphenyl | H | H | Morpholin-4-yl | H |
| H | 3,4-Dimethoxy-phenyl | H | H | Morpholin-4-yl | H |
| H | 3,5-Dimethoxy-phenyl | H | H | Morpholin-4-yl | H |
| H | Furan-2-yl | H | H | Morpholin-4-yl | H |
| H | Thiophen-2-yl | H | H | Morpholin-4-yl | H |
| H | Thiophen-3-yl | H | H | Morpholin-4-yl | H |

TABLE 2a

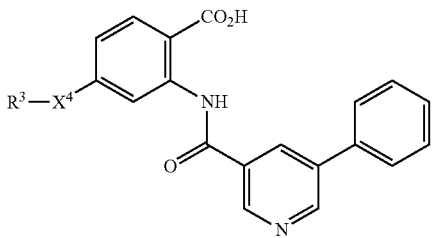

R³—X⁴

Phenyl
Anilino
Piperidin-1-yl
Morpholin-4-yl
Furan-2-yl
Furan-3-yl
Tetrahydrofuran-2-yl
Thiophen-2-yl
Thiophen-3-yl
Pyridin-2-yl
1H-Pyrrol-1-yl
1-Methyl-1H-pyrrol-2-yl
1H-Pyrazol-1-yl
2-Aminophenyl
2-Fluorophenyl
2-(Trifluoromethyl)phenyl
3-(Trifluoromethyl)phenyl
2-Nitrophenyl
2-Hydroxyphenyl
2-Methoxyphenyl
3-Methoxyphenyl
4-Methoxyphenyl
2,3-Dimethoxyphenyl
2-Ethoxyphenyl
2-Ethoxyphenyl
2-Methylphenyl
2-(Difluoromethoxy)phenyl
3-(Difluoromethoxy)phenyl
4-(Difluoromethoxy)phenyl
2-(Trifluoromethoxy)phenyl
3-(Trifluoromethoxy)phenyl
2-(Methylamino)phenyl
3-(Methylamino)phenyl
4-(Methylamino)phenyl
2-(Ethylamino)phenyl
3-(Ethylamino)phenyl
3-(Dimethylamino)phenyl
3-(Diethylamino)phenyl

TABLE 2b

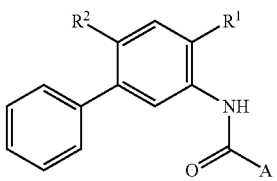

| R¹ | R² | A |
|---|---|---|
| Tetrazol-5-yl | H | 5-Phenylpyridin-3-yl |
| CO₂H | Methoxy | 5-Phenylpyridin-3-yl |
| CO₂H | H | 2-Phenylpyridin-4-yl |
| CO₂H | H | 6-Phenylpyridin-3-yl |
| CO₂H | H | 6-Phenylpyridin-2-yl |
| CO₂H | H | 5-Phenylpyridin-2-yl |
| CO₂H | H | 4-Phenylpyridin-2-yl |
| CO₂H | H | 5-(2-Fluorophenyl)pyridin-3-yl |
| CO₂H | H | 5-(Furan-2-yl)pyridin-3-yl |
| CO₂H | H | 5-(Furan-3-yl)pyridin-3-yl |
| CO₂H | H | 5-(Pyridin-3-yl)pyridin-3-yl |

TABLE 2b-continued

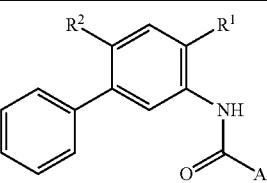

| R¹ | R² | A |
|---|---|---|
| CO₂H | H | 5-(Pyridin-4-yl)pyridin-3-yl |
| CO₂H | H | 6-(Pyridin-4-yl)pyridin-3-yl |
| CO₂H | H | 5-(Pyrimidin-2-yl)pyridin-3-yl |

Representative examples of the compound used in the present invention further include the compounds shown in Table 3a. These are compounds described in Patent Document 1. However, it has been totally unknown that these compounds have collagen production inhibitory action. These compounds are useful for the prevention, treatment and the like of diseases associated with excessive production of collagen.

TABLE 3a

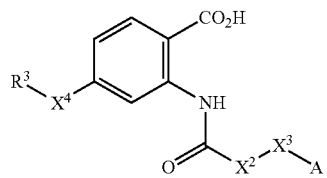

| Compound No. | R³ | X⁴ | X²—X³ | A |
|---|---|---|---|---|
| 1c | Phenyl | Bond | Bond | 2,3-Dihydrobenzo[1,4]dioxin-6-yl |
| 2c | Phenyl | Bond | Bond | 5-(1H-Pyrrol-1-y)pyridin-3-yl |
| 3c | Phenyl | Bond | Bond | Benzothiazol-2-yl |
| 4c | Phenyl | Bond | Bond | 1-Phenyl-1H-pyrazol-5-yl |
| 5c | Phenyl | Bond | Bond | 6-(Piperidin-1-yl)pyridin-3-yl |
| 6c | Phenyl | Bond | Bond | 2-(1H-Pyrrol-1-yl)pyridin-4-yl |
| 7c | Phenyl | Bond | Bond | 2-Hydroxyphenyl |
| 8c | Phenyl | Bond | Bond | 3-Biphenyl |
| 9c | Phenyl | Bond | Bond | 4-Biphenyl |
| 10c | Phenyl | Bond | Bond | 3-(1H-Pyrrol-1-yl)phenyl |
| 11c | Phenyl | Bond | Bond | 4-(1H-Pyrrol-1-yl)phenyl |
| 12c | Phenyl | Bond | CH=CH(E) | 3,4-Dimethoxyphenyl |
| 13c | Phenyl | (CH₂)₂ | Bond | 5-(1H-Pyrrol-1-yl)pyridin-3-yl |
| 14c | Benzofuran-2-yl | Bond | Bond | 5-(1H-Pyrrol-1-yl)pyridin-3-yl |
| 15c | 3-Chlorophenyl | Bond | Bond | 5-(1H-Pyrrol-1-yl)pyridin-3-yl |
| 16c | 2,4-Difluorophenyl | Bond | Bond | 5-(1H-Pyrrol-1-yl)pyridin-3-yl |
| 17c | 3-Methoxyphenyl | (CH₂)₂ | Bond | 5-(1H-Pyrrol-1-yl)pyridin-3-yl |
| 18c | Phenyl | O | Bond | 2-(1H-Pyrrol-1-yl)pyridin-4-yl |
| 19c | Phenyl | O | Bond | 2-Hydroxyphenyl |
| 20c | Phenyl | (CH₂)₂ | Bond | 2-Hydroxyphenyl |
| 21c | 1H-Indol-1-yl | Bond | Bond | Phenyl |

TABLE 3a-continued

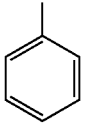

| Compound No. | R³ | X⁴ | X²—X³ | A |
|---|---|---|---|---|
| 22c | 1H-Benz-imidazol-1-yl | Bond | Bond | Phenyl |
| 23c | 4-(1H-Pyrrol-1-yl)phenyl | Bond | Bond | Phenyl |
| 24c | Phenyl | Bond | CH (phenyl-substituted) | Phenyl |

When isomers (for example, an optical isomer, a geometric isomer, a tautomer) are present in the compound of the general formula [1] or a salt thereof, the present invention includes these isomers. In addition, the present invention also includes a solvate, a hydrate, and various forms of crystals.

Next, a method for producing the compound of the present invention will be described.

The compound of the present invention is produced by combining known methods. For example, it can be produced by the following production methods.

[Production Method 1]

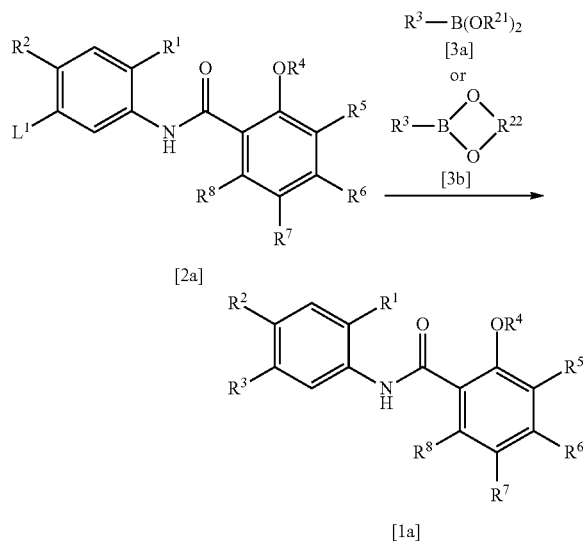

wherein, $R^{21}$ represents a hydrogen atom or a lower alkyl group; $R^{22}$ represents an optionally substituted alkylene group; $L^1$ represents a leaving group; and $R^1$, $R^2$, $R^3$, $R^4$, $R^5$, $R^6$, $R^7$, and $R^8$ represent the same meanings as above.

As compounds of the general formula [3a], for example, pyridine-3-boronic acid, 3-(methanesulfonamido)phenylboronic acid, thiophene-2-boronic acid, benzofuran-2-boronic acid, and 3-methoxyphenylboronic acid are known.

As a compound of the general formula [3b], for example, 3-(4,4,5,5-tetramethyl-1,3,2-dioxaborolan-2-yl)furan is known.

The compounds of the general formulae [3a] and [3b] can be produced, for example, from the corresponding halogeno compounds, according to the method described in JP 2003-206290 A or The Journal of Organic Chemistry, 1995, vol. 60, pp. 7508-7510.

The compound of the general formula [1a] can be produced by reacting a compound of the general formula [2a] with a compound of the general formula [3a] or [3b] in the presence or absence of a base, in the presence of a palladium catalyst, and in the presence or absence of a ligand.

The solvent used in this reaction is not particularly limited as long as it does not adversely affect the reaction, and examples thereof include water, alcohols, aromatic hydrocarbons, amides, halogenated hydrocarbons, ethers, ketones, acetonitrile, esters, and dimethyl sulfoxide. These may be used as a mixture.

Examples of the base used as appropriate in this reaction include inorganic bases such as sodium bicarbonate, sodium carbonate, potassium carbonate, cesium carbonate, and tripotassium phosphate; and organic bases such as triethylamine and N,N-diisopropylethylamine. The amount of the base used may be 1 to 50 times mol, preferably 2 to 5 times mol, of the compound of the general formula [2a].

Examples of the palladium catalyst used in this reaction include metallic palladium catalysts such as palladium-carbon and palladium black; inorganic palladium salts such as palladium chloride; organic palladium salts such as palladium acetate; and organic palladium complexes such as tetrakis(triphenylphosphine)palladium(0), bis(triphenylphosphine)palladium(II) dichloride, 1,1'-bis(diphenylphosphino)ferrocene-palladium(II) dichloride, tris(dibenzylideneacetone)dipalladium(0), and bis(di-tert-butyl(4-dimethylaminophenyl)phosphine)palladium(II) dichloride. These may be used in a combination. The amount of the palladium catalyst used may be 0.00001 to 1 times mol, preferably 0.001 to 0.1 times mol, of the compound of the general formula [2a].

Examples of the ligand used as appropriate in this reaction include trialkylphosphines such as trimethylphosphine and tri-tert-butylphosphine; tricycloalkylphosphines such as tricyclohexylphosphine; triarylphosphines such as triphenylphosphine and tritolylphosphine; trialkyl phosphites such as trimethyl phosphite, triethyl phosphite, and tributyl phosphite; tricycloalkyl phosphites such as tricyclohexyl phosphite; triaryl phosphites such as triphenyl phosphite; imidazolium salts such as 1,3-bis(2,4,6-trimethylphenyl)imidazolium chloride; diketones such as acetylacetone and octafluoroacetylacetone; amines such as trimethylamine, triethylamine, tripropylamine, and triisopropylamine; 1,1'-bis(diphenylphosphino)ferrocene, 2,2'-bis(diphenylphosphino)-1,1'-binaphthyl, 2-dicyclohexylphosphino-2,6'-dimethoxybiphenyl, 2-dicyclohexylphosphino-2',4',6'-triisopropylbiphenyl, and 2-(di-tert-butylphosphino)-2',4',6'-triisopropylbiphenyl; and 2-(di-tert-butylphosphino)biphenyl. These may be used in a combination. The amount of the ligand used may be 0.00001 to 1 times mol, preferably 0.001 to 0.1 times mol, of the compound of the general formula [2a].

The amount of the compound of the general formula [3a] or [3b] used may be 1 to 50 times mol, preferably 1 to 2 times mol, of the compound of the general formula [2a].

This reaction may be preferably performed under an atmosphere of inert gas (e.g., nitrogen or argon) at 40 to 170° C. for one minute to 96 hours.

[Production Method 2]

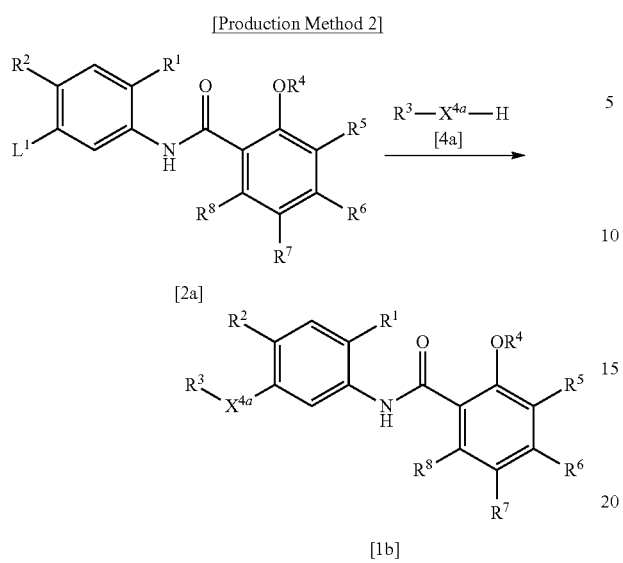

wherein, $X^{4a}$ represents an oxygen atom or an optionally protected imino group; and $R^1$, $R^2$, $R^3$, $R^4$, $R^5$, $R^6$, $R^7$, $R^8$, and $L^1$ represent the same meanings as above.

As compounds of the general formula [4a], for example, aniline, benzylamine, and phenol are known. The compound of the general formula [4a] can be produced, for example, from the corresponding halogeno compound by a common method.

The compound of the general formula [1b] can be produced according to Production Method 1 by reacting a compound of the general formula [2a] with a compound of the general formula [4a].

[Production Method 3]

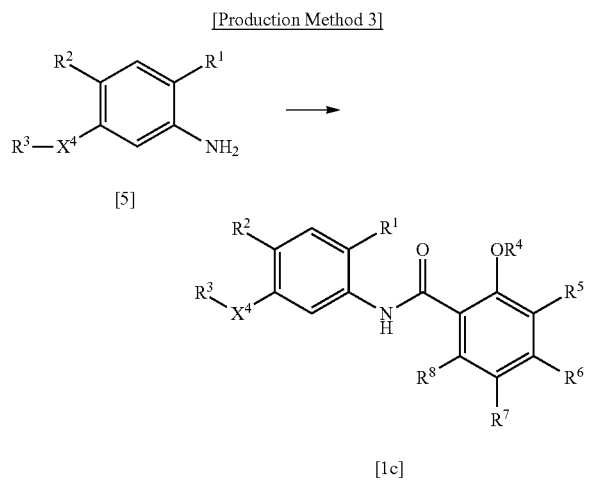

wherein, $R^1$, $R^2$, $R^3$, $R^4$, $R^5$, $R^6$, $R^7$, $R^8$, and $X^4$ represent the same meanings as above.

As compounds of the general formula [5], for example, methyl 2-amino-4-phenylbenzoate (Patent Document 1); and tert-butyl 2-amino-4-phenylbenzoate, tert-butyl 2-amino-4-phenoxybenzoate, and tert-butyl 2-amino-4-phenethylbenzoate (WO2006/098308) are known.

The compound of the general formula [1c] can be produced by acylating a compound of the general formula [5]. Specific examples thereof include a method using an acid halide in the presence or absence of a base.

The solvent used in this reaction is not particularly limited as long as it does not adversely affect the reaction, and examples thereof include amides, halogenated hydrocarbons, aromatic hydrocarbons, ethers, acetonitrile, ketones, esters, sulfolane, and dimethyl sulfoxide. These may be used as a mixture.

The acid halide used in this reaction can be produced by reacting a compound represented by a general formula [6]:

[Formula 5]

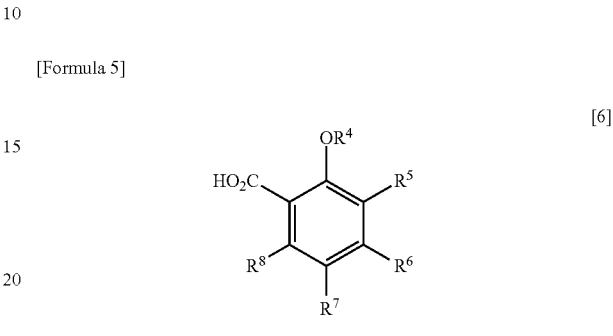

(wherein, $R^4$, $R^5$, $R^6$, $R^7$, and $R^8$ represent the same meanings as above) with, for example, thionyl chloride or oxalyl chloride.

The amount of the acid halide used may be 1 to 50 times mol, preferably 1 to 5 times mol, of the compound of the general formula [5].

As compounds of the general formula [6], for example, 2-acetoxy-3-chlorobenzoic acid, 2-acetoxy-5-bromobenzoic acid, 2-acetoxy-5-iodobenzoic acid, 2-acetoxy-5-methylbenzoic acid, 2-acetoxy-5-nitrobenzoic acid, 2-(benzyloxy)-5-bromobenzoic acid, 2-(benzyloxy)-5-nitrobenzoic acid, 2-(benzyloxy)-5-(pyridin-2-yl)benzoic acid, and 2-(benzyloxy)-5-(pyridin-3-yl)benzoic acid are known.

Examples of the base used as appropriate in this reaction include inorganic bases such as sodium hydroxide, potassium hydroxide, and lithium hydroxide; organic bases such as sodium methoxide, sodium ethoxide, potassium tert-butoxide, triethylamine, N,N-diisopropylethylamine, and pyridine; and carbonates such as sodium bicarbonate, sodium carbonate, potassium carbonate, and cesium carbonate. The amount of the base used may be 1 to 50 times mol, preferably 1 to 5 times mol, of the compound of the general formula [5].

This reaction may be usually performed at −78 to 100° C., preferably at 0 to 80° C., for 10 minutes to 24 hours.

[Production Method 4]

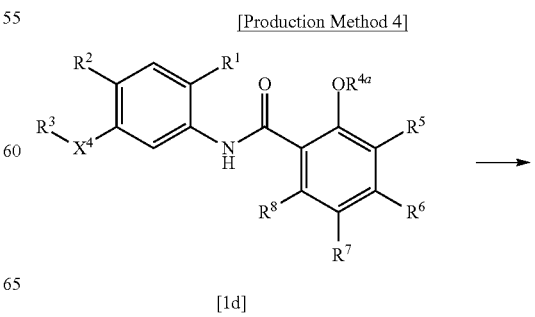

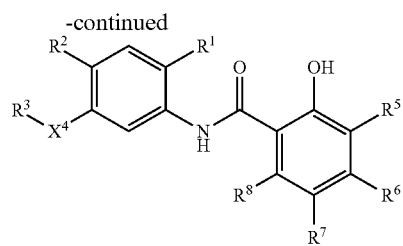

[1e]

wherein, $R^{4a}$ represents a phenolic hydroxyl protecting group; and $R^1$, $R^2$, $R^3$, $R^5$, $R^6$, $R^7$, $R^8$, and $X^4$ represent the same meanings as above.

The compound of the general formula [1e] can be produced by deprotecting a compound of the general formula [1d].

Examples of the method include that described in W. Greene, et al., Protective Groups in Organic Synthesis, 4th Edition, pp. 370-424, 2007 (John Wiley & Sons, Inc.).

Specific examples thereof include a hydrolysis reaction using an acid or a base, a dealkylation reaction using a salt, and a reductive dealkylation reaction including a catalytic hydrogenation reaction using a metal catalyst.

(4-1)

Examples of the acid used in the hydrolysis reaction using an acid include formic acid, hydrochloric acid, sulfuric acid, hydrobromic acid, trifluoroacetic acid, methanesulfonic acid, aluminum chloride, and trimethylsilane iodide. The amount of the acid used may be 1 to 100000 times mol, preferably 1 to 1000 times mol, of the compound of the general formula [1d].

Examples of the base used in the hydrolysis reaction using a base include inorganic bases such as sodium hydroxide, potassium hydroxide, and lithium hydroxide; organic bases such as sodium methoxide, sodium ethoxide, and potassium tert-butoxide; carbonates such as potassium carbonate and sodium carbonate; and tetrabutylammonium fluoride. The amount of the base used may be 1 to 1000 times mol, preferably 1 to 50 times mol, of the compound of the general formula [1d].

Examples of the salt used in the dealkylation reaction using a salt include lithium iodide and sodium chloride. The amount of the salt used may be 1 to 100 times mol, preferably 1 to 10 times mol, of the compound of the general formula [1d].

The solvent used in this reaction is not particularly limited as long as it does not adversely affect the reaction, and examples thereof include water, alcohols, amides, halogenated hydrocarbons, aromatic hydrocarbons, ethers, acetonitrile, ketones, and esters. These may be used as a mixture.

(4-2)

The solvent used in the catalytic hydrogenation reaction using a metal catalyst is not particularly limited as long as it does not adversely affect the reaction, and examples thereof include water, alcohols, amides, halogenated hydrocarbons, aromatic hydrocarbons, ethers, acetonitrile, ketones, esters, acetic acid, and pyridine. These may be used as a mixture.

Examples of the metal catalyst used in this reaction include metallic palladium catalysts such as palladium-carbon and palladium black; palladium salts such as palladium oxide and palladium hydroxide; nickel metal catalysts such as Raney nickel; and platinum salts such as platinum oxide. The amount of the metal catalyst used may be 0.001 to 5 times quantity (W/W), preferably 0.01 to 1 times quantity (W/W), of the compound of the general formula [1d].

Examples of the hydrogen source include hydrogens; formic acid; formates such as sodium formate, ammonium formate, and triethylammonium formate; cyclohexene; and cyclohexadiene. The amount of the hydrogen source used may be 2 to 100 times mol, preferably 2 to 10 times mol, of the compound of the general formula [1d].

This reaction may be performed at 0 to 200° C., preferably at 0 to 100° C., for one minute to 24 hours.

[Production Method 5]

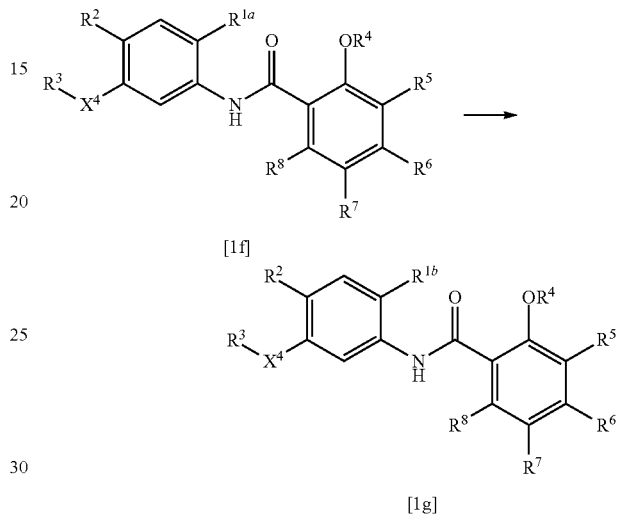

wherein, $R^{1a}$ represents a protected carboxyl group or a protected 1H-tetrazol-5-yl group; $R^{1b}$ represents a carboxyl group or a 1H-tetrazol-5-yl group; and $R^2$, $R^3$, $R^4$, $R^5$, $R^6$, $R^7$, $R^8$, and $X^4$ represent the same meanings as above.

The compound of the general formula [1g] can be produced by deprotecting a compound of the general formula [1f].

The deprotection of the carboxyl protecting group can be performed by, for example, the method described in W. Greene, et al., Protective Groups in Organic Synthesis, 4th Edition, pp. 533-643, 2007 (John Wiley & Sons, Inc.).

The deprotection of the tetrazole protecting group can be performed by, for example, the method described in W. Greene, et al., Protective Groups in Organic Synthesis, 4th Edition, pp. 872-894, 2007 (John Wiley & Sons, Inc.).

Specifically, the compound of the general formula [1g] can be produced according to Production Method 4.

[Production Method 6]

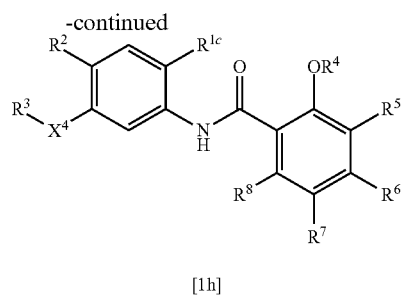

[1h]

wherein, $R^{1c}$ represents an optionally protected 1H-tetrazol-5-yl group; and $R^2$, $R^3$, $R^4$, $R^5$, $R^6$, $R^7$, $R^8$, and $X^4$ represent the same meanings as above.

The compound of the general formula [1h] can be produced by, for example, the method described in Shinpen Heterokan Kagobutsu, Oyo-hen (New Heterocyclic Compounds, Advanced), pp. 98-100, 2004, Kodansha, or a method according thereto. Specifically, the compound of the general formula [1 h] can be produced by subjecting a compound of the general formula [7a] to a cycloaddition reaction with an azide in the presence or absence of a salt.

The solvents used in these reactions are not particularly limited as long as they do not adversely affect the reactions, and examples thereof include ethers, halogenated hydrocarbons, aliphatic hydrocarbons, aromatic hydrocarbons, dimethyl sulfoxide, and amides. These may be used as a mixture.

Examples of the azide used include sodium azide and trimethylsilyl azide. The amount of the azide used may be 1 to 100 times mol, preferably 1 to 10 times mol, of the compound of the general formula [7a].

Examples of the salt used include ammonium chloride. The amount of the salt used may be 1 to 100 times mol, preferably 1 to 10 times mol, of the compound of the general formula [7a].

This reaction may be usually performed at −78 to 150° C., preferably at 0 to 120° C., for 10 minutes to 24 hours.

[Production Method 7]

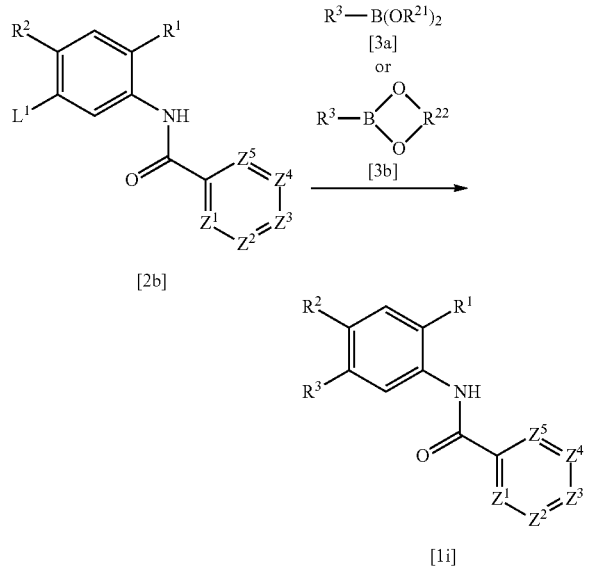

wherein, $R^1$, $R^2$, $R^3$, $R^{21}$, $R^{22}$, $L^1$, $Z^1$, $Z^2$, $Z^3$, $Z^4$, and $Z^5$ represent the same meanings as above.

As compounds of the general formula [3a], for example, pyridine-3-boronic acid, 3-(methanesulfonamido)phenylboronic acid, thiophene-2-boronic acid, benzofuran-2-boronic acid, and 3-methoxyphenylboronic acid are known. As a compound of the general formula [3b], for example, 3-(4,4,5,5-tetramethyl-1,3,2-dioxaborolan-2-yl)furan is known. Furthermore, the compounds of the general formulae [3a] and [3b] can be produced, for example, from the corresponding halogeno compounds, according to the method described in JP 2003-206290 A or The Journal of Organic Chemistry, 1995, vol. 60, pp. 7508-7510.

The compound of the general formula [1i] can be produced by reacting a compound of the general formula [2b] with a compound of the general formula [3a] or [3b] in the presence or absence of a base, in the presence of a palladium catalyst, and in the presence or absence of a ligand.

The solvent used in this reaction is not particularly limited as long as it does not adversely affect the reaction, and examples thereof include water, alcohols, aromatic hydrocarbons, amides, halogenated hydrocarbons, ethers, ketones, acetonitrile, esters, and dimethyl sulfoxide. These may be used as a mixture.

Examples of the base used as appropriate in this reaction include inorganic bases such as sodium bicarbonate, sodium carbonate, potassium carbonate, cesium carbonate, and tripotassium phosphate; and organic bases such as triethylamine and N,N-diisopropylethylamine. The amount of the base used may be 1 to 50 times mol, preferably 2 to 5 times mol, of the compound of the general formula [2b].

Examples of the palladium catalyst used in this reaction include metallic palladium catalysts such as palladium-carbon and palladium black; inorganic palladium salts such as palladium chloride; organic palladium salts such as palladium acetate; and organic palladium complexes such as tetrakis(triphenylphosphine)palladium(0), bis(triphenylphosphine)palladium(II) dichloride, 1,1'-bis(diphenylphosphino)ferrocene-palladium(II) dichloride, tris(dibenzylideneacetone)dipalladium(0), and bis(di-tert-butyl(4-dimethylaminophenyl)phosphine)palladium(II) dichloride. These may be used in a combination. The amount of the palladium catalyst used may be 0.00001 to 1 times mol, preferably 0.001 to 0.1 times mol, of the compound of the general formula [2b].

Examples of the ligand used as appropriate in this reaction include trialkylphosphines such as trimethylphosphine and tri-tert-butylphosphine; tricycloalkylphosphines such as tricyclohexylphosphine; triarylphosphines such as triphenylphosphine and tritolylphosphine; trialkyl phosphites such as trimethyl phosphite, triethyl phosphite, and tributyl phosphite; tricycloalkyl phosphites such as tricyclohexyl phosphite; triaryl phosphites such as triphenyl phosphite; imidazolium salts such as 1,3-bis(2,4,6-trimethylphenyl)imidazolium chloride; diketones such as acetylacetone and octafluoroacetylacetone; amines such as trimethylamine, triethylamine, tripropylamine, and triisopropylamine; 1,1'-bis(diphenylphosphino)ferrocene, 2,2'-bis(diphenylphosphino)-1,1'-binaphthyl, 2-dicyclohexylphosphino-2',6'-dimethoxybiphenyl, 2-dicyclohexylphosphino-2',4',6'-triisopropylbiphenyl, and 2-(di-tert-butylphosphino)-2',4',6'-triisopropylbiphenyl; and 2-(di-tert-butylphosphino)biphenyl. These may be used in a combination. The amount of the ligand used may be 0.00001 to 1 time mol, preferably 0.001 to 0.1 times mol, of the compound of the general formula [2b].

The amount of the compound of the general formula [3a] or [3b] used may be 1 to 50 times mol, preferably 1 to 2 times mol, of the compound of the general formula [2b].

This reaction may be preferably performed under an atmosphere of inert gas (e.g., nitrogen or argon) at 40 to 170° C. for one minute to 96 hours.

[Production Method 8]

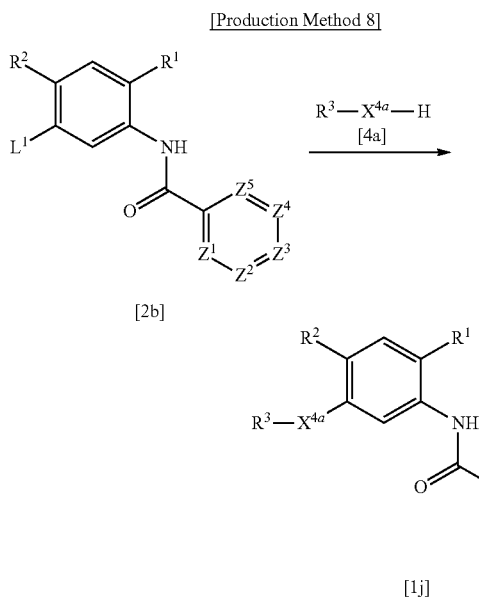

wherein, $R^1$, $R^2$, $R^3$, $Z^1$, $Z^2$, $Z^3$, $Z^4$, $Z^5$, $L^1$, and $X^{4a}$ represent the same meanings as above.

As the compound of the general formula [4a], for example, aniline, benzylamine, and phenol are known. Furthermore, the compound of the general formula [4a] can be produced, for example, from the corresponding halogeno compound by a common method.

The compound of the general formula [1j] can be produced according to Production Method 7 by reacting a compound of the general formula [2b] with a compound of the general formula [4a].

[Production Method 9]

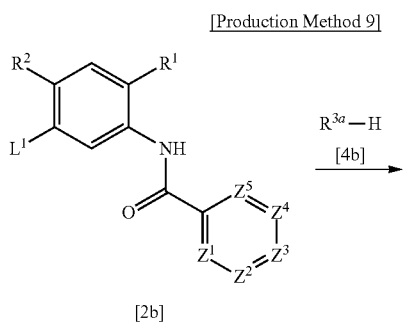

wherein, $R^{3a}$ represents a monocyclic heterocyclic ring or bicyclic heterocyclic ring, which binds through the nitrogen atom forming the ring; and $R^1$, $R^2$, $Z^1$, $Z^2$, $Z^3$, $Z^4$, $Z^5$, and $L^1$ represent the same meanings as above.

As the compound of the general formula [4b], for example, piperidine, morpholine, thiomorpholine, and 1H-pyrazole are known.

The compound of the general formula [1k] can be produced by reacting a compound of the general formula [2b] with a compound of the general formula [4b]. Specific examples of the reaction include a reaction using a palladium catalyst and a reaction using a copper catalyst.

In the reaction using a palladium catalyst, the compound of the general formula [1k] can be produced according to Production Method 7 by reacting a compound of the general formula [2b] with a compound of the general formula [4b].

In the reaction using a copper catalyst, the compound of the general formula [1k] can be produced by reacting a compound of the general formula [2b] with a compound of the general formula [4b] in the presence or absence of a base, in the presence or absence of a ligand, and in the presence of a copper catalyst.

The solvent used in this reaction is not particularly limited as long as it does not adversely affect the reaction, and examples thereof include water, alcohols, aromatic hydrocarbons, amides, halogenated hydrocarbons, ethers, ketones, acetonitrile, esters, and dimethyl sulfoxide. These may be used as a mixture.

Examples of the base used as appropriate in this reaction include inorganic bases such as sodium bicarbonate, sodium carbonate, potassium carbonate, and cesium carbonate; and organic bases such as triethylamine, N,N-diisopropylethylamine, and N-methylmorpholine. The amount of the base used may be 1 to 50 times mol, preferably 2 to 5 times mol, of the compound of the general formula [2b].

Examples of the ligand used as appropriate in this reaction include amino acids such as proline, N,N-dimethylglycine, and alanine. The amount of the ligand used may be 1 to 50 times mol, preferably 2 to 5 times mol, of the compound of the general formula [2b].

Examples of the copper catalyst used in this reaction include copper, copper bromide, and copper iodide. These may be used in a combination. The amount of the copper catalyst used may be 0.01 to 50 times mol, preferably 0.1 to 5 times mol, of the compound of the general formula [2b].

The amount of the compound of the general formula [4b] used may be 1 to 50 times mol, preferably 1 to 2 times mol, of the compound of the general formula [2b].

This reaction may be preferably performed under an atmosphere of inert gas (e.g., nitrogen or argon) at 10 to 180° C. for one minute to 24 hours.

[Production Method 10]

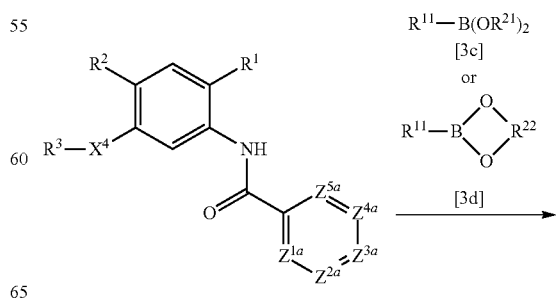

-continued

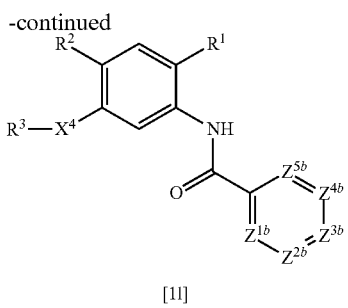

[11]

wherein, one of $Z^{1a}$, $Z^{2a}$, $Z^{3a}$, $Z^{4a}$ and $Z^{5a}$ represents a nitrogen atom, one of the remaining four represents a group represented by a general formula C-L² (wherein L² represents a leaving group), and the remaining three each represent CH; one of $Z^{1b}$, $Z^{2b}$, $Z^{3b}$, $Z^{4b}$ and $Z^{5b}$ represents a nitrogen atom, one of the remaining four represents a group represented by a general formula C—R¹¹ (wherein R¹¹ represents the same meanings as above), and the remaining three each represent CH; and R¹, R², R³, R¹¹, R²¹, R²² and X⁴ represent the same meanings as above.

The compound of the general formula [11] can be produced according to Production Method 7 by reacting a compound of the general formula [2c] with a compound of the general formula [3c] or [3d].

The acid halide used in this reaction can be produced by reacting a compound represented by a general formula [8]:

[Formula 6]

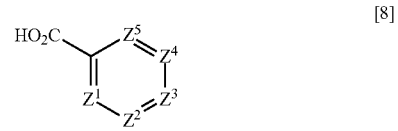

[8]

(wherein, $Z^1$, $Z^2$, $Z^3$, $Z^4$, and $Z^5$ represent the same meanings as above) with, for example, thionyl chloride or oxalyl chloride.

The amount of the acid halide used may be 1 to 50 times mol, preferably 1 to 5 times mol, of the compound of the general formula [5].

Examples of the base used as appropriate in this reaction include inorganic bases such as sodium bicarbonate, sodium carbonate, potassium carbonate, and cesium carbonate; and organic bases such as triethylamine, pyridine, and N,N-diisopropylethylamine.

The amount of the base used may be 1 to 50 times mol, preferably 1 to 5 times mol, of the compound of the general formula [5].

This reaction may be usually performed at −78 to 100° C., preferably at 0 to 80° C., for 10 minutes to 24 hours.

[Production Method 11]

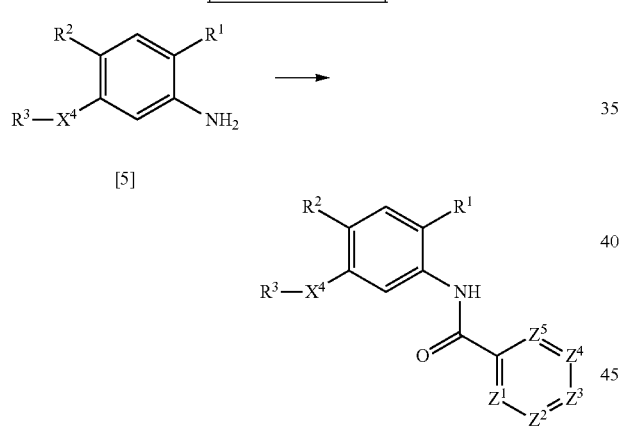

wherein, R¹, R², R³, Z¹, Z², Z³, Z⁴, Z⁵ and X⁴ represent the same meanings as above.

As compounds of the general formula [5], for example, methyl 2-amino-4-phenylbenzoate (Patent Document 1) and tert-butyl 2-amino-4-phenylbenzoate (WO2006/098308) are known.

The compound of the general formula [1m] can be produced by acylating a compound of the general formula [5]. Specific examples thereof include a method using an acid halide in the presence or absence of a base.

The solvent used in this reaction is not particularly limited as long as it does not adversely affect the reaction, and examples thereof include amides, halogenated hydrocarbons, aromatic hydrocarbons, ethers, acetonitrile, ketones, esters, sulfolane, and dimethyl sulfoxide. These may be used as a mixture.

[Production Method 12]

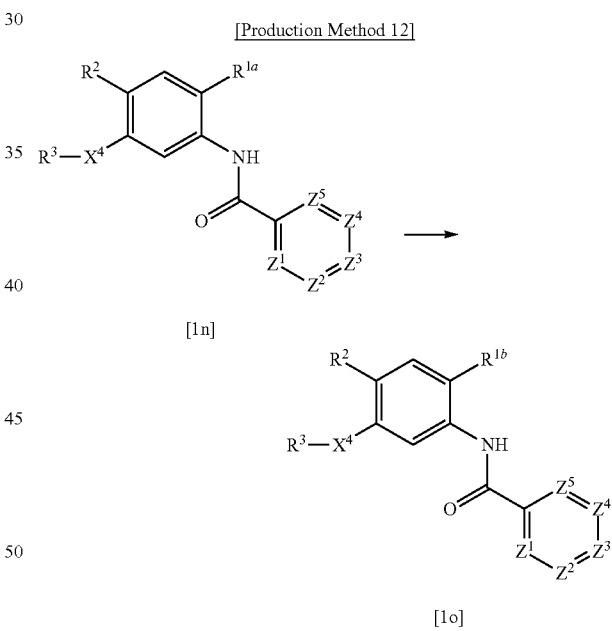

wherein, $R^{1a}$, $R^{1b}$, R², R³, $Z^1$, $Z^2$, $Z^3$, $Z^4$, $Z^5$, and X⁴ represent the same meanings as above.

The compound of the general formula [1o] can be produced by deprotecting a compound of the general formula [1n].

The deprotection of the carboxyl protecting group can be performed by, for example, the method described in W. Greene, et al., Protective Groups in Organic Synthesis, 4th Edition, pp. 533-643, 2007 (John Wiley & Sons, Inc.).

The deprotection of the tetrazole protecting group can be performed by, for example, the method described in W. Greene, et al., Protective Groups in Organic Synthesis, 4th Edition, pp. 872-894, 2007 (John Wiley & Sons, Inc.).

Specific examples thereof include a hydrolysis reaction using an acid or a base, a dealkylation reaction using a salt, and a reductive dealkylation reaction including a catalytic hydrogenation reaction using a metal catalyst.

(12-1)

Examples of the acid used in the hydrolysis reaction using an acid include formic acid, hydrochloric acid, sulfuric acid, hydrobromic acid, trifluoroacetic acid, methanesulfonic acid, aluminum chloride, and trimethylsilane iodide. The amount of the acid used may be 1 to 100000 times mol, preferably 1 to 1000 times mol, of the compound of the general formula [1n].

Examples of the base used in the hydrolysis reaction using a base include inorganic bases such as sodium hydroxide, potassium hydroxide, and lithium hydroxide; organic bases such as sodium methoxide, sodium ethoxide, and potassium tert-butoxide; carbonates such as potassium carbonate and sodium carbonate; and tetrabutylammonium fluoride.

The amount of the base used may be 1 to 1000 times mol, preferably 1 to 50 times mol, of the compound of the general formula [1n].

Examples of the salt used in the dealkylation reaction using a salt include lithium iodide and sodium chloride. The amount of the salt used may be 1 to 100 times mol, preferably 1 to 10 times mol, of the compound of the general formula [1n].

The solvent used in this reaction is not particularly limited as long as it does not adversely affect the reaction, and examples thereof include water, alcohols, amides, halogenated hydrocarbons, aromatic hydrocarbons, ethers, acetonitrile, ketones, and esters. These may be used as a mixture.

(12-2)

The solvent used in the catalytic hydrogenation reaction using a metal catalyst is not particularly limited as long as it does not adversely affect the reaction, and examples thereof include water, alcohols, amides, halogenated hydrocarbons, aromatic hydrocarbons, ethers, acetonitrile, ketones, esters, acetic acid, and pyridine. These may be used as a mixture.

Examples of the metal catalyst used in this reaction include metallic palladium catalysts such as palladium-carbon and palladium black; palladium salts such as palladium oxide and palladium hydroxide; nickel metal catalysts such as Raney nickel; and platinum salts such as platinum oxide. The amount of the metal catalyst used may be 0.001 to 5 times quantity (W/W), preferably 0.01 to 1 times quantity (W/W), of the compound of the general formula [1n].

Examples of the hydrogen source include hydrogens; formic acid; formates such as sodium formate, ammonium formate, and triethylammonium formate; cyclohexene; and cyclohexadiene. The amount of the hydrogen source used may be 2 to 100 times mol, preferably 2 to 10 times mol, of the compound of the general formula [1n].

This reaction may be performed at 0 to 200° C., preferably at 0 to 100° C., for one minute to 24 hours.

[Production Method 13]

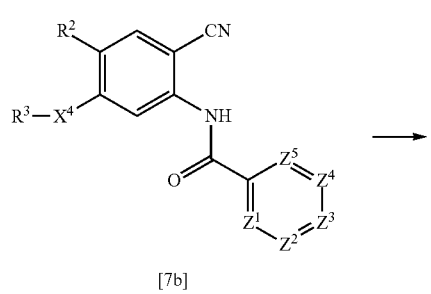

[7b]

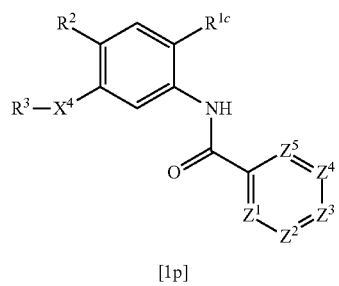

[1p]

wherein, $R^{1c}$, $R^2$, $R^3$, $Z^1$, $Z^2$, $Z^3$, $Z^4$, $Z^5$ and $X^4$ represent the same meanings as above.

The compound of the general formula [1p] can be produced by, for example, the method described in Shinpen Heterokan Kagobutsu, Oyo-hen (New Heterocyclic Compounds, Advanced), pp. 98-100, 2004, Kodansha, or a method according thereto. Specifically, the compound of the general formula [1p] can be produced by subjecting a compound of the general formula [7b] to a cycloaddition reaction with an azide in the presence or absence of a salt.

The solvents used in these reactions are not particularly limited as long as they do not adversely affect the reactions, and examples thereof include ethers, halogenated hydrocarbons, aliphatic hydrocarbons, aromatic hydrocarbons, dimethyl sulfoxide, and amides. These may be used as a mixture.

Examples of the azide used include sodium azide and trimethylsilyl azide.

The amount of the azide used may be 1 to 100 times mol, preferably 1 to 10 times mol, of the compound of the general formula [7b].

Examples of the salt used include ammonium chloride. The amount of the salt used may be 1 to 100 times mol, preferably 1 to 10 times mol, of the compound of the general formula [7b].

This reaction may be usually performed at −78 to 150° C., preferably at 0 to 120° C., for 10 minutes to 24 hours.

The thus-obtained compounds of the general formula [1] or salts thereof can be derived to other compounds of the general formula [1] or their salts by a known reaction such as condensation, addition, oxidation, reduction, rearrangement, substitution, halogenation, dehydration, or hydrolysis, or by an appropriate combination of such reactions.

Next, methods for producing materials for producing the compounds of the present invention will be described.

[Production Method A]

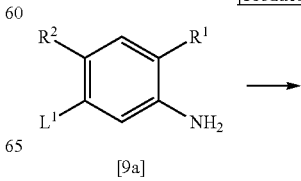

[9a]

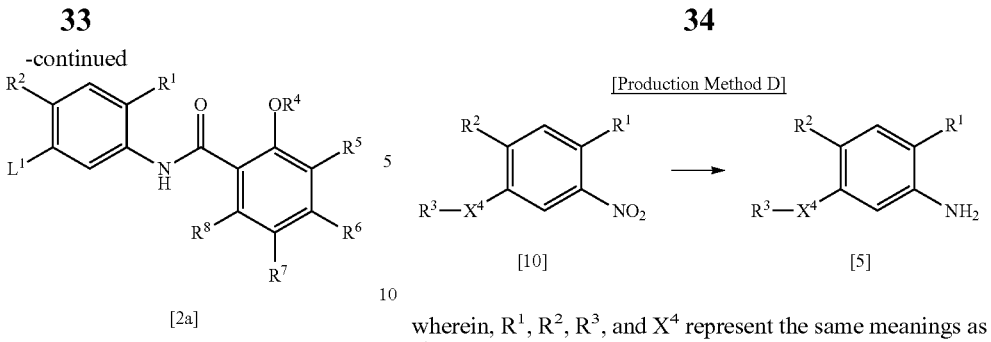

[2a]

wherein, $R^1$, $R^2$, $R^4$, $R^5$, $R^6$, $R^7$, $R^8$, and $L^1$ represent the same meanings as above.

As compounds of the general formula [9a], for example, methyl 2-amino-4-bromobenzoate and tert-butyl 2-amino-4-bromobenzoate (Patent Document 1) are known.

The compound of the general formula [2a] can be produced according to Production Method 3 by acylating a compound of the general formula [9a].

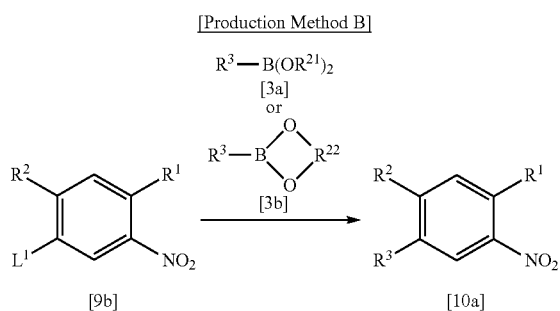

wherein, $R^1$, $R^2$, $R^3$, $R^{21}$, $R^{22}$, and $L^1$ represent the same meanings as above.

As compounds of the general formula [9b], for example, methyl 4-bromo-2-nitrobenzoate, tert-butyl 4-chloro-2-nitrobenzoate, and tert-butyl 4-bromo-2-nitrobenzoate (Patent Document 1) are known.

The compound of the general formula [10a] can be produced according to Production Method 1 by reacting a compound of the general formula [9b] with a compound of the general formula [3a] or [3b].

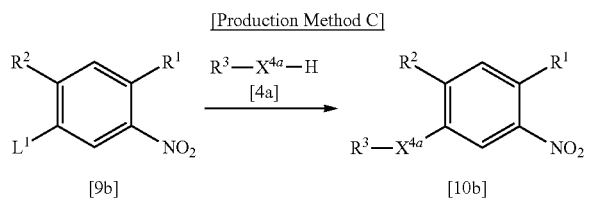

wherein, $R^1$, $R^2$, $R^3$, $X^{4a}$, and $L^1$ represent the same meanings as above.

The compound of the general formula [10b] can be produced according to Production Method 2 by reacting a compound of the general formula [9b] with a compound of the general formula [4a].

[Production Method D]

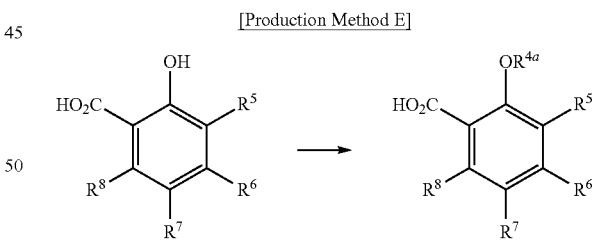

wherein, $R^1$, $R^2$, $R^3$, and $X^4$ represent the same meanings as above.

The compound of the general formula [5] can be produced by reducing a compound of the general formula [10]. This reaction may be performed by the method described in Richard C. Larock, et al., Comprehensive Organic Transformations, 2nd Edition, pp. 823-827, 1999 (John Wiley & Sons, Inc.), or a method according thereto. Specific examples thereof include a catalytic hydrogenation reaction using a metal catalyst and a reduction reaction using a metal such as iron or zinc.

The catalytic hydrogenation reaction of a compound of the general formula [10] may be performed according to Production Method (4-2).

In the case of subjecting a compound of the general formula [10] to a reduction reaction using a metal, the solvent used is not particularly limited as long as it does not affect the reaction, and examples thereof include water, alcohols, amides, halogenated hydrocarbons, aromatic hydrocarbons, ethers, acetonitrile, ketones, and esters. These may be used as a mixture.

Examples of the metal used in this reaction include iron, zinc, tin, and tin(II) chloride. The amount of the metal used may be 1 to 50 times mol, preferably 1 to 10 times mol, of the compound of the general formula [10].

Examples of the acid used as appropriate in this reaction include hydrogen chloride, hydrogen bromide, and acetic acid. The amount of the acid used may be 0.001 to 100 times quantity (V/W), preferably 0.01 to 20 times quantity (V/W), of the compound of the general formula [10].

This reaction may be performed at 0 to 200° C., preferably at 0 to 100° C., for one minute to 24 hours.

[Production Method E]

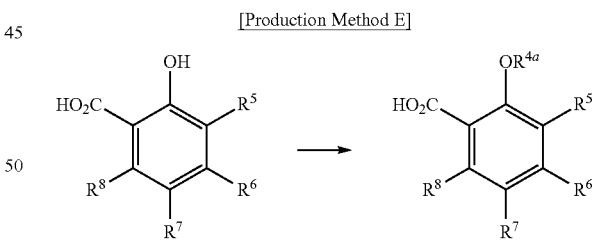

wherein, $R^{4a}$, $R^5$, $R^6$, $R^7$, and $R^8$ represent the same meanings as above.

As compounds of the general formula [6a], for example, 5-ethoxysalicylic acid and 5-isopropoxysalicylic acid are known.

The compound of the general formula [6b] can be produced by, for example, protecting the phenolic hydroxyl group of a compound of the general formula [6a] by the method described in W. Greene, et al., Protective Groups in Organic Synthesis, 4th Edition, pp. 370-424, 2007 (John Wiley & Sons, Inc.).

[Production Method F]

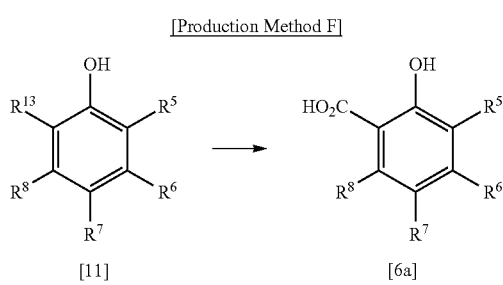

wherein, $R^{13}$ represents a protected carboxyl group; and $R^5$, $R^6$, $R^7$, and $R^8$ represent the same meanings as above.

As compounds of the general formula [11], for example, methyl 2-hydroxy-4-iodobenzoate and methyl 2-hydroxy-5-isopropoxybenzoate are known.

The compound of the general formula [6a] can be produced according to Production Method 4 by deprotecting the carboxyl protecting group of a compound of the general formula [11].

[Production Method G]

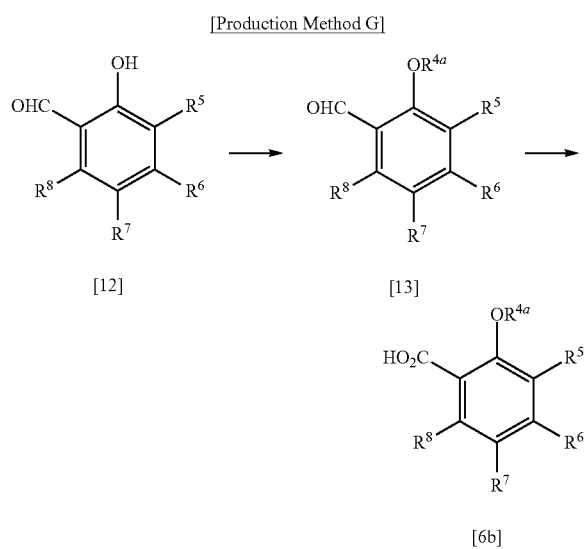

wherein, $R^{4a}$, $R^5$, $R^6$, $R^7$, and $R^8$ represent the same meanings as above.

As compounds of the general formula [12], for example, 7-hydroxy-2,3-dihydrobenzo[1,4]dioxine-6-carbaldehyde and 3-formyl-4-hydroxyphenethyl acetate are known.

(G-1)
The Compound of the General Formula [13] can be Produced According to Production Method E by protecting the phenolic hydroxyl group of a compound of the general formula [12].

(G-2)
The Compound of the General Formula [6b] can be Produced by Reacting a compound of the general formula [13] with an oxidizing agent in the presence or absence of an acid and in the presence or absence of a salt.

The solvent used in this reaction is not particularly limited as long as it does not adversely affect the reaction, and examples thereof include water, halogenated hydrocarbons, aliphatic hydrocarbons, acetonitrile, and pyridine. These may be used as a mixture.

Examples of the acid used as appropriate in this reaction include mineral acids such as hydrochloric acid and sulfuric acid; and organic acids such as acetic acid. The amount of the acid used may be 1 to 1000 times mol of the compound of the general formula [13].

Examples of the salt used as appropriate in this reaction include sodium dihydrogen phosphate, magnesium sulfate, ammonium sulfate, and magnesium chloride. The amount of the salt used is 1 to 50 times mol, preferably 1 to 10 times mol, of the compound of the general formula [13].

Examples of the oxidizing agent used in this reaction include chromates such as sodium dichromate, and chromium(VI) oxide; permanganates such as potassium permanganate, barium permanganate, calcium permanganate, and magnesium permanganate; hydrogen peroxide solution; and sodium chlorite. These may be used as a mixture. The amount of the oxidizing agent used may be 1 to 50 times mol, preferably 1 to 10 times mol, of the compound of the general formula [13].

This reaction may be usually performed at 0 to 150° C., preferably at 40 to 130° C., for 30 minutes to 48 hours.

[Production Method H]

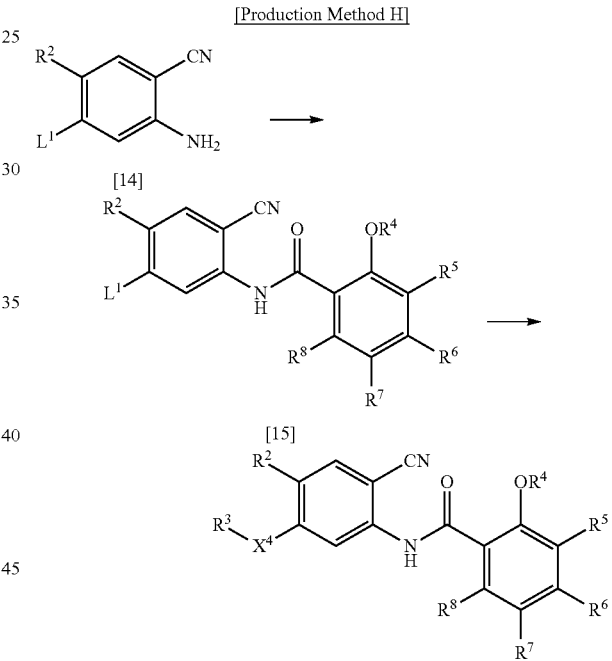

wherein, $R^2$, $R^3$, $R^4$, $R^5$, $R^6$, $R^7$, $X^4$, and $L^1$ represent the same meanings as above.

As a compound of the general formula [14], for example, 2-amino-4-chlorobenzonitrile is known.

(H-1)
The Compound of the General Formula [15] can be Produced According to Production Method 3 by acylating a compound of the general formula [14]

(H-2)
When $X^4$ is a Bonding Hand, the Compound of the General Formula [7a] can be produced according to Production Method 1 by reacting a compound of the general formula [15] with a compound of the general formula [3a] or [3b].

(H-3)
When $X^4$ is an Oxygen Atom or an Optionally Protected Imino Group, the compound of the general formula [7a] can be produced according to Production Method 2 by reacting a compound of the general formula [15] with a compound of the general formula [4a].

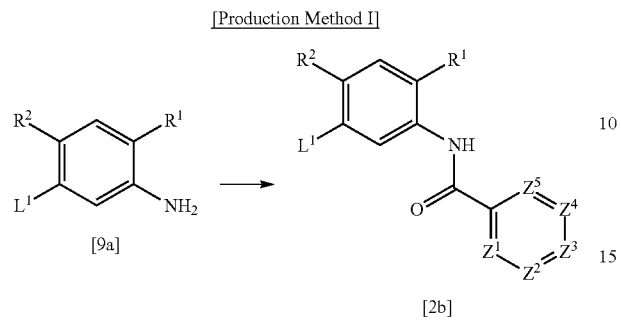

wherein, $R^1$, $R^2$, $Z^1$, $Z^2$, $Z^3$, $Z^4$, $Z^5$, and $L^1$ represent the same meanings as above.

As compounds of the general formula [9a], for example, methyl 2-amino-4-bromobenzoate and tert-butyl 2-amino-4-bromobenzoate (Patent Document 1) are known.

The compound of the general formula [2b] can be produced according to Production Method 11 by acylating a compound of the general formula [9a].

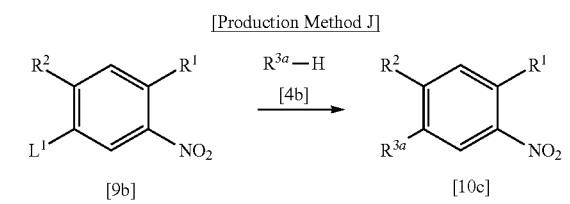

wherein, $R^1$, $R^2$, $R^{3a}$, and $L^1$ represent the same meanings as above.

The compound of the general formula [10c] can be produced according to Production Method 9 by reacting a compound of the general formula [9b] with a compound of the general formula [4b].

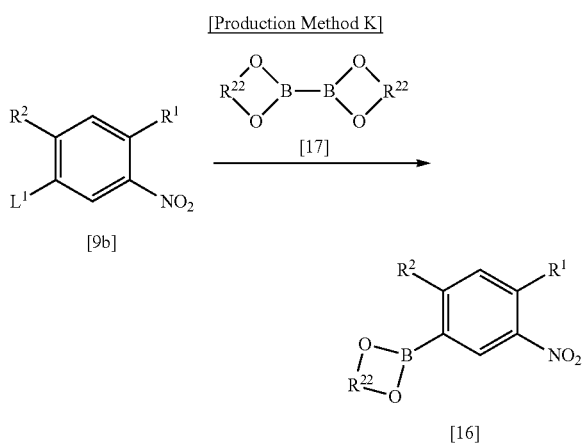

wherein, $R^1$, $R^2$, $R^{22}$, and $L^1$ represent the same meanings as above.

As compounds of the general formula [17], for example, bis(pinacolato)diboron, bis(neopentylglylato)diboron, and bis(hexyleneglycolato)diboron are known.

The compound of the general formula [16] can be produced according to Production Method 7 by reacting a compound of the general formula [9b] with a compound of the general formula [17].

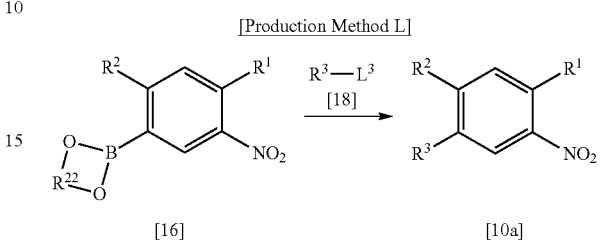

wherein, $L^3$ represents a leaving group; and $R^1$, $R^2$, $R^3$, and $R^{22}$ represent the same meanings as above.

As compounds of the general formula [18], for example, 2-bromopyridine and 1-bromo-2-(difluoromethoxy)benzene are known.

The compound of the general formula [10a] can be produced according to Production Method 7 by reacting a compound of the general formula [16] with a compound of the general formula [18].

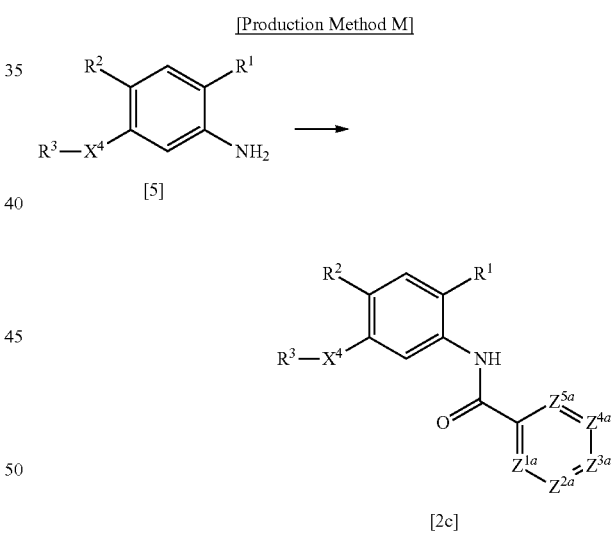

wherein, $R^1$, $R^2$, $R^3$, $X^4$, $Z^{1a}$, $Z^{2a}$, $Z^{3a}$, $Z^{4a}$, and $Z^{5a}$ represent the same meanings as above.

The compound of the general formula [2c] can be produced by acylating a compound of the general formula [5]. Specific examples thereof include a method using an acid halide in the presence or absence of a base.

The solvent used in this reaction is not particularly limited as long as it does not adversely affect the reaction, and examples thereof include amides, halogenated hydrocarbons, aromatic hydrocarbons, ethers, acetonitrile, ketones, esters, sulfolane, and dimethyl sulfoxide. These may be used as a mixture.

The acid halide used in this reaction can be produced by reacting a compound represented by a general formula [8a]:

[Formula 7]

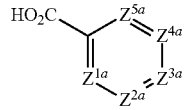

[8a]

(wherein, $Z^{1a}$, $Z^{2a}$, $Z^{3a}$, $Z^{4a}$, and $Z^{5a}$ represent the same meanings as above) with, for example, thionyl chloride or oxalyl chloride.

The amount of the acid halide used may be 1 to 50 times mol, preferably 1 to 5 times mol, of the compound of the general formula [5].

Examples of the base used as appropriate in this reaction include inorganic bases such as sodium bicarbonate, sodium carbonate, potassium carbonate, and cesium carbonate; and organic bases such as triethylamine, pyridine, and N,N-diisopropylethylamine.

The amount of the base used may be 1 to 50 times mol, preferably 1 to 5 times mol, of the compound of the general formula [5].

This reaction may be usually performed at −78 to 100° C., preferably at 0 to 80° C., for 10 minutes to 24 hours.

[Production Method N]

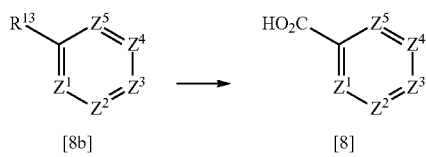

wherein, $R^{13}$, $Z^1$, $Z^2$, $Z^3$, $Z^4$, and $Z^5$ represent the same meanings as above.

As a compound of the general formula [8b], for example, methyl 5-(furan-3-yl)pyridine-3-carboxylate is known.

The compound of the general formula [8] can be produced according to Production Method 12 by deprotecting the carboxyl protecting group of a compound of the general formula [8b].

[Production Method O]

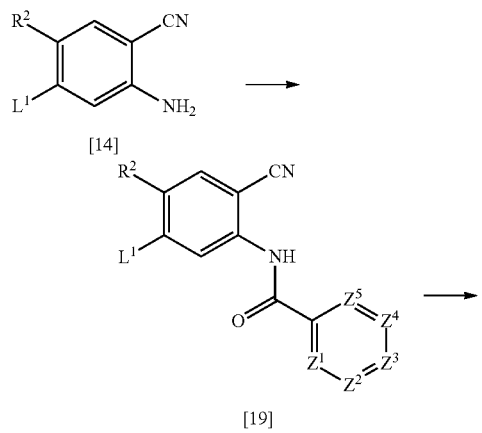

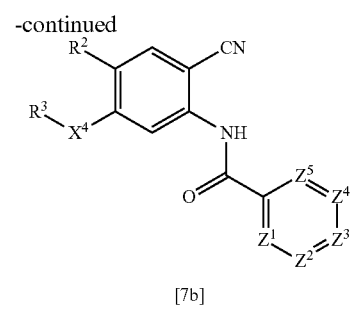

wherein, $R^2$, $R^3$, $Z^1$, $Z^2$, $Z^3$, $Z^4$, $Z^5$, $X^4$, and $L^1$ represent the same meanings as above.

As a compound of the general formula [14], for example, 2-amino-4-chlorobenzonitrile is known.

(O-1)

The compound of the general formula [19] can be produced according to Production Method 11 by acylating a compound of the general formula [14].

(O-2)

When $X^4$ is a bonding hand, the compound of the general formula [7b] can be produced according to Production Method 7 by reacting a compound of the general formula [19] with a compound of the general formula [3a] or [3b].

(O-3)

When $X^4$ is an oxygen atom or an optionally protected imino group, the compound of the general formula [7b] can be produced according to Production Method 8 by reacting a compound of the general formula [19] with a compound of the general formula [4a].

[Production Method P]

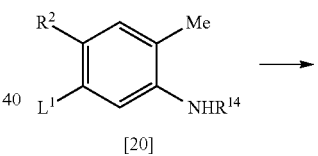

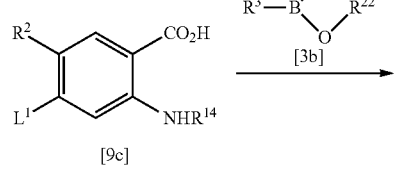

wherein, $R^{14}$ represents an amino protecting group; and $R^2$, $R^3$, $R^{21}$, $R^{22}$, and $L^1$ represent the same meanings as above.

As a compound of the general formula [20], for example, N-(5-bromo-4-methoxy-2-methylphenyl)acetamide is known.

(P-1)

The compound of the general formula [9c] can be produced by reacting a compound of the general formula [20] with an oxidizing agent in the presence or absence of an acid or a base and in the presence or absence of a salt.

The solvent used in this reaction is not particularly limited as long as it does not adversely affect the reaction, and examples thereof include water, halogenated hydrocarbons, aliphatic hydrocarbons, and pyridine. These may be used as a mixture.

Examples of the acid used as appropriate in this reaction include mineral acids such as hydrochloric acid and sulfuric acid; and organic acids such as acetic acid.

The amount of the acid used may be 1 to 1000 times mol of the compound of the general formula [20].

Examples of the base used as appropriate in this reaction include inorganic bases such as sodium hydroxide and potassium hydroxide; and organic bases such as pyridine.

The amount of the base used may be 1 to 1000 times mol of the compound of the general formula [20].

Examples of the salt used as appropriate in this reaction include magnesium sulfate, ammonium sulfate, and magnesium chloride.

The amount of the salt used is 1 to 50 times mol, preferably 1 to 10 times mol, of the compound of the general formula [20].

Examples of the oxidizing agent used in this reaction include chromates such as chromium(VI) oxide and sodium dichromate; and permanganates such as potassium permanganate, barium permanganate, calcium permanganate, and magnesium permanganate.

The amount of the oxidizing agent used may be 1 to 50 times mol, preferably 1 to 10 times mol, of the compound of the general formula [20].

This reaction may be usually performed at 0 to 150° C., preferably at 40 to 130° C., for 30 minutes to 48 hours.

(P-2)

The Compound of the General Formula [10d] can be Produced According to Production Method 7 by reacting a compound of the general formula [9c] with a compound of the general formula [3a] or [3b].

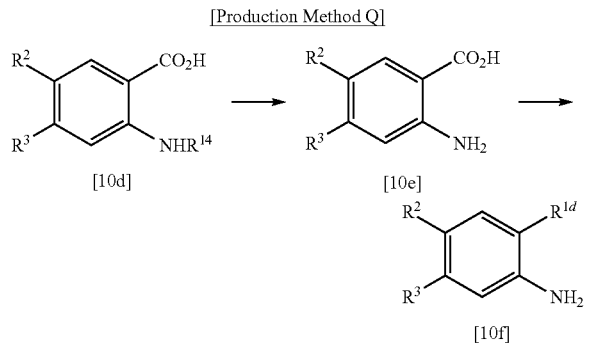

[Production Method Q]

wherein, $R^{1d}$ represents a protected carboxyl group; and $R^2$, $R^3$, and $R^{14}$ represent the same meanings as above.

(Q-1)

The Compound of the General Formula [10e] can be Produced by Deprotecting the amino protecting group of a compound of the general formula [10d].

The deprotection of the amino protecting group can be performed by, for example, the method described in W. Greene, et al., Protective Groups in Organic Synthesis, 4th Edition, pp. 696-868, 2007 (John Wiley & Sons, Inc.).

(Q-2)

The Compound of the General Formula [10f] can be Produced by Protecting the carboxyl group of a compound of the general formula [10e].

The protection of the carboxyl group can be performed by, for example, the method described in W. Greene, et al., Protective Groups in Organic Synthesis, 4th Edition, pp. 533-643, 2007 (John Wiley & Sons, Inc.).

In the compounds used in the above-described production methods, the compound that can form a salt can be also used as a salt. Examples of such a salt include the same salts as those of the compound of the general formula [1].

When isomers (for example, optical isomer, geometrical isomer, and tautomer) are present for the compounds used in the above-described production methods, these isomers can be also used. In addition, when solvates, hydrates, and crystals in various shapes are present, these solvates, hydrates, and crystals in various shapes can be also used. Furthermore, when the compounds used in the above-described production methods have substituents that can be protected, for example, in a compound having an amino group, a hydroxyl group, or a carboxyl group, such a group is protected in advance with a usual protecting group, and the protecting group may be detached by a known method after the reaction.

The compounds obtained by the above-described production methods or salts thereof can be derived to other compounds or their salts by a known reaction such as condensation, addition, oxidation, reduction, rearrangement, substitution, halogenation, dehydration, or hydrolysis, or by an appropriate combination of such reactions.

When the compound of the present invention is used as a pharmaceutical drug, pharmaceutical aids usually used for pharmaceutical formulation, such as an excipient, a carrier, and a diluent, may be appropriately mixed. The compound can be administered orally or parenterally in a form of a tablet, capsule, powder, syrup, granule, pill, suspension, emulsion, solution, powder preparation, suppository, eye drop, nose drop, eardrop, patch, ointment, or injection, according to a common method. The administration method, dosage, and administration frequency can be appropriately selected depending on the age, weight, and conditions of a patient. Usually, 0.01 to 1000 mg/kg per day can be administered to an adult orally or parenterally (for example, injection, intravenous drip, or administration to a rectal part) at a time or divided to several times.

Next, usefulness of typical compounds of the present invention will be described in the following Test Examples.

Test Example 1

Type I Collagen α1 Chain mRNA Expression Inhibition Test

Human embryonic lung fibroblast cell line WI-38 cells were suspended in a Dulbecco's modified Eagle's medium containing 10% fetal calf serum, and $7.5 \times 10^4$ cells were inoculated on a 12-well plate and cultured for 3 days, or $1.5 \times 10^5$ cells were inoculated and cultured for 2 days. After the growth of the cells to a subconfluent state, the culture medium was changed to a Dulbecco's modified Eagle's medium containing 0.4% fetal calf serum and 50 μg/mL ascorbic acid, and the cells were further cultured for 24 hours. Then, a test compound was added thereto, and, one hour later, TGF-β1 was added at a final concentration of 1 ng/mL. Twenty-four hours after the addition, the total RNA was extracted from the cells using an RNA extraction kit (SV Total RNA Isolation System, Promega), and cDNA was synthesized using a reverse transcriptase (ReverTra Ace, TOYOBO). The expression level of the type I collagen α1 chain mRNA was analyzed with a real-time PCR instrument (ABI PRISM 7700 Sequence Detection System, Applied Biosystems) by a real-time PCR method using a premix reagent of real-time PCR (SYBR Premix Ex Taq or SYBR Premix Ex Taq II (Perfect Real Time), TaKaRa). A PCR reaction was conducted with diluted cDNA as a template, using primers specific for a type I collagen α1 chain gene or a GAPDH gene as an internal standard, and the reaction product was measured. The PCR reaction was conducted by incubation at 95° C. for 10 seconds and 45 cycles of denaturation at 95° C. for 5 seconds and annealing/extension at 60° C. for 30 seconds. The expression level of the type I collagen α1 chain mRNA was corrected with GAPDH and was expressed as a relative value when the expression level obtained in the absence of the test compound was defined as 100%.

The results are shown in Tables 4a, 4b, and 4c.

TABLE 4a

| Example No. | Inhibition rate (%) at 10 μmol/L |
| --- | --- |
| 2a | 99 |
| 4a | 97 |
| 6a | 95 |
| 7a | 94 |
| 13a | 93 |
| 16a | 80 |
| 19a | 83 |
| 22a | 97 |
| 23a | 91 |
| 27a | 98 |
| 29a | 90 |
| 34a | 82 |
| 35a | 90 |
| 37a | 94 |
| 41a | 99 |
| 44a | 89 |
| 46a | 91 |
| 50a | 75 |
| 65a | 71 |
| 68a | 98 |
| 73a | 96 |
| 76a | 72 |
| 80a | 95 |
| 83a | 88 |
| 86a | 85 |
| 89a | 98 |
| 92a | 84 |
| 95a | 88 |
| 97a | 83 |
| 100a | 99 |
| 102a | 89 |
| 104a | 92 |
| 108a | 94 |
| 109a | 91 |
| 115a | 98 |
| 117a | 90 |
| 122a | 88 |
| 126a | 79 |
| 134a | 90 |
| 139a | 85 |
| 141a | 92 |
| 142a | 90 |
| 143a | 89 |
| 144a | 96 |
| 148a | 93 |
| 149a | 97 |
| 150a | 93 |
| 157a | 84 |
| 166a | 95 |
| 174a | 86 |
| 177a | 82 |
| 180a | 85 |
| 181a | 74 |
| 182a | 82 |
| 183a | 81 |
| 189a | 95 |
| 190a | 86 |
| 193a | 85 |
| 198a | 81 |
| 201a | 94 |
| 204a | 89 |
| 207a | 83 |
| 217a | 91 |
| 222a | 85 |
| 225a | 86 |

TABLE 4b

| Example No. | Inhibition rate (%) at 10 μmol/L |
| --- | --- |
| 1b | 72 |
| 3b | 83 |
| 4b | 93 |
| 5b | 72 |
| 9b | 84 |
| 11b | 80 |
| 12b | 87 |
| 13b | 92 |
| 16b | 84 |
| 19b | 90 |
| 27b | 72 |
| 29b | 86 |
| 32b | 81 |
| 33b | 78 |
| 35b | 96 |
| 38b | 94 |
| 40b | 96 |
| 44b | 93 |
| 45b | 90 |
| 46b | 69 |
| 51b | 92 |
| 57b | 84 |
| 58b | 78 |
| 61b | 86 |
| 63b | 65 |

TABLE 4c

| Compound No. | Inhibition rate (%) at 10 μmol/L |
| --- | --- |
| 2c | 82 |
| 6c | 89 |
| 7c | 94 |
| 8c | 92 |
| 9c | 76 |
| 11c | 75 |
| 16c | 89 |
| 18c | 82 |
| 23c | 78 |

The compounds used in the present invention showed excellent collagen production inhibitory activity.

Test Example 2

Mouse Bleomycin-Induced Lung Fibrosis

The test was conducted using 8- to 10.5-week-old male mice C57BL/6N (Charles River Laboratories Japan, Inc.). Bleomycin (Nippon Kayaku Co., Ltd.) was dissolved in physiological saline in a concentration of 1.0 or 1.5 mg/mL, and 2 μL/g thereof was intranasally administered to each mouse to evoke lung fibrosis. A test compound was dissolved or suspended in a 10% aqueous solution of polyoxyethylene castor oil (trade name: Cremophor EL) or in water and orally administered in an amount of 10 mg/kg twice a day from the 14th to the 28th day from the evocation. In a control group, a 10% aqueous solution of polyoxyethylene castor oil or water was administered in the same manner. The lung was extracted from each mouse on the 28th day from the evocation, and collagen was quantitatively measured. The extracted lung was homogenized in a 0.5 mol/L aqueous solution of acetic acid containing a protease inhibitor cocktail (Complete, EDTA-free, Roche Diagnostics) in an amount of one tablet/ 50 mL, and water-soluble collagen was extracted in the presence of 10 mg/mL pepsin (Sigma) overnight. The amount of collagen was measured using a kit (Sircol Soluble Collagen assay kit, Biocolor).

The inhibition rate was determined by the following expression: Inhibition rate (%)=[1−(lung collagen amount in test compound administration group)/(lung collagen amount in control group)]×100

The lung collagen amounts of administration groups in which the compound of Example 23a, 80a, 83a, 108a, 122a, 143a, 1b, 16b, 19b, 57b, or 7c was administered were low by 30% or more compared with that of the control group.

Note that the compounds of Examples 23a, 1b, and 7c were used in the forms of their sodium salts.

In addition, the compounds of Examples 122a and 143a were used in the forms of hydrochloric acid salts.

Test Example 3

Repeated Administration Toxicity Test in Rat (Oral Administration, Two Weeks)

As test compounds, the compounds of Examples 80a, 122a, 139a, 1b, 16b, and 19b were used. Note that the compounds of Examples 80a and 1b were used in the forms of sodium salts.

Each test compound was suspended in a 0.5% methylcellulose solution or distilled water to prepare a 100 mg/mL suspension. The suspension of the test compound was orally administered (10 mL/kg, test compound: 1000 mg/kg) to SD-line male rats (6-week-old, 5 rats for each group). As a result, all rats survived on the 14th day from the administration.

Test Example 4

Hepatic Drug-Metabolizing Enzyme Inhibitory Activity in Humans (CYP2C9)

As test compounds, the compounds of Examples 80a, 83a, 108a, 117a, 123a, 128a, 139a, 142a, and 143a were used. Note that the compound of Example 80a was used in the form of free base.

Pooled human liver microsome was used, and tolbutamide was used as a substrate. The reaction was performed in a phosphate buffer (100 mmol/L, pH 7.4), and the final concentrations in the reaction system were adjusted to 0.5 mg/mL of human liver microsome protein, 200 μmol/L of the substrate, 1.55 mmol/L of oxidized nicotinamide adenine dinucleotide phosphate (NADP+), 3.3 mmol/L of glucose-6-phosphate, 3.3 mmol/L of magnesium chloride, and 0.4 Units/mL of glucose-6-phosphate dehydrogenase (G6PDH). The final concentration of each compound in the reaction solution was adjusted to 0.08 to 50 μg/mL. These reaction solutions were each subjected to reaction at 37° C. for 30 minutes. The reaction was terminated with an equal amount of acetonitrile. After centrifugation, the concentration of a tolbutamide metabolite in the supernatant was quantitatively measured by LC-MS/MS. The inhibitory activity was determined as $IC_{50}$. As a positive control, sulfaphenazole was used.

The compounds of Examples 80a, 83a, 108a, 117a, 123a, 128a, 139a, 142a, and 143a each had an $IC_{50}$ of higher than 50 μg/mL.

The compounds of the present invention were low in hepatic drug-metabolizing enzyme inhibitory activity and therefore excellent in safety.

Next, the present invention will be described with reference to Reference Examples and Examples, but is not limited thereto.

The mixing ratios in eluents are volume ratios. Unless indicated otherwise, the carrier in silica gel column chromatography is Purif-Pack SI (60 μm), manufactured by Fuji Silysia Chemical Ltd.

Each of the symbols in each Example has the following meaning:

Ac: acetyl, Bn: benzyl, Boc: tert-butoxycarbonyl, $^tBu$: tert-butyl, Bz: benzoyl, Et: ethyl, $^iPr$: isopropyl, Me: methyl, Pr: propyl, and DMSO-$d_6$: deuterated dimethyl sulfoxide Reference Example 1a

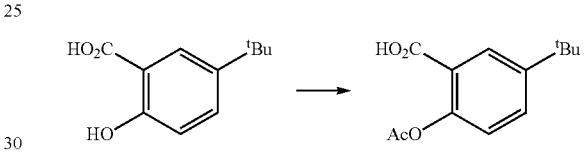

Pyridine (0.034 mL) and acetic anhydride (0.034 mL) were sequentially added to a methylene chloride (0.54 mL) solution of 5-tert-butylsalicylic acid (0.054 g), followed by stirring at room temperature for 2 hours. The solvent was evaporated under reduced pressure, and 1 mol/L hydrochloric acid and ethyl acetate were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 100-90% chloroform/methanol] to obtain 0.049 g of 2-acetoxy-5-tert-butylbenzoic acid as a white solid.

$^1$H-NMR (CDCl$_3$) δ: 1.35 (9H, s), 2.35 (3H, s), 7.06 (1H, d, J=8.3 Hz), 7.63 (1H, dd, J=8.3, 2.4 Hz), 8.12 (1H, d, J=2.4 Hz).

Reference Examples 2a to 4a

As in Reference Example 1a, the compounds shown in Table 5a were prepared.

TABLE 5a

| Reference Example No. | |
|---|---|
| 2a | HO₂C—⟨⟩—OEt, AcO |
| 3a | HO₂C—⟨⟩—O$^i$Pr, AcO |

TABLE 5a-continued

| Reference Example No. | |
|---|---|
| 4a | HO₂C-[benzene]-Ac with AcO |

2-Acetoxy-5-ethoxybenzoic acid

¹H-NMR (DMSO-d₆) δ: 1.33 (3H, t, J=7.0 Hz), 2.21 (3H, s), 4.06 (2H, q, J=7.0 Hz), 7.09 (1H, d, J=8.8 Hz), 7.17 (1H, dd, J=8.8, 3.2 Hz), 7.37 (1H, d, J=3.2 Hz), 13.06-13.16 (1H, broad).

2-Acetoxy-5-isopropoxybenzoic acid

¹H-NMR (DMSO-d₆) δ: 1.27 (6H, d, J=6.1 Hz), 2.21 (3H, s), 4.56-4.68 (1H, m), 7.08 (1H, d, J=8.8 Hz), 7.16 (1H, dd, J=8.8, 2.9 Hz), 7.35 (1H, d, J=2.8 Hz).

2-acetoxy-5-acetylbenzoic acid

¹H-NMR (CDCl₃) δ: 2.38 (3H, s), 2.66 (3H, s), 7.26 (1H, d, J=8.6 Hz), 8.23 (1H, dd, J=8.6, 2.2 Hz), 8.69 (1H, d, J=2.2 Hz).

Reference Example 5a

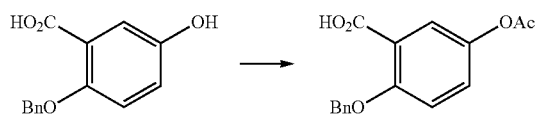 [SMILES: O=C(O)c1cc(O)ccc1OCc1ccccc1 ; CC(=O)Oc1ccc(OCc2ccccc2)c(C(=O)O)c1]

As in Reference Example 1a, the following compound was prepared.

5-Acetoxy-2-(benzyloxy)benzoic acid

¹H-NMR (CDCl₃) δ: 2.30 (3H, s), 5.29 (2H, s), 7.13 (1H, d, J=8.9 Hz), 7.30 (1H, dd, J=8.9, 3.0 Hz), 7.38-7.48 (5H, m), 7.91 (1H, d, J=3.0 Hz), 10.60-10.95 (1H, m).

Reference Example 6a

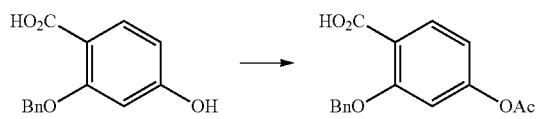 [SMILES: O=C(O)c1ccc(O)cc1OCc1ccccc1 ; CC(=O)Oc1ccc(C(=O)O)c(OCc2ccccc2)c1]

As in Reference Example 1a, the following compound was prepared.

4-Acetoxy-2-(benzyloxy)benzoic acid

¹H-NMR (DMSO-d₆) δ: 2.28 (3H, s), 5.17 (2H, s), 6.77-6.84 (1H, m), 7.04 (1H, d, J=1.7 Hz), 7.29-7.35 (1H, m), 7.36-7.43 (2H, m), 7.46-7.53 (2H, m), 7.72 (1H, d, J=8.5 Hz), 12.68 (1H, s).

Reference Example 7a

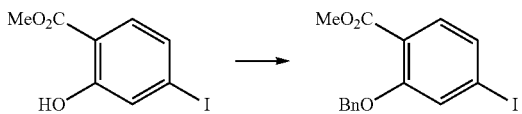 [SMILES: COC(=O)c1ccc(I)cc1O ; COC(=O)c1ccc(I)cc1OCc1ccccc1]

Potassium carbonate (1.9 g) and benzyl bromide (1.2 mL) were sequentially added to an N,N-dimethylacetamide (20 mL) solution of methyl 2-hydroxy-4-iodobenzoate (2.5 g), followed by stirring at 80° C. for 1 hour. The reaction mixture was cooled to room temperature, and then 1 mol/L hydrochloric acid and ethyl acetate were added thereto. The organic layer was separated, washed with 1 mol/L hydrochloric acid and a saturated aqueous solution of sodium chloride sequentially, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 90-80% hexane/ethyl acetate] to obtain 3.3 g of methyl 2-(benzyloxy)-4-iodobenzoate as a yellow oily substance.

¹H-NMR (CDCl₃) δ: 3.88 (3H, s), 5.15 (2H, s), 7.30-7.43 (5H, m), 7.47-7.51 (2H, m), 7.53 (1H, d, J=8.1 Hz).

Reference Example 8a

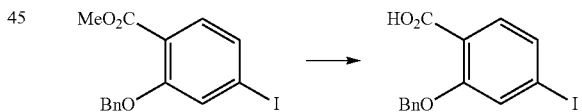

A 2.0 mol/L aqueous solution of sodium hydroxide (4.1 mL) was added to a solution mixture of methyl 2-(benzyloxy)-4-iodobenzoate (1.0 g) in dioxane (5.0 mL) and methanol (5.0 mL), followed by stirring at room temperature for 2 hours. The solvent was evaporated under reduced pressure, and water was added to the residue. After adjusting the pH to 2.5 with 6.0 mol/L hydrochloric acid under ice-cooling, ethyl acetate was added. The organic layer was separated, washed with a saturated aqueous solution of sodium chloride, and dried over anhydrous magnesium sulfate, and the solvent was evaporated under reduced pressure. Hexane and diisopropyl ether were added to the obtained residue, and the resulting solid substance was collected by filtration to obtain 0.93 g of 2-(benzyloxy)-4-iodobenzoic acid as a white solid.

¹H-NMR (CDCl₃) δ: 5.27 (2H, s), 7.40-7.55 (7H, m), 7.88 (1H, d, J=8.3 Hz), 10.35-10.55 (1H, broad).

Reference Example 9a

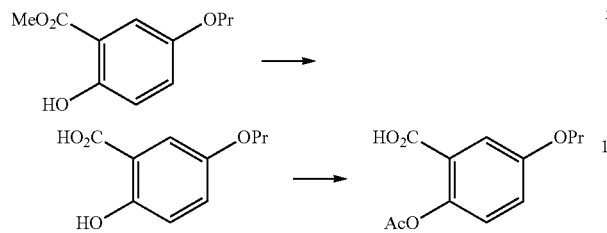

A 4 mol/L aqueous solution of sodium hydroxide (0.67 mL) was added to a dioxane (3.0 mL) solution of methyl 2-hydroxy-5-propoxybenzoate (0.19 g), followed by stirring at room temperature for 1 hour and 30 minutes and then at 55 to 60° C. for 3 hours. The reaction mixture was cooled to room temperature, and then a 10% aqueous solution of citric acid (15 mL) was added thereto. The solvent was evaporated under reduced pressure, and ethyl acetate was added to the residue. The organic layer was separated, washed with a saturated aqueous solution of sodium chloride, and dried over anhydrous magnesium sulfate, and the solvent was evaporated under reduced pressure. Hexane was added to the obtained residue, and the solid substance was collected by filtration to obtain 0.13 g of 2-hydroxy-5-propoxybenzoic acid as a light yellow solid.

Acetic anhydride (0.069 mL) was added to a solution mixture of the obtained 2-hydroxy-5-propoxybenzoic acid (0.12 g) in methylene chloride (3.0 mL) and pyridine (0.12 mL) under ice-cooling, followed by stirring at room temperature for 2 hours and 30 minutes. Pyridine (0.050 mL) and acetic anhydride (0.058 mL) were added to the reaction mixture, followed by stirring at room temperature for 50 minutes. The solvent was evaporated under reduced pressure, and 1 mol/L hydrochloric acid and ethyl acetate were added to the obtained residue. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 65-55% hexane/ethyl acetate] to obtain 0.091 g of 2-acetoxy-5-propoxybenzoic acid as a white solid.

$^1$H-NMR (DMSO-$d_6$) δ: 0.98 (3H, t, J=7.4 Hz), 1.67-1.79 (2H, m), 2.21 (3H, s), 3.96 (2H, t, J=6.5 Hz), 7.09 (1H, d, J=8.8 Hz), 7.17 (1H, dd, J=8.8, 3.2 Hz), 7.37 (1H, d, J=3.2 Hz), 13.00-13.24 (1H, broad).

Reference Example 10a

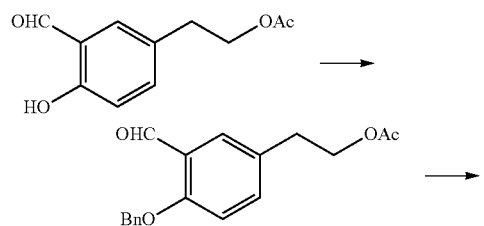

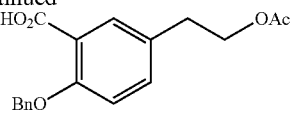

Potassium carbonate (0.40 g) and benzyl bromide (0.25 mL) were sequentially added to a 2-butanone (4.0 mL) solution of 3-formyl-4-hydroxyphenethyl acetate (0.40 g), followed by heating to reflux for 2 hours. The reaction mixture was cooled to room temperature, and then a saturated aqueous solution of sodium bicarbonate and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 95-85% hexane/ethyl acetate] to obtain 0.36 g of 4-(benzyloxy)-3-formyl phenethyl acetate as a colorless oily substance.

A 30% hydrogen peroxide solution (0.21 mL) and a water (0.5 mL) solution of sodium chlorite (0.18 g) were sequentially added to a solution mixture of acetonitrile (3.6 mL) containing the obtained 4-(benzyloxy)-3-formyl phenethyl acetate (0.36 g) and water (1.5 mL) containing sodium dihydrogen phosphate dihydrate (0.51 g) under ice-cooling, followed by stirring at the same temperature for 10 minutes and then at room temperature for 1 hour. Water and methylene chloride were added to the reaction mixture. After adjusting the pH to 3.5 with 6.0 mol/L hydrochloric acid, the organic layer was separated, washed with water and a saturated aqueous solution of sodium chloride sequentially, and dried over anhydrous magnesium sulfate. The solvent was evaporated under reduced pressure to obtain 0.38 g of 5-(2-acetoxyethyl)-2-(benzyloxy)benzoic acid as a colorless oily substance.

$^1$H-NMR (CDCl$_3$) δ: 2.03 (3H, s), 2.94 (2H, t, J=6.8 Hz), 4.27 (2H, t, J=6.8 Hz), 5.29 (2H, s), 7.08 (1H, d, J=8.6 Hz), 7.38-7.46 (6H, m), 8.08 (1H, d, J=2.2 Hz), 10.75-10.90 (1H, broad).

Reference Example 11a

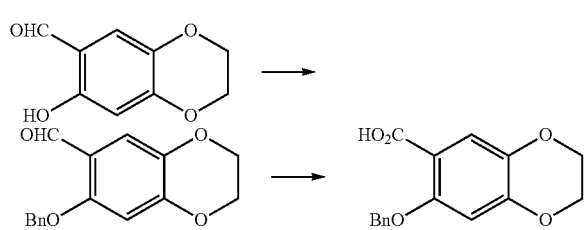

Potassium carbonate (0.27 g) and benzyl bromide (0.17 mL) were sequentially added to an N,N-dimethylformamide (2 mL) solution of 7-hydroxy-2,3-dihydrobenzo[1,4]dioxine-6-carbaldehyde (0.23 g), followed by stirring at 65° C. for 2 hours. Benzyl bromide (0.077 mL) was added to the reaction mixture, followed by stirring at 65° C. for 30 minutes. The reaction mixture was cooled to room temperature, and then water and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 75-60% hexane/ethyl acetate] to obtain 0.32 g of 7-(benzyloxy)-2,3-dihydrobenzo[1,4]dioxine-6-carbaldehyde as a light yellow solid.

A water (0.60 mL) solution of sodium dihydrogen phosphate dihydrate (0.50 g) was added to an acetonitrile (1.6 mL) suspension of the obtained 7-(benzyloxy)-2,3-dihydrobenzo[1,4]dioxine-6-carbaldehyde (0.32 g), and a 30% hydrogen peroxide solution (0.20 mL) and a water (0.30 mL) solution of sodium chlorite (0.17 g) were sequentially added thereto under ice-cooling, followed by stirring at the same temperature for 15 minutes and then at room temperature for 1 hour and 30 minutes. The reaction mixture was adjusted to a pH of 1.4 with 1 mol/L hydrochloric acid, and water and ethyl acetate were added thereto. The organic layer was separated, washed with a saturated aqueous solution of sodium chloride, and dried over anhydrous magnesium sulfate, and the solvent was evaporated under reduced pressure to obtain 0.34 g of 7-(benzyloxy)-2,3-dihydrobenzo[1,4]dioxine-6-carboxylic acid as a white solid.

$^1$H-NMR (DMSO-$d_6$) δ: 4.17-4.24 (2H, m), 4.25-4.32 (2H, m), 5.11 (2H, s), 6.70 (1H, s), 7.23 (1H, s), 7.27-7.34 (1H, m), 7.34-7.42 (2H, m), 7.45-7.53 (2H, m), 12.34 (1H, s).

Reference Example 12a

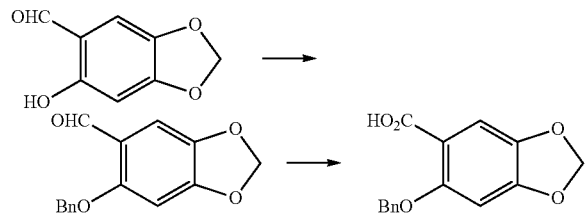

As in Reference Example 11a, the following compound was prepared.

6-(Benzyloxy)benzo[1,3]dioxole-5-carboxylic acid $^1$H-NMR (CDCl$_3$) δ: 5.23 (2H, s), 6.04 (2H, s), 6.67 (1H, s), 7.38-7.46 (5H, m), 7.59 (1H, s), 10.64-10.96 (1H, broad).

Reference Example 13a

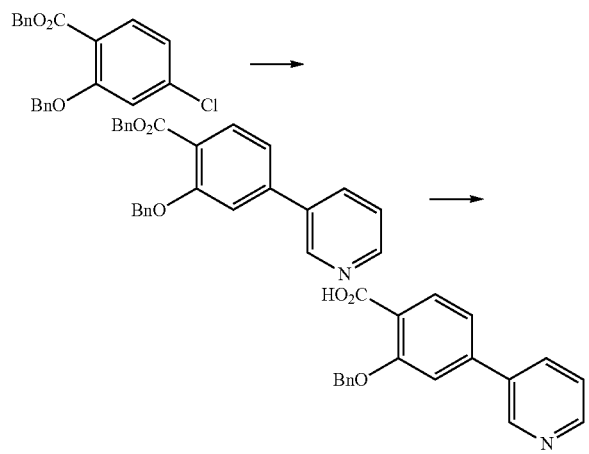

3-(4,4,5,5-Tetramethyl-1,3,2-dioxaborolan-2-yl)-pyridine (0.24 g), tripotassium phosphate (0.46 g), palladium(II) acetate (4.5 mg) and 2-dicyclohexylphosphino-2',6'-dimethoxybiphenyl (4.1 mg) were added to a toluene (5.3 mL) solution of benzyl 2-(benzyloxy)-4-chlorobenzoate (0.35 g), followed by heating to reflux under a nitrogen atmosphere for 3 hours and 30 minutes. The reaction mixture was cooled to room temperature, and then 3-(4,4,5,5-tetramethyl-1,3,2-dioxaborolan-2-yl)pyridine (0.16 g), tripotassium phosphate (0.25 g), palladium(II) acetate (4.5 mg), and 2-dicyclohexylphosphino-2',6'-dimethoxybiphenyl (4.1 mg) were added thereto, followed by heating to reflux under a nitrogen atmosphere for 3 hours and 30 minutes. After cooling the reaction mixture to room temperature, a 10% aqueous solution of citric acid and ethyl acetate were added thereto, and the insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 90-50% hexane/ethyl acetate] to obtain 0.35 g of benzyl 2-(benzyloxy)-4-(pyridin-3-yl) benzoate.

A 2 mol/L aqueous solution of sodium hydroxide (1.3 mL) was added to a solution mixture of the obtained benzyl 2-(benzyloxy)-4-(pyridin-3-yl)benzoate (0.35 g) in dioxane (1.8 mL) and methanol (1.8 mL), followed by stirring at room temperature for 1 hour. Water was added to the reaction mixture. After adjusting the pH to 4.5 with 6 mol/L hydrochloric acid, ethyl acetate was added thereto. The organic layer was separated, washed with a saturated aqueous solution of sodium chloride, and dried over anhydrous magnesium sulfate, and the solvent was evaporated under reduced pressure. Diisopropyl ether was added to the obtained residue, and the solid substance was collected by filtration to obtain 0.20 g of 2-(benzyloxy)-4-(pyridin-3-yl)benzoic acid as a light yellow solid.

$^1$H-NMR (DMSO-$d_6$) δ: 5.35 (2H, s), 7.29-7.44 (4H, m), 7.50-7.57 (4H, m), 7.78 (1H, d, J=8.0 Hz), 8.12-8.18 (1H, m), 8.62 (1H, dd, J=4.6, 1.5 Hz), 8.96 (1H, d, J=2.2 Hz).

Reference Examples 14a to 16a

As in Reference Example 13a, the compounds shown in Table 6a were prepared.

TABLE 6a

| Reference Example No. | Structure |
|---|---|
| 14a | ![structure with HO2C, BnO, and phenyl group] |
| 15a | ![structure with HO2C, BnO, and furan group] |

TABLE 6a-continued

| Reference Example No. | |
|---|---|
| 16a | 2-(Benzyloxy)-4-(pyridin-4-yl)benzoic acid structure with HO₂C, BnO, and pyridine groups |

2-(Benzyloxy)-4-phenylbenzoic acid $^1$H-NMR (CDCl$_3$) δ: 5.37 (2H, s), 7.32 (1H, d, J=1.5 Hz), 7.34-7.52 (9H, m), 7.55-7.61 (2H, m), 8.26 (1H, d, J=8.0 Hz), 10.62-10.96 (1H, broad).

2-(Benzyloxy)-4-(furan-3-yl)benzoic acid $^1$H-NMR (DMSO-d$_6$) δ: 5.29 (2H, s), 7.04-7.07 (1H, m), 7.27 (1H, dd, J=8.1, 1.0 Hz), 7.28-7.36 (1H, m), 7.37-7.46 (3H, m), 7.52-7.58 (2H, m), 7.70 (1H, d, J=8.1 Hz), 7.76-7.81 (1H, m), 8.31-8.35 (1H, m), 12.56 (1H, s).

2-(Benzyloxy)-4-(pyridin-4-yl)benzoic acid $^1$H-NMR (DMSO-d$_6$) δ: 5.36 (2H, s), 7.30-7.36 (1H, m), 7.38-7.47 (3H, m), 7.51-7.57 (2H, m), 7.59 (1H, d, J=1.5 Hz), 7.75-7.81 (3H, m), 8.66-8.71 (2H, m).

Reference Example 17a

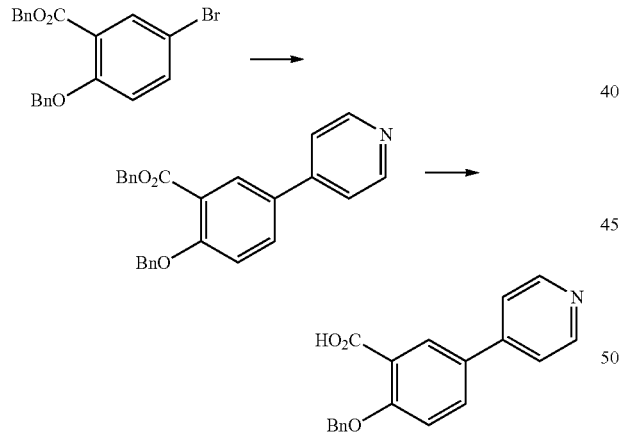

Water (1.2 mL), 4-(4,4,5,5-tetramethyl-1,3,2-dioxaborolan-2-yl)pyridine (0.25 g), sodium bicarbonate (0.21 g), and bis(triphenylphosphine)palladium(II) dichloride (14 mg) were added to an ethylene glycol dimethyl ether (4 mL) solution of benzyl 2-(benzyloxy)-5-bromobenzoate (0.40 g), followed by heating to reflux under a nitrogen atmosphere for 2 hours. The reaction mixture was cooled to room temperature, and then 4-(4,4,5,5-tetramethyl-1,3,2-dioxaborolan-2-yl)pyridine (0.12 g), sodium bicarbonate (0.10 g), and bis(triphenylphosphine)palladium(II) dichloride (14 mg) were added thereto, followed by heating to reflux under a nitrogen atmosphere for 2 hours. After cooling the reaction mixture to room temperature, water and ethyl acetate were added thereto, and the insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 90-45% hexane/ethyl acetate] to obtain 0.29 g of benzyl 2-(benzyloxy)-5-(pyridin-4-yl)benzoate as a white solid.

An 2 mol/L aqueous solution of sodium hydroxide (1.1 mL) was added to a solution mixture of the obtained benzyl 2-(benzyloxy)-5-(pyridin-4-yl)benzoate (0.29 g) in dioxane (2.9 mL) and methanol (2.9 mL), followed by stirring at room temperature for 1 hour. The solvent was evaporated under reduced pressure, and water was added to the residue. After adjusting the pH to 4 with 6 mol/L hydrochloric acid, ethyl acetate was added thereto. The reaction mixture was filtrated to collect the solid substance to obtain 0.19 g of 2-(benzyloxy)-5-(pyridin-4-yl)benzoic acid as a white solid.

$^1$H-NMR (DMSO-d$_6$) δ: 5.30 (2H, s), 7.30-7.44 (4H, m), 7.49-7.55 (2H, m), 7.69-7.74 (2H, m), 7.96 (1H, dd, J=8.7, 2.6 Hz), 8.06 (1H, d, J=2.7 Hz), 8.58-8.64 (2H, m), 12.85-13.00 (1H, broad).

Reference Example 18a

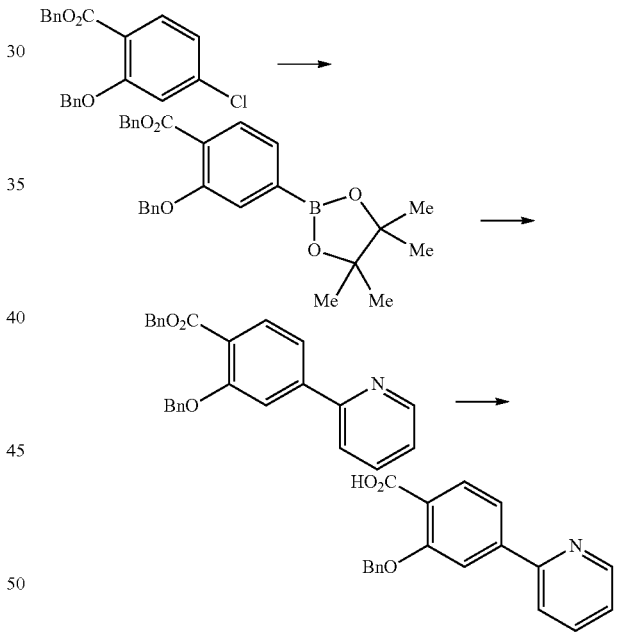

Bis(pinacolato)diboron (0.41 g), potassium acetate (0.25 g), tris(dibenzylideneacetone)dipalladium(0) (46 mg), and a 15% tricyclohexylphosphine-toluene solution (0.25 mL) were added to a dioxane (3.5 mL) solution of benzyl 2-(benzyloxy)-4-chlorobenzoate (0.35 g), followed by stirring under a nitrogen atmosphere at room temperature for 30 minutes and then at 80° C. for 5 hours and 30 minutes. After cooling the reaction mixture to room temperature, tris(dibenzylideneacetone)dipalladium(0) (46 mg) and a 15% tricyclohexylphosphine-toluene solution (0.25 mL) were added thereto, followed by stirring under a nitrogen atmosphere at 90° C. for 8 hours. After cooling the reaction mixture to room temperature, a saturated aqueous solution of sodium bicarbonate and ethyl acetate were added thereto, and the insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 100-75% hexane/ethyl acetate] to obtain benzyl 2-(benzyloxy)-4-(4,4,5,5-tetramethyl-1,3,2-dioxaborolan-2-yl)benzoate.

Water (1.1 mL), 2-bromopyridine (0.11 mL), sodium carbonate (0.21 g), and bis(triphenylphosphine)palladium(II) dichloride (14 mg) were added to a solution of ethylene glycol dimethyl ether (3.5 mL) of the obtained benzyl 2-(benzyloxy)-4-(4,4,5,5-tetramethyl-1,3,2-dioxaborolan-2-yl)benzoate, followed by heating to reflux under a nitrogen atmosphere for 1 hour and 30 minutes. After cooling the reaction mixture to room temperature, 2-bromopyridine (0.11 mL), sodium carbonate (0.21 g), and bis(triphenylphosphine)palladium(II) dichloride (14 mg) were added thereto, followed by heating to reflux under a nitrogen atmosphere for 1 hour and 30 minutes. After cooling the reaction mixture to room temperature, water and ethyl acetate were added thereto, and the insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 100-80% hexane/ethyl acetate] to obtain 0.18 g of benzyl 2-(benzyloxy)-4-(pyridin-2-yl)benzoate.

A 2 mol/L aqueous solution of sodium hydroxide (0.69 mL) was added to a solution mixture of the obtained benzyl 2-(benzyloxy)-4-(pyridin-2-yl)benzoate (0.18 g) in dioxane (0.9 mL) and methanol (0.9 mL), followed by stirring at room temperature for 2 hours. Water was added to the reaction mixture. After adjusting the pH to 4 with 6 mol/L hydrochloric acid, ethyl acetate was added thereto. The organic layer was separated, washed with a saturated aqueous solution of sodium chloride, and dried over anhydrous magnesium sulfate, and the solvent was evaporated under reduced pressure. Diisopropyl ether and hexane were added to the obtained residue, and the solid substance was collected by filtration to obtain 0.12 g of 2-(benzyloxy)-4-(pyridin-2-yl)benzoic acid as a white solid.

$^1$H-NMR (CDCl$_3$) δ: 5.43 (2H, s), 7.31-7.36 (1H, m), 7.40-7.53 (5H, m), 7.69 (1H, dd, J=8.2, 1.5 Hz), 7.78-7.86 (2H, m), 8.02 (1H, d, J=1.5 Hz), 8.30 (1H, d, J=8.2 Hz), 8.71-8.77 (1H, m), 10.70-10.95 (1H, broad).

Reference Examples 19a and 20a

As in Reference Example 18a, the compounds shown in Table 7a were prepared.

TABLE 7a

| Reference Example No. | |
|---|---|
| 19a | ![structure: HO2C-phenyl(BnO)-pyrimidin-2-yl] |

TABLE 7a-continued

| Reference Example No. | |
|---|---|
| 20a | ![structure: HO2C-phenyl(BnO)-pyrimidin-5-yl] |

2-(Benzyloxy)-4-(pyrimidin-2-yl)benzoic acid $^1$H-NMR (CDCl$_3$) δ: 5.44 (2H, s), 7.30 (1H, t, J=4.9 Hz), 7.40-7.53 (5H, m), 8.27 (1H, dd, J=8.3, 1.2 Hz), 8.31-8.36 (2H, m), 8.87 (2H, d, J=4.9 Hz), 10.75-10.95 (1H, broad).

2-(Benzyloxy)-4-(pyrimidin-5-yl)benzoic acid $^1$H-NMR (CDCl$_3$) δ: 5.41 (2H, s), 7.28 (1H, d, J=1.7 Hz), 7.37 (1H, dd, J=8.1, 1.7 Hz), 7.42-7.50 (5H, m), 8.36 (1H, d, J=8.1 Hz), 8.94 (2H, s), 9.28 (1H, s), 10.55-10.70 (1H, broad).

Reference Example 21a

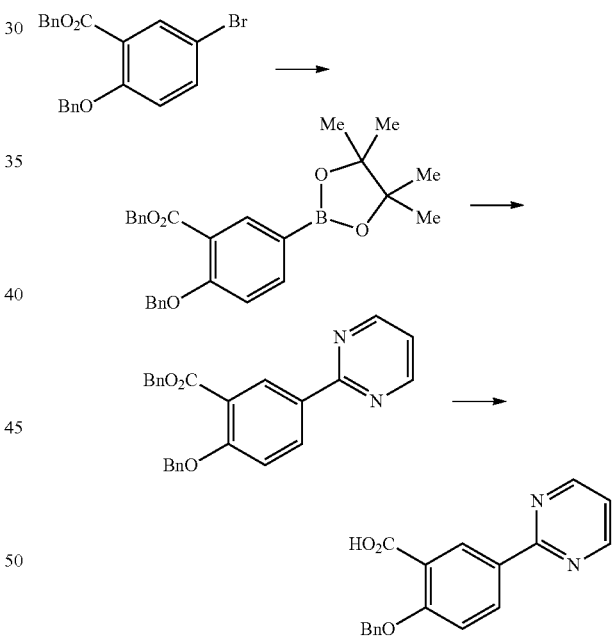

Dioxane (53 mL), bis(pinacolato)diboron (4.0 g), potassium acetate (2.6 g), and (1,1'-bis(diphenylphosphino)ferrocene)palladium(II) dichloride methylene chloride complex (0.54 g) were added to benzyl 2-(benzyloxy)-5-bromobenzoate (5.3 g), followed by heating to reflux under a nitrogen atmosphere for 2 hours and 30 minutes. After cooling the reaction mixture to room temperature, the insoluble substance was removed by filtration, and the solvent was evaporated under reduced pressure. The obtained residue was purified by silica gel column chromatography [Fuji Silysia Chemical Ltd., PSQ100B (spherical), eluent: 98-82% hexane/ethyl acetate] to obtain 5.3 g of benzyl 2-(benzyloxy)-5-(4,4,5,5-tetramethyl-1,3,2-dioxaborolan-2-yl)benzoate.

Water (5.3 mL), 2-bromopyrimidine (0.95 g), sodium carbonate (1.3 g), and bis(triphenylphosphine)palladium(II) dichloride (0.14 g) were added to an ethylene glycol dimethyl ether (18 mL) solution of the obtained benzyl 2-(benzyloxy)-5-(4,4,5,5-tetramethyl-1,3,2-dioxaborolan-2-yl)benzoate (1.8 g), followed by heating to reflux under a nitrogen atmosphere for 4 hours. The reaction mixture was cooled to room temperature, an then bis(triphenylphosphine)palladium(II) dichloride (0.14 g) was added thereto, followed by heating to reflux under a nitrogen atmosphere for 5 hours. The reaction mixture was cooled to room temperature, and then water and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 80-50% hexane/ethyl acetate] to obtain 1.4 g of benzyl 2-(benzyloxy)-5-(pyrimidin-2-yl)benzoate.

A 2 mol/L aqueous solution of sodium hydroxide (8.6 mL) was added to a solution mixture of the obtained benzyl 2-(benzyloxy)-5-(pyrimidin-2-yl)benzoate (1.4 g) in dioxane (10 mL) and methanol (5 mL), followed by stirring at room temperature for 4 hours. Toluene was added to the reaction mixture, and the aqueous layer was separated. After adjusting the pH to 1 with 6 mol/L hydrochloric acid, the solid substance was collected by filtration to obtain 0.65 g of 2-(benzyloxy)-5-(pyrimidin-2-yl)benzoic acid as a white solid.

$^1$H-NMR (DMSO-$d_6$) δ: 5.31 (2H, s), 7.30-7.45 (5H, m), 7.50-7.57 (2H, m), 8.50 (1H, dd, J=8.8, 2.4 Hz), 8.74 (1H, d, J=2.4 Hz), 8.88 (2H, d, J=4.9 Hz), 12.82-12.88 (1H, broad).

Reference Example 22a

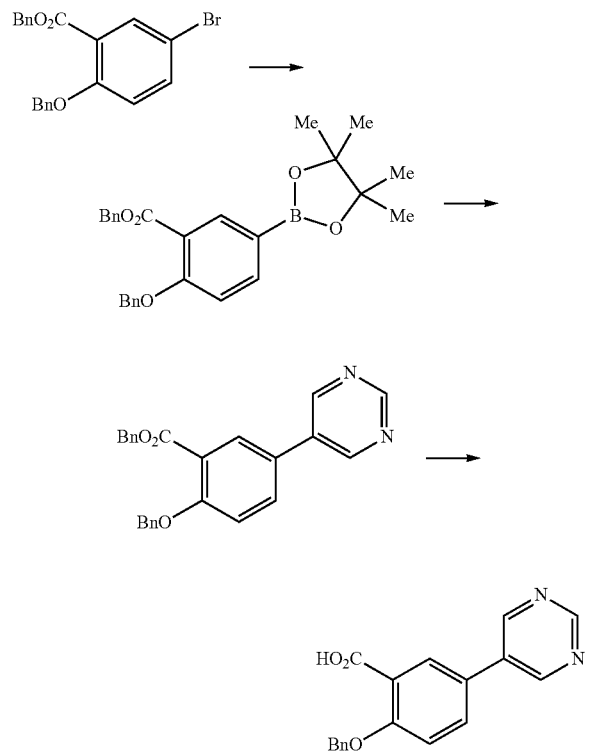

As in Reference Example 21a, the following compound was prepared.

2-(Benzyloxy)-5-(pyrimidin-5-yl)benzoic acid $^1$H-NMR (DMSO-$d_6$) δ: 5.30 (2H, s), 7.29-7.45 (4H, m), 7.49-7.55 (2H, m), 7.94 (1H, dd, J=8.8, 2.4 Hz), 8.04 (1H, d, J=2.4 Hz), 9.13 (2H, s), 9.15 (1H, s), 12.93 (1H, s).

Reference Example 23a

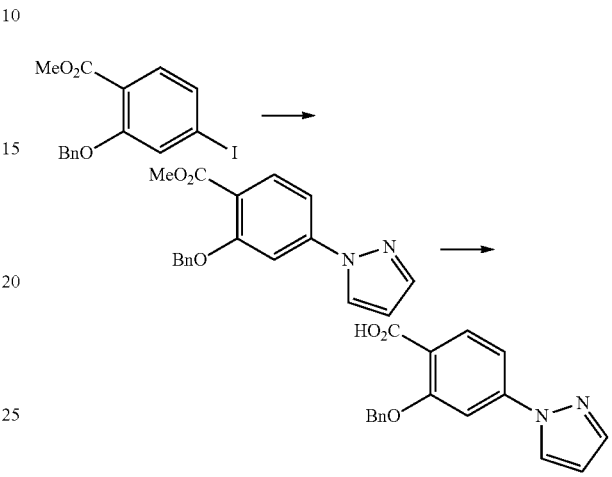

1H-Pyrazole (0.044 g), D-proline (0.013 g), potassium carbonate (0.15 g), and copper(I) iodide (0.010 g) were added to a dimethyl sulfoxide (1.5 mL) solution of methyl 2-(benzyloxy)-4-iodobenzoate (0.20 g), followed by stirring under a nitrogen atmosphere at 90° C. for 2 hours. The reaction mixture was cooled to room temperature, and then D-proline (0.013 g) and copper(I) iodide (0.010 g) were added thereto, followed by stirring under a nitrogen atmosphere at 100° C. for 2 hours. After cooling the reaction mixture to room temperature, water and ethyl acetate were added thereto, and the insoluble substance was removed by filtration. The organic layer was separated, washed with water and a saturated aqueous solution of sodium chloride sequentially, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 100-60% hexane/ethyl acetate] to obtain 0.12 g of methyl 2-(benzyloxy)-4-(1H-pyrazol-1-yl)benzoate as a white solid.

A 2 mol/L aqueous solution of sodium hydroxide (0.56 mL) was added to a solution mixture of the obtained methyl 2-(benzyloxy)-4-(1H-pyrazol-1-yl)benzoate (0.11 g) in dioxane (1.1 mL) and methanol (1.1 mL), followed by stirring at room temperature for 2 hours. Water was added to the reaction mixture. After adjusting the pH to 3 with 6 mol/L hydrochloric acid, ethyl acetate was added thereto. The organic layer was separated, washed with a saturated aqueous solution of sodium chloride, and dried over anhydrous magnesium sulfate, and the solvent was evaporated under reduced pressure. Diisopropyl ether and hexane were added to the obtained residue, and the solid substance was collected by filtration to obtain 0.10 g of 2-(benzyloxy)-4-(1H-pyrazol-1-yl)benzoic acid as a white solid.

$^1$H-NMR (CDCl$_3$) δ: 5.39 (2H, s), 6.50-6.57 (1H, m), 7.34 (1H, dd, J=8.6, 2.2 Hz), 7.40-7.51 (5H, m), 7.74-7.80 (2H, m), 8.01 (1H, d, J=2.2 Hz), 8.28 (1H, d, J=8.6 Hz), 10.50-10.70 (1H, broad).

Reference Example 24a

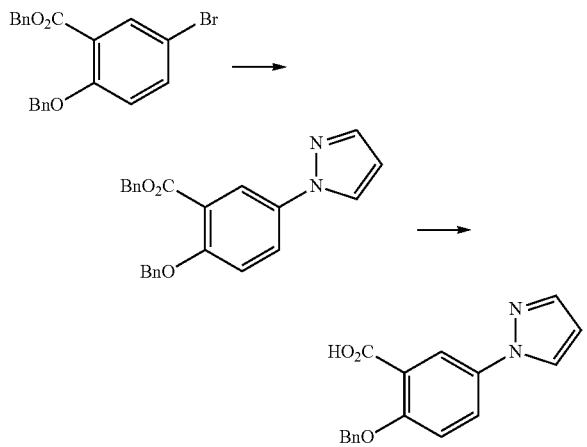

As in Reference Example 23a, the following compound was prepared.

2-(Benzyloxy)-5-(1H-pyrazol-1-yl)benzoic acid $^1$H-NMR (CDCl$_3$) δ: 5.35 (2H, s), 6.49 (1H, dd, J=2.4, 1.9 Hz), 7.23-7.28 (1H, m), 7.41-7.48 (5H, m), 7.72 (1H, d, J=1.4 Hz), 7.95-7.99 (1H, m), 8.07 (1H, dd, J=9.0, 2.9 Hz), 8.39 (1H, d, J=2.9 Hz), 10.75-10.90 (1H, broad).

Reference Example 25a

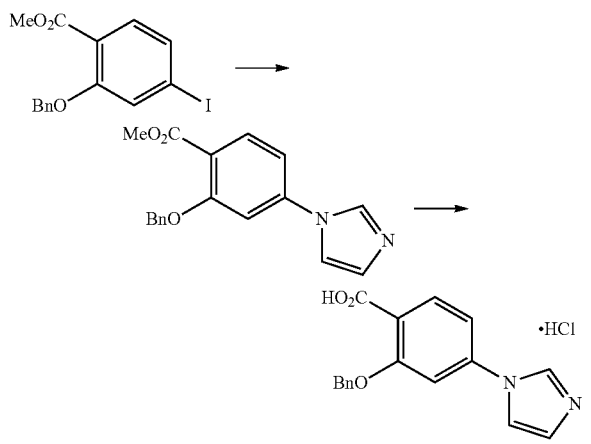

1H-Imidazole (0.044 g), D-proline (0.013 g), potassium carbonate (0.15 g), and copper(I) iodide (0.010 g) were added to a dimethyl sulfoxide (1 mL) solution of methyl 2-(benzyloxy)-4-iodobenzoate (0.20 g), followed by stirring under a nitrogen atmosphere at 90° C. for 1 hour. The reaction mixture was cooled to room temperature, and then dimethyl sulfoxide (0.5 mL), D-proline (0.013 g), and copper(I) iodide (0.010 g) were added thereto, followed by stirring under a nitrogen atmosphere at 90° C. for 2 hours. After cooling the reaction mixture to room temperature, water and ethyl acetate were added thereto, and the insoluble substance was removed by filtration. The organic layer was separated, washed with water and a saturated aqueous solution of sodium chloride sequentially, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 90-20% hexane/ethyl acetate] to obtain 0.13 g of methyl 2-(benzyloxy)-4-(1H-imidazol-1-yl)benzoate as a white solid.

A 2 mol/L aqueous solution of sodium hydroxide (0.63 mL) was added to a solution mixture of the obtained methyl 2-(benzyloxy)-4-(1H-imidazol-1-yl)benzoate (0.13 g) in dioxane (0.65 mL) and methanol (0.65 mL), followed by stiffing at room temperature for 3 hours. Under ice-cooling, 6 mol/L hydrochloric acid (0.21 mL) was added to the reaction mixture, and the solvent was evaporated under reduced pressure. Water was added to the obtained residue, and the solid substance was collected by filtration. Dioxane (1 mL) and a 4 mol/L hydrogen chloride-dioxane solution (0.5 mL) were added to the obtained solid substance, followed by stirring at room temperature for 1 hour. The solid substance was collected from the reaction mixture by filtration to obtain 0.097 g of 2-(benzyloxy)-4-(1H-imidazol-1-yl)benzoic acid hydrochloride as a white solid.

$^1$H-NMR (DMSO-d$_6$) δ: 5.33 (2H, s), 7.32-7.38 (1H, m), 7.39-7.45 (2H, m), 7.47 (1H, dd, J=8.3, 2.0 Hz), 7.50-7.55 (2H, m), 7.71 (1H, d, J=2.0 Hz), 7.86-7.91 (2H, m), 8.35 (1H, s), 9.68 (1H, s).

Reference Example 26a

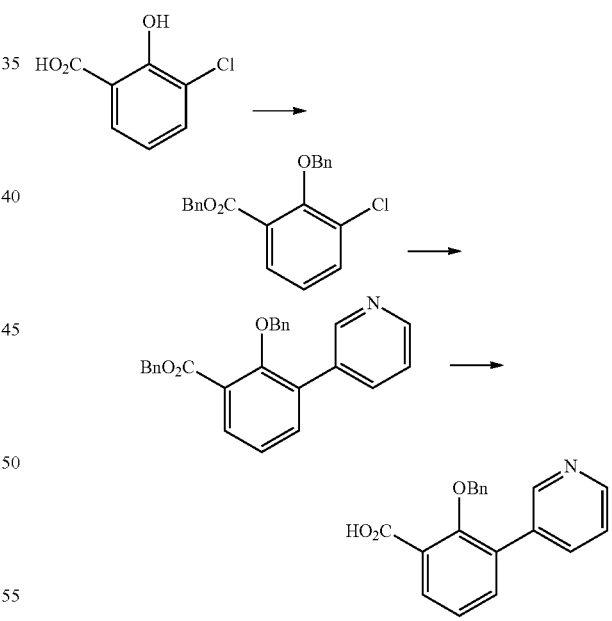

N,N-Dimethylacetamide (9.2 mL), potassium carbonate (2.2 g), and benzyl bromide (1.4 mL) were sequentially added to 3-chlorosalicylic acid (0.92 g), followed by stirring at 80° C. for 1 hour. The reaction mixture was cooled to room temperature, and then potassium carbonate (0.37 g) and benzyl bromide (0.19 mL) were sequentially added thereto, followed by stirring at 80° C. for 1 hour. The reaction mixture was cooled to room temperature, and then a 10% aqueous solution of citric acid and ethyl acetate were added thereto. The organic layer was separated, washed with a 10% aqueous solution of citric acid and a saturated aqueous solution of sodium chloride sequentially, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 100-95% hexane/ethyl acetate] to obtain 1.8 g of benzyl 2-(benzyloxy)-3-chlorobenzoate as a colorless oily substance.

3-(4,4,5,5-Tetramethyl-1,3,2-dioxaborolan-2-yl)-pyridine (0.25 g), tripotassium phosphate (0.47 g), palladium(II) acetate (4.5 mg), and 2-dicyclohexylphosphino-2',6'-dimethoxybiphenyl (4.1 mg) were added to a toluene (5.3 mL) solution of the obtained benzyl 2-(benzyloxy)-3-chlorobenzoate (0.35 g), followed by heating to reflux under a nitrogen atmosphere for 1 hour and 40 minutes. The reaction mixture was cooled to room temperature, and then 3-(4,4,5,5-tetramethyl-1,3,2-dioxaborolan-2-yl)pyridine (0.12 g), tripotassium phosphate (0.23 g), palladium(II) acetate (4.5 mg), and 2-dicyclohexylphosphino-2',6'-dimethoxybiphenyl (4.1 mg) were added thereto, followed by heating to reflux under a nitrogen atmosphere for 3 hours. After cooling the reaction mixture to room temperature, a 10% aqueous solution of citric acid and ethyl acetate were added thereto, and the insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 90-65% hexane/ethyl acetate] to obtain 0.35 g of benzyl 2-(benzyloxy)-3-(pyridin-3-yl)benzoate.

A 2 mol/L aqueous solution of sodium hydroxide (1.3 mL) was added to a solution mixture of the obtained benzyl 2-(benzyloxy)-3-(pyridin-3-yl)benzoate (0.35 g) in dioxane (3.5 mL) and methanol (3.5 mL), followed by stirring at room temperature for 1 hour. A 2 mol/L aqueous solution of sodium hydroxide (1.3 mL) was added to the reaction mixture, followed by stirring at room temperature for 1 hour. The solvent was evaporated under reduced pressure, and water was added to the residue. After adjusting the pH to 4.5 with 6 mol/L hydrochloric acid, ethyl acetate was added thereto. The organic layer was separated, washed with a saturated aqueous solution of sodium chloride, and dried over anhydrous magnesium sulfate, and the solvent was evaporated under reduced pressure. Diisopropyl ether was added to the obtained residue, and the solid substance was collected by filtration to obtain 0.18 g of 2-(benzyloxy)-3-(pyridin-3-yl)benzoic acid as a white solid.

$^1$H-NMR (CDCl$_3$) δ: 4.61 (2H, s), 7.02-7.08 (2H, m), 7.22-7.39 (3H, m), 7.39-7.47 (2H, m), 7.62 (1H, dd, J=7.6, 2.0 Hz), 7.95 (1H, ddd, J=7.8, 2.0, 2.0 Hz), 8.21 (1H, dd, J=7.9, 1.8 Hz), 8.72 (1H, dd, J=4.9, 1.4 Hz), 8.85-8.90 (1H, m).

Reference Example 27a

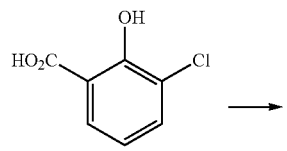

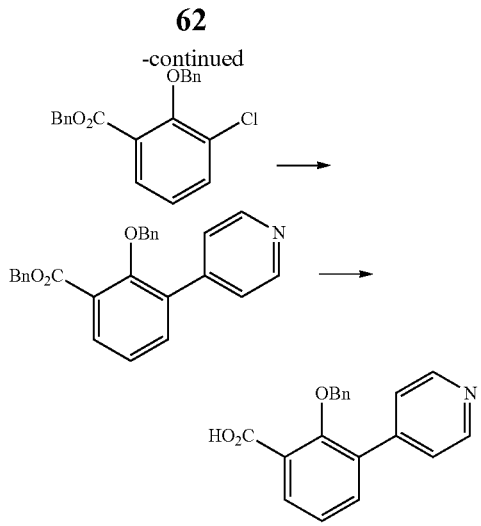

As in Reference Example 26a, the following compound was prepared.

2-(Benzyloxy)-3-(pyridin-4-yl)benzoic acid $^1$H-NMR (CDCl$_3$) δ: 4.62 (2H, s), 7.03-7.08 (2H, m), 7.23-7.38 (3H, m), 7.43 (1H, dd, J=7.8, 7.8 Hz), 7.54-7.58 (2H, m), 7.62 (1H, dd, J=7.7, 1.8 Hz), 8.23 (1H, dd, J=7.9, 1.8 Hz), 8.74-8.78 (2H, m).

Reference Example 28a

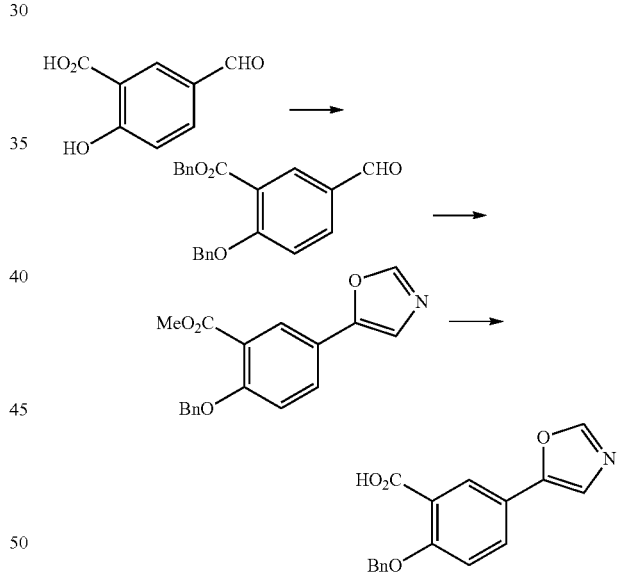

Potassium carbonate (1.2 g) and benzyl bromide (0.79 mL) were sequentially added to an N,N-dimethylformamide (5 mL) solution of 5-formyl-2-hydroxybenzoic acid (0.50 g), followed by stirring at room temperature for 10 minutes and then at 100° C. for 2 hours. The reaction mixture was cooled to room temperature, and then water and ethyl acetate were added thereto. The organic layer was separated, washed with a saturated aqueous solution of sodium chloride, and dried over anhydrous magnesium sulfate, and the solvent was evaporated under reduced pressure. Diisopropyl ether was added to the obtained residue, the solid substance was collected by filtration to obtain 0.93 g of benzyl 2-(benzyloxy)-5-formylbenzoate as a white solid.

p-Toluenesulfonylmethyl isocyanide (0.55 g) and potassium carbonate (0.39 g) were added to a methanol (9 mL)

suspension of the obtained benzyl 2-(benzyloxy)-5-formylbenzoate (0.93 g), followed by heating to reflux for 1 hour and 40 minutes. The reaction mixture was cooled to room temperature, and then p-toluenesulfonylmethyl isocyanide (0.079 g) and potassium carbonate (0.058 g) were added thereto, followed by heating to reflux for 1 hour and 30 minutes. The reaction mixture was cooled to room temperature, and then water and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 70-50% hexane/ethyl acetate] to obtain 0.56 g of methyl 2-(benzyloxy)-5-(oxazol-5-yl)benzoate as a light yellow solid.

A 2 mol/L aqueous solution of sodium hydroxide (4.5 mL) was added to a dioxane (5 mL) solution of the obtained methyl 2-(benzyloxy)-5-(oxazol-5-yl)benzoate (0.55 g), followed by stirring at room temperature for 2 hours and 40 minutes. The solvent was evaporated under reduced pressure, and water was added to the residue. After adjusting the pH to 4.0 with 6 mol/L hydrochloric acid, the solid substance was collected by filtration to obtain 0.46 g of 2-(benzyloxy)-5-(oxazol-5-yl)benzoic acid as a light yellow solid.

$^1$H-NMR (DMSO-$d_6$) δ: 5.27 (2H, s), 7.28-7.45 (4H, m), 7.47-7.55 (2H, m), 7.65 (1H, s), 7.84 (1H, dd, J=8.7, 2.1 Hz), 7.99 (1H, d, J=2.1 Hz), 8.41 (1H, s), 12.95 (1H, s).

Reference Example 29a

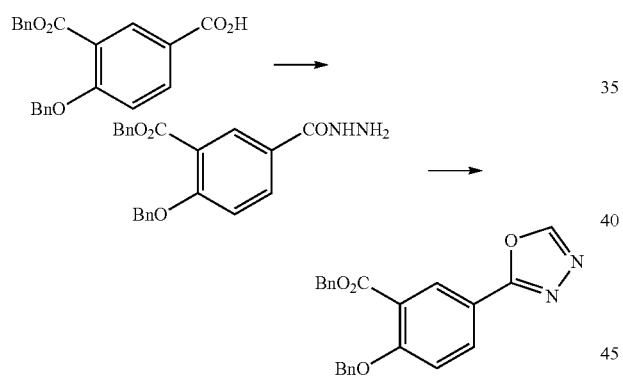

N,N-Dimethylformamide (0.011 mL) and oxalyl chloride (0.18 mL) were added to a methylene chloride (5 mL) suspension of 4-(benzyloxy)-3-(benzyloxycarbonyl)benzoic acid (0.50 g), followed by stirring at room temperature for 1 hour. The solvent was evaporated under reduced pressure, and toluene was added to the residue. The solvent was evaporated under reduced pressure, and dioxane (5 mL) was added to the residue. The resulting mixture was added to a water (6.7 mL) solution of hydrazine monohydrate (0.67 mL), followed by stirring at room temperature for 30 minutes. The solid substance was collected from the reaction mixture by filtration, and the obtained solid was washed with ethanol to obtain 0.38 g of benzyl 2-(benzyloxy)-5-(hydrazinocarbonyl)benzoate as a light yellow solid.

A trimethyl orthoformate (2 mL) suspension of the obtained benzyl 2-(benzyloxy)-5-(hydrazinocarbonyl)benzoate (0.20 g) was heated to reflux for 1 hour and 30 minutes. The reaction mixture was cooled to room temperature, and then the solvent was evaporated under reduced pressure. Ethyl acetate and diisopropyl ether were added to the obtained residue, and 0.16 g of the solid substance was collected by filtration. The obtained solid substance (0.11 g) was stirred at 200° C. for 15 minutes. The reaction mixture was cooled to room temperature and then purified by silica gel column chromatography [Kanto Chemical Co., Inc., silica gel 60 (spherical), eluent: 90-50% hexane/ethyl acetate] to obtain 0.079 g of benzyl 2-(benzyloxy)-5-(1,3,4-oxadiazol-2-yl)benzoate as a white solid.

$^1$H-NMR (CDCl$_3$) δ: 5.26 (2H, s), 5.38 (2H, s), 7.16 (1H, d, J=8.8 Hz), 7.30-7.47 (10H, m), 8.18 (1H, dd, J=8.8, 2.3 Hz), 8.43 (1H, s), 8.53 (1H, d, J=2.3 Hz).

Reference Example 30a

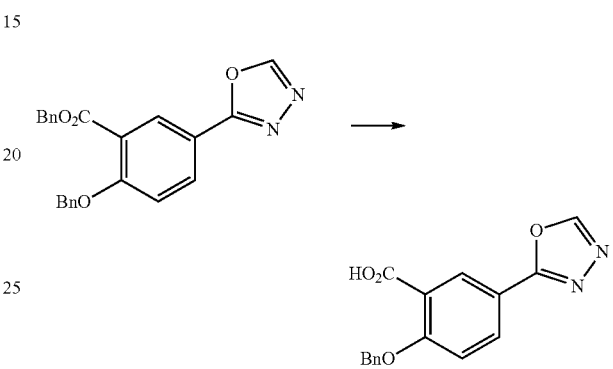

As in Reference Example 8a, the following compound was prepared.

2-(Benzyloxy)-5-(1,3,4-oxadiazol-2-yl)benzoic acid
$^1$H-NMR (DMSO-$d_6$) δ: 5.33 (2H, s), 7.30-7.37 (1H, m), 7.38-7.47 (3H, m), 7.49-7.55 (2H, m), 8.13 (1H, dd, J=8.8, 2.3 Hz), 8.28 (1H, d, J=2.3 Hz), 9.31 (1H, s).

Reference Example 31a

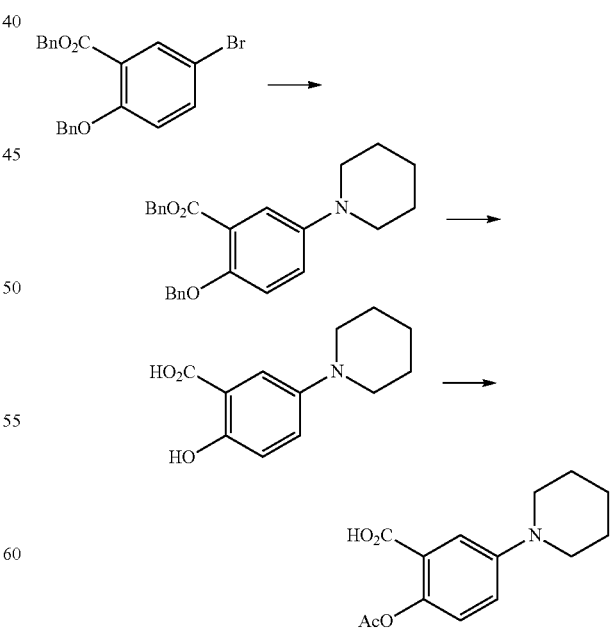

Piperidine (1.1 mL), cesium carbonate (4.9 g), tris(dibenzylideneacetone)dipalladium(0) (0.069 g), 2-dicyclohexylphosphino-2',4',6'-triisopropylbiphenyl (0.18 g), and palladium(II) acetate (0.034 g) were added to a toluene (30 mL) solution of benzyl 2-(benzyloxy)-5-bromobenzoate (3.0 g), followed by heating to reflux under a nitrogen atmosphere for 4 hours. The reaction mixture was cooled to room temperature, and then piperidine (0.37 mL), cesium carbonate (1.2 g), tris(dibenzylideneacetone)dipalladium(0) (0.069 g), 2-dicyclohexylphosphino-2',4',6'-triisopropylbiphenyl (0.18 g), and palladium(II) acetate (0.034 g) were added thereto, followed by heating to reflux under a nitrogen atmosphere for 5 hours and 30 minutes. After cooling the reaction mixture to room temperature, water and ethyl acetate were added thereto, and the insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 100-80% hexane/ethyl acetate] to obtain 2.4 g of benzyl 2-(benzyloxy)-5-(piperidin-1-yl)benzoate as a light yellow solid.

To a solution mixture of the obtained benzyl 2-(benzyloxy)-5-(piperidin-1-yl)benzoate (2.2 g) in dioxane (11 mL), ethyl acetate (17 mL), and methanol (5.5 mL), 10% palladium-carbon (1.1 g) was added, followed by stirring under a hydrogen atmosphere at room temperature for 2 hours. Tetrahydrofuran was added to the reaction mixture, and the insoluble substance was removed by filtration. The solvent was evaporated under reduced pressure. Diisopropyl ether was added to the obtained residue, and the solid substance was collected by filtration to obtain 1.1 g of 2-hydroxy-5-(piperidin-1-yl)benzoic acid as a light yellow solid.

Methylene chloride (9.0 mL), pyridine (0.82 mL), and acetic anhydride (0.46 mL) were sequentially added to the obtained 2-hydroxy-5-(piperidin-1-yl)benzoic acid (0.90 g), followed by stirring at room temperature for 2 hours. The solvent was evaporated under reduced pressure, and a 10% aqueous solution of citric acid and ethyl acetate were added thereto. The organic layer was separated, and the aqueous layer was extracted with ethyl acetate. The organic layer and the extract were combined, and the resulting mixture was washed with water and a saturated aqueous solution of sodium chloride sequentially, and dried over anhydrous magnesium sulfate. The solvent was evaporated under reduced pressure, and diisopropyl ether was added to the obtained residue. The solid substance was collected by filtration to obtain 0.55 g of 2-acetoxy-5-(piperidin-1-yl)benzoic acid as a light yellow solid.

$^1$H-NMR (CDCl$_3$) δ: 1.55-1.63 (2H, m), 1.67-1.77 (4H, m), 2.31 (3H, s), 3.15-3.22 m), 6.99 (1H, d, J=8.8 Hz), 7.11-7.20 (1H, m), 7.60 (1H, d, J=2.9 Hz).

Reference Example 32a

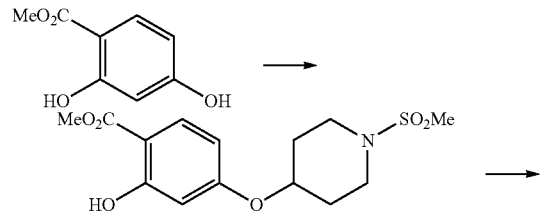

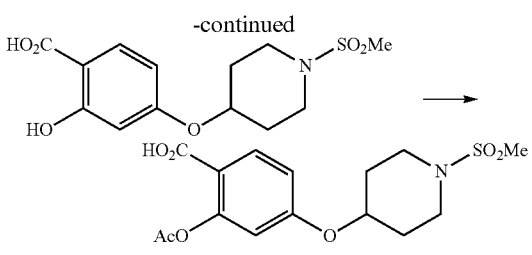

Potassium carbonate (0.31 g) and 1-(methylsulfonyl)piperidin-4-yl methanesulfonate (0.46 g) were added to an N,N-dimethylacetamide (5 mL) solution of methyl 2,4-dihydroxybenzoate (0.25 g), followed by stirring at 90° C. for 1 hour. The reaction mixture was cooled to room temperature, and then sodium iodide (0.045 g) was added thereto, followed by stirring at 90° C. for 1 hour. The reaction mixture was cooled to room temperature, and then potassium carbonate (0.10 g) and 1-(methylsulfonyl)piperidin-4-yl methanesulfonate (0.12 g) were added thereto, followed by stirring at 90° C. for 1 hour. The reaction mixture was cooled to room temperature, and then a 10% aqueous solution of citric acid and ethyl acetate were added thereto. The organic layer was separated, washed with a 10% aqueous solution of citric acid and saturated aqueous solution of sodium chloride sequentially, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 90-60% hexane/ethyl acetate] to obtain 0.19 g of methyl 2-hydroxy-4-((1-(methylsulfonyl)piperidin-4-yl)oxy)benzoate as a white solid.

A 2 mol/L aqueous solution of sodium hydroxide (0.87 mL) was added to a solution mixture of the obtained methyl 2-hydroxy-4-((1-(methylsulfonyl)piperidin-4-yl)oxy)benzoate (0.19 g) in dioxane (0.95 mL) and methanol (0.95 mL), followed by stirring at room temperature for 3 hours. A 2 mol/L aqueous solution of sodium hydroxide (0.58 mL) was added to the reaction mixture, followed by heating to reflux for 1 hour and 30 minutes. The reaction mixture was cooled to room temperature, and then water was added thereto. After adjusting the pH to 3 with 6 mol/L hydrochloric acid, ethyl acetate was added thereto. The organic layer was separated, washed with a saturated aqueous solution of sodium chloride, and dried over anhydrous magnesium sulfate. The solvent was evaporated under reduced pressure to obtain 0.18 g of 2-hydroxy-4-((1-(methylsulfonyl)piperidin-4-yl)oxy)benzoic acid as a white solid.

Under ice-cooling, pyridine (0.12 mL) and acetic anhydride (0.065 mL) were sequentially added to a methylene chloride (1.8 mL) suspension of the obtained 2-hydroxy-4-((1-(methylsulfonyl)piperidin-4-yl)oxy)benzoic acid (0.18 g), followed by stirring at room temperature for 1 hour. Under ice-cooling, pyridine (0.023 mL) and acetic anhydride (0.016 mL) were sequentially added to the reaction mixture, followed by stirring at room temperature for 2 hours. The solvent was evaporated under reduced pressure, and 1 mol/L hydrochloric acid and ethyl acetate were added to the residue. The organic layer was separated, washed with 1 mol/L hydrochloric acid, water, and a saturated aqueous solution of sodium chloride sequentially, and dried over anhydrous magnesium sulfate, and the solvent was evaporated under reduced pressure. Diisopropyl ether was added to the obtained residue, and the solid substance was collected by filtration to obtain 0.18 g of 2-acetoxy-4-((1-(methylsulfonyl)piperidin-4-yl)oxy)benzoic acid as a white solid.

$^1$H-NMR (CDCl$_3$) δ: 1.97-2.13 (4H, m), 2.34 (3H, s), 2.82 (3H, s), 3.27-3.47 (4H, m), 4.59-4.67 (1H, m), 6.63 (1H, d, J=2.5 Hz), 6.84 (1H, dd, J=8.8, 2.5 Hz), 8.07 (1H, d, J=8.8 Hz).

Reference Example 33a

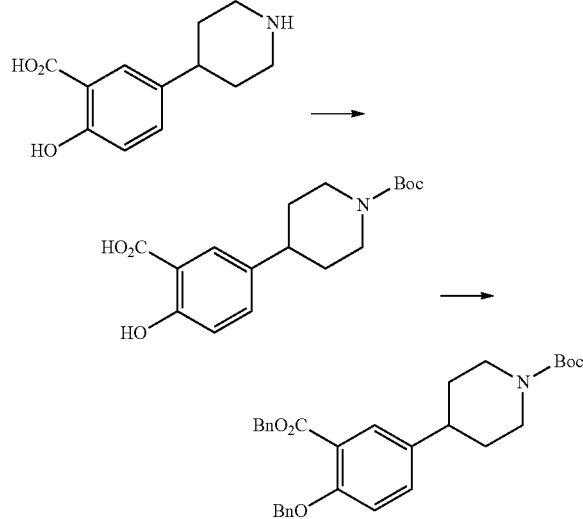

A 2.0 mol/L aqueous solution of sodium hydroxide (25 mL) and (di-tert-butyl)dicarbonate (2.1 g) were added to 2-hydroxy-5-(piperidin-4-yl)benzoic acid (1.6 g), followed by stirring at room temperature for 19 hours. The reaction mixture was adjusted to a pH of 3.0 with a 10% aqueous solution of citric acid, and then the solid substance was collected by filtration. Potassium carbonate (2.6 g) and benzyl bromide (1.6 mL) were sequentially added to an N,N-dimethylacetamide (20 mL) solution of the obtained solid substance, followed by stirring at 55° C. for 1 hour and 45 minutes. The reaction mixture was cooled to room temperature, and then water and chloroform were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [AB., KP-Sil, eluent: 97-80% chloroform/methanol] and then purified by silica gel column chromatography [Biotage AB, KP-Sil, eluent: 95-80% hexane/ethyl acetate] to obtain 0.42 g of tert-butyl 4-(4-(benzyloxy)-3-(benzyloxycarbonyl)phenylpiperidine-1-carboxylate as a colorless oily substance.

$^1$H-NMR (CDCl$_3$) δ: 1.48 (9H, s), 1.50-1.65 (2H, m), 1.72-1.83 (2H, m), 2.54-2.66 (1H, m), 2.68-2.86 (2H, m), 4.14-4.32 (2H, m), 5.14 (2H, s), 5.35 (2H, s), 6.96 (1H, d, J=8.6 Hz), 7.21-7.45 (11H, m), 7.67 (1H, d, J=2.4 Hz).

Reference Example 34a

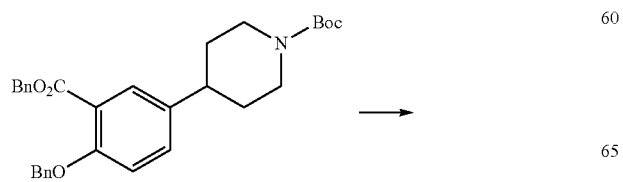

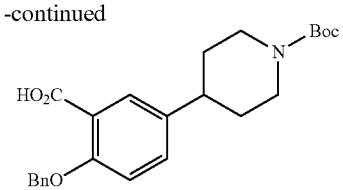

As in Reference Example 8a, the following compound was prepared.

2-(Benzyloxy)-5-(1-(tert-butoxycarbonyl)piperidin-4-yl)benzoic acid $^1$H-NMR (DMSO-d$_6$) δ: 1.34-1.50 (2H, m), 1.41 (9H, s), 1.67-1.79 (2H, m), 2.60-2.90 (3H, m), 3.97-4.13 (2H, m), 5.17 (2H, s), 7.11 (1H, d, J=8.6 Hz), 7.27-7.42 (4H, m), 7.44-7.52 (3H, m), 12.62 (1H, s).

Reference Example 35a

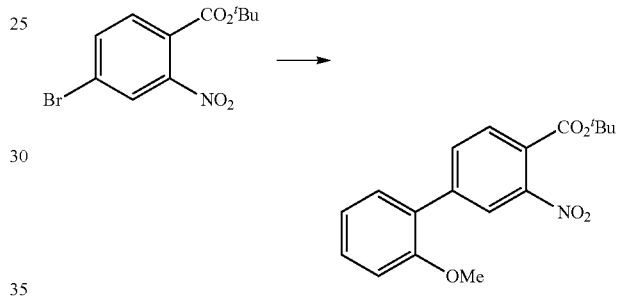

Water (9.0 mL), sodium carbonate (2.6 g), 2-methoxyphenylboronic acid (1.8 g), and bis(triphenylphosphine)palladium(II) dichloride (0.14 g) were added to an ethylene glycol dimethyl ether (30 mL) solution of tert-butyl 4-bromo-2-nitrobenzoate (3.0 g), followed by heating to reflux under a nitrogen atmosphere for 2 hours and 30 minutes. The reaction mixture was cooled to room temperature, and then a 10% aqueous solution of citric acid and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 99-91% hexane/ethyl acetate] to obtain 3.3 g of tert-butyl 4-(2-methoxyphenyl)-2-nitrobenzoate as a light yellow oily substance.

$^1$H-NMR (CDCl$_3$) δ: 1.58 (9H, s), 3.83 (3H, s), 6.99-7.04 (1H, m), 7.04-7.10 (1H, m), 7.32 (1H, dd, J=7.6, 1.7 Hz), 7.40 (1H, ddd, J=8.3, 7.6, 1.7 Hz), 7.73-7.77 (1H, m), 7.78 (1H, dd, J=7.9, 1.6 Hz), 8.01 (1H, d, J=1.0 Hz).

Reference Example 36a

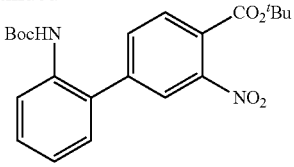

Water (0.6 mL), sodium carbonate (0.16 g), tert-butyl 2-(4,4,5,5-tetramethyl-1,3,2-dioxaborolan-2-yl)phenylcarbamate (0.19 g), and tetrakis(triphenylphosphine)palladium(0) (29 mg) were added to an ethylene glycol dimethyl ether (2.0 mL) solution of tert-butyl 4-bromo-2-nitrobenzoate (0.15 g), followed by heating to reflux under a nitrogen atmosphere for 2 hours and 30 minutes. The reaction mixture was cooled to room temperature, and then ethyl acetate and a 10% aqueous solution of citric acid were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 91-80% hexane/ethyl acetate] to obtain 0.21 g of tert-butyl 4-(2-(tert-butoxycarbonylamino)phenyl)-2-nitrobenzoate as a yellow solid.

$^1$H-NMR (CDCl$_3$) δ: 1.46 (9H, s), 1.60 (9H, s), 6.14-6.22 (1H, broad), 7.16-7.23 (2H, m), 7.38-7.45 (1H, m), 7.67 (1H, dd, J=8.1, 1.7 Hz), 7.84 (1H, d, J=8.1 Hz), 7.85 (1H, d, J=1.7 Hz), 7.96 (1H, d, J=8.5 Hz).

Reference Example 37a

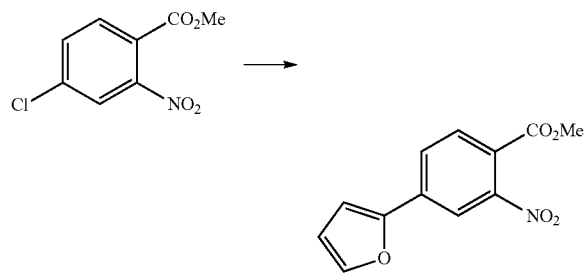

As in Reference Example 36a, the following compound was prepared.

Methyl 4-(furan-2-yl)-2-nitrobenzoate $^1$H-NMR (CDCl$_3$) δ: 3.92 (3H, s), 6.55 (1H, dd, J=3.4, 1.7 Hz), 6.87 (1H, d, J=3.4 Hz), 7.57 (1H, d, J=1.7 Hz), 7.80 (1H, d, J=8.1 Hz), 7.88 (1H, dd, J=8.1, 1.7 Hz), 8.08 (1H, d, J=1.7 Hz).

Reference Example 38a

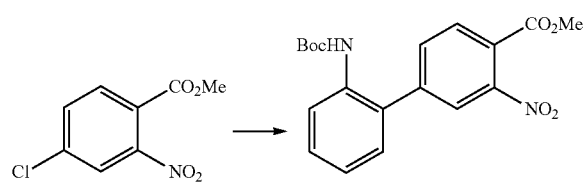 [SMILES: COC(=O)c1ccc(Cl)cc1[N+](=O)[O-] ; COC(=O)c1ccc(-c2ccccc2NC(=O)OC(C)(C)C)cc1[N+](=O)[O-]]

Water (3.0 mL), sodium carbonate (1.1 g), tert-butyl 2-(4,4,5,5-tetramethyl-1,3,2-dioxaborolan-2-yl)phenylcarbamate (1.5 g), and bis(di-tert-butyl(4-dimethylaminophenyl)phosphine)palladium(II) dichloride (30 mg) were added to an ethylene glycol dimethyl ether (10 mL) solution of methyl 4-chloro-2-nitrobenzoate (0.90 g), followed by heating to reflux under a nitrogen atmosphere for 1 hour and 30 minutes. The reaction mixture was cooled to room temperature, and then ethyl acetate and a 10% aqueous solution of citric acid were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 95-85% hexane/ethyl acetate] to obtain 1.5 g of methyl 4-(2-(tert-butoxycarbonylamino)phenyl)-2-nitrobenzoate as a light yellow solid.

$^1$H-NMR (CDCl$_3$) δ: 1.45 (9H, s), 3.97 (3H, s), 6.13-6.21 (1H, broad), 7.17-7.25 (2H, m), 7.40-7.46 (1H, m), 7.71 (1H, dd, J=8.1, 1.7 Hz), 7.86 (1H, d, J=8.1 Hz), 7.91-7.97 (2H, m).

Reference Example 39a

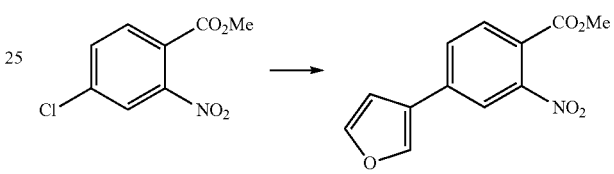

As in Reference Example 38a, the following compound was prepared.

Methyl 4-(furan-3-yl)-2-nitrobenzoate $^1$H-NMR (DMSO-d$_6$) δ: 3.85 (3H, s), 7.15-7.22 (1H, m), 7.84 (1H, dd, J=1.7, 1.7 Hz), 7.92 (1H, d, J=8.1 Hz), 8.07 (1H, dd, J=8.1, 1.7 Hz), 8.30 (1H, d, J=1.7 Hz), 8.49-8.55 (1H, m).

Reference Example 40a

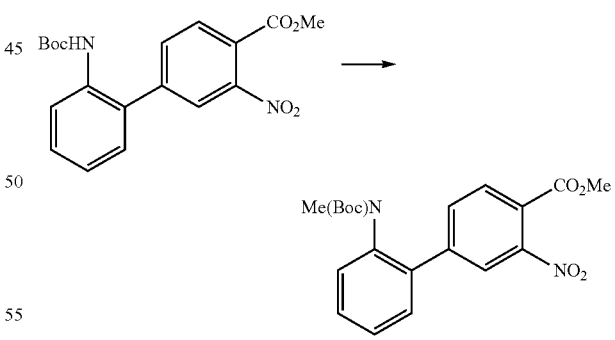

Under ice-cooling, 60% sodium hydride (0.21 g) was added to an N,N-dimethylformamide (15 mL) solution of methyl 4-(2-(tert-butoxycarbonylamino)phenyl)-2-nitrobenzoate (1.3 g), followed by stirring at room temperature for 10 minutes. Then, methyl iodide (0.32 mL) was added thereto under ice-cooling, followed by stirring at room temperature for 1 hour. Water, a 10% aqueous solution of citric acid, and diethyl ether were added to the reaction mixture. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 95-85% hexane/ethyl acetate] to obtain 1.1 g of methyl 4-(2-((tert-butoxycarbonyl)(methyl)amino)phenyl)-2-nitrobenzoate as a light yellow solid.

$^1$H-NMR (CDCl$_3$) δ: 1.17-1.43 (9H, m), 2.94-3.08 (3H, m), 3.94 (3H, s), 7.24-7.31 (1H, m), 7.33-7.41 (2H, m), 7.42-7.49 (1H, m), 7.60-7.72 (1H, m), 7.80 (1H, d, J=7.8 Hz), 7.89 (1H, d, J=1.5 Hz).

Reference Example 41a

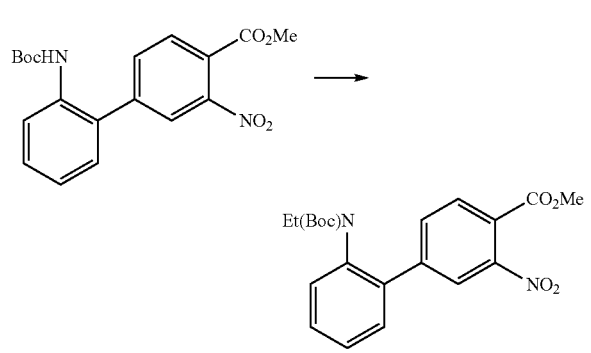

As in Reference Example 40a, the following compound was prepared.

Methyl 4-(2-((tert-butoxycarbonyl)(ethyl)amino)phenyl)-2-nitrobenzoate $^1$H-NMR (CD$_3$OD) δ: 1.06 (3H, t, J=7.1 Hz), 1.22-1.45 (9H, m), 2.85-3.05 (1H, m), 3.50-3.70 (1H, m), 3.91 (3H, s), 7.26-7.39 (1H, m), 7.42-7.54 (3H, m), 7.72-7.80 (1H, m), 7.88 (1H, d, J=7.8 Hz), 7.90-7.98 (1H, m).

Reference Example 42a

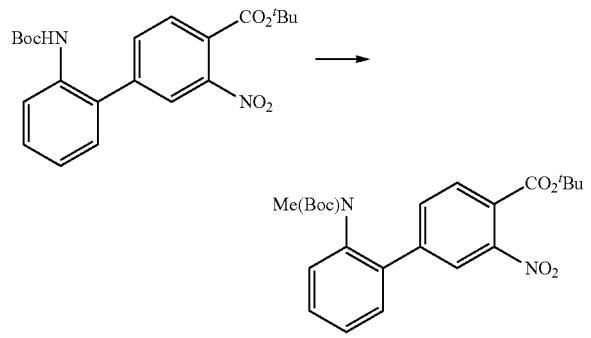

Potassium carbonate (0.16 g) and dimethyl sulfate (0.094 mL) were added to an acetone (4.0 mL) solution of tert-butyl 4-(2-(tert-butoxycarbonylamino)phenyl)-2-nitrobenzoate (0.27 g), followed by heating to reflux for 2 hours. The reaction mixture was cooled to room temperature, and then water and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 95-85% hexane/ethyl acetate] and then purified by silica gel column chromatography [eluent: 91-85% hexane/ethyl acetate] to obtain 0.061 g of tert-butyl 4-(2-((tert-butoxycarbonyl)(methyl)amino)phenyl)-2-nitrobenzoate as a colorless oily substance.

$^1$H-NMR (DMSO-d$_6$) δ: 0.99-1.28 (9H, m), 1.51 (9H, m), 3.00-3.11 (3H, m), 7.39-7.54 (4H, m), 7.74 (1H, d, J=8.3 Hz), 7.83-7.94 (2H, m).

Reference Example 43a

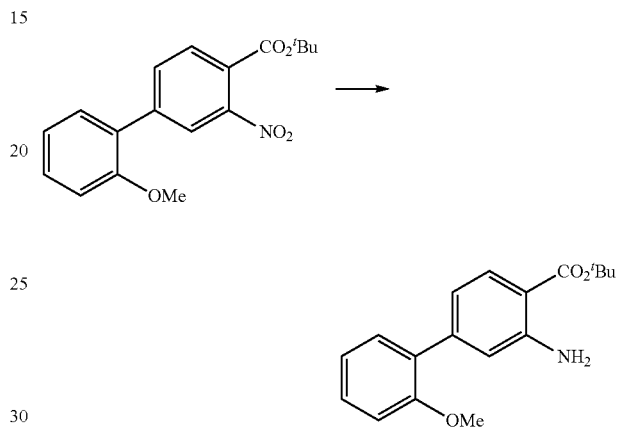

Sodium formate (2.7 g) and 10% palladium-carbon (0.65 g) were sequentially added to a solution mixture of tert-butyl 4-(2-methoxyphenyl)-2-nitrobenzoate (3.3 g) in 2-propanol (40 mL), water (10 mL), and acetic acid (2.6 mL), followed by heating to reflux for 2 hours. The reaction mixture was cooled to room temperature, and then the insoluble substance was removed by filtration. The solvent was evaporated under reduced pressure, and a saturated aqueous solution of sodium bicarbonate and ethyl acetate were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 99-91% hexane/ethyl acetate] to obtain 3.0 g of tert-butyl 2-amino-4-(2-methoxyphenyl)benzoate as a white oily substance.

$^1$H-NMR (CDCl$_3$) δ: 1.59 (9H, s), 3.80 (3H, s), 5.65-5.78 (2H, broad), 6.77-6.83 (2H, m), 6.97 (1H, d, J=8.0 Hz), 7.01 (1H, dd, J=7.4, 7.4 Hz), 7.27-7.36 (2H, m), 7.81-7.87 (1H, m).

Reference Example 44a

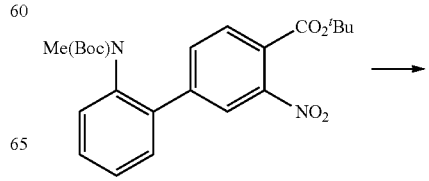

-continued

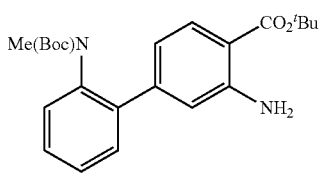

To a solution mixture of tert-butyl 4-(2-((tert-butoxycarbonyl)(methyl)amino)phenyl)-2-nitrobenzoate (0.057 g) in ethyl acetate (2.5 mL) and methanol (2.5 mL), 10% palladium-carbon (0.011 g) was added. The mixture was stirred under a hydrogen atmosphere at room temperature for 3 hours. The insoluble substance was removed by filtration, and the solvent was evaporated under reduced pressure. The obtained residue was purified by silica gel column chromatography [eluent: 95-85% hexane/ethyl acetate] to obtain 0.048 g of tert-butyl 2-amino-4-(2-((tert-butoxycarbonyl)(methyl)amino)phenyl)benzoate as a white solid.

$^1$H-NMR (DMSO-$d_6$) δ: 1.02-1.38 (9H, m), 1.54 (9H, s), 2.83-3.05 (3H, m), 6.44 (1H, dd, J=8.2, 1.3 Hz), 6.56-6.74 (3H, m), 7.26-7.43 (4H, m), 7.61-7.70 (1H, m).

Reference Examples 45a and 46a

As in Reference Example 44a, the compounds shown in Table 8a were prepared.

TABLE 8a

| Reference Example No. | R$^3$ |
|---|---|
| 45a | Et with methyl) |
| 46a | Me with methyl) |

Methyl 2-amino-4-(2-((tert-butoxycarbonyl)(ethyl)amino)phenyl)benzoate $^1$H-NMR (CD$_3$OD) δ: 0.96-1.11 (3H, m), 1.24-1.50 (9H, m), 2.77-2.95 (1H, m), 3.45-3.75 (1H, m), 3.86 (3H, s), 6.56 (1H, dd, J=8.3, 1.7 Hz), 6.73 (1H, d, J=1.7 Hz), 7.17-7.27 (1H, m), 7.33-7.42 (3H, m), 7.75-7.83 (1H, m).

Methyl 2-amino-4-(2-((tert-butoxycarbonyl)(methyl)amino)phenyl)benzoate $^1$H-NMR (CDCl$_3$) δ: 1.21-1.49 (9H, m), 2.80-3.04 (3H, m), 3.89 (3H, s), 6.60-6.72 (2H, m), 7.17-7.23 (1H, m), 7.24-7.40 (3H, m), 7.83-7.91 (1H, m).

Reference Example 47a

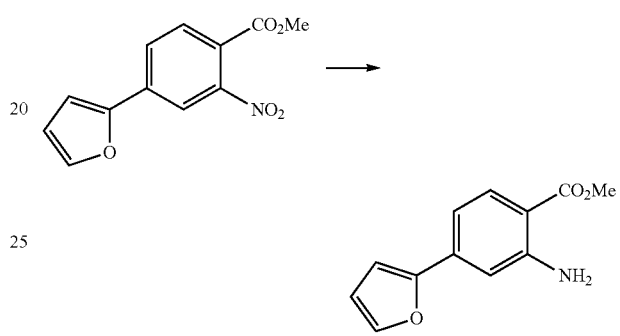

Water (0.56 mL), ammonium chloride (18 mg), and iron powder (94 mg) were added to an ethanol (2.1 mL) suspension of methyl 4-(furan-2-yl)-2-nitrobenzoate (0.14 g), followed by heating to reflux for 2 hours and 30 minutes. The reaction mixture was cooled to room temperature, and then ammonium chloride (18 mg), iron powder (31 mg), and water (0.28 mL) were added thereto, followed by heating to reflux for 1 hour. The reaction mixture was cooled to room temperature, and then the solvent was evaporated under reduced pressure. A saturated aqueous solution of sodium bicarbonate and ethyl acetate were added to the obtained residue, and the insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 99-95% hexane/ethyl acetate] to obtain 78 mg of methyl 2-amino-4-(furan-2-yl)benzoate as a light yellow solid.

$^1$H-NMR (CDCl$_3$) δ: 3.88 (3H, s), 5.72-5.86 (2H, broad), 6.49 (1H, dd, J=3.3, 1.8 Hz), 6.72 (1H, d, J=3.3 Hz), 6.94 (1H, dd, J=8.5, 1.7 Hz), 6.99 (1H, d, J=1.7 Hz), 7.47-7.51 (1H, m), 7.86 (1H, d, J=8.5 Hz).

Reference Example 48a

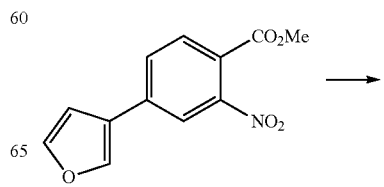

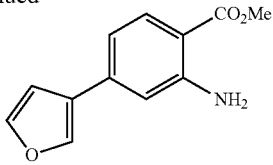

As in Reference Example 47a, the following compound was prepared.

Methyl 2-amino-4-(furan-3-yl)benzoate $^1$H-NMR (DMSO-d$_6$) δ: 3.78 (3H, s), 6.61-6.70 (2H, broad), 6.80 (1H, dd, J=8.6, 1.7 Hz), 6.84 (1H, dd, J=1.8.0.7 Hz), 6.97 (1H, d, J=1.7 Hz), 7.70 (1H, d, J=8.6 Hz), 7.76 (1H, dd, J=1.8, 1.7 Hz), 8.15-8.19 m).

Reference Example 49a

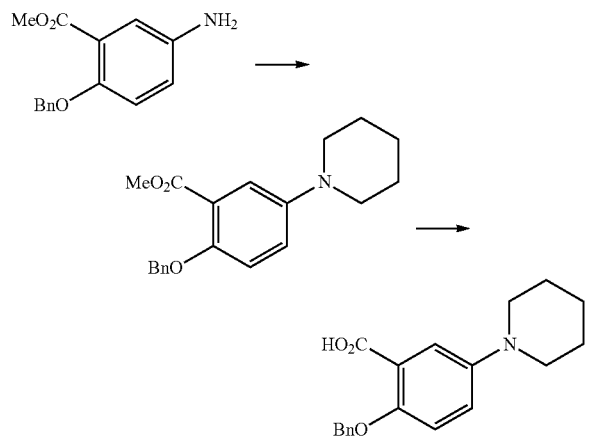

Potassium carbonate (5.1 g) and 1,5-dibromopentane (2.5 mL) were sequentially added to an N,N-dimethylformamide (23 mL) solution of methyl 5-amino-2-(benzyloxy)benzoate (4.6 g), followed by stirring at 50 to 55° C. for 1 hour, at 55 to 60° C. for 1 hour, at 70° C. for 1 hour and 30 minutes, and then at 75 to 80° C. for 1 hour and 30 minutes. The reaction mixture was cooled to room temperature, and then water and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 95-65% hexane/ethyl acetate] to obtain 4.3 g of methyl 2-(benzyloxy)-5-(piperidin-1-yl)benzoate as a light yellow oily substance.

A 4 mol/L aqueous solution of sodium hydroxide (9.8 mL) was added to a dioxane (45 mL) solution of the obtained methyl 2-(benzyloxy)-5-(piperidin-1-yl)benzoate (4.3 g), followed by stirring at room temperature for 1 hour and then at 50 to 55° C. for 2 hours. After cooling the reaction mixture to room temperature, the reaction mixture was adjusted to a pH of 6.3 with acetic acid, and the solvent was evaporated under reduced pressure. Water was added to the obtained residue, and the solid substance was collected by filtration to obtain 3.7 g of 2-(benzyloxy)-5-(piperidin-1-yl)benzoic acid as a white solid.

$^1$H-NMR (CDCl$_3$) δ: 1.52-1.62 (2H, m), 1.65-1.76 (4H, m), 3.08-3.16 (4H, m), 5.23 (2H, s), 7.03 (1H, d, J=9.0 Hz), 7.08-7.16 (1H, m), 7.36-7.45 (5H, m), 7.75 (1H, d, J=3.2 Hz).

Reference Example 50a

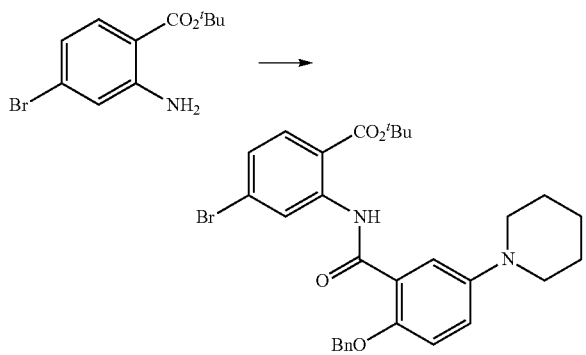

Under ice-cooling, oxalyl chloride (0.96 mL) was added to a solution mixture of 2-(benzyloxy)-5-(piperidin-1-yl)benzoic acid (2.5 g) in methylene chloride (25 mL) and N,N-dimethylformamide (0.050 mL), followed by stirring at room temperature for 30 minutes. The solvent was evaporated under reduced pressure, and methylene chloride (25 mL) was added to the residue. Then, under ice-cooling, the resulting mixture was added to a solution mixture of tert-butyl 2-amino-4-bromobenzoate (2.0 g) in pyridine (0.89 mL) and methylene chloride (20 mL), followed by stirring at room temperature for 1 hour and 30 minutes. The solvent was evaporated under reduced pressure, and a saturated aqueous solution of sodium bicarbonate and ethyl acetate were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 80-70% hexane/ethyl acetate] to obtain 3.8 g of tert-butyl 2-(2-(benzyloxy)-5-(piperidin-1-yl)benzamido)-4-bromobenzoate as a yellow solid.

$^1$H-NMR (DMSO-d$_6$) δ: 1.44-1.54 (2H, m), 1.46 (9H, s), 1.57-1.66 (4H, m), 2.99-3.08 (4H, m), 5.39 (2H, s), 7.04-7.14 (2H, m), 7.21-7.34 (3H, m), 7.38-7.50 (4H, m), 7.86-7.92 (1H, m), 9.00-9.05 (1H, m), 12.17 (1H, s).

Reference Example 51a

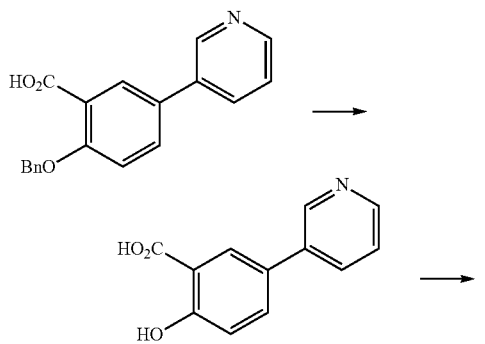

-continued

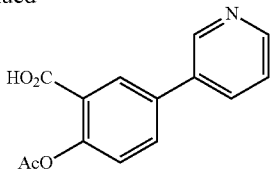

Trifluoroacetic acid (6.0 mL) was added to 2-(benzyloxy)-5-(pyridin-3-yl)benzoic acid (0.31 g), followed by stirring at room temperature for 3 hours. The solvent was evaporated under reduced pressure, and ethyl acetate was added to the obtained residue. The solid substance was collected by filtration to obtain 2-hydroxy-5-(pyridin-3-yl)benzoic acid as a white solid.

Methylene chloride (5.0 mL), pyridine (0.25 mL), and acetic anhydride (0.19 mL) were sequentially added to the obtained 2-hydroxy-5-(pyridin-3-yl)benzoic acid, followed by heating to reflux for 1 hour. The reaction mixture was cooled to room temperature, and then pyridine (0.082 mL) and acetic anhydride (0.095 mL) were added thereto, followed by heating to reflux for 30 minutes. The reaction mixture was cooled to room temperature, and then the solvent was evaporated under reduced pressure. The obtained residue was purified by silica gel column chromatography [Kanto Chemical Co., Inc., silica gel 60 (spherical), eluent: 99-93% chloroform/methanol] to obtain 0.035 g of 2-acetoxy-5-(pyridin-3-yl)benzoic acid as a white solid.

$^1$H-NMR (DMSO-$d_6$) δ: 2.28 (3H, s), 7.35 (1H, d, J=8.4 Hz), 7.52 (1H, dd, J=8.0, 4.8 Hz), 8.00 (1H, dd, J=8.4, 2.4 Hz), 8.13 (1H, ddd, J=8.0, 2.2, 1.8 Hz), 8.19 (1H, d, J=2.4 Hz), 8.62 (1H, dd, J=4.8, 1.8 Hz), 8.92 (1H, d, J=2.2 Hz), 13.10-13.60 (1H, broad).

Reference Example 52a

Pyridine (1.0 mL) and acetyl chloride (0.67 mL) were sequentially added to a methylene chloride (17 mL) solution of 5-bromo-4-fluoro-2-methylaniline (1.74 g), followed by stirring at room temperature for 1 hour. Water, 1 mol/L hydrochloric acid, and chloroform were added to the reaction mixture. The organic layer was separated, washed with a saturated aqueous solution of sodium chloride, and dried over anhydrous magnesium sulfate, and the solvent was evaporated under reduced pressure. Hexane was added to the obtained residue, and the solid substance was collected by filtration to obtain 1.83 g of N-(5-bromo-4-fluoro-2-methylphenyl)acetamide as a white solid.

$^1$H-NMR (DMSO-$d_6$) δ: 2.06 (3H, s), 2.18 (3H, s), 7.27 (1H, d, J=9.5 Hz), 7.74 (1H, d, J=6.8 Hz), 9.38 (1H, s).

Reference Example 53a

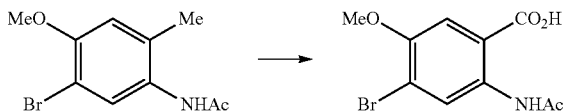 [SMILES: COc1cc(C)c(NC(C)=O)cc1Br ; COc1cc(C(=O)O)c(NC(C)=O)cc1Br]

Under heating to reflux, potassium permanganate (0.98 g) was added to a solution mixture of N-(5-bromo-4-methoxy-2-methylphenyl)acetamide (1.0 g) in water (10 mL), tert-butyl alcohol (10 mL), and magnesium sulfate (0.79 g), followed by heating to reflux under a nitrogen atmosphere for 6 hours and 20 minutes. After cooling the reaction mixture to room temperature, the insoluble substance was removed by filtration. The solvent was evaporated under reduced pressure, and water and ethyl acetate were added to the residue. The aqueous layer was separated, and 1 mol/L hydrochloric acid (4 mL) and chloroform were added thereto. The organic layer was separated, and the aqueous layer was extracted with chloroform. The organic layer and the extract were combined, and the resulting mixture was washed with a saturated aqueous solution of sodium chloride and dried over anhydrous magnesium sulfate. The solvent was evaporated under reduced pressure, and diisopropyl ether was added to the obtained residue. The solid substance was collected by filtration to obtain 0.36 g of 2-(acetamido)-4-bromo-5-methoxybenzoic acid as a white solid.

$^1$H-NMR (DMSO-$d_6$) δ: 2.11 (3H, s), 3.86 (3H, s), 7.53 (1H, s), 8.68 (1H, s), 10.78 (1H, s).

Reference Example 54a

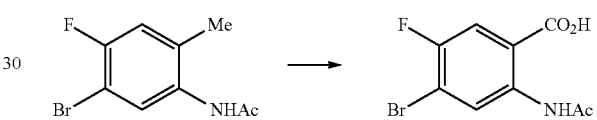

As in Reference Example 53a, the following compound was prepared.

2-(Acetamido)-4-bromo-5-fluorobenzoic acid $^1$H-NMR (DMSO-$d_6$) δ: 2.14 (3H, s), 7.81 (1H, d, J=9.3 Hz), 8.77 (1H, d, J=6.8 Hz), 10.92 (1H, s), 13.70-14.44 (1H, broad).

Reference Example 55a

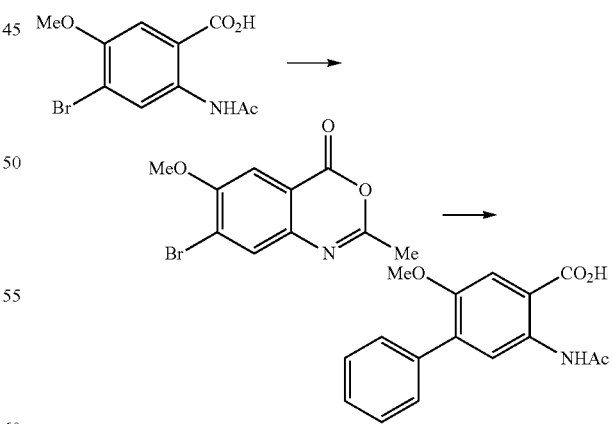

4-(Dimethylamino)pyridine (63 mg) and 2-(acetamido)-4-bromo-5-methoxybenzoic acid (0.49 g) were added to a tetrahydrofuran (1.5 mL) solution of di-tert-butyl dicarbonate (0.75 g) at room temperature, followed by stirring at the same temperature for 4 hours and 15 minutes. Tetrahydrofuran (2 mL) was added to the reaction mixture at room temperature, followed by stirring at the same temperature for 3 days. (Di-tert-butyl)dicarbonate (0.37 g) was added to the reaction mixture at room temperature, followed by stirring at the same temperature for one day. The solvent was evaporated under reduced pressure, and ethyl acetate and a saturated aqueous solution of sodium bicarbonate were added to the residue. The organic layer was separated, washed with a 10% aqueous solution of citric acid and a saturated aqueous solution of sodium chloride sequentially, and dried over anhydrous magnesium sulfate, and the solvent was evaporated under reduced pressure. Hexane and diisopropyl ether were added to the obtained residue, and the solid substance was collected by filtration to obtain 0.40 g of 7-bromo-6-methoxy-2-methyl-4H-3,1-benzoxazin-4-one as a brown solid.

Water (1.2 mL), phenylboranic acid (0.22 g), sodium carbonate (0.38 g), and bis(triphenylphosphine)palladium(II) dichloride (21 mg) were added to an ethylene glycol dimethyl ether (4 mL) suspension of the obtained 7-bromo-6-methoxy-2-methyl-4H-3,1-benzoxazin-4-one (0.40 g), followed by heating to reflux under a nitrogen atmosphere for 4 hours and 30 minutes. The reaction mixture was cooled to room temperature, and then water and ethyl acetate were added thereto. The aqueous layer was separated, and the organic layer was extracted with a 2 mol/L aqueous solution of sodium hydroxide. The aqueous layer and the extract were combined. The resulting mixture was adjusted to a pH of 1 with 6 mol/L hydrochloric acid, and ethyl acetate was added thereto. The organic layer was separated, washed with a saturated aqueous solution of sodium chloride, and dried over anhydrous magnesium sulfate, and the solvent was evaporated under reduced pressure. Diisopropyl ether was added to the obtained residue, and the solid substance was collected by filtration to obtain 0.27 g of 2-(acetamido)-5-methoxy-4-phenylbenzoic acid as a yellow solid.

$^1$H-NMR (DMSO-$d_6$) δ: 2.11 (3H, s), 3.78 (3H, s), 7.35-7.52 (5H, m), 7.57 (1H, s), 8.39 (1H, s), 10.79 (1H, s).

Reference Example 56a

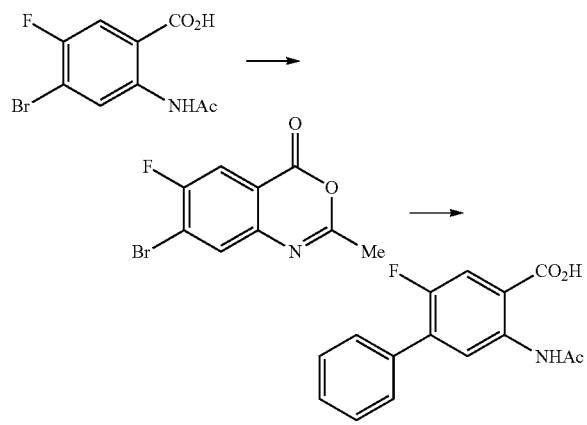

As in Reference Example 55a, the following compound was prepared.

2-(Acetamido)-5-fluoro-4-phenylbenzoic acid $^1$H-NMR (DMSO-$d_6$) δ: 2.15 (3H, s), 7.45-7.59 (5H, m), 7.79 (1H, d, J=11.2 Hz), 8.60 (1H, d, J=7.3 Hz), 10.93 (1H, s), 13.60-14.28 (1H, broad).

Reference Example 57a

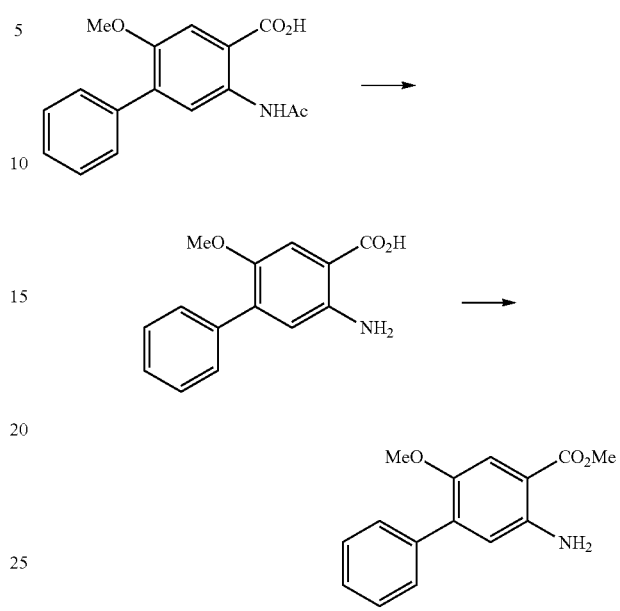

A solution mixture of 2-(acetamido)-5-methoxy-4-phenyl-benzoic acid (0.41 g) in dioxane (1.2 mL) and concentrated hydrochloric acid (1.2 mL) was heated to reflux for 3 hours and 40 minutes. After cooling the reaction mixture to room temperature, the solvent was evaporated under reduced pressure, and water was added to the residue. After adjusting the pH to 7 with a 1 mol/L aqueous solution of sodium hydroxide, chloroform was added thereto. The organic layer was separated and dried over anhydrous magnesium sulfate, and the solvent was evaporated under reduced pressure to obtain 2-amino-5-methoxy-4-phenylbenzoic acid as a brown solid.

Under ice-cooling, concentrated sulfuric acid (1 mL) was added to a methanol (10 mL) suspension of the obtained 2-amino-5-methoxy-4-phenylbenzoic acid, followed by heating to reflux for 6 hours. The reaction mixture was cooled to room temperature and adjusted to a pH of 8.0 with a saturated aqueous solution of sodium bicarbonate, and then chloroform was added thereto. The organic layer was separated and dried over anhydrous magnesium sulfate, and the solvent was evaporated under reduced pressure. Hexane was added to the obtained residue, and the solid substance was collected by filtration to obtain 0.24 g of methyl 2-amino-5-methoxy-4-phenylbenzoate as a brown solid.

$^1$H-NMR (DMSO-$d_6$) δ: 3.65 (3H, s), 3.82 (3H, s), 6.35 (2H, s), 6.78 (1H, s), 7.30 (1H, s), 7.32-7.49 (5H, m).

Reference Example 58a

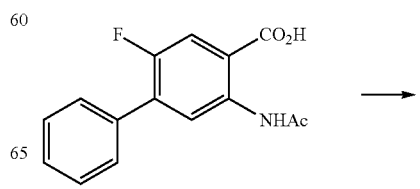

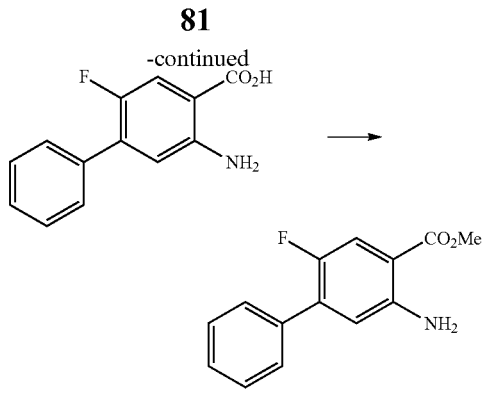

As in Reference Example 57a, the following compound was prepared.

Methyl 2-amino-5-fluoro-4-phenylbenzoate $^1$H-NMR (CDCl$_3$) δ: 3.90 (3H, s), 5.42-5.81 (2H, broad), 6.71 (1H, d, J=6.3 Hz), 7.36-7.47 (3H, m), 7.51-7.56 (2H, m), 7.63 (1H, d, J=11.5 Hz).

Reference Example 59a

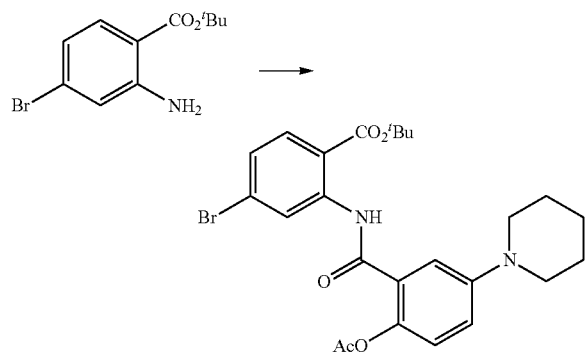

As in Reference Example 50a, the following compound was prepared.

Tert-butyl 2-(2-acetoxy-5-(piperidin-1-yl)benzamido)-4-bromobenzoate $^1$H-NMR (DMSO-d$_6$) δ: 1.52-1.67 (6H, m), 1.54 (9H, s), 2.19 (3H, s), 3.18-3.26 (4H, m), 7.09 (1H, d, J=9.0 Hz), 7.17 (1H, dd, J=8.5, 2.9 Hz), 7.32 (1H, d, J=2.9 Hz), 7.41-7.48 (1H, m), 7.89 (1H, d, J=8.5 Hz), 8.78 (1H, d, J=1.7 Hz), 11.47 (1H, s).

Reference Example 60a

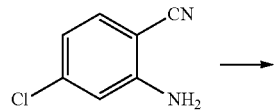

N,N-Dimethylformamide (0.010 mL) and oxalyl chloride (0.21 mL) were sequentially added to a methylene chloride (3.0 mL) suspension of 2-(benzyloxy)-5-(piperidin-1-yl)benzoic acid (0.56 g), followed by stirring at room temperature for 1 hour and 20 minutes. Under ice-cooling, the reaction mixture was added to a solution mixture of 2-amino-4-chlorobenzonitrile (0.23 g) in methylene chloride (3.0 mL) and pyridine (0.30 mL), followed by stirring at room temperature for 2 hours and 30 minutes. The solvent was evaporated under reduced pressure, and a 10% aqueous solution of citric acid and chloroform were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 95-85% hexane/ethyl acetate] to obtain 2-(benzyloxy)-N-(5-chloro-2-cyanophenyl)-5-(piperidin-1-yl)benzamide as a yellow solid.

Water (0.74 mL), phenylboranic acid (0.12 g), sodium carbonate (0.21 g), and bis(di-tert-butyl(4-dimethylaminophenyl)phosphine)palladium(II) dichloride (3.0 mg) were added to an ethylene glycol dimethyl ether (3.0 mL) suspension of the obtained 2-(benzyloxy)-N-(5-chloro-2-cyanophenyl)-5-(piperidin-1-yl)benzamide, followed by heating to reflux under a nitrogen atmosphere for 1 hour. After cooling the reaction mixture to room temperature, phenylboranic acid (0.12 g), sodium carbonate (0.21 g), and bis(di-tert-butyl(4-dimethylaminophenyl)phosphine)palladium(II) dichloride (3.0 mg) were added thereto, followed by heating to reflux under a nitrogen atmosphere for 40 minutes. The reaction mixture was cooled to room temperature, and then chloroform and a 10% aqueous solution of citric acid were added thereto. The organic layer was separated and dried over anhydrous magnesium sulfate, and the solvent was evaporated under reduced pressure. The obtained residue was purified by silica gel column chromatography [eluent: 90-50% hexane/ethyl acetate] to obtain 0.32 g of 2-(benzyloxy)-N-(4-cyanobiphenyl-3-yl)-5-(piperidin-1-yl)benzamide as a yellow solid.

$^1$H-NMR (CDCl$_3$) δ: 1.50-1.59 (2H, m), 1.65-1.73 (4H, m), 3.07-3.12 (4H, m), 5.54 (2H, s), 6.92 (1H, d, J=9.0 Hz), 7.01 (1H, dd, J=9.0, 3.2 Hz), 7.26-7.50 (9H, m), 7.64-7.71 (3H, m), 7.87 (1H, d, J=3.2 Hz), 9.05 (1H, d, J=1.4 Hz), 11.08 (1H, s).

Reference Example 61a

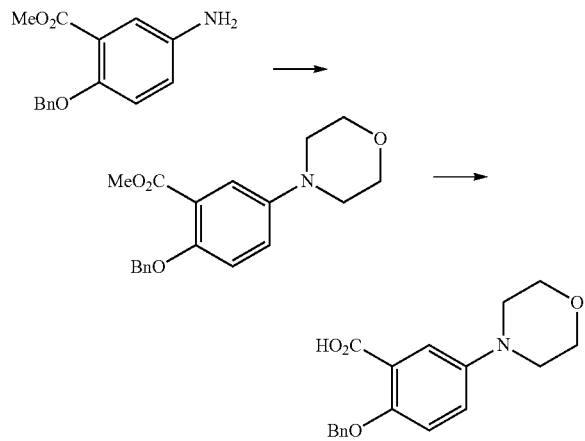

Potassium carbonate (0.54 g), potassium iodide (0.11 g), and bis(2-chloroethyl)ether (0.22 mL) were sequentially added to an N,N-dimethylacetamide (3.2 mL) solution of methyl 5-amino-2-(benzyloxy)benzoate (0.40 g), followed by stirring at 100° C. for 3 hours. The reaction mixture was cooled to room temperature, and then water and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 85-60% hexane/ethyl acetate] to obtain 0.27 g of methyl 2-(benzyloxy)-5-(morpholin-4-yl)benzoate as a light yellow oily substance.

A 4 mol/L aqueous solution of sodium hydroxide (0.3 mL) was added to an ethanol (2.1 mL) solution of the obtained methyl 2-(benzyloxy)-5-(morpholin-4-yl)benzoate (0.26 g), followed by stirring at 50° C. for 1 hour. The reaction mixture was cooled to room temperature, and then a 10% aqueous solution of citric acid and ethyl acetate were sequentially added thereto. The organic layer was separated, washed with a saturated aqueous solution of sodium chloride, and dried over anhydrous magnesium sulfate, and the solvent was evaporated under reduced pressure. Diisopropyl ether was added to the obtained residue, and the solid substance was collected by filtration to obtain 0.17 g of 2-(benzyloxy)-5-(morpholin-4-yl)benzoic acid as a white solid.

$^1$H-NMR (CDCl$_3$) δ: 3.10-3.16 (4H, m), 3.82-3.89 (4H, m), 5.25 (2H, s), 7.04-7.13 (2H, m), 7.39-7.45 (5H, m), 7.73 (1H, d, J=2.9 Hz), 10.80-11.20 (1H, broad).

Reference Example 62a

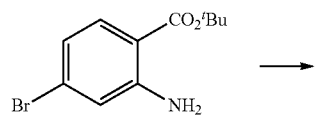

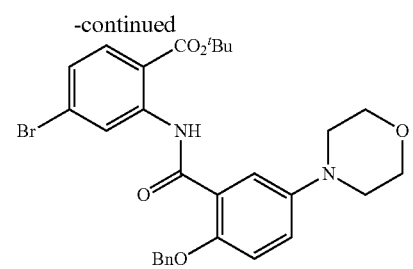

Oxalyl chloride (3.4 mL) was added to a solution mixture of 2-(benzyloxy)-5-(morpholin-4-yl)benzoic acid (11.4 g) in tetrahydrofuran (57 mL) and N,N-dimethylformamide (0.013 mL), followed by stirring at room temperature for 40 minutes and then heating to reflux for 1 hour. The reaction mixture was cooled to room temperature, and then tetrahydrofuran (23 mL) was added thereto, followed by heating to reflux for 30 minutes. After cooling the reaction mixture to room temperature, the solvent was evaporated under reduced pressure, and toluene was added to the residue. The solvent was evaporated under reduced pressure, and tetrahydrofuran (23 mL) was added to the residue. The resulting mixture was added to a solution mixture of tert-butyl 2-amino-4-bromobenzoate (9.0 g) in pyridine (6.7 mL) and tetrahydrofuran (45 mL) under ice-cooling, followed by stirring at room temperature for 30 minutes and then at 50° C. for 30 minutes. After cooling the reaction mixture to room temperature, the solvent was evaporated under reduced pressure, and a saturated aqueous solution of sodium bicarbonate and ethyl acetate were added to the residue. The insoluble substance was removed by filtration, and the organic layer was separated, washed with a 10% aqueous solution of citric acid and a saturated aqueous solution of sodium chloride sequentially, and dried over anhydrous magnesium sulfate. The solvent was evaporated under reduced pressure. The obtained residue was purified by silica gel column chromatography [Kanto Chemical Co., Inc., silica gel 60 (spherical), eluent: 90-60% hexane/ethyl acetate] to obtain 13.8 g of tert-butyl 2-(2-(benzyloxy)-5-(morpholin-4-yl)benzamido)-4-bromobenzoate as a light yellow solid.

$^1$H-NMR (DMSO-d$_6$) δ: 1.46 (9H, s), 3.00-3.07 (4H, m), 3.69-3.77 (4H, m), 5.41 (2H, s), 7.09-7.17 (2H, m), 7.22-7.34 (3H, m), 7.40-7.50 (4H, m), 7.89 (1H, d, J=8.6 Hz), 9.03 (1H, d, J=2.0 Hz), 12.19 (1H, s).

Reference Example 63a

Under ice-cooling, oxalyl chloride (0.29 mL) was added to a solution mixture of 2-(benzyloxy)-5-(1-(tert-butoxycarbonyl)piperidin-4-yl)benzoic acid (0.93 g) in methylene chloride (9.0 mL) and N,N-dimethylformamide (0.017 mL), followed by stirring at room temperature for 30 minutes. The solvent was evaporated under reduced pressure, and toluene was added to the residue. The solvent was evaporated under reduced pressure, and methylene chloride (4.5 mL) was added to the residue. The resulting mixture was added to a solution mixture of methyl 2-amino-4-bromobenzoate (0.45 g) in pyridine (0.40 mL) and methylene chloride (9.0 mL) under ice-cooling, followed by stirring at room temperature for 1 hour. Chloroform and a 10% aqueous solution of citric acid were added to the reaction mixture. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 100-70% hexane/ethyl acetate] to obtain 0.65 g of methyl 2-(2-(benzyloxy)-5-(1-(tert-butoxycarbonyl)piperidin-4-yl)benzamido)-4-bromobenzoate as a white solid.

$^1$H-NMR (DMSO-$d_6$) δ: 1.35-1.51 (2H, m), 1.41 (9H, s), 1.69-1.79 (2H, m), 2.65-2.90 (3H, m), 3.73 (3H, s), 4.00-4.12 (2H, m), 5.43 (2H, s), 7.18 (1H, d, J=8.8 Hz), 7.24-7.36 (3H, m), 7.38-7.48 (4H, m), 7.78 (1H, d, J=2.2 Hz), 7.90 (1H, d, J=8.6 Hz), 8.99 (1H, d, J=2.2 Hz), 12.00 (1H, s).

Reference Example 64a

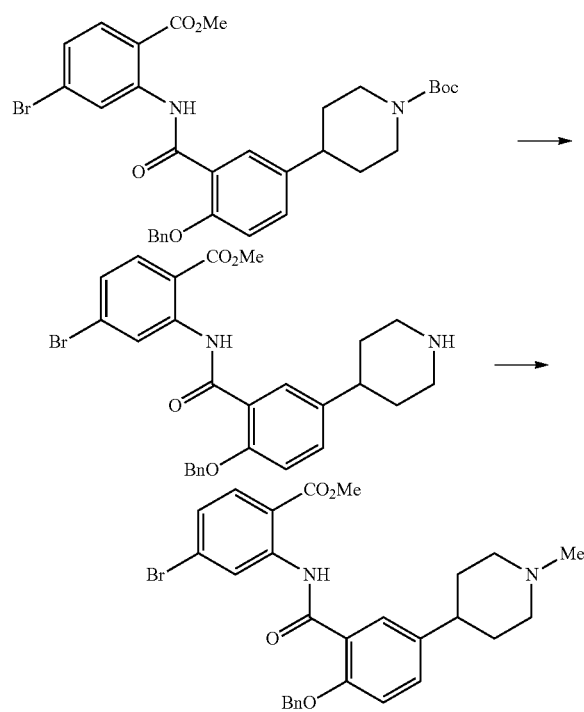

Under ice-cooling, trifluoroacetic acid (1.3 mL) was added to a methylene chloride (6.5 mL) solution of methyl 2-(2-(benzyloxy)-5-(1-(tert-butoxycarbonyl)piperidin-4-yl)benzamido)-4-bromobenzoate (0.65 g), followed by stirring at room temperature for 30 minutes. The reaction mixture was added to a saturated aqueous solution of sodium bicarbonate under ice-cooling. The organic layer was separated, washed with a saturated aqueous solution of sodium bicarbonate, and dried over anhydrous sodium sulfate. The solvent was evaporated under reduced pressure to obtain 0.54 g of methyl 2-(2-(benzyloxy)-5-(piperidin-4-yl)benzamido)-4-bromobenzoate as a white solid.

Acetic acid (0.12 mL), a 37% aqueous solution of formaldehyde (0.10 mL), and sodium triacetoxyborohydride (0.54 g) were sequentially added to a tetrahydrofuran (5.4 mL) solution of the obtained methyl 2-(2-(benzyloxy)-5-(piperidin-4-yl)benzamido)-4-bromobenzoate (0.54 g), followed by stirring at room temperature for 1 hour. The solvent was evaporated under reduced pressure, and a saturated aqueous solution of sodium bicarbonate and ethyl acetate were added to the residue. The organic layer was separated, washed with a saturated aqueous solution of sodium chloride, and dried over anhydrous sodium sulfate, and the solvent was evaporated under reduced pressure. The obtained residue was purified by silica gel column chromatography [eluent: 100-90% chloroform/methanol] to obtain 0.48 g of methyl 2-(2-(benzyloxy)-5-(1-methylpiperidin-4-yl)benzamido)-4-bromobenzoate as a light yellow solid.

$^1$H-NMR (CD$_3$OD) δ: 1.70-1.91 (4H, m), 2.14-2.24 (2H, m), 2.34 (3H, s), 2.52-2.62 (1H, m), 2.97-3.05 (2H, m), 3.75 (3H, s), 5.43 (2H, s), 7.12 (1H, d, J=8.8 Hz), 7.22-7.40 (5H, m), 7.41-7.46 (2H, m), 7.89 (1H, d, J=2.4 Hz), 7.93 (1H, d, J=8.6 Hz), 9.09 (1H, d, J=2.0 Hz).

Reference Example 1b

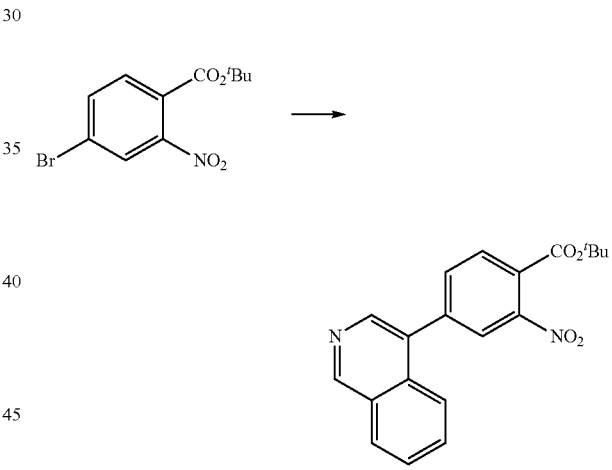

Water (15 mL), sodium carbonate (4.6 g), 4-(4,4,5,5-tetramethyl-1,3,2-dioxaborolan-2-yl)isoquinoline (5.1 g), and bis(triphenylphosphine)palladium(II) dichloride (0.24 g) were added to an ethylene glycol dimethyl ether (50 mL) solution of tert-butyl 4-bromo-2-nitrobenzoate (5.0 g), followed by heating to reflux under a nitrogen atmosphere for 2 hours. The reaction mixture was cooled to room temperature, and then ethyl acetate and water were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 85-75% hexane/ethyl acetate] to obtain 5.8 g of tert-butyl 4-(isoquinolin-4-yl)-2-nitrobenzoate as a brown oily substance.

$^1$H-NMR (DMSO-$d_6$) δ: 1.55 (9H, s), 7.76-7.83 (1H, m), 7.83-7.88 (2H, m), 7.99-8.02 (2H, m), 8.21 (1H, s), 8.28 (1H, d, J=8.0 Hz), 8.55 (1H, s), 9.44 (1H, s).

Reference Example 2b

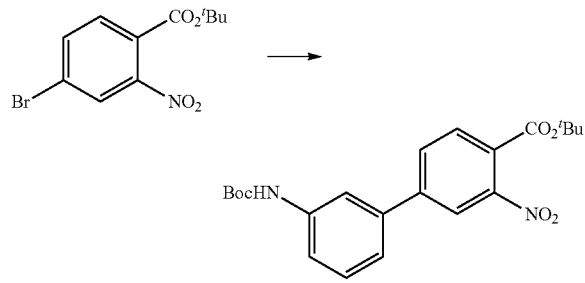

Water (0.6 mL), sodium carbonate (0.16 g), 3-(tert-butoxycarbonylamino)phenylboronic acid (0.14 g), and tetrakis(triphenylphosphine)palladium(0) (29 mg) were added to an ethylene glycol dimethyl ether (2.0 mL) solution of tert-butyl 4-bromo-2-nitrobenzoate (0.15 g), followed by heating to reflux under a nitrogen atmosphere for 2 hours. The reaction mixture was cooled to room temperature, and then ethyl acetate and a saturated aqueous solution of sodium bicarbonate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 95-91% hexane/ethyl acetate] to obtain 0.17 g of tert-butyl 4-(3-(tert-butoxycarbonylamino)phenyl)-2-nitrobenzoate as a light yellow solid.

$^1$H-NMR (CDCl$_3$) δ: 1.54 (9H, s), 1.58 (9H, s), 6.55-6.63 (1H, broad), 7.24-7.28 (1H, m), 7.33 (1H, d, J=8.6 Hz), 7.39 (1H, d, J=7.8 Hz), 7.74 (1H, s), 7.80 (1H, d, J=8.1 Hz), 7.84 (1H, dd, J=7.9, 1.6 Hz), 7.99 (1H, d, J=1.7 Hz).

Reference Example 3b

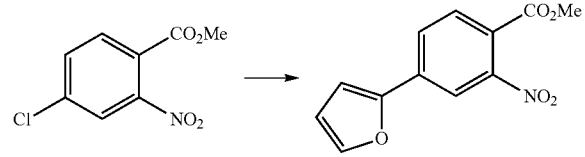 [SMILES: COC(=O)c1ccc(Cl)cc1[N+](=O)[O-] ; COC(=O)c1ccc(-c2ccco2)cc1[N+](=O)[O-]]

As in Reference Example 2b, the following compound was prepared.

Methyl 4-(furan-2-yl)-2-nitrobenzoate $^1$H-NMR (CDCl$_3$) δ: 3.92 (3H, s), 6.55 (1H, dd, J=3.4, 1.7 Hz), 6.87 (1H, d, J=3.4 Hz), 7.57 (1H, d, J=1.7 Hz), 7.80 (1H, d, J=8.1 Hz), 7.88 (1H, dd, J=8.1, 1.7 Hz), 8.08 (1H, d, J=1.7 Hz).

Reference Example 4b

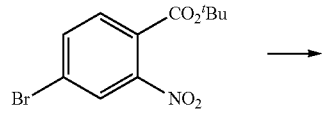

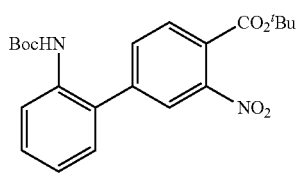

Water (0.6 mL), sodium carbonate (0.16 g), tert-butyl 2-(4,4,5,5-tetramethyl-1,3,2-dioxaborolan-2-yl)-phenylcarbamate (0.19 g), and tetrakis(triphenylphosphine)palladium(0) (29 mg) were added to an ethylene glycol dimethyl ether (2.0 mL) solution of tert-butyl 4-bromo-2-nitrobenzoate (0.15 g), followed by heating to reflux under a nitrogen atmosphere for 2 hours and 30 minutes. The reaction mixture was cooled to room temperature, and then ethyl acetate and a 10% aqueous solution of citric acid were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 91-80% hexane/ethyl acetate] to obtain 0.21 g of tert-butyl 4-(2-(tert-butoxycarbonylamino)phenyl)-2-nitrobenzoate as a yellow solid.

$^1$H-NMR (CDCl$_3$) δ: 1.46 (9H, s), 1.60 (9H, s), 6.14-6.22 (1H, broad), 7.16-7.23 (2H, m), 7.38-7.45 (1H, m), 7.67 (1H, dd, J=8.1, 1.7 Hz), 7.84 (1H, d, J=8.1 Hz), 7.85 (1H, d, J=1.7 Hz), 7.96 (1H, d, J=8.5 Hz).

Reference Example 5b

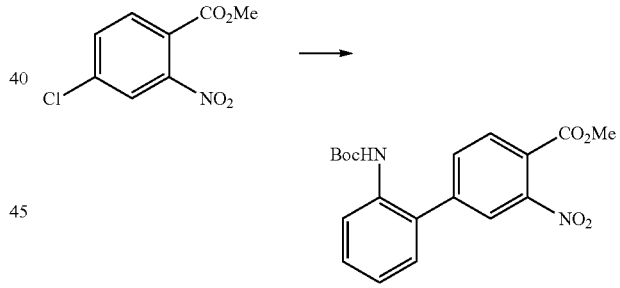

Water (3.0 mL), sodium carbonate (1.1 g), tert-butyl 2-(4,4,5,5-tetramethyl-1,3,2-dioxaborolan-2-yl)phenylcarbamate (1.5 g), and bis(di-tert-butyl(4-dimethylaminophenyl)phosphine)palladium(II) dichloride (30 mg) were added to an ethylene glycol dimethyl ether (10 mL) solution of methyl 4-chloro-2-nitrobenzoate (0.90 g), followed by heating to reflux under a nitrogen atmosphere for 1 hour and 30 minutes. The reaction mixture was cooled to room temperature, and then ethyl acetate and a 10% aqueous solution of citric acid were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 95-85% hexane/ethyl acetate] to obtain 1.5 g of methyl 4-(2-(tert-butoxycarbonylamino)phenyl)-2-nitrobenzoate as a light yellow solid.

¹H-NMR (CDCl₃): 1.45 (9H, s), 3.97 (3H, s), 6.13-6.22 (1H, broad), 7.17-7.25 (2H, m), 7.40-7.46 (1H, m), 7.71 (1H dd, J=8.0, 1.7 Hz), 7.86 (1H, d, J=8.1 Hz), 7.91-7.97 (2H, m).

Reference Example 6b

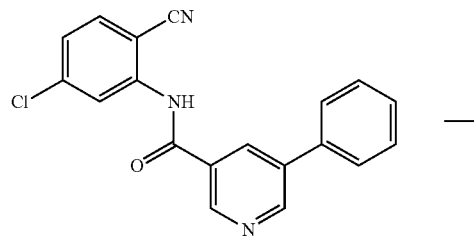

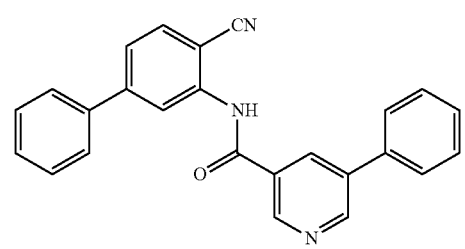

Phenylboranic acid (88 mg), tripotassium phosphate (0.28 g), 2-dicyclohexylphosphino-2',6'-dimethoxybiphenyl (2.5 mg), and palladium(II) acetate (2.7 mg) were added to a toluene (3.0 mL) suspension of N-(5-chloro-2-cyanophenyl)-5-phenylpyridine-3-carboxamide (0.20 g), followed by heating to reflux under a nitrogen atmosphere for 1 hour and 30 minutes. The reaction mixture was cooled to room temperature, and then 2-dicyclohexylphosphino-2',6'-dimethoxybiphenyl (2.5 mg) and palladium(II) acetate (2.7 mg) were added thereto, followed by heating to reflux under a nitrogen atmosphere for 6 hours. After cooling the reaction mixture to room temperature, ethyl acetate and a 10% aqueous solution of citric acid were added thereto, and the insoluble substance was removed by filtration. The organic layer was separated, washed with a saturated aqueous solution of sodium chloride, and dried over anhydrous magnesium sulfate, and the solvent was evaporated under reduced pressure. Diisopropyl ether was added to the obtained residue, and the solid substance was collected by filtration to obtain 0.23 g of N-(2-cyano-5-phenylphenyl)-5-phenylpyridine-3-carboxamide as a light yellow solid.

¹H-NMR (DMSO-d₆) δ: 7.45-7.62 (6H, m), 7.75-7.83 (3H, m), 7.84-7.90 (2H, m), 7.96 (1H, d, J=1.7 Hz), 8.01 (1H, d, J=8.0 Hz), 8.65 (1H, dd, J=2.2, 2.2 Hz), 9.13-9.18 (2H, m), 11.01 (1H, s).

Reference Example 7b

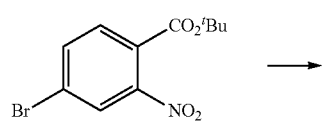

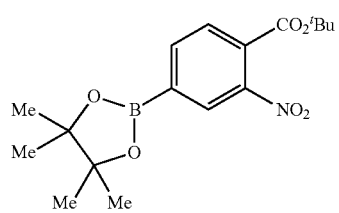

Potassium acetate (2.0 g), bis(pinacolato)diboron (3.4 g), and (1,1'-bis(diphenylphosphino)ferrocene)palladium(II) dichloride methylene chloride complex (0.27 g) were added to a dioxane (20 mL) solution of tert-butyl 4-bromo-2-nitrobenzoate (2.0 g), followed by stirring under a nitrogen atmosphere at 95 to 100° C. for 2 hours. After cooling the reaction mixture to room temperature, the insoluble substance was removed by filtration, and the solvent was evaporated under reduced pressure. The obtained residue was purified by silica gel column chromatography [eluent: 80% hexane/ethyl acetate] and then purified by silica gel column chromatography [eluent: 95-90% hexane/ethyl acetate] to obtain 2.0 g of tert-butyl 2-nitro-4-(4,4,5,5-tetramethyl-1,3,2-dioxaborolan-2-yl)benzoate as a white solid.

¹H-NMR (CDCl₃) δ: 1.26 (12H, s), 1.36 (9H, s), 7.69 (1H, d, J=7.6 Hz), 7.99-8.06 (1H, m), 8.23-8.27 (1H, m).

Reference Example 8b

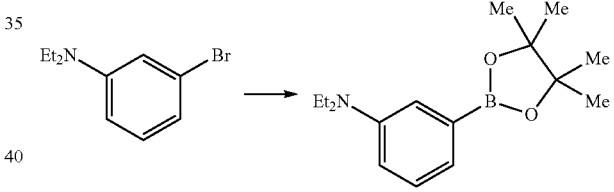

As in Reference Example 7b, the following compound was prepared.

N,N-Diethyl-3-(4,4,5,5-tetramethyl-1,3,2-dioxaborolan-2-yl)aniline

¹H-NMR (CDCl₃) δ: 1.15 (6H, t, J=7.1 Hz), 1.33 (12H, s), 3.37 (4H, q, J=7.1 Hz), 6.75-6.84 (1H, m), 7.07-7.17 (2H, m), 7.18-7.25 (1H, m).

Reference Example 9b

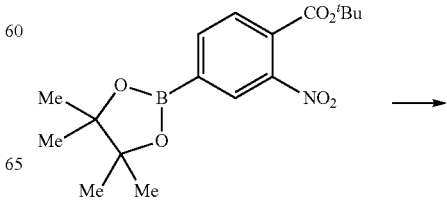

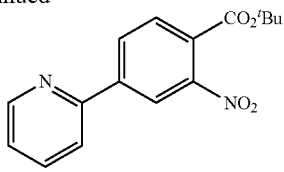

Water (3 mL), sodium carbonate (0.76 g), 2-bromopyridine (0.42 mL), and tetrakis(triphenylphosphine)palladium(0) (0.17 g) were added to an ethylene glycol dimethyl ether (10 mL) solution of tert-butyl 2-nitro-4-(4,4,5,5-tetramethyl-1,3,2-dioxaborolan-2-yl)benzoate (1.0 g), followed by heating to reflux under a nitrogen atmosphere for 2 hours and 30 minutes. The reaction mixture was cooled to room temperature, and then a 10% aqueous solution of citric acid and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 90-85% hexane/ethyl acetate] to obtain 0.32 g of tert-butyl 2-nitro-4-(pyridin-2-yl)benzoate as a light yellow oily substance.

$^1$H-NMR (CDCl$_3$) δ: 1.59 (9H, s), 7.32-7.38 (1H, m), 7.78-7.87 (3H, m), 8.28 (1H, dd, J=8.1, 1.7 Hz), 8.50 (1H, d, J=1.7 Hz), 8.72-8.77 (1H, m).

Reference Example 10b

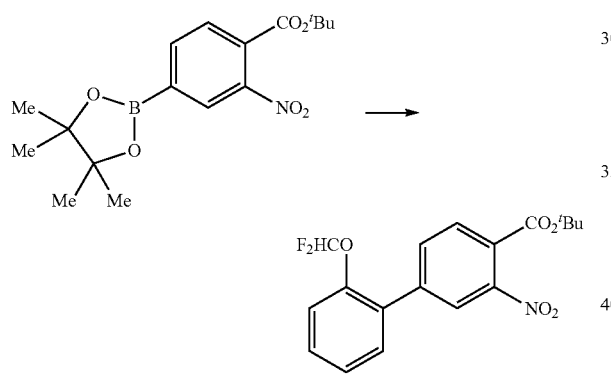

As in Reference Example 9b, the following compound was prepared.

Tert-butyl 4-(2-(difluoromethoxy)phenyl)-2-nitrobenzoate $^1$H-NMR (CDCl$_3$): 1.59 (9H, s), 6.44 (1H, t, J=73.5 Hz), 7.24-7.37 (2H, m), 7.39-7.49 (2H, m), 7.74-7.82 (2H, m), 7.93-7.97 (1H, m).

Reference Example 11b

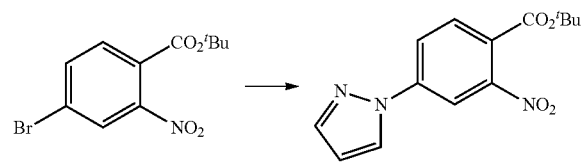 [SMILES: CC(C)(C)OC(=O)c1ccc(Br)cc1[N+](=O)[O-] ; CC(C)(C)OC(=O)c1ccc(-n2cccn2)cc1[N+](=O)[O-]]

1H-Pyrazole (0.14 g), potassium carbonate (0.46 g), D-proline (38 mg), and copper(I) iodide (32 mg) were added to a dimethyl sulfoxide (5 mL) solution of tert-butyl 4-bromo-2-nitrobenzoate (0.50 g), followed by stirring under a nitrogen atmosphere at 100° C. for 3 hours. After cooling the reaction mixture to room temperature, ethyl acetate and water were added thereto, and the insoluble substance was removed by filtration. The organic layer was separated, washed with water and a saturated aqueous solution of sodium chloride sequentially, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 100-80% hexane/ethyl acetate] to obtain 0.20 g of tert-butyl 2-nitro-4-(1H-pyrazol-1-yl)benzoate as a white solid.

$^1$H-NMR (CDCl$_3$) δ: 1.57 (9H, s), 6.56 (1H, dd, J=2.6, 1.8 Hz), 7.79 (1H, d, J=1.8 Hz), 7.88 (1H, d, J=8.5 Hz), 7.95 (1H, dd, J=8.5, 2.1 Hz), 8.01 (1H, d, J=2.6 Hz), 8.15 (1H, d, J=2.1 Hz).

Reference Example 12b

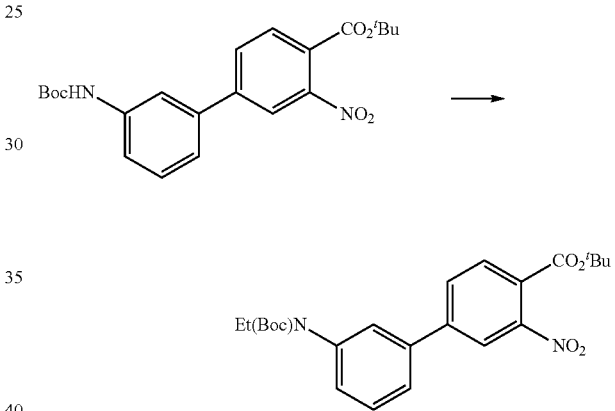

Under ice-cooling, 60% sodium hydride (43 mg) was added to a tetrahydrofuran (5.0 mL) solution of tert-butyl 4-(3-(tert-butoxycarbonylamino)phenyl)-2-nitrobenzoate (0.30 g), followed by stirring at the same temperature for 20 minutes. Ethyl iodide (0.087 mL) was added to the reaction mixture under ice-cooling, followed by stirring at the same temperature for 30 minutes and then at room temperature for 2 hours and 40 minutes. N,N-Dimethylformamide (3.0 mL) was added to the reaction mixture at room temperature, and then 60% sodium hydride (14 mg) and ethyl iodide (0.058 mL) were sequentially added thereto under ice-cooling, followed by stirring at room temperature for 1 hour. Water and diethyl ether were added to the reaction mixture, and the organic layer was separated, washed with a 10% aqueous solution of citric acid and a saturated aqueous solution of sodium chloride sequentially, and dried over anhydrous magnesium sulfate. The solvent was evaporated under reduced pressure, and the obtained residue was purified by silica gel column chromatography [eluent: 85-60% hexane/ethyl acetate] to obtain 0.16 g of tert-butyl 4-(3-((tert-butoxycarbonyl)(ethyl)amino)phenyl)-2-nitrobenzoate as a colorless oily substance.

$^1$H-NMR (CDCl$_3$) δ: 1.19 (3H, t, J=7.1 Hz), 1.46 (9H, s), 1.58 (9H, s), 3.73 (2H, q, J=7.1 Hz), 7.26-7.32 (1H, m), 7.38-7.50 (3H, m), 7.80-7.83 (2H, m), 7.98 (1H, s).

Reference Example 13b

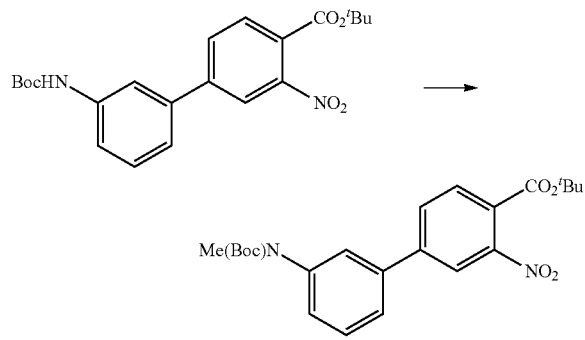

Under ice-cooling, 60% sodium hydride (24 mg) was added to an N,N-dimethylformamide (3.0 mL) solution of tert-butyl 4-(3-(tert-butoxycarbonylamino)phenyl)-2-nitrobenzoate (0.17 g), followed by stirring at the same temperature for 15 minutes and then at room temperature for 20 minutes. Methyl iodide (0.037 mL) was added to the reaction mixture under ice-cooling, followed by stirring at room temperature for 1 hour. Water and diethyl ether was added to the reaction mixture, and the organic layer was separated, and the aqueous layer was extracted with diethyl ether. The organic layer and the extract were combined, and the resulting mixture was washed with a 10% aqueous solution of citric acid and a saturated aqueous solution of sodium chloride sequentially and dried over anhydrous magnesium sulfate. The solvent was evaporated under reduced pressure, and the obtained residue was purified by silica gel column chromatography [eluent: 95-85% hexane/ethyl acetate] to obtain 0.17 g of tert-butyl 4-(3-((tert-butoxycarbonyl)(methyl)amino)phenyl)-2-nitrobenzoate as a brown oily substance.

$^1$H-NMR (CDCl$_3$): 1.48 (9H, s), 1.58 (9H, s), 3.32 (3H, s), 7.30-7.36 (1H, m), 7.36-7.41 (1H, m), 7.42-7.53 (2H, m), 7.80-7.84 (2H, m), 7.99 (1H, s).

Reference Example 14b

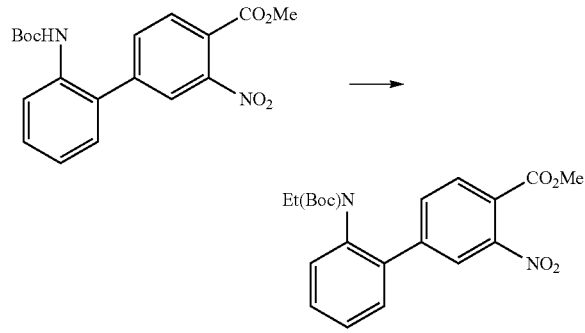

As in Reference Example 13b, the following compound was prepared.

Methyl 4-(2-((tert-butoxycarbonyl)(ethyl)amino)phenyl)-2-nitrobenzoate $^1$H-NMR (CD$_3$OD): 1.06 (3H, t, J=7.1 Hz), 1.22-1.45 (9H, m), 2.85-3.05 (1H, broad), 3.50-3.70 (1H, broad), 3.91 (3H, s), 7.26-7.39 (1H, m), 7.42-7.54 (3H, m), 7.72-7.80 (1H, m), 7.88 (1H, d, J=7.8 Hz), 7.90-7.98 (1H, broad).

Reference Example 15b

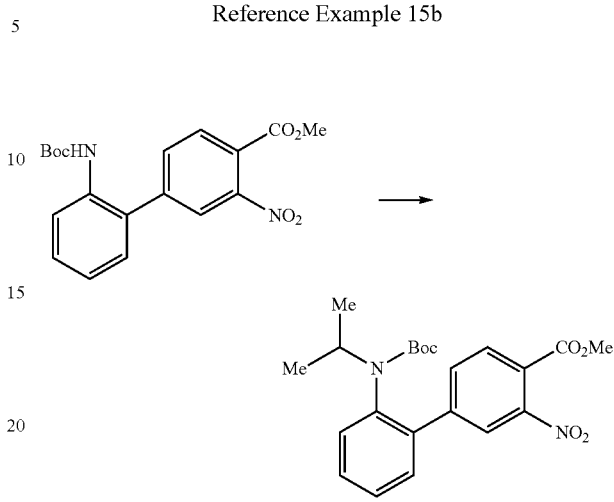

As in Reference Example 13b, the following compound was prepared.

Methyl 4-(2-((tert-butoxycarbonyl)(isopropyl)amino)phenyl)-2-nitrobenzoate $^1$H-NMR (CD$_3$OD): 0.73 (3H, d, J=6.8 Hz), 1.05 (3H, d, J=6.6 Hz), 1.26-1.50 (9H, broad), 3.91 (3H, s), 3.89-4.05 (1H, broad), 7.21-7.30 (1H, m), 7.46-7.54 (3H, m), 7.78 (1H, dd, J=7.9, 1.6 Hz), 7.88 (1H, d, J=7.9 Hz), 7.99 (1H, s).

Reference Example 16b

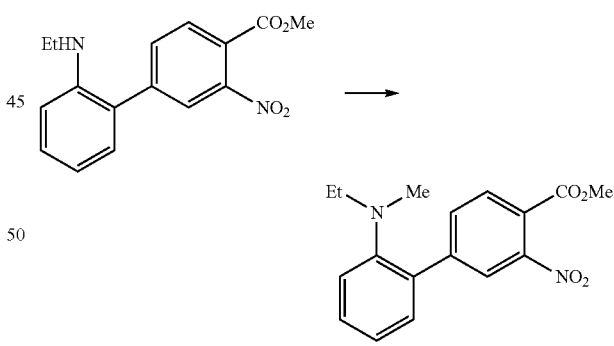

Under ice-cooling, 60% sodium hydride (54 mg) was added to an N,N-dimethylformamide (3.0 mL) solution of methyl 4-(2-(ethylamino)phenyl)-2-nitrobenzoate (0.27 g), followed by stirring at the same temperature for 5 minutes and then at room temperature for 15 minutes. Methyl iodide (0.083 mL) was added to the reaction mixture under ice-cooling, followed by stirring at room temperature for 1 hour and then at 50° C. for 1 hour. The reaction mixture was cooled to room temperature, and then methyl iodide (0.11 mL) was added thereto, followed by stirring at 40 to 50° C. for 2 hours. The reaction mixture was cooled to room temperature, and then water and diethyl ether were added thereto. The organic layer was separated, washed with a saturated aqueous solution of sodium bicarbonate and a saturated aqueous solution of sodium chloride sequentially, and dried over anhydrous magnesium sulfate, and the solvent was evaporated under reduced pressure. The obtained residue was purified by silica gel column chromatography [eluent: 99-95% hexane/ethyl acetate] to obtain 0.12 g of methyl 4-(2-((ethyl)(methyl)amino)phenyl)-2-nitrobenzoate as a yellow oily substance.

$^1$H-NMR (CDCl$_3$): 0.92 (3H, t, J=7.2 Hz), 2.58 (3H, s), 2.80 (2H, q, J=7.2 Hz), 3.94 (3H, s), 7.05-7.15 (2H, m), 7.23 (1H, dd, J=7.6, 1.7 Hz), 7.31-7.39 (1H, m), 7.78 (1H, d, J=8.0 Hz), 7.88 (1H, dd, J=8.0, 1.7 Hz), 8.18 (1H, d, J=1.7 Hz).

Reference Example 17b

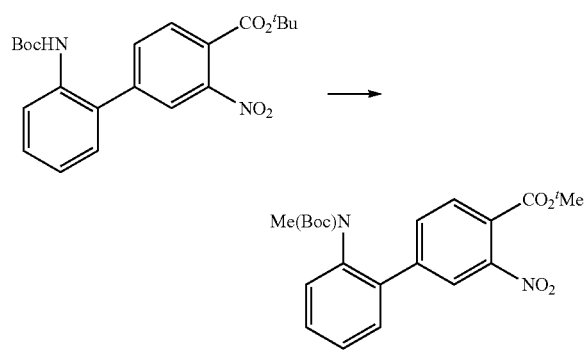

Potassium carbonate (0.16 g) and dimethyl sulfate (0.094 mL) were added to an acetone (4.0 mL) solution of tert-butyl 4-(2-(tert-butoxycarbonylamino)phenyl)-2-nitrobenzoate (0.27 g), followed by heating to reflux for 2 hours. The reaction mixture was cooled to room temperature, and then water and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 95-85% hexane/ethyl acetate] and then purified by silica gel column chromatography [eluent: 91-85% hexane/ethyl acetate] to obtain 0.061 g of tert-butyl 4-(2-((tert-butoxycarbonyl)(methyl)amino)phenyl)-2-nitrobenzoate as a colorless oily substance.

$^1$H-NMR (DMSO-d$_6$) δ: 0.99-1.28 (9H, m), 1.51 (9H, s), 3.00-3.11 (3H, m), 7.39-7.54 (4H, m), 7.74 (1H, d, J=8.3 Hz), 7.83-7.94 (2H, m).

Reference Example 18b

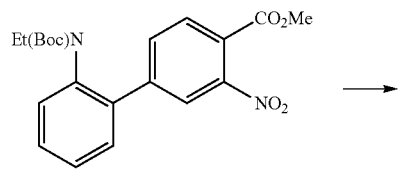

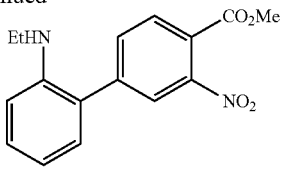

Trifluoroacetic acid (4.5 mL) was added to a methylene chloride (2.0 mL) solution of methyl 4-(2-((tert-butoxycarbonyl)(ethyl)amino)phenyl)-2-nitrobenzoate (0.39 g) at room temperature, followed by stirring at the same temperature for 1 hour. The solvent was evaporated under reduced pressure, and ethyl acetate and a saturated aqueous solution of sodium bicarbonate were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 91-85% hexane/ethyl acetate] to obtain 0.27 g of methyl 4-(2-(ethylamino)phenyl)-2-nitrobenzoate as an orange oily substance.

$^1$H-NMR (CDCl$_3$): 1.16-1.23 (3H, m), 3.15 (2H, q, J=7.1 Hz), 3.52-3.68 (1H, broad), 3.93-3.97 (3H, m), 6.74 (1H, d, J=8.3 Hz), 6.76-6.83 (1H, m), 7.03-7.09 (1H, m), 7.27-7.33 (1H, m), 7.74-7.79 (1H, m), 7.80-7.86 (1H, m), 7.95-7.99 (1H, m).

Reference Example 19b

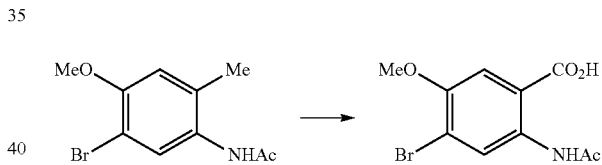

Under heating to reflux, potassium permanganate (0.98 g) was added to a solution mixture of N-(5-bromo-4-methoxy-2-methylphenyl)acetamide (1.0 g) in water (10 mL), tert-butyl alcohol (10 mL), and magnesium sulfate (0.79 g), followed by heating to reflux under a nitrogen atmosphere for 6 hours and 20 minutes. After cooling the reaction mixture to room temperature, the insoluble substance was removed by filtration. The solvent was evaporated under reduced pressure, and water and ethyl acetate were added to the residue. The aqueous layer was separated, and 1 mol/L hydrochloric acid (4 mL) and chloroform were added to thereto. The organic layer was separated, and the aqueous layer was extracted with chloroform. The organic layer and the extract were combined, and the resulting mixture was washed with a saturated aqueous solution of sodium chloride and dried over anhydrous magnesium sulfate. The solvent was evaporated under reduced pressure, and diisopropyl ether was added to the obtained residue. The solid substance was collected by filtration to obtain 0.36 g of 2-(acetamido)-4-bromo-5-methoxybenzoic acid as a white solid.

$^1$H-NMR (DMSO-d$_6$) δ: 2.11 (3H, s), 3.86 (3H, s), 7.53 (1H, s), 8.68 (1H, s), 10.78 (1H, s).

Reference Example 20b

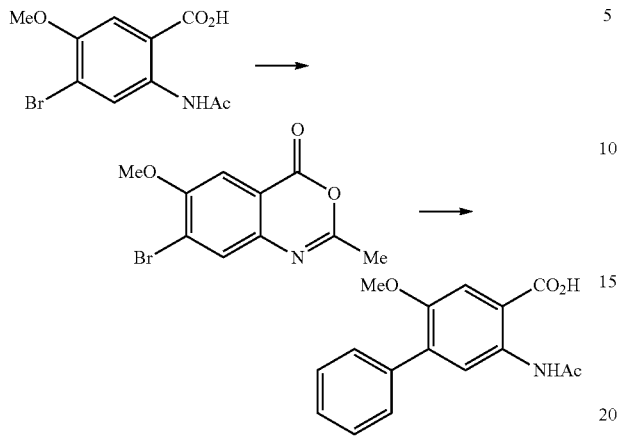

4-(Dimethylamino)pyridine (63 mg) and 2-acetamide-4-bromo-5-methoxybenzoic acid (0.49 g) were added to a tetrahydrofuran (1.5 mL) solution of di-tert-butyl dicarbonate (0.75 g) at room temperature, followed by stirring at the same temperature for 4 hours and 15 minutes. Tetrahydrofuran (2 mL) was added to the reaction mixture at room temperature, followed by stirring at the same temperature for 3 days. Di-tert-butyl dicarbonate (0.37 g) was added to the reaction mixture at room temperature, followed by stirring at the same temperature for 1 day. The solvent was evaporated under reduced pressure, ethyl acetate and a saturated aqueous solution of sodium bicarbonate were added to the residue. The organic layer was separated, washed with a 10% aqueous solution of citric acid and a saturated aqueous solution of sodium chloride sequentially, and dried over anhydrous magnesium sulfate, and the solvent was evaporated under reduced pressure. Hexane and diisopropyl ether were added to the obtained residue, and the solid substance was collected by filtration to obtain 0.40 g of 7-bromo-6-methoxy-2-methyl-4H-3,1-benzoxazin-4-one as a brown solid.

Water (1.2 mL), phenylboranic acid (0.22 g), sodium carbonate (0.38 g), and bis(triphenylphosphine)palladium(II) dichloride (21 mg) were added to an ethylene glycol dimethyl ether (4 mL) suspension of the obtained 7-bromo-6-methoxy-2-methyl-4H-3,1-benzoxazin-4-one (0.40 g), followed by heating to reflux under a nitrogen atmosphere for 4 hours and 30 minutes. The reaction mixture was cooled to room temperature, and then water and ethyl acetate were added thereto. The aqueous layer was separated, and the organic layer was extracted with a 2 mol/L aqueous solution of sodium hydroxide. The aqueous layer and the extract were combined, and the resulting mixture was adjusted to a pH of 1 with 6 mol/L hydrochloric acid, and ethyl acetate was added thereto. The organic layer was separated, washed with a saturated aqueous solution of sodium chloride, and dried over anhydrous magnesium sulfate, and the solvent was evaporated under reduced pressure. Diisopropyl ether was added to the obtained residue, and the solid substance was collected by filtration to obtain 0.27 g of 2-acetamide-5-methoxy-4-phenylbenzoic acid as a yellow solid.

$^1$H-NMR (DMSO-$d_6$) δ: 2.11 (3H, s), 3.78 (3H, s), 7.35-7.52 (5H, m), 7.57 (1H, s), 8.39 (1H, s), 10.79 (1H, s).

Reference Example 21b

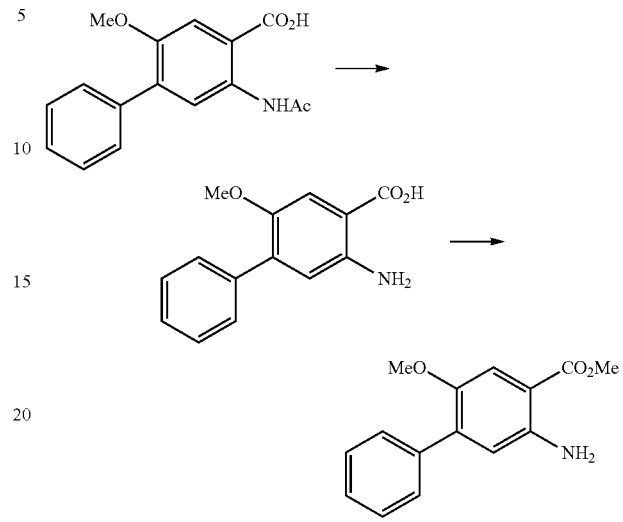

A solution mixture of 2-acetamide-5-methoxy-4-phenylbenzoic acid (0.41 g) in dioxane (1.2 mL) and concentrated hydrochloric acid (1.2 mL) was heated to reflux for 3 hours and 40 minutes. After cooling the reaction mixture to room temperature, the solvent was evaporated under reduced pressure, and water was added to the residue. After adjusting the pH to 7 with a 1 mol/L aqueous solution of sodium hydroxide, chloroform was added thereto. The organic layer was separated and dried over anhydrous magnesium sulfate, and the solvent was evaporated under reduced pressure to obtain 2-amino-5-methoxy-4-phenylbenzoic acid as a brown solid.

Under ice-cooling, concentrated sulfuric acid (1 mL) was added to a methanol (10 mL) suspension of the obtained 2-amino-5-methoxy-4-phenylbenzoic acid, followed by heating to reflux for 6 hours. The reaction mixture was cooled to room temperature and was adjusted to a pH of 8.0 with a saturated aqueous solution of sodium bicarbonate, and chloroform was added thereto. The organic layer was separated and dried over anhydrous magnesium sulfate, and the solvent was evaporated under reduced pressure. Hexane was added to the obtained residue, and the solid substance was collected by filtration to obtain 0.24 g of methyl 2-amino-5-methoxy-4-phenylbenzoate as a brown solid.

$^1$H-NMR (DMSO-$d_6$) δ3.65 (3H, s), 3.82 (3H, s), 6.35 (2H, s), 6.78 (1H, s), 7.30 (1H, s), 7.32-7.49 (5H, m).

Reference Example 22b

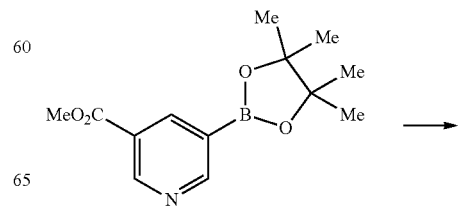

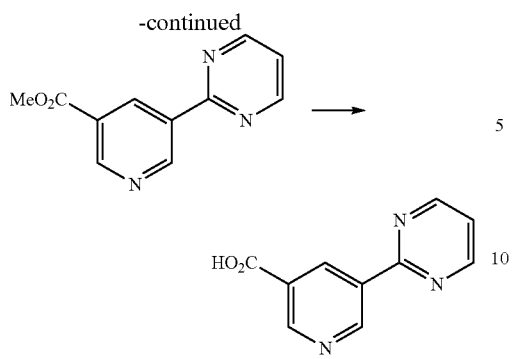

2-Bromopyrimidine (73 mg), sodium carbonate (81 mg), water (0.3 mL), and bis(triphenylphosphine)palladium(II) dichloride (5.3 mg) were added to an ethylene glycol dimethyl ether (1 mL) solution of methyl 5-(4,4,5,5-tetramethyl-1,3,2-dioxaborolan-2-yl)pyridine-3-carboxylate (0.10 g), followed by heating to reflux under a nitrogen atmosphere for 1 hour and 30 minutes. After cooling the reaction mixture to room temperature, ethyl acetate and water were added thereto, and the insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 90-50% hexane/ethyl acetate] to obtain 30 mg of methyl 5-(pyrimidin-2-yl)pyridine-3-carboxylate as a yellow solid.

A 2 mol/L aqueous solution of sodium hydroxide (0.21 mL) was added to a solution mixture of the obtained methyl 5-(pyrimidin-2-yl)pyridine-3-carboxylate (30 mg) in dioxane (0.3 mL) and methanol (0.3 mL) at room temperature, followed by stirring at the same temperature for 1 hour and 30 minutes. The solvent was evaporated under reduced pressure, and water and toluene were added to the residue. The aqueous layer was separated and adjusted to a pH of 3.8 with 1 mol/L hydrochloric acid. The solid substance was collected by filtration to obtain 7.0 mg of 5-(pyrimidin-2-yl)pyridine-3-carboxylic acid as a white solid.

$^1$H-NMR (DMSO-$d_6$) δ: 7.58 (1H, t, J=4.9 Hz), 9.00 (2H, d, J=4.9 Hz), 9.13 (1H, dd, J=2.0, 2.0 Hz), 9.20 (1H, d, J=2.0 Hz), 9.68 (1H, d, J=2.0 Hz).

Reference Example 23b

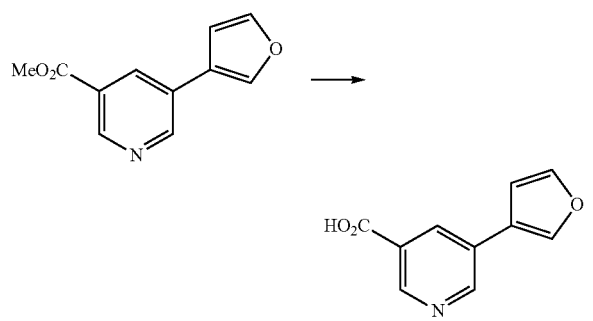

A 4 mol/L aqueous solution of sodium hydroxide (2.0 mL) was added to a methanol (10 mL) solution of methyl 5-(furan-3-yl)pyridine-3-carboxylate (0.54 g) at room temperature, followed by stirring at the same temperature for 2 hours and 50 minutes. A 10% aqueous solution of citric acid (8 mL) was added to the reaction mixture at room temperature, and the solvent was evaporated under reduced pressure. Water was added to the obtained residue, and the solid substance was collected by filtration to obtain 0.33 g of 5-(furan-3-yl)pyridine-3-carboxylic acid as a light yellow solid.

$^1$H-NMR (DMSO-$d_6$) δ: 7.13-7.17 m), 7.80-7.84 (1H, m), 8.41-8.48 (2H, m), 8.92-8.96 (1H, m), 9.05-9.11 (1H, m).

Reference Example 24b

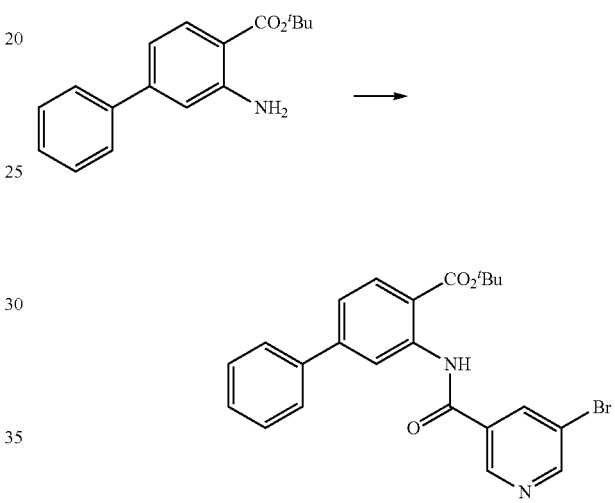

N,N-Dimethylformamide (8.6 μL) and oxalyl chloride (0.14 mL) were added to a methylene chloride (5 mL) suspension of 5-bromopyridine-3-carboxylic acid (0.23 g) at room temperature, followed by stirring at the same temperature for 1 hour. The solvent was evaporated under reduced pressure, and methylene chloride (2.5 mL) was added to the residue. The reaction mixture was added to a solution mixture of tert-butyl 2-amino-4-phenylbenzoate (0.25 g) in methylene chloride (5 mL) and pyridine (0.19 mL) at room temperature, followed by stirring at the same temperature for 1 hour. A saturated aqueous solution of sodium bicarbonate was added to the reaction mixture. The organic layer was separated, and the solvent was evaporated under reduced pressure. The obtained residue was purified by silica gel column chromatography [Fuji Silysia Chemical Ltd., PSQ100B (spherical), eluent: 100-80% hexane/ethyl acetate] to obtain 0.39 g of tert-butyl 2-(5-bromopyridine-3-carboxamido)-4-phenylbenzoate as a white solid.

$^1$H-NMR (CDCl$_3$) δ: 1.65 (9H, s), 7.37-7.45 (2H, m), 7.45-7.53 (2H, m), 7.68-7.74 (2H, m), 8.10 (1H, d, J=8.6 Hz), 8.52 (1H, dd, J=2.1, 2.1 Hz), 8.86 (1H, d, J=2.2 Hz), 9.17 (1H, d, J=2.0 Hz), 9.22 (1H, d, J=1.9 Hz), 12.52 (1H, s).

Reference Examples 25b to 27b

As in Reference Example 24b, the compounds shown in Table 5b were prepared.

TABLE 5b

| Reference Example No. | A |
|---|---|
| 25b | pyridine with methyl and Br |
| 26b | pyridine with methyl and Cl |
| 27b | pyridine with methyl and Cl |

Tert-butyl 2-(5-bromopyridine-2-carboxamido)-4-phenylbenzoate $^1$H-NMR (CDCl$_3$) δ: 1.67 (9H, s), 7.35-7.43 (2H, m), 7.43-7.50 (2H, m), 7.69-7.75 (2H, m), 8.04 (1H, dd, J=8.5, 2.2 Hz), 8.09 (1H, d, J=8.3 Hz), 8.19 (1H, d, J=8.3 Hz), 8.84 (1H, d, J=2.0 Hz), 9.24 (1H, d, J=2.0 Hz), 12.90 (1H, s).

Tert-butyl 2-(4-chloropyridine-2-carboxamido)-4-phenylbenzoate $^1$H-NMR (CDCl$_3$) δ: 1.68 (9H, s), 7.36-7.44 (2H, m), 7.44-7.53 (3H, m), 7.69-7.75 (2H, m), 8.09 (1H, d, J=8.3 Hz), 8.31 (1H, d, J=1.4 Hz), 8.67 (1H, d, J=5.2 Hz), 9.25 (1H, d, J=1.9 Hz), 12.94 (1H, s).

Tert-butyl 2-(6-chloropyridine-3-carboxamido)-4-phenylbenzoate $^1$H-NMR (DMSO-d$_6$) δ: 1.55 (9H, s), 7.43-7.50 (1H, m), 7.51-7.58 (2H, m), 7.60 (1H, dd, J=8.3, 1.8 Hz), 7.71-7.76 (2H, m), 7.81 (1H, d, J=8.3 Hz), 8.02 (1H, d, J=8.3 Hz), 8.37 (1H, dd, J=8.3, 2.6 Hz), 8.60 (1H, d, J=1.8 Hz), 8.99 (1H, d, J=2.6 Hz), 11.56 (1H, s).

Reference Example 28b

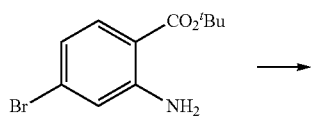

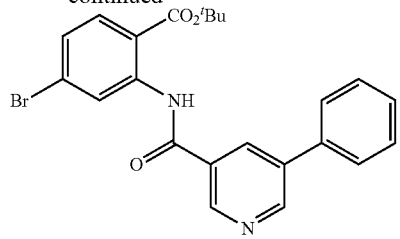

As in Reference Example 24b, the following compound was prepared.

Tert-butyl 4-bromo-2-(5-phenylpyridine-3-carboxamido)benzoate $^1$H-NMR (CDCl$_3$) δ: 1.64 (9H, s), 7.24-7.31 (1H, m), 7.43-7.49 (1H, m), 7.50-7.58 (2H, m), 7.66-7.73 (2H, m), 7.89 (1H, d, J=8.5 Hz), 8.56 (1H, dd, J=2.2, 2.2 Hz), 9.04 (1H, d, J=2.2 Hz), 9.17 (1H, d, J=1.9 Hz), 9.24 (1H, d, J=2.2 Hz), 12.52 (1H, s).

Reference Example 29b

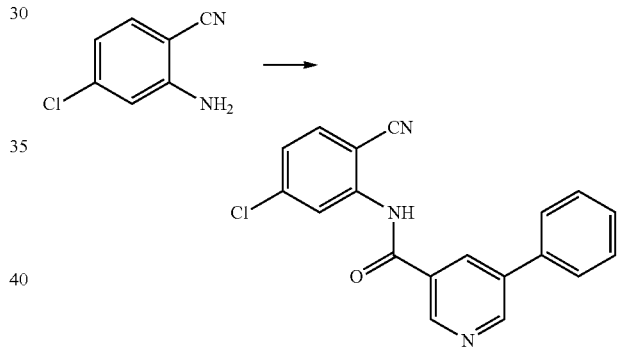

As in Reference Example 24b, the following compound was prepared.

N-(5-Chloro-2-cyanophenyl)-5-phenylpyridine-3-carboxamide $^1$H-NMR (DMSO-d$_6$) δ: 7.46-7.64 (4H, m), 7.78-7.90 (3H, m), 7.98 (1H, d, J=8.3 Hz), 8.59-8.64 (1H, m), 9.09-9.19 (2H, m), 11.03 (1H, s).

Reference Example 30b

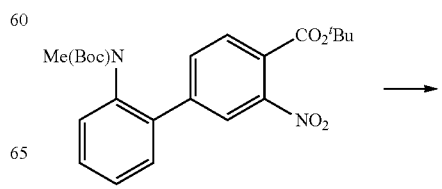

-continued

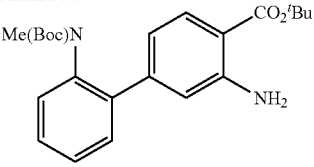

To a solution mixture of tert-butyl 4-(2-((tert-butoxycarbonyl)(methyl)amino)phenyl)-2-nitrobenzoate (57 mg) in ethyl acetate (2.5 mL) and methanol (2.5 mL), 10% palladium-carbon (11 mg) was added. The resulting mixture was stirred at room temperature for 3 hours under a hydrogen atmosphere. The insoluble substance was removed by filtration, and the solvent was evaporated under reduced pressure. The obtained residue was purified by silica gel column chromatography [eluent: 95-85% hexane/ethyl acetate] to obtain 48 mg of tert-butyl 2-amino-4-(2-((tert-butoxycarbonyl)(methyl)amino)phenyl)benzoate as a white solid.

$^1$H-NMR (DMSO-$d_6$) δ: 1.02-1.38 (9H, m), 1.54 (9H, s), 2.83-3.01 (3H, m), 6.44 (1H, dd, J=8.2, 1.3 Hz), 6.56-6.74 (3H, m), 7.26-7.43 (4H, m), 7.61-7.70 (1H, m).

Reference Examples 31b to 34b

As in Reference Example 30b, the compounds shown in Table 6b were prepared.

TABLE 6b

| Reference Example No. | $R^3$ |
|---|---|
| 31b | pyridin-2-yl |
| 32b | 1-methyl-1H-pyrazol-5-yl |
| 33b | 3-(Et(Boc)N)-phenyl (methyl-substituted) |
| 34b | 3-(Me(Boc)N)-phenyl (methyl-substituted) |

Tert-butyl 2-amino-4-(pyridin-2-yl)benzoate $^1$H-NMR (CDCl$_3$) δ: 1.61 (9H, s), 5.74-5.86 (2H, broad), 7.18 (1H, dd, J=8.3, 1.7 Hz), 7.23-7.29 (1H, m), 7.36 (1H, d, J=1.4 Hz), 7.69-7.79 (2H, m), 7.90 (1H, d, J=8.3 Hz), 8.67-8.72 (1H, m).

Tert-butyl 2-amino-4-(1H-pyrazol-1-yl)benzoate $^1$H-NMR (CDCl$_3$) δ: 1.60 (9H, s), 5.82-5.95 (2H, broad), 6.47 (1H, dd, J=2.3, 2.0 Hz), 6.90 (1H, dd, J=8.8, 2.2 Hz), 7.08 (1H, d, J=2.2 Hz), 7.72 (1H, d, J=2.0 Hz), 7.88 (1H, d, J=8.8 Hz), 7.93 (1H, d, J=2.3 Hz).

Tert-butyl 2-amino-4-(3-((tert-butoxycarbonyl)(ethyl)amino)phenyl)benzoate $^1$H-NMR (CDCl$_3$) δ: 1.18 (3H, t, J=7.1 Hz), 1.45 (9H, s), 1.60 (9H, s), 3.71 (2H, q, J=7.1 Hz), 5.78 (2H, s), 6.81-6.87 (2H, m), 7.15-7.24 (1H, m), 7.34-7.44 (3H, m), 7.84-7.90 (1H, m).

Tert-butyl 2-amino-4-(3-((tert-butoxycarbonyl)(methyl)amino)phenyl)benzoate $^1$H-NMR (CDCl$_3$): 1.47 (9H, s), 1.60 (9H, s), 3.30 (3H, s), 5.72-5.83 (2H, broad), 6.81-6.86 (2H, m), 7.21-7.27 (1H, m), 7.34-7.41 (2H, m), 7.42-7.45 (1H, m), 7.84-7.89 (1H, m).

Reference Example 35b

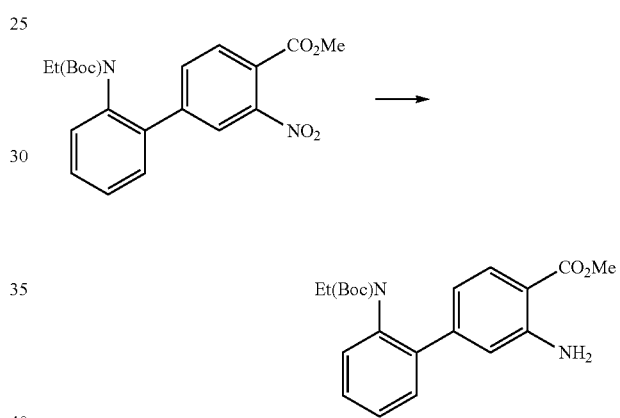

As in Reference Example 30b, the following compound was prepared.

Methy 2-amino-4-(2-((tert-butoxycarbonyl)(ethyl)amino)phenyl)benzoate $^1$H-NMR (CD$_3$OD): 0.96-1.11 (3H, m), 1.24-1.50 (9H, m), 2.77-2.95 (1H, m), 3.45-3.75 (1H, m), 3.86 (3H, s), 6.56 (1H, dd, J=8.3, 1.7 Hz), 6.73 (1H, d, J=1.7 Hz), 7.17-7.27 (1H, m), 7.33-7.42 (3H, m), 7.75-7.83 (1H, m).

Reference Example 36b

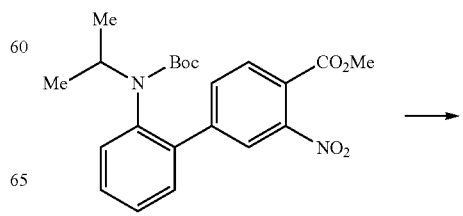

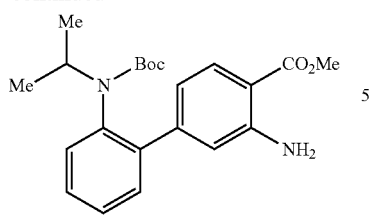

As in Reference Example 30b, the following compound was prepared.

Methyl 2-amino-4-(2-((tert-butoxycarbonyl)(isopropyl)amino)phenyl)benzoate $^1$H-NMR (CD$_3$OD): 0.82 (3H, d, J=6.8 Hz), 0.93-1.13 (3H, m), 1.22-1.57 (9H, m), 3.80-4.07 (1H, m), 3.86 (3H, s), 6.60-6.70 (1H, m), 6.77 (1H, d, J=1.4 Hz), 7.08-7.24 (1H, broad), 7.33-7.44 (3H, m), 7.77 (1H, d, J=8.3 Hz).

Reference Example 37b

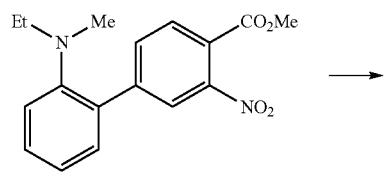

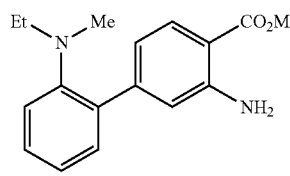

As in Reference Example 30b, the following compound was prepared.

Methyl 2-amino-4-(2-((ethyl)(methyl)amino)phenyl)benzoate $^1$H-NMR (CDCl$_3$): 0.90 (3H, t, J=7.0 Hz), 2.61 (3H, s), 2.84 (2H, q, J=7.0 Hz), 3.88 (3H, s), 6.85-6.91 (2H, m), 6.99 (1H, dd, J=7.4, 7.4 Hz), 7.03 (1H, d, J=8.3 Hz), 7.20 (1H, dd, J=7.6, 1.7 Hz), 7.23-7.30 (1H, m), 7.86 (1H, d, J=8.6 Hz).

Reference Example 38b

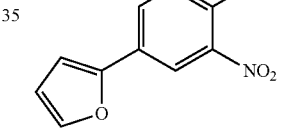

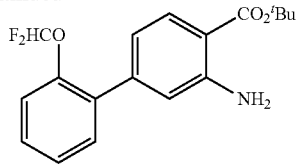

Water (0.53 mL), sodium formate (0.13 g), acetic acid (0.13 mL), and 10% palladium-carbon (35 mg) were added to a 2-propanol (2.1 mL) solution of tert-butyl 4-(2-(difluoromethoxy)phenyl)-2-nitrobenzoate (0.18 g), followed by heating to reflux for 2 hours. The reaction mixture was cooled to room temperature, and then the insoluble substance was removed by filtration. The solvent was evaporated under reduced pressure, and ethyl acetate and a saturated aqueous solution of sodium bicarbonate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 99-91% hexane/ethyl acetate] to obtain 0.15 g of tert-butyl 2-amino-4-(2-(difluoromethoxy)phenyl)benzoate as a yellow oily substance.

$^1$H-NMR (CDCl$_3$): 1.60 (9H, s), 6.33 (1H, t, J=74.2 Hz), 6.72-6.78 (2H, m), 7.20-7.32 (2H, m), 7.33-7.42 (2H, m), 7.83-7.90 (1H, m).

Reference Example 39b

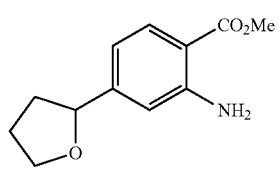

As in Reference Example 38b, the following compound was prepared.

Methyl 2-amino-4-(tetrahydrofuran-2-yl)benzoate $^1$H-NMR (CDCl$_3$): 1.70-1.82 (1H, m), 1.93-2.03 (2H, m), 2.25-2.37 (1H, m), 3.85 (3H, s), 3.89-3.97 (1H, m), 4.02-4.11 (1H, m), 4.82 (1H, dd, J=7.2, 7.2 Hz), 5.65-5.82 (2H, broad), 6.53-6.60 (1H, m), 6.64-6.70 (1H, m), 7.80 (1H, d, J=8.3 Hz).

Reference Example 40b

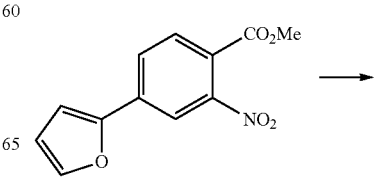

107
-continued

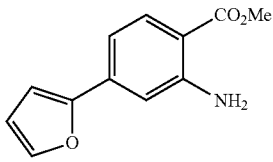

Water (0.56 mL), ammonium chloride (18 mg), and iron powder (94 mg) were added to an ethanol (2.1 mL) suspension of methyl 4-(furan-2-yl)-2-nitrobenzoate (0.14 g), followed by heating to reflux for 2 hours and 30 minutes. The reaction mixture was cooled to room temperature, and then ammonium chloride (18 mg), iron powder (31 mg), and water (0.28 mL) were added thereto, followed by heating to reflux for 1 hour. The reaction mixture was cooled to room temperature, and then the solvent was evaporated under reduced pressure. A saturated aqueous solution of sodium bicarbonate and ethyl acetate were added to the obtained residue, and the insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 99-95% hexane/ethyl acetate] to obtain 78 mg of methyl 2-amino-4-(furan-2-yl) benzoate as a light yellow solid.

$^1$H-NMR (CDCl$_3$): 3.88 (3H, s), 5.72-5.86 (2H, broad), 6.49 (1H, dd, J=3.3, 1.8 Hz), 6.72 (1H, d, J=3.3 Hz), 6.94 (1H, dd, J=8.5, 1.7 Hz), 6.99 (1H, d, J=1.7 Hz), 7.47-7.51 (1H, m), 7.86 (1H, d, J=8.5 Hz).

Reference Example 41b

108

As in Reference Example 40b, the following compound was prepared.

Tert-butyl 2-amino-4-(isoquinolin-4-yl)benzoate $^1$H-NMR (DMSO-d$_6$) δ: 1.58 (9H, s), 6.64-6.72 (1H, m), 6.72-6.84 (2H, broad), 6.91 (1H, s), 7.72-7.96 (4H, m), 8.23 (1H, d, J=7.8 Hz), 8.42 (1H, d, J=1.0 Hz), 9.35 (1H, s).

Example 1a

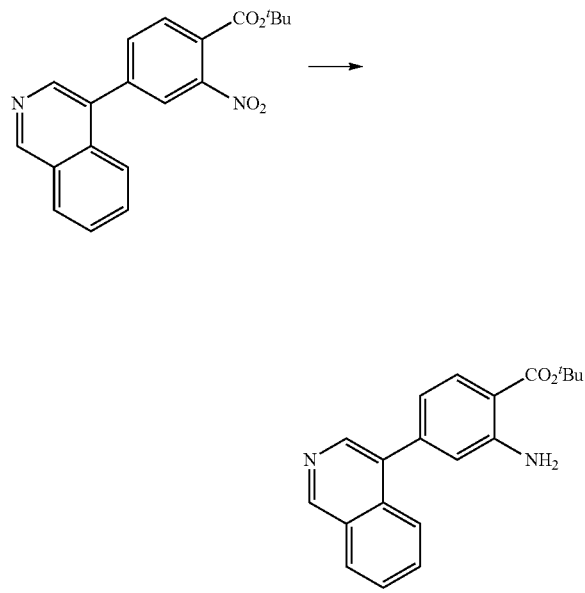

N,N-Dimethylformamide (2.7 μL) and oxalyl chloride (0.046 mL) were sequentially added to a methylene chloride (1.6 mL) suspension of 2-acetoxy-4-chlorobenzoic acid (0.076 g), followed by stirring at room temperature for 1 hour. The solvent was evaporated under reduced pressure, and toluene was added the residue. The solvent was evaporated under reduced pressure, and methylene chloride (1 mL) was added to the residue. The resulting mixture was added to a solution mixture of tert-butyl 2-amino-4-phenylbenzoate (0.080 g) in pyridine (0.060 mL) and methylene chloride (1.6 mL), followed by stirring at room temperature for 2 hours. The reaction mixture was purified by silica gel column chromatography [Fuji Silysia Chemical Ltd., PSQ100B (spherical), eluent: 100-85% hexane/ethyl acetate] to obtain 0.13 g of tert-butyl 2-(2-acetoxy-4-chlorobenzamido)-4-phenylbenzoate.

Potassium carbonate (0.12 g) was added to a solution mixture of the obtained tert-butyl 2-(2-acetoxy-4-chlorobenzamido)-4-phenylbenzoate (0.13 g) in methanol (2.5 mL) and dioxane (2.5 mL), followed by stirring at room temperature for 2 hours. The solvent was evaporated under reduced pressure, and a 10% aqueous solution of citric acid and ethyl acetate were added to the residue. The organic layer was separated, washed with a saturated aqueous solution of sodium chloride, and dried over anhydrous magnesium sulfate, and the solvent was evaporated under reduced pressure to obtain 0.11 of tert-butyl 2-(4-chloro-2-hydroxybenzamido)-4-phenylbenzoate as a white solid.

A solution mixture of the obtained tert-butyl 2-(4-chloro-2-hydroxybenzamido)-4-phenylbenzoate (0.11 g) in trifluoroacetic acid (5 mL) and methylene chloride (2.5 mL) was stirred at room temperature for 3 hours. The solvent was evaporated under reduced pressure, and diisopropyl ether was added to the residue. The solid substance was collected by filtration to obtain 0.077 g of 2-(4-chloro-2-hydroxybenzamido)-4-phenylbenzoic acid as a white solid.

$^1$H-NMR (DMSO-$d_6$) δ: 7.03-7.09 (2H, m), 7.43-7.58 (4H, m), 7.70-7.76 (2H, m), 7.93 (1H, d, J=9.0 Hz), 8.10 (1H, d, J=8.3 Hz), 9.02 (1H, d, J=1.7 Hz), 11.75-12.05 (1H, broad), 12.15-12.40 (1H, broad), 13.30-13.60 (1H, broad).

Example 2a to 10a

As in Example 1a, the compounds shown in Table 9a were prepared.

TABLE 9a

| Example No. | A |
|---|---|
| 2a | 2-methyl-4-chloro-phenol (2-Me, 4-Cl, 1-OH) |
| 3a | 2-methyl-6-chloro-phenol |
| 4a | 2,4-dimethylphenol |
| 5a | 2-methyl-6-methoxyphenol |
| 6a | 2-methyl-5-methoxyphenol |

TABLE 9a-continued

| Example No. | A |
|---|---|
| 7a | 2-methyl-4-methoxyphenol |
| 8a | 2-methyl-3-methoxyphenol |
| 9a | 2-methyl-4-acetylphenol |
| 10a | 4-methyl-3-hydroxyphenyl 1-(methylsulfonyl)piperidin-4-yl ether |

2-(5-Chloro-2-hydroxybenzamido)-4-phenylbenzoic acid $^1$H-NMR (DMSO-$d_6$) δ: 7.05 (1H, d, J=8.8 Hz), 7.43-7.58 (5H, m), 7.70-7.76 (2H, m), 7.90 (1H, d, J=2.9 Hz), 8.10 (1H, d, J=8.3 Hz), 9.00 (1H, d, J=1.7 Hz), 11.60-11.75 (1H, broad), 12.25-12.40 (1H, broad), 13.35-13.60 (1H, broad).

2-(3-Chloro-2-hydroxybenzamido)-4-phenylbenzoic acid $^1$H-NMR (DMSO-$d_6$) δ: 7.08 (1H, dd, J=7.9, 7.9 Hz), 7.44-7.50 (1H, m), 7.51-7.58 (2H, m), 7.60 (1H, dd, J=8.2, 1.8 Hz), 7.71 (1H, dd, J=7.9, 1.1 Hz), 7.72-7.78 (2H, m), 7.82-7.88 (1H, m), 8.14 (1H, d, J=8.2 Hz), 8.80 (1H, d, J=1.8 Hz), 12.25-12.50 (2H, broad).

2-(2-Hydroxy-5-methylbenzamido)-4-phenylbenzoic acid $^1$H-NMR (DMSO-$d_6$) δ: 2.28 (3H, s), 6.92 (1H, d, J=8.3 Hz), 7.26 (1H, dd, J=8.3, 1.7 Hz), 7.43-7.58 (4H, m), 7.69-7.76 (3H, m), 8.10 (1H, d, J=8.3 Hz), 9.01 (1H, d, J=1.7 Hz), 11.24 (1H, s), 12.30 (1H, s), 13.40-13.65 (1H, broad).

2-(2-Hydroxy-3-methoxybenzamido)-4-phenylbenzoic acid $^1$H-NMR (DMSO-$d_6$) δ: 3.81-3.87 (3H, m), 6.91-6.95 (1H, m), 7.17-7.23 (1H, m), 7.40-7.50 (2H, m), 7.50-7.58 (3H, m), 7.70-7.77 (2H, m), 8.11 (1H, dd, J=8.3, 2.4 Hz), 8.92-8.96 (1H, m), 11.25 (1H, s), 12.27 (1H, s).

2-(2-Hydroxy-4-methoxybenzamido)-4-phenylbenzoic acid $^1$H-NMR (DMSO-d$_6$) δ: 3.80 (3H, s), 6.53 (1H, d, J=2.3 Hz), 6.60 (1H, dd, J=8.9, 2.3 Hz), 7.42-7.57 (4H, m), 7.70-7.75 (2H, m), 7.85 (1H, d, J=8.9 Hz), 8.10 (1H, d, J=8.3 Hz), 8.97 (1H, d, J=1.7 Hz), 11.82 (1H, s), 12.21 (1H, s).

2-(2-Hydroxy-5-methoxybenzamido)-4-phenylbenzoic acid $^1$H-NMR (DMSO-d$_6$) δ: 3.76 (3H, s), 6.96 (1H, d, J=8.9 Hz), 7.08 (1H, dd, J=8.9, 3.1 Hz), 7.43-7.49 (2H, m), 7.49-7.58 (3H, m), 7.71-7.76 (2H, m), 8.10 (1H, d, J=8.3 Hz), 9.03 (1H, d, J=1.7 Hz), 11.00 (1H, s), 12.33 (1H, s), 13.35-13.65 (1H, broad).

2-(2-Hydroxy-6-methoxybenzamido)-4-phenylbenzoic acid $^1$H-NMR (DMSO-d$_6$) δ: 3.98 (3H, s), 6.59 (1H, dd, J=8.3, 1.0 Hz), 6.66 (1H, d, J=8.4 Hz), 7.40 (1H, dd, J=8.4, 8.3 Hz), 7.43-7.50 (1H, m), 7.51-7.58 (3H, m), 7.70-7.76 (2H, m), 8.11 (1H, d, J=8.1 Hz), 8.94 (1H, s), 12.35 (1H, s), 12.62 (1H, s), 13.60-13.78 (1H, broad).

2-(5-Acetyl-2-hydroxybenzamido)-4-phenylbenzoic acid $^1$H-NMR (DMSO-d$_6$) δ: 2.57 (3H, s), 7.12 (1H, d, J=8.7 Hz), 7.43-7.50 (1H, m), 7.51-7.58 (3H, m), 7.71-7.78 (2H, m), 8.04 (1H, dd, J=8.7, 2.2 Hz), 8.11 (1H, d, J=8.3 Hz), 8.58 (1H, d, J=2.2 Hz), 9.06 (1H, d, J=1.7 Hz), 12.25-12.48 (2H, m), 13.40-13.65 (1H, broad).

2-(2-Hydroxy-4-(1-(methylsulfonyl)piperidin-4-yloxy)benzamido)-4-phenylbenzoic acid $^1$H-NMR (DMSO-d$_6$), (40° C.) δ: 1.70-1.84 (2H, m), 1.96-2.10 (2H, m), 2.90 (3H, s), 3.10-3.22 (2H, m), 3.30-3.42 (2H, m), 4.59-4.70 (1H, m), 6.57 (1H, d, J=2.4 Hz), 6.65 (1H, dd, J=8.9, 2.4 Hz), 7.42-7.57 (4H, m), 7.69-7.75 (2H, m), 7.84 (1H, d, J=8.9 Hz), 8.10 (1H, d, J=8.3 Hz), 8.95 (1H, d, J=1.7 Hz), 11.79 (1H, s), 12.19 (1H, s).

Example 11a

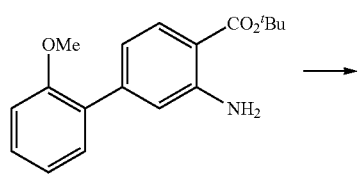

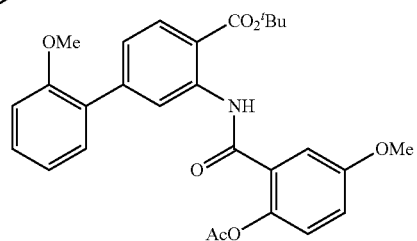

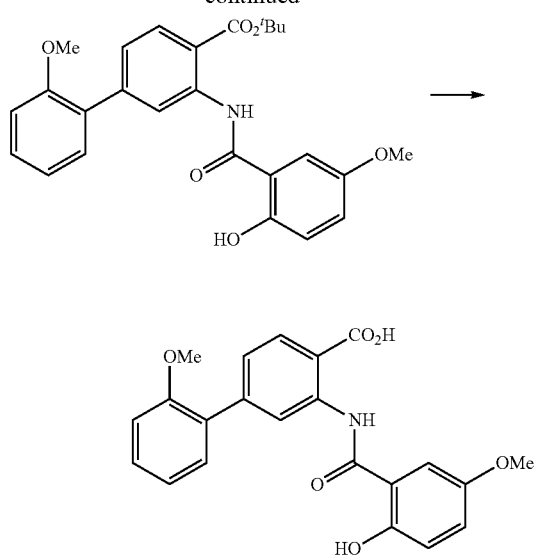

As in Example 1a, the following compound was prepared.

2-(2-Hydroxy-5-methoxybenzamido)-4-(2-methoxyphenyl)benzoic acid $^1$H-NMR (DMSO-d$_6$) δ: 3.75 (3H, s), 3.80 (3H, s), 6.95 (1H, d, J=9.0 Hz), 7.04-7.12 (2H, m), 7.16 (1H, d, J=8.6 Hz), 7.30-7.45 (4H, m), 8.03 (1H, d, J=8.3 Hz), 8.78 (1H, d, J=1.7 Hz), 11.00 (1H, s), 12.28 (1H, s).

Example 12a

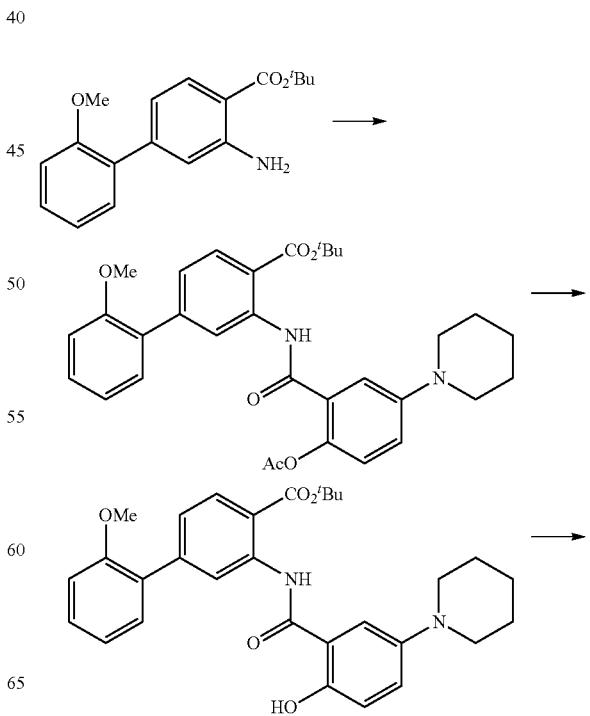

-continued

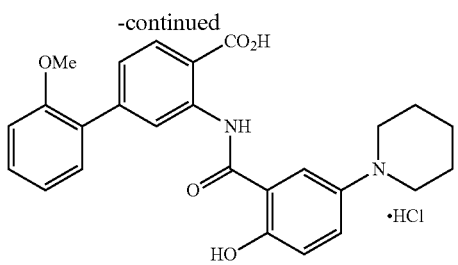 ·HCl

Under ice-cooling, N,N-dimethylformamide (0.010 mL) and oxalyl chloride (0.044 mL) were sequentially added to a methylene chloride (2.0 mL) suspension of 2-acetoxy-5-(piperidin-1-yl)benzoic acid (0.11 g), followed by stirring at room temperature for 30 minutes. The solvent was evaporated under reduced pressure, and methylene chloride (2.0 mL) was added to the residue. The resulting mixture was added to a methylene chloride (1.0 mL) solution of tert-butyl 2-amino-4-(2-methoxyphenyl)benzoate (0.10 g) and pyridine (0.054 mL) under ice-cooling, followed by stirring at room temperature for 1 hour and 30 minutes. The solvent was evaporated under reduced pressure, and a saturated aqueous solution of sodium bicarbonate and ethyl acetate were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 91-80% hexane/ethyl acetate] to obtain 0.11 g of tert-butyl 2-(2-acetoxy-5-(piperidin-1-yl)benzamido)-4-(2-methoxyphenyl)benzoate as a light yellow solid.

Dioxane (4.0 mL) and a 4 mol/L aqueous solution of sodium hydroxide (0.25 mL) were added to the obtained tert-butyl 2-(2-acetoxy-5-(piperidin-1-yl)benzamido)-4-(2-methoxyphenyl)benzoate (0.11 g), followed by stirring at 50 to 55° C. for 2 hours. The reaction mixture was cooled to room temperature, and a 10% aqueous solution of citric acid and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 95-60% hexane/ethyl acetate] to obtain 0.025 g of tert-butyl 2-(2-hydroxy-5-(piperidin-1-yl)benzamido)-4-(2-methoxyphenyl)benzoate as a yellow solid.

A 4 mol/L hydrogen chloride-dioxane solution (3.0 mL) was added to the obtained tert-butyl 2-(2-hydroxy-5-(piperidin-1-yl)benzamido)-4-(2-methoxyphenyl)benzoate (0.025 g), followed by stirring at room temperature for 3 hours and then at 50 to 55° C. for 1 hour. The reaction mixture was cooled to room temperature, and then the solvent was evaporated under reduced pressure. Diisopropyl ether was added to the obtained residue, and the solid substance was collected by filtration to obtain 0.020 g of 2-(2-hydroxy-5-(piperidin-1-yl)benzamido)-4-(2-methoxyphenyl)benzoic acid hydrochloride as a white solid.

$^1$H-NMR (CD$_3$OD) δ: 1.72-1.84 (2H, m), 1.96-2.06 (4H, m), 3.52-3.62 (4H, m), 3.85 (3H, s), 7.03-7.16 (3H, m), 7.35-7.43 (3H, m), 7.64 (1H, dd, J=8.8, 2.7 Hz), 8.04-8.09 (1H, m), 8.15 (1H, d, J=8.3 Hz), 8.88 (1H, d, J=1.5 Hz).

Example 13a

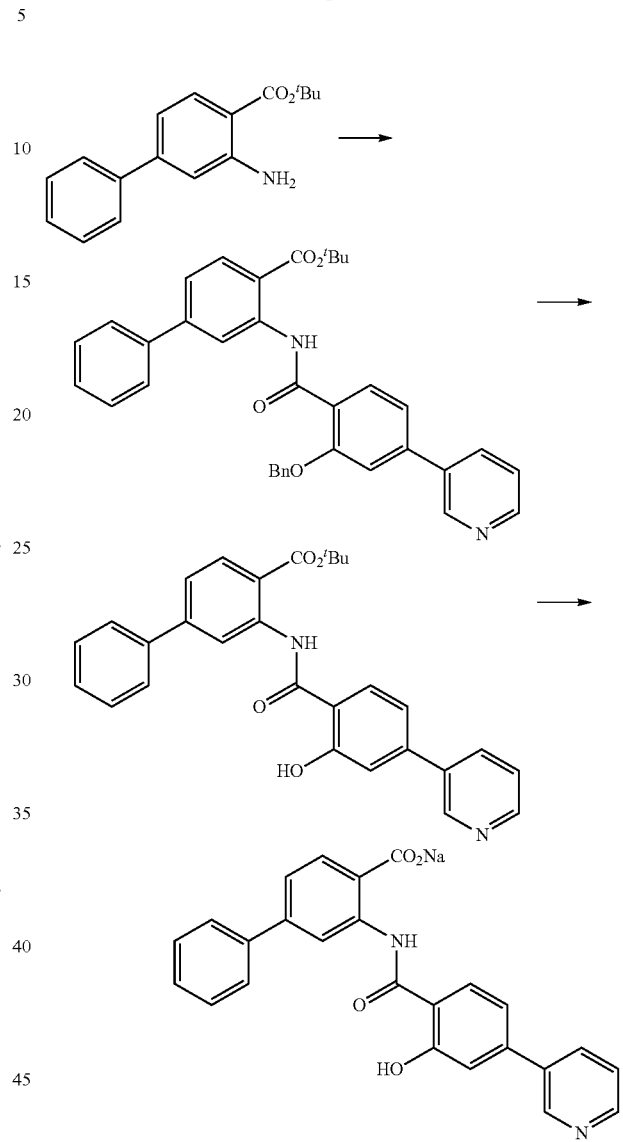

N,N-Dimethylformamide (2.4 μL) and oxalyl chloride (0.040 mL) were sequentially added to a methylene chloride (1.4 mL) suspension of 2-(benzyloxy)-4-(pyridin-3-yl)benzoic acid (0.095 g), followed by stirring at room temperature for 2 hours. The solvent was evaporated under reduced pressure, and toluene was added to the residue. The solvent was evaporated under reduced pressure, and methylene chloride (1.4 mL) was added to the residue. The resulting mixture was added to a solution mixture of tert-butyl 2-amino-4-phenylbenzoate (0.070 g) in pyridine (0.053 mL) and methylene chloride (1.4 mL), followed by stirring at room temperature for 1 hour. A 1 mol/L aqueous solution of sodium hydroxide added to the reaction mixture. The organic layer was separated, washed with a 1 mol/L aqueous solution of sodium hydroxide, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 90-50% hexane/ethyl acetate] to obtain 0.13 g of tert-butyl 2-(2-(benzyloxy)-4-(pyridin-3-yl)benzamido)-4-phenylbenzoate as a white solid.

To a solution mixture of the obtained tert-butyl 2-(2-(benzyloxy)-4-(pyridin-3-yl)benzamido)-4-phenylbenzoate (0.13 g) in methanol (2 mL), dioxane (4 mL), and ethyl acetate (4 mL), 10% palladium-carbon (63 mg) was added, followed by stirring under a hydrogen atmosphere at room temperature for 2 hours. The insoluble substance was removed by filtration, and the solvent was evaporated under reduced pressure. The obtained residue was purified by silica gel column chromatography [Fuji Silysia Chemical Ltd., PSQ100B (spherical), eluent: 90-40% hexane/ethyl acetate] to obtain 0.077 g of tert-butyl 2-(2-hydroxy-4-(pyridin-3-yl)benzamido)-4-phenylbenzoate as a white solid.

A trifluoroacetic acid (5 mL) solution of the obtained tert-butyl 2-(2-hydroxy-4-(pyridin-3-yl)benzamido)-4-phenylbenzoate (0.077 g) was stirred at room temperature for 2 hours and 30 minutes. The solvent was evaporated under reduced pressure, and water and ethyl acetate were added to the obtained residue. After adjusting the pH to 6.5 with a saturated aqueous solution of sodium bicarbonate, the solid substance was collected by filtration. Methanol (3 mL), dioxane (3 mL), and a 2 mol/L aqueous solution of sodium hydroxide (0.073 mL) were added to the obtained solid substance. The insoluble substance was removed by filtration, and the solvent was evaporated under reduced pressure. Diisopropyl ether was added to the obtained residue. The solid substance was collected by filtration to obtain 0.063 g of sodium 2-(2-hydroxy-4-(pyridin-3-yl)benzamido)-4-phenylbenzoate as a light yellow solid.

$^1$H-NMR (DMSO-$d_6$) δ: 7.31-7.43 (4H, m), 7.47-7.55 (3H, m), 7.66-7.72 (2H, m), 8.10-8.22 (3H, m), 8.60-8.65 (1H, m), 8.91 (1H, d, J=2.0 Hz), 8.99 (1H, d, J=1.9 Hz).

Examples 14a to 17a

As in Example 13a, the compounds shown in Table 10a were prepared.

TABLE 10a

| Example No. | A |
|---|---|
| 14a | (3-methyl-5-(pyridin-4-yl)phenol structure) |
| 15a | (3-methyl-5-(pyrimidin-5-yl)phenol structure) |

TABLE 10a-continued

| Example No. | A |
|---|---|
| 16a | (2-methyl-6-(pyridin-3-yl)phenol structure) |
| 17a | (2-methyl-6-(pyridin-4-yl)phenol structure) |

Sodium 2-(2-hydroxy-4-(pyridin-4-yl)benzamido)-4-phenylbenzoate $^1$H-NMR (DMSO-$d_6$) δ: 7.33-7.44 (4H, m), 7.47-7.54 (2H, m), 7.66-7.72 (2H, m), 7.76-7.83 (2H, m), 8.12 (1H, d, J=7.8 Hz), 8.15 (1H, d, J=8.3 Hz), 8.60-8.76 (2H, m), 8.91 (1H, d, J=1.7 Hz).

Sodium 2-(2-hydroxy-4-(pyrimidin-5-yl)benzamido)-4-phenylbenzoate $^1$H-NMR (DMSO-$d_6$) δ: 7.34-7.54 (6H, m), 7.66-7.72 (2H, m), 8.12 (1H, d, J=8.1 Hz), 8.16 (1H, d, J=8.1 Hz), 8.91 (1H, d, J=1.7 Hz), 9.22-9.26 (3H, m).

Sodium 2-(2-hydroxy-3-(pyridin-3-yl)benzamido)-4-phenylbenzoate $^1$H-NMR (DMSO-$d_6$) δ: 7.12 (1H, dd, J=7.8, 7.8 Hz), 7.34-7.43 (2H, m), 7.45-7.53 (3H, m), 7.61 (1H, dd, J=7.4, 1.1 Hz), 7.65-7.71 (2H, m), 8.00-8.06 (1H, m), 8.10-8.16 (2H, m), 8.52-8.59 (1H, m), 8.79 (1H, d, J=1.7 Hz), 8.88 (1H, d, J=1.7 Hz).

Sodium 2-(2-hydroxy-3-(pyridin-4-yl)benzamido)-4-phenylbenzoate $^1$H-NMR (DMSO-$d_6$) δ: 7.04-7.21 (1H, m), 7.32-7.43 (2H, m), 7.46-7.54 (2H, m), 7.61-7.72 (5H, m), 8.06-8.22 (2H, m), 8.56-8.70 (2H, m), 8.86-8.92 (1H, m).

Example 18a

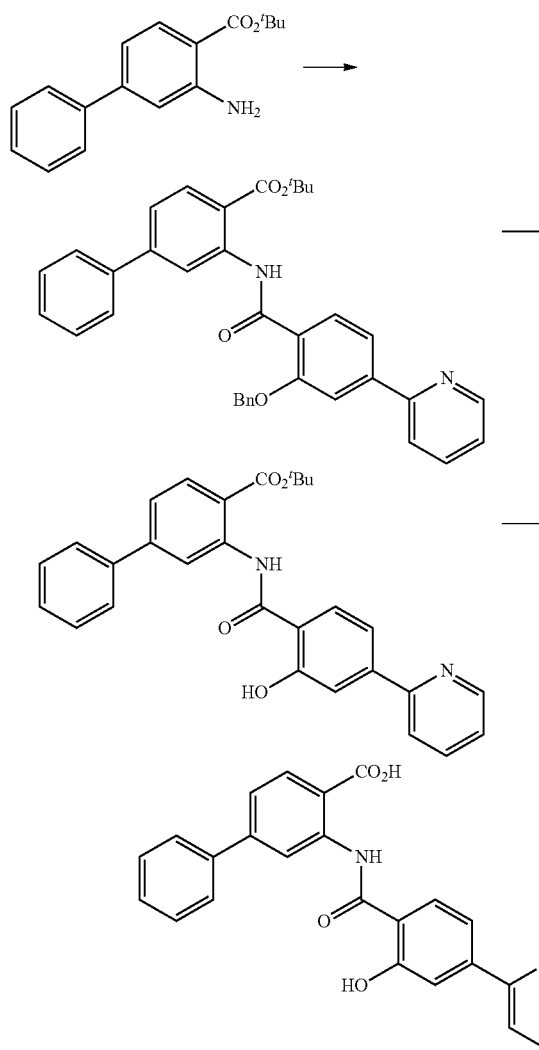

N,N-Dimethylformamide (2.4 μL) and oxalyl chloride (0.040 mL) were sequentially added to a methylene chloride (1.4 mL) suspension of 2-(benzyloxy)-4-(pyridin-2-yl)benzoic acid (0.095 g), followed by stirring at room temperature for 1 hour. The solvent was evaporated under reduced pressure, and toluene was added to the residue. The solvent was evaporated under reduced pressure, and methylene chloride (1.4 mL) was added to the residue. The resulting mixture was added to a solution mixture of tert-butyl 2-amino-4-phenylbenzoate (0.070 g) in pyridine (0.053 mL) and methylene chloride (1.4 mL), followed by stirring at room temperature for 2 hours. A 1 mol/L aqueous solution of sodium hydroxide was added to the reaction mixture. The organic layer was separated, washed with a 1 mol/L aqueous solution of sodium hydroxide, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 95-60% hexane/ethyl acetate] to obtain 0.13 g of tert-butyl 2-(2-(benzyloxy)-4-(pyridin-2-yl)benzamido)-4-phenylbenzoate as a white solid.

To a solution mixture of the obtained tert-butyl 2-(2-(benzyloxy)-4-(pyridin-2-yl)benzamido)-4-phenylbenzoate (0.13 g) in methanol (2 mL), dioxane (2 mL), and ethyl acetate (4 mL), 10% palladium-carbon (67 mg) was added, followed by stirring under a hydrogen atmosphere at room temperature for 2 hours and 30 minutes. Chloroform was added to the reaction mixture. The insoluble substance was removed by filtration, and the solvent was evaporated under reduced pressure. The obtained residue was purified by silica gel column chromatography [Fuji Silysia Chemical Ltd., PSQ100B (spherical), eluent: chloroform] to obtain 0.11 g of tert-butyl 2-(2-hydroxy-4-(pyridin-2-yl)benzamido)-4-phenylbenzoate as a white solid.

A trifluoroacetic acid (5 mL) solution of the obtained tert-butyl 2-(2-hydroxy-4-(pyridin-2-yl)benzamido)-4-phenylbenzoate (0.11 g) was stirred at room temperature for 3 hours. The solvent was evaporated under reduced pressure, and water and ethyl acetate were added to the obtained residue. After adjusting the pH to 6.0 with a saturated aqueous solution of sodium bicarbonate, the solid substance was collected by filtration. Water (4 mL), methanol (4 mL), and dioxane (4 mL) were added to the obtained solid substance, and carbon dioxide gas was introduced thereinto at room temperature. The solvent was evaporated under reduced pressure, and water was added to the obtained residue. The solid substance was collected by filtration to obtain 0.072 g of 2-(2-hydroxy-4-(pyridin-2-yl)benzamido)-4-phenylbenzoic acid as a light yellow solid.

$^1$H-NMR (DMSO-$d_6$) δ: 7.40-7.58 (5H, m), 7.69 (1H, dd, J=8.3, 1.7 Hz), 7.72-7.77 (2H, m), 7.80 (1H, d, J=1.4 Hz), 7.93 (1H, ddd, J=7.8, 7.8, 1.8 Hz), 7.98-8.06 (2H, m), 8.11 (1H, d, J=8.3 Hz), 8.69-8.74 (1H, m), 9.05 (1H, d, J=1.7 Hz), 11.55-11.78 (1H, broad), 12.40-12.62 (1H, broad).

Example 19a

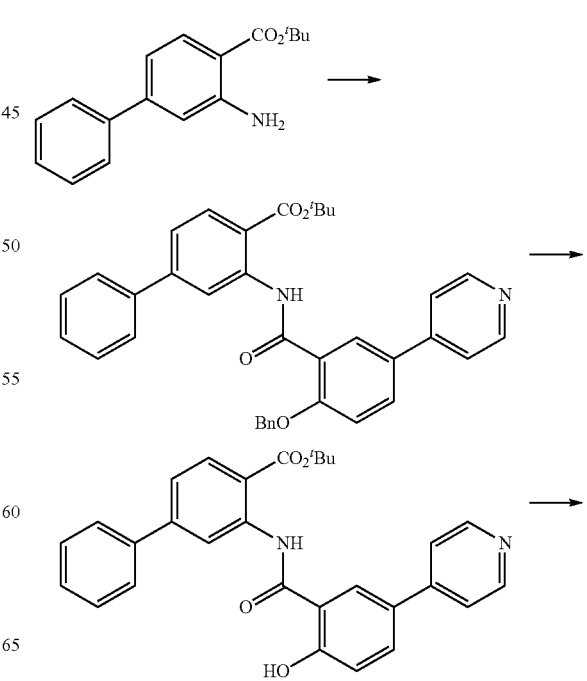

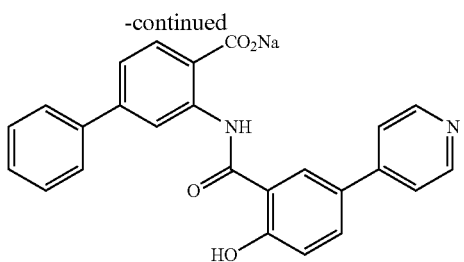

N,N-Dimethylformamide (2.4 µL) and oxalyl chloride (0.040 mL) were sequentially added to a methylene chloride (2 mL) suspension of 2-(benzyloxy)-5-(pyridin-4-yl)benzoic acid (0.095 g), followed by stirring at room temperature for 2 hours and 30 minutes. The solvent was evaporated under reduced pressure, and toluene was added to the residue. The solvent was evaporated under reduced pressure, and methylene chloride (1.5 mL) was added to the residue. The resulting mixture was added to a solution mixture of tert-butyl 2-amino-4-phenylbenzoate (0.070 g) in pyridine (0.053 mL) and methylene chloride (2 mL), followed by stirring at room temperature for 1 hour. A 1 mol/L aqueous solution of sodium hydroxide was added to the reaction mixture. The organic layer was separated, washed with a 1 mol/L aqueous solution of sodium hydroxide, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 90-40% hexane/ethyl acetate] to obtain 0.11 g of tert-butyl 2-(2-(benzyloxy)-5-(pyridin-4-yl)benzamido)-4-phenylbenzoate.

$^1$H-NMR (DMSO-d$_6$) δ: 1.51 (9H, s), 5.59 (2H, s), 7.26-7.42 (4H, m), 7.44-7.62 (6H, m), 7.67-7.80 (4H, m), 7.97 (1H, dd, J=8.8, 2.4 Hz), 8.07 (1H, d, J=8.3 Hz), 8.39 (1H, d, J=2.4 Hz), 8.58-8.67 (2H, m), 9.14 (1H, s), 12.25 (1H, s).

To an acetic acid (2 mL) solution of the obtained tert-butyl 2-(2-(benzyloxy)-5-(pyridin-4-yl)benzamido)-4-phenylbenzoate (0.11 g), 10% palladium-carbon (0.11 g) was added, followed by stirring under a hydrogen atmosphere at room temperature for 2 hours. The insoluble substance was removed by filtration, and the solvent was evaporated under reduced pressure. Ethyl acetate and a saturated aqueous solution of sodium bicarbonate were added to the residue. The organic layer was separated, washed with a saturated aqueous solution of sodium bicarbonate and a saturated aqueous solution of sodium chloride sequentially, and dried over anhydrous magnesium sulfate, and the solvent was evaporated under reduced pressure. Trifluoroacetic acid (5 mL) was added to the obtained residue, followed by stirring at room temperature for 5 hours. The solvent was evaporated under reduced pressure, and water and ethyl acetate were added to the residue. After adjusting the pH to 6.5 with a saturated aqueous solution of sodium bicarbonate, the solid substance was collected by filtration, and methanol (10 mL), dioxane (10 mL), and a 2 mol/L aqueous solution of sodium hydroxide (0.078 mL) were added to the obtained solid substance. Then, the insoluble substance was removed by filtration, and the solvent was evaporated under reduced pressure. Diisopropyl ether was added to the obtained residue, and the solid substance was collected by filtration to obtain 0.067 g of sodium 2-(2-hydroxy-5-(pyridin-4-yl)benzamido)-4-phenylbenzoate as a yellow solid.

$^1$H-NMR (DMSO-d$_6$) δ: 7.08 (1H, d, J=8.8 Hz), 7.36 (1H, dd, J=8.1, 1.7 Hz), 7.35-7.43 (1H, m), 7.47-7.54 (2H, m), 7.66-7.72 (2H, m), 7.73-7.79 (2H, m), 7.92-8.00 (1H, m), 8.12 (1H, d, J=8.1 Hz), 8.54 (1H, d, J=2.2 Hz), 8.60-8.70 (2H, m), 8.91 (1H, d, J=1.7 Hz).

Example 20a

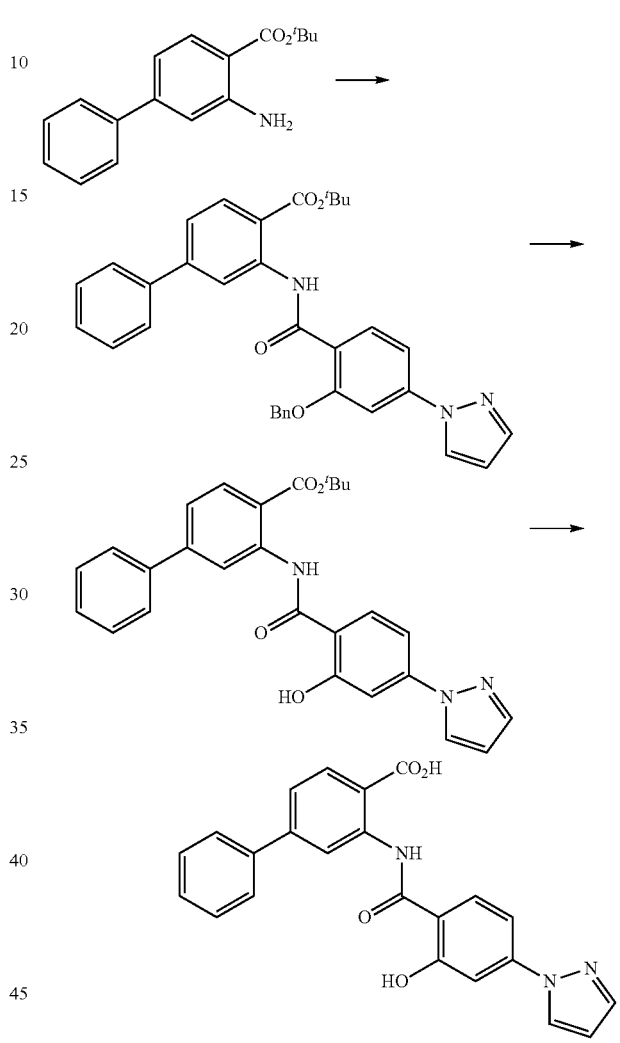

N,N-Dimethylformamide (2.4 µL) and oxalyl chloride (0.040 mL) were sequentially added to a methylene chloride (1.4 mL) suspension of 2-(benzyloxy)-4-(1H-pyrazol-1-yl)benzoic acid (0.092 g), followed by stirring at room temperature for 1 hours. The solvent was evaporated under reduced pressure, and toluene was added to the residue. The solvent was evaporated under reduced pressure, and methylene chloride (1.4 mL) was added to the residue. The resulting mixture was added to a solution mixture of tert-butyl 2-amino-4-phenylbenzoate (0.070 g) in pyridine (0.053 mL) and methylene chloride (1.4 mL), followed by stirring at room temperature for 1 hour. A saturated aqueous solution of sodium bicarbonate was added to the reaction mixture, and the organic layer was separated. The obtained organic layer was purified by silica gel column chromatography [Fuji Silysia Chemical Ltd., PSQ100B (spherical), eluent: 95-70% hexane/ethyl acetate] to obtain 0.098 g of tert-butyl 2-(2-(benzyloxy)-4-(1H-pyrazol-1-yl)benzamido)-4-phenylbenzoate as a white solid.

To a solution mixture of the obtained tert-butyl 2-(2-(benzyloxy)-4-(1H-pyrazol-1-yl)benzamido)-4-phenylbenzoate (0.098 g) in ethyl acetate (2 mL), methanol (1 mL), and dioxane (1 mL), 10% palladium-carbon (49 mg) was added, followed by stirring under a hydrogen atmosphere at room temperature for 2 hours. Chloroform was added to the reaction mixture, and the insoluble substance was removed by filtration. The solvent was evaporated under reduced pressure. The obtained residue was purified by silica gel column chromatography [Fuji Silysia Chemical Ltd., PSQ100B (spherical), eluent: chloroform] to obtain tert-butyl 2-(2-hydroxy-4-(1H-pyrazol-1-yl)benzamido)-4-phenylbenzoate.

A trifluoroacetic acid (5 mL) solution of the obtained tert-butyl 2-(2-hydroxy-4-(1H-pyrazol-1-yl)benzamido)-4-phenylbenzoate was stirred at room temperature for 3 hours and 30 minutes. The solvent was evaporated under reduced pressure, and methanol was added to the obtained residue. The solid substance was collected by filtration to obtain 0.056 g of 2-(2-hydroxy-4-(1H-pyrazol-1-yl)benzamido)-4-phenylbenzoic acid as a white solid.

$^1$H-NMR (DMSO-d$_6$) δ: 6.60 (1H, dd, J=2.6, 1.8 Hz), 7.43-7.58 (6H, m), 7.71-7.77 (2H, m), 7.81 (1H, d, J=1.7 Hz), 8.03 (1H, d, J=8.8 Hz), 8.11 (1H, d, J=8.3 Hz), 8.58 (1H, d, J=2.4 Hz), 9.02 (1H, d, J=1.7 Hz), 11.90 (1H, s), 12.33 (1H, s), 13.38-13.64 (1H, broad).

Examples 21a and 22a

As in Example 20a, the compounds shown in Table 11a were prepared.

TABLE 11a

| Example No. | A |
|---|---|
| 21a | (3-hydroxy-4-(pyrimidin-2-yl)phenyl) |
| 22a | (4-hydroxy-3-methyl-phenyl with pyrazole) |

2-(2-Hydroxy-4-(pyrimidin-2-yl)benzamido)-4-phenylbenzoic acid $^1$H-NMR (DMSO-d$_6$) δ: 7.43-7.58 (5H, m), 7.71-7.77 (2H, m), 7.99 (1H, dd, J=8.4, 1.6 Hz), 8.04-8.14 (3H, m), 8.96 (2H, d, J=4.9 Hz), 9.07 (1H, d, J=1.7 Hz), 11.62 (1H, s), 12.42 (1H, s), 13.35-13.60 (1H, broad).

2-(2-hydroxy-5-(1H-pyrazol-1-yl)benzamido)-4-phenylbenzoic acid $^1$H-NMR (DMSO-d$_6$) δ: 6.53 (1H, dd, J=2.1, 2.1 Hz), 7.14 (1H, d, J=9.0 Hz), 7.43-7.50 (1H, m), 7.51-7.58 (3H, m), 7.71-7.77 (3H, m), 7.90 (1H, dd, J=8.8, 2.9 Hz), 8.11 (1H, d, J=8.3 Hz), 8.34 (1H, d, J=2.7 Hz), 8.42 (1H, d, J=2.4 Hz), 9.06 (1H, d, J=1.7 Hz), 11.52-11.70 (1H, broad), 12.35-12.50 (1H, broad).

Example 23a

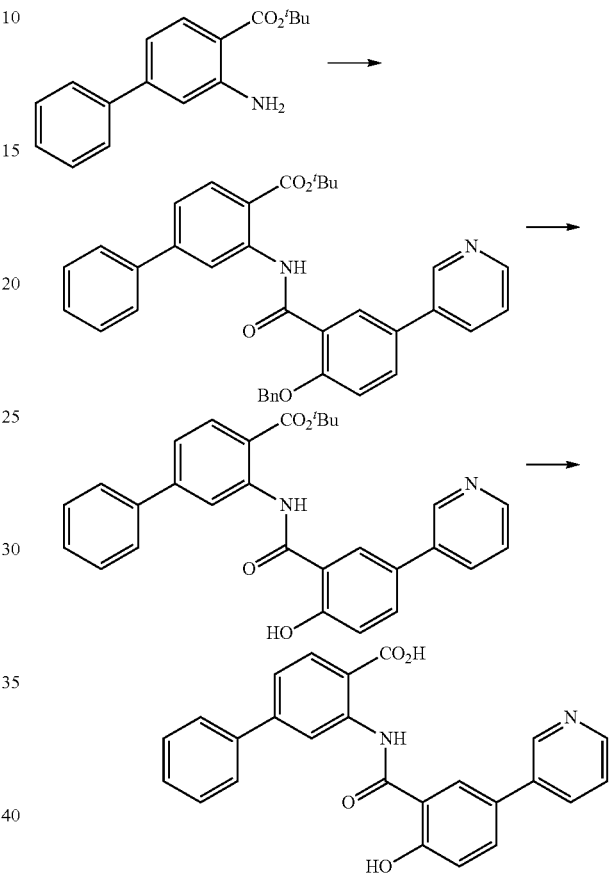

N,N-Dimethylformamide (2.4 µL) and oxalyl chloride (0.040 mL) were sequentially added to a methylene chloride (2 mL) suspension of 2-(benzyloxy)-5-(pyridin-3-yl)benzoic acid (0.095 g), followed by stirring at room temperature for 2 hours and 30 minutes. The solvent was evaporated under reduced pressure, and toluene was added to the residue. The solvent was evaporated under reduced pressure, and methylene chloride (1.5 mL) was added to the residue. The resulting mixture was added to a solution mixture of tert-butyl 2-amino-4-phenylbenzoate (0.070 g) in pyridine (0.053 mL) and methylene chloride (2 mL), followed by stirring at room temperature for 1 hour. A 1 mol/L aqueous solution of sodium hydroxide was added to the reaction mixture. The organic layer was separated, washed with a 1 mol/L aqueous solution of sodium hydroxide, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 90-50% hexane/ethyl acetate] to obtain 0.14 g of tert-butyl 2-(2-(benzyloxy)-5-(pyridin-3-yl)benzamido)-4-phenylbenzoate.

$^1$H-NMR (DMSO-d$_6$) δ: 1.51 (9H, s), 5.58 (2H, s), 7.26-7.42 (4H, m), 7.44-7.63 (7H, m), 7.70-7.78 (2H, m), 7.89 (1H, dd, J=8.8, 2.4 Hz), 8.04-8.13 (2H, m), 8.28 (1H, d, J=2.4 Hz), 8.56 (1H, dd, J=4.6, 1.4 Hz), 8.89 (1H, d, J=2.4 Hz), 9.12-9.17 (1H, m), 12.25 (1H, s).

To a solution mixture of the obtained tert-butyl 2-(2-(benzyloxy)-5-(pyridin-3-yl)benzamido)-4-phenylbenzoate (0.14 g) in ethyl acetate (1 mL) and methanol (1 mL), 10% palladium-carbon (14 mg) was added, followed by stirring under a hydrogen atmosphere at room temperature for 1 hour and 30 minutes. To the reaction mixture, 10% palladium-carbon (14 mg) was added. The resulting mixture was stirred under a hydrogen atmosphere at room temperature for 2 hours and 30 minutes. Acetic acid (2 mL) and 10% palladium-carbon (0.11 g) were added to the reaction mixture, followed by stirring under a hydrogen atmosphere at room temperature for 2 hours. The insoluble substance was removed by filtration, and the solvent was evaporated under reduced pressure. Ethyl acetate and a saturated aqueous solution of sodium bicarbonate were added to the residue. The organic layer was separated, washed with a saturated aqueous solution of sodium bicarbonate and a saturated aqueous solution of sodium chloride sequentially, and dried over anhydrous magnesium sulfate, and the solvent was evaporated under reduced pressure. Trifluoroacetic acid (5 mL) was added to the obtained residue, followed by stirring at room temperature for 5 hours. The solvent was evaporated under reduced pressure, and water and ethyl acetate were added to the residue. After adjusting the pH to 5 with a saturated aqueous solution of sodium bicarbonate, the solid substance was collected by filtration to obtain 0.070 g of 2-(2-hydroxy-5-(pyridin-3-yl)benzamido)-4-phenylbenzoic acid as a white solid.

$^1$H-NMR (DMSO-$d_6$) δ: 7.16 (1H, d, J=8.5 Hz), 7.43-7.59 (5H, m), 7.70-7.78 (2H, m), 7.86 (1H, dd, J=8.5, 2.3 Hz), 8.05-8.11 (1H, m), 8.12 (1H, d, J=8.0 Hz), 8.26 (1H, d, J=2.3 Hz), 8.53-8.59 (1H, m), 8.91 (1H, d, J=2.0 Hz), 9.03 (1H, d, J=1.5 Hz).

Example 24a

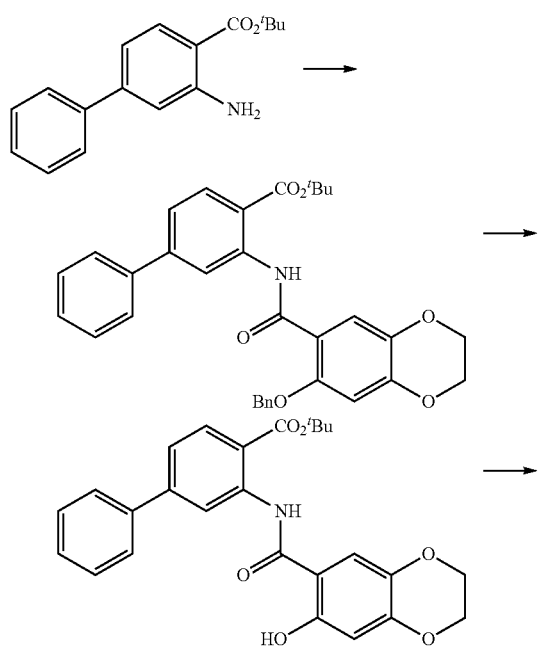

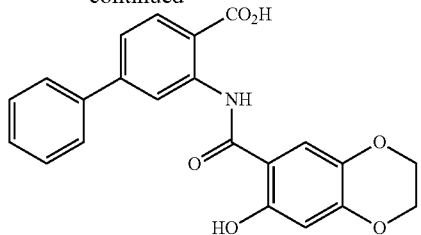

-continued

N,N-Dimethylformamide (8.8 μL) and oxalyl chloride (0.15 mL) were sequentially added to a methylene chloride (3.0 mL) suspension of 7-(benzyloxy)-2,3-dihydrobenzo[1,4]dioxine-6-carboxylic acid (0.33 g), followed by stirring at room temperature for 40 minutes. The solvent was evaporated under reduced pressure, and methylene chloride (3 mL) was added to the residue. The resulting mixture was added to a solution mixture of tert-butyl 2-amino-4-phenylbenzoate (0.26 g) in pyridine (0.20 mL) and methylene chloride (3.0 mL), followed by stirring at room temperature for 40 minutes. The solvent was evaporated under reduced pressure, and 1 mol/L hydrochloric acid and chloroform were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 90-65% hexane/ethyl acetate] to obtain 0.49 g of tert-butyl 2-(7-(benzyloxy)-2,3-dihydrobenzo[1,4]dioxine-6-carboxamido)-4-phenylbenzoate as a white solid.

To a solution mixture of the obtained tert-butyl 2-(7-(benzyloxy)-2,3-dihydrobenzo[1,4]dioxine-6-carboxamido)-4-phenylbenzoate (0.49 g) in methanol (4 mL) and ethyl acetate (4 mL), 10% palladium-carbon (0.24 g) was added, followed by stirring under a hydrogen atmosphere at room temperature for 3 hours. The insoluble substance was removed by filtration, and the solvent was evaporated under reduced pressure. Diisopropyl ether was added to the obtained residue, and the solid substance was collected by filtration to obtain 0.37 g of tert-butyl 2-(7-hydroxy-2,3-dihydrobenzo[1,4]dioxine-6-carboxamido)-4-phenylbenzoate as a white solid.

A trifluoroacetic acid (4 mL) solution of the obtained tert-butyl 2-(7-hydroxy-2,3-dihydrobenzo[1,4]dioxine-6-carboxamido)-4-phenylbenzoate (0.37 g) was stirred at room temperature for 15 minutes. Methylene chloride (10 mL) was added to the reaction mixture, followed by stirring at room temperature for 1 hour and 15 minutes. The solvent was evaporated under reduced pressure, and ethyl acetate was added to the obtained residue. The solid substance was collected by filtration to obtain 0.30 g of 2-(7-hydroxy-2,3-dihydrobenzo[1,4]dioxine-6-carboxamido)-4-phenylbenzoic acid as a white solid.

$^1$H-NMR (DMSO-$d_6$) δ: 4.18-4.26 (2H, m), 4.26-4.35 (2H, m), 6.48 (1H, s), 7.39 (1H, s), 7.41-7.57 (4H, m), 7.68-7.75

(2H, m), 8.08 (1H, d, J=8.3 Hz), 8.97 (1H, d, J=2.0 Hz), 11.24 (1H, s), 12.19 (1H, s), 13.35-13.60 (1H, broad).

Example 25a

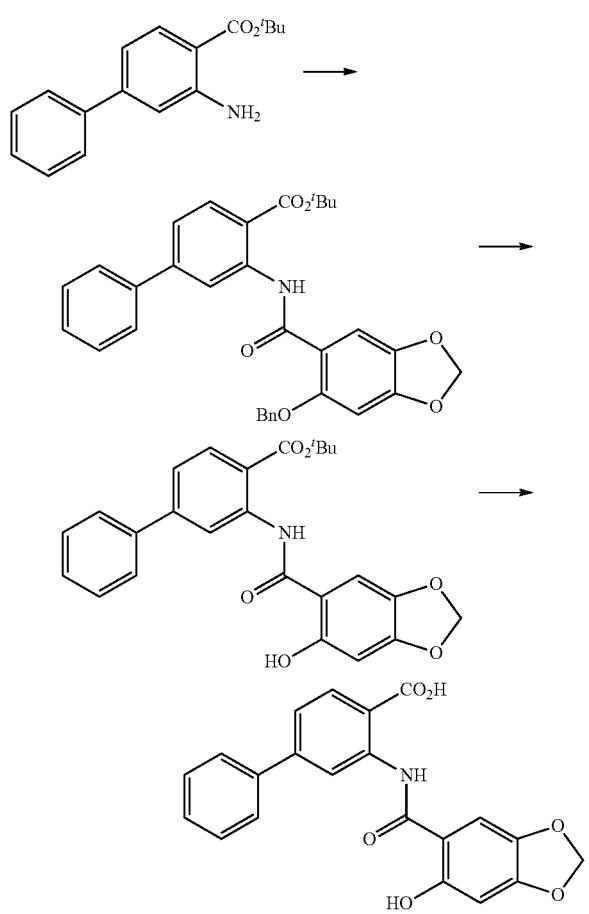

As in Example 24a, the following compound was prepared.

2-(6-Hydroxy-benzo[1,3]dioxazole-5-carboxamido)-4-phenylbenzoic acid $^1$H-NMR (DMSO-d$_6$) δ: 6.07 (1H, s), 6.60 (1H, d, J=0.7 Hz), 7.34 (1H, d, J=0.7 Hz), 7.42-7.59 (4H, m), 7.68-7.78 (2H, m), 8.09 (1H, d, J=8.0 Hz), 8.90-8.96 (1H, m), 11.85 (1H, s), 12.17 (1H, s), 13.40-13.70 (1H, broad).

Example 26a

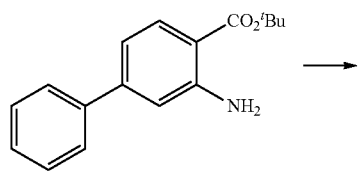

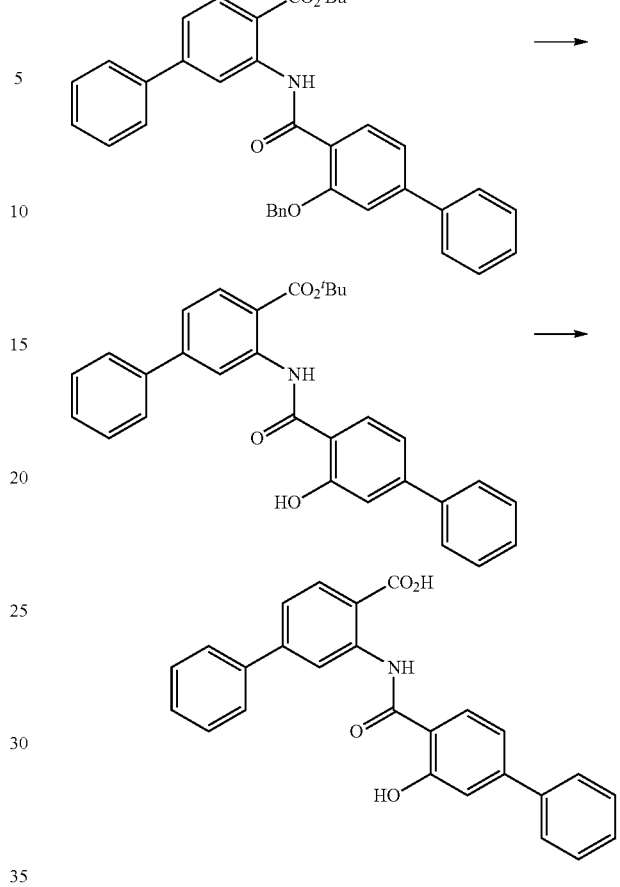

N,N-Dimethylformamide (4.6 and oxalyl chloride (0.077 mL) were sequentially added to a methylene chloride (2 mL) solution of 2-(benzyloxy)-4-phenylbenzoic acid (0.18 g), followed by stirring at room temperature for 25 minutes. The solvent was evaporated under reduced pressure, and methylene chloride (2 mL) was added to the residue. The resulting mixture was added to a solution mixture of tert-butyl 2-amino-4-phenylbenzoate (0.14 g) in pyridine (0.10 mL) and methylene chloride (2 mL), followed by stirring at room temperature for 30 minutes. The solvent was evaporated under reduced pressure, and water and chloroform were added to the residue. The organic layer was separated, washed with a saturated aqueous solution of sodium chloride, and dried over anhydrous magnesium sulfate, and the solvent was evaporated under reduced pressure. The reaction mixture was purified by silica gel column chromatography [Kanto Chemical Co., Inc., silica gel 60 (spherical), eluent: 90-75% hexane/ethyl acetate to chloroform] to obtain 0.11 g of tert-butyl 2-(2-(benzyloxy)-4-phenylbenzamido)-4-phenylbenzoate as a white solid.

To a solution mixture of the obtained tert-butyl 2-(2-(benzyloxy)-4-phenylbenzamido)-4-phenylbenzoate (0.11 g) in methanol (4 mL) and chloroform (4 mL), 10% palladium-carbon (40 mg) was added, followed by stirring under a hydrogen atmosphere at room temperature for 5 hours and 30 minutes and then at 35° C. for 1 hour. To the reaction mixture, 10% palladium-carbon (40 mg) was added, followed by stirring under a hydrogen atmosphere at 35° C. for 2 hours. The insoluble substance was removed by filtration, and the solvent was evaporated under reduced pressure. Diisopropyl ether and hexane were added to the obtained residue, and the solid substance was collected by filtration to obtain tert-butyl 2-(2-hydroxy-4-phenylbenzamido)-4-phenylbenzoate.

A solution mixture of the obtained tert-butyl 2-(2-hydroxy-4-phenylbenzamido)-4-phenylbenzoate in methylene chloride (6 mL) and trifluoroacetic acid (1 mL) was stirred at room temperature for 3 hours and 10 minutes. Trifluoroacetic acid (2 mL) was added to the reaction mixture, followed by stirring at room temperature for 1 hour. The solvent was evaporated under reduced pressure, and diisopropyl ether was added to the obtained residue. The solid substance was collected by filtration to obtain 0.076 g of 2-(2-hydroxy-4-phenylbenzamido)-4-phenylbenzoic acid as a white solid.

$^1$H-NMR (DMSO-$d_6$) δ: 7.29 (1H, d, J=1.7 Hz), 7.31 (1H, dd, J=8.2, 1.8 Hz), 7.40-7.60 (7H, m), 7.66-7.79 (4H, m), 8.00 (1H, d, J=8.3 Hz), 8.11 (1H, d, J=8.1 Hz), 9.04 (1H, d, J=2.0 Hz), 11.66 (1H, s), 12.36 (1H, s), 13.35-13.70 (1H, broad).

Example 27a

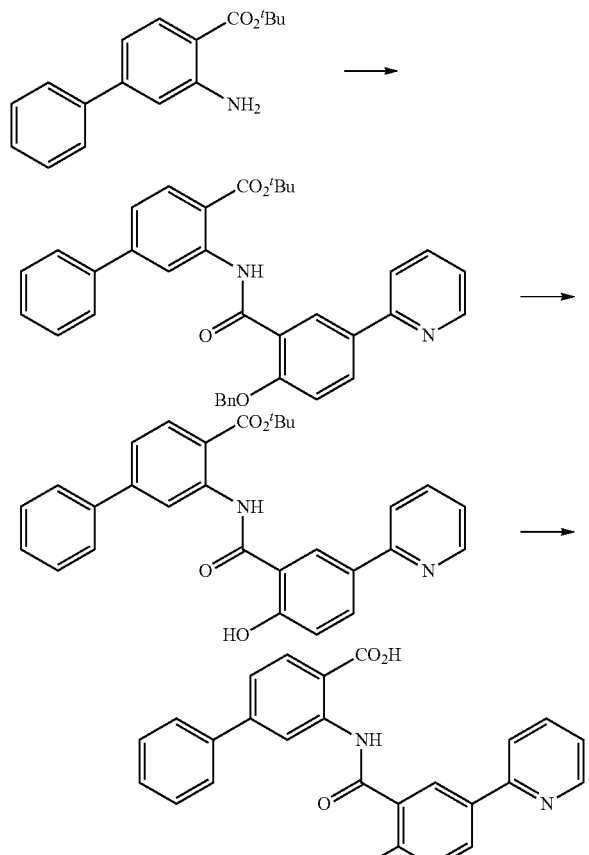

N,N-Dimethylformamide (1.5 µL) and oxalyl chloride (0.023 mL) were sequentially added to a methylene chloride (2 mL) suspension of 2-(benzyloxy)-5-(pyridin-2-yl)benzoic acid (0.050 g), followed by stirring at room temperature for 1 hour. The solvent was evaporated under reduced pressure, and toluene was added to the residue. The solvent was evaporated under reduced pressure, and methylene chloride (2 mL) was added to the residue. The resulting mixture was added to a solution mixture of tert-butyl 2-amino-4-phenylbenzoate (0.053 g) in pyridine (0.033 mL) and methylene chloride (2 mL), followed by stirring at room temperature for 1 hour. The solvent was evaporated under reduced pressure, and the obtained residue was purified by silica gel column chromatography [eluent: 95-70% hexane/ethyl acetate] to obtain 0.038 g of tert-butyl 2-(2-(benzyloxy)-5-(pyridin-2-yl)benzamido)-4-phenylbenzoate as a white solid.

$^1$H-NMR (CDCl$_3$) δ: 1.53 (9H, s), 5.56 (2H, s), 7.08 (1H, d, J=8.8 Hz), 7.18 (1H, ddd, J=7.4, 4.8, 1.2 Hz), 7.23-7.52 (9H, m), 7.68-7.81 (4H, m), 8.07 (1H, d, J=8.3 Hz), 8.15 (1H, dd, J=8.8, 2.4 Hz), 8.61-8.66 (1H, m), 8.74 (1H, d, J=2.4 Hz), 9.31-9.35 (1H, m), 12.54 (1H, s).

To a solution mixture of the obtained tert-butyl 2-(2-(benzyloxy)-5-(pyridin-2-yl)benzamido)-4-phenylbenzoate (0.038 g) in ethyl acetate (2 mL) and methanol (4 mL), 10% palladium-carbon (20 mg) was added, followed by stirring under a hydrogen atmosphere at room temperature for 2 hours and 45 minutes. The insoluble substance was removed by filtration, and the solvent was evaporated under reduced pressure. The obtained residue was purified by silica gel column chromatography [eluent: 95-70% hexane/ethyl acetate] to obtain 0.021 g of tert-butyl 2-(2-hydroxy-5-(pyridin-2-yl)benzamido)-4-phenylbenzoate as a white solid.

A solution mixture of the obtained tert-butyl 2-(2-hydroxy-5-(pyridin-2-yl)benzamido)-4-phenylbenzoate (0.021 g) in methylene chloride (1 mL) and trifluoroacetic acid (0.5 mL) was stirred at room temperature for 1 hour and 10 minutes. The solvent was evaporated under reduced pressure, and water was added to the obtained residue. After adjusting the pH to 7 with a saturated aqueous solution of sodium bicarbonate, the solid substance was collected by filtration to obtain 0.013 g of 2-(2-hydroxy-5-(pyridin-2-yl)benzamido)-4-phenylbenzoic acid as a white solid.

$^1$H-NMR (DMSO-$d_6$) δ: 7.15 (1H, d, J=8.6 Hz), 7.31-7.39 (1H, m), 7.43-7.60 (4H, m), 7.71-7.79 (2H, m), 7.86-8.00 (2H, m), 8.12 (1H, d, J=8.1 Hz), 8.18 (1H, dd, J=8.5, 2.2 Hz), 8.66 (1H, d, J=4.9 Hz), 8.69 (1H, d, J=2.0 Hz), 9.04-9.10 (1H, m), 11.81 (1H, s), 12.39 (1H, s).

Example 28a

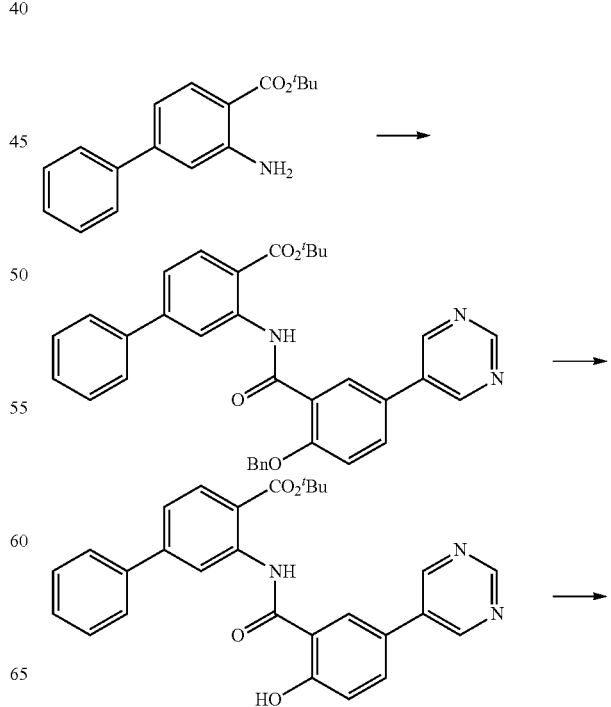

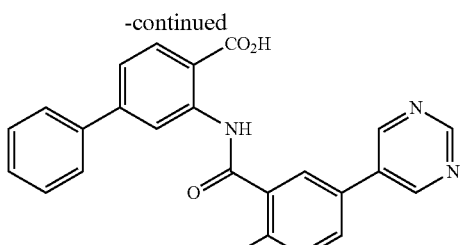

9.04 (1H, d, J=1.7 Hz), 9.14 (2H, s), 9.17 (1H, s), 11.72-11.92 (1H, broad), 12.28-12.50 (1H, broad), 13.44-13.72 (1H, broad).

Example 29a

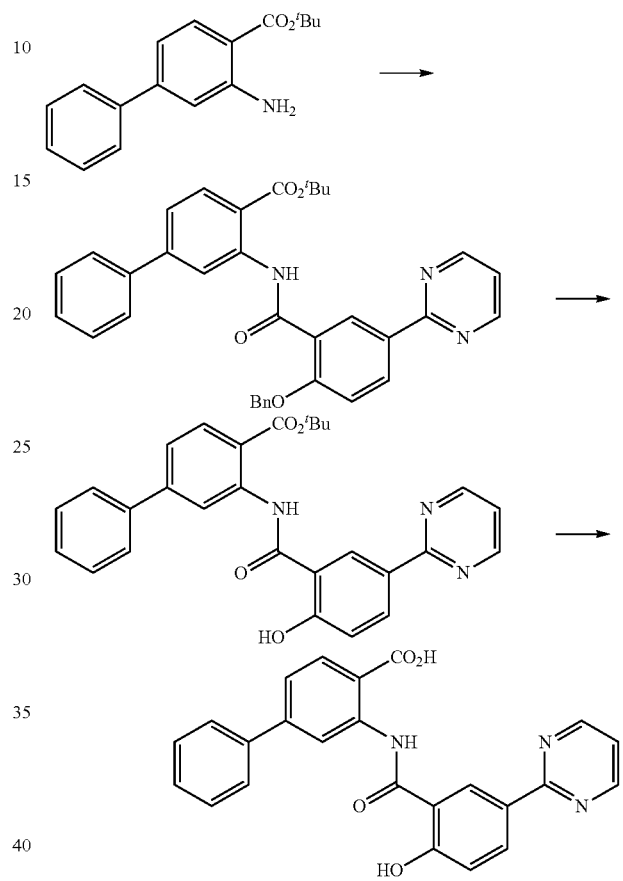

N,N-Dimethylformamide (0.024 mL) and oxalyl chloride (0.40 mL) were sequentially added to a methylene chloride (20 mL) suspension of 2-(benzyloxy)-5-(pyrimidin-5-yl)benzoic acid (0.80 g), followed by stirring at room temperature for 1 hour and 30 minutes. The solvent was evaporated under reduced pressure, and methylene chloride (20 mL) was added to the residue. The resulting mixture was added to a solution mixture of tert-butyl 2-amino-4-phenylbenzoate (0.74 g) in pyridine (0.59 mL) and methylene chloride (20 mL), followed by stirring at room temperature for 1 hour and 10 minutes. The solvent was evaporated under reduced pressure, and water and chloroform were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 80-50% hexane/ethyl acetate] to obtain 1.1 g of tert-butyl 2-(2-(benzyloxy)-5-(pyrimidin-5-yl)benzamido)-4-phenylbenzoate as a white solid.

To a solution mixture of the obtained tert-butyl 2-(2-(benzyloxy)-5-(pyrimidin-5-yl)benzamido)-4-phenylbenzoate (1.1 g) in ethyl acetate (10 mL), methanol (20 mL), and dioxane (20 mL), 10% palladium-carbon (0.57 g) was added, followed by stirring under a hydrogen atmosphere at room temperature for 2 hours and 20 minutes. The insoluble substance was removed by filtration, and the solvent was evaporated under reduced pressure. The obtained residue was purified by silica gel column chromatography [Fuji Silysia Chemical Ltd., PSQ100B (spherical), eluent: 70-0% hexane/ethyl acetate] to obtain 0.73 g of tert-butyl 2-(2-hydroxy-5-(pyrimidin-5-yl)benzamido)-4-phenylbenzoate as a white solid.

A solution mixture of the obtained tert-butyl 2-(2-hydroxy-5-(pyrimidin-5-yl)benzamido)-4-phenylbenzoate (0.73 g) in methylene chloride (25 mL) and trifluoroacetic acid (10 mL) was stirred at room temperature overnight. The solvent was evaporated under reduced pressure, and water was added to the obtained residue. After adjusting the pH to 6.5 with a saturated aqueous solution of sodium bicarbonate, the solid substance was collected by filtration to obtain 0.49 g of 2-(2-hydroxy-5-(pyrimidin-5-yl)benzamido)-4-phenylbenzoic acid as a white solid.

$^1$H-NMR (DMSO-$d_6$) δ: 7.19 (1H, d, J=8.5 Hz), 7.43-7.50 (1H, m), 7.51-7.60 (3H, m), 7.70-7.78 (2H, m), 7.93 (1H, dd, J=8.5, 2.4 Hz), 8.12 (1H, d, J=8.3 Hz), 8.31 (1H, d, J=2.2 Hz),

N,N-Dimethylformamide (0.019 mL) and oxalyl chloride (0.32 mL) were sequentially added to a methylene chloride (20 mL) suspension of 2-(benzyloxy)-5-(pyrimidin-2-yl)benzoic acid (0.64 g), followed by stirring at room temperature for 1 hour and 10 minutes. The solvent was evaporated under reduced pressure, and methylene chloride (20 mL) was added to the residue. The resulting mixture was added to a solution mixture of tert-butyl 2-amino-4-phenylbenzoate (0.59 g) in pyridine (0.47 mL) and methylene chloride (20 mL), followed by stirring at room temperature for 1 hour and 20 minutes. The solvent was evaporated under reduced pressure, and water and ethyl acetate were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 70-50% hexane/ethyl acetate] to obtain 0.94 g of tert-butyl 2-(2-(benzyloxy)-5-(pyrimidin-2-yl)benzamido)-4-phenylbenzoate.

To a solution mixture of the obtained tert-butyl 2-(2-(benzyloxy)-5-(pyrimidin-2-yl)benzamido)-4-phenylbenzoate (0.072 g) in ethyl acetate (4 mL) and methanol (4 mL), 10% palladium-carbon (36 mg) was added, followed by stirring under a hydrogen atmosphere at room temperature for 2 hours and 45 minutes. The insoluble substance was removed by filtration, and the solvent was evaporated under reduced pressure. The obtained residue was purified by silica gel column chromatography [eluent: 75-60% hexane/ethyl acetate] to obtain 5 mg of tert-butyl 2-(2-hydroxy-5-(pyrimidin-2-yl)benzamido)-4-phenylbenzoate as a white solid.

A solution mixture of the obtained tert-butyl 2-(2-hydroxy-5-(pyrimidin-2-yl)benzamido)-4-phenylbenzoate (5 mg) in methylene chloride (2 mL) and trifluoroacetic acid (0.50 mL) was stirred at room temperature for 3 hours and 30 minutes. The solvent was evaporated under reduced pressure, and water and chloroform were added to the residue. The organic layer was separated and dried over anhydrous magnesium sulfate, and the solvent was evaporated under reduced pressure. Diisopropyl ether was added to the obtained residue, and the solid substance was collected by filtration to obtain 4 mg of 2-(2-hydroxy-5-(pyrimidin-2-yl)benzamido)-4-phenylbenzoic acid as a white solid.

$^1$H-NMR (DMSO-$d_6$) δ: 7.20-7.57 (6H, m), 7.64-7.77 (2H, m), 7.96-8.54 (2H, m), 8.64-9.14 (4H, m).

Example 30a

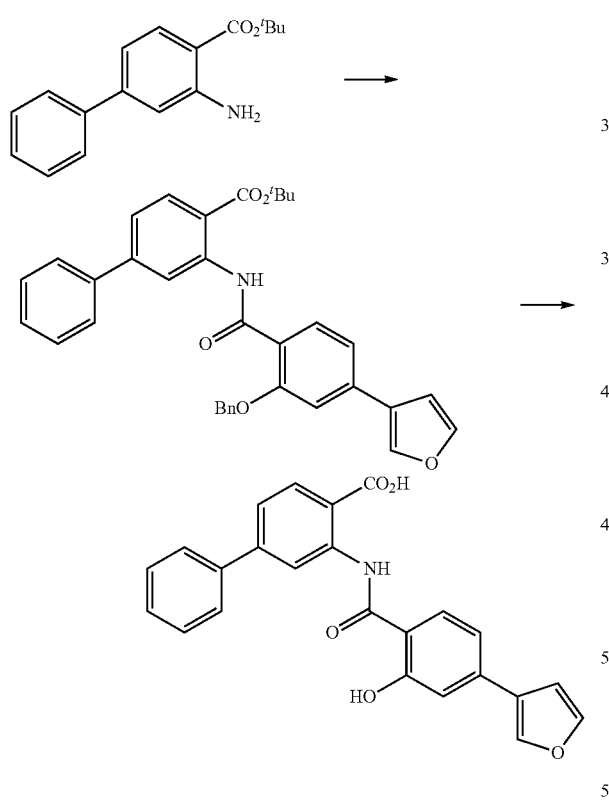

Methylene chloride (2 mL) was added to 2-(benzyloxy)-4-(furan-3-yl)benzoic acid (0.099 g), and N,N-dimethylformamide (3 μL) and oxalyl chloride (0.043 mL) were sequentially added thereto under ice-cooling, followed by stirring at the same temperature for 10 minutes and then at room temperature for 50 minutes. Oxalyl chloride (0.043 mL) was added to the reaction mixture at room temperature, followed by stirring at the same temperature for 20 minutes. The solvent was evaporated under reduced pressure, and methylene chloride (2 mL) was added to the residue. The resulting mixture was added to a solution mixture of tert-butyl 2-amino-4-phenylbenzoate (0.075 g) in pyridine (0.057 mL) and methylene chloride (2 mL) under ice-cooling, followed by stirring at room temperature for 1 hour and 30 minutes. The solvent was evaporated under reduced pressure, and 1 mol/L hydrochloric acid and ethyl acetate were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 95-80% hexane/ethyl acetate] and further purified by silica gel column chromatography [eluent: toluene] to obtain 0.077 g of tert-butyl 2-(2-(benzyloxy)-4-(furan-3-yl)benzamido)-4-phenylbenzoate as a light yellow solid.

Thioanisole (0.82 mL) and trifluoroacetic acid (2.6 mL) were added to the obtained tert-butyl 2-(2-(benzyloxy)-4-(furan-3-yl)benzamido)-4-phenylbenzoate (0.076 g), followed by stirring at room temperature for 3 hours and 20 minutes. The solvent was evaporated under reduced pressure, and a 2 mol/L aqueous solution of sodium hydroxide and toluene were added to the residue. The aqueous layer was separated and adjusted to a pH of 4.5 with 6 mol/L hydrochloric acid. The solid substance was collected by filtration to obtain 0.016 g of 2-(4-(furan-3-yl)-2-hydroxybenzamido)-4-phenylbenzoic acid as a brown solid.

$^1$H-NMR (DMSO-$d_6$) δ: 6.98 (1H, s), 7.23 (1H, s), 7.28 (1H, d, J=8.3 Hz), 7.41-7.59 (4H, m), 7.68-7.82 (3H, m), 7.92 (1H, d, J=8.3 Hz), 8.11 (1H, d, J=8.3 Hz), 8.29 (1H, s), 8.99 (1H, s), 11.73 (1H, s), 12.38 (1H, s), 13.30-13.80 (1H, broad).

Example 31a

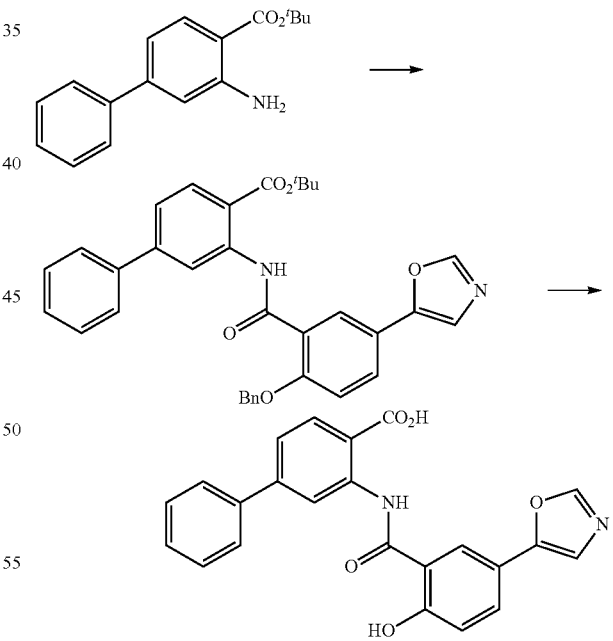

N,N-Dimethylformamide (4.6 μL) and oxalyl chloride (0.077 mL) were sequentially added to a methylene chloride (2 mL) suspension of 2-(benzyloxy)-5-(oxazol-5-yl)benzoic acid (0.18 g), followed by stirring at the same temperature for 40 minutes. The solvent was evaporated under reduced pressure, and methylene chloride (2 mL) was added to the residue. The resulting mixture was added to a solution mixture of tert-butyl 2-amino-4-phenylbenzoate (0.14 g) in pyridine (0.10 mL) and methylene chloride (2 mL), followed by stirring at room temperature for 1 hour and 40 minutes. The solvent was evaporated under reduced pressure, and 1 mol/L hydrochloric acid, water, and ethyl acetate were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 70-50% hexane/ethyl acetate] to obtain 0.22 g of tert-butyl 2-(2-(benzyloxy)-5-(oxazol-5-yl)benzamido)-4-phenylbenzoate as a white solid.

Thioanisole (2.3 mL) and trifluoroacetic acid (7.7 mL) were added to the obtained tert-butyl 2-(2-(benzyloxy)-5-(oxazol-5-yl)benzamido)-4-phenylbenzoate (0.21 g), followed by stirring at room temperature for 9 hours and 40 minutes. The solvent was evaporated under reduced pressure, and methanol was added to the residue. The solid substance was collected by filtration to obtain 0.12 g of 2-(2-hydroxy-5-(oxazol-5-yl)benzamido)-4-phenylbenzoic acid as a white solid.

$^1$H-NMR (DMSO-$d_6$) δ: 7.14 (1H, d, J=8.8 Hz), 7.42-7.64 (5H, m), 7.69-7.87 (3H, m), 8.11 (1H, d, J=8.1 Hz), 8.28 (1H, s), 8.42 (1H, s), 9.07 (1H, s), 11.80 (1H, s), 12.38 (1H, s), 13.35-13.70 (1H, broad).

Example 32a

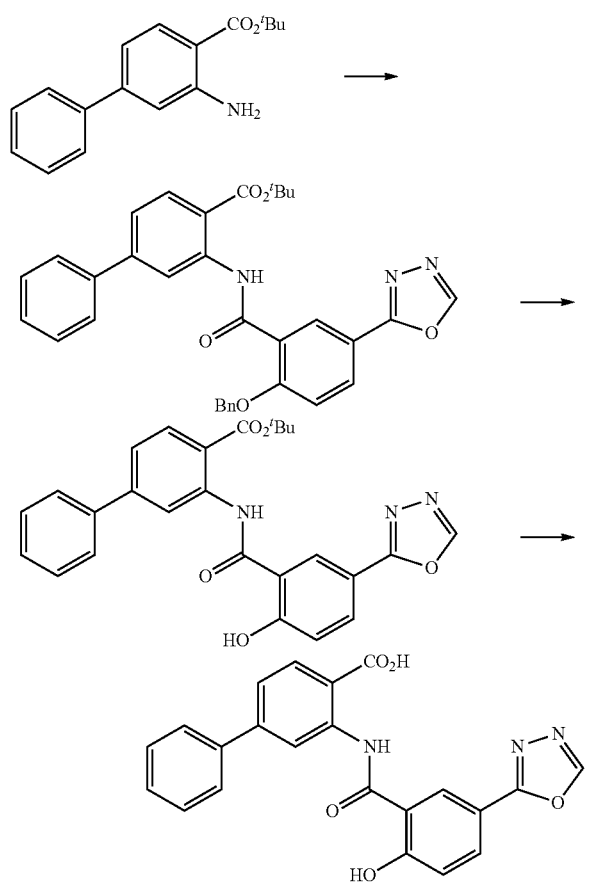

N,N-Dimethylformamide (1.8 μL) and oxalyl chloride (0.030 mL) were sequentially added to a methylene chloride (1.2 mL) suspension of 2-(benzyloxy)-5-(1,3,4-oxadiazol-2-yl)benzoic acid (0.069 g), followed by stirring at room temperature for 1 hour. The solvent was evaporated under reduced pressure, and toluene was added to the residue. The solvent was evaporated under reduced pressure, and methylene chloride (1.2 mL) was added to the residue. The resulting mixture was added to a solution mixture of tert-butyl 2-amino-4-phenylbenzoate (0.060 g) in pyridine (0.045 mL) and methylene chloride (1.2 mL), followed by stirring at room temperature for 1 hour. A 10% aqueous solution of citric acid was added to the reaction mixture, and the organic layer was separated and the obtained organic layer was purified by silica gel column chromatography [Kanto Chemical Co., Inc., silica gel 60 (spherical), eluent: 95-60% hexane/ethyl acetate] to obtain 0.099 g of tert-butyl 2-(2-(benzyloxy)-5-(1,3,4-oxadiazol-2-yl)benzamido)-4-phenylbenzoate as a white solid.

To a solution mixture of the obtained tert-butyl 2-(2-(benzyloxy)-5-(1,3,4-oxadiazol-2-yl)benzamido)-4-phenylbenzoate (0.049 g) in ethyl acetate (1 mL) and methanol (1 mL), 10% palladium-carbon (25 mg) was added, followed by stirring under a hydrogen atmosphere at room temperature for 2 hours. Ethyl acetate was added to the reaction mixture, and the insoluble substance was removed by filtration. The solvent was evaporated under reduced pressure, and diisopropyl ether was added to the obtained residue. The solid substance was collected by filtration to obtain 0.034 g of tert-butyl 2-(2-hydroxy-5-(1,3,4-oxadiazol-2-yl)benzamido)-4-phenylbenzoate as a white solid.

A trifluoroacetic acid (5 mL) solution of the obtained tert-butyl 2-(2-hydroxy-5-(1,3,4-oxadiazol-2-yl)benzamido)-4-phenylbenzoate (0.034 g) was stirred at room temperature for 3 hours. The solvent was evaporated under reduced pressure, and diisopropyl ether was added to the obtained residue. The solid substance was collected by filtration to obtain 0.027 g of 2-(2-hydroxy-5-(1,3,4-oxadiazol-2-yl)benzamido)-4-phenylbenzoic acid as a white solid.

$^1$H-NMR (DMSO-$d_6$) δ: 7.24 (1H, d, J=8.8 Hz), 7.43-7.51 (1H, m), 7.51-7.59 (3H, m), 7.71-7.78 (2H, m), 8.06-8.14 (2H, m), 8.61 (1H, d, J=2.2 Hz), 9.06 (1H, d, J=1.7 Hz), 9.31 (1H, s), 12.30 (1H, s), 12.43 (1H, s), 13.40-13.62 (1H, broad).

Example 33a

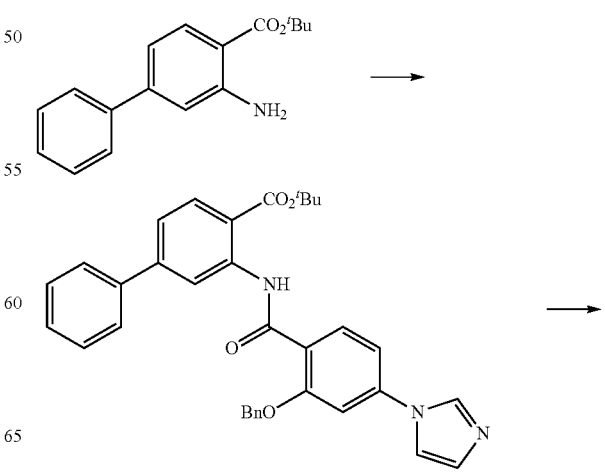

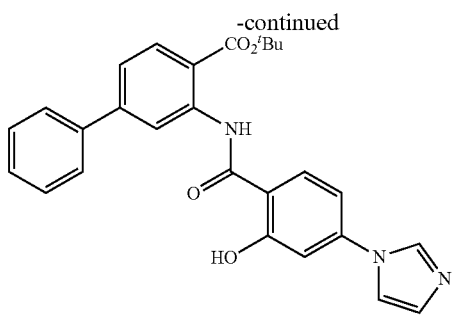

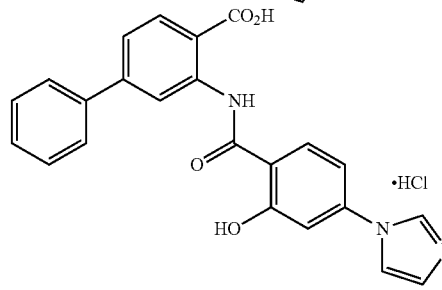

N,N-Dimethylformamide (2.04) and oxalyl chloride (0.033 mL) were sequentially added to a methylene chloride (1.4 mL) suspension of 2-(benzyloxy)-4-(1H-imidazol-1-yl)benzoic acid hydrochloride (0.086 g), followed by stirring at room temperature for 1 hour and 30 minutes. The solvent was evaporated under reduced pressure, and toluene was added to the residue. The solvent was evaporated under reduced pressure, and methylene chloride (1.4 mL) was added to the residue. The resulting mixture was added to a solution mixture of tert-butyl 2-amino-4-phenylbenzoate (0.070 g) in pyridine (0.053 mL) and methylene chloride (1.4 mL), followed by stirring at room temperature for 1 hour. The solvent was evaporated under reduced pressure, and ethyl acetate and a saturated aqueous solution of sodium bicarbonate were added to the residue. The organic layer was separated, washed with a saturated aqueous solution of sodium chloride, and dried over anhydrous magnesium sulfate, and the solvent was evaporated under reduced pressure. The obtained organic layer was purified by silica gel column chromatography [Fuji Silysia Chemical Ltd., PSQ100B (spherical), eluent: 90-20% hexane/ethyl acetate] to obtain 0.12 g of tert-butyl 2-(2-(benzyloxy)-4-(1H-imidazol-1-yl)benzamido)-4-phenylbenzoate as a white solid.

To a solution mixture of the obtained tert-butyl 2-(2-(benzyloxy)-4-(1H-imidazol-1-yl)benzamido)-4-phenylbenzoate (0.12 g) in ethyl acetate (3.6 mL), methanol (1.8 mL), and dioxane (1.8 mL), 10% palladium-carbon (61 mg) was added, followed by stirring under a hydrogen atmosphere at room temperature for 2 hours. To the reaction mixture, 10% palladium-carbon (30 mg) was added, followed by stirring under a hydrogen atmosphere at room temperature for 2 hours. Chloroform was added to the reaction mixture, and the insoluble substance was removed by filtration. The solvent was evaporated under reduced pressure, and the obtained residue was purified by silica gel column chromatography [Fuji Silysia Chemical Ltd., PSQ100B (spherical), eluent: chloroform] to obtain 0.084 g of tert-butyl 2-(2-hydroxy-4-(1H-imidazol-1-yl)benzamido)-4-phenylbenzoate as a white solid.

A trifluoroacetic acid (5 mL) solution of the obtained tert-butyl 2-(2-hydroxy-4-(1H-imidazol-1-yl)benzamido)-4-phenylbenzoate (0.084 g) was stirred at room temperature for 3 hours. The solvent was evaporated under reduced pressure, and dioxane (2 mL) and a 4 mol/L hydrogen chloride-dioxane solution (0.5 mL) were added to the residue, followed by stirring at room temperature for 4 hours. The solid substance was collected by filtration to obtain 0.064 g of 2-(2-hydroxy-4-(1H-imidazol-1-yl)benzamido)-4-phenylbenzoic acid hydrochloride as a white solid.

$^1$H-NMR (DMSO-$d_6$) δ: 7.38-7.50 (3H, m), 7.51-7.59 (3H, m), 7.71-7.77 (2H, m), 7.84-7.88 (1H, m), 8.12 (1H, d, J=8.3 Hz), 8.13 (1H, d, J=8.5 Hz), 8.26 (1H, dd, J=1.7, 1.7 Hz), 9.02 (1H, d, J=1.7 Hz), 9.60 (1H, s), 12.23 (1H, s), 12.36 (1H, s).

Example 34a

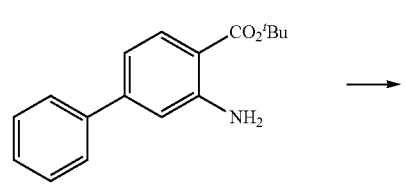

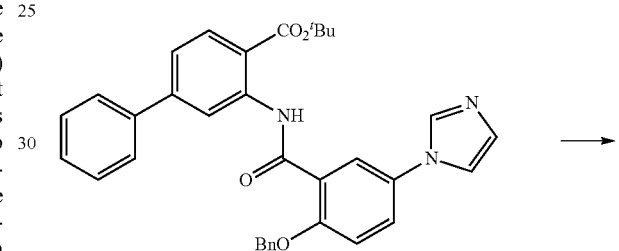

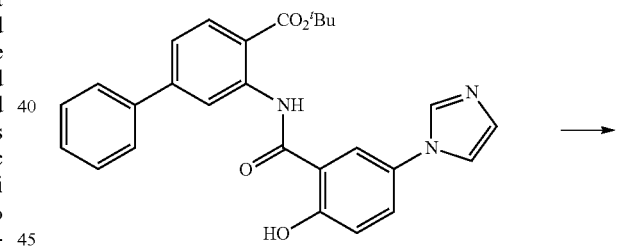

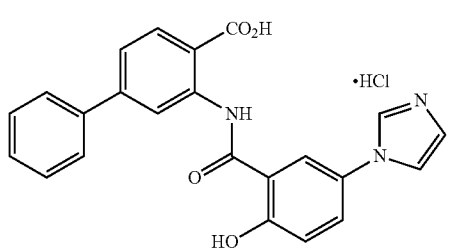

As in Example 33a, the following compound was prepared.

2-(2-Hydroxy-5-(1H-imidazol-1-yl)benzamido)-4-phenylbenzoic acid hydrochloride $^1$H-NMR (DMSO-$d_6$) δ: 7.27 (1H, d, J=8.8 Hz), 7.43-7.50 (1H, m), 7.51-7.58 (3H, m), 7.70-7.76 (2H, m), 7.83 (1H, dd, J=8.8, 2.9 Hz), 7.85-7.89 (1H, m), 8.11 (1H, d, J=8.3 Hz), 8.23 (1H, dd, J=1.7, 1.7 Hz), 8.29 (1H, d, J=2.9 Hz), 9.09 (1H, d, J=1.7 Hz), 9.58 (1H, s), 12.08 (1H, s), 12.42 (1H, s).

Example 35a

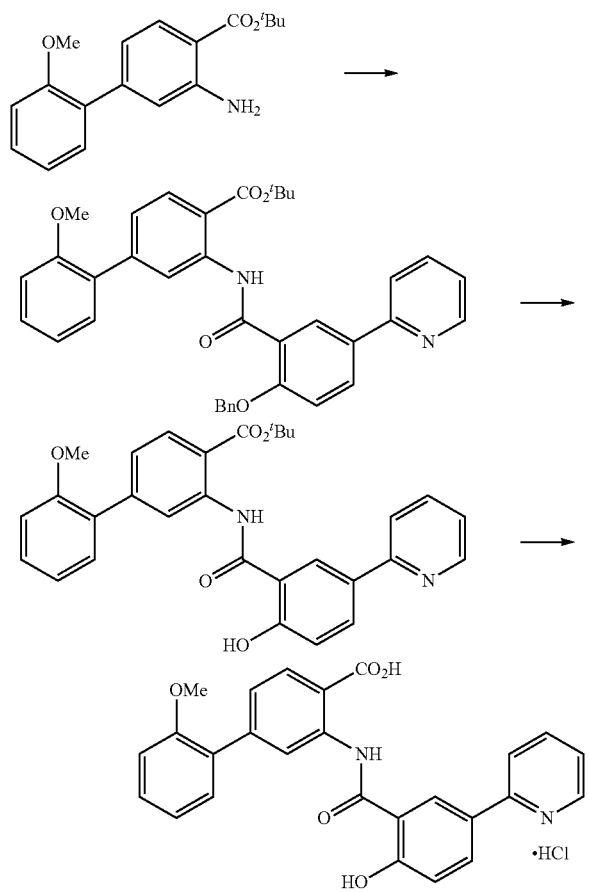

As in Example 33a, the following compound was prepared.

2-(2-Hydroxy-5-(pyridin-2-yl)benzamido)-4-(2-methoxyphenyl)benzoic acid hydrochloride $^1$H-NMR (DMSO-$d_6$) δ: 3.81 (3H, s), 7.06-7.12 (1H, m), 7.15-7.22 (2H, m), 7.32-7.46 (3H, m), 7.50-7.57 (1H, m), 8.05 (1H, d, J=8.3 Hz), 8.06-8.18 (2H, m), 8.16 (1H, dd, J=8.6, 2.3 Hz), 8.64 (1H, d, J=2.3 Hz), 8.69-8.73 (1H, m), 8.85 (1H, d, J=1.7 Hz), 11.99 (1H, s), 12.33 (1H, s).

Example 36a

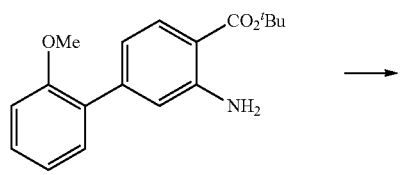

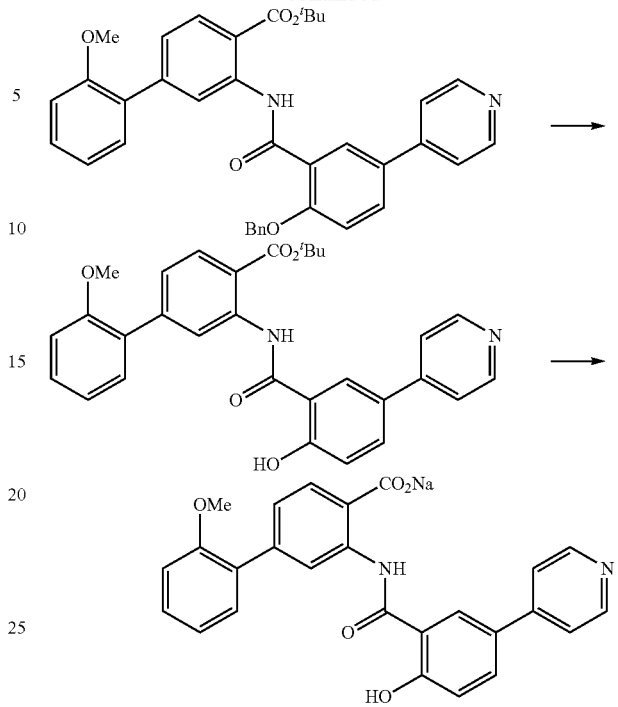

N,N-Dimethylformamide (0.010 mL) and oxalyl chloride (0.031 mL) were sequentially added to a methylene chloride (1.5 mL) suspension of 2-(benzyloxy)-5-(pyridin-4-yl)benzoic acid (0.086 g) under ice-cooling, followed by stirring at room temperature for 30 minutes. The solvent was evaporated under reduced pressure, and methylene chloride (2.5 mL) was added to the residue. The resulting mixture was added to a solution mixture of tert-butyl 2-amino-4-(2-methoxyphenyl)benzoate (0.070 g) in pyridine (0.028 mL) and methylene chloride (1.0 mL) under ice-cooling, followed by stirring at room temperature for 2 hours. The solvent was evaporated under reduced pressure, and a saturated aqueous solution of sodium bicarbonate and ethyl acetate were added to the residue. The organic layer was separated, washed with a 10% aqueous solution of citric acid and a saturated aqueous solution of sodium chloride sequentially, and dried over anhydrous magnesium sulfate, and the solvent was evaporated under reduced pressure. The obtained residue was purified by silica gel column chromatography [eluent: 50-0% hexane/ethyl acetate] to obtain 0.094 g of tert-butyl 2-(2-(benzyloxy)-5-(pyridin-4-yl)benzamido)-4-(2-methoxyphenyl)benzoate as a white solid.

To a solution mixture of the obtained tert-butyl 2-(2-(benzyloxy)-5-(pyridin-4-yl)benzamido)-4-(2-methoxyphenyl)benzoate (0.094 g) in ethyl acetate (2.5 mL) and methanol (3.5 mL), 10% palladium-carbon (19 mg) was added, followed by stirring under a hydrogen atmosphere at room temperature for 3 hours. To the reaction mixture, 10% palladium-carbon (19 mg) was added, followed by stirring under a hydrogen atmosphere at room temperature for 3 hours. The insoluble substance was removed by filtration, and the residue was washed with ethyl acetate and tetrahydrofuran. The filtrate and the washing liquid were combined, and the solvent was evaporated under reduced pressure. The obtained residue was purified by silica gel column chromatography [Kanto Chemical Co., Inc., silica gel 60 (spherical), PSQ100B (spherical), eluent: 65-45% hexane/ethyl acetate] to obtain tert-butyl 2-(2-hydroxy-5-(pyridin-4-yl)benzamido)-4-(2-methoxyphenyl)benzoate.

A trifluoroacetic acid (4.0 mL) solution of the obtained tert-butyl 2-(2-hydroxy-5-(pyridin-4-yl)benzamido)-4-(2-methoxyphenyl)benzoate was stirred at room temperature for 1 hour and 30 minutes. The solvent was evaporated under reduced pressure, and toluene was added to the residue. The solvent was evaporated under reduced pressure, and diisopropyl ether was added to the obtained residue. The solid substance was collected by filtration to obtain 0.027 g of 2-(2-hydroxy-5-(pyridin-4-yl)benzamido)-4-(2-methoxyphenyl)benzoic acid as a light yellow solid.

Dioxane (2.5 mL) and a 2 mol/L aqueous solution of sodium hydroxide (0.031 mL) were added to the obtained 2-(2-hydroxy-5-(pyridin-4-yl)benzamido)-4-(2-methoxyphenyl)benzoic acid (0.027 g), followed by stirring at room temperature for 2 hours and 30 minutes. The solid substance was collected by filtration to obtain 0.012 g of sodium 2-(2-hydroxy-5-(pyridin-4-yl)benzamido)-4-(2-methoxyphenyl)benzoic acid as a yellow solid.

$^1$H-NMR (DMSO-$d_6$) δ: 3.79 (3H, s), 7.02-7.16 (3H, m), 7.16-7.22 (1H, m), 7.30-7.41 (2H, m), 7.73-7.79 (2H, m), 7.97 (1H, dd, J=8.6, 2.2 Hz), 8.07 (1H, d, J=8.0 Hz), 8.53 (1H, s), 8.63-8.68 (2H, m), 8.68-8.71 (1H, m).

Example 37a

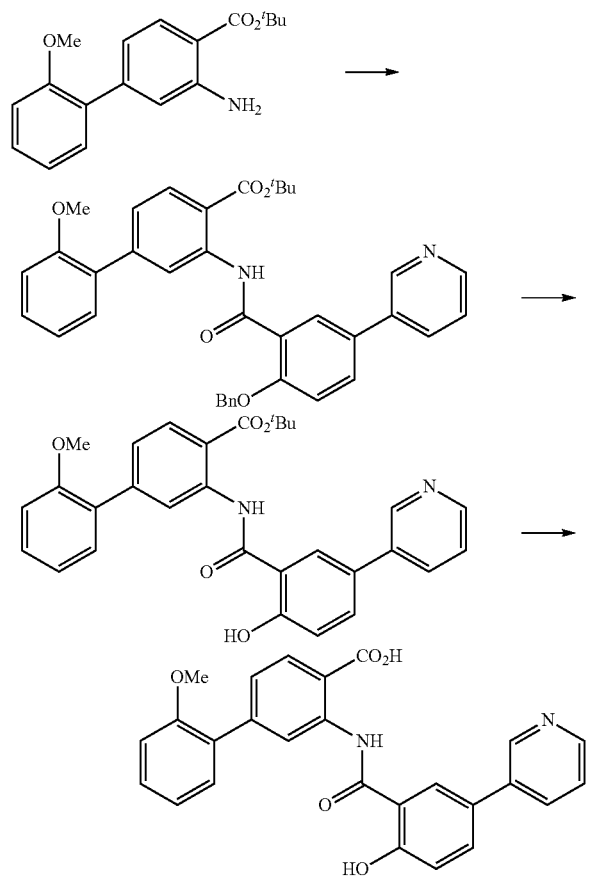

N,N-Dimethylformamide (0.010 mL) and oxalyl chloride (0.053 mL) were sequentially added to a tetrahydrofuran (2.0 mL) suspension of 2-(benzyloxy)-5-(pyridin-3-yl)benzoic acid (0.15 g) under ice-cooling, followed by stirring at room temperature for 30 minutes. The solvent was evaporated under reduced pressure, and tetrahydrofuran (3.0 mL) was added to the residue. The resulting mixture was added to a solution mixture of tert-butyl 2-amino-4-(2-methoxyphenyl) benzoate (0.12 g) in pyridine (0.049 mL) and tetrahydrofuran (2.0 mL) under ice-cooling, followed by stirring at room temperature for 1 hour and 30 minutes. A saturated aqueous solution of sodium bicarbonate and ethyl acetate were added to the reaction mixture. The organic layer was separated, washed with a 10% aqueous solution of citric acid and a saturated aqueous solution of sodium chloride sequentially, and dried over anhydrous magnesium sulfate, and the solvent was evaporated under reduced pressure. The obtained residue was purified by silica gel column chromatography [eluent: 70-35% hexane/ethyl acetate] to obtain 0.19 g of tert-butyl 2-(2-(benzyloxy)-5-(pyridin-3-yl)benzamido)-4-(2-methoxyphenyl)benzoate as a white solid.

To a solution mixture of the obtained tert-butyl 2-(2-(benzyloxy)-5-(pyridin-3-yl)benzamido)-4-(2-methoxyphenyl)benzoate (0.19 g) in ethyl acetate (5.0 mL) and methanol (5.0 mL), 10% palladium-carbon (39 mg) was added, followed by stirring under a hydrogen atmosphere at room temperature for 2 hours. To the reaction mixture, 10% palladium-carbon (39 mg) was added, followed by stirring under a hydrogen atmosphere at room temperature for 2 hours and 30 minutes. Tetrahydrofuran was added to the reaction mixture, and the insoluble substance was removed by filtration. The solvent was evaporated under reduced pressure. The obtained residue was purified by silica gel column chromatography [Kanto Chemical Co., Inc., silica gel 60 (spherical), PSQ100B (spherical), eluent: 100-91% chloroform/methanol] to obtain tert-butyl 2-(2-hydroxy-5-(pyridin-3-yl)benzamido)-4-(2-methoxyphenyl)benzoate as a white solid.

A trifluoroacetic acid (4.0 mL) solution of the obtained tert-butyl 2-(2-hydroxy-5-(pyridin-3-yl)benzamido)-4-(2-methoxyphenyl)benzoate was stirred at room temperature for 2 hours. The solvent was evaporated under reduced pressure, and toluene was added to the residue. The solvent was evaporated under reduced pressure, and diisopropyl ether was added to the obtained residue. The solid substance was collected by filtration. Dioxane (2.0 mL) and a 2 mol/L aqueous solution of sodium hydroxide (0.49 mL) were added to the obtained solid substance, followed by stirring at room temperature for 45 minutes. A 10% aqueous solution of citric acid was added to the reaction mixture, and the solid substance was collected by filtration. Ethanol and water were added to the obtained solid substance, and the solid substance was collected by filtration to obtain 0.053 g of 2-(2-hydroxy-5-(pyridin-3-yl)benzamido)-4-(2-methoxyphenyl)benzoic acid as a white solid.

$^1$H-NMR (DMSO-$d_6$) δ: 3.81 (3H, s), 7.06-7.12 (1H, m), 7.12-7.20 (2H, m), 7.33-7.39 (2H, m), 7.39-7.46 (1H, m), 7.46-7.52 (1H, m), 7.85 (1H, dd, J=8.6, 2.4 Hz), 8.02-8.10 (2H, m), 8.22 (1H, d, J=2.4 Hz), 8.55 (1H, dd, J=4.6, 1.5 Hz), 8.80 (1H, d, J=1.7 Hz), 8.90 (1H, d, J=1.9 Hz), 11.69-11.80 (1H, broad), 12.31-12.43 (1H, broad).

Example 38a

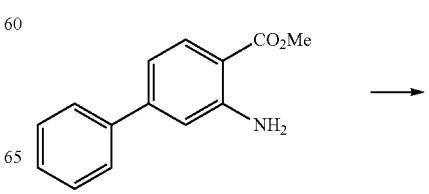

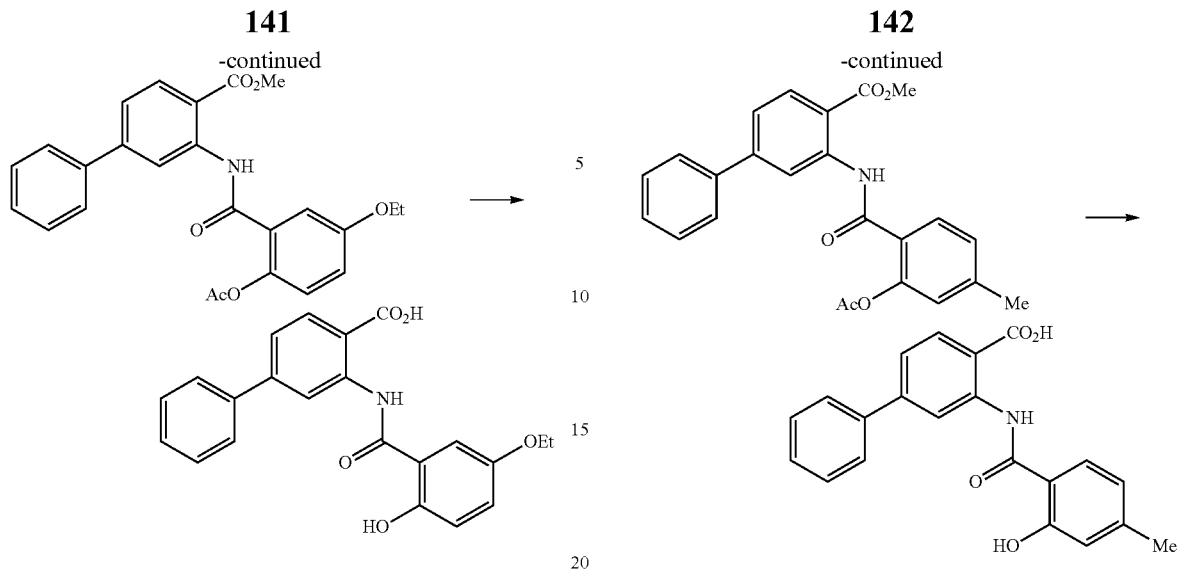

N,N-Dimethylformamide (4.64) and oxalyl chloride (0.077 mL) were sequentially added to a methylene chloride (2 mL) suspension of 2-acetoxy-5-ethoxybenzoic acid (0.14 g), followed by stirring at room temperature for 30 minutes. The solvent was evaporated under reduced pressure, and methylene chloride (2 mL) was added to the residue. The resulting mixture was added to a solution mixture of methyl 2-amino-4-phenylbenzoate (0.11 g) in pyridine (0.10 mL) and methylene chloride (2 mL), followed by stirring at room temperature for 2 hours and 10 minutes. The solvent was evaporated under reduced pressure, and water and ethyl acetate were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 90-70% hexane/ethyl acetate] to obtain 0.082 g of methyl 2-(2-acetoxy-5-ethoxybenzamido)-4-phenylbenzoate as a white solid.

Methanol (4 mL) and a 2 mol/L aqueous solution of sodium hydroxide (0.95 mL) were added to the obtained methyl 2-(2-acetoxy-5-ethoxybenzamido)-4-phenylbenzoate (0.082 g), followed by stirring at room temperature for 3 hours and 30 minutes and then heating to reflux for 30 minutes. The reaction mixture was cooled to room temperature and adjusted to a pH of 1.2 with 6 mol/L hydrochloric acid. The solid substance was collected by filtration to obtain 0.055 g of 2-(5-ethoxy-2-hydroxybenzamido)-4-phenylbenzoic acid as a white solid.

$^1$H-NMR (DMSO-d$_6$) δ: 1.33 (3H, t, J=6.9 Hz), 4.01 (2H, q, J=6.9 Hz), 6.95 (1H, d, J=9.0 Hz), 7.07 (1H, dd, J=9.0, 3.2 Hz), 7.40-7.58 (5H, m), 7.70-7.78 (2H, m), 8.10 (1H, d, J=8.3 Hz), 9.01 (1H, d, J=1.7 Hz), 11.01 (1H, s), 12.33 (1H, s), 13.40-13.65 (1H, broad).

N,N-Dimethylformamide (4.6 μL) and oxalyl chloride (0.077 mL) were sequentially added to a methylene chloride (2 mL) solution of 2-acetoxy-4-methylbenzoic acid (0.12 g), followed by stirring at room temperature for 1 hour. The solvent was evaporated under reduced pressure, and methylene chloride (2 mL) was added to the residue. The resulting mixture was added to a solution mixture of methyl 2-amino-4-phenylbenzoate (0.11 g) in pyridine (0.10 mL) and methylene chloride (2 mL), followed by stirring at room temperature for 1 hour and 10 minutes. The solvent was evaporated under reduced pressure, and water and chloroform were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 90-70% hexane/ethyl acetate] to obtain 0.14 g of methyl 2-(2-acetoxy-4-methylbenzamido)-4-phenylbenzoate as a white solid.

Dioxane (3 mL) and a 2 mol/L aqueous solution of sodium hydroxide (1.7 mL) were added to the obtained methyl 2-(2-acetoxy-4-methylbenzamido)-4-phenylbenzoate (0.14 g), followed by stirring at room temperature for 2 hours and 30 minutes. The reaction mixture was adjusted to a pH of 3.0 with 6 mol/L hydrochloric acid. The solid substance was collected by filtration to obtain 0.042 g of 2-(2-hydroxy-4-methylbenzamido)-4-phenylbenzoic acid as a white solid.

$^1$H-NMR (DMSO-d$_6$) δ: 2.31 (3H, s), 6.79-6.86 (2H, m), 7.42-7.58 (4H, m), 7.69-7.76 (2H, m), 7.80 (1H, d, J=7.8 Hz), 8.10 (1H, d, J=8.3 Hz), 9.00 (1H, d, J=1.7 Hz), 11.47 (1H, s), 12.29 (1H, s), 13.40-13.65 (1H, broad).

Example 39a

Example 40a

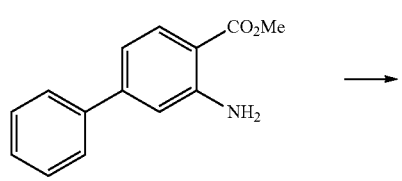

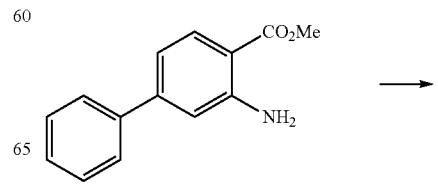

-continued

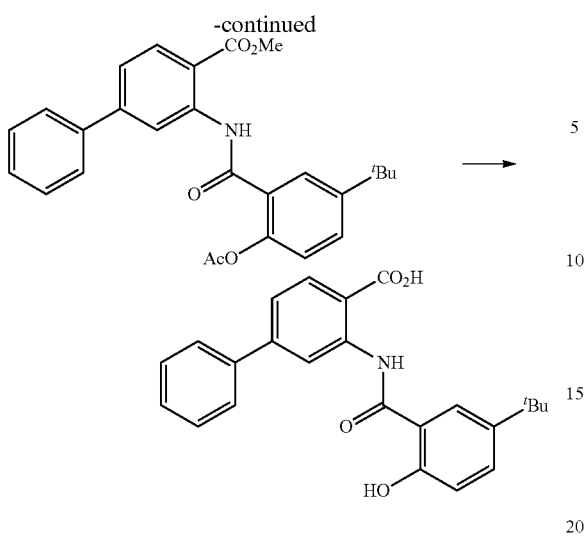

N,N-Dimethylformamide (2 μL) and oxalyl chloride (0.026 mL) were sequentially added to a methylene chloride (1.5 mL) solution of 2-acetoxy-5-tert-butylbenzoic acid (0.049 g), followed by stirring at room temperature for 25 minutes. The solvent was evaporated under reduced pressure, and methylene chloride (2 mL) was added to the residue. The resulting mixture was added to a solution mixture of methyl 2-amino-4-phenylbenzoate (0.038 g) in pyridine (0.034 mL) and methylene chloride (1.5 mL), followed by stirring at room temperature for 1 hour and 15 minutes. Water, 1 mol/L hydrochloric acid, and chloroform were added to the reaction mixture. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 90-75% hexane/ethyl acetate] to obtain 0.023 g of methyl 2-(2-acetoxy-5-tert-butylbenzamido)-4-phenylbenzoate as a white solid.

Methanol (2 mL) and a 2 mol/L aqueous solution of sodium hydroxide (0.26 mL) were added to the obtained methyl 2-(2-acetoxy-5-tert-butylbenzamido)-4-phenylbenzoate (0.023 g), followed by stirring at room temperature for 15 hours. Toluene was added to the reaction mixture. The aqueous layer was separated and adjusted to a pH of 3.0 with 6 mol/L hydrochloric acid. The solid substance was collected by filtration to obtain 0.010 g of 2-(5-tert-butyl-2-hydroxybenzamido)-4-phenylbenzoic acid as a white solid.

$^1$H-NMR (DMSO-$d_6$) δ: 1.31 (9H, s), 6.96 (1H, d, J=8.5 Hz), 7.42-7.60 (5H, m), 7.70-7.79 (2H, m), 7.93 (1H, d, J=2.4 Hz), 8.11 (1H, d, J=8.3 Hz), 9.05 (1H, d, J=1.7 Hz), 11.35 (1H, s), 12.42 (1H, s), 13.45-13.80 (1H, broad).

Example 41a

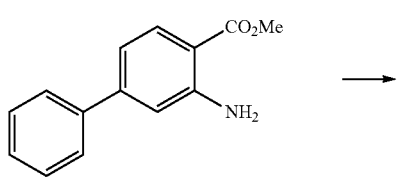

-continued

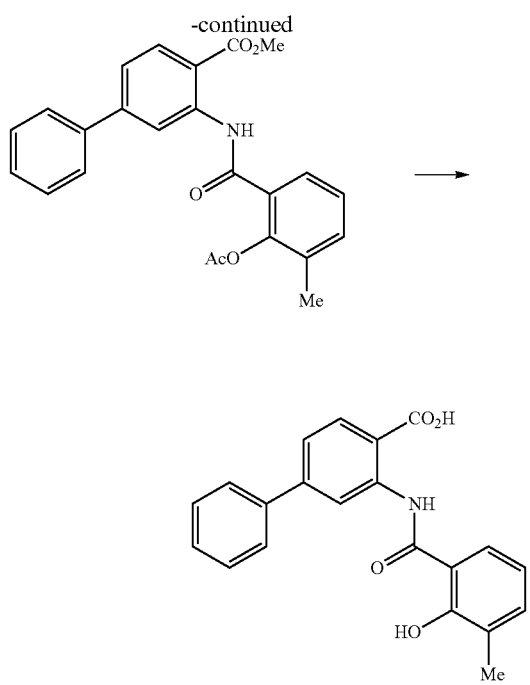

N,N-Dimethylformamide (4.6 μL) and oxalyl chloride (0.077 mL) were sequentially added to a methylene chloride (2 mL) solution of 2-acetoxy-3-methylbenzoic acid (0.12 g), followed by stirring at room temperature for 30 minutes. The solvent was evaporated under reduced pressure, and methylene chloride (2 mL) was added to the residue. The resulting mixture was added to a solution mixture of methyl 2-amino-4-phenylbenzoate (0.11 g) in pyridine (0.10 mL) and methylene chloride (2 mL), followed by stirring at room temperature for 20 minutes. The solvent was evaporated under reduced pressure, and the obtained residue was purified by silica gel column chromatography [eluent: 85-70% hexane/ethyl acetate] to obtain 0.063 g of methyl 2-(2-acetoxy-3-methylbenzamido)-4-phenylbenzoate as a white solid.

Methanol (2 mL), dioxane (4 mL), and a 2 mol/L aqueous solution of sodium hydroxide (0.77 mL) were added to the obtained methyl 2-(2-acetoxy-3-methylbenzamido)-4-phenylbenzoate (0.062 g), followed by stirring at room temperature for 7 hours. The reaction mixture was adjusted to a pH of 1.1 with 6 mol/L hydrochloric acid. The solid substance was collected by filtration to obtain 0.044 g of 2-(2-hydroxy-3-methylbenzamido)-4-phenylbenzoic acid as a white solid.

$^1$H-NMR (DMSO-$d_6$) δ: 2.22 (3H, s), 6.95 (1H, dd, J=7.6, 7.6 Hz), 7.38-7.51 (2H, m), 7.51-7.63 (3H, m), 7.66-7.80 (3H, m), 8.14 (1H, d, J=8.3 Hz), 8.83-8.89 (1H, m), 8.85 (1H, s), 12.24 (1H, s), 12.34-12.46 (1H, broad).

Example 42a

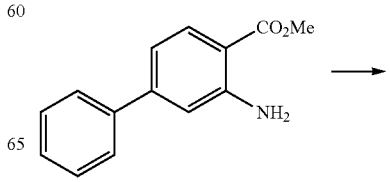

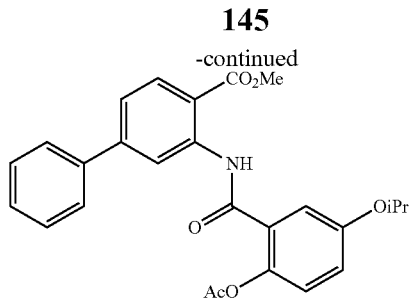

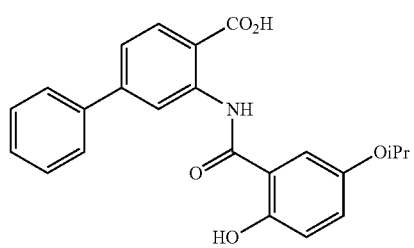

Under ice-cooling, oxalyl chloride (0.040 mL) was added to a solution mixture of 2-acetoxy-5-isopropoxybenzoic acid (0.081 g) in methylene chloride (2.0 mL) and N,N-dimethylformamide (0.010 mL), followed by stirring at room temperature for 20 minutes. The solvent was evaporated under reduced pressure, and methylene chloride (2.0 mL) was added to the residue. The resulting mixture was added to a solution mixture of methyl 2-amino-4-phenylbenzoate (0.070 g) in pyridine (0.037 mL) and methylene chloride (1.0 mL) under ice-cooling, followed by stirring at room temperature for 1 hour and 45 minutes. The solvent was evaporated under reduced pressure, and a saturated aqueous solution of sodium bicarbonate and ethyl acetate were added to the residue. The organic layer was separated, washed with a 10% aqueous solution of citric acid and a saturated aqueous solution of sodium chloride sequentially, and dried over anhydrous magnesium sulfate, and the solvent was evaporated under reduced pressure. The obtained residue was purified by silica gel column chromatography [eluent: 95-80% hexane/ethyl acetate] to obtain 0.072 g of methyl 2-(2-acetoxy-5-isopropoxybenzamido)-4-phenylbenzoate as a white solid.

Dioxane (5.0 mL) and a 4 mol/L aqueous solution of sodium hydroxide (0.20 mL) were added to the obtained methyl 2-(2-acetoxy-5-isopropoxybenzamido)-4-phenylbenzoate (0.072 g), followed by stirring at 50 to 60° C. for 4 hours. The reaction mixture was cooled to room temperature, and a 4 mol/L aqueous solution of sodium hydroxide (0.081 mL) was added thereto, followed by stirring at 55 to 60° C. for 2 hours. The reaction mixture was cooled to room temperature, and a 4 mol/L aqueous solution of sodium hydroxide (0.040 mL) was added thereto, followed by stirring at 60° C. for 1 hour and 30 minutes. The reaction mixture was cooled to room temperature, and a 10% aqueous solution of citric acid (9 mL) was added thereto. The solid substance was collected by filtration to obtain 0.039 g of 2-(2-hydroxy-5-isopropoxybenzamido)-4-phenylbenzoic acid as a white solid.

$^1$H-NMR (DMSO-$d_6$) δ: 1.23-1.29 (6H, m), 4.45-4.56 (1H, m), 6.94 (1H, d, J=8.8 Hz), 7.03-7.10 (1H, m), 7.40-7.49 (2H, m), 7.49-7.58 (3H, m), 7.70-7.77 (2H, m), 8.10 (1H, d, J=8.3 Hz), 8.98-9.04 (1H, m), 11.03 (1H, s), 12.32 (1H, s), 13.40-13.64 (1H, broad).

Example 43a

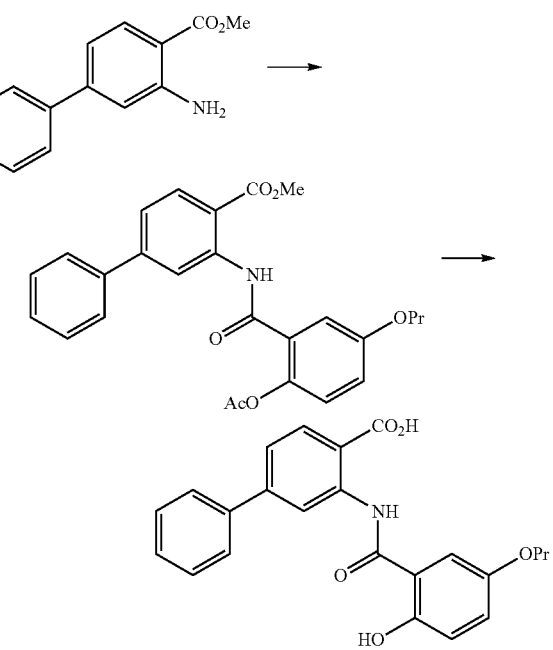

As in Example 42a, the following compound was prepared.

2-(2-Hydroxy-5-propoxybenzamido)-4-phenylbenzoic acid $^1$H-NMR (DMSO-$d_6$) δ: 0.99 (3H, t, J=7.4 Hz), 1.66-1.79 (2H, m), 3.91 (2H, t, J=6.5 Hz), 6.95 (1H, d, J=8.8 Hz), 7.04-7.11 (1H, m), 7.41-7.49 (2H, m), 7.49-7.58 (3H, m), 7.69-7.77 (2H, m), 8.10 (1H, d, J=8.3 Hz), 9.01 (1H, s), 11.02 (1H, s), 12.33 (1H, s).

Example 44a

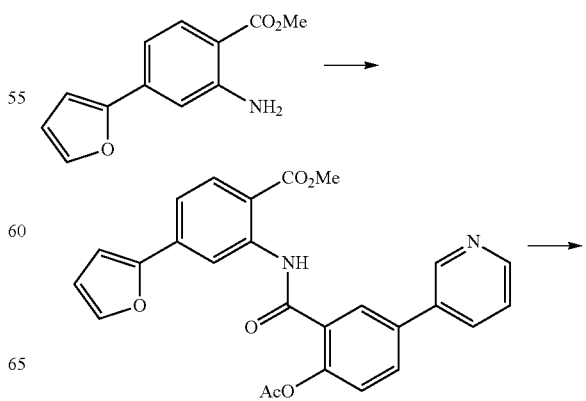

-continued

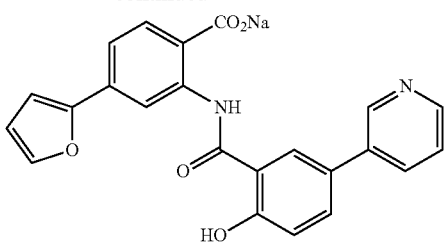

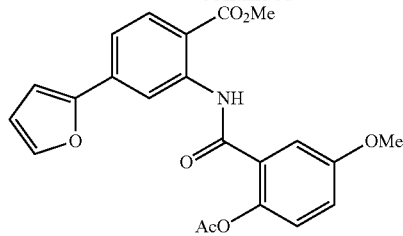 

N,N-Dimethylformamide (5 μL) and oxalyl chloride (0.077 mL) were added to a methylene chloride (2 mL) suspension of 2-acetoxy-5-(pyridin-3-yl)benzoic acid (0.15 g), followed by stirring at room temperature for 1 hour. The solvent was evaporated under reduced pressure, and methylene chloride (2 mL) was added to the residue. The resulting mixture was added to a solution mixture of methyl 2-amino-4-(furan-2-yl)benzoate (0.11 g) in pyridine (0.14 mL) and methylene chloride (2 mL), followed by stirring at room temperature for 4 hours. The solvent was evaporated under reduced pressure, and a saturated aqueous solution of sodium bicarbonate and chloroform were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 55-20% hexane/ethyl acetate] to obtain 0.18 g of methyl 2-(2-acetoxy-5-(pyridin-3-yl)benzamido)-4-(furan-2-yl)benzoate as a white solid.

Dioxane (3 mL) and a 2 mol/L aqueous solution of sodium hydroxide (0.19 mL) were added to the obtained methyl 2-(2-acetoxy-5-(pyridin-3-yl)benzamido)-4-(furan-2-yl)benzoate (0.18 g), followed by stirring at room temperature for 3 hours and 10 minutes and then at 70° C. for 1 hour and 30 minutes. The reaction mixture was cooled to room temperature and adjusted to a pH of 6.0 with a 10% aqueous solution of citric acid. The solid substance was collected by filtration, and methanol (1.0 mL) and a 1 mol/L aqueous solution of sodium hydroxide (0.055 mL) were added thereto. The solid substance was collected by filtration to obtain 0.044 g of sodium 4-(furan-2-yl)-2-(2-hydroxy-5-(pyridin-3-yl)benzamido)benzoate as a white solid.

$^{1}$H-NMR (DMSO-d$_{6}$) δ: 6.62 (1H, dd, J=3.4, 2.0 Hz), 6.96 (1H, d, J=3.4 Hz), 7.10 (1H, d, J=8.7 Hz), 7.42 (1H, dd, J=8.1, 1.7 Hz), 7.52 (1H, ddd, J=7.9, 4.8, 0.7 Hz), 7.78-7.83 (1H, m), 7.89 (1H, dd, J=8.7, 2.3 Hz), 8.08 (1H, d, J=8.1 Hz), 8.08-8.15 (1H, m), 8.41 (1H, d, J=2.2 Hz), 8.58 (1H, dd, J=4.8, 1.6 Hz), 8.92-8.99 (2H, m).

Example 45a

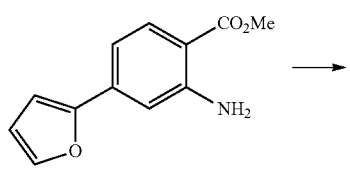

Under ice-cooling, oxalyl chloride (0.036 mL) was added to a solution mixture of 2-acetoxy-5-methoxybenzoic acid (0.070 g) in methylene chloride (1.0 mL) and N,N-dimethylformamide (0.010 mL), followed by stirring at room temperature for 30 minutes. The solvent was evaporated under reduced pressure, and methylene chloride (2 mL) was added to the residue. The resulting mixture was added to a solution mixture of methyl 2-amino-4-(furan-2-yl)benzoate (0.060 g) in pyridine (0.034 mL) and methylene chloride (1.0 mL) under ice-cooling, followed by stirring at room temperature for 1 hour and 30 minutes. The solvent was evaporated under reduced pressure, and a saturated aqueous solution of sodium bicarbonate and ethyl acetate were added to the residue. The organic layer was separated, washed with a 10% aqueous solution of citric acid and a saturated aqueous solution of sodium chloride sequentially, and dried over anhydrous magnesium sulfate, and the solvent was evaporated under reduced pressure. The obtained residue was purified by silica gel column chromatography [eluent: 95-85% hexane/ethyl acetate] to obtain 0.073 g of methyl 2-(2-acetoxy-5-methoxybenzamido)-4-(furan-2-yl)benzoate as a white solid.

Dioxane (2.0 mL) and a 4 mol/L aqueous solution of sodium hydroxide (0.22 mL) were added to the obtained methyl 2-(2-acetoxy-5-methoxybenzamido)-4-(furan-2-yl)benzoate (0.073 g), followed by stirring at 50 to 55° C. for 2 hours and 30 minutes. The reaction mixture was cooled to room temperature, and a 10% aqueous solution of citric acid (6 mL) was added thereto. The solid substance was collected by filtration to obtain 0.062 g of 4-(furan-2-yl)-2-(2-hydroxy-5-methoxybenzamido)benzoic acid as a white solid.

Ethanol (2.5 mL) and a 1 mol/L aqueous solution of sodium hydroxide (0.17 mL) were added to the obtained 4-(furan-2-yl)-2-(2-hydroxy-5-methoxybenzamido)benzoic acid (0.062 g), followed by stirring at room temperature for 35 minutes. The solid substance was collected by filtration to obtain 0.046 g of sodium 4-(furan-2-yl)-2-(2-hydroxy-5-methoxybenzamido)benzoate as a white solid.

$^{1}$H-NMR (DMSO-d$_{6}$) δ: 3.78 (3H, s), 6.62 (1H, dd, J=3.4, 1.8 Hz), 6.90 (1H, d, J=9.0 Hz), 6.95 (1H, d, J=3.4 Hz), 7.10

(1H, dd, J=9.0, 3.0 Hz), 7.40 (1H, dd, J=8.0, 1.7 Hz), 7.58 (1H, d, J=3.0 Hz), 7.78-7.82 (1H, m), 8.06 (1H, d, J=8.0 Hz), 8.94 (1H, d, J=1.7 Hz).

Example 46a

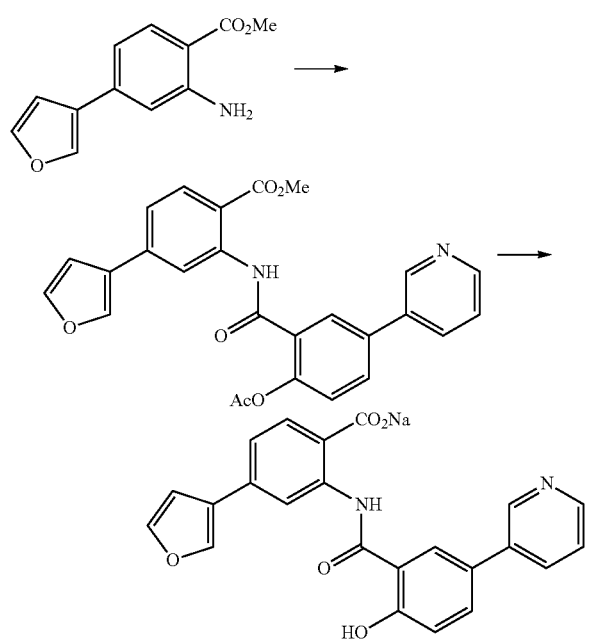

N,N-Dimethylformamide (0.010 mL) and oxalyl chloride (0.060 mL) were added to a tetrahydrofuran (4.0 mL) suspension of 2-acetoxy-5-(pyridin-3-yl)benzoic acid (0.14 g), followed by stirring at room temperature for 50 minutes. Oxalyl chloride (0.060 mL) was added to the reaction mixture, followed by stirring at room temperature for 40 minutes. Oxalyl chloride (0.020 mL) was added the reaction mixture, followed by stirring at room temperature for 15 minutes. The solvent was evaporated under reduced pressure, and tetrahydrofuran (3.0 mL) was added to the residue. The resulting mixture was added to a solution mixture of methyl 2-amino-4-(furan-3-yl)benzoate (0.10 g) in pyridine (0.093 mL) and tetrahydrofuran (1.0 mL) under ice-cooling, followed by stirring at room temperature for 2 hours. A saturated aqueous solution of sodium bicarbonate and ethyl acetate were added to the reaction mixture. The organic layer was separated and washed with a saturated aqueous solution of sodium chloride. The insoluble substance was removed by filtration. The obtained filtrate was dried over anhydrous magnesium sulfate, and the solvent was evaporated under reduced pressure. Diisopropyl ether and ethyl acetate were added to the obtained residue. The solid substance was collected by filtration to obtain 0.11 g of methyl 2-(2-acetoxy-5-(pyridin-3-yl) benzamido)-4-(furan-3-yl)benzoate as a white solid.

Dioxane (5.0 mL) and a 4 mol/L aqueous solution of sodium hydroxide (0.31 mL) were added to the obtained methyl 2-(2-acetoxy-5-(pyridin-3-yl)benzamido)-4-(furan-3-yl)benzoate (0.11 g), followed by stirring at 50 to 55° C. for 1 hours. The reaction mixture was cooled to room temperature, and a 10% aqueous solution of citric acid (6 mL) was added thereto. The solid substance was collected by filtration to obtain 0.081 g of 4-(furan-3-yl)-2-(2-hydroxy-5-(pyridin-3-yl)benzamido)-benzoic acid as a yellow solid.

Ethanol (1.5 mL) and a 1 mol/L aqueous solution of sodium hydroxide (0.19 mL) were added to the obtained 4-(furan-3-yl)-2-(2-hydroxy-5-(pyridin-3-yl)benzamido) benzoic acid (0.081 g), followed by stirring at room temperature for 1 hour. The solid substance was collected by filtration to obtain 0.048 g of sodium 4-(furan-3-yl)-2-(2-hydroxy-5-(pyridin-3-yl)benzamido)benzoate as a white solid.

$^1$H-NMR (DMSO-d$_6$) δ: 6.92-6.98 (1H, m), 7.13 (1H, d, J=8.5 Hz), 7.40 (1H, dd, J=8.1, 1.5 Hz), 7.50 (1H, dd, J=7.9, 4.7 Hz), 7.80 (1H, s), 7.87 (1H, dd, J=8.5, 2.2 Hz), 8.03-8.13 (1H, m), 8.06 (1H, d, J=8.3 Hz), 8.24 (1H, s), 8.34 (1H, d, J=1.7 Hz), 8.51-8.60 (1H, m), 8.83 (1H, d, J=1.4 Hz), 8.91-8.97 (1H, m).

Example 47a

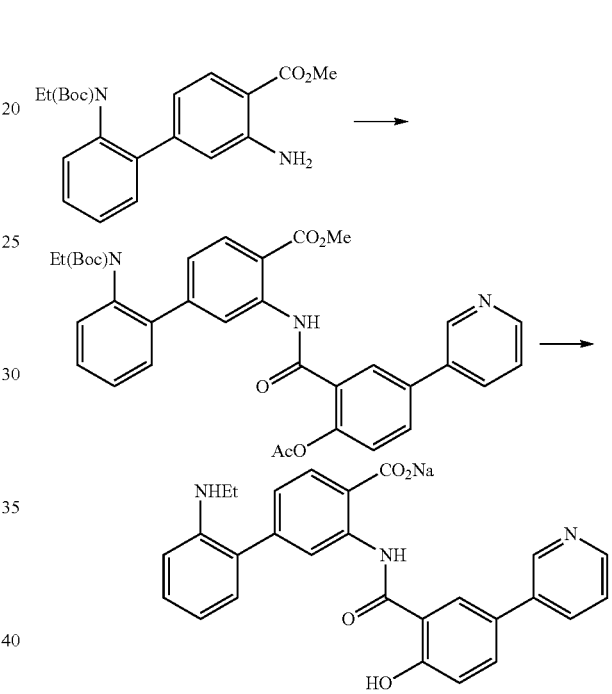

Under ice-cooling, oxalyl chloride (0.035 mL) was added to a solution mixture of 2-acetoxy-5-(pyridin-3-yl)benzoic acid (0.083 g) in tetrahydrofuran (2.0 mL) and N,N-dimethylformamide (0.010 mL), followed by stirring at room temperature for 1 hour. The solvent was evaporated under reduced pressure, and tetrahydrofuran (3.0 mL) was added to the residue. The resulting mixture was added to a solution mixture of methyl 2-amino-4-(2-((tert-butoxycarbonyl) (ethyl)amino)phenyl)benzoate (0.10 g) in pyridine (0.054 mL) and tetrahydrofuran (1.5 mL) under ice-cooling, followed by stirring at room temperature for 1 hour and 40 minutes. A saturated aqueous solution of sodium bicarbonate and ethyl acetate were added to the reaction mixture. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 70-45% hexane/ethyl acetate] to obtain methyl 2-(2-acetoxy-5-(pyridin-3-yl)benzamido)-4-(2-((tert-butoxycarbonyl)(ethyl)amino)phenyl)benzoate.

A trifluoroacetic acid (4.0 mL) solution of the obtained methyl 2-(2-acetoxy-5-(pyridin-3-yl)benzamido)-4-(2-((tert-butoxycarbonyl)(ethyl)amino)phenyl)benzoate was stirred at room temperature for 2 hours and 30 minutes. The solvent was evaporated under reduced pressure, and toluene was added thereto. The solvent was evaporated under reduced pressure, and diisopropyl ether was added to the obtained residue. The solid substance was collected by filtration. Dioxane (4.0 mL) and a 1 mol/L aqueous solution of sodium hydroxide (0.40 mL) were added to the obtained solid substance, followed by stirring at 50 to 55° C. for 2 hours. The reaction mixture was cooled to room temperature and then adjusted to a pH of 7.4 with 1 mol/L hydrochloric acid. The solvent was evaporated under reduced pressure, and water was added to the obtained residue. The solid substance was collected by filtration to obtain 0.032 g of 4-(2-(ethylamino)phenyl)-2-(2-hydroxy-5-(pyridin-3-yl)benzamido)benzoic acid as a white solid.

Ethanol (2.0 mL) and a 1 mol/L aqueous solution of sodium hydroxide (0.067 mL) were added to the obtained 4-(2-(ethylamino)phenyl)-2-(2-hydroxy-5-(pyridin-3-yl)benzamido)benzoic acid (0.032 g), followed by stirring at room temperature for 2 hours and 30 minutes. The solvent was evaporated under reduced pressure, and water was added to the obtained residue. The solid substance was collected by filtration to obtain 0.024 g of sodium 4-(2-(ethylamino)phenyl)-2-(2-hydroxy-5-(pyridin-3-yl)benzamido)benzoate as a white solid.

$^1$H-NMR (DMSO-$d_6$) δ: 1.12 (3H, t, J=7.1 Hz), 3.06-3.15 (2H, m), 4.49 (1H, t, J=5.5 Hz), 6.65-6.72 (2H, m), 7.02-7.11 (3H, m), 7.16-7.22 (1H, m), 7.53 (1H, dd, J=7.9, 4.8 Hz), 7.84-7.92 (1H, m), 8.08-8.15 (2H, m), 8.39-8.45 (1H, m), 8.55-8.63 (2H, m), 8.93-8.99 (1H, m).

Example 48a

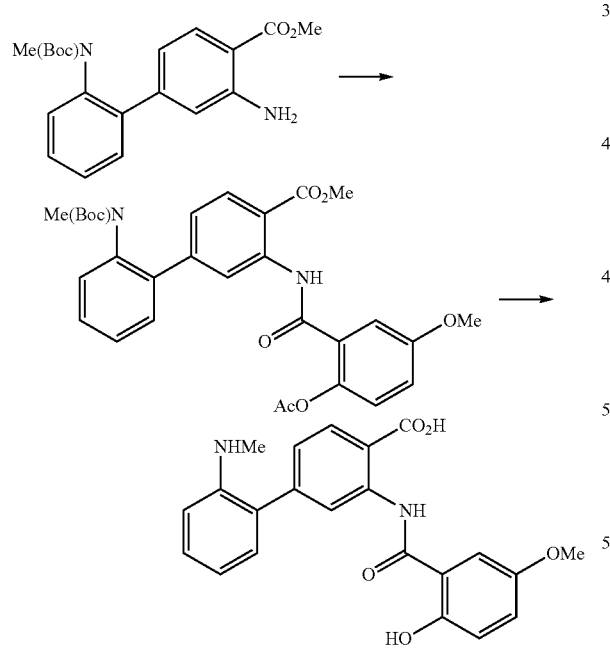

Under ice-cooling, oxalyl chloride (0.026 mL) was added to a solution mixture of 2-acetoxy-5-methoxybenzoic acid (0.049 g) in methylene chloride (1.0 mL) and N,N-dimethylformamide (0.010 mL), followed by stirring at room temperature for 30 minutes. The solvent was evaporated under reduced pressure, and methylene chloride (2.0 mL) was added to the residue. The resulting mixture was added to a solution mixture of methyl 2-amino-4-(2-((tert-butoxycarbonyl)(methyl)amino)phenyl)benzoate (0.070 g) in pyridine (0.024 mL) and methylene chloride (1.0 mL) under ice-cooling, followed by stirring at room temperature for 1 hour and 30 minutes. The solvent was evaporated under reduced pressure, and a saturated aqueous solution of sodium bicarbonate and ethyl acetate were added to the residue. The organic layer was separated, washed with a 10% aqueous solution of citric acid and a saturated aqueous solution of sodium chloride sequentially, and dried over anhydrous magnesium sulfate, and the solvent was evaporated under reduced pressure. The obtained residue was purified by silica gel column chromatography [Kanto Chemical Co., Inc., silica gel 60 (spherical), eluent: 91-60% hexane/ethyl acetate] to obtain methyl 2-(2-acetoxy-5-methoxybenzamido)-4-(2-((tert-butoxycarbonyl)(methyl)amino)phenyl)benzoate.

A trifluoroacetic acid (3.0 mL) solution of the obtained methyl 2-(2-acetoxy-5-methoxybenzamido)-4-(2-((tert-butoxycarbonyl)(methyl)amino)phenyl)benzoate was stirred at room temperature for 1 hour and 40 minutes. The solvent was evaporated under reduced pressure, and toluene was added to the residue. The solvent was evaporated under reduced pressure, and dioxane (3.0 mL) and a 4 mol/L aqueous solution of sodium hydroxide (0.25 mL) were added to the obtained residue, followed by stirring at 50 to 55° C. for 1 hour and 30 minutes and then at 55 to 60° C. for 2 hours and 30 minutes. The reaction mixture was cooled to room temperature, and water added thereto. After adjusting the pH to 7.0 with 1 mol/L hydrochloric acid, the solvent was evaporated under reduced pressure. Water was added to the obtained residue, and the solid substance was collected by filtration to obtain 0.025 g of 2-(2-hydroxy-5-methoxybenzamido)-4-(2-(methylamino)phenyl)benzoic acid as a white solid.

$^1$H-NMR (DMSO-$d_6$) δ: 2.69 (3H, s), 3.75 (3H, s), 4.80-5.10 (1H, broad), 6.65 (1H, d, J=8.1 Hz), 6.70 (1H, dd, J=7.4, 7.4 Hz), 6.95 (1H, d, J=8.8 Hz), 7.01-7.10 (2H, m), 7.19-7.27 (2H, m), 7.40 (1H, d, J=3.2 Hz), 8.06 (1H, d, J=8.0 Hz), 8.70 (1H, d, J=1.2 Hz), 10.99 (1H, s), 12.32-12.43 (1H, broad), 13.24-13.66 (1H, broad).

Example 49a

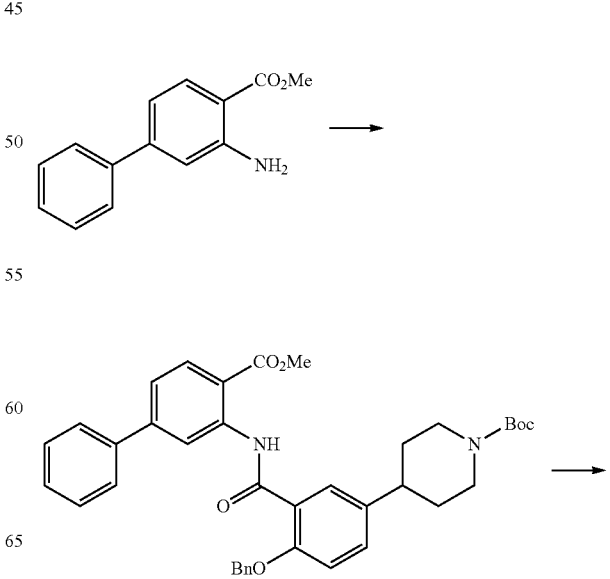

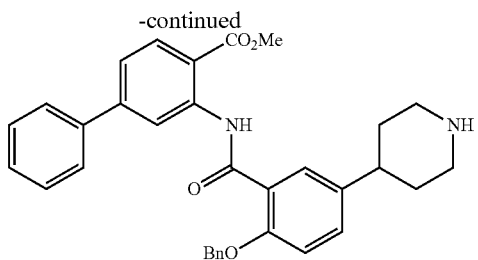

N,N-Dimethylformamide (5 µL) and oxalyl chloride (0.093 mL) were added to a methylene chloride (3.0 mL) solution of 2-(benzyloxy)-5-(1-(tert-butoxycarbonyl)piperidin-4-yl)benzoic acid (0.30 g), followed by stirring at room temperature for 65 minutes. The solvent was evaporated under reduced pressure, and methylene chloride (3.0 mL) was added to the residue. The resulting mixture was added to a solution mixture of methyl 2-amino-4-phenylbenzoate (0.14 g) in pyridine (0.12 mL) and methylene chloride (3.0 mL) under ice-cooling, followed by stirring at room temperature for 3 hours. The solvent was evaporated under reduced pressure, and water and chloroform were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 85-60% hexane/ethyl acetate] to obtain 0.19 g of methyl 2-(2-(benzyloxy)-5-(1-(tert-butoxycarbonyl)piperidin-4-yl)benzamido)-4-phenylbenzoate as a white solid.

Trifluoroacetic acid (1.0 mL) was added to a chloroform (2.0 mL) solution of the obtained methyl 2-(2-(benzyloxy)-5-(1-(tert-butoxycarbonyl)piperidin-4-yl)benzamido)-4-phenylbenzoate (0.19 g), followed by stirring at room temperature for 1 hour and 30 minutes. The solvent was evaporated under reduced pressure, and water was added to the residue. After adjusting the pH to 7.4 with a saturated aqueous solution of sodium bicarbonate, chloroform was added thereto. The organic layer was separated, washed with a saturated aqueous solution of sodium chloride, and dried over anhydrous magnesium sulfate, and the solvent was evaporated under reduced pressure to obtain 0.15 g of methyl 2-(2-(benzyloxy)-5-(piperidin-4-yl)benzamido)-4-phenylbenzoate as a white solid.

$^1$H-NMR (CDCl$_3$) δ: 1.50-1.92 m), 2.56-2.80 (3H, m), 3.10-3.26 (2H, m), 3.75 (3H, s), 5.42 (2H, s), 6.95 (1H, d, J=8.6 Hz), 7.20-7.52 (1H, m), 7.70-7.78 (2H, m), 8.02 (1H, d, J=2.4 Hz), 8.07 (1H, d, J=8.3 Hz), 9.29 (1H, d, J=1.7 Hz), 12.27 (1H, s).

Example 50a

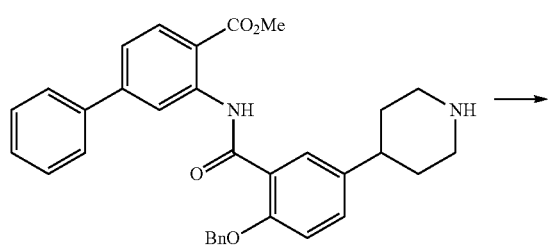

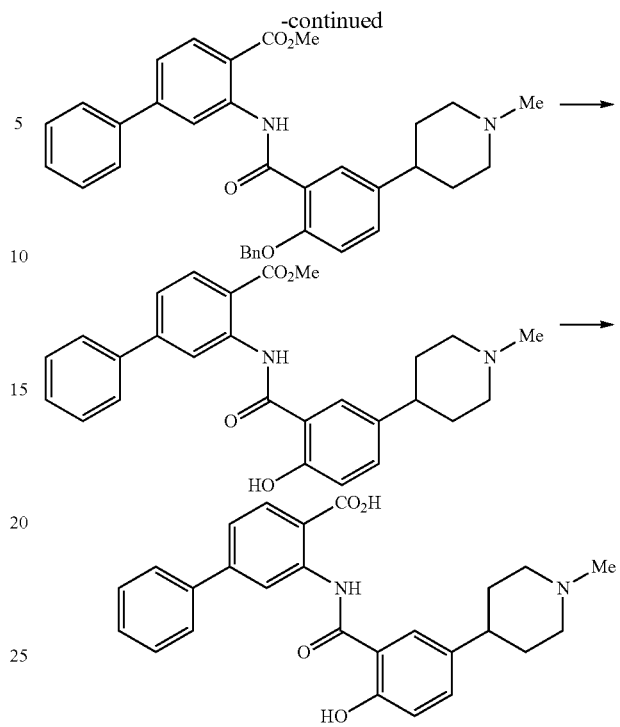

A 37% formaldehyde aqueous solution (6.3 µL), acetic acid (0.022 mL), and sodium triacetoxyborohydride (0.10 g) were sequentially added to a tetrahydrofuran (3.0 mL) solution of methyl 2-(2-(benzyloxy)-5-(piperidin-4-yl)benzamido)-4-phenylbenzoate (0.10 g), followed by stirring at room temperature for 3 hours and 30 minutes. The solvent was evaporated under reduced pressure, and a saturated aqueous solution of sodium bicarbonate and chloroform were added to the residue. The organic layer was separated and dried over anhydrous magnesium sulfate, and the solvent was evaporated under reduced pressure. The obtained residue was purified by silica gel column chromatography [eluent: 98-90% chloroform/methanol] to obtain 0.086 g of methyl 2-(2-(benzyloxy)-5-(1-methylpiperidin-4-yl)benzamido)-4-phenylbenzoate as a white solid.

To a methanol (3.0 mL) solution of the obtained methyl 2-(2-(benzyloxy)-5-(1-methylpiperidin-4-yl)benzamido)-4-phenylbenzoate (0.086 g), 10% palladium-carbon (43 mg) was added, followed by stirring under a hydrogen atmosphere at room temperature for 2 hours and 10 minutes. The insoluble substance was removed by filtration, and the solvent was evaporated under reduced pressure. Ethyl acetate was added to the obtained residue, and the solid substance was collected by filtration to obtain 0.058 g of methyl 2-(2-hydroxy-5-(1-methylpiperidin-4-yl)benzamido)-4-phenylbenzoate as a white solid.

A 2.0 mol/L aqueous solution of sodium hydroxide (0.33 mL) was added to a methanol (2.0 mL) suspension of the obtained methyl 2-(2-hydroxy-5-(1-methylpiperidin-4-yl)benzamido)-4-phenylbenzoate (0.058 g), followed by stirring at 60° C. for 9 hours and 20 minutes. The reaction mixture was cooled to room temperature, and 6 mol/L hydrochloric acid (0.11 mL) was added thereto. The solvent was evaporated under reduced pressure. The obtained residue was purified by silica gel column chromatography [eluent: 95-85% chloroform/methanol] to obtain 0.019 g of 2-(2-hydroxy-5-(1-methylpiperidin-4-yl)benzamido)-4-phenylbenzoic acid as a white solid.

¹H-NMR (DMSO-d₆) δ: 1.83-2.11 (4H, m), 2.66-2.85 (4H, m), 2.87-3.11 (2H, m), 6.94 (1H, d, J=8.6 Hz), 7.33-7.44 (3H, m), 7.46-7.54 (2H, m), 7.64-7.72 (2H, m), 7.87-7.96 (1H, m), 8.13 (1H, d, J=8.0 Hz), 8.91 (1H, d, J=1.7 Hz).

¹H-NMR(CF₃COD) δ: 2.18-2.43 (4H, m), 2.95-3.38 (6H, m), 3.84-4.06 (2H, m), 7.17-7.29 (1H, m), 7.46-7.89 (8H, m), 8.38-8.50 (1H, m), 8.79-8.90 (1H, m).

Example 51a

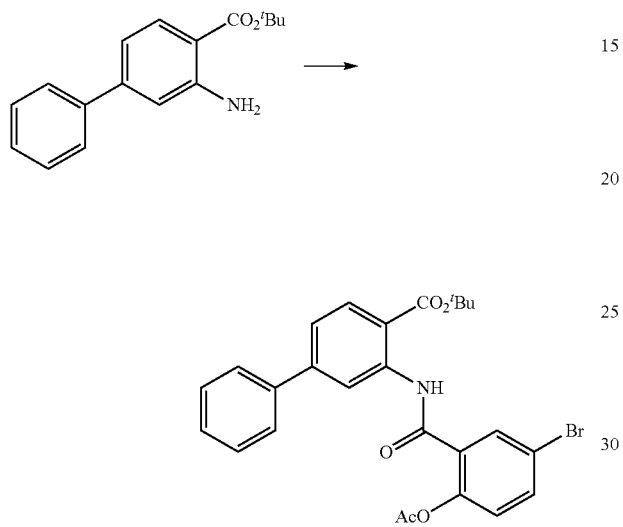

N,N-Dimethylformamide (0.15 mL) and oxalyl chloride (2.5 mL) were added to a methylene chloride (49 mL) suspension of 2-acetoxy-5-bromobenzoic acid (5.0 g), followed by stirring at room temperature for 1 hour. The solvent was evaporated under reduced pressure, and toluene was added to the residue. The solvent was evaporated under reduced pressure, and methylene chloride (10 mL) was added to the residue. The resulting mixture was added to a solution mixture of tert-butyl 2-amino-4-phenylbenzoate (4.9 g) in pyridine (3.7 mL) and methylene chloride (49 mL) under ice-cooling, followed by stirring at room temperature for 30 minutes. A 10% aqueous solution of citric acid was added to the reaction mixture. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 100-80% hexane/ethyl acetate] to obtain 8.9 g of tert-butyl 2-(2-acetoxy-5-bromobenzamido)-4-phenylbenzoate as a white solid.

¹H-NMR (CDCl₃) δ: 1.62 (9H, s), 2.30 (3H, s), 7.11 (1H, d, J=8.7 Hz), 7.36 (1H, dd, J=8.3, 1.8 Hz), 7.36-7.44 (1H, m), 7.44-7.51 (2H, m), 7.63 (1H, dd, J=8.7, 2.4 Hz), 7.67-7.73 (2H, m), 8.05 (1H, d, J=2.4 Hz), 8.07 (1H, d, J=8.3 Hz), 9.12 (1H, d, J=1.8 Hz), 11.89 (1H, s).

Examples 52a to 57a

As in Example 51a, the compounds shown in Table 12a were prepared.

TABLE 12a

| Example No. | A |
|---|---|
| 52a | 2-BnO, 4-I, methyl-substituted phenyl |
| 53a | 2-BnO, 4-NO₂, methyl-substituted phenyl |
| 54a | 2-BnO, 4-Br, methyl-substituted phenyl |
| 55a | 2-BnO, 4-I, methyl-substituted phenyl |
| 56a | 2-BnO, 4-OAc, methyl-substituted phenyl |
| 57a | 2-BnO, 4-(CH₂CH₂OAc), methyl-substituted phenyl |

Tert-butyl 2-(2-(benzyloxy)-4-iodobenzamido)-4-phenylbenzoate

¹H-NMR (DMSO-d₆) δ: 1.49 (9H, s), 5.52 (2H, s), 7.25-7.37 (3H, m), 7.43-7.58 (7H, m), 7.61 (1H, d, J=1.2 Hz), 7.66-7.75 (3H, m), 8.05 (1H, d, J=8.3 Hz), 9.01-9.06 (1H, m), 12.08 (1H, s).

Tert-butyl 2-(2-(benzyloxy)-5-nitrobenzamido)-4-phenylbenzoate

¹H-NMR (CDCl₃) δ: 1.55 (9H, s), 5.61 (2H, s), 7.05 (1H, d, J=9.3 Hz), 7.28-7.44 (5H, m), 7.44-7.53 (4H, m), 7.70-7.76 (2H, m), 8.09 (1H, d, J=8.3 Hz), 8.23 (1H, dd, J=9.3, 2.9 Hz), 9.09 (1H, d, J=2.9 Hz), 9.29 (1H, d, J=1.7 Hz), 12.60 (1H, s).

Tert-butyl 2-(2-(benzyloxy)-5-bromobenzamido)-4-phenylbenzoate $^1$H-NMR (CDCl$_3$) δ: 1.53 (9H, s), 5.48 (2H, s), 6.83 (1H, d, J=8.8 Hz), 7.22-7.50 (10H, m), 7.70-7.75 (2H, m), 8.06 (1H, d, J=8.3 Hz), 8.29 (1H, d, J=2.7 Hz), 9.26 (1H, d, J=1.7 Hz), 12.49 (1H, s).

Tert-butyl 2-(2-(benzyloxy)-5-iodobenzamido)-4-phenylbenzoate $^1$H-NMR (DMSO-d$_6$) δ: 1.50 (9H, s), 5.51 (2H, s), 7.08 (1H, d, J=8.8 Hz), 7.24-7.36 (3H, m), 7.44-7.58 (6H, m), 7.68-7.75 (2H, m), 7.81 (1H, dd, J=8.8, 2.3 Hz), 8.05 (1H, d, J=8.3 Hz), 8.21 (1H, d, J=2.3 Hz), 9.00-9.06 (1H, m), 12.15 (1H, s).

Tert-butyl 2-(5-acetoxy-2-(benzyloxy)benzamido)-4-phenylbenzoate $^1$H-NMR (CDCl$_3$) δ: 1.53 (9H, s), 2.28 (3H, s), 5.48 (2H, s), 6.94 (1H, d, J=9.0 Hz), 7.09 (1H, dd, J=9.0, 3.0 Hz), 7.24-7.51 (9H, m), 7.69-7.75 (2H, m), 7.89 (1H, d, J=3.0 Hz), 8.05 (1H, d, J=8.3 Hz), 9.25 (1H, d, J=1.9 Hz), 12.52 (1H, s).

Tert-butyl 2-(5-(2-acetoxyethyl)-2-(benzyloxy)benzamido)-4-phenylbenzoate $^1$H-NMR (DMSO-d$_6$) δ: 1.49 (9H, s), 1.97 (3H, s), 2.88 (2H, t, J=6.8 Hz), 4.19 (2H, t, J=6.8 Hz), 5.48 (2H, s), 7.17 (1H, d, J=8.7 Hz), 7.23-7.36 (3H, m), 7.39 (1H, dd, J=8.7, 2.4 Hz), 7.43-7.59 (6H, m), 7.69-7.75 (2H, m), 7.84 (1H, d, J=2.4 Hz), 8.05 (1H, d, J=8.3 Hz), 9.06-9.11 (1H, m), 12.16 (1H, s).

Example 58a

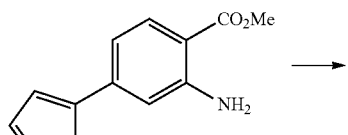

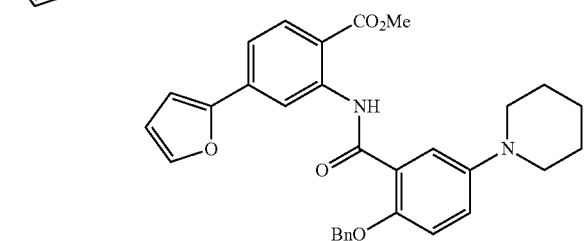

As in Example 51a, the following compound was prepared.

Methyl 2-(2-(benzyloxy)-5-(piperidin-1-yl)benzamido)-4-(furan-2-yl)benzoate $^1$H-NMR (CDCl$_3$) δ: 1.40-2.50 (6H, m), 3.10-3.60 (4H, m), 3.77 (3H, s), 5.46 (2H, s), 6.53 (1H, dd, J=3.4, 1.6z), 6.89 (1H, d, J=3.4 Hz), 6.98-7.12 (1H, m), 7.25-7.37 (4H, m), 7.40-7.49 (3H, m), 7.52-7.58 (1H, m), 8.00-8.22 (1H, m), 8.05 (1H, d, J=8.3 Hz), 9.30 (1H, d, J=1.4 Hz), 12.43 (1H, s).

Example 59a

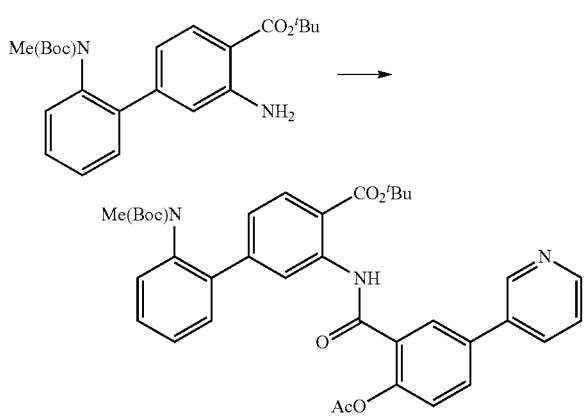

As in Example 51a, the following compound was prepared.

Tert-butyl 2-(2-acetoxy-5-(pyridin-3-yl)benzamido)-4-(2-((tert-butoxycarbonyl)(methyl)amino)phenyl)benzoate $^1$H-NMR (CDCl$_3$) δ: 1.21 (9H, s), 1.63 (9H, s), 2.32 (3H, s), 3.10 (3H, s), 7.05-7.13 (1H, m), 7.18-7.29 (1H, m), 7.31-7.48 (5H, m), 7.74 (1H, dd, J=8.4, 2.3 Hz), 7.95 (1H, ddd, J=7.9, 2.4, 1.7 Hz), 8.04 (1H, d, J=8.3 Hz), 8.15 (1H, d, J=2.2 Hz), 8.63 (1H, dd, J=4.8, 1.6 Hz), 8.88-8.98 (2H, m), 12.06 (1H, s).

Example 60a

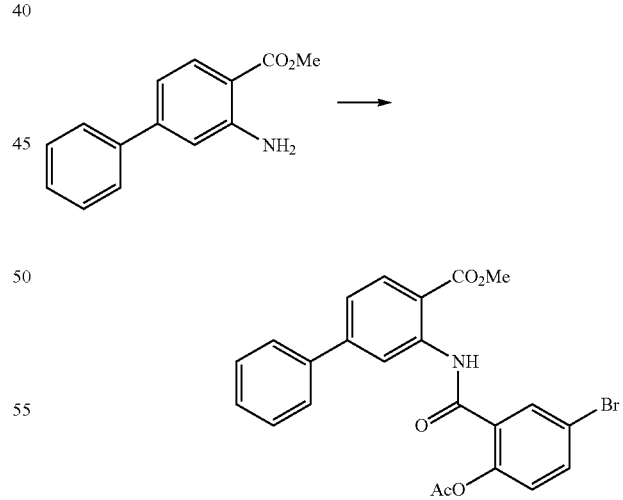

N,N-Dimethylformamide (5 μL) and oxalyl chloride (0.077 mL) were added to a methylene chloride (2 mL) suspension of 2-acetoxy-5-bromobenzoic acid (0.16 g), followed by stirring at room temperature for 1 hour. The solvent was evaporated under reduced pressure, and methylene chloride (2 mL) was added to the residue. The resulting mixture was added to a solution mixture of methyl 2-amino-4-phenylbenzoate (0.11 g) in pyridine (0.10 mL) and methylene chloride (2 mL), followed by stirring at room temperature for 1 hour and 20 minutes. The solvent was evaporated under reduced pressure, and water and chloroform were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 70-50% hexane/ethyl acetate] to obtain 0.23 g of methyl 2-(2-acetoxy-5-bromobenzamido)-4-phenylbenzoate as a white solid.

$^1$H-NMR (CDCl$_3$) δ: 2.31 (3H, s), 3.96 (3H, s), 7.10 (1H, d, J=8.8 Hz), 7.36-7.53 (4H, m), 7.64 (1H, dd, J=8.8, 2.4 Hz), 7.67-7.74 (2H, m), 8.04 (1H, d, J=2.4 Hz), 8.13 (1H, d, J=8.3 Hz), 9.13 (1H, d, J=1.7 Hz), 11.75 (1H, s).

Examples 61a and 62a

As in Example 60a, the compounds shown in Table 13a were prepared.

TABLE 13a

| Example No. | A |
| --- | --- |
| 61a | (4-methyl-1,3-phenylene diacetate: AcO, OAc) |
| 62a | (4-methyl-3-benzyloxy-phenyl acetate: BnO, OAc) |

4-(2-(Methoxycarbonyl)-5-phenylphenylcarbamoyl)-1,3-phenylene diacetate $^1$H-NMR (CDCl$_3$) δ: 2.32 (3H, s), 2.33 (3H, s), 3.95 (3H, s), 7.06 (1H, d, J=2.2 Hz), 7.16 (1H, dd, J=8.5, 2.2 Hz), 7.38 (1H, dd, J=8.4, 1.8 Hz), 7.38-7.44 (1H, m), 7.44-7.51 (2H, m), 7.68-7.74 (2H, m), 7.95 (1H, d, J=8.5 Hz), 8.12 (1H, d, J=8.6 Hz), 9.15 (1H, d, J=1.8 Hz), 11.75 (1H, s).

Methyl 2-(5-acetoxy-2-(benzyloxy)benzamido)-4-phenylbenzoate $^1$H-NMR (CDCl$_3$) δ: 2.28 (3H, s), 3.77 (3H, s), 5.45 (2H, s), 6.98 (1H, d, J=9.0 Hz), 7.12 (1H, dd, J=8.9, 3.1 Hz), 7.26-7.51 (9H, m), 7.68-7.75 (2H, m), 7.89 (1H, d, J=3.0 Hz), 8.07 (1H, d, J=8.3 Hz), 9.25 (1H, d, J=2.0 Hz), 12.33 (1H, s).

Example 63a

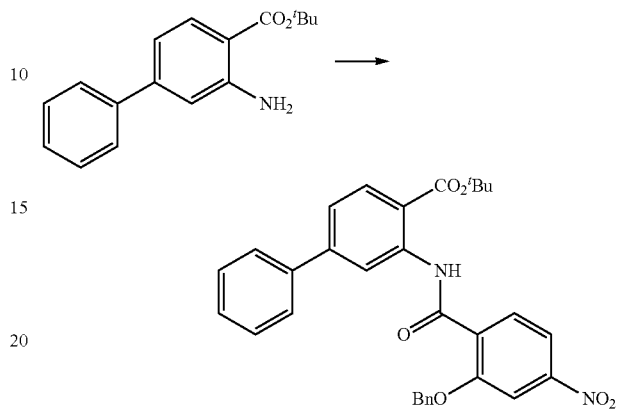

As in Example 60a, the following compound was prepared.

Tert-butyl 2-(2-(benzyloxy)-4-nitrobenzamido)-4-phenylbenzoate $^1$H-NMR (CDCl$_3$) δ: 1.55 (9H, s), 5.56 (2H, s), 7.24-7.57 (9H, m), 7.69-7.77 (2H, m), 7.85-7.94 (2H, m), 8.09 (1H, d, J=8.3 Hz), 8.28 (1H, d, J=8.3 Hz), 9.26 (1H, s), 12.55 (1H, s).

Example 64a

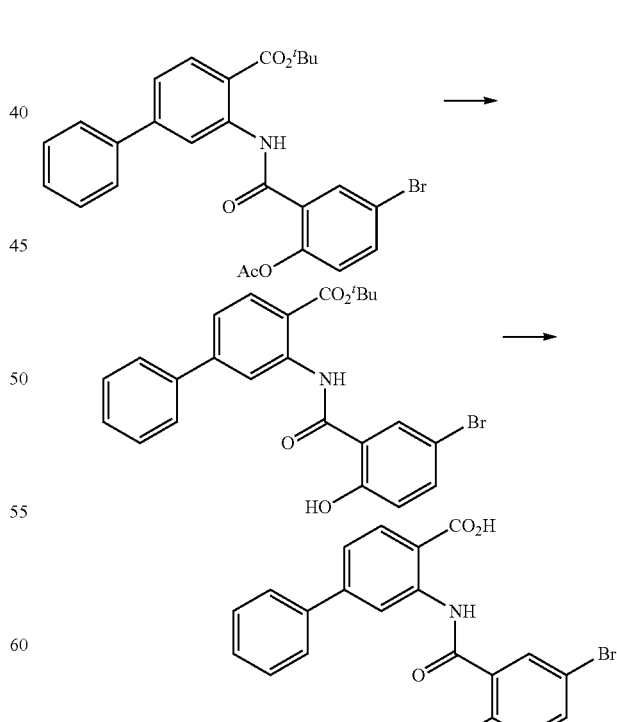

Potassium carbonate (0.049 g) was added to a solution mixture of tert-butyl 2-(2-acetoxy-5-bromobenzamido)-4- phenylbenzoate (0.060 g) in methanol (1 mL) and dioxane (1 mL), followed by stirring at room temperature for 1 hour. A 10% aqueous solution of citric acid and ethyl acetate were added to the reaction mixture. The organic layer was separated, washed with a saturated aqueous solution of sodium chloride, and dried over anhydrous magnesium sulfate, and the solvent was evaporated under reduced pressure. Trifluoroacetic acid (5 mL) was added to the obtained residue, followed by stirring at room temperature for 2 hours. The solvent was evaporated under reduced pressure, and methanol was added to the obtained residue. The solid substance was collected by filtration to obtain 0.034 g of 2-(5-bromo-2-hydroxybenzamido)-4-phenylbenzoic acid as a white solid.

$^1$H-NMR (DMSO-$d_6$) δ: 7.00 (1H, d, J=8.7 Hz), 7.43-7.49 (1H, m), 7.50-7.58 (3H, m), 7.60 (1H, dd, J=8.7, 2.6 Hz), 7.70-7.75 (2H, m), 8.03 (1H, d, J=2.6 Hz), 8.09 (1H, d, J=8.0 Hz), 9.00 (1H, d, J=1.7 Hz), 11.62-11.80 (1H, broad), 12.24-12.40 (1H, broad), 13.38-13.60 (1H, broad).

Example 65a 4-(furan-2-yl)-2-(2-hydroxy-5-(piperidin-1-yl)benzamido) benzoate (0.043 g) in methanol (1.0 mL) and dioxane (4.0 mL), followed by stirring at room temperature for 5 hours. Water and toluene were added to the reaction mixture, and the aqueous layer was separated. After adjusting the pH to 1.8 with methanesulfonic acid, 0.036 g of a solid substance was collected by filtration. Ethyl acetate (2.0 mL) and methanesulfonic acid (5.7 µL) were added to the obtained solid substance (0.036 g), and the solid substance was collected by filtration to obtain 0.034 g of 4-(furan-2-yl)-2-(2-hydroxy-5-(piperidin-1-yl)benzamido)benzoic acid methanesulfonate as a white solid.

$^1$H-NMR (DMSO-$d_6$-$D_2O$) δ: 1.56-1.76 (2H, m), 1.83-1.98 (4H, m), 2.38 (3H, s), 3.46-3.57 (4H, m), 6.69 (1H, dd, J=3.4, 1.9 Hz), 7.11 (1H, d, J=3.4 Hz), 7.18 (1H, d, J=8.9 Hz), 7.57 (1H, dd, J=8.4, 1.8 Hz), 7.72 (1H, dd, J=8.9, 2.9 Hz), 7.87 (1H, d, J=1.2 Hz), 8.07 (1H, d, J=8.4 Hz), 8.14-8.22 (1H, m), 9.08 (1H, d, J=1.8 Hz).

Example 66a

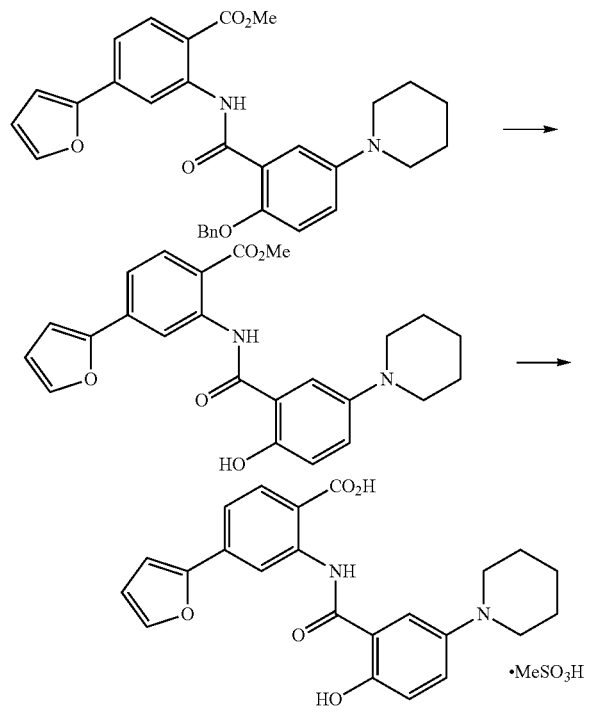

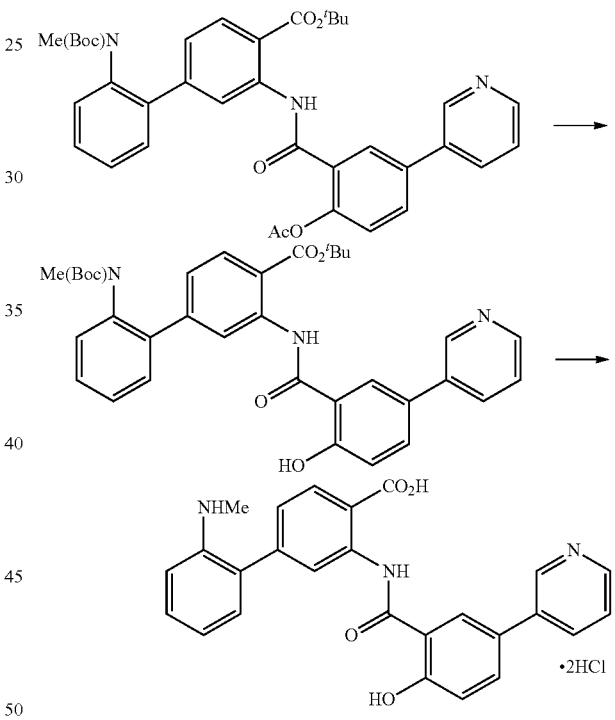

Water (0.20 mL), sodium formate (0.045 g), acetic acid (0.043 mL) and 10% palladium-carbon (8 mg) were added to a dioxane (1 mL) solution of methyl 2-(2-(benzyloxy)-5-(piperidin-1-yl)benzamido)-4-(furan-2-yl)benzoate (0.085 g), followed by stirring at room temperature for 3 hours and 30 minutes and then at 60° C. for 50 minutes. To the reaction mixture, 10% palladium-carbon (8 mg) was added, followed by stirring at 70° C. for 50 minutes. After cooling the reaction mixture to room temperature, the insoluble substance was removed by filtration, and the solvent was evaporated under reduced pressure. Diisopropyl ether was added to the obtained residue, and the solid substance was collected by filtration to obtain 0.048 g of methyl 4-(furan-2-yl)-2-(2-hydroxy-5-(piperidin-1-yl)benzamido)benzoate.

A 2 mol/L aqueous solution of sodium hydroxide (0.51 mL) was added to a solution mixture of the obtained methyl A 2 mol/L aqueous solution of sodium hydroxide (2.3 mL) was added to a solution mixture of tert-butyl 2-(2-acetoxy-5-(pyridin-3-yl)benzamido)-4-(2-((tert-butoxycarbonyl)(methyl)amino)phenyl)benzoate (0.28 g) in methanol (2 mL) and dioxane (4 mL), followed by stirring at room temperature for 6 hours. The reaction mixture was adjusted to a pH of 5.5 with a 10% aqueous solution of citric acid, and chloroform was added thereto. The organic layer was separated, washed with a saturated aqueous solution of sodium chloride, and dried over anhydrous magnesium sulfate, and the solvent was evaporated under reduced pressure. Trifluoroacetic acid (4 mL) was added to the obtained residue, followed by stirring at room temperature for 20 minutes. The solvent was evaporated under reduced pressure, and toluene was added to the residue. The solvent was evaporated under reduced pressure, and a 4 mol/L hydrogen chloride-dioxane solution (5 mL) was added to the residue, followed by stirring at room temperature for 5 minutes. The solvent was evaporated under reduced pressure, and diethyl ether was added to the residue. The solid substance was collected by filtration to obtain 0.18 g of 2-(2-hydroxy-5-(pyridin-3-yl)benzamido)-4-(2-(methylamino)phenyl)benzoic acid dihydrochloride as a light yellow solid.

$^1$H-NMR (DMSO-$d_6$) δ: 2.74 (3H, s), 6.86-7.02 (2H, m), 7.12-7.20 (1H, m), 7.25-7.39 (3H, m), 7.98 (1H, dd, J=8.7, 2.6 Hz), 8.05-8.15 (2H, m), 8.38 (1H, d, J=2.4 Hz), 8.75 (1H, d, J=1.7 Hz), 8.81-8.90 (2H, m), 9.25 (1H, d, J=2.0 Hz), 11.95-12.10 (1H, broad), 12.34 (1H, s).

Example 67a

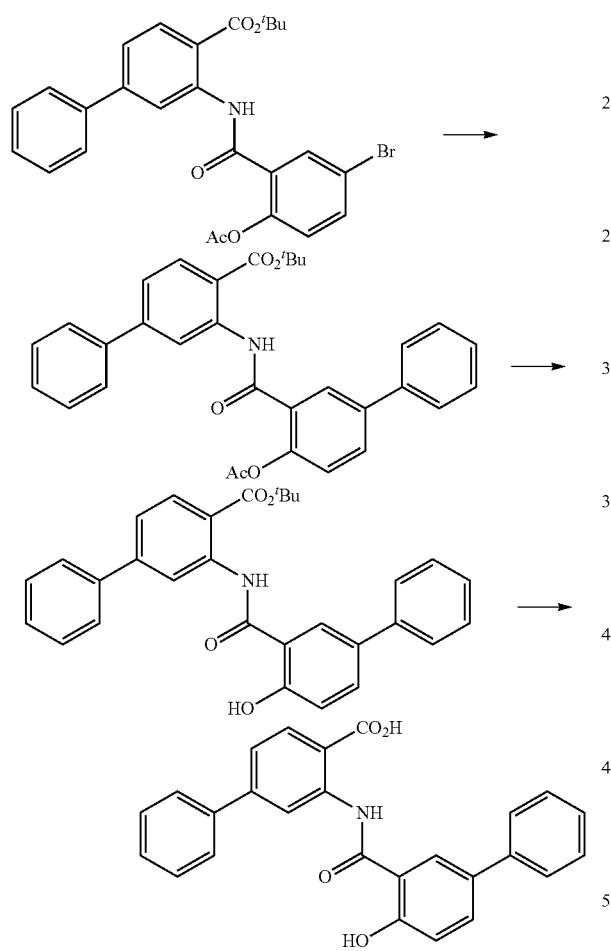

Ethylene glycol dimethyl ether (1.4 mL), water (0.42 mL), phenylboranic acid (0.045 g), sodium bicarbonate (0.063 g), and bis(triphenylphosphine)palladium(II) dichloride (4 mg) were added to tert-butyl 2-(2-acetoxy-5-bromobenzamido)-4-phenylbenzoate (0.15 g), followed by heating to reflux under a nitrogen atmosphere for 45 minutes. The reaction mixture was cooled to room temperature, and potassium carbonate (0.12 g) was added thereto, followed by stirring under a nitrogen atmosphere at room temperature for 2 hours. Water and ethyl acetate were added to the reaction mixture. The organic layer was separated, washed with a saturated aqueous solution of sodium chloride, and dried over anhydrous magnesium sulfate, and the solvent was evaporated under reduced pressure. Methanol (2 mL), dioxane (4 mL), and a 2 mol/L aqueous solution of sodium hydroxide (1.5 mL) were added to the obtained residue, followed by stirring at room temperature for 1 hour and 40 minutes. The solvent was evaporated under reduced pressure, and 1 mol/L hydrochloric acid and ethyl acetate were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 95-80% hexane/ethyl acetate] and further purified by silica gel column chromatography [eluent: chloroform] to obtain 0.086 g of tert-butyl 2-(2-hydroxy-5-phenylbenzamido)-4-phenylbenzoate as a white solid.

Trifluoroacetic acid (1 mL) was added to a methylene chloride (3 mL) solution of the obtained tert-butyl 2-(2-hydroxy-5-phenylbenzamido)-4-phenylbenzoate (0.085 g), followed by stirring at room temperature for 17 hours. The solvent was evaporated under reduced pressure, and ethyl acetate was added to the residue. The solid substance was collected by filtration to obtain 0.072 g of 2-(2-hydroxy-5-phenylbenzamido)-4-phenylbenzoic acid as a white solid.

$^1$H-NMR (DMSO-$d_6$) δ: 7.13 (1H, d, J=8.6 Hz), 7.31-7.39 (1H, m), 7.43-7.51 (3H, m), 7.51-7.58 (3H, m), 7.64-7.70 (2H, m), 7.72-7.77 (2H, m), 7.78 (1H, dd, J=8.6, 2.3 Hz), 8.12 (1H, d, J=8.3 Hz), 8.21 (1H, d, J=2.3 Hz), 9.05 (1H, d, J=1.7 Hz), 11.64 (1H, s), 12.40 (1H, s), 13.45-13.70 (1H, broad).

Example 68a

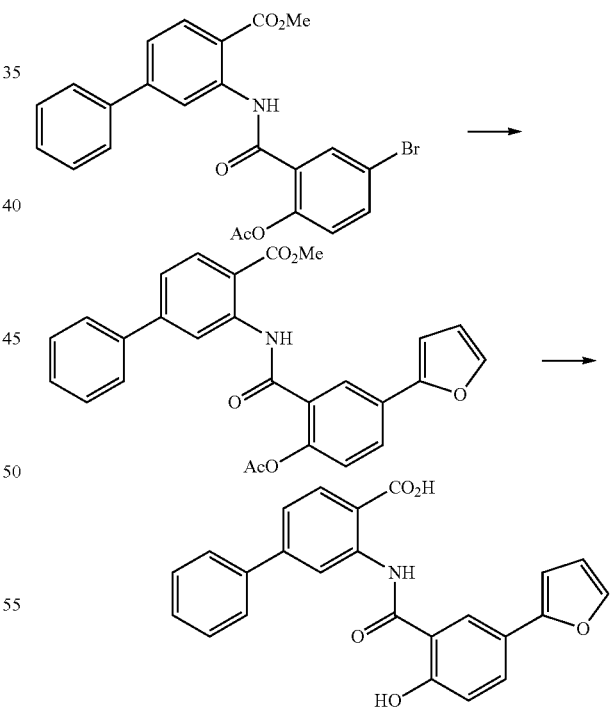

Water (0.42 mL), 2-furanboronic acid (0.040 g), sodium bicarbonate (0.060 g), and bis(triphenylphosphine)palladium(II) dichloride (4 mg) were added to an ethylene glycol dimethyl ether (1.4 mL) suspension of methyl 2-(2-acetoxy-5-bromobenzamido)-4-phenylbenzoate (0.14 g), followed by heating to reflux under a nitrogen atmosphere for 1 hour and 10 minutes. The reaction mixture was cooled to room temperature, and water and ethyl acetate were added thereto. The insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 95-70% hexane/ethyl acetate] and further purified by silica gel column chromatography [eluent: 90-70% hexane/ethyl acetate] to obtain 0.073 g of methyl 2-(2-acetoxy-5-(furan-2-yl)benzamido)-4-phenylbenzoate.

Dioxane (2 mL) and a 2 mol/L aqueous solution of sodium hydroxide (0.79 mL) were added to the obtained methyl 2-(2-acetoxy-5-(furan-2-yl)benzamido)-4-phenylbenzoate (0.072 g), followed by stirring at room temperature for 6 hours. The reaction mixture was adjusted to a pH of 1.5 with 2 mol/L hydrochloric acid, and the solid substance was collected by filtration to obtain 0.055 g of 2-(5-(furan-2-yl)-2-hydroxybenzamido)-4-phenylbenzoic acid as a yellow solid.

$^1$H-NMR (DMSO-$d_6$) δ: 6.56-6.62 (1H, m), 6.83 (1H, d, J=3.4 Hz), 7.08 (1H, d, J=8.3 Hz), 7.42-7.60 (4H, m), 7.69-7.77 (3H, m), 7.78 (1H, dd, J=8.5, 2.2 Hz), 8.11 (1H, d, J=8.3 Hz), 8.25 (1H, d, J=1.9 Hz), 9.05 (1H, d, J=1.4 Hz), 11.55-11.80 (1H, broad), 12.30-12.60 (1H, broad), 13.45-13.65 (1H, broad).

Example 69a

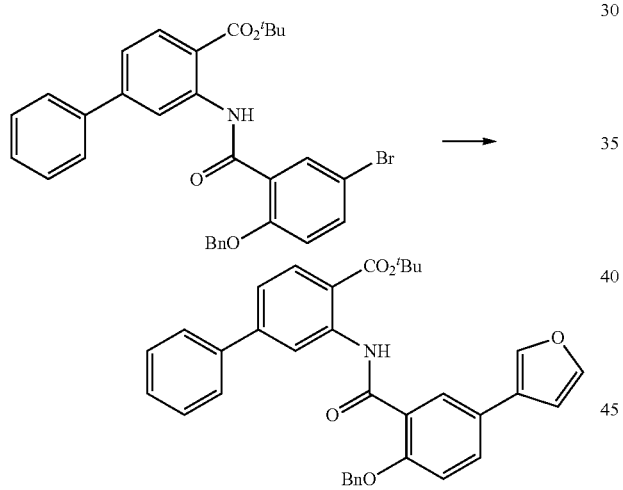

Water (0.5 mL), 3-(4,4,5,5-tetramethyl-1,3,2-dioxaborolan-2-yl)furan (0.070 g), sodium carbonate (0.076 g), and bis(triphenylphosphine)palladium(II) dichloride (4.2 mg) were added to an ethylene glycol dimethyl ether (1.7 mL) solution of tert-butyl 2-(2-(benzyloxy)-5-bromobenzamido)-4-phenylbenzoate (0.17 g), followed by heating to reflux under a nitrogen atmosphere for 1 hour and 40 minutes. The reaction mixture was cooled to room temperature, and water and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 95-80% hexane/ethyl acetate] to obtain 0.14 g of tert-butyl 2-(2-(benzyloxy)-5-(furan-3-yl)benzamido)-4-phenylbenzoate as a white solid.

$^1$H-NMR (CDCl$_3$) δ: 1.53 (9H, s), 5.50 (2H, s), 6.67-6.73 (1H, m), 6.97 (1H, d, J=8.8 Hz), 7.24-7.53 (11H, m), 7.67-7.79 (3H, m), 8.07 (1H, d, J=8.3 Hz), 8.31 (1H, d, J=2.4 Hz), 9.31 (1H, d, J=1.7 Hz), 12.52 (1H, s).

Example 70a

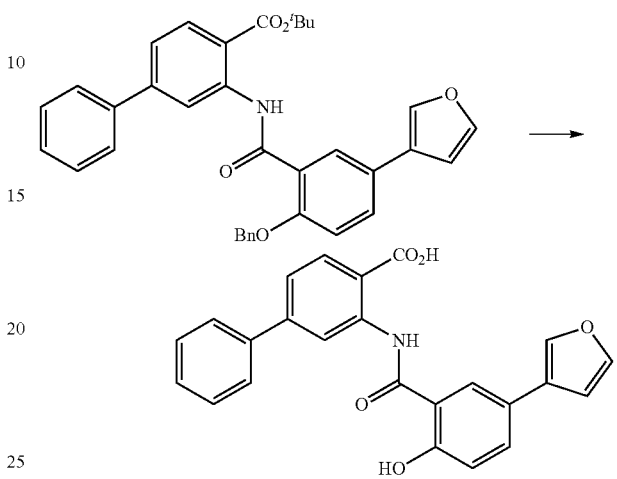

Thioanisole (1.6 mL) and trifluoroacetic acid (5.2 mL) were added to tert-butyl 2-(2-(benzyloxy)-5-(furan-3-yl)benzamido)-4-phenylbenzoate (0.14 g), followed by stirring at room temperature for 4 hours. The solvent was evaporated under reduced pressure, and dioxane was added to the residue. The solvent was evaporated under reduced pressure, and ethyl acetate was added to the residue. The solid substance was collected by filtration to obtain 0.020 g of 2-(5-(furan-3-yl)-2-hydroxybenzamido)-4-phenylbenzoic acid as a white solid.

$^1$H-NMR (DMSO-$d_6$) δ: 6.89-6.95 (1H, m), 7.05 (1H, d, J=8.5 Hz), 7.42-7.50 (1H, m), 7.50-7.59 (3H, m), 7.70 (1H, dd, J=8.5, 2.4 Hz), 7.72-7.78 (3H, m), 8.08-8.15 (3H, m), 9.05 (1H, d, J=1.7 Hz), 11.45-11.58 (1H, broad), 12.30-12.50 (1H, broad), 13.45-13.65 (1H, broad).

Example 71a

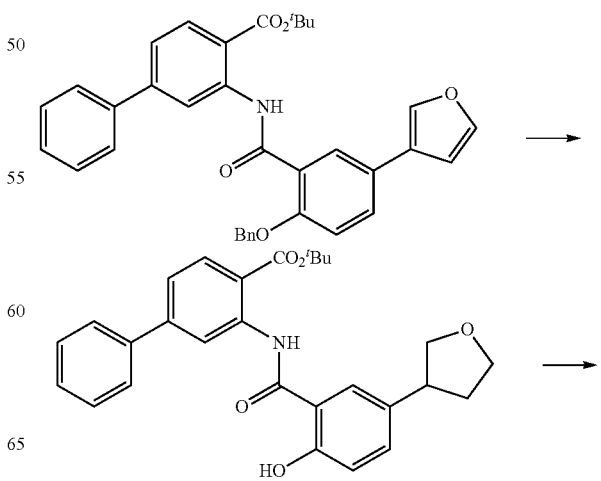

-continued

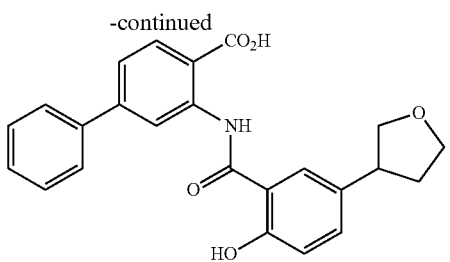

To a solution mixture of tert-butyl 2-(2-(benzyloxy)-5-(furan-3-yl)benzamido)-4-phenylbenzoate (0.048 g) in methanol (2 mL) and dioxane (2 mL), 10% palladium-carbon (20 mg) was added, followed by stirring under a hydrogen atmosphere at room temperature for 2 hours. The insoluble substrate was removed by filtration, and the solvent was evaporated under reduced pressure. The obtained residue was purified by silica gel column chromatography [Fuji Silysia Chemical Ltd., PSQ100B (spherical), eluent: 97-85% hexane/ethyl acetate] to obtain 0.027 g of tert-butyl 2-(2-hydroxy-5-(tetrahydrofuran-3-yl)benzamido)-4-phenylbenzoate as a white solid.

Trifluoroacetic acid (2 mL) was added to a methylene chloride (5 mL) solution of the obtained tert-butyl 2-(2-hydroxy-5-(tetrahydrofuran-3-yl)benzamido)-4-phenylbenzoate (0.027 g), followed by stirring at room temperature for 3 hours. The solvent was evaporated under reduced pressure, and diisopropyl ether was added to the obtained residue. The solid substance was collected by filtration to obtain 0.023 g of 2-(2-hydroxy-5-(tetrahydrofuran-3-yl)benzamido)-4-phenylbenzoic acid as a white solid.

$^1$H-NMR (DMSO-$d_6$) δ: 1.85-2.00 (1H, m), 2.25-2.38 (1H, m), 3.27-3.44 (1H, m), 3.53 (1H, dd, J=7.9, 7.9 Hz), 3.81 (1H, ddd, J=7.8, 7.8, 7.8 Hz), 3.96 (1H, ddd, J=8.3, 8.3, 4.4 Hz), 4.04 (1H, dd, J=7.7, 7.7 Hz), 6.97 (1H, d, J=8.5 Hz), 7.37 (1H, dd, J=8.4, 2.3 Hz), 7.42-7.59 (4H, m), 7.70-7.77 (2H, m), 7.81 (1H, d, J=2.2 Hz), 8.10 (1H, d, J=8.3 Hz), 9.03 (1H, d, J=1.7 Hz), 11.35 (1H, s), 12.34 (1H, s), 13.45-13.65 (1H, broad).

Example 72a

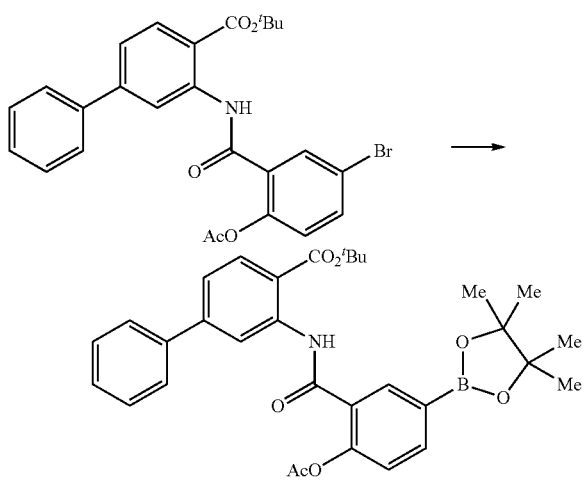

Potassium acetate (1.4 g), bis(pinacolato)diboron (1.5 g), and (1,1'-bis(diphenylphosphino)ferrocene)palladium(II) dichloride methylene chloride complex (0.20 g) were sequentially added to a dioxane (25 mL) suspension of tert-butyl 2-(2-acetoxy-5-bromobenzamido)-4-phenylbenzoate (2.5 g), followed by heating to reflux under a nitrogen atmosphere for 1 hour and 30 minutes. The reaction mixture was cooled to room temperature, and a saturated aqueous solution of sodium bicarbonate and ethyl acetate were added thereto. The insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [Biotage AB, KP-Sil, eluent: 95-50% hexane/ethyl acetate] to obtain 1.4 g of tert-butyl 2-(2-acetoxy-5-(4,4,5,5-tetramethyl-1,3,2-dioxaborolan-2-yl)benzamido)-4-phenylbenzoate as a white solid.

$^1$H-NMR (DMSO-$d_6$) δ: 1.32 (12H, s), 1.56 (9H, s), 2.25 (3H, s), 7.34 (1H, d, J=8.1 Hz), 7.43-7.50 (1H, m), 7.51-7.58 (3H, m), 7.68-7.74 (2H, m), 7.90 (1H, dd, J=8.1, 1.7 Hz), 8.03 (1H, d, J=8.3 Hz), 8.18 (1H, d, J=1.7 Hz), 8.78 (1H, d, J=1.7 Hz), 11.47 (1H, s).

Example 73a

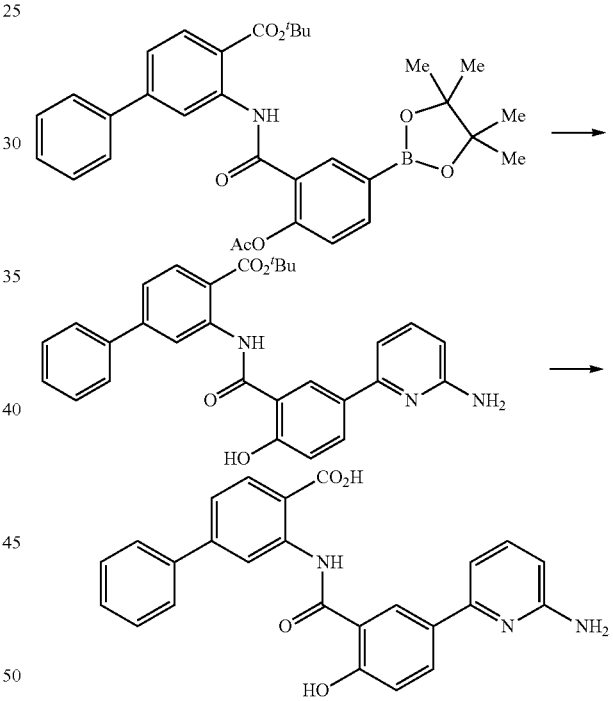

Water (0.3 mL), 2-amino-6-bromopyridine (0.037 g), sodium bicarbonate (0.036 g), and bis(triphenylphosphine)palladium(II) dichloride (5.0 mg) were added to an ethylene glycol dimethyl ether (1 mL) suspension of tert-butyl 2-(2-acetoxy-5-(4,4,5,5-tetramethyl-1,3,2-dioxaborolan-2-yl)benzamido)-4-phenylbenzoate (0.080 g), followed by heating to reflux under a nitrogen atmosphere for 1 hour and 30 minutes. The reaction mixture was cooled to room temperature, and then bis(triphenylphosphine)palladium(II) dichloride (5.0 mg) was added thereto, followed by heating to reflux under a nitrogen atmosphere for 2 hours. The reaction mixture was cooled to room temperature, and methanol (0.3 mL) and sodium carbonate (0.046 g) were added thereto, followed by heating to reflux under a nitrogen atmosphere for 20 minutes. The reaction mixture was cooled to room temperature, and water and ethyl acetate were added thereto. The insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 90-60% hexane/ethyl acetate] to obtain 0.032 g of tert-butyl 2-(5-(6-aminopyridin-2-yl)-2-hydroxybenzamido)-4-phenylbenzoate.

Trifluoroacetic acid (5 mL) was added to the obtained tert-butyl 2-(5-(6-aminopyridin-2-yl)-2-hydroxybenzamido)-4-phenylbenzoate (0.032 g), followed by stirring at room temperature for 12 hours. The solvent was evaporated under reduced pressure, and water and ethyl acetate were added thereto. After adjusting the pH to 6 with a saturated aqueous solution of sodium bicarbonate, the solid substance was collected by filtration. Carbon dioxide gas was introduced into a solution mixture of water (1 mL), methanol (0.5 mL), and dioxane (0.5 mL) containing the obtained solid substance, and the solid substance was collected by filtration to obtain 0.018 g of 2-(5-(6-aminopyridin-2-yl)-2-hydroxybenzamido)-4-phenylbenzoic acid as a white solid.

$^1$H-NMR (DMSO-$d_6$) δ: 5.90-6.15 (2H, broad), 6.41 (1H, d, J=8.0 Hz), 7.02 (1H, d, J=7.3 Hz), 7.07 (1H, d, J=8.6 Hz), 7.43-7.58 (5H, m), 7.71-7.77 (2H, m), 8.05 (1H, dd, J=8.6, 2.4 Hz), 8.11 (1H, d, J=8.3 Hz), 8.59 (1H, d, J=2.4 Hz), 9.06 (1H, d, J=1.7 Hz).

Example 74a

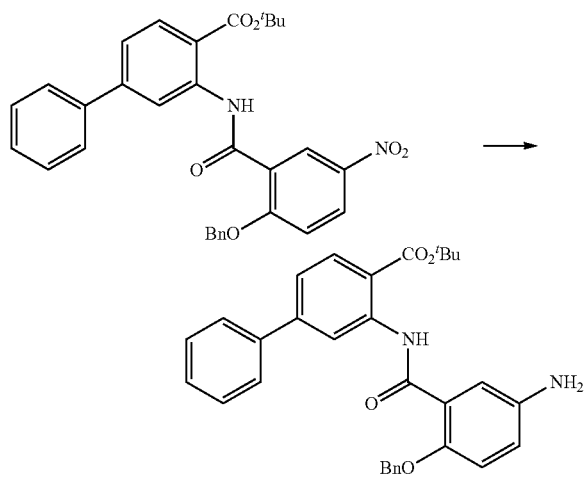

Iron powder (43 mg) was added to a solution mixture of tert-butyl 2-(2-(benzyloxy)-5-nitrobenzamido)-4-phenylbenzoate (0.14 g) in methanol (1.4 mL) and acetic acid (1.4 mL), followed by heating to reflux for 1 hour. The reaction mixture was cooled to room temperature, and iron powder (14 mg) was added thereto, followed by heating to reflux for 30 minutes. The reaction mixture was cooled to room temperature, and a saturated aqueous solution of sodium bicarbonate and ethyl acetate were added thereto. The insoluble substance was removed by filtration. The organic layer was separated, washed with a saturated aqueous solution of sodium bicarbonate and a saturated aqueous solution of sodium chloride sequentially, and dried over anhydrous magnesium sulfate, and the solvent was evaporated under reduced pressure. The obtained residue was purified by silica gel column chromatography [Kanto Chemical Co., Inc., silica gel 60 (spherical), eluent: 90-50% hexane/ethyl acetate] to obtain 0.065 g of tert-butyl 2-(5-amino-2-(benzyloxy)benzamido)-4-phenylbenzoate as a yellow solid.

$^1$H-NMR (CDCl$_3$) δ: 1.52 (9H, s), 5.38 (2H, s), 6.71 (1H, dd, J=8.7, 2.6 Hz), 6.79 (1H, d, J=8.7 Hz), 7.20-7.53 (10H, m), 7.70-7.75 (2H, m), 8.04 (1H, d, J=8.3 Hz), 9.25 (1H, d, J=1.7 Hz), 12.40 (1H, s).

Example 75a

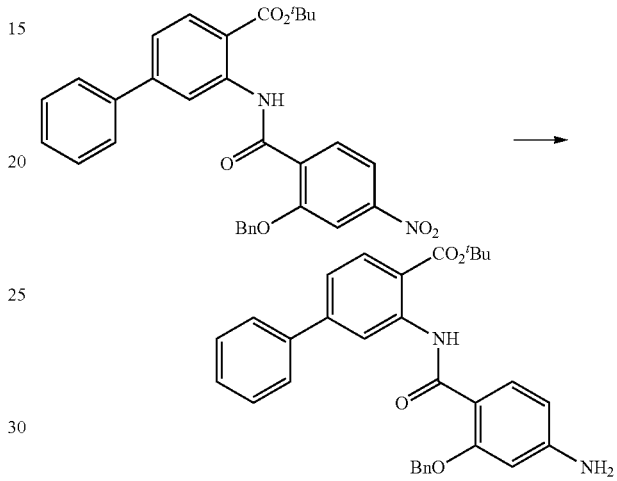

As in Example 74a, the following compound was prepared.

Tert-butyl 2-(4-amino-2-(benzyloxy)benzamido)-4-phenylbenzoate $^1$H-NMR (CDCl$_3$) δ: 1.51 (9H, s), 5.47 (2H, s), 6.16 (1H, d, J=2.2 Hz), 6.33 (1H, dd, J=8.5, 2.2 Hz), 7.25-7.41 (5H, m), 7.41-7.50 (4H, m), 7.70-7.76 (2H, m), 8.02 (1H, d, J=8.1 Hz), 8.05 (1H, d, J=8.5 Hz), 9.28 (1H, d, J=1.7 Hz), 12.36 (1H, s).

Example 76a

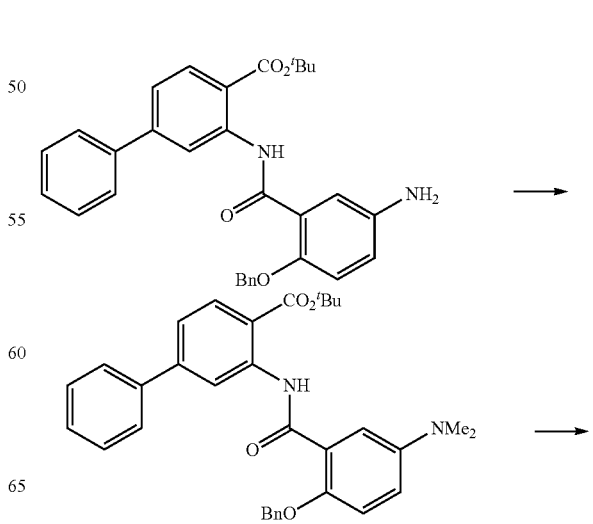

-continued

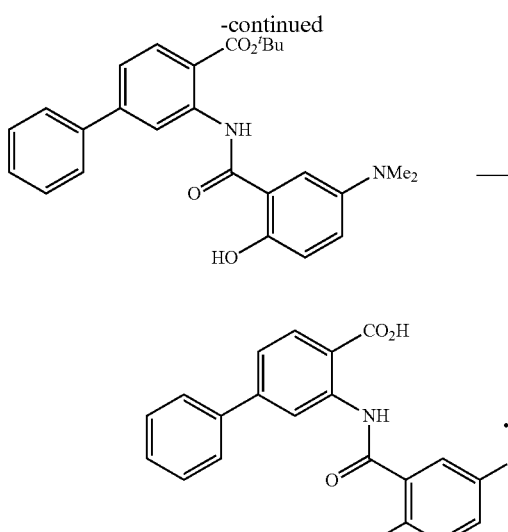

A 37% aqueous solution of formaldehyde (0.24 mL) and sodium triacetoxyborohydride (0.082 g) were sequentially added to a chloroform (1.5 mL) solution of tert-butyl 2-(5-amino-2-(benzyloxy)benzamido)-4-phenylbenzoate (0.064 g), followed by stirring at room temperature for 4 hours and 30 minutes. Water and chloroform were added to the reaction mixture. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 95-70% hexane/ethyl acetate] to obtain 0.063 g of tert-butyl 2-(2-(benzyloxy)-5-(dimethylamino)benzamido)-4-phenylbenzoate.

To a solution mixture of the obtained tert-butyl 2-(2-(benzyloxy)-5-(dimethylamino)benzamido)-4-phenylbenzoate (0.063 g) in methanol (1.5 mL) and ethyl acetate (2.5 mL), 10% palladium-carbon (32 mg) was added, followed by stirring under a hydrogen atmosphere at room temperature for 2 hours. To the reaction mixture, 10% palladium-carbon (13 mg) was added, followed by stirring under a hydrogen atmosphere at room temperature for 1 hour and 30 minutes. Ethyl acetate was added to the reaction mixture. The insoluble substance was removed by filtration, and the solvent was evaporated under reduced pressure. The obtained residue was purified by silica gel column chromatography [eluent: 95-85% hexane/ethyl acetate] to obtain 0.036 g of tert-butyl 2-(5-(dimethylamino)-2-hydroxybenzamido)-4-phenylbenzoate.

Trifluoroacetic acid (5 mL) was added to the obtained tert-butyl 245-(dimethylamino)-2-hydroxybenzamido)-4-phenylbenzoate (0.036 g), followed by stirring at room temperature for 12 hours. The solvent was evaporated under reduced pressure, and ethyl acetate (1.5 mL) and a 4 mol/L hydrogen chloride-dioxane solution (0.5 mL) were added thereto, followed by stirring at room temperature for 2 hours and 30 minutes. The solid substance was collected by filtration to obtain 0.029 g of 2-(5-(dimethylamino)-2-hydroxybenzamido)-4-phenylbenzoic acid hydrochloride as a white solid.

$^1$H-NMR (DMSO-$d_6$) δ: 3.08 (6H, s), 7.08-7.16 (1H, m), 7.43-7.51 (2H, m), 7.51-7.58 (4H, m), 7.70-7.76 (2H, m), 8.10 (1H, d, J=8.3 Hz), 9.07 (1H, d, J=1.7 Hz), 12.37 (1H, s).

Example 77a

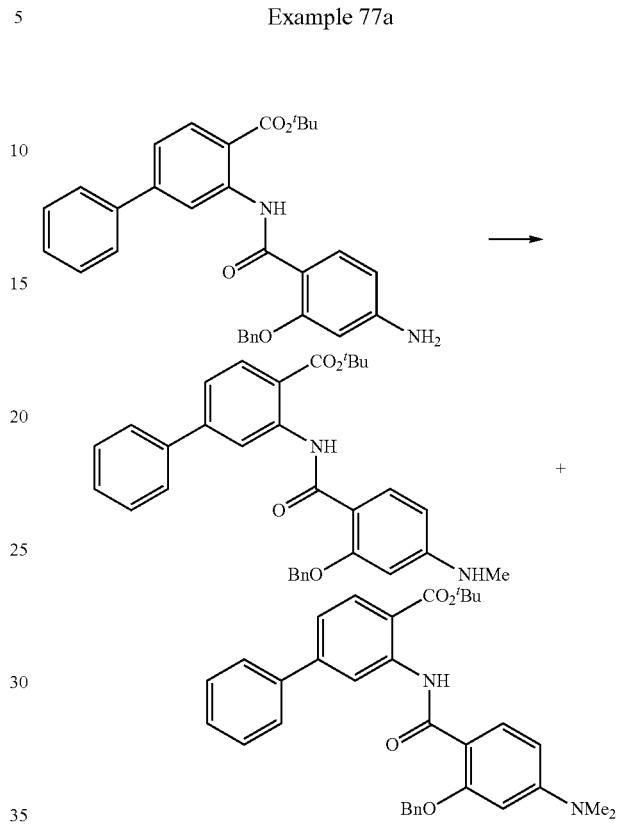

Potassium carbonate (0.084 g) and methyl iodide (0.028 mL) were added to an N,N-dimethylacetamide (1.5 mL) solution of tert-butyl 2-(4-amino-2-(benzyloxy)benzamido)-4-phenylbenzoate (0.15 g), followed by stirring at room temperature for 1 hour and then at 80° C. for 30 minutes. The reaction mixture was cooled to room temperature, and then potassium carbonate (0.042 g) and methyl iodide (0.019 mL) were added thereto, followed by stirring at 80° C. for 20 minutes. The reaction mixture was cooled to room temperature, and a 10% aqueous solution of citric acid and ethyl acetate were added thereto. The organic layer was separated, washed with a 10% aqueous solution of citric acid and a saturated aqueous solution of sodium chloride sequentially, and dried over anhydrous magnesium sulfate, and the solvent was evaporated under reduced pressure. The obtained residue was purified by silica gel column chromatography [eluent: 90-70% hexane/ethyl acetate] to obtain 0.056 g of tert-butyl 2-(2-(benzyloxy)-4-(methylamino)benzamido)-4-phenylbenzoate as a white solid and 0.049 g of tert-butyl 2-(2-(benzyloxy)-4-(dimethylamino)benzamido)-4-phenylbenzoate as a white solid.

Tert-butyl 2-(2-(benzyloxy)-4-(methylamino)benzamido)-4-phenylbenzoate $^1$H-NMR (CDCl$_3$) δ: 1.52 (9H, s), 2.77 (3H, s), 3.98-4.06 (1H, broad), 5.49 (2H, s), 6.05 (1H, d, J=2.1 Hz), 6.25 (1H, dd, J=8.7, 2.1 Hz), 7.22-7.41 (5H, m), 7.41-7.53 (4H, m), 7.70-7.76 (2H, m), 8.03 (1H, d, J=8.3 Hz), 8.08 (1H, d, J=8.7 Hz), 9.29 (1H, d, J=1.7 Hz), 12.37 (1H, s).

Tert-butyl 2-(2-(benzyloxy)-4-(dimethylamino)benzamido)-4-phenylbenzoate $^1$H-NMR (CDCl$_3$) δ: 1.53 (9H, s), 2.91 (6H, s), 5.51 (2H, s), 6.11 (1H, d, J=2.3 Hz), 6.34 (1H, dd, J=9.0, 2.3 Hz), 7.22-7.40 (5H, m), 7.41-7.48 (2H, m), 7.50-7.55 (2H, m), 7.71-7.76 (2H, m), 8.03 (1H, d, J=8.3 Hz), 8.11 (1H, d, J=9.0 Hz), 9.31 (1H, d, J=2.0 Hz), 12.38-12.41 (1H, broad).

Example 78a

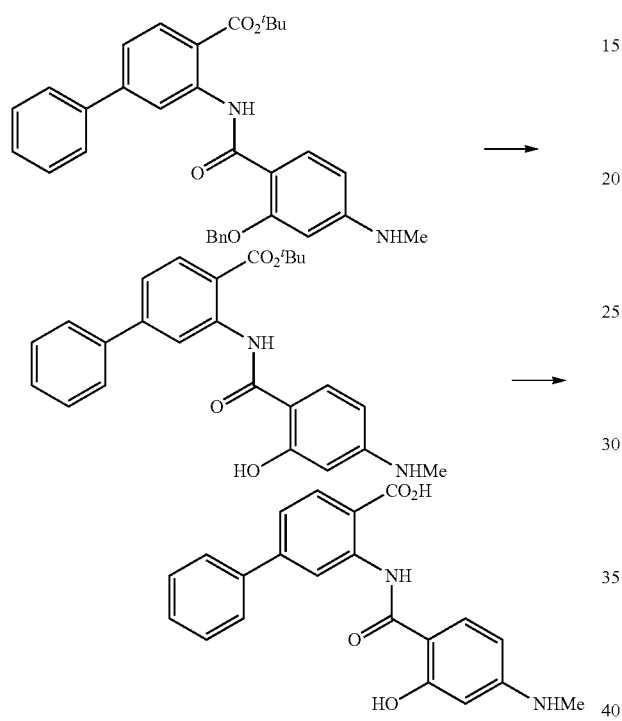

To a solution mixture of tert-butyl 2-(2-(benzyloxy)-4-(methylamino)benzamido)-4-phenylbenzoate (0.053 g) in methanol (1.5 mL), ethyl acetate (3 mL), and dioxane (4.5 mL), 10% palladium-carbon (27 mg) was added, followed by stirring under a hydrogen atmosphere at room temperature for 2 hours. The insoluble substance was removed by filtration, and the solvent was evaporated under reduced pressure. Diisopropyl ether was added to the obtained residue, and then the solid substance was collected by filtration to obtain 0.027 g of tert-butyl 2-(2-hydroxy-4-(methylamino)benzamido)-4-phenylbenzoate as a white solid.

Trifluoroacetic acid (5 mL) was added to the obtained tert-butyl 2-(2-hydroxy-4-(methylamino)benzamido)-4-phenylbenzoate (0.027 g), followed by stirring at room temperature for 3 hours. The solvent was evaporated under reduced pressure, and water and ethyl acetate were added to the residue, followed by adjusting the pH to 6 with a saturated aqueous solution of sodium bicarbonate. The organic layer was separated, washed with a saturated aqueous solution of sodium chloride, and dried over anhydrous magnesium sulfate, and the solvent was evaporated under reduced pressure. Hexane and diisopropyl ether were added to the obtained residue, and the solid substance was collected by filtration to obtain 0.014 g of 2-(2-hydroxy-4-(methylamino)benzamido)-4-phenylbenzoic acid as a light yellow solid.

$^1$H-NMR (DMSO-d$_6$) δ: 2.72 (3H, s), 5.99 (1H, d, J=2.1 Hz), 6.22 (1H, dd, J=8.9, 2.1 Hz), 6.50-6.64 (1H, broad), 7.42-7.49 (2H, m), 7.49-7.57 (2H, m), 7.58 (1H, d, J=8.9 Hz), 7.69-7.75 (2H, m), 8.09 (1H, d, J=8.3 Hz), 8.94 (1H, d, J=1.7 Hz), 12.03 (1H, s), 12.08-12.26 (1H, broad).

Example 79a

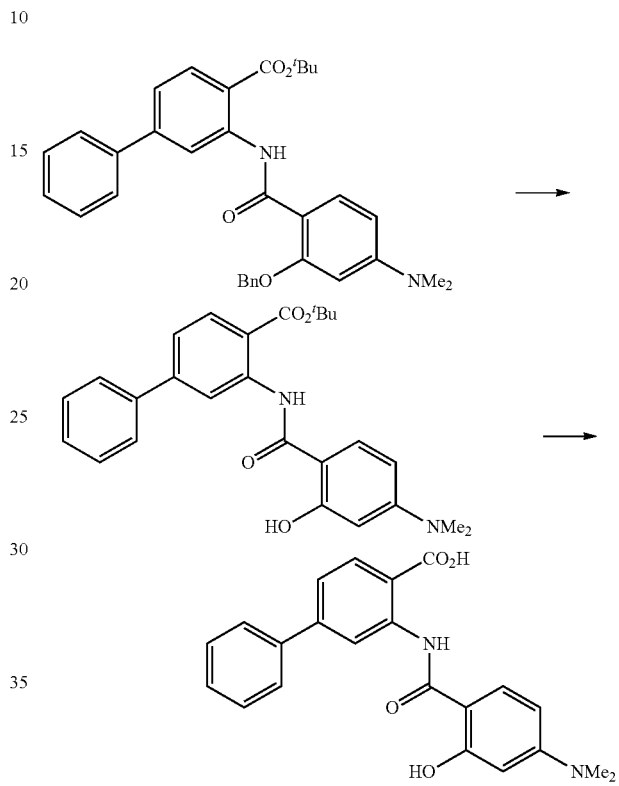

As in Example 78a, the following compound was prepared.

2-(4-(Dimethylamino)-2-hydroxybenzamido)-4-phenylbenzoic acid $^1$H-NMR (DMSO-d$_6$) δ: 2.99 (6H, s), 6.14 (1H, d, J=2.7 Hz), 6.40 (1H, dd, J=9.0, 2.7 Hz), 7.42-7.50 (2H, m), 7.50-7.57 (2H, m), 7.68 (1H, d, J=9.0 Hz), 7.69-7.75 (2H, m), 8.10 (1H, d, J=8.3 Hz), 8.96 (1H, d, J=1.7 Hz), 11.95 (1H, s), 12.18-12.32 (1H, broad).

Example 80a

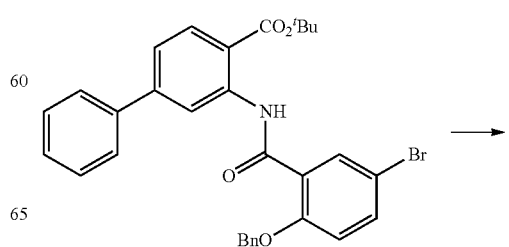

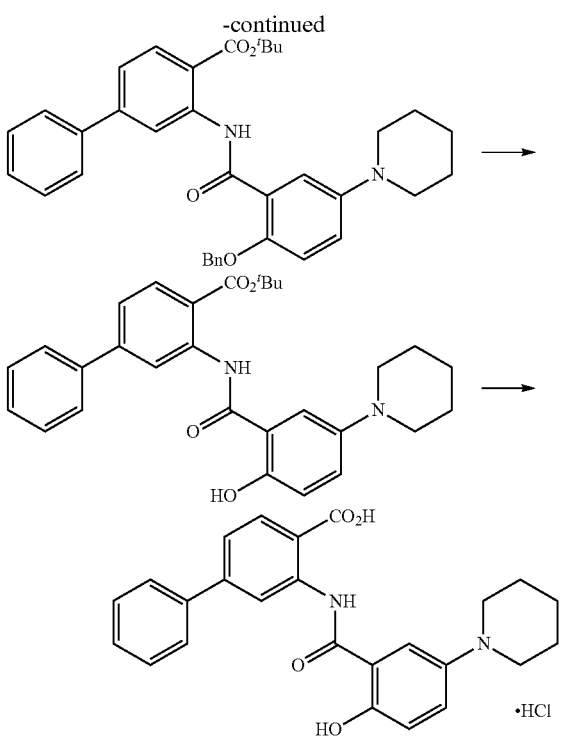

Piperidine (0.040 mL), cesium carbonate (0.18 g), tris(dibenzylideneacetone)dipalladium(0) (2.5 mg), 2-dicyclohexylphosphino-2',4',6'-triisopropylbiphenyl (6.4 mg), and palladium(II) acetate (1.2 mg) were added to a toluene (2.3 mL) suspension of tert-butyl 2-(2-(benzyloxy)-5-bromobenzamido)-4-phenylbenzoate (0.15 g), followed by heating to reflux under a nitrogen atmosphere for 4 hours. The reaction mixture was cooled to room temperature, and then piperidine (0.040 mL), cesium carbonate (0.18 g), tris(dibenzylideneacetone)dipalladium(0) (2.5 mg), 2-dicyclohexylphosphino-2',4',6'-triisopropylbiphenyl (6.4 mg), and palladium(II) acetate (1.2 mg) were added thereto, followed by heating to reflux under a nitrogen atmosphere for 5 hours and 30 minutes. The reaction mixture was cooled to room temperature, and a 10% aqueous solution of citric acid and ethyl acetate were added thereto. The insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 100-70% hexane/ethyl acetate] to obtain 0.13 g of tert-butyl 2-(2-(benzyloxy)-5-(piperidin-1-yl)benzamido)-4-phenylbenzoate as an orange oily substance.

To a solution mixture of the obtained tert-butyl 2-(2-(benzyloxy)-5-(piperidin-1-yl)benzamido)-4-phenylbenzoate (0.13 g) in ethyl acetate (1 mL) and methanol (1 mL), 10% palladium-carbon (63 mg) was added, followed by stirring under a hydrogen atmosphere at room temperature for 2 hours and 30 minutes. Ethyl acetate was added to the reaction mixture, and the insoluble substance was removed by filtration. The solvent was evaporated under reduced pressure, and diisopropyl ether was added to the obtained residue. The solid substance was collected by filtration to obtain 0.081 g of tert-butyl 2-(2-hydroxy-5-(piperidin-1-yl)benzamido)-4-phenylbenzoate as a yellow solid.

Trifluoroacetic acid (5 mL) was added to the obtained tert-butyl 2-(2-hydroxy-5-(piperidin-1-yl)benzamido)-4-phenylbenzoate (0.081 g), followed by stirring at room temperature for 4 hours. The solvent was evaporated under reduced pressure, and ethyl acetate (2 mL) and a 4 mol/L hydrogen chloride-dioxane solution (0.5 mL) were added to the residue, followed by stirring at room temperature for 3 hours. The solid substance was collected from the reaction mixture by filtration to obtain 0.066 g of 2-(2-hydroxy-5-(piperidin-1-yl)benzamido)-4-phenylbenzoic acid hydrochloride as a white solid.

$^1$H-NMR(CD$_3$OD) δ: 1.75-1.88 (2H, m), 1.98-2.12 (4H, m), 3.65 (4H, dd, J=5.6, 5.6 Hz), 7.18 (1H, d, J=9.0 Hz), 7.40-7.46 (1H, m), 7.47-7.54 (3H, m), 7.70-7.76 (3H, m), 8.19 (1H, d, J=3.2 Hz), 8.22 (1H, d, J=8.3 Hz), 9.06 (1H, d, J=2.0 Hz).

Examples 81a to 86a

As in Example 80a, the compounds shown in Table 14a were prepared.

TABLE 14a

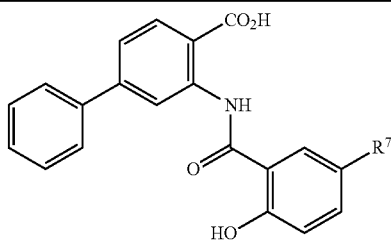

| Example No. | R$^7$ |
|---|---|
| 81a | (N-methyl azocane) ·HCl |
| 82a | (1,4-dimethylpiperidin-4-yl, Me) ·HCl |
| 83a | (N-methyl morpholine) ·HCl |
| 84a | CH$_2$NEt$_2$ ·HCl |
| 85a | N(Me)CH$_2$CH$_2$OH ·HCl |
| 86a | (N-methyl azetidine) ·HCl |

2-(2-Hydroxy-5-((octahydroazocin)-1-yl)benzamido)-4-phenylbenzoic acid hydrochloride $^1$H-NMR (DMSO-$d_6$) δ: 1.42-1.61 (6H, m), 1.65-1.80 (4H, m), 3.36-3.50 (4H, m), 6.82-7.02 (2H, m), 7.08-7.30 (1H, m), 7.43-7.58 (4H, m), 7.70-7.77 (2H, m), 8.10 (1H, d, J=8.3 Hz), 9.04 (1H, d, J=1.9 Hz), 12.31 (1H, s).

2-(2-Hydroxy-5-(4-methylpiperidin-1-yl)benzamido)-4-phenylbenzoic acid hydrochloride $^1$H-NMR (CD$_3$OD) δ: 1.11 (3H, d, J=6.6 Hz), 1.64-1.78 (2H, m), 1.84-1.97 (1H, m), 2.02-2.13 (2H, m), 3.60-3.74 (4H, m), 7.18 (1H, d, J=9.0 Hz), 7.40-7.46 (1H, m), 7.47-7.54 (3H, m), 7.70-7.77 (3H, m), 8.18-8.24 (2H, m), 9.06 (1H, d, J=1.7 Hz).

2-(2-Hydroxy-5-(morpholin-4-yl)benzamido)-4-phenylbenzoic acid hydrochloride $^1$H-NMR (DMSO-$d_6$) δ: 3.16-3.27 (4H, m), 3.80-3.91 (4H, m), 7.03 (1H, d, J=9.0 Hz), 7.36-7.59 (5H, m), 7.67-7.78 (3H, m), 8.10 (1H, d, J=8.3 Hz), 9.03 (1H, d, J=1.7 Hz), 11.22-11.40 (1H, broad), 12.31 (1H, s).

2-(5-(Diethylamino)-2-hydroxybenzamido)-4-phenylbenzoic acid hydrochloride $^1$H-NMR (DMSO-$d_6$) δ: 1.04 (6H, t, J=7.1 Hz), 3.43-3.68 (4H, m), 7.15-7.28 (1H, m), 7.43-7.50 (1H, m), 7.50-7.58 (3H, m), 7.68-7.86 (3H, m), 8.10 (1H, d, J=8.3 Hz), 8.16-8.34 (1H, m), 9.08 (1H, d, J=1.7 Hz), 11.93-12.15 (1H, broad), 12.39 (1H, s).

2-(2-Hydroxy-5-((2-hydroxyethyl)(methyl)amino)benzamido)-4-phenylbenzoic acid hydrochloride $^1$H-NMR (DMSO-$d_6$), (50° C.) δ: 3.04 (3H, s), 3.42-3.58 (4H, m), 7.02 (1H, d, J=9.0 Hz), 7.26-7.38 (1H, m), 7.41-7.57 (4H, m), 7.61-7.76 (3H, m), 8.10 (1H, d, J=8.3 Hz), 9.03 (1H, d, J=2.0 Hz), 12.17-12.35 (1H, broad).

2-(5-(Azetidin-1-yl)-2-hydroxybenzamido)-4-phenylbenzoic acid hydrochloride $^1$H-NMR (CD$_3$OD) δ: 2.66 (2H, qn, J=8.0 Hz), 4.57 (4H, t, J=8.0 Hz), 7.14 (1H, d, J=9.0 Hz), 7.39-7.46 (1H, m), 7.46-7.54 (3H, m), 7.59 (1H, dd, J=9.0, 2.8 Hz), 7.70-7.76 (2H, m), 7.96-8.02 (1H, m), 8.22 (1H, d, J=8.3 Hz), 9.06 (1H, d, J=1.7 Hz).

Example 87a

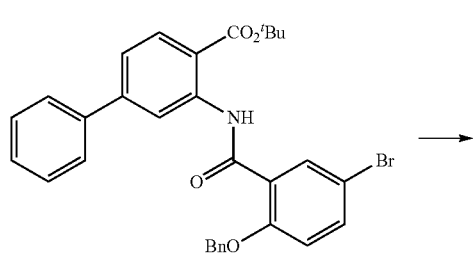

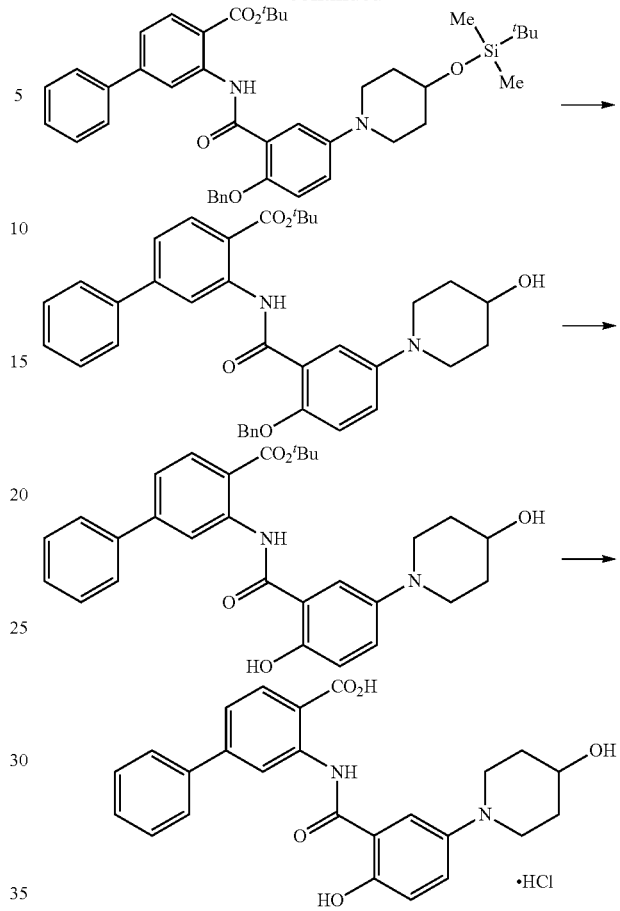

4-(Tert-butyldimethylsilyloxy)piperidine (0.23 g), cesium carbonate (0.44 g), tris(dibenzylideneacetone)dipalladium (0) (9.8 mg), 2-dicyclohexylphosphino-2',4',6'-triisopropylbiphenyl (26 mg), and palladium(II) acetate (4.8 mg) were added to a toluene (4.5 mL) solution of tert-butyl 2-(2-(benzyloxy)-5-bromobenzamido)-4-phenylbenzoate (0.30 g), followed by heating to reflux under a nitrogen atmosphere for 4 hours and 30 minutes. The reaction mixture was cooled to room temperature, and water and ethyl acetate were added thereto. The insoluble substance was removed by filtration. The organic layer was separated, washed with saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 100-90% hexane/ethyl acetate] to obtain 0.32 g of tert-butyl 2-(2-(benzyloxy)-5-(4-(tert-butyldimethylsilyloxy)piperidin-1-yl)benzamido)-4-phenylbenzoate.

A 1.0 mol/L tetrabutylammonium fluoride-tetrahydrofuran solution (0.56 mL) was added to a tetrahydrofuran (3.2 mL) solution of the obtained tert-butyl 2-(2-(benzyloxy)-5-(4-(tert-butyldimethylsilyloxy)piperidin-1-yl)benzamido)-4-phenylbenzoate (0.32 g), followed by stirring at room temperature for 1 hour. A 1.0 mol/L tetrabutylammonium fluoride-tetrahydrofuran solution (0.28 mL) was added to the reaction mixture, followed by stirring at room temperature for 4 hours. Water was added to the reaction mixture under ice-cooling, and chloroform was added thereto at room temperature. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 90-40% hexane/ethyl acetate] to obtain 0.23 g of tert-butyl 2-(2-(benzyloxy)-5-(4-hydroxypiperidin-1-yl)benzamido)-4-phenylbenzoate.

To a solution mixture of the obtained tert-butyl 2-(2-(benzyloxy)-5-(4-hydroxypiperidin-1-yl)benzamido)-4-phenylbenzoate (0.22 g) in methanol (2.2 mL) and ethyl acetate (1.1 mL), 10% palladium-carbon (0.11 g) was added, followed by stirring under a hydrogen atmosphere at room temperature for 1 hour. Ethyl acetate was added to the reaction mixture, and the insoluble substance was removed by filtration. The solvent was evaporated under reduced pressure, and diisopropyl ether was added to the obtained residue. The solid substance was collected by filtration to obtain 0.18 g of tert-butyl 2-(2-hydroxy-5-(4-hydroxypiperidin-1-yl)benzamido)-4-phenylbenzoate.

A trifluoroacetic acid (5 mL) solution of the obtained tert-butyl 2-(2-hydroxy-5-(4-hydroxypiperidin-1-yl)benzamido)-4-phenylbenzoate (0.18 g) was stirred at room temperature for 30 minutes. The solvent was evaporated under reduced pressure, and ethyl acetate (2 mL) and a 4 mol/L hydrogen chloride-dioxane solution (0.5 mL) were added to the residue, followed by stirring at room temperature for 30 minutes. The solid substance was collected from the reaction mixture by filtration to obtain 0.15 g of 2-(2-hydroxy-5-(4-hydroxypiperidin-1-yl)benzamido)-4-phenylbenzoic acid hydrochloride as a light yellow solid.

$^1$H-NMR (CD$_3$OD) δ: 1.97-2.10 (2H, m), 2.18-2.32 (2H, m), 3.56-3.72 (2H, m), 3.78-3.94 (2H, m), 4.05-4.16 (1H, m), 7.18 (1H, d, J=9.0 Hz), 7.40-7.46 (1H, m), 7.47-7.54 (3H, m), 7.70-7.78 (3H, m), 8.19-8.24 (2H, m), 9.06 (1H, d, J=2.0 Hz).

Example 88a

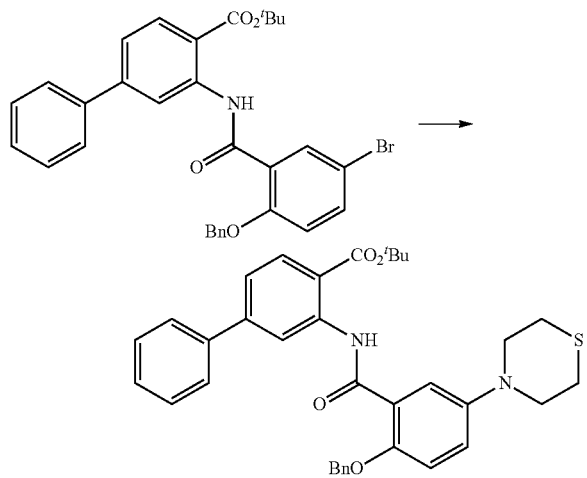

Thiomorpholine (0.14 mL), cesium carbonate (0.58 g), tris(dibenzylideneacetone)dipalladium(0) (8.2 mg), 2-dicyclohexylphosphino-2',4',6'-triisopropylbiphenyl (21 mg), and palladium(II) acetate (4.0 mg) were added to a toluene (5.0 mL) solution of tert-butyl 2-(2-(benzyloxy)-5-bromobenzamido)-4-phenylbenzoate (0.50 g), followed by heating to reflux under a nitrogen atmosphere for 2 hours. The reaction mixture was cooled to room temperature, and then thiomorpholine (0.045 mL), cesium carbonate (0.15 g), tris(dibenzylideneacetone)dipalladium(0) (8.2 mg), 2-dicyclohexylphosphino-2',4',6'-triisopropylbiphenyl (21 mg), and palladium(II) acetate (4.0 mg) were added thereto, followed by heating to reflux under a nitrogen atmosphere for 3 hours. The reaction mixture was cooled to room temperature, and then water and ethyl acetate were added thereto. The insoluble substance was removed by filtration. The organic layer was separated, washed with a 10% aqueous solution of citric acid and a saturated aqueous solution of sodium chloride sequentially, and dried over anhydrous magnesium sulfate, and the solvent was evaporated under reduced pressure. The obtained residue was purified by silica gel column chromatography [Kanto Chemical Co., Inc., silica gel 60 (spherical), eluent: 100-80% hexane/ethyl acetate] to obtain 0.36 g of tert-butyl 2-(2-(benzyloxy)-5-(thiomorpholin-4-yl)benzamido)-4-phenylbenzoate as a yellow solid.

$^1$H-NMR (DMSO-d$_6$) δ: 1.49 (9H, s), 2.65-2.73 (4H, m), 3.36-3.44 (4H, m), 5.42 (2H, s), 7.09-7.15 (2H, m), 7.23-7.35 (3H, m), 7.43-7.59 (7H, m), 7.69-7.76 (2H, m), 8.04 (1H, d, J=8.3 Hz), 9.08-9.12 (1H, m), 12.16 (1H, s).

Example 89a

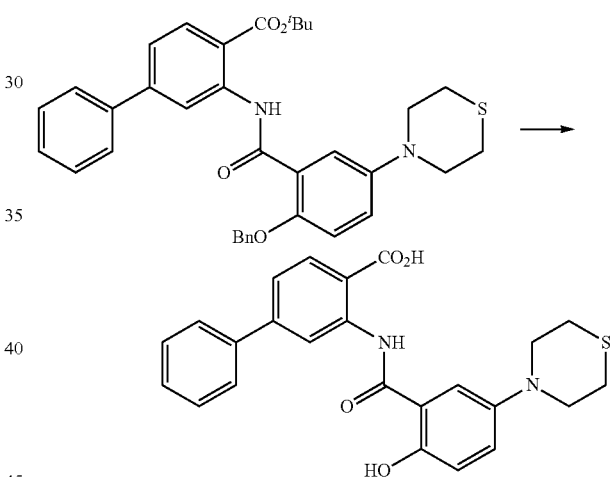

Thioanisole (1.0 mL) was added to a trifluoroacetic acid (2.0 mL) solution of tert-butyl 2-(2-(benzyloxy)-5-(thiomorpholin-4-yl)benzamido)-4-phenylbenzoate (0.10 g), followed by stirring at room temperature for 24 hours. The solvent was evaporated under reduced pressure, and a 4 mol/L hydrogen chloride-dioxane solution (0.5 mL) and ethyl acetate (1.0 mL) were added to the residue, followed by stirring at room temperature for 3 hours. The solid substance was collected by filtration, and water and ethyl acetate were added to the obtained solid substance. After adjusting the pH to 6.5 with a saturated aqueous solution of sodium bicarbonate, the organic layer was separated, washed with a saturated aqueous solution of sodium chloride, and dried over anhydrous magnesium sulfate. The solvent was evaporated under reduced pressure, and the obtained residue was purified by silica gel column chromatography [Kanto Chemical Co., Inc., silica gel 60 (spherical), eluent: chloroform] to obtain 0.047 g of 2-(2-hydroxy-5-(thiomorpholin-4-yl)benzamido)-4-phenylbenzoic acid as a yellow solid.

$^1$H-NMR (DMSO-d$_6$), (40° C.) δ: 2.70-2.76 (4H, m), 3.33-3.39 (4H, m), 6.92 (1H, d, J=8.8 Hz), 7.15 (1H, dd, J=8.8, 3.1

Hz), 7.41-7.57 (5H, m), 7.70-7.76 (2H, m), 8.10 (1H, d, J=8.1 Hz), 8.99 (1H, d, J=1.9 Hz), 10.99 (1H, s), 12.20-12.40 (1H, broad).

Example 90a

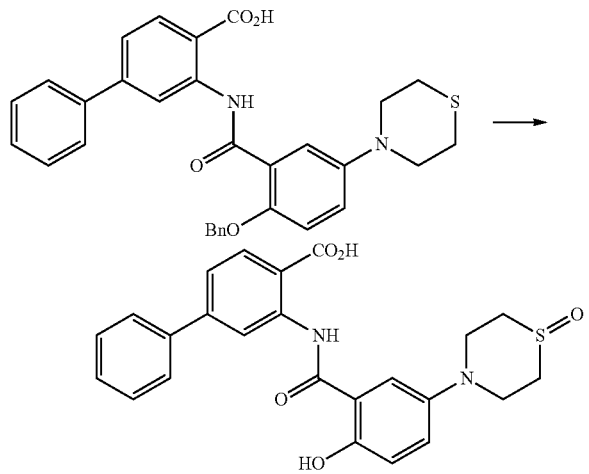

Under ice-cooling, m-chloroperbenzoic acid (7.9 mg) was added to a solution mixture of 2-(2-hydroxy-5-(thiomorpholin-4-yl)benzamido)-4-phenylbenzoic acid (0.015 g) in methylene chloride (1.0 mL) and tetrahydrofuran (0.50 mL), followed by stirring at room temperature for 10 minutes. 2-Propanol (2.0 mL) was added to the reaction mixture, and the solid substance was collected by filtration to obtain 0.011 g of 2-(2-hydroxy-5-(1-oxidethiomorpholin-4-yl)benzamido)-4-phenylbenzoic acid as a light yellow solid.

$^1$H-NMR (DMSO-d$_6$) δ: 2.71-2.84 (2H, m), 2.92-3.04 (2H, m), 3.38-3.50 (2H, m), 3.56-3.70 (2H, m), 6.95 (1H, d, J=9.0 Hz), 7.24 (1H, dd, J=9.0, 2.8 Hz), 7.42-7.57 (5H, m), 7.70-7.76 (2H, m), 8.10 (1H, d, J=8.3 Hz), 9.01 (1H, d, J=1.7 Hz), 11.07 (1H, s), 12.32-12.54 (1H, broad).

Example 91a

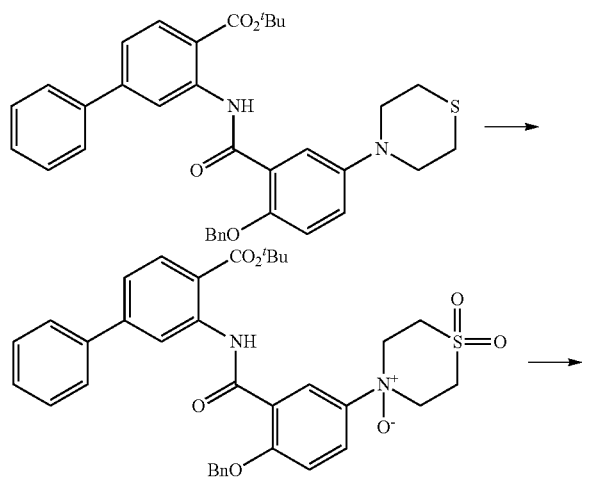

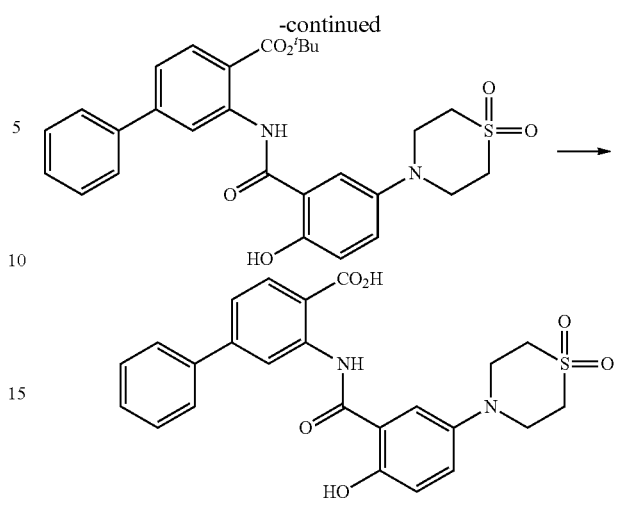

Under ice-cooling, m-chloroperbenzoic acid (79 mg) was added to a methylene chloride (1.5 mL) solution of tert-butyl 2-(2-(benzyloxy)-5-(thiomorpholin-4-yl)benzamido)-4-phenylbenzoate (0.10 g), followed by stirring at room temperature for 30 minutes. Under ice-cooling, m-chloroperbenzoic acid (20 mg) was added to the reaction mixture, followed by stirring at room temperature for 30 minutes. Under ice-cooling, m-chloroperbenzoic acid (40 mg) was added to the reaction mixture, followed by stirring at room temperature for 30 minutes. Under ice-cooling, m-chloroperbenzoic acid (20 mg) was added to the reaction mixture, followed by stirring at room temperature for 30 minutes. A saturated aqueous solution of sodium bicarbonate and methylene chloride were added to the reaction mixture. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 100-90% chloroform/methanol] to obtain 0.089 g of tert-butyl 2-(2-(benzyloxy)-5-(1,14-trioxidethiomorpholin-4-yl)benzamido)-4-phenylbenzoate as a light yellow solid.

To a solution mixture of the obtained tert-butyl 2-(2-(benzyloxy)-5-(1,1,4-trioxidethiomorpholin-4-yl)benzamido)-4-phenylbenzoate (0.086 g) in methanol (2.0 mL) and ethyl acetate (3.0 mL), 10% palladium-carbon (43 mg) was added, followed by stirring under a hydrogen atmosphere at room temperature for 2 hours and 30 minutes. Dioxane and ethyl acetate were added to the reaction mixture, and the insoluble substance was removed by filtration. The solvent was evaporated under reduced pressure to obtain 0.061 g of tert-butyl 2-(2-hydroxy-5-(1,1-dioxidethiomorpholin-4-yl)benzamido)-4-phenylbenzoate.

A trifluoroacetic acid (5.0 mL) solution of the obtained tert-butyl 2-(2-hydroxy-5-(1,1-dioxidethiomorpholin-4-yl)benzamido)-4-phenylbenzoate (0.059 g) was stirred at room temperature for 3 hours. The solvent was evaporated under reduced pressure, and water and ethyl acetate were added to the residue, followed by adjusting the pH to 6.5 with a saturated aqueous solution of sodium bicarbonate. The organic layer was separated, washed with a saturated aqueous solution of sodium chloride, and dried over anhydrous magnesium sulfate, and the solvent was evaporated under reduced pressure. Diisopropyl ether was added to the obtained residue, and the solid substance was collected by filtration to obtain 0.048 g of 2-(2-hydroxy-5-(1,1-dioxidethiomorpholin-4-yl)benzamido)-4-phenylbenzoic acid as a yellow solid.

¹H-NMR (DMSO-d₆) δ: 3.13-3.25 (4H, m), 3.58-3.70 (4H, m), 6.95 (1H, d, J=8.9 Hz), 7.25 (1H, dd, J=8.9, 3.0 Hz), 7.42-7.57 (5H, m), 7.70-7.76 (2H, m), 8.10 (1H, d, J=8.0 Hz), 9.00 (1H, d, J=1.7 Hz), 11.04-11.20 (1H, broad).

Example 92a

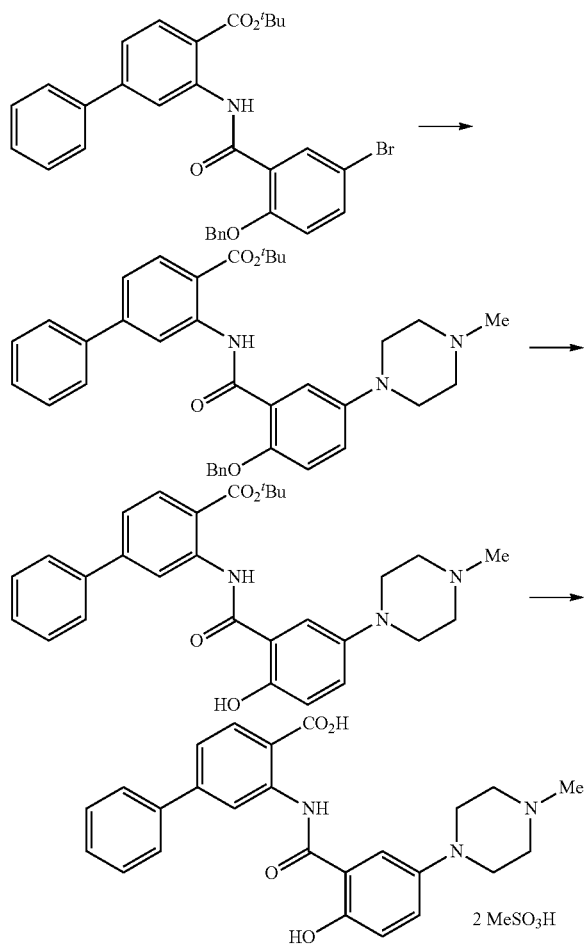

1-Methylpiperazine (0.089 mL), cesium carbonate (0.35 g), tris(dibenzylideneacetone)dipalladium(0) (4.9 mg), 2-dicyclohexylphosphino-2',4',6'-triisopropylbiphenyl (13 mg), and palladium(II) acetate (2.4 mg) were added to a toluene (4.5 mL) solution of tert-butyl 2-(2-(benzyloxy)-5-bromobenzamido)-4-phenylbenzoate (0.30 g), followed by heating to reflux under a nitrogen atmosphere for 3 hours. The reaction mixture was cooled to room temperature, and then 1-methylpiperazine (0.060 mL), cesium carbonate (0.18 g), tris(dibenzylideneacetone)dipalladium(0) (4.9 mg), 2-dicyclohexylphosphino-2',4',6'-triisopropylbiphenyl (13 mg), and palladium(II) acetate (2.4 mg) were added thereto, followed by heating to reflux under a nitrogen atmosphere for 3 hours. After cooling the reaction mixture to room temperature, the solvent was evaporated under reduced pressure, and water and chloroform were added to the residue. The insoluble substance was removed by filtration. The organic layer was separated, washed with a 1 mol/L aqueous solution of sodium hydroxide and a saturated aqueous solution of sodium chloride sequentially, and dried over anhydrous magnesium sulfate, and the solvent was evaporated under reduced pressure. The obtained residue was purified by silica gel column chromatography [Kanto Chemical Co., Inc., silica gel 60 (spherical), eluent: 100-90% chloroform/methanol] to obtain 0.26 g of tert-butyl 2-(2-(benzyloxy)-5-(4-methylpiperazin-1-yl)benzamido)-4-phenylbenzoate.

To a solution mixture of the obtained tert-butyl 2-(2-(benzyloxy)-5-(4-methylpiperazin-1-yl)benzamido)-4-phenylbenzoate (0.26 g) in methanol (2.6 mL) and ethyl acetate (1.3 mL), 10% palladium-carbon (0.26 g) was added, followed by stirring under a hydrogen atmosphere at room temperature for 2 hours. Chloroform was added to the reaction mixture, and the insoluble substance was removed by filtration. The solvent was evaporated under reduced pressure, and the obtained residue was purified by silica gel column chromatography [Kanto Chemical Co., Inc., silica gel 60 (spherical), eluent: 100-90% chloroform/methanol] to obtain 0.13 g of tert-butyl 2-(2-hydroxy-5-(4-methylpiperazin-1-yl)benzamido)-4-phenylbenzoate.

Trifluoroacetic acid (5 mL) was added to the obtained tert-butyl 2-(2-hydroxy-5-(4-methylpiperazin-1-yl)benzamido)-4-phenylbenzoate (0.13 g), followed by stirring at room temperature for 3 hours. The solvent was evaporated under reduced pressure, and methanesulfonic acid (0.034 mL) and ethyl acetate (3 mL) were added to the residue, followed by stirring at room temperature for 1 hour and 30 minutes. The solid substance was collected by filtration to obtain 0.12 g of 2-(2-hydroxy-5-(4-methylpiperazin-1-yl)benzamido)-4-phenylbenzoic acid dimethanesulfonate as a white solid.

¹H-NMR (DMSO-d₆) δ: 2.33 (6H, s), 2.84-2.98 (5H, m), 3.13-3.26 (2H, m), 3.49-3.57 (2H, m), 3.65-3.74 (2H, m), 6.97 (1H, d, J=8.9 Hz), 7.21 (1H, dd, J=8.9, 2.9 Hz), 7.43-7.58 (5H, m), 7.70-7.75 (2H, m), 8.09 (1H, d, J=8.3 Hz), 9.04 (1H, d, J=1.7 Hz), 9.48-9.62 (1H, broad), 10.94-11.06 (1H, broad), 12.27 (1H, s).

Example 93a

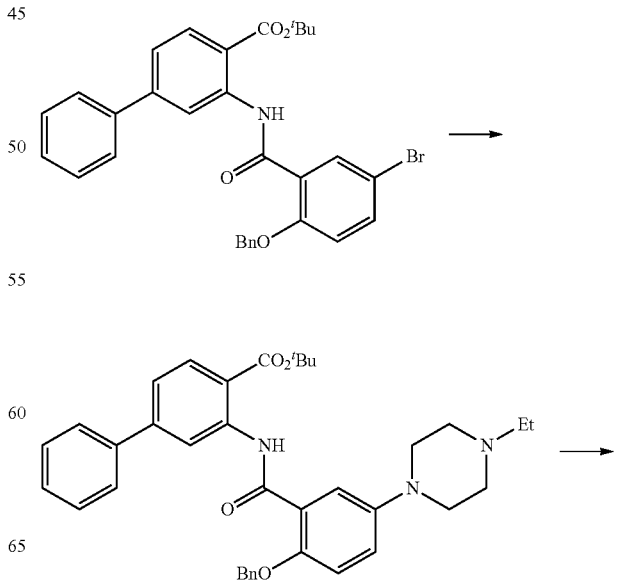

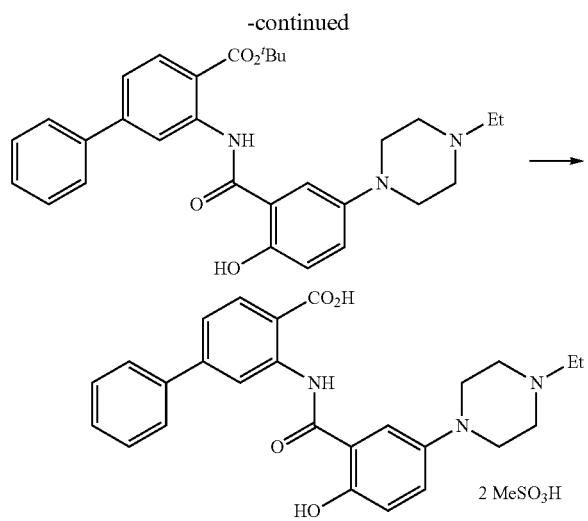

As in Example 92a, the following compound was prepared.

2-(5-(4-Ethylpiperazin-1-yl)-2-hydroxybenzamido)-4-phenylbenzoic acid dimethanesulfonate $^1$H-NMR (DMSO-$d_6$) δ: 1.26 (3H, t, J=7.3 Hz), 2.33 (6H, s), 2.87-2.98 (2H, m), 3.08-3.28 (4H, m), 3.54-3.65 (2H, m), 3.65-3.80 (2H, m), 6.98 (1H, d, J=9.0 Hz), 7.22 (1H, dd, J=9.0, 3.1 Hz), 7.43-7.57 (5H, m), 7.70-7.75 (2H, m), 8.09 (1H, d, J=8.3 Hz), 9.04 (1H, d, J=1.7 Hz), 9.26-9.38 (1H, broad), 10.94-11.04 (1H, broad), 12.27 (1H, s).

Example 94a

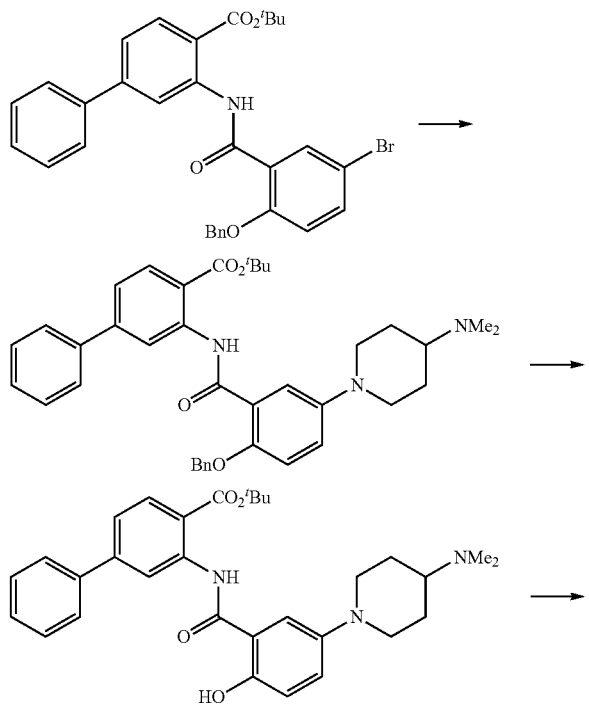

4-(Dimethylamino)piperidine dihydrochloride (0.11 g), cesium carbonate (0.44 g), tris(dibenzylideneacetone)dipalladium(0) (2.5 mg), 2-dicyclohexylphosphino-2',4',6'-triisopropylbiphenyl (6.4 mg), and palladium(II) acetate (1.2 mg) were added to a toluene (2.3 mL) solution of tert-butyl 2-(2-(benzyloxy)-5-bromobenzamido)-4-phenylbenzoate (0.15 g), followed by heating to reflux under a nitrogen atmosphere for 3 hours. The reaction mixture was cooled to room temperature, and cesium carbonate (0.13 g), tris(dibenzylideneacetone)dipalladium(0) (2.5 mg), 2-dicyclohexylphosphino-2',4',6'-triisopropylbiphenyl (6.4 mg), and palladium(II) acetate (1.2 mg) were added to the reaction mixture, followed by heating to reflux under a nitrogen atmosphere for 7 hours. The reaction mixture was cooled to room temperature, and tripotassium phosphate (0.29 g), tris(dibenzylideneacetone)dipalladium(0) (2.5 mg), 2-dicyclohexylphosphino-2',4',6'-triisopropylbiphenyl (6.4 mg), and palladium(II) acetate (1.2 mg) were added to the reaction mixture, followed by heating to reflux under a nitrogen atmosphere for 2 hours and 30 minutes. The reaction mixture was cooled to room temperature, and water and chloroform were added thereto. The insoluble substance was removed by filtration. The organic layer was separated and dried over anhydrous sodium sulfate, and the solvent was evaporated under reduced pressure. The obtained residue was purified by silica gel column chromatography [Kanto Chemical Co., Inc., silica gel 60 (spherical), eluent: 100-90% chloroform/methanol] to obtain 0.13 g of tert-butyl 2-(2-(benzyloxy)-5-(4-(dimethylamino)piperidin-1-yl)benzamido)-4-phenylbenzoate.

To a solution mixture of the obtained tert-butyl 2-(2-(benzyloxy)-5-(4-(dimethylamino)piperidin-1-yl)benzamido)-4-phenylbenzoate (0.13 g) in methanol (1.5 mL) and ethyl acetate (1.5 mL), 10% palladium-carbon (0.13 g) was added, followed by stirring under a hydrogen atmosphere at room temperature for 2 hours. Chloroform was added to the reaction mixture, and the insoluble substance was removed by filtration. The solvent was evaporated under reduced pressure, and the obtained residue was purified by silica gel column chromatography [Kanto Chemical Co., Inc., silica gel 60 (spherical), eluent: 100-90% chloroform/methanol] to obtain 0.066 g of tert-butyl 2-(5-(4-(dimethylamino)piperidin-1-yl)-2-hydroxybenzamido)-4-phenylbenzoate.

Trifluoroacetic acid (5.0 mL) was added to the obtained tert-butyl 24544-(dimethylamino)piperidin-1-yl)-2-hydroxybenzamido)-4-phenylbenzoate (0.066 g), followed by stirring at room temperature for 5 hours. The solvent was evaporated under reduced pressure, and the obtained residue was purified by reversed-phase silica gel column chromatography [YMC Co., Ltd., ODS-AM12S05-2520WT, eluent: 40-85% acetonitrile/0.1% trifluoroacetic acid aqueous solution] to obtain 0.060 g of a solid substance. Ethyl acetate (3.0 mL) and methanesulfonic acid (0.011 mL) were added to the obtained solid substance (0.060 g), followed by stirring at room temperature for 5 hours. The solid substance was collected by filtration to obtain 0.045 g of 2-(5-(4-(dimethylamino)piperidin-1-yl)-2-hydroxybenzamido)-4-phenylbenzoic acid dimethanesulfonate as a white solid.

¹H-NMR (CD₃OD) δ: 2.17-2.32 (2H, m), 2.36-2.50 (2H, m), 2.73 (6H, s), 2.98 (6H, s), 3.50-3.70 (3H, m), 3.82-3.94 (2H, m), 7.13 (1H, d, J=9.0 Hz), 7.39-7.46 (1H, m), 7.46-7.54 (3H, m), 7.64 (1H, dd, J=9.0, 2.9 Hz), 7.70-7.76 (2H, m), 8.06 (1H, d, J=2.9 Hz), 8.21 (1H, d, J=8.3 Hz), 9.06 (1H, d, J=1.7 Hz).

Example 95a

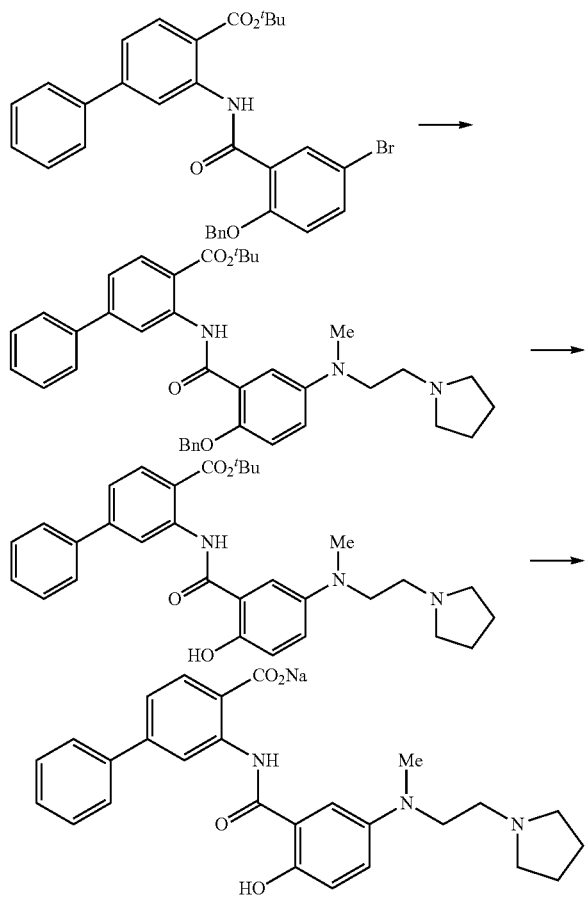

N-Methyl-2-(pyrrolidin-1-yl)ethylamine (0.086 g), tripotassium phosphate (0.17 g), tris(dibenzylideneacetone)dipalladium(0) (2.5 mg), 2-dicyclohexylphosphino-2',4',6'-triisopropylbiphenyl (6.4 mg), and palladium(II) acetate (1.2 mg) were added to a toluene (2.3 mL) solution of tert-butyl 2-(2-(benzyloxy)-5-bromobenzamido)-4-phenylbenzoate (0.15 g), followed by heating to reflux under a nitrogen atmosphere for 1 hour and 30 minutes. The reaction mixture was cooled to room temperature, and then N-methyl-2-(pyrrolidin-1-yl)ethylamine (0.017 g), tripotassium phosphate (0.029 g), tris(dibenzylideneacetone)dipalladium(0) (2.5 mg), 2-dicyclohexylphosphino-2',4',6'-triisopropylbiphenyl (6.4 mg), and palladium(II) acetate (1.2 mg) were added to the reaction mixture, followed by heating to reflux under a nitrogen atmosphere for 7 hours and 30 minutes. The reaction mixture was cooled to room temperature, and then N-methyl-2-(pyrrolidin-1-yl)ethylamine (0.017 g), tripotassium phosphate (0.029 g), tris(dibenzylideneacetone)dipalladium(0) 2.5 mg, 2-dicyclohexylphosphino-2',4',6'-triisopropylbiphenyl (6.4 mg), and palladium(II) acetate (1.2 mg) were added to the reaction mixture, followed by heating to reflux under a nitrogen atmosphere for 3 hours. The reaction mixture was cooled to room temperature, and water and chloroform were added thereto. The insoluble substance was removed by filtration. The organic layer was separated and dried over anhydrous sodium sulfate, and the solvent was evaporated under reduced pressure. The obtained residue was purified by silica gel column chromatography [eluent: 100-90% chloroform/methanol] to obtain 0.097 g of tert-butyl 2-(2-(benzyloxy)-5-(methyl(2-(pyrrolidin-1-yl)ethyl)amino)benzamido)-4-phenylbenzoate.

To a solution mixture of the obtained tert-butyl 2-(2-(benzyloxy)-5-(methyl(2-(pyrrolidin-1-yl)ethyl)amino)benzamido)-4-phenylbenzoate (0.097 g) in methanol (1.5 mL) and ethyl acetate (1.5 mL), 10% palladium-carbon (0.097 g) was added, followed by stirring under a hydrogen atmosphere at room temperature for 2 hours. Chloroform was added to the reaction mixture, and the insoluble substance was removed by filtration. The solvent was evaporated under reduced pressure. The obtained residue was purified by silica gel column chromatography [eluent: 100-95% chloroform/methanol] to obtain 0.048 g of tert-butyl 2-(2-hydroxy-5-(methyl(2-(pyrrolidin-1-yl)ethyl)amino)benzamido)-4-phenylbenzoate.

Trifluoroacetic acid (5.0 mL) was added to the obtained tert-butyl 2-(2-hydroxy-5-(methyl(2-(pyrrolidin-1-yl)ethyl)amino)benzamido)-4-phenylbenzoate (0.048 g), followed by stirring at room temperature for 3 hours. The solvent was evaporated under reduced pressure, and water and ethyl acetate were added to the residue, followed by adjusting the pH to 7 with a saturated aqueous solution of sodium bicarbonate. The organic layer was separated, washed with a saturated aqueous solution of sodium chloride, and dried over anhydrous sodium sulfate, and the solvent was evaporated under reduced pressure. Methanol (1.5 mL), dioxane (1.5 mL), and a 1.0 mol/L aqueous solution of sodium hydroxide (0.067 mL) were added to the obtained residue, and the solvent was evaporated under reduced pressure. Diisopropyl ether was added to the obtained residue, and the solid substance was collected by filtration to obtain 0.028 g of sodium 2-(2-hydroxy-5-(methyl(2-(pyrrolidin-1-yl)ethyl)amino)benzamido)-4-phenylbenzoate as a yellow solid.

¹H-NMR (CD₃OD) δ: 1.76-1.90 (4H, m), 2.58-2.78 (6H, m), 2.99 (3H, s), 3.43-3.54 (2H, m), 6.85 (1H, d, J=9.0 Hz), 7.06 (1H, dd, J=9.0, 2.9 Hz), 7.32-7.40 (3H, m), 7.43-7.50 (2H, m), 7.67-7.74 (2H, m), 8.18 (1H, d, J=8.1 Hz), 9.00 (1H, d, J=1.7 Hz).

Example 96a

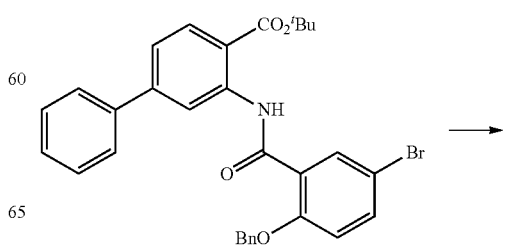

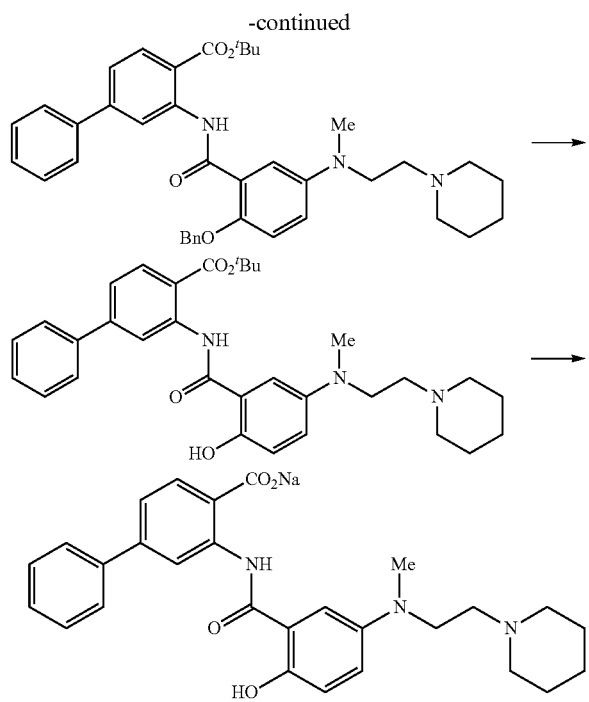

As in Example 95a, the following compound was prepared.

Sodium 2-(2-hydroxy-5-(methyl(2-(piperidin-1-yl)ethyl)amino)benzamido)-4-phenylbenzoate $^1$H-NMR (CD$_3$OD) δ: 1.42-1.54 (2H, m), 1.56-1.72 (4H, m), 2.46-2.68 (6H, m), 2.98 (3H, s), 3.45-3.56 (2H, m), 6.85 (1H, d, J=9.0 Hz), 7.06 (1H, dd, J=9.0, 2.9 Hz), 7.32-7.40 (3H, m), 7.43-7.50 (2H, m), 7.68-7.73 (2H, m), 8.18 (1H, d, J=8.3 Hz), 9.01 (1H, d, J=1.7 Hz).

Example 97a

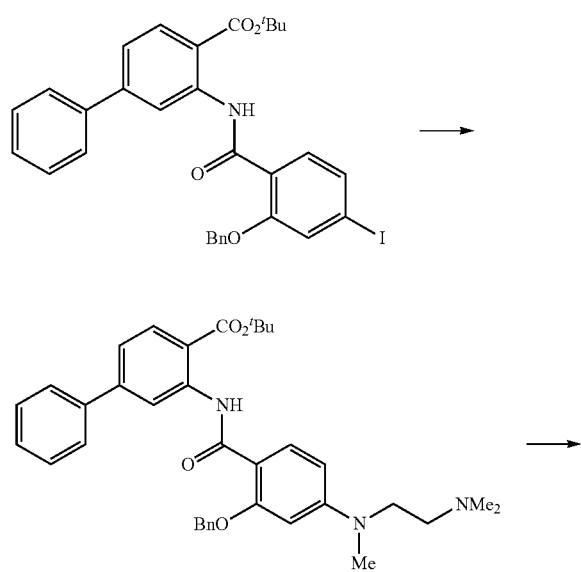

N,N,N'-Trimethylethylenediamine (0.12 mL), cesium carbonate (0.35 g), tris(dibenzylideneacetone)dipalladium(0) (3.3 mg), 2-dicyclohexylphosphino-2',4',6'-triisopropylbiphenyl (8.6 mg), and palladium(II) acetate (1.6 mg) were added to a toluene (3.0 mL) suspension of tert-butyl 2-(2-(benzyloxy)-4-iodobenzamido)-4-phenylbenzoate (0.22 g), followed by heating to reflux under a nitrogen atmosphere for 4 hours and 10 minutes. The reaction mixture was cooled to room temperature, and then N,N,N'-trimethylethylenediamine (0.12 mL), cesium carbonate (0.35 g), tris(dibenzylideneacetone)dipalladium(0) (3.3 mg), 2-dicyclohexylphosphino-2',4',6'-triisopropylbiphenyl (8.6 mg), and palladium(II) acetate (1.6 mg) were added to the reaction mixture, followed by heating to reflux under a nitrogen atmosphere for 8 hours. The reaction mixture was cooled to room temperature, and then water and chloroform were added thereto. The insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 100-93% chloroform/methanol] to obtain 0.072 g of tert-butyl 2-(2-(benzyloxy)-4-((2-(dimethylamino)ethyl)(methyl)amino)benzamido)-4-phenylbenzoate.

To a methanol (3.0 mL) solution of the obtained tert-butyl 2-(2-(benzyloxy)-4-((2-(dimethylamino)ethyl)(methyl)amino)benzamido)-4-phenylbenzoate (0.071 g), 10% palladium-carbon (0.035 g) was added, followed by stirring under a hydrogen atmosphere at room temperature for 1 hour and 45 minutes. Methanol (2.0 mL) and chloroform (1.0 mL) were added to the reaction mixture, followed by stirring under a hydrogen atmosphere at room temperature for 2 hours. The insoluble substance was removed by filtration, and then the solvent was evaporated under reduced pressure. Ethyl acetate was added to the obtained residue, and the solid substance was collected by filtration to obtain 0.045 g of tert-butyl 2-(4-((2-(dimethylamino)ethyl)(methyl)amino)-2-hydroxybenzamido)-4-phenylbenzoate as a white solid.

Trifluoroacetic acid (2.0 mL) was added to the obtained tert-butyl 2-(4-((2-(dimethylamino)ethyl)(methyl)amino)-2-hydroxybenzamido)-4-phenylbenzoate (0.045 g), followed by stirring at room temperature for 2 hours. The solvent was removed under reduced pressure, and then methanol was added to the residue. After adjusting the pH to 8.0 with a saturated aqueous solution of sodium bicarbonate, the solid substance was collected from the reaction mixture by filtration to obtain 0.028 g of sodium 2-(4-((2-(dimethylamino)ethyl)(methyl)amino)-2-hydroxybenzamido)-4-phenylbenzoate as a yellow solid.

$^1$H-NMR (DMSO-$d_6$) δ: 2.70 (6H, s), 2.96 (3H, s), 3.00-3.10 (2H, m), 3.63-3.77 (2H, m), 6.15 (1H, d, J=2.2 Hz), 6.40 (1H, dd, J=9.0, 2.2 Hz), 7.35 (1H, dd, J=8.1, 1.7 Hz), 7.37-7.44 (1H, m), 7.46-7.55 (2H, m), 7.63-7.73 (2H, m), 7.77 (1H, d, J=9.0 Hz), 8.11 (1H, d, J=8.1 Hz), 8.89 (1H, d, J=1.7 Hz), 12.65-12.90 (1H, broad).

Example 98a

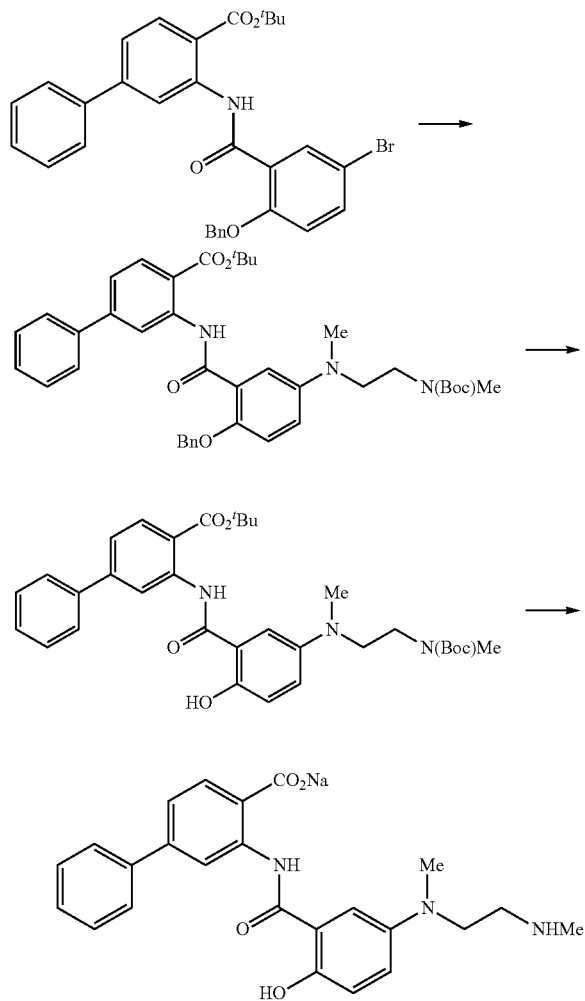

As in Example 97a, the following compound was prepared.

Sodium 2-(2-hydroxy-5-(methyl(2-(methylamino)ethyl)amino)benzamido)-4-phenylbenzoate $^1$H-NMR (DMSO-$d_6$) δ: 2.66 (3H, s), 2.95 (3H, s), 3.05-3.16 (2H, m), 3.53-3.61 (2H, m), 6.88 (1H, d, J=8.9 Hz), 7.00 (1H, dd, J=8.9, 2.7 Hz), 7.36-7.46 (3H, m), 7.47-7.56 (2H, m), 7.65-7.75 (2H, m), 8.14 (1H, d, J=8.0 Hz), 8.89 (1H, d, J=1.7 Hz), 9.55-10.00 (1H, broad), 11.55-11.80 (1H, broad).

Example 99a

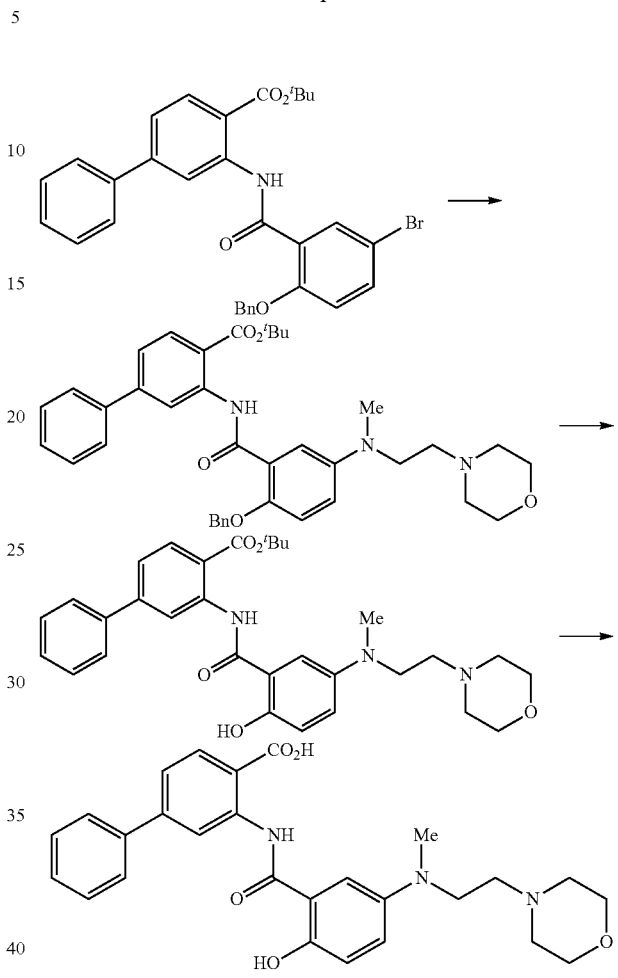

N-Methyl-2-(morpholin-4-yl)ethylamine (0.097 g), tripotassium phosphate (0.17 g), tris(dibenzylideneacetone)dipalladium(0) (2.5 mg), 2-dicyclohexylphosphino-2',4',6'-triisopropylbiphenyl (6.4 mg), and palladium(II) acetate (1.2 mg) were added to a toluene (2.3 mL) solution of tert-butyl 2-(2-(benzyloxy)-5-bromobenzamido)-4-phenylbenzoate (0.15 g), followed by heating to reflux under a nitrogen atmosphere for 1 hour and 30 minutes. The reaction mixture was cooled to room temperature, and then N-methyl-2-(morpholin-4-yl)ethylamine (0.019 g), tripotassium phosphate (0.029 g), tris(dibenzylideneacetone)dipalladium(0) (2.5 mg), 2-dicyclohexylphosphino-2',4',6'-triisopropylbiphenyl (6.4 mg) and palladium(II) acetate (1.2 mg) were added to the reaction mixture, followed by heating to reflux under a nitrogen atmosphere for 6 hours. The reaction mixture was cooled to room temperature, and then water and chloroform were added thereto. The insoluble substance was removed by filtration. The organic layer was separated and dried over anhydrous sodium sulfate, and the solvent was evaporated under reduced pressure. The obtained residue was purified by silica gel column chromatography [Kanto Chemical Co., Inc., silica gel 60 (spherical), eluent: 100-90% chloroform/methanol] to obtain 0.12 g of tert-butyl 2-(2-(benzyloxy)-5-(methyl(2-(morpholin-4-yl)ethyl)amino)benzamido)-4-phenylbenzoate.

To a solution mixture of the obtained tert-butyl 2-(2-(benzyloxy)-5-(methyl(2-(morpholin-4-yl)ethyl)amino)benzamido)-4-phenylbenzoate (0.12 g) in methanol (1.5 mL) and ethyl acetate (1.5 mL), 10% palladium-carbon (0.12 g) was added, followed by stirring under a hydrogen atmosphere at room temperature for 2 hours and 30 minutes. Ethyl acetate was added to the reaction mixture. The insoluble substance was removed by filtration, and the solvent was evaporated under reduced pressure. The obtained residue was purified by silica gel column chromatography [Kanto Chemical Co., Inc., silica gel 60 (spherical), eluent: 100-95% chloroform/methanol] to obtain 0.074 g of tert-butyl 2-(2-hydroxy-5-(methyl(2-(morpholin-4-yl)ethyl)amino)benzamido)-4-phenylbenzoate.

Trifluoroacetic acid (5.0 mL) was added to the obtained tert-butyl 2-(2-hydroxy-5-(methyl(2-(morpholin-4-yl)ethyl)amino)benzamido)-4-phenylbenzoate (0.074 g), followed by stirring at room temperature for 3 hours. The solvent was evaporated under reduced pressure, and water and chloroform were added to the residue. After adjusting the pH to 7.0 with a saturated aqueous solution of sodium bicarbonate, the organic layer was separated, and the aqueous layer was extracted with chloroform. The organic layer and the extract were combined, and the resulting mixture was dried over anhydrous sodium sulfate. The solvent was evaporated under reduced pressure, and diisopropyl ether was added to the obtained residue. The solid substance was collected by filtration to obtain 0.024 g of 2-(2-hydroxy-5-(methyl(2-(morpholin-4-yl)ethyl)amino)benzamido)-4-phenylbenzoic acid as a yellow solid.

$^1$H-NMR (DMSO-$d_6$), (60° C.) δ: 2.95 (3H, s), 3.00-3.14 (6H, m), 3.60-3.70 (2H, m), 3.96-4.08 (4H, m), 6.88 (1H, d, J=9.0 Hz), 6.99 (1H, dd, J=9.0, 2.9 Hz), 7.36 (1H, d, J=2.9 Hz), 7.38-7.45 (2H, m), 7.47-7.54 (2H, m), 7.66-7.73 (2H, m), 8.17 (1H, d, J=8.3 Hz), 8.93 (1H, d, J=2.0 Hz).

Example 100a

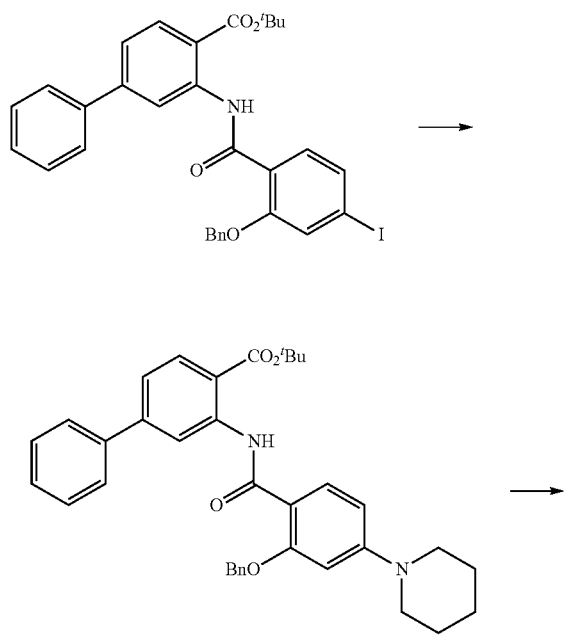

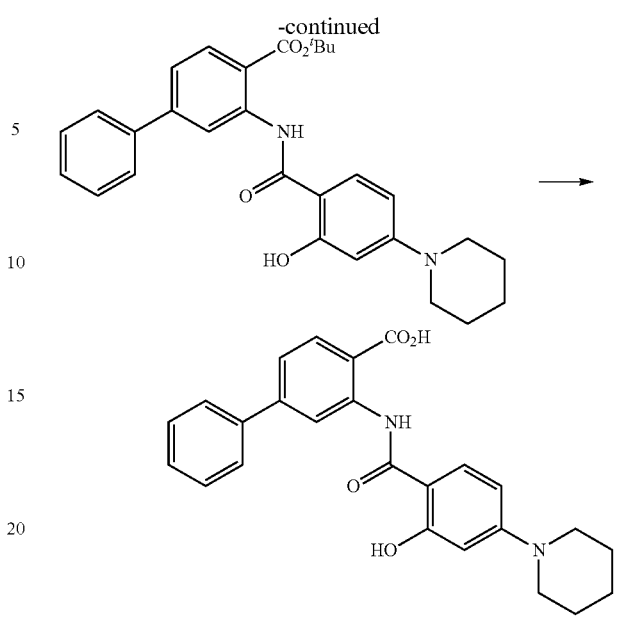

Piperidine (0.049 mL), cesium carbonate (0.22 g), tris(dibenzylideneacetone)dipalladium(0) (3.0 mg), 2-dicyclohexylphosphino-2',4',6'-triisopropylbiphenyl (7.9 mg), and palladium(II) acetate (1.5 mg) were added to a toluene (2.0 mL) suspension of tert-butyl 2-(2-(benzyloxy)-4-iodobenzamido)-4-phenylbenzoate (0.20 g), followed by heating to reflux under a nitrogen atmosphere for 2 hours. The reaction mixture was cooled to room temperature, and then piperidine (0.033 mL), cesium carbonate (0.11 g), tris(dibenzylideneacetone)dipalladium(0) (3.0 mg), 2-dicyclohexylphosphino-2',4',6'-triisopropylbiphenyl (7.9 mg), and palladium(II) acetate (1.5 mg) were added thereto, followed by heating to reflux under a nitrogen atmosphere for 4 hours and 30 minutes. The reaction mixture was cooled to room temperature, and then a 10% aqueous solution of citric acid and ethyl acetate were added thereto. The insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 100-85% hexane/ethyl acetate] to obtain 0.13 g of tert-butyl 2-(2-(benzyloxy)-4-(piperidin-1-yl)benzamido)-4-phenylbenzoate.

To a solution mixture of the obtained tert-butyl 2-(2-(benzyloxy)-4-(piperidin-1-yl)benzamido)-4-phenylbenzoate (0.13 g) in methanol (1.5 mL) and ethyl acetate (3.0 mL), 10% palladium-carbon (0.063 g) was added, followed by stirring under a hydrogen atmosphere at room temperature for 2 hours. Ethyl acetate was added to the reaction mixture. The insoluble substance was removed by filtration, and then the solvent was evaporated under reduced pressure. Diisopropyl ether was added to the obtained residue, and the solid substance was collected by filtration to obtain 0.084 g of tert-butyl 2-(2-hydroxy-4-(piperidin-1-yl)benzamido)-4-phenylbenzoate as a white solid.

Trifluoroacetic acid (5.0 mL) was added to the obtained tert-butyl 2-(2-hydroxy-4-(piperidin-1-yl)benzamido)-4-phenylbenzoate (0.084 g), followed by stirring at room temperature for 4 hours. The solvent was evaporated under reduced pressure, and water and ethyl acetate were added to the residue, followed by adjusting the pH to 6.5 with a saturated aqueous solution of sodium bicarbonate. The organic layer was separated, washed with a saturated aqueous solution of sodium chloride, and dried over anhydrous magnesium sulfate, and the solvent was evaporated under reduced pressure. Diisopropyl ether was added to the obtained residue. The solid substance was collected by filtration to obtain 0.063 g of 2-(2-hydroxy-4-(piperidin-1-yl)benzamido)-4-phenylbenzoic acid as a light yellow solid.

$^1$H-NMR (DMSO-$d_6$), (40° C.) δ: 1.52-1.66 (6H, m), 3.26-3.40 (4H, m), 6.34 (1H, d, J=2.5 Hz), 6.58 (1H, dd, J=9.1, 2.5 Hz), 7.41-7.49 (2H, m), 7.49-7.56 (2H, m), 7.67 (1H, d, J=9.1 Hz), 7.69-7.74 (2H, m), 8.10 (1H, d, J=8.3 Hz), 8.94 (1H, d, J=1.7 Hz), 11.80-11.94 (1H, broad), 12.20-12.35 (1H, broad).

Example 101a

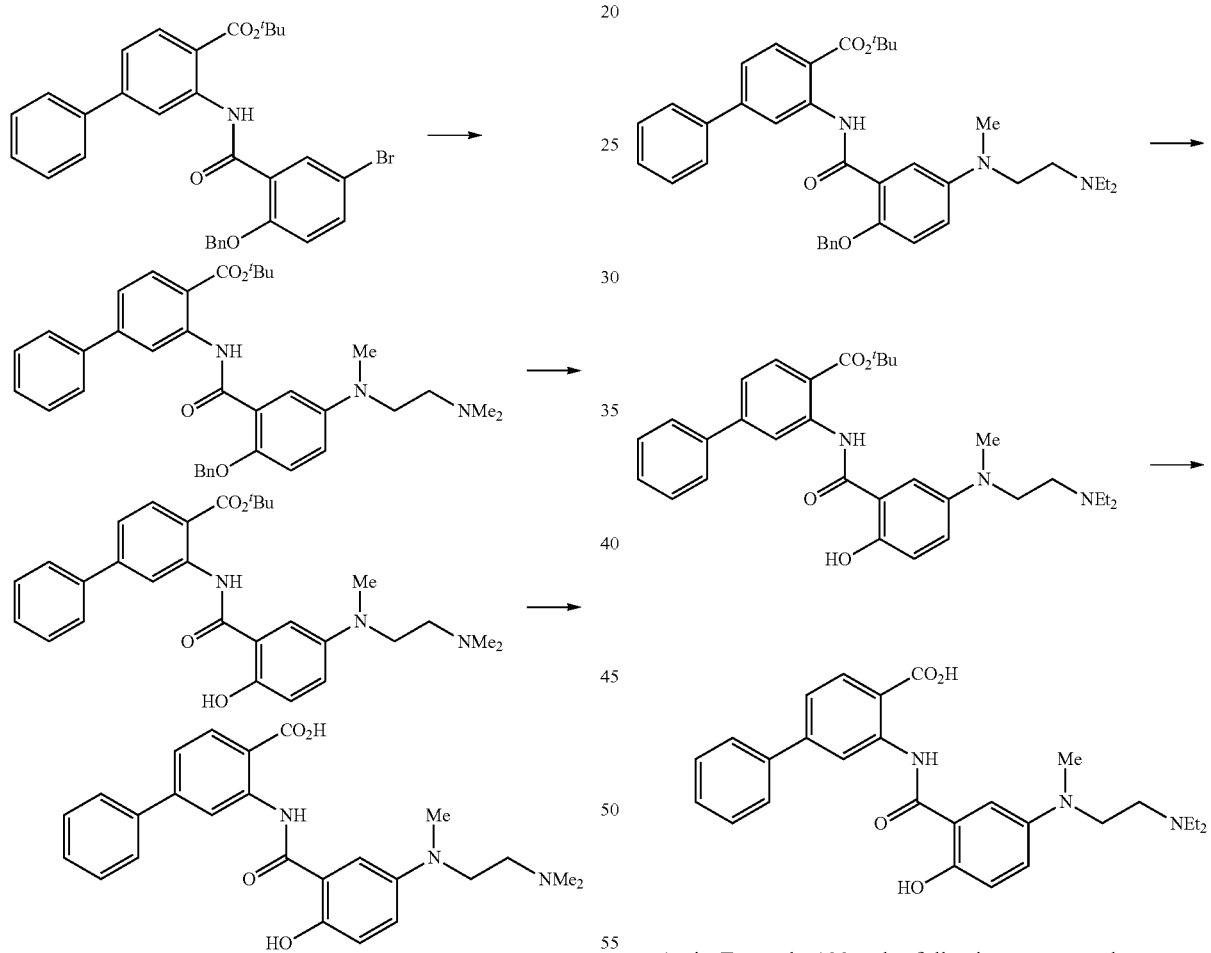

As in Example 100a, the following compound was prepared.

2-(5-((2-(Dimethylamino)ethyl)(methyl)amino)-2-hydroxybenzamido)-4-phenylbenzoic acid $^1$H-NMR (DMSO-$d_6$) δ: 2.83 (6H, s), 2.95 (3H, s), 3.16-3.26 (2H, m), 3.62-3.74 (2H, m), 6.89 (1H, d, J=9.0 Hz), 7.00 (1H, dd, J=9.0, 2.7 Hz), 7.36-7.45 (3H, m), 7.48-7.55 (2H, m), 7.67-7.73 (2H, m), 8.13 (1H, d, J=8.1 Hz), 8.88 (1H, d, J=2.0 Hz), 11.53-11.67 (1H, broad).

Example 102a

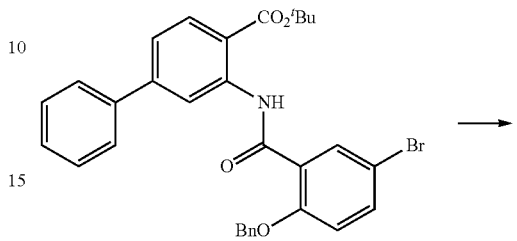

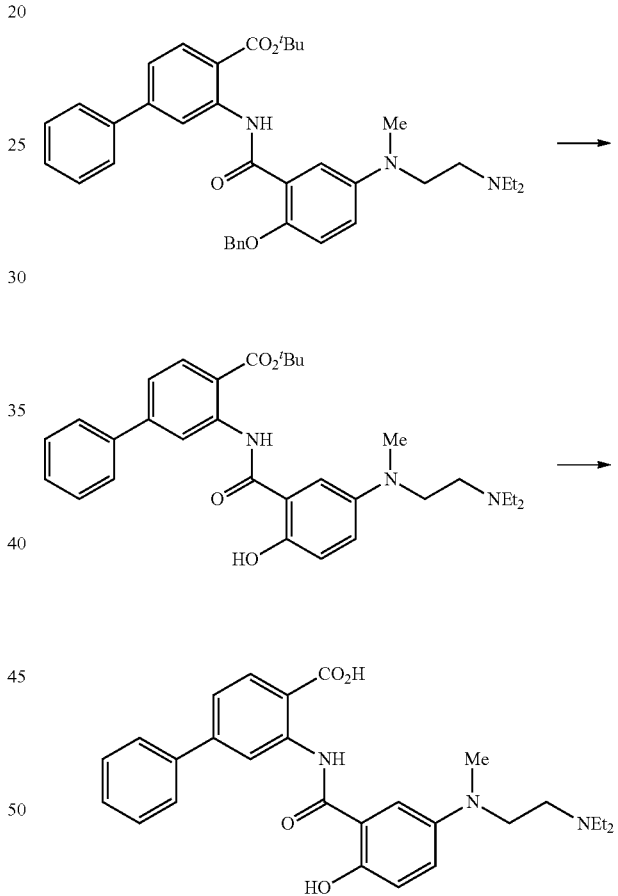

As in Example 100a, the following compound was prepared.

2-(5-((2-(Diethylamino)ethyl)(methyl)amino)-2-hydroxybenzamido)-4-phenylbenzoic acid $^1$H-NMR (DMSO-$d_6$) δ: 1.18-1.39 (6H, m), 2.97 (3H, s), 3.07-3.54 (6H, m), 3.63-3.80 (2H, m), 6.89 (1H, d, J=8.9 Hz), 7.00 (1H, dd, J=8.9, 2.4 Hz), 7.36-7.45 (3H, m), 7.47-7.55 (2H, m), 7.66-7.73 (2H, m), 8.15 (1H, d, J=8.0 Hz), 8.90 (1H, d, J=1.7 Hz), 11.56-11.70 (1H, broad).

Example 103a

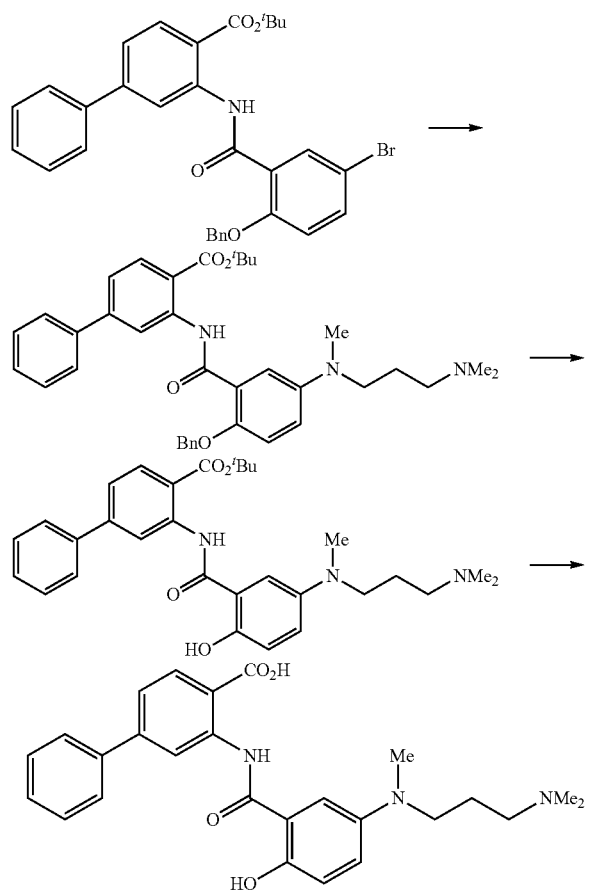

As in Example 100a, the following compound was prepared.

2-(5-((3-(Dimethylamino)propyl)(methyl)amino)-2-hydroxybenzamido)-4-phenylbenzoic acid $^1$H-NMR (CD$_3$OD) δ: 2.07-2.21 (2H, m), 2.92 (6H, s), 2.95 (3H, s), 3.21 (21-1, t, J=7.4 Hz), 3.37 (2H, t, J=8.3 Hz), 6.87 (1H, d, J=9.0 Hz), 7.01 (1H, dd, J=9.0, 3.0 Hz), 7.26 (1H, d, J=3.0 Hz), 7.35-7.42 (2H, m), 7.44-7.51 (2H, m), 7.68-7.74 (2H, m), 8.19 (1H, d, J=8.0 Hz), 9.03 (1H, d, J=2.0 Hz).

Example 104a

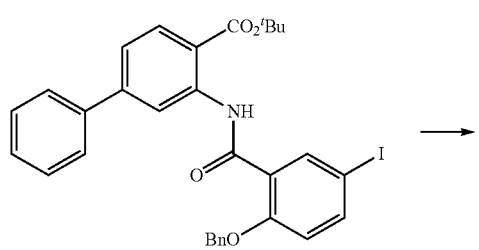

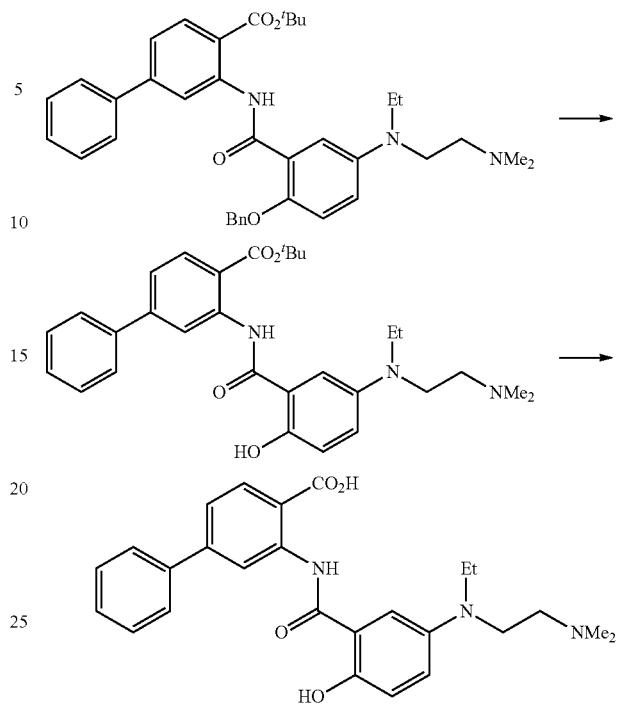

As in Example 100a, the following compound was prepared.

2-(5-((2-(Dimethylamino)ethyl)(ethyl)amino)-2-hydroxybenzamido)-4-phenylbenzoic acid $^1$H-NMR (CD$_3$OD) δ: 1.11 (3H, t, J=7.1 Hz), 2.95 (6H, s), 3.27-3.34 (2H, m), 3.40 (21-1, q, J=7.1 Hz), 3.64 (2H, t, J=7.1 Hz), 6.93 (1H, d, J=9.0 Hz), 7.15 (1H, dd, J=9.0, 2.8 Hz), 7.37-7.53 (5H, m), 7.69-7.75 (2H, m), 8.22 (1H, d, J=8.3 Hz), 9.05 (1H, d, J=1.7 Hz).

Example 105a

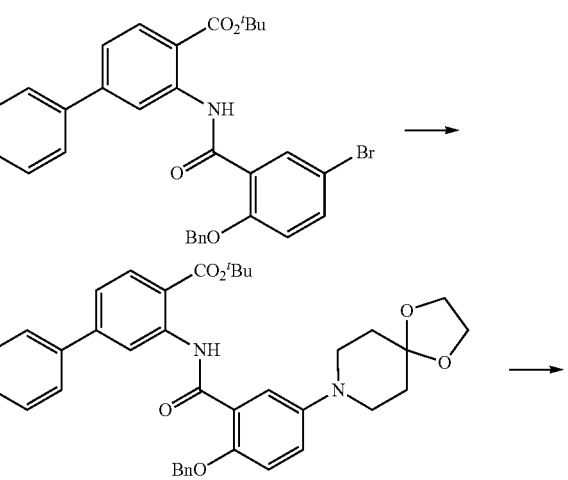

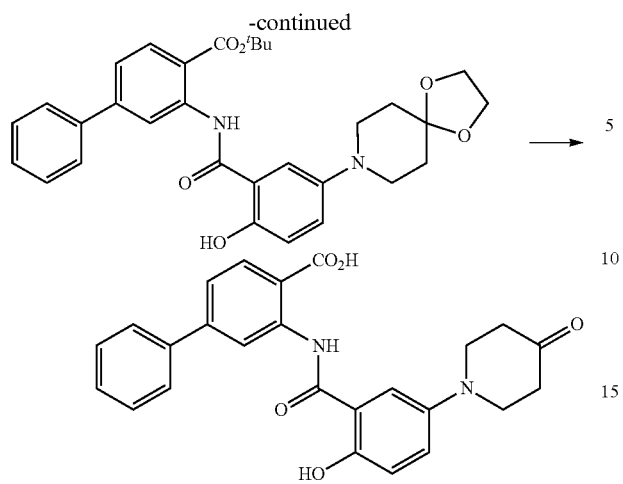

1,4-Dioxa-8-azaspiro[4,5]decane (0.12 mL), cesium carbonate (0.35 g), tris(dibenzylideneacetone)dipalladium(0) (3.3 mg), 2-dicyclohexylphosphino-2',4',6'-triisopropylbiphenyl (8.5 mg), and palladium(II) acetate (1.6 mg) were added to a toluene (3.0 mL) solution of tert-butyl 2-(2-(benzyloxy)-5-bromobenzamido)-4-phenylbenzoate (0.20 g), followed by heating to reflux under a nitrogen atmosphere for 2 hours. The reaction mixture was cooled to room temperature, and then tris(dibenzylideneacetone)dipalladium(0) (3.3 mg), 2-dicyclohexylphosphino-2',4',6'-triisopropylbiphenyl (8.5 mg), and palladium(II) acetate (1.6 mg) were added to the reaction mixture, followed by heating to reflux under a nitrogen atmosphere for 5 hours. The reaction mixture was cooled to room temperature, and water and ethyl acetate were added thereto. The insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 90-65% hexane/ethyl acetate] to obtain 0.18 g of tert-butyl 2-(2-(benzyloxy)-5-(1,4-dioxa-8-azaspiro[4,5]decan-8-yl)benzamido)-4-phenylbenzoate.

To a solution mixture of the obtained tert-butyl 2-(2-(benzyloxy)-5-(1,4-dioxa-8-azaspiro[4,5]decan-8-yl)benzamido)-4-phenylbenzoate (0.18 g) in methanol (1.5 mL) and ethyl acetate (1.5 mL), 10% palladium-carbon (0.091 g) was added, followed by stirring under a hydrogen atmosphere at room temperature for 3 hours. Ethyl acetate was added to the reaction mixture. The insoluble substance was removed by filtration, and then the solvent was evaporated under reduced pressure. Diisopropyl ether was added to the obtained residue, and the solid substance was collected by filtration to obtain 0.12 g of tert-butyl 2-(5-(1,4-dioxa-8-azaspiro[4,5]decan-8-yl)-2-hydroxybenzamido)-4-phenylbenzoate as a yellow solid.

Dioxane (1.0 mL) and 6 mol/L hydrochloric acid (1.0 mL) were added to the obtained tert-butyl 2-(5-(1,4-dioxa-8-azaspiro[4,5]decan-8-yl)-2-hydroxybenzamido)-4-phenylbenzoate (0.070 g), followed by heating to reflux for 25 minutes. The reaction mixture was cooled to room temperature, and water and ethyl acetate were added thereto, followed by adjusting the pH to 5.2 with a saturated aqueous solution of sodium bicarbonate. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: chloroform] to obtain 0.026 g of 2-(2-hydroxy-5-(4-oxopiperidin-1-yl)benzamido)-4-phenylbenzoic acid as a yellow solid.

$^1$H-NMR (DMSO-d$_6$) δ: 2.46 (4H, t, J=6.0 Hz), 3.49 (4H, t, J=6.0 Hz), 6.96 (1H, d, J=8.8 Hz), 7.27 (1H, dd, J=8.8, 3.1 Hz), 7.43-7.57 (5H, m), 7.70-7.76 (2H, m), 8.10 (1H, d, J=8.3 Hz), 9.02 (1H, d, J=1.7 Hz), 10.97 (1H, s), 12.33 (1H, s).

Example 106a

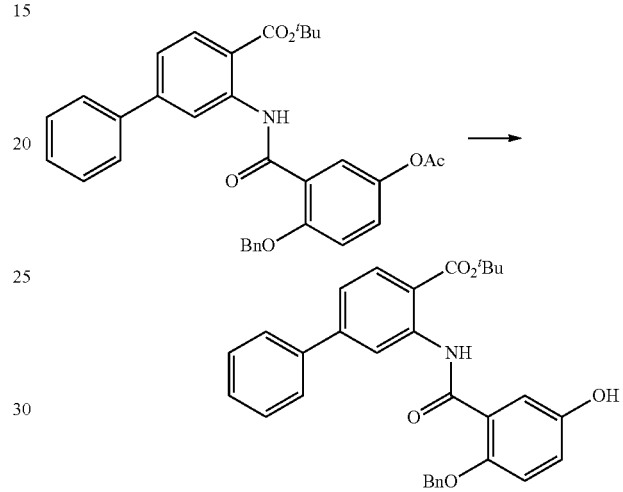

A 2.0 mol/L aqueous solution of sodium hydroxide (1.6 mL) was added to a solution mixture of tert-butyl 2-(5-acetoxy-2-(benzyloxy)benzamido)-4-phenylbenzoate (0.58 g) in methanol (3.0 mL) and dioxane (2.0 mL), followed by stirring at room temperature for 30 minutes. The solvent was evaporated under reduced pressure, and water and chloroform were added to the residue, followed by adjusting the pH to 4.0 with 2.0 mol/L hydrochloric acid. The organic layer was separated, washed with a saturated aqueous solution of sodium chloride, and dried over anhydrous magnesium sulfate. The solvent was evaporated under reduced pressure to obtain 0.52 g of tert-butyl 2-(2-(benzyloxy)-5-hydroxybenzamido)-4-phenylbenzoate as a white solid.

$^1$H-NMR (CDCl$_3$) δ: 1.52 (9H, s), 5.41 (2H, s), 6.40 (1H, s), 6.80-6.93 (2H, m), 7.21-7.50 (9H, m), 7.72-7.79 (2H, m), 7.88 (1H, d, J=2.9 Hz), 8.01-8.08 (1H, m), 9.13 (1H, d, J=1.7 Hz), 12.51 (1H, s).

Example 107a

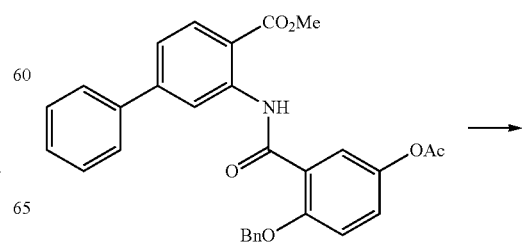

201
-continued

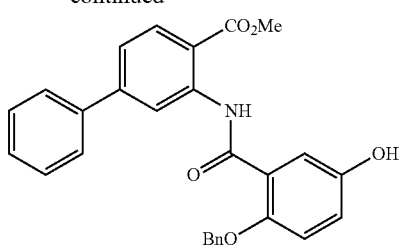

Potassium carbonate (1.6 g) was added to a solution mixture of methyl 2-(5-acetoxy-2-(benzyloxy)benzamido)-4-phenylbenzoate (3.8 g) in chloroform (5.0 mL), methanol (10 mL), and acetone (10 mL), followed by stirring at room temperature for 1 hour. The insoluble substance was removed by filtration, and then the solvent was evaporated under reduced pressure, and 1.0 mol/L hydrochloric acid and chloroform were added to the residue. The organic layer was separated, washed with a saturated aqueous solution of sodium chloride, and dried over anhydrous magnesium sulfate. The solvent was evaporated under reduced pressure to obtain 3.4 g of methyl 2-(2-(benzyloxy)-5-hydroxybenzamido)-4-phenylbenzoate as a white solid.

$^1$H-NMR (CDCl$_3$) δ: 3.76 (3H, s), 5.36 (2H, s), 6.55 (1H, s), 6.85-6.95 (2H, m), 7.22-7.51 (9H, m), 7.70-7.81 (3H, m), 8.07 (1H, d, J=8.3 Hz), 9.16 (1H, d, J=1.7 Hz), 12.30 (1H, s).

Example 108a

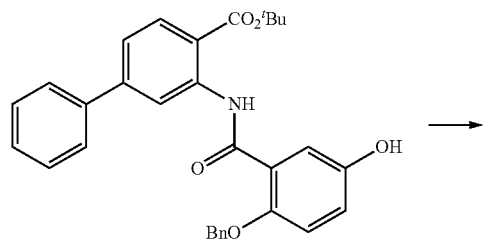

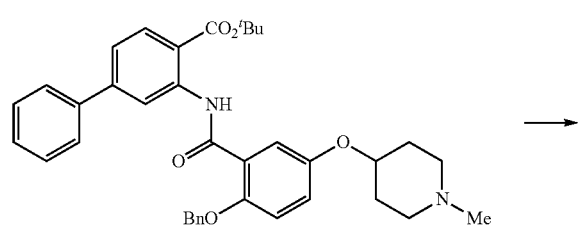

202
-continued

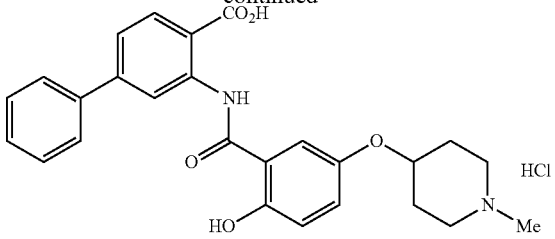

4-Hydroxy-1-methylpiperidine (0.17 g), triphenylphosphine (0.39 g), and diisopropyl azodicarboxylate (0.30 mL) were added to a tetrahydrofuran (3.0 mL) solution of tert-butyl 2-(2-(benzyloxy)-5-hydroxybenzamido)-4-phenylbenzoate (0.15 g), followed by stirring at room temperature for 3 hours and 20 minutes. The solvent was evaporated under reduced pressure, and the obtained residue was purified by silica gel column chromatography [eluent: 60-50% hexane/ethyl acetate to 100-90% chloroform/methanol] to obtain tert-butyl 2-(2-(benzyloxy)-5-((1-methylpiperidin-4-yl)oxy)benzamido)-4-phenylbenzoate.

To a methanol (5.0 mL) solution of the obtained tert-butyl 2-(2-(benzyloxy)-5-((1-methylpiperidin-4-yl)oxy)benzamido)-4-phenylbenzoate, 10% palladium-carbon (0.11 g) was added, followed by stirring under a hydrogen atmosphere at room temperature for 2 hours and 40 minutes. The insoluble substance was removed by filtration, and the obtained residue was purified by silica gel column chromatography [eluent: 100-90% chloroform/methanol] to obtain 0.13 g of tert-butyl 2-(2-hydroxy-5-((1-methylpiperidin-4-yl)oxy)benzamido)-4-phenylbenzoate as a light yellow solid.

A trifluoroacetic acid (2.0 mL) solution of the obtained tert-butyl 2-(2-hydroxy-5-((1-methylpiperidin-4-yl)oxy)benzamido)-4-phenylbenzoate (0.13 g) was stirred at room temperature for 2 hours and 20 minutes. The solvent was evaporated under reduced pressure, and a 4.0 mol/L hydrogen chloride-dioxane solution (2.0 mL) was added to the residue, followed by stirring at room temperature for 40 minutes. The solvent was evaporated under reduced pressure, and diisopropyl ether was added to the obtained residue. The solid substance was collected by filtration to obtain 0.12 g of 2-(2-hydroxy-5-((1-methylpiperidin-4-yl)oxy)benzamido)-4-phenylbenzoic acid hydrochloride as a white solid.

$^1$H-NMR (DMSO-d$_6$) δ: 1.77-1.93 (1H, m), 2.00-2.12 (2H, m), 2.17-2.28 (1H, m), 2.72-2.86 (3H, m), 3.01-3.54 (4H, m), 4.39-4.68 (1H, m), 6.99 (1H, dd, J=8.9, 5.5 Hz), 7.10-7.22 (1H, m), 7.42-7.60 (5H, m), 7.68-7.78 (2H, m), 8.10 (1H, d, J=8.3 Hz), 9.03 (1H, d, J=2.0 Hz), 10.25-10.45 (1H, broad), 11.10 (1H, s), 12.25-12.40 (1H, m), 13.35-13.65 (1H, broad).

Example 109a

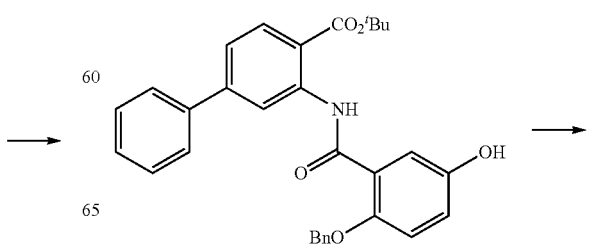

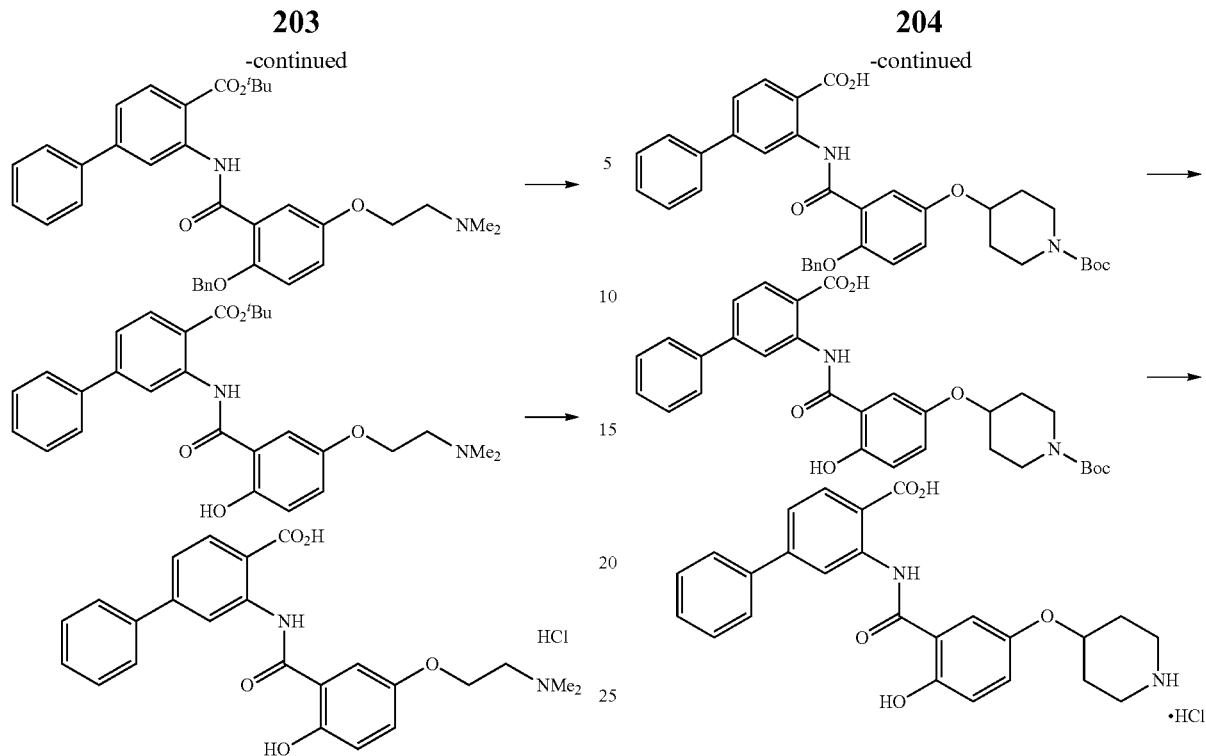

As in Example 108a, the following compound was prepared.

2-(5-(2-(Dimethylamino)ethoxy)-2-hydroxybenzamido)-4-phenylbenzoic acid hydrochloride $^1$H-NMR (DMSO-$d_6$) δ: 2.86 (6H, s), 3.46-3.54 (2H, m), 4.34 (2H, t, J=5.0 Hz), 7.02 (1H, d, J=9.0 Hz), 7.15 (1H, dd, J=9.0, 3.2 Hz), 7.42-7.59 (5H, m), 7.67-7.78 (2H, m), 8.09 (1H, d, J=8.3 Hz), 9.04 (1H, d, J=1.7 Hz), 10.10-10.35 (1H, broad), 11.10 (1H, s), 12.33 (1H, s), 13.25-13.60 (1H, broad).

Example 110a

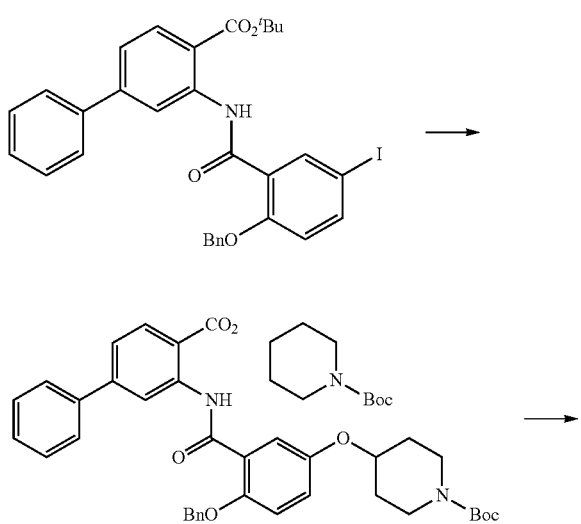

1-(tert-Butoxycarbonyl)-4-hydroxypiperidine (0.047 g), cesium carbonate (0.075 g), 1,10-phenanthroline (4.2 mg), and copper(I) iodide (2.2 mg) were added to a toluene (1 mL) solution of tert-butyl 2-(2-(benzyloxy)-5-iodobenzamido)-4-phenylbenzoate (0.070 g), followed by heating to reflux under a nitrogen atmosphere for 4 hours. The reaction mixture was cooled to room temperature, and then 1-(tert-butoxycarbonyl)-4-hydroxypiperidine (0.047 g), cesium carbonate (0.075 g), 1,10-phenanthroline (4.2 mg), and copper(I) iodide (2.2 mg) were added to the reaction mixture, followed by heating to reflux under a nitrogen atmosphere for 2 hours. The reaction mixture was cooled to room temperature, and then 1,10-phenanthroline (4.2 mg) and copper(I) iodide (2.2 mg) were added to the reaction mixture, followed by heating to reflux under a nitrogen atmosphere for 5 hours and 30 minutes. The reaction mixture was cooled to room temperature, and then a 10% aqueous solution of citric acid and ethyl acetate were added thereto. The insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 95-60% hexane/ethyl acetate] to obtain 0.074 g of tert-butyl 4-(2-(2-(benzyloxy)-5-((1-(tert-butoxycarbonyl)piperidin-4-yl)oxy)benzamido)-4-phenylbenzoyloxy)piperidine-1-carboxylate.

A 2 mol/L aqueous solution of sodium hydroxide (0.13 mL) was added to a solution mixture of the obtained tert-butyl 4-(2-(2-(benzyloxy)-5-((1-(tert-butoxycarbonyl)piperidin-4-yl)oxy)benzamido)-4-phenylbenzoyloxy)piperidine-1-carboxylate (0.072 g) in methanol (1 mL) and dioxane (1 mL), followed by stirring at room temperature for 1 hour. A 2 mol/L aqueous solution of sodium hydroxide (0.089 mL) was added to the reaction mixture, followed by heating to reflux for 20 minutes. After cooling the reaction mixture to room temperature, the solvent was evaporated under reduced pressure, and water was added to the obtained residue. After adjusting the pH to 3.5 with a 10% aqueous solution of citric acid, ethyl acetate was added thereto. The organic layer was separated, washed with a saturated aqueous solution of sodium chloride, and dried over anhydrous magnesium sulfate, and the solvent was evaporated under reduced pressure. To a solution mixture of the obtained residue, 10% palladium-carbon (0.039 g) in methanol (1.5 mL) and ethyl acetate (1.5 mL) was added, followed by stirring under a hydrogen atmosphere at room temperature for 2 hours. Ethyl acetate was added to the reaction mixture, and the insoluble substance was removed by filtration. The solvent was evaporated under reduced pressure, and diisopropyl ether was added to the obtained residue. The solid substance was collected by filtration to obtain 0.024 g of 2-(5-((1-(tert-butoxycarbonyl)piperidin-4-yl)oxy)-2-hydroxybenzamido)-4-phenylbenzoic acid as a light yellow solid.

Trifluoroacetic acid (2 mL) was added to the obtained 2-(5-((1-(tert-butoxycarbonyl)piperidin-4-yl)oxy)-2-hydroxybenzamido)-4-phenylbenzoic acid (0.024 g), followed by stirring at room temperature for 2 hours. The solvent was evaporated under reduced pressure, and ethyl acetate (0.7 mL) and a 4 mol/L hydrogen chloride-dioxane solution (0.3 mL) were added to the residue, followed by stirring at room temperature for 5 hours. The solid substance was collected from the reaction mixture by filtration to obtain 0.017 g of 2-(2-hydroxy-5-(piperidin-4-yloxy)benzamido)-4-phenylbenzoic acid hydrochloride as a white solid.

$^1$H-NMR (DMSO-$d_6$) δ: 1.78-1.89 (2H, m), 2.03-2.14 (2H, m), 3.02-3.14 (2H, m), 3.19-3.32 (2H, m), 4.51-4.60 (1H, m), 6.98 (1H, d, J=8.9 Hz), 7.14 (1H, dd, J=8.9, 3.2 Hz), 7.43-7.49 (1H, m), 7.49-7.58 (4H, m), 7.70-7.75 (2H, m), 8.09 (1H, d, J=8.3 Hz), 8.60-8.80 (2H, m), 9.02 (1H, d, J=1.7 Hz), 11.09 (1H, s), 12.30-12.40 (1H, broad), 13.35-13.60 (1H, broad).

Example 111a

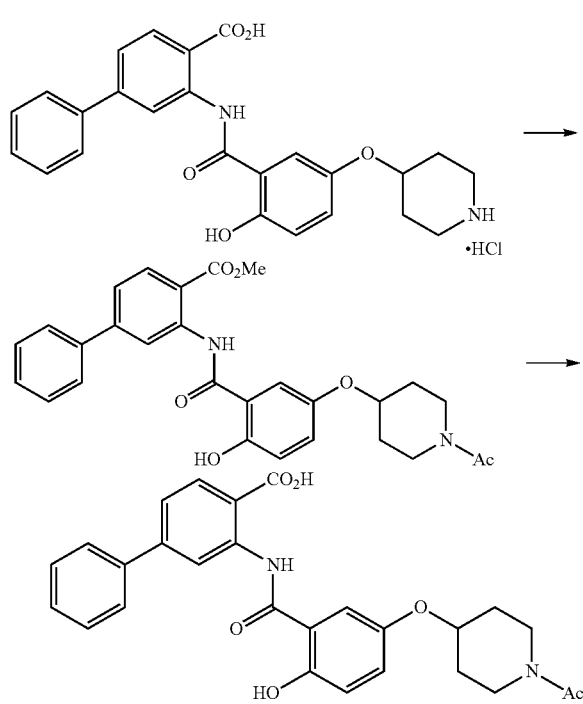

Under ice-cooling, pyridine (0.30 mL) and acetic anhydride (6.7 µL) were sequentially added to a methylene chloride (1 mL) suspension of 2-(2-hydroxy-5-(piperidin-4-yloxy)benzamido)-4-phenylbenzoic acid hydrochloride (0.030 g), followed by stirring at room temperature for 1 hour. Pyridine (0.20 mL) and acetic anhydride (5.4 µL) were sequentially added to the reaction mixture, followed by stirring at room temperature for 1 hour and 30 minutes. The solvent was evaporated under reduced pressure, and methanol (0.5 mL) and a 2 mol/L aqueous solution of sodium hydroxide (0.19 mL) were added to the residue, followed by stirring at room temperature for 1 hour. To the reaction mixture, 1 mol/L hydrochloric acid (5 mL) and ethyl acetate were added. The organic layer was separated, washed with 1 mol/L hydrochloric acid, water, and a saturated aqueous solution of sodium chloride sequentially, and dried over anhydrous magnesium sulfate, and the solvent was evaporated under reduced pressure. Dioxane (0.5 mL), methanol (0.5 mL), and a 2 mol/L aqueous solution of sodium hydroxide (0.32 mL) were added to the obtained residue, followed by stirring at 70° C. for 30 minutes. After cooling the reaction mixture to room temperature, the solvent was evaporated under reduced pressure, and water was added to the obtained residue. After adjusting the pH to 3 with 6 mol/L hydrochloric acid, the solid substance was collected by filtration to obtain 0.022 g of 2-(5-(1-acetylpiperidin-4-yloxy)-2-hydroxybenzamido)-4-phenylbenzoic acid as a white solid.

$^1$H-NMR (DMSO-$d_6$) δ: 1.44-1.67 (2H, m), 1.83-2.06 (2H, m), 2.02 (3H, s), 3.19-3.40 (2H, m), 3.63-3.73 (1H, m), 3.79-3.89 (1H, m), 4.46-4.55 (1H, m), 6.95 (1H, d, J=8.8 Hz), 7.13 (1H, dd, J=8.8, 2.9 Hz), 7.43-7.58 (5H, m), 7.70-7.76 (2H, m), 8.10 (1H, d, J=8.1 Hz), 9.01 (1H, d, J=1.2 Hz), 11.07 (1H, s), 12.34 (1H, s), 13.40-13.57 (1H, broad).

Example 112a

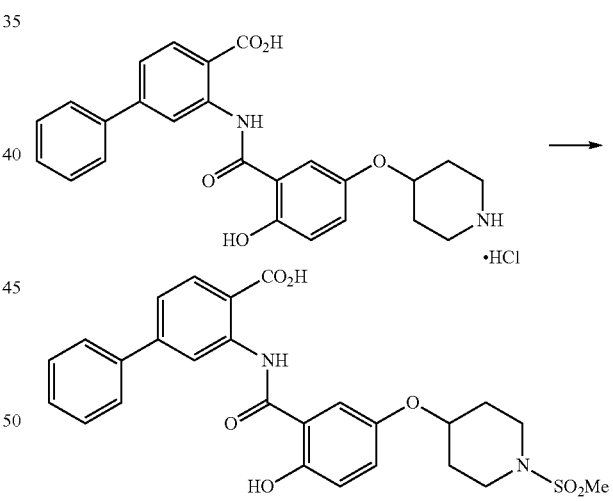

Under ice-cooling, pyridine (0.5 mL) and methanesulfonyl chloride (9.9 µL) were sequentially added to a methylene chloride (1 mL) suspension of 2-(2-hydroxy-5-(piperidin-4-yloxy)benzamido)-4-phenylbenzoic acid hydrochloride (0.030 g), followed by stirring at room temperature for 5 hours and 30 minutes. The solvent was evaporated under reduced pressure, and methanol (0.5 mL) and a 2 mol/L aqueous solution of sodium hydroxide (0.5 mL) were added to the residue, followed by stirring at 70° C. for 45 minutes. The reaction mixture was cooled to room temperature, and then 1 mol/L hydrochloric acid (5 mL) was added thereto. The solid substance was collected by filtration and the obtained solid substance was purified by silica gel column chromatography [Kanto Chemical Co., Inc., silica gel 60 (spherical), eluent: chloroform] to obtain 8.0 mg of 2-(2-hydroxy-5-(1-(methylsulfonyl)piperidin-4-yloxy)benzamido)-4-phenylbenzoic acid as a white solid.

$^1$H-NMR (DMSO-$d_6$), (40° C.) δ: 1.67-1.82 (2H, m), 1.94-2.06 (2H, m), 2.90 (3H, s), 3.06-3.20 (2H, m), 3.32-3.44 (2H, m), 4.40-4.50 (1H, m), 6.95 (1H, d, J=9.0 Hz), 7.13 (1H, dd, J=9.0, 3.1 Hz), 7.42-7.56 (5H, m), 7.69-7.75 (2H, m), 8.10 (1H, d, J=8.1 Hz), 8.98 (1H, d, J=1.7 Hz).

Example 113a

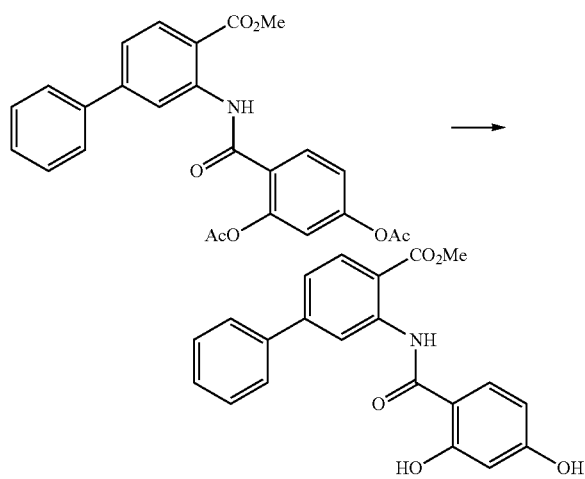

Under ice-cooling, a 28% sodium methoxide-methanol solution (0.34 g) was added to a methanol (3.1 mL) suspension of 4-(2-(methoxycarbonyl)-5-phenylphenylcarbamoyl)-1,3-phenylene diacetate (0.31 g), followed by stirring at room temperature for 1 hour. The reaction mixture was added to 0.5 mol/L hydrochloric acid (20 mL) under ice-cooling, and then ethyl acetate was added thereto. The organic layer was separated, washed with water and a saturated aqueous solution of sodium chloride sequentially, and dried over anhydrous magnesium sulfate, and the solvent was evaporated under reduced pressure. Diisopropyl ether was added to the obtained residue to obtain 0.24 g of methyl 2-(2,4-dihydroxybenzamido)-4-phenylbenzoate as a white solid.

$^1$H-NMR (CDCl$_3$) δ: 4.01 (3H, s), 5.26 (1H, s), 6.45 (1H, d, J=2.4 Hz), 6.49 (1H, dd, J=8.8, 2.4 Hz), 7.35-7.53 (4H, m), 7.67-7.74 (2H, m), 7.75 (1H, d, J=8.8 Hz), 8.15 (1H, d, J=8.3 Hz), 9.09 (1H, d, J=1.7 Hz), 12.14 (1H, s), 12.54 (1H, s).

Example 114a

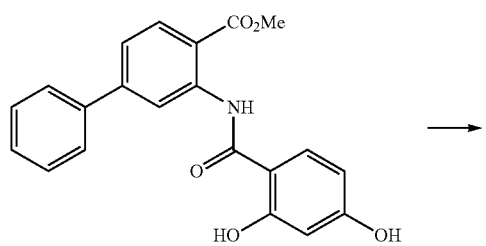

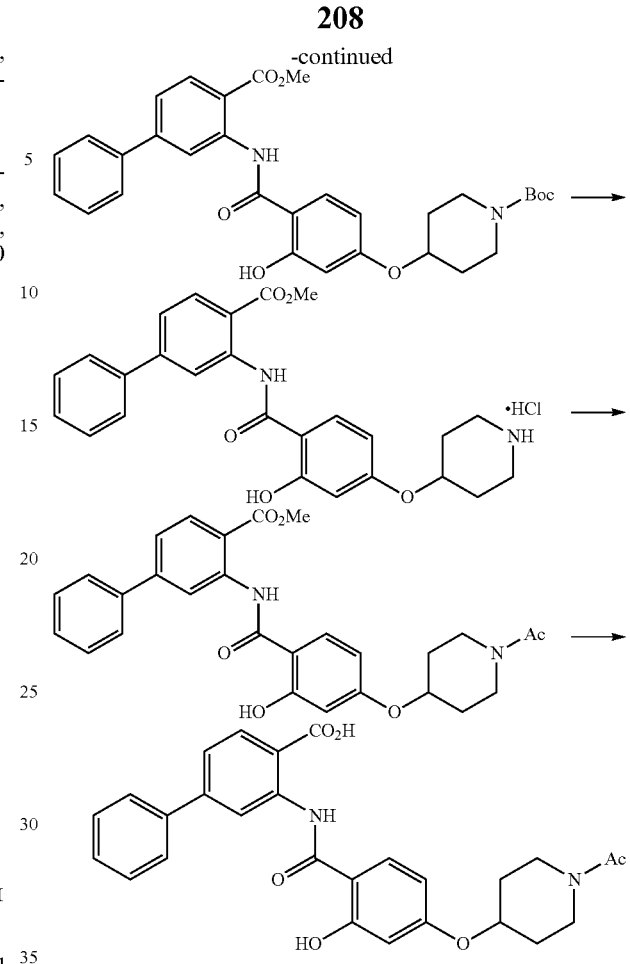

1-(tert-Butoxycarbonyl)-4-hydroxypiperidine (0.15 g), triphenylphosphine (0.21 g), and diisopropyl azodicarboxylate (0.16 mL) were added to a tetrahydrofuran (3.6 mL) suspension of methyl 2-(2,4-dihydroxybenzamido)-4-phenylbenzoate (0.24 g), followed by stirring at room temperature for 1 hour. 1-(tert-Butoxycarbonyl)-4-hydroxypiperidine (0.066 g), triphenylphosphine (0.086 g), and diisopropyl azodicarboxylate (0.064 mL) were added to the reaction mixture, followed by stirring at room temperature for 1 hour. The solvent was evaporated under reduced pressure, and the obtained residue was purified by silica gel column chromatography [eluent: 100-75% hexane/ethyl acetate] to obtain 0.050 g of tert-butyl 4-(3-hydroxy-4-(2-(methoxycarbonyl)-5-phenylphenylcarbamoyl)phenoxy)piperidine-1-carboxylate as a white solid.

Ethyl acetate (1 mL) and a 4 mol/L hydrogen chloride-dioxane solution (0.50 mL) were added to the obtained tert-butyl 4-(3-hydroxy-4-(2-(methoxycarbonyl)-5-phenylphenylcarbamoyl)phenoxy)piperidine-1-carboxylate (0.025 g), followed by stirring at room temperature for 3 hours. The solid substance was collected from the reaction mixture by filtration to obtain 0.018 g of methyl 2-(2-hydroxy-4-(piperidin-4-yloxy)benzamido)-4-phenylbenzoate hydrochloride as a white solid.

Under ice-cooling, pyridine (0.010 mL) and acetic anhydride (4.0 μL) were sequentially added to a methylene chloride (1 mL) suspension of the obtained methyl 2-(2-hydroxy-4-(piperidin-4-yloxy)benzamido)-4-phenylbenzoate hydrochloride (0.017 g), followed by stirring at room temperature for 1 hour. Pyridine (0.49 mL) and acetic anhydride (4.0 μL) were sequentially added to the reaction mixture, followed by stirring at room temperature for 1 hour. The solvent was evaporated under reduced pressure, and a 10% aqueous solution of citric acid and ethyl acetate were added to the residue. The organic layer was separated, washed with a 10% aqueous solution of citric acid, and a saturated aqueous solution of sodium chloride sequentially, and dried over anhydrous magnesium sulfate, and the solvent was evaporated under reduced pressure to obtain 0.016 g of methyl 2-(4-((1-acetylpiperidin-4-yl)oxy)-2-hydroxybenzamido)-4-phenylbenzoate as a white solid.

A 2 mol/L aqueous solution of sodium hydroxide (0.082 mL) was added to a solution mixture of the obtained methyl 2-(4-((1-acetylpiperidin-4-yl)oxy)-2-hydroxybenzamido)-4-phenylbenzoate (0.016 g) in methanol (0.5 mL) and dioxane (0.5 mL), followed by stirring at 60° C. for 1 hour and 30 minutes. The reaction mixture was cooled to room temperature, and then methanol (1 mL), dioxane (1 mL), and a 2 mol/L aqueous solution of sodium hydroxide (0.082 mL) were added to the reaction mixture, followed by stirring at 60° C. for 3 hours. The reaction mixture was cooled to room temperature, and then the solvent was evaporated under reduced pressure. Water was added to the obtained residue, followed by adjusting the pH to 3 with 6 mol/L hydrochloric acid. The solid substance was collected from the reaction mixture by filtration to obtain 0.014 g of 2-(4-((1-acetylpiperidin-4-yl)oxy)-2-hydroxybenzamido)-4-phenylbenzoic acid as a white solid.

$^1$H-NMR (DMSO-d$_6$) δ: 1.46-1.70 (2H, m), 1.87-2.07 (2H, m), 2.02 (3H, s), 3.18-3.44 (2H, m), 3.63-3.74 (1H, m), 3.81-3.91 (1H, m), 4.64-4.74 (1H, m), 6.57 (1H, d, J=2.4 Hz), 6.66 (1H, dd, J=8.8, 2.4 Hz), 7.43-7.57 (4H, m), 7.70-7.75 (2H, m), 7.84 (1H, d, J=8.8 Hz), 8.10 (1H, d, J=8.3 Hz), 8.96 (1H, d, J=1.7 Hz), 11.81 (1H, s), 12.24 (1H, s).

Example 115a

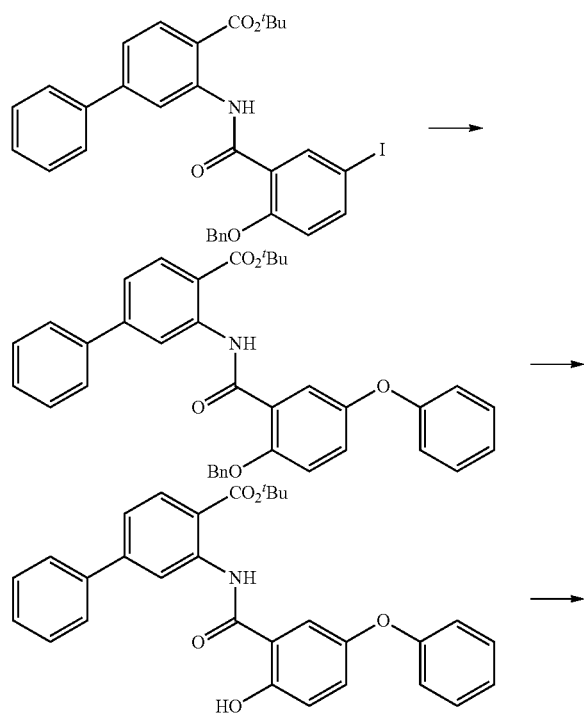

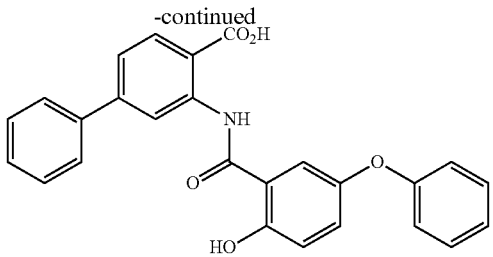

Phenol (0.029 mL), cesium carbonate (0.11 g), 2,2,6,6-tetramethylheptane-3,5-dione (3.4 µL), and copper(I) chloride (8.2 mg) were added to a 1-methyl-2-pyrrolidone (0.60 mL) solution of tert-butyl 2-(2-(benzyloxy)-5-iodobenzamido)-4-phenylbenzoate (0.10 g), followed by stirring under a nitrogen atmosphere at 100° C. for 2 hours. The reaction mixture was cooled to room temperature, and then 2,2,6,6-tetramethylheptane-3,5-dione (3.4 µL) and copper(I) chloride (8.2 mg) were added thereto, followed by stirring under a nitrogen atmosphere at 100° C. for 2 hours. The reaction mixture was cooled to room temperature, and then a 10% aqueous solution of citric acid and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 100-95% hexane/ethyl acetate] to obtain 0.049 g of tert-butyl 2-(2-(benzyloxy)-5-phenoxybenzamido)-4-phenylbenzoate (0.049 g).

To a solution mixture of the obtained tert-butyl 2-(2-(benzyloxy)-5-phenoxybenzamido)-4-phenylbenzoate (0.049 g) in methanol (1.5 mL) and ethyl acetate (1.5 mL), 10% palladium-carbon (0.025 g) was added, followed by stirring under a hydrogen atmosphere at room temperature for 2 hours. To the reaction mixture, 10% palladium-carbon (0.050 g) was added, followed by stirring under a hydrogen atmosphere at room temperature for 2 hours. Ethyl acetate was added to the reaction mixture, and the insoluble substance was removed by filtration. The solvent was evaporated under reduced pressure, and hexane was added to the obtained residue. The solid substance was collected by filtration to obtain 0.017 g of tert-butyl 2-(2-hydroxy-5-phenoxybenzamido)-4-phenylbenzoate as a white solid.

Trifluoroacetic acid (2.0 mL) was added to the obtained tert-butyl 2-(2-hydroxy-5-phenoxybenzamido)-4-phenylbenzoate (0.017 g), followed by stirring at room temperature for 3 hours. The solvent was evaporated under reduced pressure, and diisopropyl ether was added to the obtained residue. The solid substance was collected by filtration to obtain 0.012 g of 2-(2-hydroxy-5-phenoxybenzamido)-4-phenylbenzoic acid as a white solid.

$^1$H-NMR (DMSO-d$_6$) δ: 6.95-7.01 (2H, m), 7.07 (1H, d, J=8.8 Hz), 7.07-7.14 (1H, m), 7.21 (1H, dd, J=8.8, 2.9 Hz), 7.34-7.41 (2H, m), 7.41-7.48 (1H, m), 7.48-7.57 (4H, m), 7.68-7.75 (2H, m), 8.08 (1H, d, J=8.0 Hz), 8.98 (1H, d, J=1.7 Hz), 11.37 (1H, s), 12.26-12.44 (1H, broad), 13.30-13.55 (1H, broad).

7.60 (6H, m), 7.68-7.77 (2H, m), 7.87 (1H, d, J=2.4 Hz), 8.05 (1H, d, J=8.5 Hz), 9.06-9.14 (1H, m), 12.17 (1H, s).

Example 116a

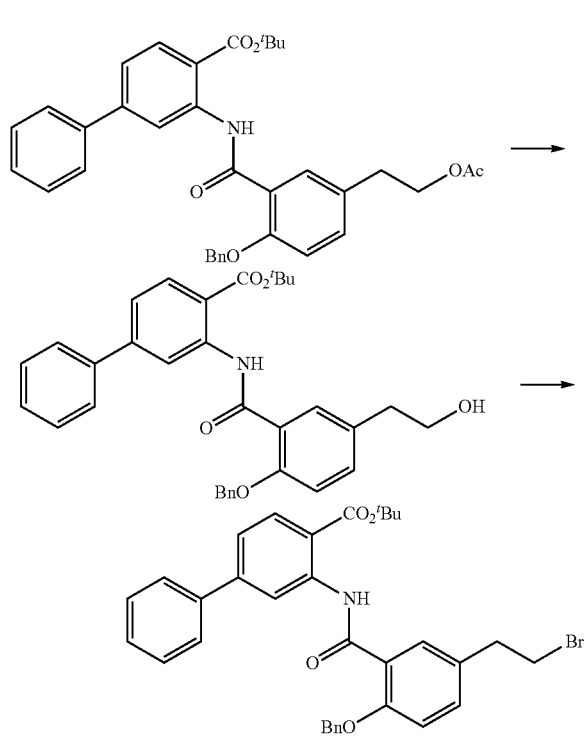

Example 117a

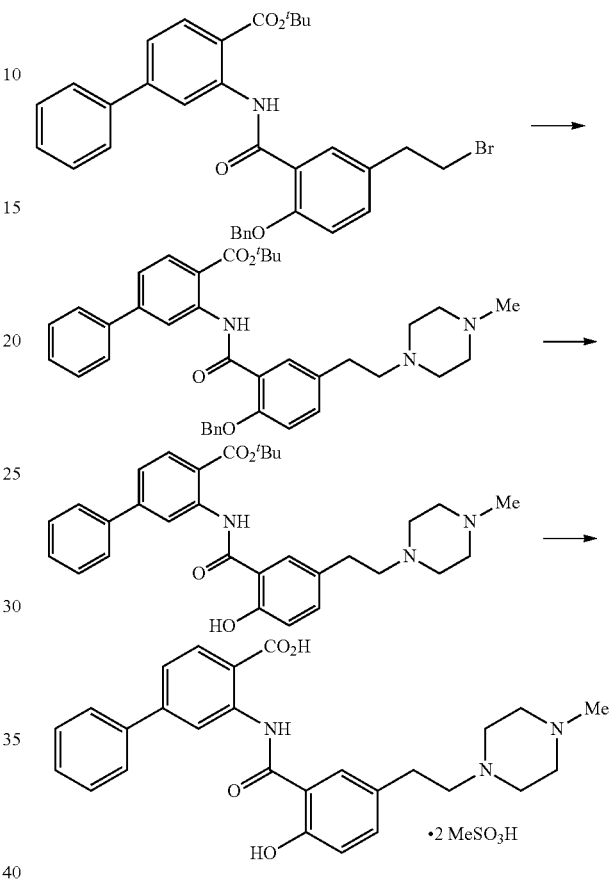

A 2.0 mol/L aqueous solution of sodium hydroxide (0.37 mL) was added to a solution mixture of tert-butyl 2-(5-(2-acetoxyethyl)-2-(benzyloxy)benzamido)-4-phenylbenzoate (0.38 g) in methanol (1.9 mL) and dioxane (1.9 mL), followed by stirring at room temperature for 2 hours. Acetic acid (0.012 mL) was added to the reaction mixture. The solvent was evaporated under reduced pressure, and a saturated aqueous solution of sodium bicarbonate and ethyl acetate were added to the residue. The organic layer was separated, washed with a saturated aqueous solution of sodium chloride, and dried over anhydrous magnesium sulfate. The solvent was evaporated under reduced pressure to obtain 0.35 g of tert-butyl 2-(2-(benzyloxy)-5-(2-hydroxyethyl)benzamido)-4-phenylbenzoate as a white solid.

Triphenylphosphine (0.13 g) and carbon tetrabromide (0.16 g) were added to a methylene chloride (3.4 mL) solution of the obtained tert-butyl 2-(2-(benzyloxy)-5-(2-hydroxyethyl)benzamido)-4-phenylbenzoate (0.17 g), followed by stirring at room temperature for 50 minutes. The reaction mixture was purified by silica gel column chromatography [Kanto Chemical Co., Inc., silica gel 60 (spherical), eluent: chloroform] and then purified by silica gel column chromatography [eluent: 100-85% hexane/ethyl acetate] to obtain 0.16 g of tert-butyl 2-(2-(benzyloxy)-5-(2-bromoethyl)benzamido)-4-phenylbenzoate as a white solid.

$^1$H-NMR (DMSO-$d_6$) δ: 1.50 (9H, s), 3.12 (2H, t, J=7.0 Hz), 3.72 (2H, t, J=7.0 Hz), 5.49 (2H, s), 7.18 (1H, d, J=8.6 Hz), 7.24-7.37 (3H, m), 7.42 (1H, dd, J=8.6, 2.4 Hz), 7.43-

Under ice-cooling, 1-methylpiperazine (0.095 mL) was addedd to an acetone (1.5 mL) solution of tert-butyl 2-(2-(benzyloxy)-5-(2-bromoethyl)benzamido)-4-phenylbenzoate (0.10 g), followed by stirring at room temperature for 30 minutes. Potassium carbonate (0.035 g) was added thereto, followed by stirring at room temperature for 1 hour. 1-Methylpiperazine (0.095 mL) and potassium carbonate (0.035 g) were added to the reaction mixture, followed by stirring at room temperature for 1 hour. The reaction mixture was left to stand overnight. The solvent was evaporated under reduced pressure, and a saturated aqueous solution of sodium bicarbonate and ethyl acetate were added to the residue. The organic layer was separated, washed with a saturated aqueous solution of sodium chloride, and dried over anhydrous sodium sulfate, and the solvent was evaporated under reduced pressure. The obtained residue was purified by silica gel column chromatography [eluent: 100-90% chloroform/methanol] to obtain 0.10 g of tert-butyl 2-(2-(benzyloxy)-5-(2-(4-methylpiperazin-1-yl)ethyl)benzamido)-4-phenylbenzoate.

To a solution mixture of the obtained tert-butyl 2-(2-(benzyloxy)-5-(2-(4-methylpiperazin-1-yl)ethyl)benzamido)-4-phenylbenzoate (0.10 g) in methanol (1.5 mL) and ethyl acetate (1.5 mL), 10% palladium-carbon (0.10 g) was added, followed by stirring under a hydrogen atmosphere at room temperature for 1 hour. The insoluble substance was removed by filtration, and the solvent was evaporated under reduced pressure. The obtained residue was purified by silica gel column chromatography [Kanto Chemical Co., Inc., silica gel 60 (spherical), eluent: 100-90% chloroform/methanol] to obtain 0.056 g of tert-butyl 2-(2-hydroxy-5-(2-(4-methylpiperazin-1-yl)ethyl)benzamido)-4-phenylbenzoate as a light yellow solid.

Trifluoroacetic acid (5.0 mL) was added to the obtained tert-butyl 2-(2-hydroxy-5-(2-(4-methylpiperazin-1-yl)ethyl)benzamido)-4-phenylbenzoate (0.056 g), followed by stirring at room temperature for 19 hours. The solvent was evaporated under reduced pressure, and ethyl acetate (3.0 mL) and methanesulfonic acid (0.018 mL) were sequentially added to the residue, followed by stirring at room temperature for 1 hour. The solid substance was collected from the reaction mixture by filtration to obtain 0.059 g of 2-(2-hydroxy-5-(2-(4-methylpiperazin-1-yl)ethyl)benzamido)-4-phenylbenzoic acid dimethanesulfonate as a white solid.

$^1$H-NMR (CD$_3$OD) δ: 2.74 (6H, s), 3.04 (3H, s), 3.09-3.17 (2H, m), 3.40-3.95 (10H, m), 7.00 (1H, d, J=8.5 Hz), 7.39-7.53 (5H, m), 7.69-7.76 (2H, m), 7.83 (1H, d, J=2.0 Hz), 8.22 (1H, d, J=8.3 Hz), 9.06 (1H, d, J=1.9 Hz).

Example 118a

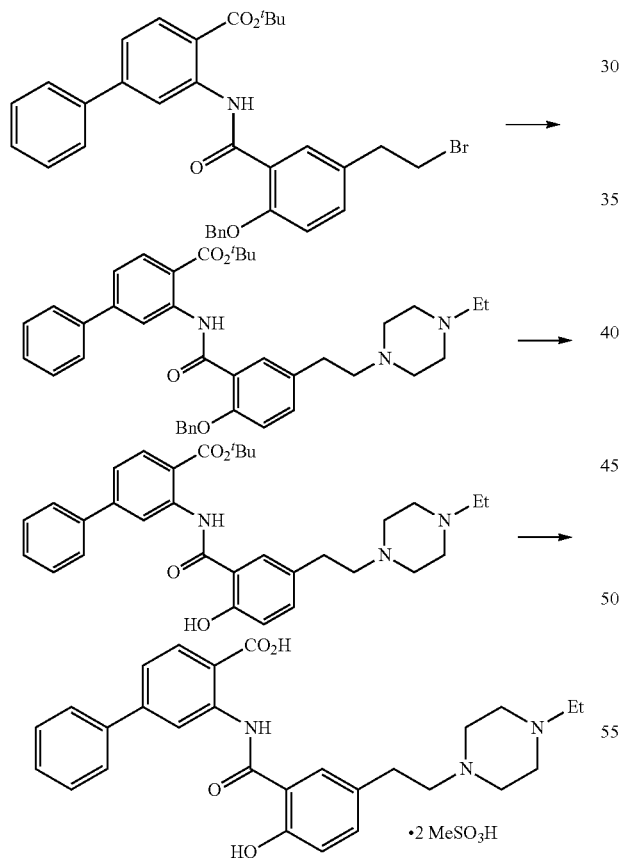

1-Ethylpiperazine (0.065 mL) and potassium carbonate (0.042 g) were added to an acetone (1.2 mL) solution of tert-butyl 2-(2-(benzyloxy)-5-(2-bromoethyl)benzamido)-4-phenylbenzoate (0.060 g), followed by stirring at room temperature for 6 hours. 1-Ethylpiperazine (0.065 mL) was added to the reaction mixture, followed by stirring at room temperature for 9 hours. The solvent was evaporated under reduced pressure, and a saturated aqueous solution of sodium bicarbonate and chloroform were added to the residue. The organic layer was separated and dried over anhydrous sodium sulfate, and then the solvent was evaporated under reduced pressure. The obtained residue was purified by silica gel column chromatography [eluent: 100-90% chloroform/methanol] to obtain 0.062 g of tert-butyl 2-(2-(benzyloxy)-5-(2-(4-ethylpiperazin-1-yl)ethyl)benzamido)-4-phenylbenzoate.

To a solution mixture of the obtained tert-butyl 2-(2-(benzyloxy)-5-(2-(4-ethylpiperazin-1-yl)ethyl)benzamido)-4-phenylbenzoate (0.062 g) in methanol (1.5 mL) and ethyl acetate (1.5 mL), 10% palladium-carbon (0.062 g) was added, followed by stirring under a hydrogen atmosphere at room temperature for 2 hours and 30 minutes. The insoluble substance was removed by filtration, and the solvent was evaporated under reduced pressure to obtain 0.047 g of tert-butyl 2-(5-(2-(4-ethylpiperazin-1-yl)ethyl)-2-hydroxybenzamido)-4-phenylbenzoate.

Trifluoroacetic acid (5.0 mL) was added to the obtained tert-butyl 2-(5-(2-(4-ethylpiperazin-1-yl)ethyl)-2-hydroxybenzamido)-4-phenylbenzoate (0.047 g), followed by stirring at room temperature for 4 hours. The solvent was evaporated under reduced pressure, and ethyl acetate (3.0 mL) and methanesulfonic acid (0.013 mL) were sequentially added to the residue, followed by stirring at room temperature for 5 hours and 30 minutes. The solid substance was collected from the reaction mixture by filtration to obtain 0.048 g of 2-(5-(2-(4-ethylpiperazin-1-yl)ethyl)-2-hydroxybenzamido)-4-phenylbenzoic acid dimethanesulfonate as a white solid.

$^1$H-NMR (DMSO-d$_6$) δ: 1.23 (3H, t, J=7.2 Hz), 2.34 (6H, s), 2.40-3.90 (14H, m), 7.00 (1H, d, J=8.3 Hz), 7.32-7.38 (1H, m), 7.43-7.58 (4H, m), 7.69-7.75 (2H, m), 7.83-7.91 (1H, m), 8.10 (1H, d, J=8.3 Hz), 9.05 (1H, d, J=1.2 Hz), 11.31 (1H, s), 12.30 (1H, s).

Example 119a

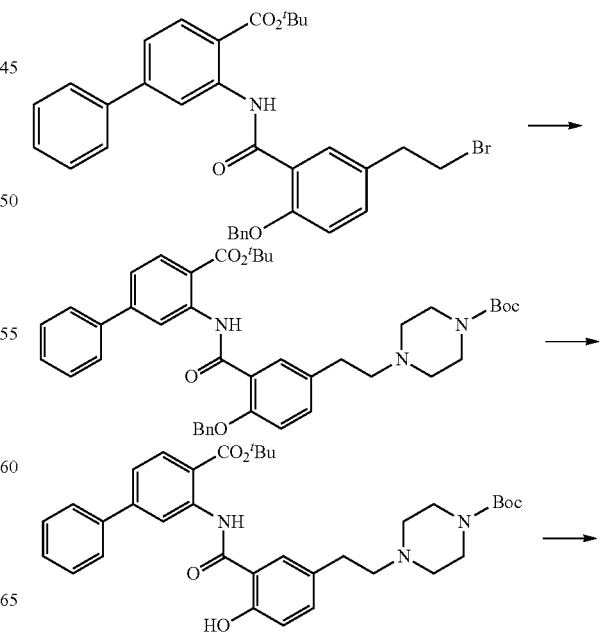

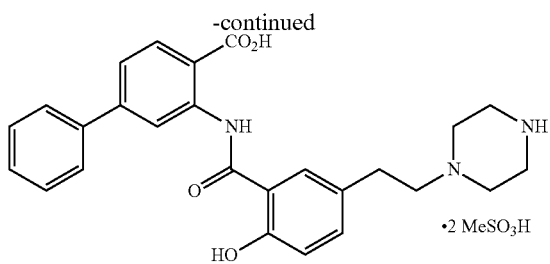

As in Example 118a, the following compound was prepared.

2-(2-Hydroxy-5-(2-(piperazin-1-yl)ethyl)benzamido)-4-phenylbenzoic acid dimethanesulfonate $^1$H-NMR (DMSO-$d_6$) δ: 2.35 (6H, s), 2.80-3.70 (12H, m), 7.00 (1H, d, J=8.3 Hz), 7.36 (1H, dd, J=8.4, 2.3 Hz), 7.43-7.58 (4H, m), 7.69-7.75 (2H, m), 7.84-7.90 (1H, m), 8.10 (1H, d, J=8.3 Hz), 8.75-9.10 (1H, broad), 9.05 (1H, d, J=1.7 Hz), 11.31 (1H, s), 12.30 (1H, s).

Example 120a

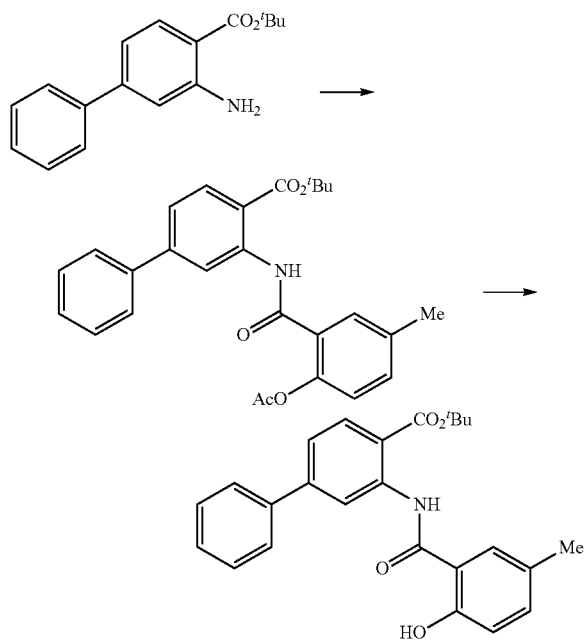

N,N-Dimethylformamide (0.019 mL) and oxalyl chloride (0.32 mL) were sequentially added to a methylene chloride (6.0 mL) suspension of 2-acetoxy-5-methylbenzoic acid (0.48 g), followed by stirring at room temperature for 1 hour. The solvent was evaporated under reduced pressure, and toluene was added to the residue. The solvent was evaporated under reduced pressure, and methylene chloride (6.0 mL) was added to the residue. The resulting mixture was added to a solution mixture of tert-butyl 2-amino-4-phenylbenzoate (0.60 g) under ice-cooling in pyridine (0.45 mL) and methylene chloride (6.0 mL), followed by stirring at room temperature for 1 hour. The solvent was evaporated under reduced pressure, and methanol (5.0 mL) and potassium carbonate (1.54 g) were added to the residue, followed by stirring at room temperature for 2 hours and 30 minutes. The solvent was evaporated under reduced pressure, and water and chloroform were added to the residue. The organic layer was separated, washed with a 10% aqueous solution of citric acid and a saturated aqueous solution of sodium chloride sequentially, and dried over anhydrous magnesium sulfate, and the solvent was evaporated under reduced pressure. Diisopropyl ether was added to the obtained residue, and the solid substance was collected by filtration to obtain 0.80 g of tert-butyl 2-(2-hydroxy-5-methylbenzamido)-4-phenylbenzoate as a white solid.

$^1$H-NMR (DMSO-$d_6$) δ: 1.56 (9H, s), 2.28 (3H, s), 6.93 (1H, d, J=8.3 Hz), 7.26 (1H, dd, J=8.3, 2.2 Hz), 7.42-7.49 (1H, m), 7.50-7.57 (3H, m), 7.69-7.78 (3H, m), 7.99 (1H, d, J=8.3 Hz), 8.81 (1H, d, J=1.7 Hz), 11.25 (1H, s), 11.81 (1H, s).

Example 121a

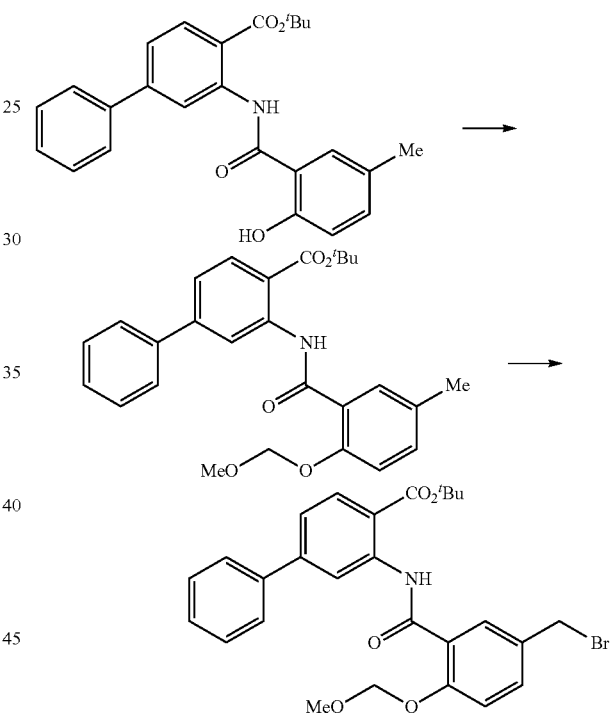

Potassium carbonate (0.51 g) and methoxymethyl chloride (0.23 mL) were sequentially added to an acetone (9.0 mL) suspension of tert-butyl 2-(2-hydroxy-5-methylbenzamido)-4-phenylbenzoate (0.60 g), followed by stirring at room temperature for 1 hour and 30 minutes. Potassium carbonate (0.21 g) and methoxymethyl chloride (0.11 mL) were sequentially added to the reaction mixture, followed by stirring at room temperature for 2 hours. Potassium carbonate (0.51 g) and methoxymethyl chloride (0.23 mL) were sequentially added to the reaction mixture, followed by stirring at room temperature for 2 hours and then heating to reflux for 20 minutes. The reaction mixture was cooled to room temperature, and then water and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 100-80% hexane/ethyl acetate] to obtain 0.64 g of tert-butyl 2-(2-(methoxymethoxy)-5-methylbenzamido)-4-phenylbenzoate.

N-Bromosuccinimide (0.25 g) and azobisisobutyronitrile (0.023 g) were sequentially added to a benzene (6.3 mL) solution of the obtained tert-butyl 2-(2-(methoxymethoxy)-5-methylbenzamido)-4-phenylbenzoate (0.63 g), followed by heating to reflux for 30 minutes. The reaction mixture was cooled to room temperature, and then a saturated aqueous solution of sodium bicarbonate and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 100-90% hexane/ethyl acetate] to obtain 0.51 g of tert-butyl 2-(5-(bromomethyl)-2-(methoxymethoxy)benzamido)-4-phenylbenzoate as a white solid.

$^1$H-NMR (DMSO-$d_6$) δ: 1.60 (9H, s), 3.49 (3H, s), 4.78 (2H, s), 5.52 (2H, s), 7.35 (1H, d, J=8.7 Hz), 7.42-7.58 (4H, m), 7.65 (1H, dd, J=8.7, 2.4 Hz), 7.70-7.76 (2H, m), 8.07 (1H, d, J=8.3 Hz), 8.13 (1H, d, J=2.4 Hz), 9.13 (1H, d, J=1.5 Hz), 12.17 (1H, s).

Example 122a

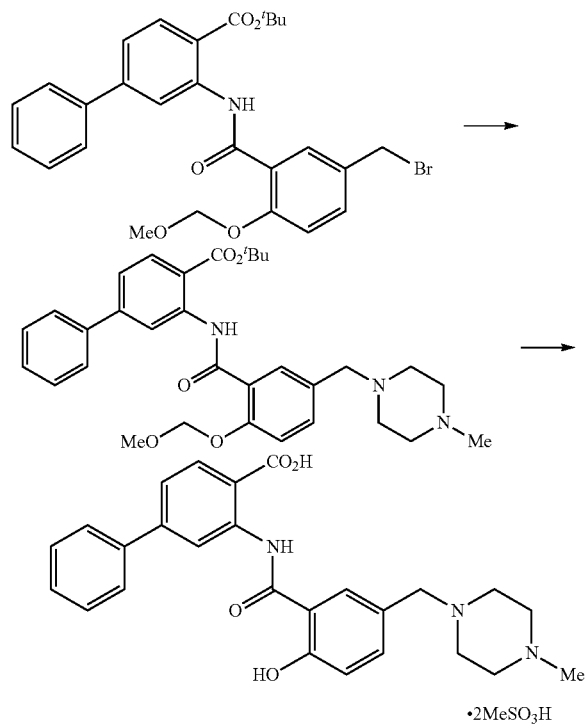

Under ice-cooling, 1-methylpiperazine (0.16 mL) was added to an acetone (2.3 mL) suspension of tert-butyl 2-(5-(bromomethyl)-2-(methoxymethoxy)benzamido)-4-phenylbenzoate (0.15 g), followed by stirring at room temperature for 2 hours. The solvent was evaporated under reduced pressure, and a 1.0 mol/L aqueous solution of sodium hydroxide and chloroform were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 100-95% chloroform/methanol] to obtain 0.14 g of tert-butyl 2-(2-(methoxymethoxy)-5-((4-methylpiperazin-1-yl)methyl)benzamido)-4-phenylbenzoate as a yellow oil substance.

Under ice-cooling, trifluoroacetic acid (1.5 mL) was added to a methylene chloride (3.0 mL) solution of the obtained tert-butyl 2-(2-(methoxymethoxy)-5-((4-methylpiperazin-1-yl)methyl)benzamido)-4-phenylbenzoate (0.14 g), followed by stirring at room temperature for 4 hours and 30 minutes. The solvent was evaporated under reduced pressure, and diisopropyl ether was added to the obtained residue. The solid substance was collected by filtration, and ethyl acetate (5.0 mL) and methanesulfonic acid (0.036 mL) were added to the obtained solid substance, followed by stirring at room temperature for 4 hours. The solid substance was collected from the reaction mixture by filtration to obtain 0.11 g of 2-(2-hydroxy-5-((4-methylpiperazin-1-yl)methyl)benzamido)-4-phenylbenzoic acid dimethanesulfonate as a white solid.

$^1$H-NMR (CD$_3$OD) δ: 2.73 (6H, s), 3.01 (3H, s), 3.20-3.90 (8H, broad), 4.38 (2H, s), 7.10 (1H, d, J=8.6 Hz), 7.40-7.46 (1H, m), 7.46-7.54 (3H, m), 7.62 (1H, dd, J=8.6, 2.1 Hz), 7.69-7.75 (2H, m), 8.06 (1H, d, J=2.1 Hz), 8.22 (1H, d, J=8.3 Hz), 9.05 (1H, d, J=1.7 Hz).

Examples 123a and 124a

As in Example 122a, the compounds shown in Table 15a were prepared.

TABLE 15a

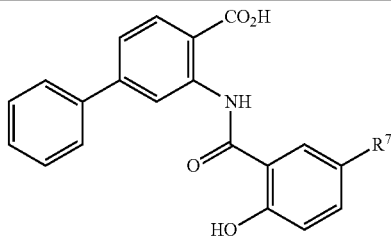

| Example No. | R$^7$ |
|---|---|
| 123a | ![structure] ·2MeSO$_3$H (4-ethylpiperazinyl with N-Et) |
| 124a | ![structure] ·2MeSO$_3$H (4-isopropylpiperazinyl with N-iPr) |

2-(5-((4-Ethylpiperazin-1-yl)methyl)-2-hydroxybenzamido)-4-phenylbenzoic acid dimethanesulfonate $^1$H-NMR (D$_2$O) δ: 1.31 (3H, t, J=7.2 Hz), 2.79 (6H, s), 3.20-3.70 (10H, m), 4.10 (2H, s), 6.82 (1H, d, J=7.8 Hz), 6.98-7.15 (1H, m), 7.18-7.48 (7H, m), 7.58-7.72 (1H, m), 8.38 (1H, s).

2-(2-Hydroxy-5-((4-isopropylpiperazin-1-yl)methyl)benzamido)-4-phenylbenzoic acid dimethanesulfonate $^1$H-NMR (DMSO-$d_6$) δ: 1.24 (6H, d, J=6.1 Hz), 2.33 (6H, s), 3.00-3.70 (11H, m), 7.08 (1H, d, J=8.8 Hz), 7.43-7.58 (5H, m), 7.68-7.76 (2H, m), 8.00-8.14 (1H, m), 8.10 (1H, d, J=8.6 Hz), 9.06 (1H, d, J=1.7 Hz), 11.52-11.75 (1H, broad), 12.33 (1H, s).

Example 125a

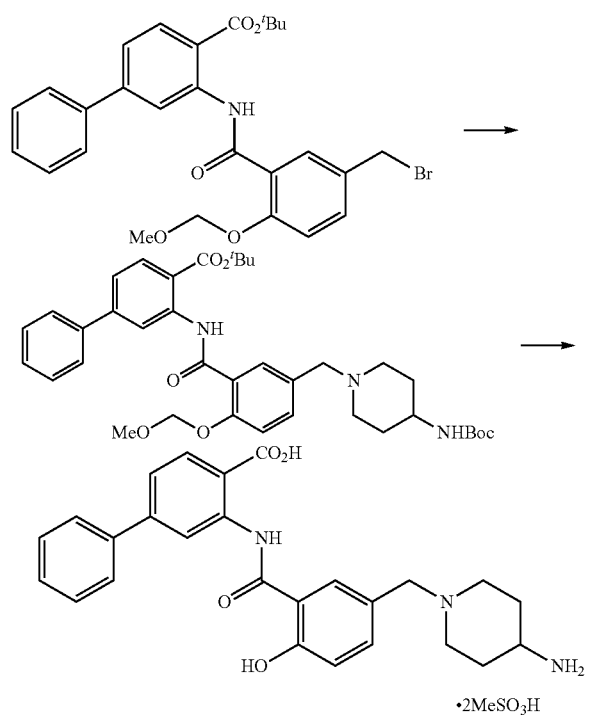

As in Example 122a, the following compound was prepared.

2-(5-((4-aminopiperidin-1-yl)methyl)-2-hydroxybenzamido)-4-phenylbenzoic acid dimethanesulfonate ¹H-NMR (CD₃OD) δ: 1.88-2.04 (2H, m), 2.23-2.34 (2H, m), 2.71 (6H, s), 3.12-3.27 (2H, m), 3.40-3.54 (1H, m), 3.58-3.70 (2H, m), 4.37 (2H, s), 7.11 (1H, d, J=8.6 Hz), 7.40-7.46 (1H, m), 7.47-7.54 (3H, m), 7.61 (1H, dd, J=8.6, 2.1 Hz), 7.70-7.75 (2H, m), 8.05 (1H, d, J=2.1 Hz), 8.22 (1H, d, J=8.3 Hz), 9.06 (1H, d, J=1.7 Hz).

Example 126a

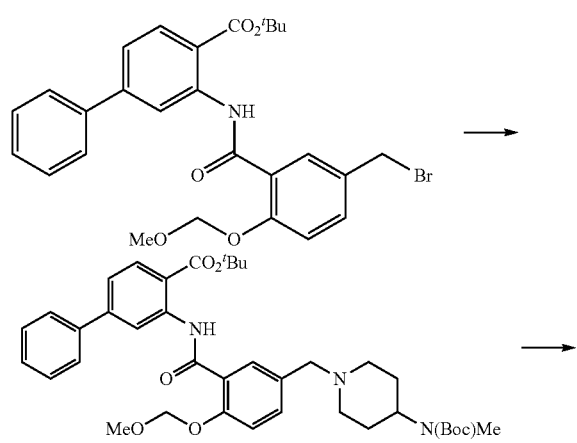

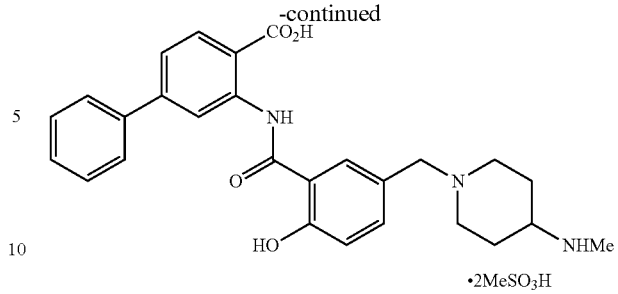

As in Example 122a, the following compound was prepared.

2-(2-Hydroxy-5-((4-(methylamino)piperidin-1-yl)methyl)benzamido)-4-phenylbenzoic acid dimethanesulfonate ¹H-NMR (DMSO-d₆) δ: 1.64-1.80 (2H, m), 2.16-2.28 (2H, m), 2.38 (6H, s), 2.55-2.60 (3H, m), 2.90-3.07 (2H, m), 3.13-3.31 (1H, m), 3.42-3.56 (2H, m), 4.24-4.34 (2H, m), 7.11 (1H, d, J=8.5 Hz), 7.42-7.60 (5H, m), 7.68-7.76 (2H, m), 8.06-8.14 (2H, m), 8.62-8.76 (1H, m), 9.06 (1H, d, J=1.7 Hz), 9.46-9.63 (1H, broad), 11.76 (1H, s), 12.33 (1H, s).

Example 127a

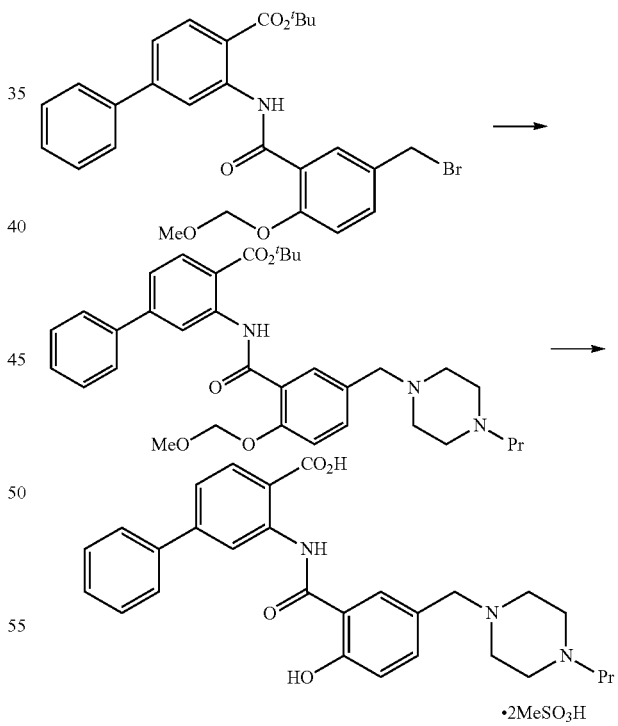

Under ice-cooling, potassium carbonate (0.19 g) and tert-butyl 2-(5-(bromomethyl)-2-(methoxymethoxy)benzamido)-4-phenylbenzoate (0.12 g) were sequentially added to an acetone (1.8 mL) suspension of 1-propylpiperazine dihydrochloride (0.13 g), followed by stirring at room temperature for 5 hours and 30 minutes. The solvent was evaporated under reduced pressure, and a saturated aqueous solution of sodium bicarbonate and chloroform were added to the residue. The organic layer was separated and dried over anhydrous sodium sulfate, and the solvent was evaporated under reduced pressure. The obtained residue was purified by silica gel column chromatography [Kanto Chemical Co., Inc., silica gel 60 (spherical), eluent: 100-90% chloroform/methanol] to obtain 0.088 g of tert-butyl 2-(2-(methoxymethoxy)-5-((4-propylpiperazin-1-yl)methyl)benzamido)-4-phenylbenzoate.

Trifluoroacetic acid (5.0 mL) was added to the obtained tert-butyl 2-(2-(methoxymethoxy)-5-((4-propylpiperazin-1-yl)methyl)benzamido)-4-phenylbenzoate (0.088 g), followed by stirring at room temperature for 3 hours. The solvent was evaporated under reduced pressure, and ethyl acetate (3.0 mL) and methanesulfonic acid (0.022 mL) were added to the residue, followed by stirring at room temperature for 2 hours and 30 minutes. The solid substance was collected from the reaction mixture by filtration to obtain 0.067 g of 2-(2-hydroxy-5-((4-propylpiperazin-1-yl)methyl)benzamido)-4-phenylbenzoic acid dimethanesulfonate as a white solid.

$^1$H-NMR (DMSO-$d_6$) δ: 0.90 (3H, t, J=7.3 Hz), 1.55-1.69 (2H, m), 2.34 (6H, s), 2.90-3.70 (12H, m), 7.08 (1H, d, J=8.0 Hz), 7.43-7.59 (5H, m), 7.67-7.76 (2H, m), 7.99-8.15 (1H, m), 8.10 (1H, d, J=8.3 Hz), 9.06 (1H, d, J=2.0 Hz), 11.55-11.75 (1H, broad), 12.33 (1H, s).

Example 128a

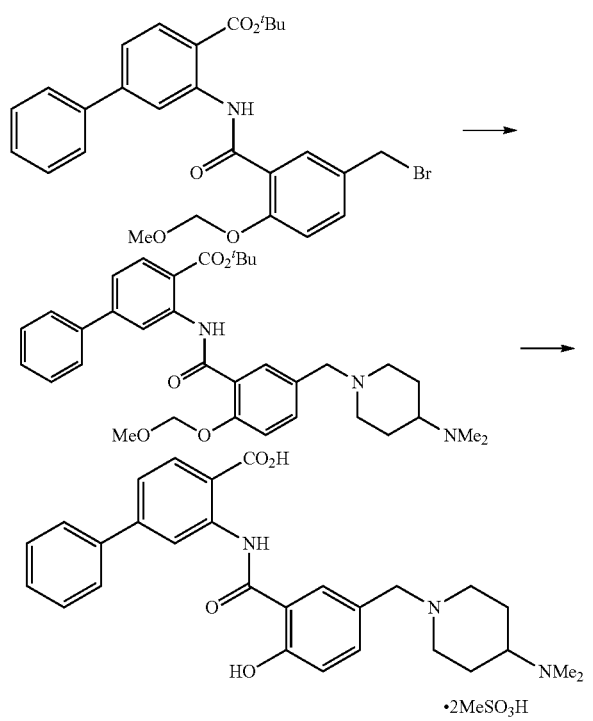

As in Example 127a, the following compound was prepared.

2-(5-((4-(Dimethylamino)piperidin-1-yl)methyl)-2-hydroxybenzamido)-4-phenylbenzoic acid dimethanesulfonate $^1$H-NMR (CD$_3$OD) δ: 1.96-2.13 (2H, m), 2.33-2.45 (2H, m), 2.72 (6H, s), 2.92 (6H, s), 3.10-3.23 (2H, m), 3.46-3.64 (1H, m), 3.66-3.78 (2H, m), 4.39 (2H, s), 7.12 (1H, d, J=8.5 Hz), 7.40-7.46 (1H, m), 7.47-7.54 (3H, m), 7.63 (1H, dd, J=8.5, 1.9 Hz), 7.70-7.76 (2H, m), 8.06 (1H, d, J=1.9 Hz), 8.22 (1H, d, J=8.6 Hz), 9.06 (1H, d, J=1.7 Hz).

Example 129a

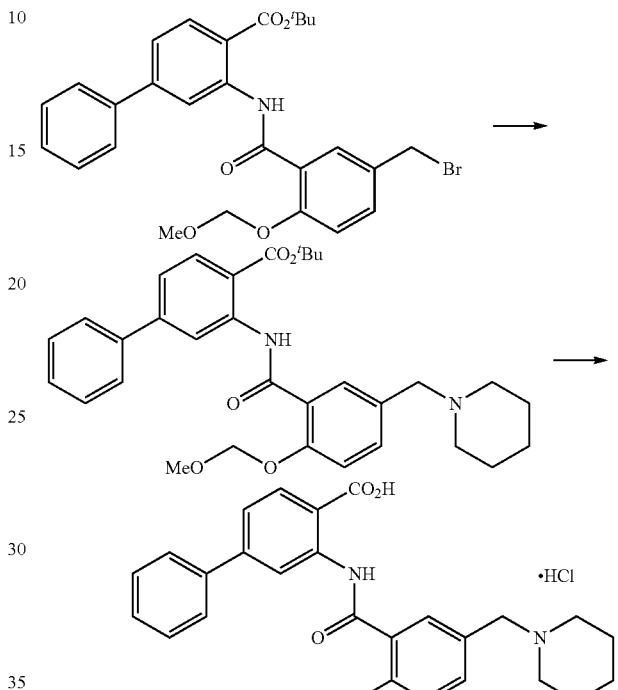

Under ice-cooling, piperidine (0.094 mL) was added to an acetone (1.5 mL) suspension of tert-butyl 2-(5-(bromomethyl)-2-(methoxymethoxy)benzamido)-4-phenylbenzoate (0.10 g), followed by stirring at room temperature for 1 hour. The solvent was evaporated under reduced pressure, and a saturated aqueous solution of sodium bicarbonate and ethyl acetate were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 100-95% chloroform/methanol] to obtain 0.080 g of tert-butyl 2-(2-(methoxymethoxy)-5-((piperidin-1-yl)methyl)benzamido)-4-phenylbenzoate.

Under ice-cooling, trifluoroacetic acid (1.0 mL) was added to a methylene chloride (2.0 mL) solution of the obtained tert-butyl 2-(2-(methoxymethoxy)-5-((piperidin-1-yl)methyl)benzamido)-4-phenylbenzoate (0.080 g), followed by stirring at room temperature for 3 hours. The solvent was evaporated under reduced pressure, and ethyl acetate was added to the obtained residue. The solid substance was collected by filtration. Ethyl acetate (1.0 mL) and a 4.0 mol/L hydrogen chloride-dioxane solution (0.20 mL) were added to the obtained solid substance, followed by stirring at room temperature for 3 hours. The solid substance was collected from the reaction mixture by filtration to obtain 0.020 g of 2-(2-hydroxy-5-((piperidin-1-yl)methyl)benzamido)-4-phenylbenzoic acid hydrochloride as a white solid.

¹H-NMR (CD₃OD) δ: 1.43-1.60 (1H, m), 1.65-1.90 (3H, m), 1.90-2.05 (2H, m), 2.92-3.06 (2H, m), 3.45-3.57 (2H, m), 4.31 (2H, s), 7.10 (1H, d, J=8.5 Hz), 7.40-7.46 (1H, m), 7.47-7.54 (3H, m), 7.58 (1H, dd, J=8.5, 2.2 Hz), 7.70-7.76 (2H, m), 8.02 (1H, d, J=2.2 Hz), 8.23 (1H, d, J=8.3 Hz), 9.06 (1H, d, J=1.7 Hz).

Example 130a

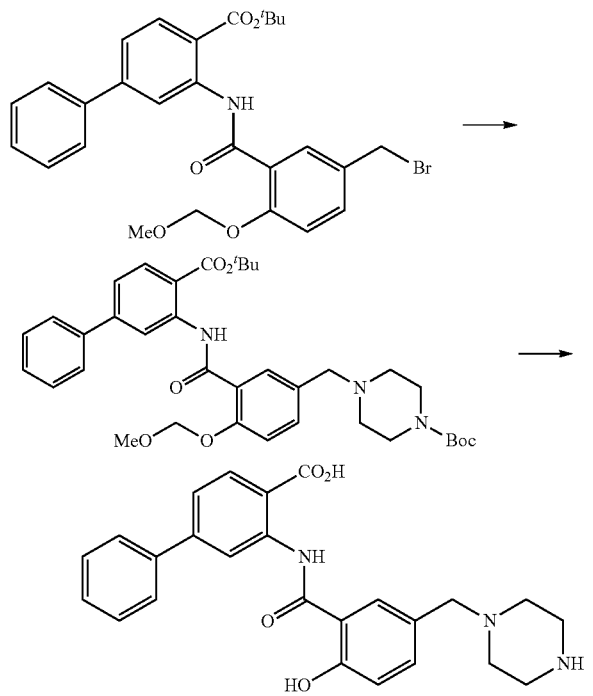

N,N-Dimethylformamide (1 mL), potassium carbonate (0.039 g), and 1-(tert-butoxycarbonyl)piperidine (0.053 g) were added to tert-butyl 2-(5-(bromomethyl)-2-(methoxymethoxy)benzamido)-4-phenylbenzoate (0.030 g), followed by stirring at 90 to 100° C. for 15 minutes. The reaction mixture was cooled to room temperature, and then water and chloroform were added thereto. The organic layer was separated and dried over anhydrous sodium sulfate, and the solvent was evaporated under reduced pressure. Trifluoroacetic acid (2 mL) was added to the obtained residue, followed by stirring at room temperature for 20 minutes. The solvent was evaporated under reduced pressure, and water was added to the residue. After adjusting the pH to 6.7 with a saturated aqueous solution of sodium bicarbonate, the solid substance was collected by filtration. Methanol and methanesulfonic acid (0.010 g) were added to the obtained solid substance. The solid substance was collected by filtration to obtain 0.015 g of 2-(2-hydroxy-5-((piperazin-1-yl)methyl)benzamido)-4-phenylbenzoic acid dimethanesulfonate as a white solid.

¹H-NMR (DMSO-d₆) δ: 2.34 (6H, s), 2.80-3.80 (10H, m), 7.09 (1H, d, J=7.8 Hz), 7.43-7.58 (5H, m), 7.69-7.75 (2H, m), 8.04-8.14 (1H, m), 8.10 (1H, d, J=8.3 Hz), 8.65-8.95 (1H, broad), 9.06 (1H, d, J=1.5 Hz), 11.60-11.80 (1H, broad), 12.33 (1H, s).

Examples 131a to 133a

As in Example 130a, the compounds shown in Table 16a were prepared.

TABLE 16a

| Example No. | R⁷ |
|---|---|
| 131a | ~NMe₂ ·MeSO₃H |
| 132a | ~N(morpholine) ·MeSO₃H |
| 133a | ~N(4-methyl-1,4-diazepan-1-yl, ethyl) ·2MeSO₃H |

2-(5-((Dimethylamino)methyl)-2-hydroxybenzamido)-4-phenylbenzoic acid methanesulfonate ¹H-NMR (DMSO-d₆) δ: 2.30 (3H, s), 2.73 (6H, s), 4.26 (2H, s), 7.10 (1H, d, J=8.6 Hz), 7.44-7.58 (5H, m), 7.69-7.75 (2H, m), 8.08-8.13 (2H, m), 9.06 (1H, d, J=1.7 Hz), 9.42-9.58 (¹H, broad), 11.68-11.78 (1H, broad), 12.28-12.38 (1H, broad).

2-(2-Hydroxy-5-((morpholin-4-yl)methyl)benzamido)-4-phenylbenzoic acid methanesulfonate ¹H-NMR (DMSO-d₆) δ: 2.32 (3H, s), 3.00-3.19 (2H, m), 3.20-3.46 (2H, m), 3.53-3.71 (2H, m), 3.88-4.05 (2H, m), 4.34 (2H, s), 7.11 (1H, d, J=8.5 Hz), 7.43-7.58 (5H, m), 7.69-7.75 (2H, m), 8.10 (1H, d, J=8.3 Hz), 8.12 (1H, d, J=2.2 Hz), 9.06 (1H, d, J=1.7 Hz), 9.62-9.85 (1H, broad), 11.74 (1H, s), 12.33 (1H, s).

2-(2-Hydroxy-5-((4-methyl-1,4-diazepan-1-yl)methyl)benzamido)-4-phenylbenzoic acid dimethanesulfonate ¹H-NMR (CD₃OD) δ: 2.27-2.41 (2H, m), 2.73 (6H, s), 3.00 (3H, s), 3.24-3.88 (8H, m), 4.48 (2H, s), 7.13 (1H, d, J=8.5 Hz), 7.39-7.56 (4H, m), 7.65 (1H, dd, J=8.5, 2.1 Hz), 7.69-7.77 (2H, m), 8.08 (1H, d, J=2.1 Hz), 8.22 (1H, d, J=8.3 Hz), 9.05 (1H, d, J=1.7 Hz).

7.44-7.52 (2H, m), 7.68-7.74 (2H, m), 8.20 (1H, d, J=8.0 Hz), 8.32 (1H, d, J=2.0 Hz), 9.00 (1H, d, J=1.9 Hz).

Examples 134a

Example 135a

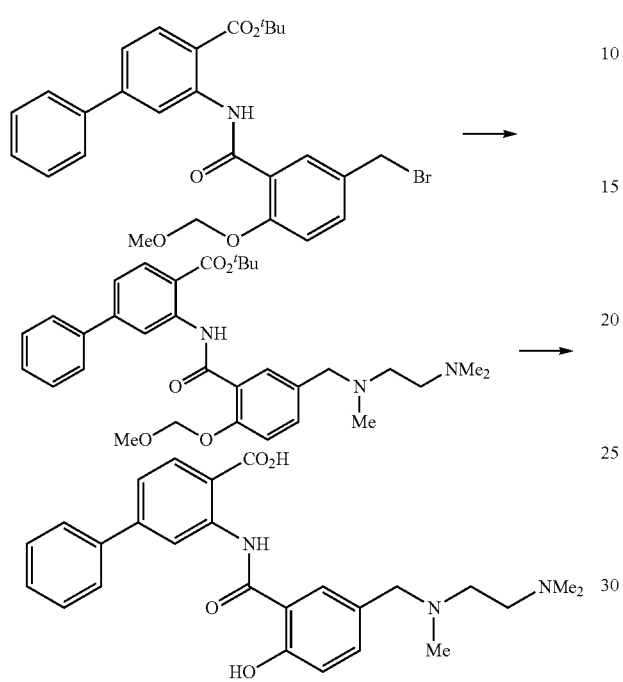

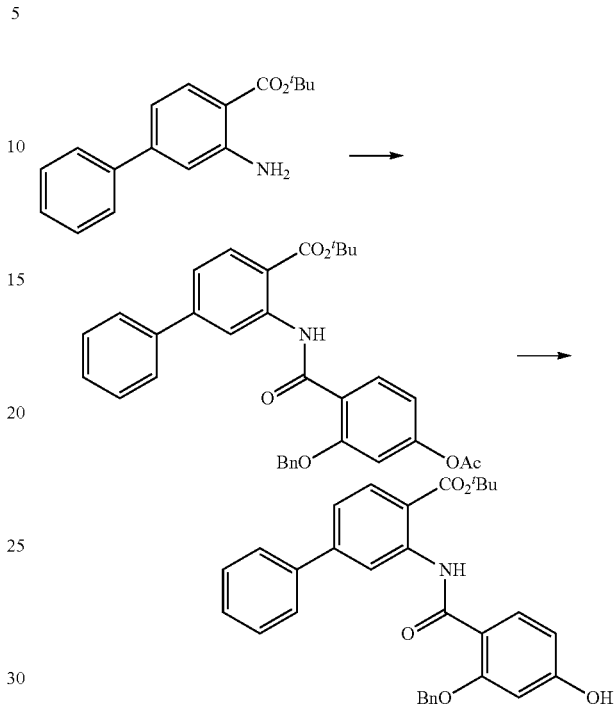

Under ice-cooling, tert-butyl 2-(5-(bromomethyl)-2-(methoxymethoxy)benzamido)-4-phenylbenzoate (0.12 g) was added to an acetone (1.8 mL) solution of N,N,N'-trimethylethylenediamine (0.089 mL), followed by stirring at room temperature for 1 hour. The solvent was evaporated under reduced pressure, and a saturated aqueous solution of sodium bicarbonate and chloroform were added to the residue. The organic layer was separated and dried over anhydrous sodium sulfate, and the solvent was evaporated under reduced pressure. The obtained residue was purified by silica gel column chromatography [eluent: 100-90% chloroform/methanol] to obtain 0.070 g of tert-butyl 2-(5-(((2-(dimethylamino)ethyl)(methyl)amino)methyl)-2-(methoxymethoxy)benzamido)-4-phenylbenzoate.

Trifluoroacetic acid (5.0 mL) was added to the obtained tert-butyl 2-(5-(((2-(dimethylamino)ethyl)(methyl)amino)methyl)-2-(methoxymethoxy)benzamido)-4-phenylbenzoate (0.070 g), followed by stirring at room temperature for 8 hours. The solvent was evaporated under reduced pressure, and water and ethyl acetate were added to the residue. After adjusting the pH to 6.3 with a saturated aqueous solution of sodium bicarbonate, the organic layer was separated, washed with a saturated aqueous solution of sodium chloride, and dried over anhydrous sodium sulfate, and the solvent was evaporated under reduced pressure. Diisopropyl ether was added to the obtained residue, and the solid substance was collected by filtration to obtain 0.045 g of 2-(5-(((2-(dimethylamino)ethyl)(methyl)amino)methyl)-2-hydroxybenzamido)-4-phenylbenzoic acid as a white solid.

$^1$H-NMR (CD$_3$OD) δ: 2.30 (3H, s), 2.91 (2H, t, J=5.9 Hz), 2.98 (6H, s), 3.37 (2H, t, J=5.9 Hz), 3.66 (2H, s), 6.90 (1H, d, J=8.3 Hz), 7.30 (1H, dd, J=8.3, 2.0 Hz), 7.35-7.43 (2H, m),

Under ice-cooling, oxalyl chloride (0.15 mL) was added to a solution mixture of 4-acetoxy-2-(benzyloxy)benzoic acid (0.35 g) in methylene chloride (5.0 mL) and N,N-dimethylformamide (0.020 mL), followed by stirring at room temperature for 30 minutes. The solvent was evaporated under reduced pressure, and methylene chloride (3.0 mL) was added to the residue. The resulting mixture was added to a solution mixture of tert-butyl 2-amino-4-phenylbenzoate (0.30 g) in pyridine (0.14 mL) and methylene chloride (2.5 mL) under ice-cooling, followed by stirring at room temperature for 3 hours and 20 minutes. The solvent was evaporated under reduced pressure, and a saturated aqueous solution of sodium bicarbonate and ethyl acetate were added to the residue. The organic layer was separated, washed with a 10% aqueous solution of citric acid and a saturated aqueous solution of sodium chloride sequentially, and dried over anhydrous magnesium sulfate, and the solvent was evaporated under reduced pressure. The obtained residue was purified by silica gel column chromatography [eluent: 91-80% hexane/ethyl acetate] to obtain 0.34 g of tert-butyl 2-(4-acetoxy-2-(benzyloxy)benzamido)-4-phenylbenzoate as a white solid.

A 4 mol/L aqueous solution of sodium hydroxide (0.47 mL) was added to a dioxane (5.0 mL) solution of the obtained tert-butyl 2-(4-acetoxy-2-(benzyloxy)benzamido)-4-phenylbenzoate (0.34 g), followed by stirring at 50 to 55° C. for 2 hours. The reaction mixture was cooled to room temperature, and a 10% aqueous solution of citric acid (15 mL) and ethyl acetate were added thereto. The organic layer was separated, washed with a saturated aqueous solution of sodium chloride, and dried over anhydrous magnesium sulfate, and the solvent was evaporated under reduced pressure. Diisopropyl ether was added to the obtained residue, and the solid substance was collected by filtration to obtain 0.29 g of tert-butyl 2-(2-(benzyloxy)-4-hydroxybenzamido)-4-phenylbenzoate as a white solid.

¹H-NMR (DMSO-d₆) δ: 1.50 (9H, s), 5.49 (2H, s), 6.46-6.55 (2H, m), 7.25-7.38 (3H, m), 7.42-7.58 (6H, m), 7.68-7.75 (2H, m), 7.89 (1H, d, J=8.6 Hz), 8.03 (1H, d, J=8.3 Hz), 9.11 (1H, d, J=1.4 Hz), 10.25 (1H, s), 12.17 (1H, s).

Example 136a

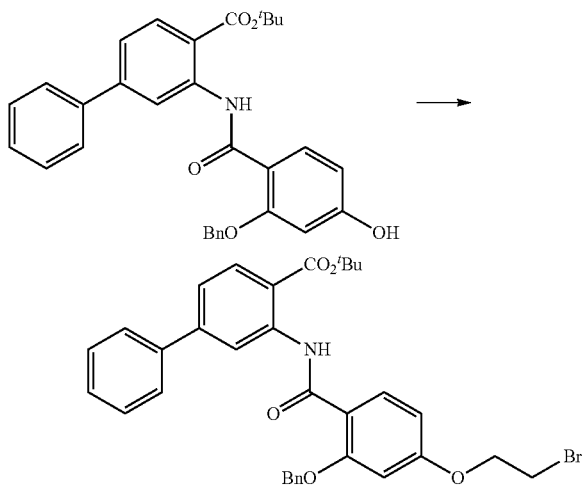

Potassium carbonate (1.6 g) and 1,2-dibromoethane (2.6 mL) were added to a N,N-dimethylformamide (5.0 mL) solution of tert-butyl 2-(2-(benzyloxy)-4-hydroxybenzamido)-4-phenylbenzoate (0.29 g), followed by stirring at 120° C. for 1 hour and 45 minutes. The reaction mixture was cooled to room temperature, and a 10% aqueous solution of citric acid and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 95-91% hexane/ethyl acetate] to obtain 0.19 g of tert-butyl 2-(2-(benzyloxy)-4-(2-bromoethoxy)benzamido)-4-phenylbenzoate as a white solid.

¹H-NMR (DMSO-d₆) δ: 1.50 (9H, s), 3.79 (2H, t, J=5.4 Hz), 4.37 (2H, t, J=5.4 Hz), 5.56 (2H, s), 6.71 (1H, dd, J=8.8, 2.2 Hz), 6.74 (1H, d, J=2.2 Hz), 7.24-7.37 (3H, m), 7.43-7.58 (6H, m), 7.68-7.75 (2H, m), 7.98 (1H, d, J=8.8 Hz), 8.04 (1H, d, J=8.3 Hz), 9.10 (1H, d, J=1.4 Hz), 12.17 (1H, s).

Example 137a

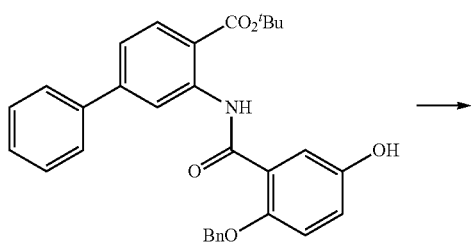

-continued

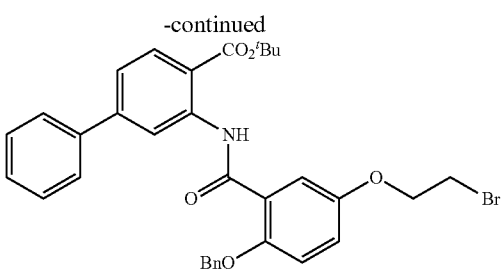

As in Example 136a, the following compound was prepared.

Tert-butyl 2-(2-(benzyloxy)-5-(2-bromoethoxy)benzamido)-4-phenylbenzoate

¹H-NMR (CDCl₃) δ: 1.52 (9H, s), 3.61 (2H, t, J=6.2 Hz), 4.30 (2H, t, J=6.2 Hz), 5.44 (2H, s), 6.90 (1H, d, J=9.0 Hz), 6.96 (1H, dd, J=9.0, 3.2 Hz), 7.26-7.50 (9H, m), 7.69-7.76 (3H, m), 8.06 (1H, d, J=8.3 Hz), 9.26 (1H, d, J=1.7 Hz), 12.50 (1H, s).

Example 138a

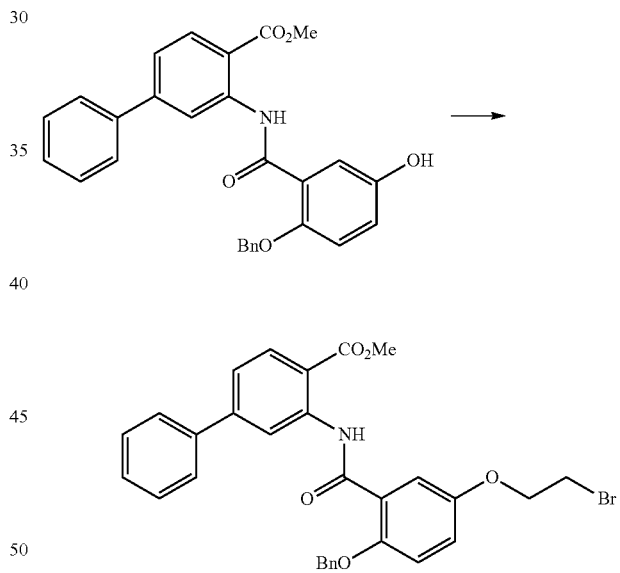

As in Example 136a, the following compound was prepared.

Methyl 2-(2-(benzyloxy)-5-(2-bromoethoxy)benzamido)-4-phenylbenzoate

¹H-NMR (CDCl₃) δ: 3.62 (2H, t, J=6.2 Hz), 3.77 (3H, s), 4.31 (2H, t, J=6.2 Hz), 5.40 (2H, s), 6.95 (1H, d, J=9.0 Hz), 7.00 (1H, dd, J=9.0, 3.2 Hz), 7.23-7.52 (9H, m), 7.69-7.77 (3H, m), 8.08 (1H, d, J=8.3 Hz), 9.25 (1H, d, J=1.7 Hz), 12.33 (1H, s).

Example 139a

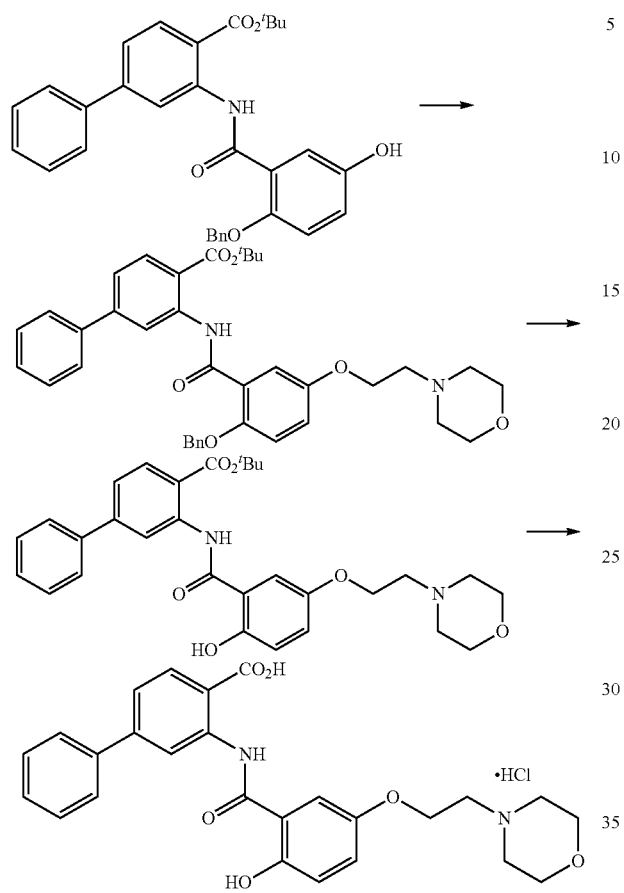

Potassium carbonate (0.075 g), potassium iodide (0.090 g), and N-(2-chloroethyl)morpholine hydrochloride (0.041 g) were added to an N,N-dimethylacetamide (1.8 mL) solution of tert-butyl 2-(2-(benzyloxy)-5-hydroxybenzamido)-4-phenylbenzoate (0.090 g), followed by stirring at 100° C. for 1 hour. The reaction mixture was cooled to room temperature, and then water and ethyl acetate were added thereto. The organic layer was separated, washed with a saturated aqueous solution of sodium bicarbonate, and dried over anhydrous sodium sulfate, and the solvent was evaporated under reduced pressure. The obtained residue was purified by silica gel column chromatography [eluent: 80-25% hexane/ethyl acetate] to obtain 0.058 g of tert-butyl 2-(2-(benzyloxy)-5-(2-(morpholin-4-yl)ethoxy)benzamido)-4-phenylbenzoate as a light yellow solid.

To a solution mixture of the obtained tert-butyl 2-(2-(benzyloxy)-5-(2-(morpholin-4-yl)ethoxy)benzamido)-4-phenylbenzoate (0.058 g) in methanol (1.5 mL) and ethyl acetate (1.5 mL), 10% palladium-carbon (0.058 g) was added, followed by stirring under a hydrogen atmosphere at room temperature for 2 hours. To the reaction mixture, 10% palladium-carbon (0.029 g) was added, followed by stirring under a hydrogen atmosphere at room temperature for 1 hour. Ethyl acetate was added to the reaction mixture. Then, the insoluble substance was removed by filtration, and the solvent was evaporated under reduced pressure. Trifluoroacetic acid (5.0 mL) was added to the obtained residue, followed by stirring at room temperature for 4 hours. The solvent was evaporated under reduced pressure, and ethyl acetate (2.5 mL) and a 4.0 mol/L hydrogen chloride-dioxane solution (0.30 mL) were added to the residue, followed by stirring at room temperature for 2 hours. The solid substance was collected from the reaction mixture by filtration to obtain 0.033 g of 2-(2-hydroxy-5-(2-(morpholin-4-yl)ethoxy)benzamido)-4-phenylbenzoic acid hydrochloride as a white solid.

$^1$H-NMR (CD$_3$OD) δ: 3.15-3.75 (4H, broad), 3.67 (2H, t, J=4.9 Hz), 3.75-4.20 (4H, broad), 4.43 (2H, t, J=4.9 Hz), 6.97 (1H, d, J=9.0 Hz), 7.21 (1H, dd, J=9.0, 3.1 Hz), 7.39-7.46 (1H, m), 7.46-7.55 (4H, m), 7.70-7.76 (2H, m), 8.21 (1H, d, J=8.3 Hz), 9.06 (1H, d, J=2.0 Hz).

Example 140a

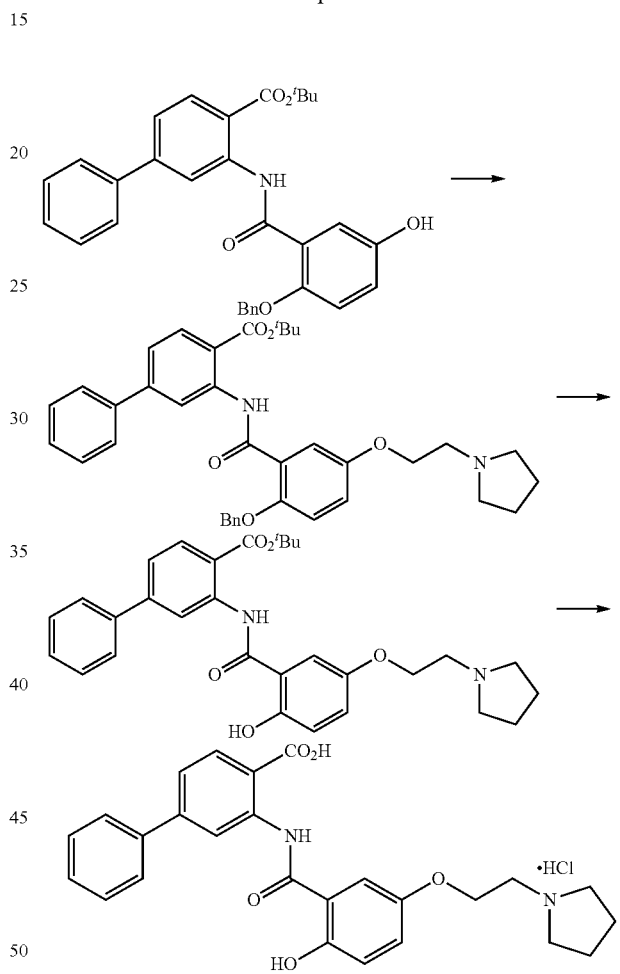

1-(2-Hydroxyethyl)pyrrolidine (0.016 mL), triphenylphosphine (0.038 g), and diisopropyl azodicarboxylate (0.029 mL) were added to a tetrahydrofuran (1.2 mL) solution of tert-butyl 2-(2-(benzyloxy)-5-hydroxybenzamido)-4-phenylbenzoate (0.060 g), followed by stirring at room temperature for 25 minutes. To the reaction mixture, 1-(2-hydroxyethyl)pyrrolidine (0.016 mL), triphenylphosphine (0.038 g), and diisopropyl azodicarboxylate (0.029 mL) were added, followed by stirring at room temperature for 20 minutes. To the reaction mixture, 1-(2-hydroxyethyl)pyrrolidine (0.016 mL), triphenylphosphine (0.038 g), and diisopropyl azodicarboxylate (0.029 mL) were added, followed by stirring at room temperature for 30 minutes. To the reaction mixture, 1-(2-hydroxyethyl)pyrrolidine (0.016 mL), triphenylphosphine (0.038 g), and diisopropyl azodicarboxylate (0.029 mL) were added, followed by stirring at room temperature for 1 hour. The solvent was evaporated under reduced pressure, and the obtained residue was purified by silica gel column chromatography [eluent: 80-0% hexane/ethyl acetate] to obtain 0.071 g of tert-butyl 2-(2-(benzyloxy)-5-(2-(pyrrolidin-1-yl)ethoxy)benzamido)-4-phenylbenzoate.

To a solution mixture of the obtained tert-butyl 2-(2-(benzyloxy)-5-(2-(pyrrolidin-1-yl)ethoxy)benzamido)-4-phenylbenzoate (0.071 g) in methanol (1.5 mL) and ethyl acetate (1.5 mL), 10% palladium-carbon (0.071 g) was added, followed by stirring under a hydrogen atmosphere at room temperature for 2 hours. The insoluble substance was removed by filtration, and the solvent was evaporated under reduced pressure. Trifluoroacetic acid (5.0 mL) was added to the obtained residue, followed by stirring at room temperature for 4 hours. The solvent was evaporated under reduced pressure, and ethyl acetate (2.5 mL) and a 4.0 mol/L hydrogen chloride-dioxane solution (0.30 mL) were added to the residue, followed by stirring at room temperature for 1 hour and 30 minutes. The solid substance was collected from the reaction mixture by filtration to obtain 0.036 g of 2-(2-hydroxy-5-(2-(pyrrolidin-1-yl)ethoxy)benzamido)-4-phenylbenzoic acid hydrochloride as a light brown solid.

$^1$H-NMR (DMSO-$d_6$) δ: 1.82-2.10 (4H, m), 3.05-3.20 (2H, m), 3.52-3.66 (4H, m), 4.31 (2H, t, J=5.0 Hz), 7.01 (1H, d, J=8.9 Hz), 7.16 (1H, dd, J=8.9, 3.2 Hz), 7.43-7.58 (5H, m), 7.69-7.75 (2H, m), 8.09 (1H, d, J=8.3 Hz), 9.04 (1H, d, J=1.7 Hz), 10.10-10.30 (1H, broad), 11.08 (1H, s), 12.32 (1H, s), 13.30-13.55 (1H, broad).

Example 141a

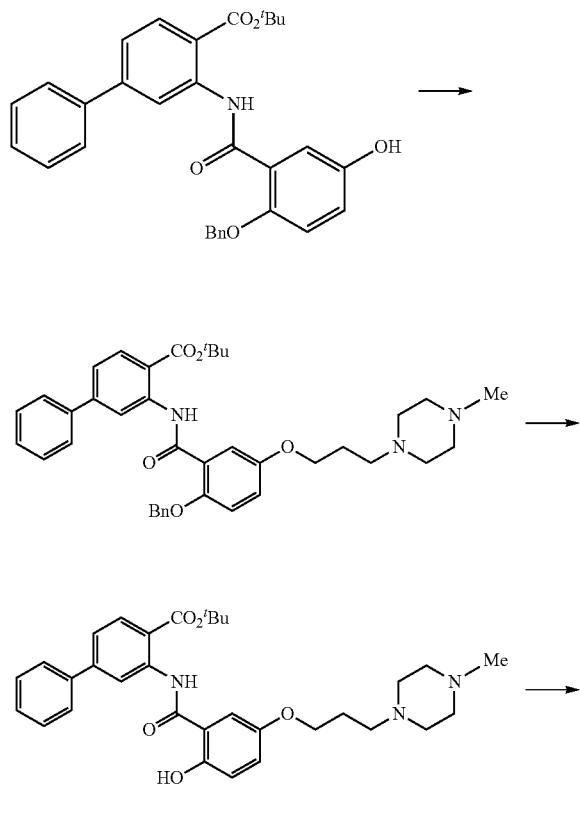

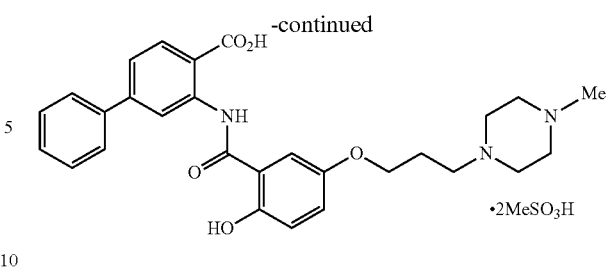

N,N-Dimethylformamide (3.0 mL), potassium carbonate (0.12 g), and 1-(3-bromopropyl)-4-methylpiperazine (0.30 g) were sequentially added to tert-butyl 2-(2-(benzyloxy)-5-hydroxybenzamido)-4-phenylbenzoate (0.15 g), followed by stirring at 100° C. for 1 hour and 20 minutes. Potassium carbonate (0.12 g) was added to the reaction mixture, followed by stirring at 100° C. for 50 minutes. Water and chloroform were added to the reaction mixture. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 100-92% chloroform/methanol] to obtain 0.060 g of tert-butyl 2-(2-(benzyloxy)-5-(3-(4-methylpiperazin-1-yl)propoxy)benzamido)-4-phenylbenzoate.

To a solution mixture of the obtained tert-butyl 2-(2-(benzyloxy)-5-(3-(4-methylpiperazin-1-yl)propoxy)benzamido)-4-phenylbenzoate (0.059 g) in methanol (1.0 mL) and chloroform (1.0 mL), 10% palladium-carbon (0.023 g) was added, followed by stirring under a hydrogen atmosphere at room temperature for 1 hour and 20 minutes. To the reaction mixture, 10% palladium-carbon (0.058 g) was added, followed by stirring under a hydrogen atmosphere at room temperature for 3 hours. Methanol (2.0 mL), chloroform (2.0 mL), and 10% palladium-carbon (0.055 g) were added to the reaction mixture, followed by stirring under a hydrogen atmosphere at room temperature for 2 hours and 50 minutes. To the reaction mixture, 10% palladium-carbon (0.025 g) was added, followed by stirring under a hydrogen atmosphere at room temperature for 4 hours and 30 minutes. The insoluble substance was removed by filtration, and then the solvent was evaporated under reduced pressure. The obtained residue was purified by silica gel column chromatography [eluent: 100-90% chloroform/methanol] to obtain 0.026 g of tert-butyl 2-(2-hydroxy-5-(3-(4-methylpiperazin-1-yl)propoxy)benzamido)-4-phenylbenzoate.

Trifluoroacetic acid (1.0 mL) was added to the obtained tert-butyl 2-(2-hydroxy-5-(3-(4-methylpiperazin-1-yl)propoxy)benzamido)-4-phenylbenzoate (0.024 g), followed by stirring at room temperature for 2 hours. The solvent was evaporated under reduced pressure, and water and methanol were added to the residue. After adjusting the pH to 7.5 with a saturated aqueous solution of sodium bicarbonate, the solid substance was collected by filtration. Ethyl acetate (2.0 mL) and methanesulfonic acid (5.0 μL) were added to the obtained solid substance, and the solvent was evaporated under reduced pressure. Ethyl acetate was added to the obtained residue, and the solid substance was collected by filtration to obtain 0.020 g of 2-(2-hydroxy-5-(3-(4-methylpiperazin-1-yl)propoxy)benzamido)-4-phenylbenzoic acid dimethanesulfonate as a white solid.

$^1$H-NMR (CD$_3$OD) δ: 2.22-2.34 (2H, m), 2.72 (6H, s), 3.02 (3H, s), 3.36-3.90 (10H, m), 4.18 (2H, t, J=5.7 Hz), 6.94 (1H, d, J=9.0 Hz), 7.14 (1H, dd, J=9.0, 3.2 Hz), 7.39-7.54 (5H, m), 7.69-7.77 (2H, m), 8.22 (1H, d, J=8.3 Hz), 9.07 (1H, d, J=1.7 Hz).

Example 142a

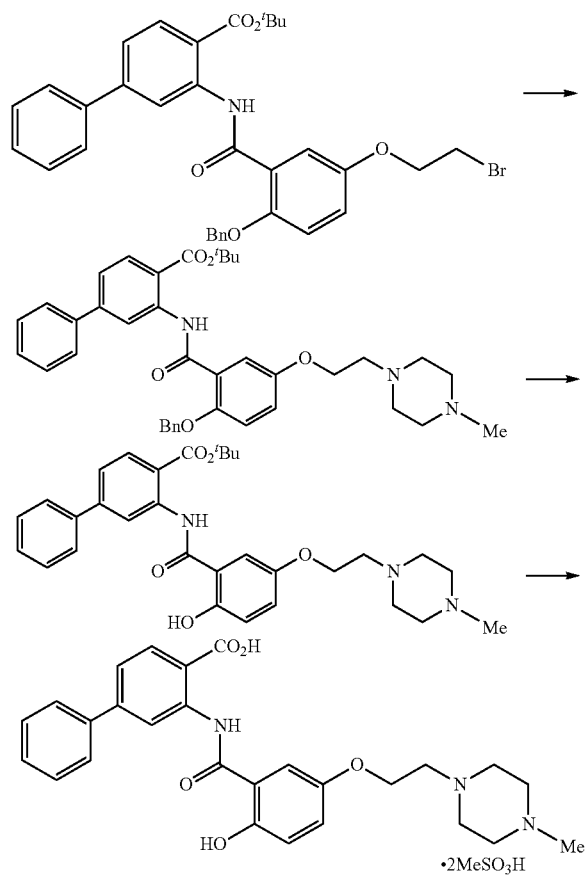

Potassium carbonate (1.0 g) and 1-methylpiperazine (0.83 mL) were added to an acetone (7.5 mL) solution of tert-butyl 2-(2-(benzyloxy)-5-(2-bromoethoxy)benzamido)-4-phenylbenzoate (1.5 g), followed by heating to reflux for 2 hours. The reaction mixture was cooled to room temperature, and potassium carbonate (0.34 g) and 1-methylpiperazine (0.28 mL) were added thereto, followed by heating to reflux for 2 hours. After cooling the reaction mixture to room temperature, the solvent was evaporated under reduced pressure, and water and chloroform were added to the residue. The organic layer was separated, and the solvent was removed under reduced pressure. The obtained residue was purified by silica gel column chromatography [eluent: 100-95% chloroform/methanol] to obtain tert-butyl 2-(2-(benzyloxy)-5-(2-(4-methylpiperazin-1-yl)ethoxy)benzamido)-4-phenylbenzoate.

To a methanol (8.0 mL) solution of the obtained tert-butyl 2-(2-(benzyloxy)-5-(2-(4-methylpiperazin-1-yl)ethoxy)benzamido)-4-phenylbenzoate, 10% palladium-carbon (0.75 g) was added, followed by stirring under a hydrogen atmosphere at room temperature for 5 hours. The insoluble substance was removed by filtration, and then the solvent was evaporated under reduced pressure. The obtained residue was purified by silica gel column chromatography [Kanto Chemical Co., Inc., silica gel 60 (spherical), eluent: 100-90% chloroform/methanol] to obtain 1.2 g of tert-butyl 2-(2-hydroxy-5-(2-(4-methylpiperazin-1-yl)ethoxy)benzamido)-4-phenylbenzoate.

Trifluoroacetic acid (10 mL) was added to the obtained tert-butyl 2-(2-hydroxy-5-(2-(4-methylpiperazin-1-yl)ethoxy)benzamido)-4-phenylbenzoate (1.2 g), followed by stirring at room temperature for 2 hours. The solvent was evaporated under reduced pressure, and a 30% aqueous solution of methanol was added to the residue. After adjusting the pH to 6.7 with a saturated aqueous solution of sodium bicarbonate, the solid substance was collected from the reaction mixture by filtration to obtain 0.86 g of 2-(2-hydroxy-5-(2-(4-methylpiperazin-1-yl)ethoxy)benzamido)-4-phenylbenzoic acid.

Water (1.0 mL), methanesulfonic acid (0.029 mL), and activated carbon (0.020 g) were added to a solution mixture of the obtained 2-(2-hydroxy-5-(2-(4-methylpiperazin-1-yl)ethoxy)benzamido)-4-phenylbenzoic acid (0.10 g) in tetrahydrofuran (2.0 mL) and ethanol (1.0 mL), followed by stirring at room temperature for 30 minutes. The insoluble substance was removed by filtration, and then the solvent was evaporated under reduced pressure. Acetone was added to the obtained residue, and the solid substance was collected by filtration to obtain 0.095 g of 2-(2-hydroxy-5-(2-(4-methylpiperazin-1-yl)ethoxy)benzamido)-4-phenylbenzoic acid dimethanesulfonate as a white solid.

$^1$H-NMR (DMSO-$d_6$) δ: 2.36 (6H, s), 2.87 (3H, s), 2.99-4.05 (10H, m), 4.22-4.34 (2H, m), 7.00 (1H, d, J=9.0 Hz), 7.14 (1H, dd, J=8.7, 3.1 Hz), 7.43-7.59 (5H, m), 7.68-7.76 (2H, m), 8.10 (1H, d, J=8.3 Hz), 9.04 (1H, d, J=1.5 Hz), 10.99-11.10 (1H, broad), 12.32 (1H, s).

Example 143a

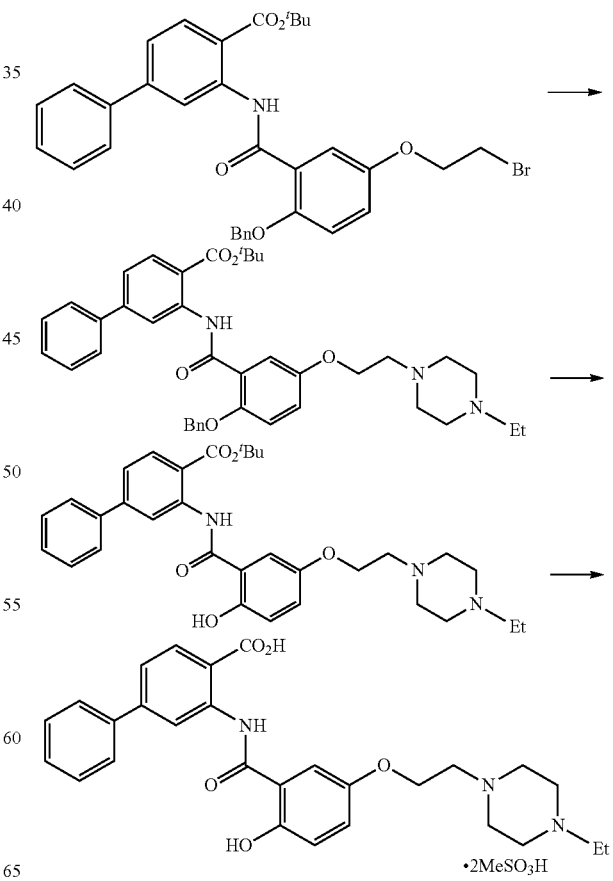

Potassium carbonate (1.5 g) and 1-ethylpiperazine (1.0 mL) were added to an acetone (8.0 mL) solution of tert-butyl 2-(2-(benzyloxy)-5-(2-bromoethoxy)benzamido)-4-phenylbenzoate (1.6 g), followed by heating to reflux for 5 hours. After cooling the reaction mixture to room temperature, the insoluble substance was removed by filtration, and the solvent was evaporated under reduced pressure. The obtained residue was purified by silica gel column chromatography [eluent: 100-90% chloroform/methanol] to obtain tert-butyl 2-(2-(benzyloxy)-5-(2-(4-ethylpiperazin-1-yl)ethoxy)benzamido)-4-phenylbenzoate as a yellow oily substance.

To a methanol (20 mL) solution of the obtained tert-butyl 2-(2-(benzyloxy)-5-(2-(4-ethylpiperazin-1-yl)ethoxy)benzamido)-4-phenylbenzoate, 10% palladium-carbon (1.7 g) was added, followed by stirring under a hydrogen atmosphere at room temperature for 2 hours and 30 minutes. To the reaction mixture, 10% palladium-carbon (0.70 g) was added, followed by stirring under a hydrogen atmosphere at room temperature for 3 hours. The insoluble substance was removed by filtration, and then the solvent was evaporated under reduced pressure to obtain tert-butyl 2-(5-(2-(4-ethylpiperazin-1-yl)ethoxy)-2-hydroxybenzamido)-4-phenylbenzoate as a white solid.

Trifluoroacetic acid (10 mL) was added to the obtained tert-butyl 2-(5-(2-(4-ethylpiperazin-1-yl)ethoxy)-2-hydroxybenzamido)-4-phenylbenzoate, followed by stirring at room temperature for 3 hours. The solvent was evaporated under reduced pressure, and a 30% aqueous solution of methanol (16 mL) was added to the residue. After adjusting the pH to 6.5 with a saturated aqueous solution of sodium bicarbonate, the solid substance was collected from the reaction mixture by filtration to obtain 1.1 g of 2-(5-(2-(4-ethylpiperazin-1-yl)ethoxy)-2-hydroxybenzamido)-4-phenylbenzoic acid as a white solid.

Methanesulfonic acid (0.027 mL), tetrahydrofuran (3.0 mL), and activated carbon (0.020 g) were added to an ethanol (2.0 mL) suspension of the obtained 2-(5-(2-(4-ethylpiperazin-1-yl)ethoxy)-2-hydroxybenzamido)-4-phenylbenzoic acid (0.10 g), followed by stirring at room temperature for 30 minutes. The insoluble substance was removed by filtration, and the solvent was evaporated under reduced pressure. Acetone was added to the obtained residue, and the solid substance was collected by filtration to obtain 0.090 g of 2-(5-(2-(4-ethylpiperazin-1-yl)ethoxy)-2-hydroxybenzamido)-4-phenylbenzoic acid dimethanesulfonate as a white solid.

$^1$H-NMR (DMSO-$d_6$) δ: 1.23 (3H, t, J=7.3 Hz), 2.36 (6H, s), 3.02-3.78 (12H, m), 4.21-4.34 (2H, m), 7.00 (1H, d, J=9.0 Hz), 7.14 (1H, dd, J=9.0, 3.2 Hz), 7.42-7.59 (5H, m), 7.68-7.76 (2H, m), 8.10 (1H, d, J=8.3 Hz), 9.01-9.07 (1H, m), 10.99-11.09 (1H, broad), 12.32 (1H, s).

Example 144a

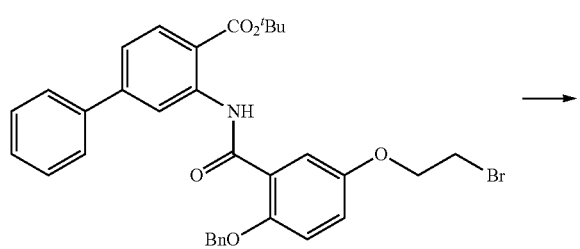

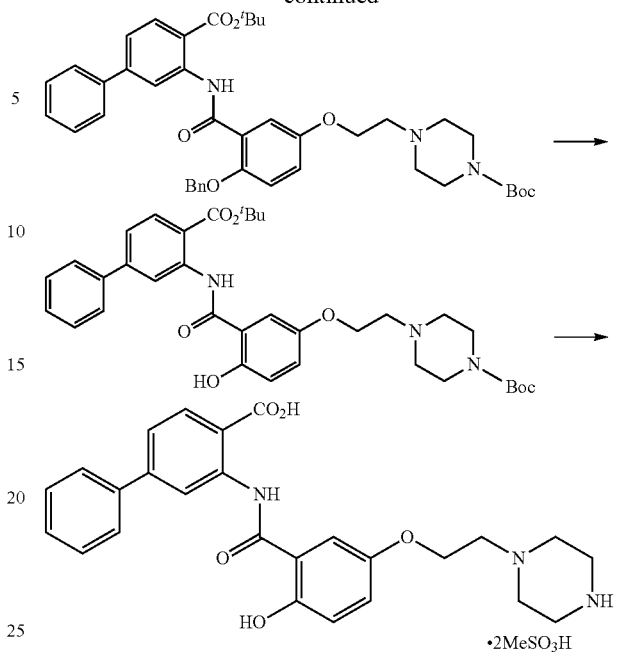

Tert-butyl 2-(2-(benzyloxy)-5-(2-bromoethoxy)benzamido)-4-phenylbenzoate (0.030 g), potassium carbonate (0.10 g), and 1-(tert-butoxycarbonyl)piperidine (0.093 g) were added to N,N-dimethylformamide (1 mL), followed by stirring at 90 to 100° C. for 3 hours. The reaction mixture was cooled to room temperature, and then water and chloroform were added thereto. The organic layer was separated and dried over anhydrous sodium sulfate, and the solvent was evaporated under reduced pressure. Tetrahydrofuran (1.5 mL), water (0.1 mL), 10% palladium-carbon (0.060 g), sodium formate (7.5 mg), and acetic acid (7.5 mg) were added to the obtained residue, followed by stirring at 60° C. for 2 hours. The insoluble substance was removed by filtration, and the solvent was evaporated under reduced pressure. A saturated aqueous solution of sodium bicarbonate and chloroform were added to the residue. The organic layer was separated and dried over anhydrous sodium sulfate, and the solvent was evaporated under reduced pressure. The obtained residue was purified by silica gel column chromatography [eluent: 80-50% hexane/ethyl acetate] to obtain 0.025 g of tert-butyl 4424342-(tert-butoxycarbonyl)-5-phenylphenylcarbamoyl)-4-hydroxyphenoxy)ethyl)piperidine-1-carboxylate.

Trifluoroacetic acid (2 mL) was added to the obtained tert-butyl 4-(2-(3-(2-(tert-butoxycarbonyl)-5-phenylphenylcarbamoyl)-4-hydroxyphenoxy)ethyl)piperidine-1-carboxylate (0.025 g), followed by stirring at room temperature for 2 hours. The solvent was evaporated under reduced pressure, and water added to the residue. After adjusting the pH to 6.3 with a saturated aqueous solution of sodium bicarbonate, the solid substance was collected by filtration. Methanol and methanesulfonic acid were added to the obtained solid substance, and then ethyl acetate was added thereto. The solid substance was collected by filtration to obtain 0.010 g of 2-(2-hydroxy-5-(2-(piperazin-1-yl)ethoxy)benzamido)-4-phenylbenzoic acid dimethanesulfonate as a white solid.

$^1$H-NMR (DMSO-$d_6$) δ: 2.31 (6H, s), 2.80-3.80 (10H, m), 4.16-4.32 (2H, m), 6.99 (1H, d, J=8.8 Hz), 7.08-7.17 (1H, m), 7.43-7.59 (5H, m), 7.68-7.76 (2H, m), 8.09 (1H, d, J=8.5 Hz), 9.01-9.07 (1H, m), 11.03 (1H, s), 12.32 (1H, s).

Example 145a

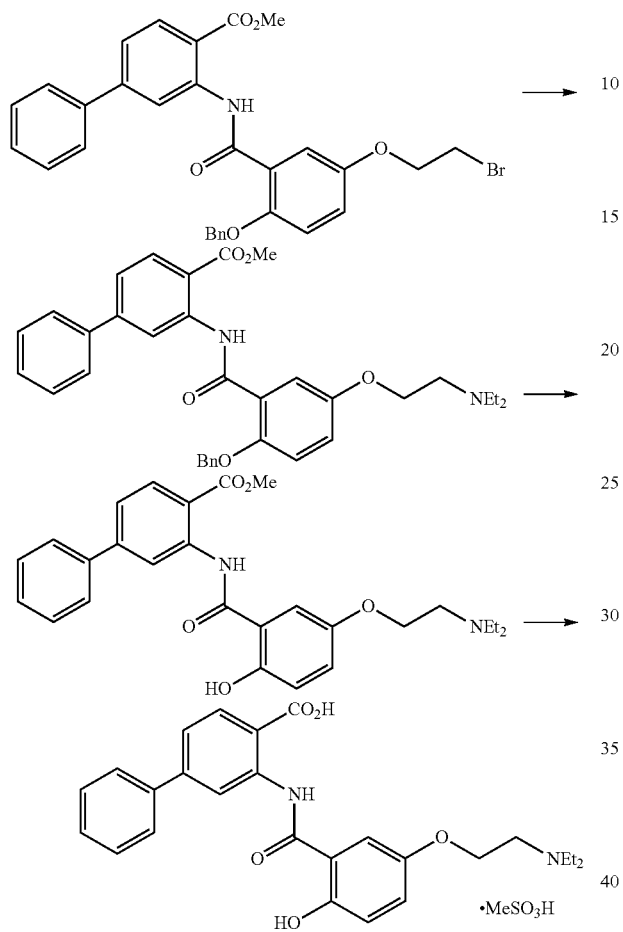

Potassium carbonate (0.15 g) and diethylamine (0.11 mL) were added to an acetone (2.0 mL) solution of methyl 2-(2-(benzyloxy)-5-(2-bromoethoxy)benzamido)-4-phenylbenzoate (0.20 g), followed by heating to reflux for 4 hour and 30 minutes. The reaction mixture was cooled to room temperature, and then potassium carbonate (0.049 g) and diethylamine (0.037 mL) were added thereto, followed by heating to reflux for 1 hour. The reaction mixture was cooled to room temperature, and then potassium carbonate (0.049 g) and diethylamine (0.037 mL) were added thereto, followed by heating to reflux for 1 hour and 15 minutes. The reaction mixture was cooled to room temperature, and then potassium carbonate (0.049 g) and diethylamine (0.037 mL) were added thereto, followed by heating to reflux for 5 hours and 30 minutes. The reaction mixture was cooled to room temperature, and water, a saturated aqueous solution of sodium bicarbonate, and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 100-97% chloroform/methanol] to obtain 0.15 g of methyl 2-(2-(benzyloxy)-5-(2-(diethylamino)ethoxy)benzamido)-4-phenylbenzoate.

To a solution mixture of the obtained methyl 2-(2-(benzyloxy)-5-(2-(diethylamino)ethoxy)benzamido)-4-phenylbenzoate (0.15 g) in methanol (3.0 mL) and ethyl acetate (3.0 mL), 10% palladium-carbon (0.030 g) was added, followed by stirring under a hydrogen atmosphere at room temperature for 3 hours. The insoluble substance was removed by filtration, and then the solvent was evaporated under reduced pressure. The obtained residue was purified by silica gel column chromatography [eluent: 100-96% chloroform/methanol] to obtain 0.087 g of methyl 2-(5-(2-(diethylamino)ethoxy)-2-hydroxybenzamido)-4-phenylbenzoate as a white solid.

Dioxane (3.0 mL) and a 4 mol/L aqueous solution of sodium hydroxide (0.19 mL) were added to the obtained methyl 2-(5-(2-(diethylamino)ethoxy)-2-hydroxybenzamido)-4-phenylbenzoate (0.087 g), followed by stirring at room temperature for 2 hours and 30 minutes and then at 50 to 55° C. for 2 hours. The reaction mixture was cooled to room temperature and adjusted to a pH of 6.9 with methanesulfonic acid, and the solvent was evaporated under reduced pressure. Water was added to the obtained residue, and the solid substance was collected by filtration to obtain 0.079 g of 2-(5-(2-(diethylamino)ethoxy)-2-hydroxybenzamido)-4-phenylbenzoic acid.

Ethanol (3.0 mL) and methanesulfonic acid (0.011 mL) were added to the obtained 2-(5-(2-(diethylamino)ethoxy)-2-hydroxybenzamido)-4-phenylbenzoic acid (0.079 g), followed by stirring at room temperature for 1 hour and 30 minutes. The solid substance was collected from the reaction mixture by filtration to obtain 0.049 g of 2-(5-(2-(diethylamino)ethoxy)-2-hydroxybenzamido)-4-phenylbenzoic acid methanesulfonate as a white solid.

$^1$H-NMR (CD$_3$OD) δ: 1.39 (6H, t, J=7.3 Hz), 2.69 (3H, s), 3.32-3.41 (4H, m), 3.62 (2H, t, J=4.9 Hz), 4.37 (2H, t, J=4.9 Hz), 6.96 (1H, d, J=9.0 Hz), 7.19 (1H, dd, J=9.0, 2.9 Hz), 7.39-7.45 (1H, m), 7.45-7.53 (4H, m), 7.69-7.75 (2H, m), 8.20 (1H, d, J=8.3 Hz), 9.05 (1H, d, J=1.7 Hz).

Example 146a

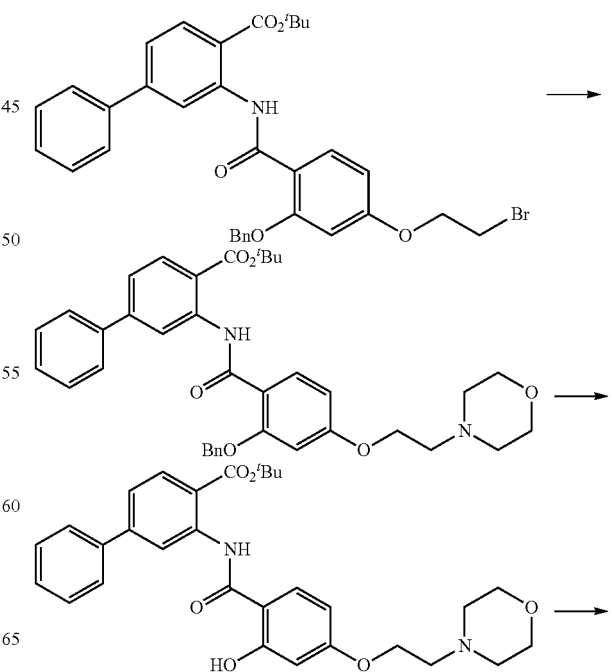

-continued

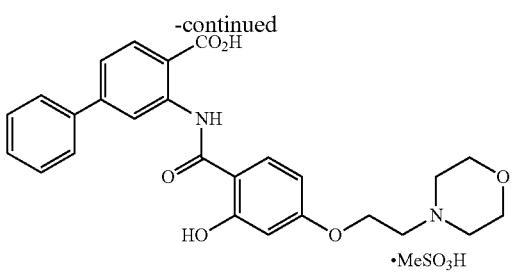
·MeSO₃H

Potassium carbonate (0.065 g) and morpholine (0.041 mL) were added to an acetone (3.0 mL) solution of tert-butyl 2-(2-(benzyloxy)-4-(2-bromoethoxy)benzamido)-4-phenylbenzoate (0.094 g), followed by heating to reflux for 45 minutes. The reaction mixture was cooled to room temperature, and potassium carbonate (0.022 g) and morpholine (0.014 mL) were added thereto, followed by heating to reflux for 2 hours and 30 minutes. The reaction mixture was cooled to room temperature, and then water, a saturated aqueous solution of sodium bicarbonate, and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 100-91% chloroform/methanol] to obtain 0.059 g of tert-butyl 2-(2-(benzyloxy)-4-(2-(morpholin-4-yl)ethoxy)benzamido)-4-phenylbenzoate.

To a solution mixture of the obtained tert-butyl 2-(2-(benzyloxy)-4-(2-(morpholin-4-yl)ethoxy)benzamido)-4-phenylbenzoate (0.059 g) in methanol (2.0 mL) and ethyl acetate (2.0 mL), 10% palladium-carbon (0.012 g) was added, followed by stirring under a hydrogen atmosphere at room temperature for 3 hours. The insoluble substance was removed by filtration, and the solvent was evaporated under reduced pressure. Diisopropyl ether was added to the obtained residue, and the solid substance was collected by filtration. Trifluoroacetic acid (4.0 mL) was added to the obtained solid substance, followed by stirring at room temperature for 3 hours. Toluene was added to the reaction mixture, and the solvent was evaporated under reduced pressure. Diisopropyl ether was added to the obtained residue, and the solid substance was collected by filtration. Ethanol (4.0 mL) was added to the obtained solid substance. After adjusting the pH to 7.7 with a 1 mol/L aqueous solution of sodium hydroxide, the solid substance was collected by filtration to obtain 0.011 g of 2-(2-hydroxy-4-(2-(morpholin-4-yl)ethoxy)benzamido)-4-phenylbenzoic acid as a white solid.

Ethanol (2.0 mL) and methanesulfonic acid (0.010 mL) were added to the obtained 2-(2-hydroxy-4-(2-(morpholin-4-yl)ethoxy)benzamido)-4-phenylbenzoic acid (0.011 g), followed by stirring at room temperature for 3 hours and 30 minutes. The solvent was evaporated under reduced pressure, and ethanol was added to the obtained residue. The solid substance was collected by filtration to obtain 6.1 mg of 2-(2-hydroxy-4-(2-(morpholin-4-yl)ethoxy)benzamido)-4-phenylbenzoic acid methanesulfonate as a white solid.

¹H-NMR (DMSO-d₆) δ: 2.31 (3H, s), 3.10-4.10 (10H, m), 4.41 (2H, t, J=4.6 Hz), 6.61 (1H, d, J=2.4 Hz), 6.68 (1H, dd, J=9.0, 2.4 Hz), 7.42-7.58 (4H, m), 7.68-7.76 (2H, m), 7.90 (1H, d, J=9.0 Hz), 8.10 (1H, d, J=8.3 Hz), 8.98 (1H, d, J=1.7 Hz), 11.87 (1H, s), 12.25 (1H, s).

Example 147a

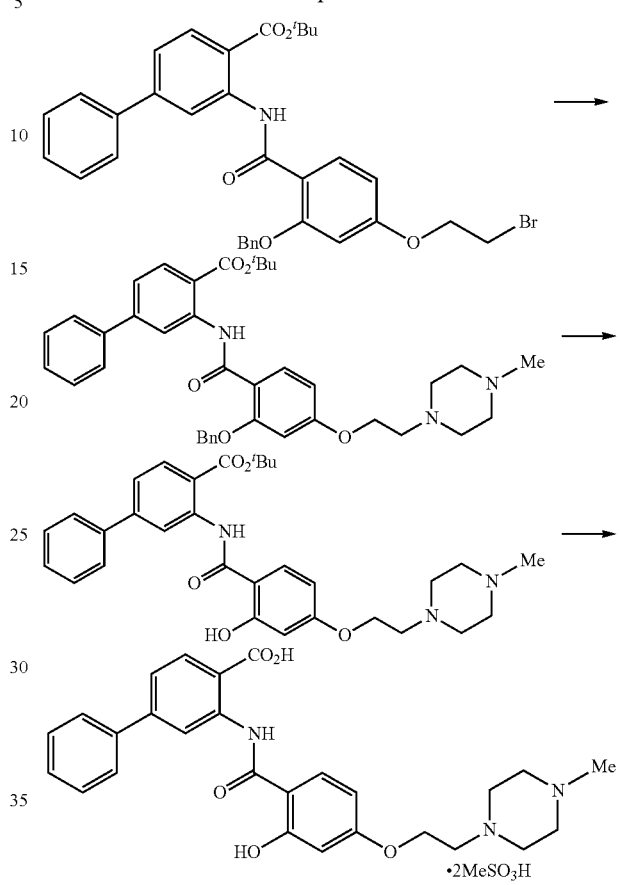
·2MeSO₃H

As in Example 146a, the following compound was prepared.

2-(2-Hydroxy-4-(2-(4-methylpiperazin-1-yl)ethoxy)benzamido)-4-phenylbenzoic acid dimethanesulfonate ¹H-NMR (DMSO-d₆) δ: 2.35 (6H, s), 2.86 (3H, s), 3.12-3.70 (10H, m), 4.24-4.38 (2H, m), 6.59 (1H, d, J=2.0 Hz), 6.62-6.70 (1H, m), 7.42-7.58 (4H, m), 7.68-7.76 (2H, m), 7.88 (1H, d, J=8.8 Hz), 8.10 (1H, d, J=8.3 Hz), 8.98 (1H, d, J=1.7 Hz), 11.86 (1H, s), 12.24 (1H, s).

Example 148a

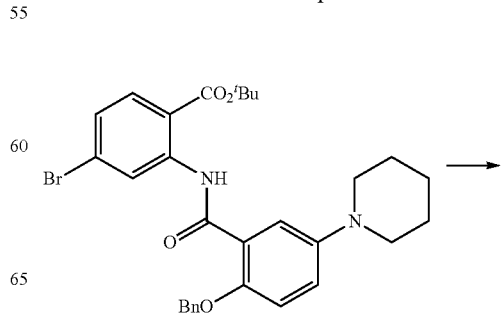

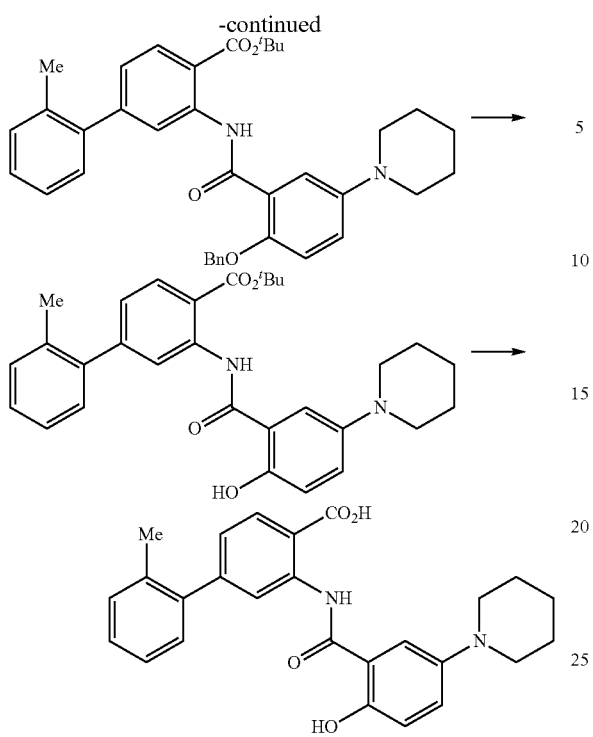

Water (0.60 mL), 2-methylphenylboronic acid (0.029 g), sodium carbonate (0.047 g), and bis(triphenylphosphine)palladium(II) dichloride (2.5 mg) were added to an ethylene glycol dimethyl ether (2.0 mL) solution of tert-butyl 2-(2-(benzyloxy)-5-(piperidin-1-yl)benzamido)-4-bromobenzoate (0.10 g), followed by heating to reflux under a nitrogen atmosphere for 2 hours. The reaction mixture was cooled to room temperature, and water and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 99-91% hexane/ethyl acetate] to obtain 0.10 g of tert-butyl 2-(2-(benzyloxy)-5-(piperidin-1-yl)benzamido)-4-(2-methylphenyl)benzoate.

To a solution mixture of the obtained tert-butyl 2-(2-(benzyloxy)-5-(piperidin-1-yl)benzamido)-4-(2-methylphenyl)benzoate (0.10 g) in methanol (2.0 mL) and ethyl acetate (2.0 mL), 10% palladium-carbon (0.020 g) was added, followed by stirring under a hydrogen atmosphere at room temperature for 2 hours and 45 minutes. The insoluble substance was removed by filtration, and then the solvent was evaporated under reduced pressure. The obtained residue was purified by silica gel column chromatography [eluent: 99-91% hexane/ethyl acetate] to obtain 0.063 g of tert-butyl 2-(2-hydroxy-5-(piperidin-1-yl)benzamido)-4-(2-methylphenyl)benzoate as a yellow solid.

A trifluoroacetic acid (3.0 mL) solution of the obtained tert-butyl 2-(2-hydroxy-5-(piperidin-1-yl)benzamido)-4-(2-methylphenyl)benzoate (0.063 g) was stirred at room temperature for 1 hour. The solvent was evaporated under reduced pressure, and water and ethanol were added thereto. After adjusting the pH to 5.5 with a saturated aqueous solution of sodium bicarbonate, the solid substance was collected by filtration to obtain 0.048 g of 2-(2-hydroxy-5-(piperidin-1-yl)benzamido)-4-(2-methylphenyl)benzoic acid as a yellow solid.

$^1$H-NMR (DMSO-$d_6$) δ: 1.46-1.56 (2H, m), 1.60-1.70 (4H, m), 2.29 (3H, s), 3.00-3.08 (4H, m), 6.91 (1H, d, J=9.0 Hz), 7.14-7.22 (2H, m), 7.24-7.38 (4H, m), 7.39-7.44 (1H, m), 8.08 (1H, d, J=8.1 Hz), 8.66 (1H, d, J=1.5 Hz), 10.91-11.08 (1H, broad), 12.24-12.40 (1H, broad).

Examples 149a to 155a

As in Example 148a, the compounds shown in Table 17a were prepared.

TABLE 17a

| Example No. | R$^3$ |
|---|---|
| 149a | 3-Me-phenyl |
| 150a | 4-Me-phenyl |
| 151a | 2-F-phenyl |
| 152a | 3-F-phenyl |
| 153a | 4-F-phenyl |
| 154a | 3-MeO-phenyl |
| 155a | 4-MeO-phenyl |

2-(2-Hydroxy-5-(piperidin-1-yl)benzamido)-4-(3-methylphenyl)benzoic acid $^1$H-NMR (CDCl$_3$) δ: 1.57-1.70 (2H, m), 1.91-2.05 (4H, m), 2.42 (3H, s), 3.30-3.43 (4H, m), 7.05 (1H, d, J=9.0 Hz), 7.19 (1H, d, J=7.6 Hz), 7.29-7.39 (3H, m), 7.41-7.47 (2H, m), 8.07 (1H, d, J=2.4 Hz), 8.11 (1H, d, J=8.3 Hz), 8.97 (1H, d, J=1.7 Hz).

2-(2-Hydroxy-5-(piperidin-1-yl)benzamido)-4-(4-methylphenyl)benzoic acid $^1$H-NMR (DMSO-d$_6$) δ: 1.47-1.56 (2H, m), 1.61-1.71 (4H, m), 2.38 (3H, s), 2.99-3.08 (4H, m), 6.91 (1H, d, J=8.9 Hz), 7.17 (1H, dd, J=8.9, 2.5 Hz), 7.34 (2H, d, J=7.9 Hz), 7.43 (1H, d, J=2.5 Hz), 7.46-7.52 (1H, m), 7.63 (2H, d, J=7.9 Hz), 8.08 (1H, d, J=8.3 Hz), 9.00 (1H, s), 10.95-11.09 (1H, broad), 12.29-12.43 (1H, broad).

4-(2-Fluorophenyl)-2-(2-hydroxy-5-(piperidin-1-yl)benzamido)benzoic acid $^1$H-NMR (DMSO-d$_6$) δ: 1.46-1.55 (2H, m), 1.60-1.69 (4H, m), 2.99-3.06 (4H, m), 6.90 (1H, d, J=9.0 Hz), 7.17 (1H, dd, J=9.0, 2.8 Hz), 7.33-7.44 (4H, m), 7.46-7.55 (1H, m), 7.56-7.64 (1H, m), 8.11 (1H, d, J=8.3 Hz), 8.90 (1H, s), 10.93-11.10 (1H, broad), 12.36-12.54 (1H, broad).

4-(3-Fluorophenyl)-2-(2-hydroxy-5-(piperidin-1-yl)benzamido)benzoic acid $^1$H-NMR (DMSO-d$_6$) δ: 1.47-1.56 (2H, m), 1.61-1.70 (4H, m), 3.00-3.07 (4H, m), 6.91 (1H, d, J=8.9 Hz), 7.17 (1H, dd, J=8.9, 2.9 Hz), 7.26-7.34 (1H, m), 7.44 (1H, d, J=2.9 Hz), 7.52-7.63 (4H, m), 8.10 (1H, d, J=8.3 Hz), 9.01 (1H, d, J=1.7 Hz), 10.92-11.12 (1H, broad), 12.28-12.48 (1H, broad).

4-(4-Fluorophenyl)-2-(2-hydroxy-5-(piperidin-1-yl)benzamido)benzoic acid $^1$H-NMR (DMSO-d$_6$) δ: 1.46-1.56 (2H, m), 1.60-1.71 (4H, m), 2.99-3.08 (4H, m), 6.91 (1H, d, J=8.9 Hz), 7.17 (1H, dd, J=8.9, 2.8 Hz), 7.33-7.41 (2H, m), 7.43 (1H, d, J=2.8 Hz), 7.46-7.53 (1H, m), 7.73-7.82 (2H, m), 8.09 (1H, d, J=8.3 Hz), 8.96-9.02 (1H, m), 10.96-11.08 (1H, broad), 12.31-12.46 (1H, broad).

2-(2-Hydroxy-5-(piperidin-1-yl)benzamido)-4-(3-methoxyphenyl)benzoic acid $^1$H-NMR (DMSO-d$_6$) δ: 1.47-1.56 (2H, m), 1.61-1.70 (4H, m), 3.00-3.06 (4H, m), 3.85 (3H, s), 6.91 (1H, d, J=9.0 Hz), 7.01-7.07 (1H, m), 7.17 (1H, dd, J=9.0, 2.9 Hz), 7.22-7.25 (1H, m), 7.26-7.32 (1H, m), 7.41-7.49 (2H, m), 7.51 (1H, dd, J=8.3, 1.7 Hz), 8.09 (1H, d, J=8.3 Hz), 8.98 (1H, d, J=1.7 Hz), 10.92-11.12 (1H, broad), 12.30-12.50 (1H, broad).

2-(2-Hydroxy-5-(piperidin-1-yl)benzamido)-4-(4-methoxyphenyl)benzoic acid $^1$H-NMR (DMSO-d$_6$) δ: 1.47-1.55 (2H, m), 1.61-1.69 (4H, m), 3.00-3.06 (4H, m), 3.83 (3H, s), 6.91 (1H, d, J=9.0 Hz), 7.07-7.12 (2H, m), 7.17 (1H, dd, J=9.0, 3.0 Hz), 7.42 (1H, d, J=3.0 Hz), 7.47 (1H, dd, J=8.3, 2.0 Hz), 7.66-7.71 (2H, m), 8.07 (1H, d, J=8.3 Hz), 8.97 (1H, d, J=2.0 Hz), 10.95-11.12 (1H, broad), 12.30-12.50 (1H, broad).

Example 156a

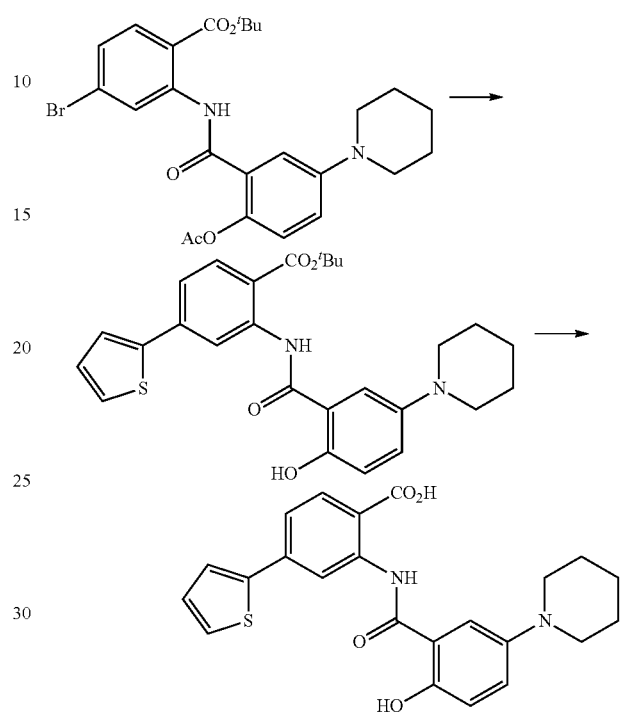

Water (0.60 mL), thiophene-2-boronic acid (0.024 g), sodium carbonate (0.041 g), and bis(triphenylphosphine)palladium(II) dichloride (2.2 mg) were added to an ethylene glycol dimethyl ether (2.0 mL) solution of tert-butyl 2-(2-acetoxy-5-(piperidin-1-yl)benzamido)-4-bromobenzoate (0.080 g), followed by heating to reflux under a nitrogen atmosphere for 1 hour and 30 minutes. The reaction mixture was cooled to room temperature, and a 10% aqueous solution of citric acid and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 95-85% hexane/ethyl acetate] to obtain 0.027 g of tert-butyl 2-(2-hydroxy-5-(piperidin-1-yl)benzamido)-4-(thiophen-2-yl)benzoate as a yellow solid.

A 1 mol/L aqueous solution of sodium hydroxide (0.17 mL) was added to a solution mixture of the obtained tert-butyl 2-(2-hydroxy-5-(piperidin-1-yl)benzamido)-4-(thiophen-2-yl)benzoate (0.027 g) in dioxane (2.0 mL) and methanol (2.0 mL), followed by stirring at 50 to 55° C. for 1 hour. The reaction mixture was cooled to room temperature, and a 1 mol/L aqueous solution of sodium hydroxide (0.11 mL) was added thereto, followed by stirring at 50 to 55° C. for 2 hours. The reaction mixture was cooled to room temperature, and a 1 mol/L aqueous solution of sodium hydroxide (0.056 mL) was added thereto, followed by stirring at 55° C. for 1 hour. The reaction mixture was cooled to room temperature, and a 1 mol/L aqueous solution of sodium hydroxide (0.056 mL) was added thereto, followed by stirring at 60° C. for 2 hours. The reaction mixture was cooled to room temperature and then adjusted to a pH of 7.7 with a 10% aqueous solution of citric acid, and water and ethyl acetate were added thereto. The organic layer was separated, and the aqueous layer was extracted with chloroform. The organic layer and the extract were combined, and the resulting mixture was dried over anhydrous magnesium sulfate. The solvent was evaporated under reduced pressure. The obtained residue was purified by silica gel column chromatography [eluent: 100-80% chloroform/methanol] to obtain 0.011 g of 2-(2-hydroxy-5-(piperidin-1-yl)benzamido)-4-(thiophen-2-yl)benzoic acid as an orange solid.

$^1$H-NMR (DMSO-$d_6$) δ 1.47-1.56 (2H, m), 1.61-1.70 (4H, m), 2.99-3.07 (4H, m), 6.90 (1H, d, J=8.8 Hz), 7.16 (1H, dd, J=8.8, 2.9 Hz), 7.21 (1H, dd, J=5.1, 3.7 Hz), 7.42 (1H, d, J=2.9 Hz), 7.52 (1H, dd, J=8.4, 2.0 Hz), 7.64 (1H, dd, J=3.7, 1.2 Hz), 7.69 (1H, dd, J=5.1, 1.2 Hz), 8.05 (1H, d, J=8.4 Hz), 9.04 (1H, d, J=2.0 Hz), 10.94-11.13 (1H, broad).

Example 157a

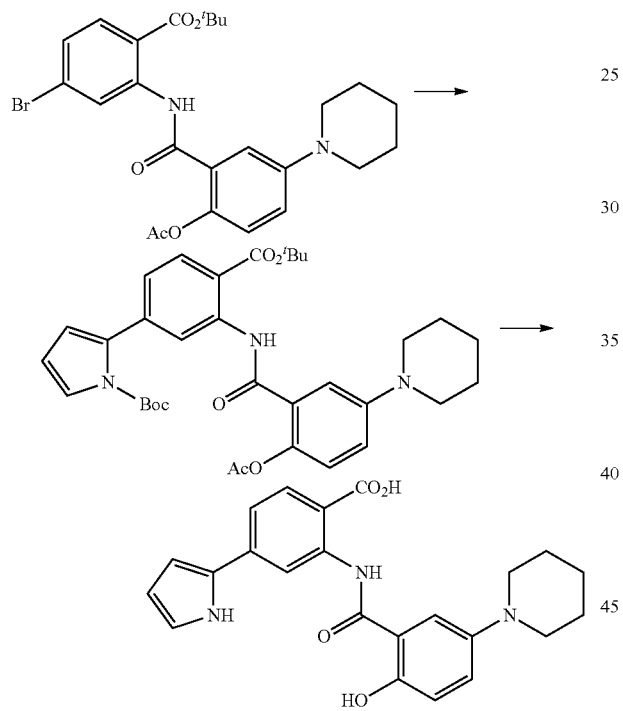

Water (0.60 mL), 1-(tert-butoxycarbonyl)-1H-pyrrole-2-boronic acid (0.024 g), sodium carbonate (0.041 g), and bis(triphenylphosphine)palladium(II) dichloride (2.2 mg) were added to an ethylene glycol dimethyl ether (2.0 mL) solution of tert-butyl 2-(2-acetoxy-5-(piperidin-1-yl)benzamido)-4-bromobenzoate (0.080 g), followed by heating to reflux under a nitrogen atmosphere for 1 hour. The reaction mixture was cooled to room temperature, and sodium carbonate (0.016 g) was added thereto, followed by heating to reflux under a nitrogen atmosphere for 1 hour. The reaction mixture was cooled to room temperature, and a 10% aqueous solution of citric acid and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 95-80% hexane/ethyl acetate] to obtain tert-butyl 2-(2-acetoxy-5-(piperidin-1-yl)benzamido)-4-(1-(tert-butoxycarbonyl)-1H-pyrrol-2-yl)benzoate.

Methanol (2.0 mL) and a 4 mol/L aqueous solution of sodium hydroxide (0.19 mL) were added to a dioxane (2.0 mL) solution of the obtained tert-butyl 2-(2-acetoxy-5-(piperidin-1-yl)benzamido)-4-(1-(tert-butoxycarbonyl)-1H-pyrrol-2-yl)benzoate, followed by stirring at 55° C. for 1 hour. The reaction mixture was cooled to room temperature, and then a 4 mol/L aqueous solution of sodium hydroxide (0.077 mL) was added thereto, followed by stirring at 60° C. for 2 hours. The reaction mixture was cooled to room temperature and then adjusted to a pH of 7.8 with a 10% aqueous solution of citric acid, and water and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 100-91% chloroform/methanol] to obtain 8 mg of 2-(2-hydroxy-5-(piperidin-1-yl)benzamido)-4-(1H-pyrrol-2-yl)benzoic acid as a yellow solid.

$^1$H-NMR (DMSO-$d_6$) δ: 1.47-1.56 (2H, m), 1.61-1.70 (4H, m), 3.00-3.06 (4H, m), 6.16-6.22 (1H, m), 6.60-6.65 (1H, m), 6.89 (1H, d, J=9.0 Hz), 6.92-6.97 (1H, m), 7.17 (1H, dd, J=9.0, 2.8 Hz), 7.39-7.47 (1H, m), 7.41 (1H, d, J=2.8 Hz), 7.99 (1H, d, J=8.5 Hz), 8.85 (1H, d, J=1.5 Hz), 11.11-11.27 (1H, broad), 11.49-11.55 (1H, broad).

Example 158a

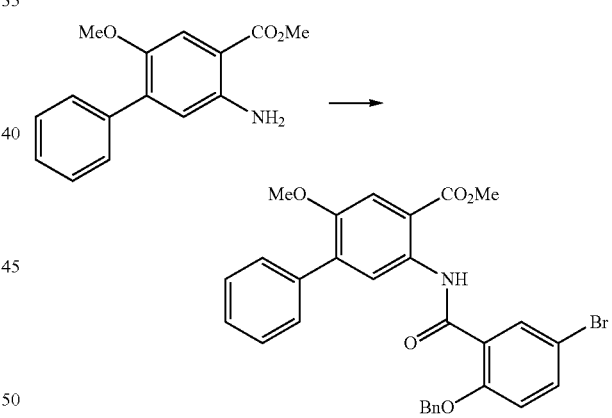

Under ice-cooling, oxalyl chloride (0.026 mL) was added to a solution mixture of 2-(benzyloxy)-5-bromobenzoic acid (0.074 g) in methylene chloride (2.0 mL) and N,N-dimethylformamide (0.010 mL), followed by stirring at room temperature for 30 minutes. The solvent was evaporated under reduced pressure, and methylene chloride (2.0 mL) was added to the residue. The resulting mixture was added to a solution mixture of methyl 2-amino-5-methoxy-4-phenylbenzoate (0.052 g) in pyridine (0.025 mL) and methylene chloride (1.0 mL), followed by stirring at room temperature for 3 hours. The reaction mixture was purified by silica gel column chromatography [eluent: 95-85% hexane/ethyl acetate] to obtain 0.045 g of methyl 2-(2-(benzyloxy)-5-bromobenzamido)-5-methoxy-4-phenylbenzoate as a white solid.

¹H-NMR (CDCl₃) δ: 3.80 (3H, s), 3.85 (3H, s), 5.45 (2H, s), 6.87 (1H, d, J=8.8 Hz), 7.27-7.40 (4H, m), 7.40-7.47 (5H, m), 7.57 (1H, s), 7.62-7.66 (2H, m), 8.28 (1H, d, J=2.7 Hz), 8.92 (1H, s), 12.08 (1H, s).

Example 159a

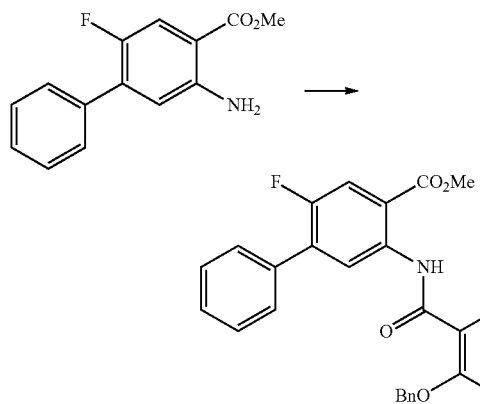

As in Example 158a, the following compound was prepared.

Methyl 2-(2-(benzyloxy)-5-bromobenzamido)-5-fluoro-4-phenylbenzoate

¹H-NMR (CDCl₃) δ: 3.79 (3H, s), 5.46 (2H, s), 6.88 (1H, d, J=8.8 Hz), 7.22-7.37 (4H, m), 7.38-7.51 (5H, m), 7.64-7.72 (2H, m), 7.80 (1H, d, J=11.2 Hz), 8.25-8.31 (1H, m), 9.11 (1H, d, J=7.1 Hz), 12.15-12.24 (1H, broad).

Example 160a

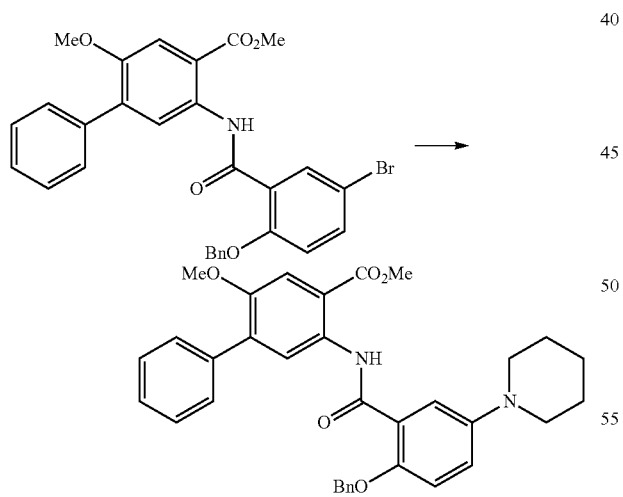

Piperidine (0.012 mL), cesium carbonate (0.054 g), tris(dibenzylideneacetone)dipalladium(0) (2.3 mg), 2-dicyclohexylphosphino-2',4',6'-triisopropylbiphenyl (5.9 mg), and palladium(II) acetate (1.1 mg) were added to a toluene (2.0 mL) solution of methyl 2-(2-(benzyloxy)-5-bromobenzamido)-5-methoxy-4-phenylbenzoate (0.045 g), followed by heating to reflux under a nitrogen atmosphere for 2 hours and 20 minutes. The reaction mixture was cooled to room temperature, and ethyl acetate and water were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 95-85% hexane/ethyl acetate] to obtain 0.034 g of methyl 2-(2-(benzyloxy)-5-(piperidin-1-yl)benzamido)-5-methoxy-4-phenylbenzoate as a yellow solid.

¹H-NMR (CDCl₃) δ: 1.49-1.60 (2H, m), 1.64-1.74 (4H, m), 3.04-3.14 (4H, m), 3.76 (3H, s), 3.84 (3H, s), 5.36 (2H, s), 6.91 (1H, d, J=9.0 Hz), 6.99 (1H, dd, J=9.0, 2.9 Hz), 7.22-7.39 (4H, m), 7.39-7.46 (4H, m), 7.56 (1H, s), 7.61-7.68 (2H, m), 7.76 (1H, d, J=3.2 Hz), 8.92 (1H, s), 12.04 (1H, s).

Example 161a

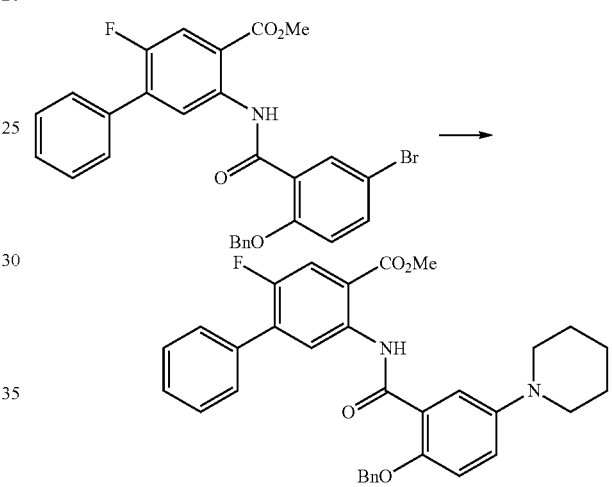

As in Example 160a, the following compound was prepared.

Methyl 2-(2-(benzyloxy)-5-(piperidin-1-yl)benzamido)-5-fluoro-4-phenylbenzoate

¹H-NMR (CDCl₃) δ: 1.49-1.59 (2H, m), 1.65-1.74 (4H, m), 3.05-3.13 (4H, m), 3.75 (3H, s), 5.37 (2H, m), 6.92 (1H, d, J=8.9 Hz), 7.00 (1H, dd, J=8.9, 3.2 Hz), 7.23-7.34 (3H, m), 7.37-7.50 (5H, m), 7.64-7.72 (2H, m), 7.73-7.81 (2H, m), 9.12 (1H, d, J=7.3 Hz), 12.15 (1H, s).

Example 162a

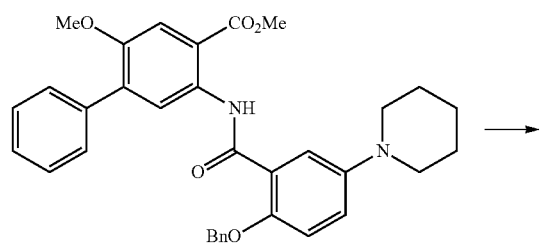

-continued

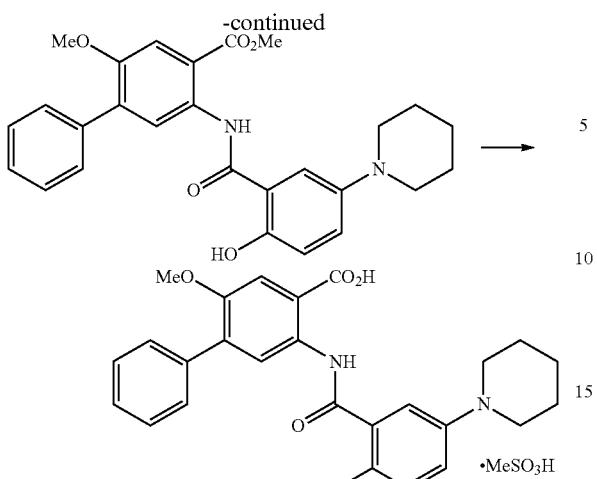

To a solution mixture of methyl 2-(2-(benzyloxy)-5-(piperidin-1-yl)benzamido)-5-methoxy-4-phenylbenzoate (0.034 g) in methanol (2.5 mL) and ethyl acetate (2.5 mL), 10% palladium-carbon (6.8 mg) was added, followed by stirring under a hydrogen atmosphere at room temperature for 2 hours. The insoluble substance was removed by filtration, and the solvent was evaporated under reduced pressure. Hexane and diisopropyl ether were added to the obtained residue, and the solid substance was collected by filtration to obtain 0.020 g of methyl 2-(2-hydroxy-5-(piperidin-1-yl)benzamido)-5-methoxy-4-phenylbenzoate as a yellow solid.

Dioxane (3.0 mL) and a 1 mol/L aqueous solution of sodium hydroxide (0.13 mL) were added to the obtained methyl 2-(2-hydroxy-5-(piperidin-1-yl)benzamido)-5-methoxy-4-phenylbenzoate (0.020 g), followed by stirring at 50 to 55° C. for 1 hour. The reaction mixture was cooled to room temperature, and a 10% aqueous solution of citric acid and ethyl acetate were added thereto. The organic layer was separated, washed with a saturated aqueous solution of sodium chloride, and dried over anhydrous magnesium sulfate, and the solvent was evaporated under reduced pressure. Ethanol (2.0 mL) and methanesulfonic acid (0.010 mL) were added to the obtained residue, followed by stirring at room temperature for 10 minutes. Then, the solid substance was collected by filtration to obtain 0.012 g of 2-(2-hydroxy-5-(piperidin-1-yl)benzamido)-5-methoxy-4-phenylbenzoic acid methanesulfonate as a light brown solid.

$^1$H-NMR (CD$_3$OD) δ: 1.70-2.20 (6H, m), 2.70 (3H, s), 3.60-3.74 (4H, m), 3.86 (3H, s), 7.17 (1H, d, J=9.0 Hz), 7.34-7.50 (3H, m), 7.54-7.64 (2H, m), 7.68-7.75 (1H, m), 7.77 (1H, s), 8.18 (1H, d, J=2.9 Hz), 8.68 (1H, s).

Example 163a

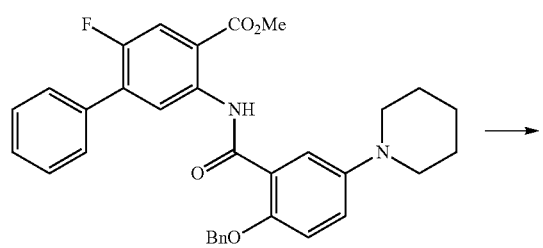

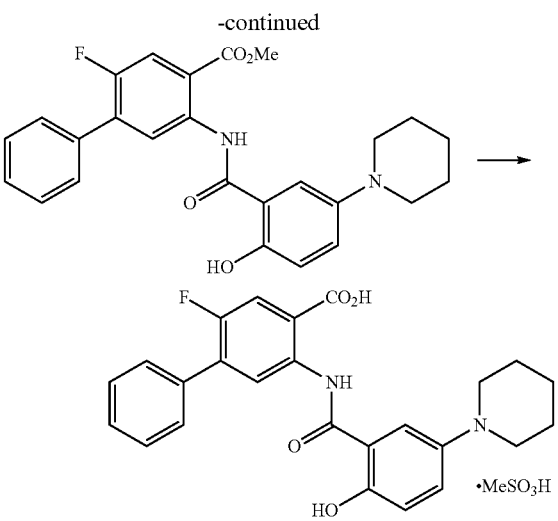

As in Example 162a, the following compound was prepared.

5-Fluoro-2-(2-(hydroxy-5-(piperidin-1-yl)benzamido)-4-phenylbenzoic acid methanesulfonate $^1$H-NMR (CD$_3$OD) δ: 1.74-1.85 (2H, m), 1.97-2.07 (4H, m), 2.69 (3H, s), 3.57-3.65 (4H, m), 7.15 (1H, d, J=9.0 Hz), 7.42-7.47 (1H, m), 7.47-7.54 (2H, m), 7.61-7.66 (2H, m), 7.68 (1H, dd, J=9.0, 3.2 Hz), 7.91 (1H, d, J=11.2 Hz), 8.15 (1H, d, J=3.2 Hz), 8.92 (1H, d, J=7.6 Hz).

Example 164a

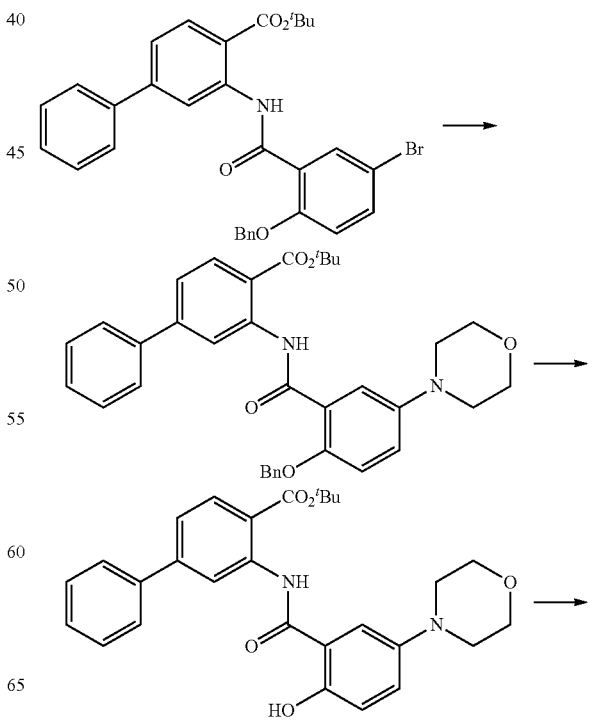

-continued

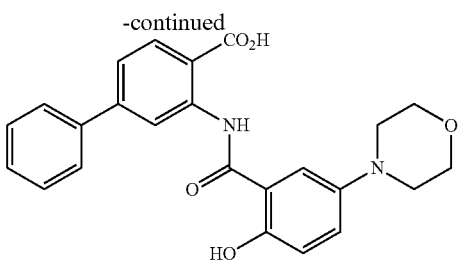

Morpholine (0.014 mL), cesium carbonate (0.070 g), tris(dibenzylideneacetone)dipalladium(0) (1.0 mg), 2-dicyclohexylphosphino-2',4',6'-triisopropylbiphenyl (2.6 mg), and palladium(II) acetate (0.5 mg) were added to a toluene (0.90 mL) solution of tert-butyl 2-(2-(benzyloxy)-5-bromobenzamido)-4-phenylbenzoate (0.060 g), followed by heating to reflux under a nitrogen atmosphere for 2 hours and 30 minutes. The reaction mixture was cooled to room temperature, and then morpholine (4.7 μL), cesium carbonate (0.035 g), tris(dibenzylideneacetone)dipalladium(0) (1.0 mg), 2-dicyclohexylphosphino-2',4',6'-triisopropylbiphenyl (2.6 mg), and palladium(II) acetate (0.5 mg) were added thereto, followed by heating to reflux under a nitrogen atmosphere for 2 hours and 30 minutes. The reaction mixture was cooled to room temperature, and a 10% aqueous solution of citric acid and ethyl acetate were added thereto. The insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 100-60% hexane/ethyl acetate] to obtain 0.060 g of tert-butyl-2-(2-(benzyloxy)-5-(morpholin-4-yl)benzamido)-4-phenylbenzoate as a light yellow solid.

To a solution mixture of the obtained tert-butyl 2-(2-(benzyloxy)-5-(morpholin-4-yl)benzamido)-4-phenylbenzoate (0.060 g) in ethyl acetate (1.5 mL) and methanol (1.5 mL), 10% palladium-carbon (0.030 g) was added, followed by stirring under a hydrogen atmosphere at room temperature for 3 hours and 30 minutes. Ethyl acetate was added to the reaction mixture. The insoluble substance was removed by filtration, and the solvent was evaporated under reduced pressure. Diisopropyl ether was added to the obtained residue. The solid substance was collected by filtration to obtain 0.036 g of tert-butyl 2-(2-hydroxy-5-(morpholin-4-yl)benzamido)-4-phenylbenzoate as a yellow solid.

Trifluoroacetic acid (3 mL) was added to the obtained tert-butyl 2-(2-hydroxy-5-(morpholin-4-yl)benzamido)-4-phenylbenzoate (0.036 g), followed by stirring at room temperature for 3 hours. The solvent was evaporated under reduced pressure, and water and 2-propanol were added to the obtained residue. After adjusting the pH to 6.0 with a saturated aqueous solution of sodium bicarbonate, the solid substance was collected by filtration to obtain 0.027 g of 2-(2-hydroxy-5-(morpholin-4-yl)benzamido)-4-phenylbenzoic acid as a yellow solid.

$^1$H-NMR (DMSO-$d_6$) δ: 2.99-3.08 (4H, m), 3.71-3.80 (4H, m), 6.94 (1H, d, J=9.0 Hz), 7.18 (1H, dd, J=9.0, 3.0 Hz), 7.40-7.58 (5H, m), 7.70-7.77 (2H, m), 8.10 (1H, d, J=8.3 Hz), 9.02 (1H, d, J=1.7 Hz), 10.99 (1H, s), 12.30-12.41 (1H, broad).

Examples 165a and 166a

As in Example 80a, the compounds shown in Table 18a were prepared.

TABLE 18a

| Example No. | R$^7$ |
|---|---|
| 165a | Me on piperidine N-methyl ·HCl |
| 166a | N-methyl piperidine with Me ·HCl |

2-(2-Hydroxy-5-(2-methylpiperidin-1-yl)benzamido)-4-phenylbenzoic acid hydrochloride $^1$H-NMR (DMSO-$d_6$) δ: 1.00 (3H, d, J=6.4 Hz), 1.62-2.15 (6H, m), 3.39-3.70 (2H, m), 3.72-3.87 (1H, m), 7.21 (1H, d, J=8.6 Hz), 7.42-7.50 (1H, m), 7.50-7.58 (3H, m), 7.70-7.76 (2H, m), 7.86-7.98 (1H, m), 8.10 (1H, d, J=8.1 Hz), 8.34-8.45 (1H, m), 9.07 (1H, d, J=1.7 Hz), 11.66-11.86 (1H, broad), 11.94-12.11 (1H, broad), 12.37 (1H, s), 13.30-13.56 (1H, broad).

2-(2-Hydroxy-5-(3-methylpiperidin-1-yl)benzamido)-4-phenylbenzoic acid hydrochloride $^1$H-NMR (DMSO-$d_6$) δ: 0.94 (3H, d, J=6.6 Hz), 1.16-1.34 (1H, m), 1.74-2.27 (4H, m), 3.03-3.60 (4H, m), 7.17 (1H, d, J=8.8 Hz), 7.43-7.50 (1H, m), 7.51-7.59 (3H, m), 7.68-7.75 (2H, m), 7.77-7.88 (1H, broad), 8.11 (1H, d, J=8.0 Hz), 8.17-8.40 (1H, broad), 9.07 (1H, d, J=1.7 Hz), 11.76-12.09 (1H, broad), 12.36 (1H, s).

$^1$H-NMR (DMSO-$d_6$-$D_2O$) δ: 0.97 (3H, d, J=6.6 Hz), 1.19-1.34 (1H, m), 1.76-2.16 (4H, m), 3.13-3.25 (1H, m), 3.35-3.60 (3H, m), 7.20 (1H, d, J=8.8 Hz), 7.45-7.63 (4H, m), 7.70-7.80 (3H, m), 8.13 (1H, d, J=8.1 Hz), 8.20 (1H, d, J=2.9 Hz), 9.01 (1H, d, J=1.5 Hz).

Examples 167a to 169a

As in Example 87a, the compounds shown in Table 19a were prepared.

TABLE 19a

| Example No. | R⁷ |
|---|---|
| 167a | ![3-hydroxy-1-methylpiperidine·HCl] |
| 168a | ![4-(hydroxymethyl)-1-methylpiperidine·HCl] |
| 169a | ![4-(2-hydroxyethyl)-1-methylpiperidine·HCl] |

2-(2-Hydroxy-5-(3-hydroxypiperidin-1-yl)benzamido)-4-phenylbenzoic acid hydrochloride $^1$H-NMR (CD$_3$OD) δ: 1.80-2.01 (3H, m), 2.31-2.47 (1H, m), 3.45-3.62 (2H, m), 3.67-3.76 (2H, m), 4.19-4.26 (1H, m), 7.18 (1H, d, J=9.0 Hz), 7.39-7.45 (1H, m), 7.47-7.53 (3H, m), 7.70-7.78 (3H, m), 8.19-8.23 (2H, m), 9.05 (1H, d, J=1.7 Hz).

2-(2-Hydroxy-5-(4-(hydroxymethyl)piperidin-1-yl)benzamido)-4-phenylbenzoic acid hydrochloride $^1$H-NMR (CD$_3$OD) δ: 1.73-1.87 (2H, m), 1.90-2.01 (1H, m), 2.10-2.19 (2H, m), 3.56 (2H, d, J=5.8 Hz), 3.63-3.79 (4H, m), 7.18 (1H, d, J=9.0 Hz), 7.40-7.45 (1H, m), 7.47-7.53 (3H, m), 7.70-7.75 (2H, m), 7.76 (1H, dd, J=9.0, 3.1 Hz), 8.21 (1H, d, J=3.1 Hz), 8.21 (1H, d, J=8.3 Hz), 9.05 (1H, d, J=1.7 Hz).

2-(2-Hydroxy-5-(4-(2-hydroxyethyl)piperidin-1-yl)benzamido)-4-phenylbenzoic acid hydrochloride $^1$H-NMR (CD$_3$OD) δ: 1.59-1.66 (2H, m), 1.68-1.83 (2H, m), 1.90-2.03 (1H, m), 2.10-2.20 (2H, m), 3.60-3.76 (6H, m), 7.17 (1H, d, J=9.0 Hz), 7.39-7.45 (1H, m), 7.47-7.53 (3H, m), 7.70-7.75 (2H, m), 7.76 (1H, dd, J=9.0, 2.9 Hz), 8.18-8.23 (2H, m), 9.05 (1H, d, J=1.7 Hz).

Example 170a

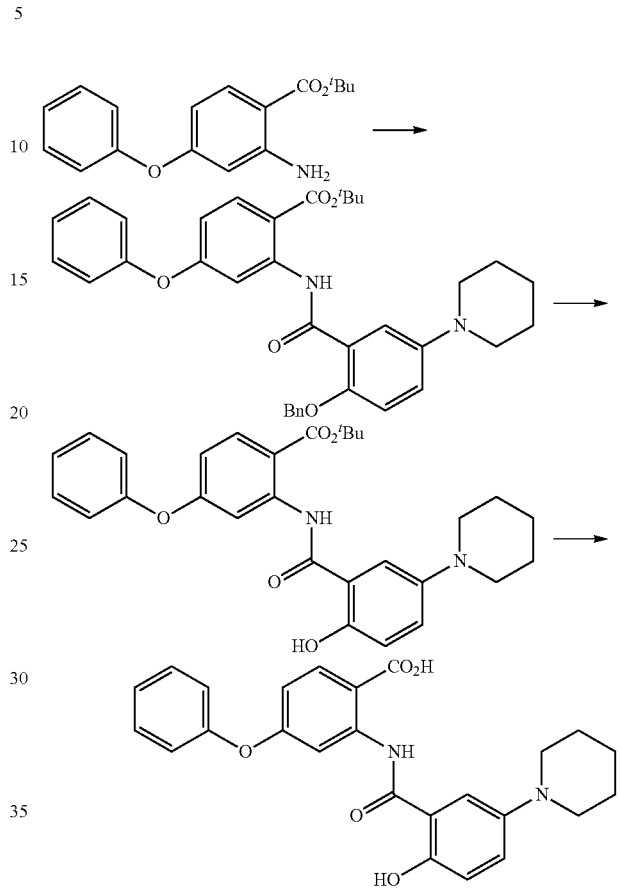

N,N-Dimethylformamide (2.1 μL) and oxalyl chloride (0.032 mL) were sequentially added to a methylene chloride (1.4 mL) solution of 2-(benzyloxy)-5-(piperidin-1-yl)benzoic acid (0.084 g), followed by stirring at room temperature for 1 hour. The solvent was evaporated under reduced pressure, and toluene was added to the obtained residue. The solvent was evaporated under reduced pressure, and methylene chloride (1.0 mL) was added to the obtained residue. The resulting mixture was added to a solution mixture of tert-butyl 2-amino-4-phenoxybenzoate (0.070 g) in pyridine (0.070 mL) and methylene chloride (1.4 mL) under ice-cooling, followed by stirring at room temperature for 1 hour. A 10% aqueous solution of citric acid was added to the reaction mixture, and the organic layer was separated and dried over anhydrous magnesium sulfate, and the solvent was evaporated under reduced pressure. The obtained residue was purified by silica gel column chromatography [Kanto Chemical Co., Inc., silica gel 60 (spherical), eluent: 90-80% hexane/ethyl acetate] to obtain 0.093 g of tert-butyl 2-(2-(benzyloxy)-5-(piperidin-1-yl)benzamido)-4-phenoxybenzoate as a yellow oily substance.

To a solution mixture of the obtained tert-butyl 2-(2-(benzyloxy)-5-(piperidin-1-yl)benzamido)-4-phenoxybenzoate (0.093 g) in ethyl acetate (1.5 mL) and methanol (1.5 mL), 10% palladium-carbon (0.047 g) was added, followed by stirring under a hydrogen atmosphere at room temperature for 2 hours. Chloroform was added to the reaction mixture. The insoluble substance was removed by filtration, and the solvent was evaporated under reduced pressure. The obtained residue was purified by silica gel column chromatography [Kanto Chemical Co., Inc., silica gel 60 (spherical), eluent: 80-70% hexane/ethyl acetate] to obtain 0.067 g of tert-butyl 2-(2-hydroxy-5-(piperidin-1-yl)benzamido)-4-phenoxybenzoate as a yellow solid.

Trifluoroacetic acid (5 mL) was added to the obtained tert-butyl 2-(2-hydroxy-5-(piperidin-1-yl)benzamido)-4-phenoxybenzoate (0.067 g), followed by stirring at room temperature for 3 hours. The solvent was evaporated under reduced pressure, and water and 2-propanol were added to the residue. After adjusting the pH to 6.0 with a saturated aqueous solution of sodium bicarbonate, the solid substance was collected by filtration to obtain 0.053 g of 2-(2-hydroxy-5-(piperidin-1-yl)benzamido)-4-phenoxybenzoic acid as a light yellow solid.

$^1$H-NMR (DMSO-d$_6$) δ: 1.46-1.54 (2H, m), 1.59-1.68 (4H, m), 2.97-3.04 (4H, m), 6.76 (1H, dd, J=9.0, 2.6 Hz), 6.88 (1H, d, J=8.8 Hz), 7.11-7.20 (3H, m), 7.23-7.30 (1H, m), 7.32 (1H, d, J=2.7 Hz), 7.44-7.52 (2H, m), 8.04 (1H, d, J=9.0 Hz), 8.39 (1H, d, J=2.6 Hz), 10.79-10.94 (1H, broad), 12.40-12.58 (1H, broad).

Example 171a

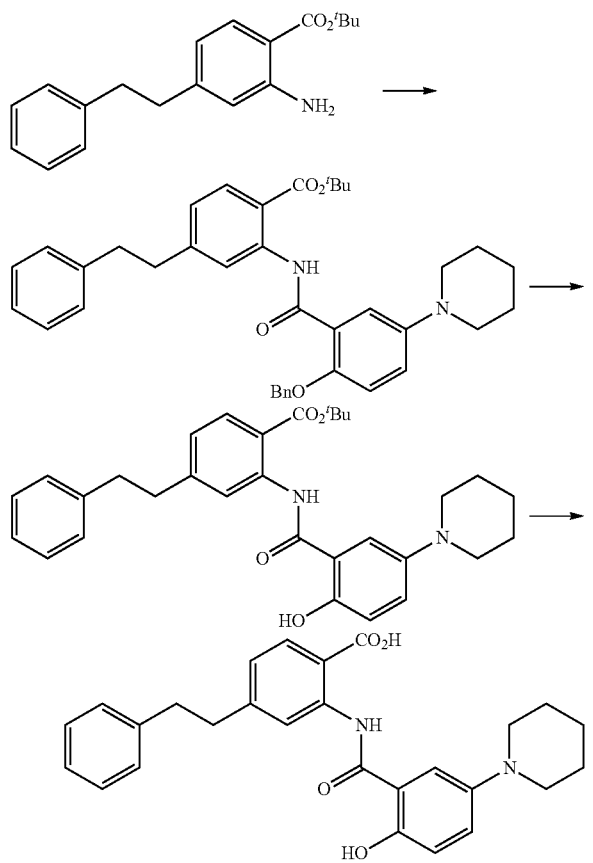

As in Example 170a, the following compound was prepared.

2-(2-Hydroxy-5-(piperidin-1-yl)benzamido)-4-phenoxybenzoic acid $^1$H-NMR (DMSO-d$_6$) δ: 1.46-1.56 (2H, m), 1.59-1.70 (4H, m), 2.88-3.06 (8H, m), 6.89 (1H, d, J=9.0 Hz), 7.07 (1H, dd, J=8.2, 1.5 Hz), 7.13-7.22 (2H, m), 7.23-7.32 (4H, m), 7.36-7.40 (1H, m), 7.92 (1H, d, J=8.4 Hz), 8.57 (1H, d, J=1.5 Hz), 10.96-11.12 (1H, broad), 12.22-12.40 (1H, broad).

Example 172a

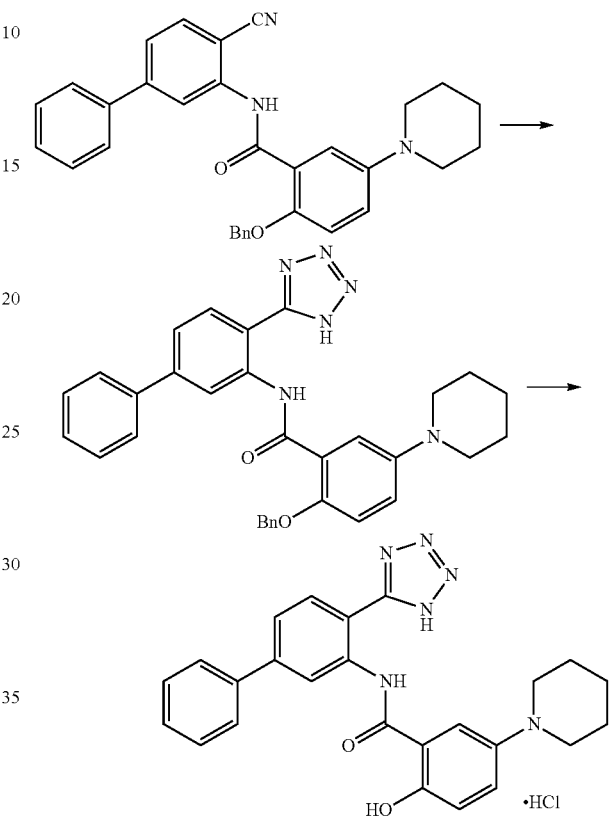

Sodium azide (0.065 g) and ammonium chloride (0.053 g) were added to an N,N-dimethylformamide (2.5 mL) suspension of 2-(benzyloxy)-N-(4-cyanobiphenyl-3-yl)-5-(piperidin-1-yl)benzamide (0.25 g), followed by stirring at 110° C. for 2 hours. The reaction mixture was cooled to room temperature, and then sodium azide (0.065 g) and ammonium chloride (0.053 g) were added thereto, followed by stirring at 110° C. for 1 hour and 30 minutes. The reaction mixture was cooled to room temperature, and then sodium azide (0.032 g) and ammonium chloride (0.026 g) were added thereto, followed by stirring at 110° C. for 1 hour and 30 minutes. The reaction mixture was cooled to room temperature, and then sodium azide (0.032 g) and ammonium chloride (0.026 g) were added thereto, followed by stirring at 110° C. for 1 hour. The reaction mixture was cooled to room temperature, and then chloroform and water were added thereto. The organic layer was separated and dried over anhydrous magnesium sulfate, and the solvent was evaporated under reduced pressure. The obtained residue was purified by silica gel column chromatography [eluent: 100-90% chloroform/methanol] and then purified by silica gel column chromatography [Kanto Chemical Co., Inc., silica gel 60 (spherical), eluent: 100-93% chloroform/methanol] to obtain 0.18 g of 2-(benzyloxy)-N-(5-phenyl-2-(1H-tetrazol-5-yl)phenyl)-5-(piperidin-1-yl)benzamide as a brown solid.

To a solution mixture of the obtained 2-(benzyloxy)-N-(5-phenyl-2-(1H-tetrazol-5-yl)phenyl)-5-(piperidin-1-yl)benzamide (0.095 g) in ethyl acetate (6.0 mL) and methanol (3.0 mL), 10% palladium-carbon (0.050 g) was added, followed by stirring under a hydrogen atmosphere at room temperature for 1 hour. To the reaction mixture, 10% palladium-carbon (0.050 g) was added, followed by stirring under a hydrogen atmosphere at room temperature for 2 hours. The insoluble substance was removed by filtration, and then the solvent was evaporated under reduced pressure. Ethyl acetate (2.0 mL) and a 4.0 mol/L hydrogen chloride-ethyl acetate solution (2.0 mL) were added to the obtained residue, followed by stirring at room temperature for 10 minutes. The solid substance was collected from the reaction mixture by filtration to obtain 0.016 g of 2-hydroxy-N-(5-phenyl-2-(1H-tetrazol-5-yl)phenyl)-5-(piperidin-1-yl)benzamide hydrochloride as a brownish red solid.

$^1$H-NMR (DMSO-$d_6$) δ: 1.56-1.74 (2H, m), 1.87-2.01 (4H, m), 3.24-3.70 (4H, m), 7.18 (1H, d, J=9.0 Hz), 7.43-7.50 (1H, m), 7.50-7.60 (2H, m), 7.72 (1H, dd, J=8.2, 1.8 Hz), 7.75-7.89 (3H, m), 8.05 (1H, d, J=8.0 Hz), 8.26-8.37 (1H, m), 8.86 (1H, d, J=2.0 Hz), 11.67 (1H, s), 11.82-12.09 (1H, broad).

$^1$H-NMR (DMSO-$d_6$-$D_2$O) δ: 1.60-1.73 (2H, m), 1.86-1.98 (4H, m), 3.54 (4H, t, J=5.4 Hz), 7.22 (1H, d, J=9.0 Hz), 7.45-7.52 (1H, m), 7.53-7.62 (2H, m), 7.73 (1H, dd, J=8.1, 1.8 Hz), 7.73-7.82 (3H, m), 8.02 (1H, d, J=8.1 Hz), 8.23 (1H, d, J=3.0 Hz), 8.81 (1H, d, J=1.8 Hz).

Example 173a

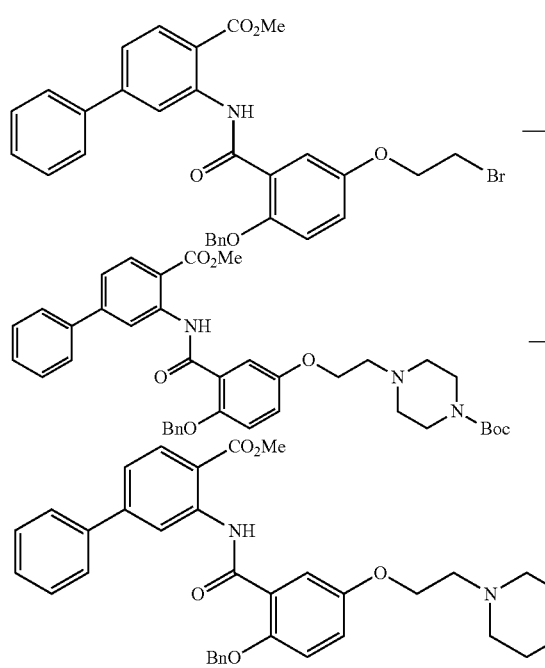

Potassium carbonate (0.12 g) and 1-(tert-butoxycarbonyl)piperidine (0.15 g) were added to a 1-methyl-2-pyrrolidone (2.0 mL) solution of methyl 2-(2-(benzyloxy)-5-(2-bromoethoxy)benzamido)-4-phenylbenzoate (0.40 g), followed by stirring at 90° C. for 45 minutes. The reaction mixture was cooled to room temperature, and then water and ethyl acetate were added thereto. The organic layer was separated, washed with a saturated aqueous solution of sodium chloride, and dried over anhydrous sodium sulfate, and the solvent was evaporated under reduced pressure. The obtained residue was purified by silica gel column chromatography [Kanto Chemical Co., Inc., silica gel 60 (spherical), eluent: 80-0% hexane/ethyl acetate] to obtain 0.36 g of tert-butyl 4-(2-(4-(benzyloxy)-3-(2-(methoxycarbonyl)-5-phenylphenylcarbamoyl)phenoxy)ethyl)piperidine-1-carboxylate as a white solid.

Under ice-cooling, trifluoroacetic acid (1.0 mL) was added to a methylene chloride (5.0 mL) solution of the obtained tert-butyl 4-(2-(4-(benzyloxy)-3-(2-(methoxycarbonyl)-5-phenylphenylcarbamoyl)phenoxy)ethyl)piperidine-1-carboxylate (0.36 g), followed by stirring at room temperature for 4 hours. Water was added to the reaction mixture. After adjusting the pH to 8.0 with a saturated aqueous solution of sodium bicarbonate, the organic layer was separated, washed with a saturated aqueous solution of sodium bicarbonate, and dried over anhydrous sodium sulfate. The solvent was evaporated under reduced pressure to obtain 0.30 g of methyl 2-(2-(benzyloxy)-5-(2-(piperazin-1-yl)ethoxy)benzamido)-4-phenylbenzoate as a yellow oily substance.

$^1$H-NMR (CDCl$_3$) δ: 2.48-2.63 (4H, m), 2.78 (2H, t, J=5.7 Hz), 2.91 (4H, t, J=4.9 Hz), 3.76 (3H, s), 4.12 (2H, t, J=5.7 Hz), 5.38 (2H, s), 6.91-7.01 (2H, m), 7.23-7.52 (9H, m), 7.68-7.77 (3H, m), 8.08 (1H, d, J=8.3 Hz), 9.26 (1H, d, J=1.7 Hz), 12.31 (1H, s).

Example 174a

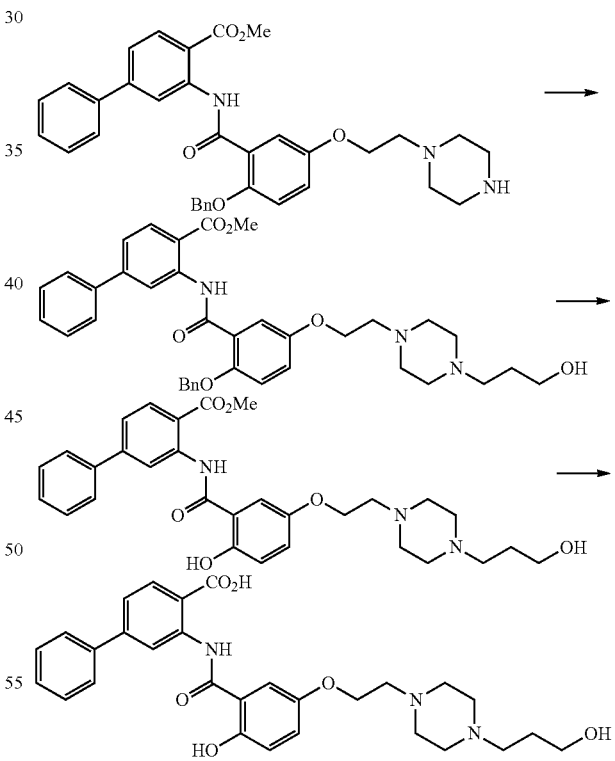

Potassium carbonate (0.031 g) and 3-bromo-1-propanol (0.013 mL) were added to a 2-butanone (1.3 mL) solution of methyl 2-(2-(benzyloxy)-5-(2-(piperazin-1-yl)ethoxy)benzamido)-4-phenylbenzoate (0.084 g), followed by heating to reflux for 1 hour. The reaction mixture was cooled to room temperature, and then a saturated aqueous solution of sodium bicarbonate and ethyl acetate were added thereto. The organic layer was separated, washed with a saturated aqueous solution of sodium chloride, and dried over anhydrous sodium sulfate, and the solvent was evaporated under reduced pressure. The obtained residue was purified by silica gel column chromatography [Kanto Chemical Co., Inc., silica gel 60 (spherical), eluent: 100-91% chloroform/methanol] to obtain 0.036 g of methyl 2-(2-(benzyloxy)-5-(2-(4-(3-hydroxypropyl)piperazin-1-yl)ethoxy)benzamido)-4-phenylbenzoate as a light yellow oily substance.

To a solution mixture of the obtained methyl 2-(2-(benzyloxy)-5-(2-(4-(3-hydroxypropyl)piperazin-1-yl)ethoxy)benzamido)-4-phenylbenzoate (0.036 g) in ethyl acetate (1.5 mL) and methanol (1.5 mL), 10% palladium-carbon (0.018 g) was added, followed by stirring under a hydrogen atmosphere at room temperature for 2 hours and 30 hours. To the reaction mixture, 10% palladium-carbon (0.018 g) was added, followed by stirring under a hydrogen atmosphere at room temperature for 3 hours. The insoluble substance was removed by filtration, and then the solvent was evaporated under reduced pressure. The obtained residue was purified by silica gel column chromatography [Kanto Chemical Co., Inc., silica gel 60 (spherical), eluent: 100-90% chloroform/methanol] to obtain 0.011 g of methyl 2-(2-hydroxy-5-(2-(4-(3-hydroxypropyl)piperazin-1-yl)ethoxy)benzamido)-4-phenylbenzoate as a light yellow solid.

A 2.0 mol/L aqueous solution of sodium hydroxide (0.031 mL) was added to a solution mixture of the obtained methyl 2-(2-hydroxy-5-(2-(4-(3-hydroxypropyl)piperazin-1-yl)ethoxy)benzamido)-4-phenylbenzoate (0.011 g) in methanol (1.0 mL) and dioxane (1.0 mL), followed by stirring at 50° C. for 1 hour. A 2.0 mol/L aqueous solution of sodium hydroxide (0.031 mL) was added to the reaction mixture, followed by stirring at 50° C. for 1 hour. The reaction mixture was cooled to room temperature, and then water was added thereto. After adjusting the pH to 6.5 with 1.0 mol/L hydrochloric acid, ethyl acetate was added thereto. The organic layer was separated, and the aqueous layer was extracted with ethyl acetate. The organic layer and the extract were combined. The resulting mixture was washed with a saturated aqueous solution of sodium chloride and dried over anhydrous sodium sulfate, and the solvent was evaporated under reduced pressure. Diisopropyl ether was added to the obtained residue, and the solid substance was collected by filtration to obtain 6.5 mg of 2-(2-hydroxy-5-(2-(4-(3-hydroxypropyl)piperazin-1-yl)ethoxy)benzamido)-4-phenylbenzoic acid as a light yellow solid.

$^1$H-NMR (DMSO-$d_6$) δ: 1.70-1.84 (2H, m), 2.84-3.90 (14H, m), 4.15 (2H, t, J=4.8 Hz), 6.91 (1H, d, J=9.0 Hz), 7.15 (1H, dd, J=8.9, 2.8 Hz), 7.38-7.45 (2H, m), 7.48-7.55 (2H, m), 7.64 (1H, d, J=2.9 Hz), 7.67-7.73 (2H, m), 8.13 (1H, d, J=8.1 Hz), 8.92 (1H, d, J=1.7 Hz).

$^1$H-NMR (DMSO-$d_6$) δ: 1.72-1.87 (2H, m), 2.75-3.35 (12H, m), 3.49 (2H, t, J=6.1 Hz), 4.13-4.22 (2H, m), 6.94 (1H, d, J=9.0 Hz), 7.17 (1H, dd, J=9.0, 2.7 Hz), 7.38-7.48 (2H, m), 7.49-7.58 (2H, m), 7.57 (1H, d, J=2.7 Hz), 7.66-7.75 (2H, m), 8.14 (1H, d, J=8.0 Hz), 8.90 (1H, d, J=1.7 Hz).

Example 175a

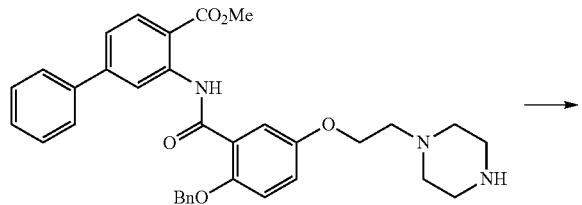

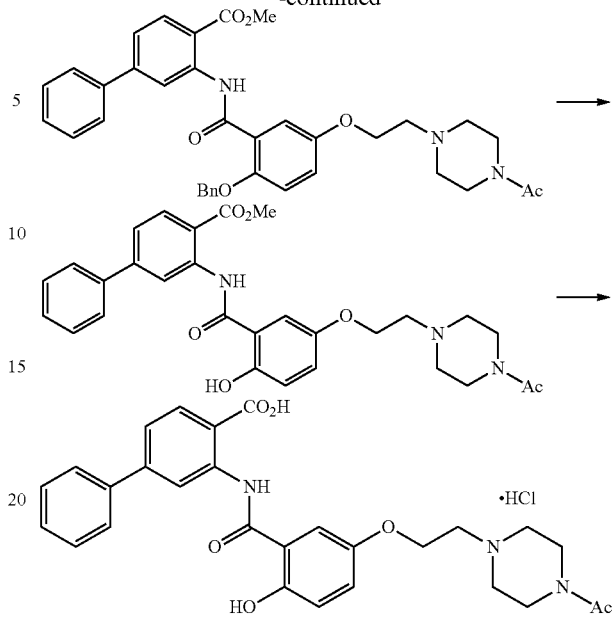

Under ice-cooling, acetic anhydride (0.025 mL) was added to a solution mixture of methyl 2-(2-(benzyloxy)-5-(2-(piperazin-1-yl)ethoxy)benzamido)-4-phenylbenzoate (0.12 g) in methylene chloride (2.4 mL) and pyridine (0.027 mL), followed by stirring at room temperature for 1 hour. The solvent was evaporated under reduced pressure, and a saturated aqueous solution of sodium bicarbonate and ethyl acetate were added to the residue. The organic layer was separated, washed with a saturated aqueous solution of sodium chloride, and dried over anhydrous sodium sulfate, and the solvent was evaporated under reduced pressure. The obtained residue was purified by silica gel column chromatography [Kanto Chemical Co., Inc., silica gel 60 (spherical), eluent: 100-95% chloroform/methanol] to obtain methyl 2-(5-(2-(4-acetylpiperazin-1-yl)ethoxy)-2-(benzyloxy)benzamido)-4-phenylbenzoate as a colorless oily substance.

To a solution mixture of the obtained methyl 2-(5-(2-(4-acetylpiperazin-1-yl)ethoxy)-2-(benzyloxy)benzamido)-4-phenylbenzoate in ethyl acetate (1.5 mL) and methanol (1.5 mL), 10% palladium-carbon (0.15 g) was added, followed by stirring under a hydrogen atmosphere at room temperature for 1 hour and 30 minutes. Chloroform and methanol were added to the reaction mixture. The insoluble substance was removed by filtration, and the solvent was evaporated under reduced pressure. Diisopropyl ether was added to the obtained residue, and the solid substance was collected by filtration to obtain 0.083 g of methyl 2-(5-(2-(4-acetylpiperazin-1-yl)ethoxy)-2-hydroxybenzamido)-4-phenylbenzoate as a light yellow solid.

A 2.0 mol/L aqueous solution of sodium hydroxide (0.24 mL) was added to a 2-propanol (1.5 mL) suspension of the obtained methyl 2-(5-(2-(4-acetylpiperazin-1-yl)ethoxy)-2-hydroxybenzamido)-4-phenylbenzoate (0.083 g), followed by stirring at 50° C. for 1 hour. The reaction mixture was cooled to room temperature, and water was added thereto. After adjusting the pH to 6.5 with 1.0 mol/L hydrochloric acid, the solvent was evaporated under reduced pressure. Water was added to the obtained residue, and the solid substance was collected by filtration. Ethyl acetate (2.0 mL) and a 4.0 mol/L hydrogen chloride-dioxane solution (0.10 mL) were added to the obtained solid substance, followed by stirring at room temperature for 3 hours and 30 minutes. The solid substance was collected from the reaction mixture by filtration to obtain 0.038 g of 2-(5-(2-(4-acetylpiperazin-1-yl)ethoxy)-2-hydroxybenzamido)-4-phenylbenzoic acid hydrochloride as a light yellow solid.

$^1$H-NMR (DMSO-$d_6$) δ: 2.05 (3H, s), 2.96-3.30 (3H, m), 3.44-3.84 (5H, m), 3.90-4.12 (1H, m), 4.34-4.49 (3H, m), 7.02 (1H, d, J=8.8 Hz), 7.15 (1H, dd, J=8.8, 2.9 Hz), 7.42-7.59 (5H, m), 7.70-7.76 (2H, m), 8.09 (1H, d, J=8.3 Hz), 9.02-9.06 (1H, m), 11.00-11.20 (2H, m), 12.31 (1H, s).

Example 176a

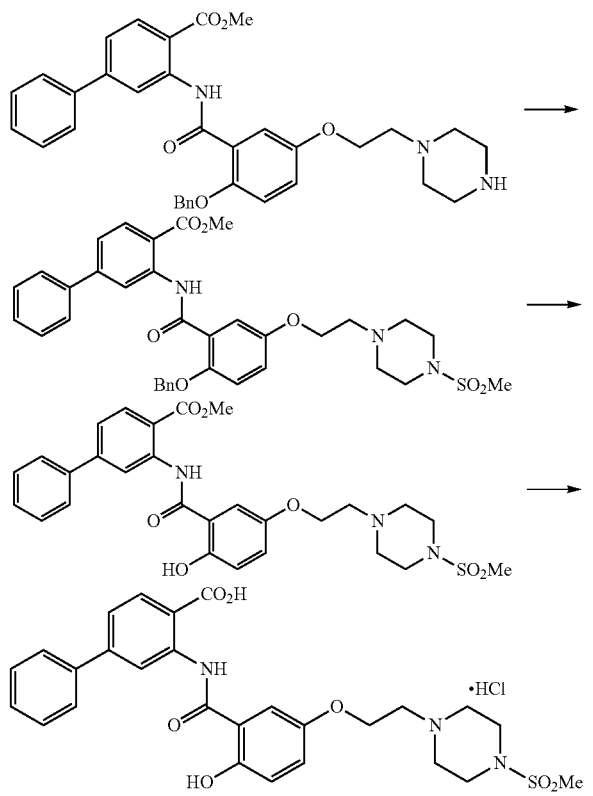

Under ice-cooling, methanesulfonyl chloride (0.018 mL) was added to a solution mixture of methyl 2-(2-(benzyloxy)-5-(2-(piperazin-1-yl)ethoxy)benzamido)-4-phenylbenzoate (0.11 g) in methylene chloride (2.2 mL) and pyridine (0.024 mL), followed by stirring at room temperature for 1 hour. Pyridine (0.016 mL) and methanesulfonyl chloride (9.0 μL) were sequentially added to the reaction mixture, followed by stirring at room temperature for 1 hour and 30 minutes. The solvent was evaporated under reduced pressure, and a saturated aqueous solution of sodium bicarbonate and ethyl acetate were added to the residue. The organic layer was separated, washed with a saturated aqueous solution of sodium chloride, and dried over anhydrous sodium sulfate, and the solvent was evaporated under reduced pressure. The obtained residue was purified by silica gel column chromatography [Kanto Chemical Co., Inc., silica gel 60 (spherical), eluent: 50-0% hexane/ethyl acetate] to obtain 0.085 g of methyl 2-(2-(benzyloxy)-5-(2-(4-(methylsulfonyl)piperazin-1-yl)ethoxy)benzamido)-4-phenylbenzoate as a white solid.

To a solution mixture of the obtained methyl 2-(2-(benzyloxy)-5-(2-(4-(methylsulfonyl)piperazin-1-yl)ethoxy)benzamido)-4-phenylbenzoate (0.085 g) in ethyl acetate (3.0 mL), methanol (1.5 mL), and dioxane (6.0 mL), 10% palladium-carbon (0.085 g) was added, followed by stirring under a hydrogen atmosphere at room temperature for 2 hours. The insoluble substance was removed by filtration, and the solvent was evaporated under reduced pressure. Diisopropyl ether was added to the obtained residue, and the solid substance was collected by filtration to obtain 0.063 g of methyl 2-(2-hydroxy-5-(2-(4-(methylsulfonyl)piperazin-1-yl)ethoxy)benzamido)-4-phenylbenzoate as a light yellow solid.

A 2.0 mol/L aqueous solution of sodium hydroxide (0.17 mL) was added to 2-propanol (1.2 mL) suspension of the obtained methyl 2-(2-hydroxy-5-(2-(4-(methylsulfonyl)piperazin-1-yl)ethoxy)benzamido)-4-phenylbenzoate (0.063 g), followed by stirring at 50° C. for 2 hours. The reaction mixture was cooled to room temperature, and then water was added thereto. After adjusting the pH to 6.5 with 1.0 mol/L hydrochloric acid, the solid substance was collected by filtration. Ethyl acetate (2.0 mL) and a 4.0 mol/L hydrogen chloride-dioxane solution (0.10 mL) were added to the obtained solid substance, followed by stirring at room temperature for 1 hour. The solid substance was collected from the reaction mixture by filtration to obtain 0.025 g of 2-(2-hydroxy-5-(2-(4-(methylsulfonyl)piperazin-1-yl)ethoxy)benzamido)-4-phenylbenzoic acid hydrochloride as a white solid.

$^1$H-NMR (CD$_3$OD) δ: 2.98 (3H, s), 3.46-3.74 (8H, m), 3.71 (2H, t, J=4.9 Hz), 4.44 (2H, t, J=4.9 Hz), 6.98 (1H, d, J=9.0 Hz), 7.22 (1H, dd, J=9.0, 3.2 Hz), 7.39-7.46 (1H, m), 7.47-7.53 (3H, m), 7.54 (1H, d, J=3.2 Hz), 7.70-7.75 (2H, m), 8.22 (1H, d, J=8.1 Hz), 9.06 (1H, d, J=1.7 Hz).

Example 177a

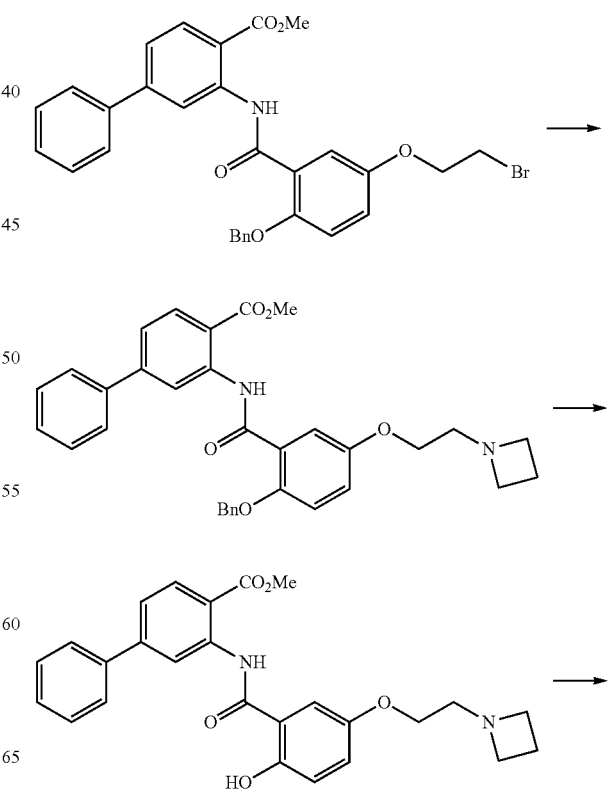

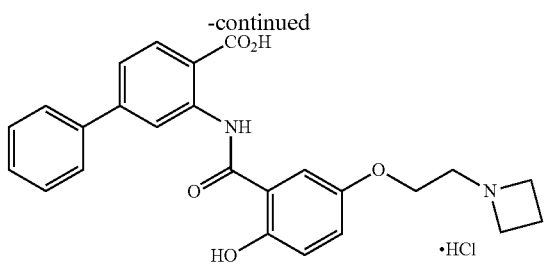

Potassium carbonate (0.15 g) and azetidine hydrochloride (0.046 g) were added to a 1-methyl-2-pyrrolidone (1.3 mL) solution of methyl 2-(2-(benzyloxy)-5-(2-bromoethoxy)benzamido)-4-phenylbenzoate (0.25 g), followed by stirring at 90° C. for 45 minutes. The reaction mixture was cooled to room temperature, and then water and ethyl acetate were added thereto. The organic layer was separated, washed with a saturated aqueous solution of sodium chloride, and dried over anhydrous sodium sulfate, and the solvent was evaporated under reduced pressure. The obtained residue was purified by silica gel column chromatography [eluent: 100-90% chloroform/methanol] to obtain 0.088 g of methyl 2-(5-(2-(azetidin-1-yl)ethoxy)-2-(benzyloxy)benzamido)-4-phenylbenzoate as a light yellow oily substance.

To a solution mixture of the obtained methyl 2-(5-(2-(azetidin-1-yl)ethoxy)-2-(benzyloxy)benzamido)-4-phenylbenzoate (0.088 g) in ethyl acetate (1.5 mL), methanol (1.5 mL), and dioxane (1.5 mL), 10% palladium-carbon (0.088 g) was added, followed by stirring under a hydrogen atmosphere at room temperature for 2 hours. To the reaction mixture, 10% palladium-carbon (0.088 g) was added, followed by stirring under a hydrogen atmosphere at room temperature for 3 hours. The insoluble substance was removed by filtration, and then the solvent was evaporated under reduced pressure. Diisopropyl ether was added to the obtained residue, and the solid substance was collected by filtration to obtain 0.033 g of methyl 2-(5-(2-(azetidin-1-yl)ethoxy)-2-hydroxybenzamido)-4-phenylbenzoate as a light yellow solid.

A 2.0 mol/L aqueous solution of sodium hydroxide (0.11 mL) was added to a 2-propanol (1.0 mL) suspension of the obtained methyl 2-(5-(2-(azetidin-1-yl)ethoxy)-2-hydroxybenzamido)-4-phenylbenzoate (0.032 g), followed by stirring at 50° C. for 1 hour. The reaction mixture was cooled to room temperature, and water was added thereto. After adjusting the pH to 6.0 with 1.0 mol/L hydrochloric acid, the solid substance was collected by filtration. Ethyl acetate (1.5 mL) and a 4.0 mol/L hydrogen chloride-dioxane solution (0.10 mL) were added to the obtained solid substance, followed by stirring at room temperature for 1 hour and 30 minutes. The solid substance was collected from the reaction mixture by filtration to obtain 0.021 g of 2-(5-(2-(azetidin-1-yl)ethoxy)-2-hydroxybenzamido)-4-phenylbenzoic acid hydrochloride as a light yellow solid.

$^1$H-NMR (CD$_3$OD) δ: 2.40-2.55 (1H, m), 2.58-2.73 (1H, m), 3.66 (2H, t, J=4.9 Hz), 4.22-4.36 (6H, m), 6.96 (1H, d, J=9.0 Hz), 7.18 (1H, dd, J=9.0, 3.1 Hz), 7.39-7.47 (1H, m), 7.47-7.55 (4H, m), 7.70-7.76 (2H, m), 8.22 (1H, d, J=8.3 Hz), 9.07 (1H, d, J=1.7 Hz).

Examples 178a to 182a

As in Example 177a, the compounds shown in Table 20a were prepared.

TABLE 20a

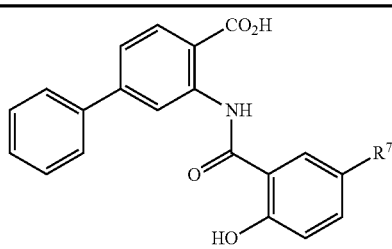

| Example No. | R$^7$ |
|---|---|
| 178a | 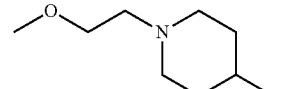 |
| 179a | 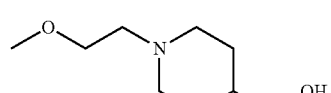 |
| 180a | 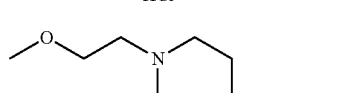 |
| 181a | 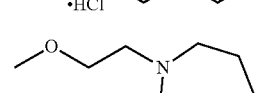 |
| 182a | 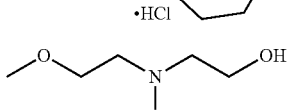 |

2-(2-Hydroxy-5-(2-(4-hydroxypiperidin-1-yl)ethoxy)benzamido)-4-phenylbenzoic acid hydrochloride $^1$H-NMR (DMSO-d$_6$) δ: 1.60-1.82 (2H, m), 1.89-2.02 (2H, m), 2.98-3.72 (7H, m), 4.30-4.40 (2H, m), 4.94-5.14 (1H, m), 7.01 (1H, d, J=8.8 Hz), 7.15 (1H, dd, J=8.8, 3.2 Hz), 7.43-7.57 (5H, m), 7.70-7.75 (2H, m), 8.09 (1H, d, J=8.0 Hz), 9.03 (1H, d, J=1.7 Hz), 9.80-10.02 (1H, broad), 11.08 (1H, s), 12.36 (1H, s).

2-(2-Hydroxy-5-(2-(4-(2-hydroxymethyl)piperidin-1-yl)ethoxy)benzamido)-4-phenylbenzoic acid hydrochloride $^1$H-NMR (DMSO-d$_6$) δ: 1.40-1.72 (3H, m), 1.78-1.90 (2H, m), 2.95-3.10 (2H, m), 3.18-3.64 (6H, m), 4.30-4.40 (2H, m), 4.58-4.74 (1H, broad), 7.01 (1H, d, J=9.0 Hz), 7.15 (1H, dd, J=9.0, 3.1 Hz), 7.43-7.58 (5H, m), 7.70-7.75 (2H, m), 8.10 (1H, d, J=8.0 Hz), 9.04 (1H, s), 9.60-9.88 (1H, broad), 11.09 (1H, s), 12.30-12.46 (1H, broad).

2-(2-Hydroxy-5-(2-(4-(hydroxyethyl)piperidin-1-yl)ethoxy)benzamido)-4-phenylbenzoic acid hydrochloride $^1$H-NMR (DMSO-d$_6$) δ: 1.30-1.74 (5H, m), 1.76-1.94 (2H, m), 2.93-3.09 (2H, m), 3.40-3.64 (6H, m), 4.28-4.56 (3H, m), 7.01 (1H, d, J=8.9 Hz), 7.14 (1H, dd, J=8.9, 3.0 Hz), 7.43-7.58 (5H, m), 7.70-7.75 (2H, m), 8.09 (1H, d, J=8.3 Hz), 9.04 (1H, d, J=1.7 Hz), 9.66-9.94 (1H, broad), 11.08 (1H, s), 12.35 (1H, s).

2-(5-(2-(Homopiperidin-1-yl)ethoxy)-2-hydroxybenzamido)-4-phenylbenzoic acid hydrochloride $^1$H-NMR (DMSO-$d_6$) δ: 1.53-1.73 (4H, m), 1.76-1.92 (4H, m), 3.18-3.60 (6H, m), 4.35 (2H, t, J=4.9 Hz), 7.01 (1H, d, J=9.0 Hz), 7.15 (1H, dd, J=9.0, 3.2 Hz), 7.42-7.58 (5H, m), 7.69-7.76 (2H, m), 8.09 (1H, d, J=8.3 Hz), 9.04 (1H, d, J=1.7 Hz), 9.98-10.14 (1H, broad), 11.08 (1H, s), 12.33 (1H, s), 13.30-13.52 (1H, broad).

2-(5-(2-(Ethyl(2-hydroxyethyl)amino)ethoxy)-2-hydroxybenzamido)-4-phenylbenzoic acid hydrochloride $^1$H-NMR (DMSO-$d_6$) δ: 1.28 (3H, t, J=7.2 Hz), 3.18-3.42 (4H, m), 3.52-3.65 (2H, m), 3.79 (2H, t, J=5.0 Hz), 4.36 (2H, t, J=5.0), 5.26-5.49 (1H, broad), 7.02 (1H, d, J=8.9 Hz), 7.14 (1H, dd, J=8.9, 3.2 Hz), 7.43-7.58 (5H, m), 7.69-7.76 (2H, m), 8.09 (1H, d, J=8.0 Hz), 9.04 (1H, d, J=1.7 Hz), 9.72-10.00 (1H, broad), 11.10 (1H, s), 12.36 (1H, s).

Example 183a

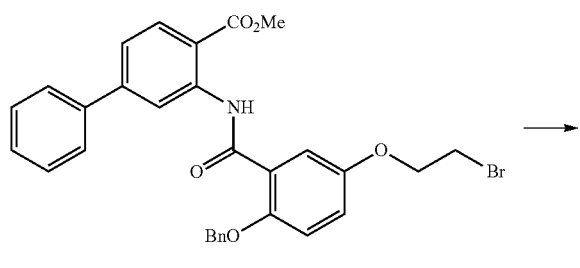

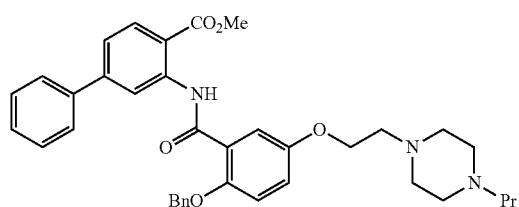

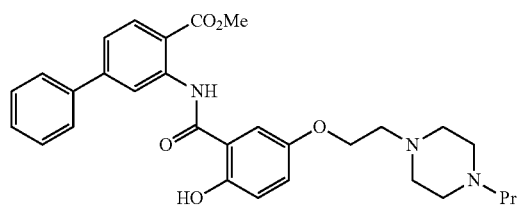

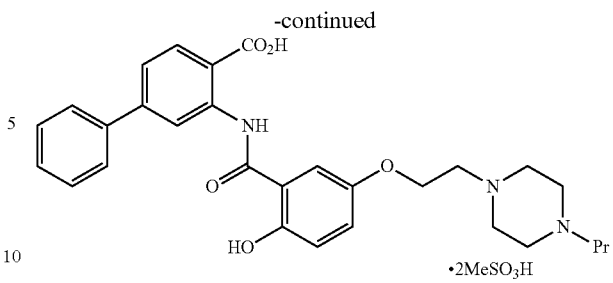

Potassium carbonate (0.14 g) and 1-propylpiperazine dihydrochloride (0.12 g) were added to an acetone (1.6 mL) solution of methyl 2-(2-(benzyloxy)-5-(2-bromoethoxy)benzamido)-4-phenylbenzoate (0.080 g), followed by heating to reflux for 4 hours. After cooling the reaction mixture to room temperature, the solvent was evaporated under reduced pressure, and a saturated aqueous solution of sodium bicarbonate and chloroform were added to the residue. The organic layer was separated and dried over anhydrous sodium sulfate, and the solvent was evaporated under reduced pressure. The obtained residue was purified by silica gel column chromatography [Kanto Chemical Co., Inc., silica gel 60 (spherical), eluent: 100-90% chloroform/methanol] to obtain 0.081 g of methyl 2-(2-(benzyloxy)-5-(2-(4-propylpiperazin-1-yl)ethoxy)benzamido)-4-phenylbenzoate as a light yellow oily substance.

To a solution mixture of methyl 2-(2-(benzyloxy)-5-(2-(4-propylpiperazin-1-yl)ethoxy)benzamido)-4-phenylbenzoate (0.081 g) in methanol (1.5 mL) and ethyl acetate (1.5 mL), 10% palladium-carbon (0.081 g) was added, followed by stirring under a hydrogen atmosphere at room temperature for 2 hours and 30 minutes. Chloroform was added to the reaction mixture. The insoluble substance was removed by filtration, and the solvent was evaporated under reduced pressure. Diisopropyl ether was added to the obtained residue, and the solid substance was collected by filtration to obtain 0.043 g of methyl 2-(2-hydroxy-5-(2-(4-propylpiperazin-1-yl)ethoxy)benzamido)-4-phenylbenzoate as an orange solid.

Methanol (2.0 mL) and a 2.0 mol/L aqueous solution of sodium hydroxide (0.12 mL) were added to the obtained methyl 2-(2-hydroxy-5-(2-(4-propylpiperazin-1-yl)ethoxy)benzamido)-4-phenylbenzoate (0.043 g), followed by stirring at 50° C. for 1 hour. A 2.0 mol/L aqueous solution of sodium hydroxide (0.25 mL) was added to the reaction mixture, followed by stirring at 50° C. for 3 hours. The reaction mixture was cooled to room temperature, and then water was added thereto. After adjusting the pH to 6.0 with 2.0 mol/L hydrochloric acid, the solid substance was collected by filtration. Ethyl acetate (3.0 mL) and methanesulfonic acid (9.2 μL) were added to the obtained solid substance, followed by stirring at room temperature for 4 hours. The solid substance was collected from the reaction mixture by filtration to obtain 0.035 g of 2-(2-hydroxy-5-(2-(4-propylpiperazin-1-yl)ethoxy)benzamido)-4-phenylbenzoic acid dimethanesulfonate as a white solid.

$^1$H-NMR (CD$_3$OD) δ: 1.05 (3H, t, J=7.4 Hz), 1.74-1.88 (2H, m), 2.72 (6H, s), 3.17-3.26 (2H, m), 3.45-3.90 (10H, m), 4.43 (2H, t, J=4.9 Hz), 6.97 (1H, d, J=9.0 Hz), 7.22 (1H, dd, J=9.0, 3.2 Hz), 7.39-7.56 (5H, m), 7.69-7.76 (2H, m), 8.22 (1H, d, J=8.3 Hz), 9.06 (1H, d, J=1.7 Hz).

Examples 184a and 185a

As in Example 183a, the compounds shown in Table 21a were prepared.

TABLE 21a

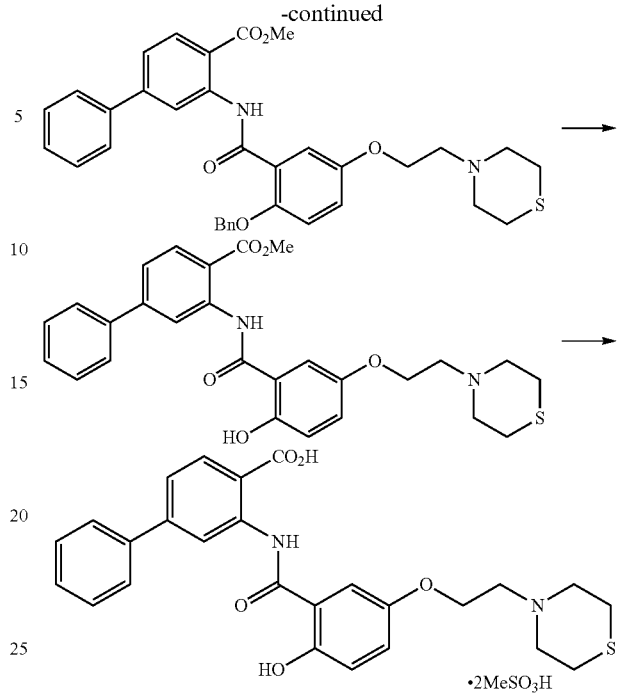

| Example No. | R[7] |
|---|---|
| 184a | (2-methoxyethyl-piperazinyl with iPr) •2MeSO₃H |
| 185a | (2-methoxyethyl-piperazinyl with ethanol) •2MeSO₃H |

2-(2-Hydroxy-5-(2-(4-isopropylpiperazin-1-yl)ethoxy)benzamido)-4-phenylbenzoic acid dimethanesulfonate $^1$H-NMR (CD$_3$OD) δ: 1.43 (6H, d, J=6.6 Hz), 2.72 (6H, s), 3.40-4.00 (11H, m), 4.43 (2H, t, J=4.9 Hz), 6.97 (1H, d, J=9.0 Hz), 7.22 (1H, dd, J=9.0, 2.9 Hz), 7.39-7.46 (1H, m), 7.47-7.56 (4H, m), 7.70-7.76 (2H, m), 8.22 (1H, d, J=8.3 Hz), 9.06 (1H, d, J=1.7 Hz).

2-(2-Hydroxy-5-(2-(4-(2-hydroxyethyl)piperazin-1-yl)ethoxy)benzamido)-4-phenylbenzoic acid dimethanesulfonate $^1$H-NMR (CD$_3$OD) δ: 2.73 (6H, s), 3.39-3.47 (2H, m), 3.60-3.90 (10H, m), 3.90-3.98 (2H, m), 4.40-4.48 (2H, m), 6.97 (1H, d, J=9.0 Hz), 7.23 (1H, dd, J=9.0, 3.1 Hz), 7.39-7.55 (5H, m), 7.68-7.75 (2H, m), 8.20 (1H, d, J=8.3 Hz), 9.05 (1H, d, J=1.7 Hz).

Example 186a

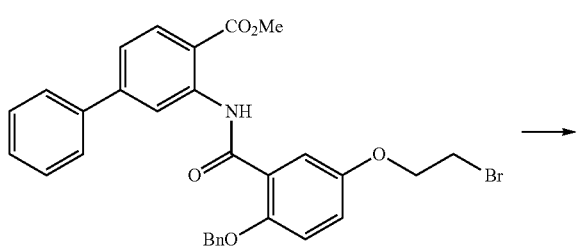

Potassium carbonate (2.0 g) and thiomorpholine (1.1 mL) were added to an acetone (20 mL) solution of methyl 2-(2-(benzyloxy)-5-(2-bromoethoxy)benzamido)-4-phenylbenzoate (2.0 g), followed by heating to reflux for 4 hours. The reaction mixture was cooled to room temperature, and thiomorpholine (0.55 mL) was added thereto, followed by heating to reflux for 2 hours and 30 minutes. After cooling the reaction mixture to room temperature, the solvent was evaporated under reduced pressure, and water and chloroform were added to the residue. The organic layer was separated and dried over anhydrous magnesium sulfate, and the solvent was evaporated under reduced pressure. The obtained residue was purified by silica gel column chromatography [Kanto Chemical Co., Inc., silica gel 60 (spherical), eluent: 70-40% hexane/ethyl acetate] to obtain 1.9 g of methyl 2-(2-(benzyloxy)-5-(2-(thiomorpholin-4-yl)ethoxy)benzamido)-4-phenylbenzoate as a white solid.

Thioanisole (3.2 mL) and trifluoroacetic acid (10 mL) were added to the obtained methyl 2-(2-(benzyloxy)-5-(2-(thiomorpholin-4-yl)ethoxy)benzamido)-4-phenylbenzoate (0.80 g), followed by stirring at room temperature for 18 hours. The solvent was evaporated under reduced pressure, and a saturated aqueous solution of sodium bicarbonate and chloroform were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 70-0% hexane/ethyl acetate to 100-95% chloroform/methanol] to obtain 0.54 g of methyl 2-(2-hydroxy-5-(2-(thiomorpholin-4-yl)ethoxy)benzamido)-4-phenylbenzoate as a brown solid.

Methanol (5.0 mL) and a 2.0 mol/L aqueous solution of sodium hydroxide (1.5 mL) were added to the obtained methyl 2-(2-hydroxy-5-(2-(thiomorpholin-4-yl)ethoxy)benzamido)-4-phenylbenzoate (0.15 g), followed by stirring at 40 to 50° C. for 1 hour and 30 minutes. After cooling the reaction mixture to room temperature and adjusting the pH to 6.8 with a 10% aqueous solution of citric acid, the solid substance was collected by filtration. Ethyl acetate (5.0 mL) and methanesulfonic acid (0.015 mL) were added to the obtained solid substance, followed by stirring at room temperature for 1 hour. The solid substance was collected from the reaction mixture by filtration to obtain 0.12 g of 2-(2-hydroxy-5-(2-(thiomorpholin-4-yl)ethoxy)benzamido)-4-phenylbenzoic acid methanesulfonate as a white solid.

$^1$H-NMR (CD$_3$OD) δ: 2.69 (3H, s), 2.95-3.11 (4H, m), 3.50-3.83 (4H, m), 3.65 (2H, t, J=5.0 Hz), 4.41 (2H, t, J=5.0 Hz), 6.95 (1H, d, J=9.0 Hz), 7.19 (1H, dd, J=9.0, 3.2 Hz), 7.38-7.53 (5H, m), 7.68-7.74 (2H, m), 8.19 (1H, d, J=8.3 Hz), 9.05 (1H, d, J=1.7 Hz).

Example 187a

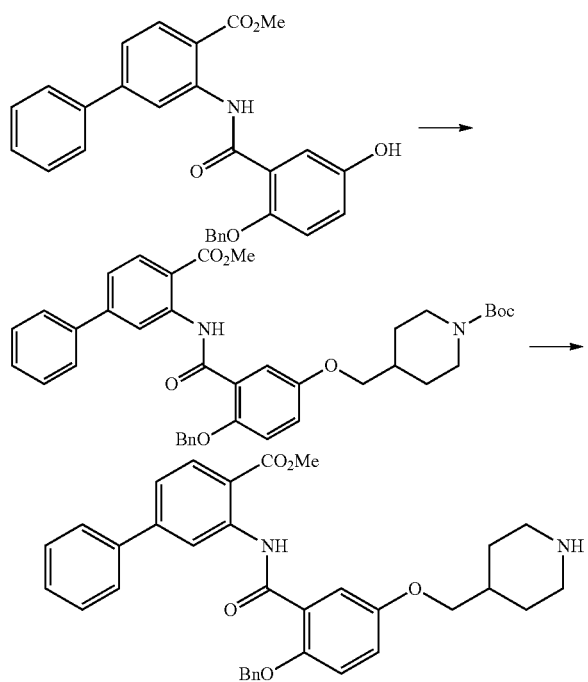

Tert-butyl 4-(hydroxymethyl)piperidine-1-carboxylate (0.26 g), triphenylphosphine (0.35 g), and diisopropyl azodicarboxylate (0.26 mL) were added to a tetrahydrofuran (5.0 mL) solution of methyl 2-(2-(benzyloxy)-5-hydroxybenzamido)-4-phenylbenzoate (0.50 g), followed by stirring at room temperature for 30 minutes. Triphenylphosphine (0.35 g) and diisopropyl azodicarboxylate (0.26 mL) were added to the reaction mixture, followed by stirring at room temperature for 30 minutes. Triphenylphosphine (0.35 g) and diisopropyl azodicarboxylate (0.26 mL) were added to the reaction mixture, followed by stirring at room temperature for 30 minutes. The solvent was evaporated under reduced pressure, and the obtained residue was purified by silica gel column chromatography [Kanto Chemical Co., Inc., silica gel 60 (spherical), eluent: 95-70% hexane/ethyl acetate] to obtain methyl 2-(2-(benzyloxy)-5-((1-(tert-butoxycarbonyl)piperidin-4-yl)methoxy)benzamido)-4-phenylbenzoate as a yellow oily substance.

Under ice-cooling, trifluoroacetic acid (1.9 mL) was added to a methylene chloride (9.4 mL) solution of the obtained methyl 2-(2-(benzyloxy)-5-(1-(tert-butoxycarbonyl)piperidin-4-yl)methoxy)benzamido)-4-phenylbenzoate, followed by stirring at room temperature for 30 minutes. The reaction mixture was added to a saturated aqueous solution of sodium bicarbonate under ice-cooling. The organic layer was separated, washed with a saturated aqueous solution of sodium bicarbonate, and dried over anhydrous sodium sulfate, and the solvent was evaporated under reduced pressure. The obtained residue was purified by silica gel column chromatography [Kanto Chemical Co., Inc., silica gel 60 (spherical), eluent: 100-90% chloroform/methanol] to obtain 0.30 g of methyl 2-(2-(benzyloxy)-5-(piperidin-4-ylmethoxy)benzamido)-4-phenylbenzoate as a light yellow solid.

$^1$H-NMR (DMSO-d$_6$-D$_2$O) δ: 1.10-1.23 (2H, m), 1.64-1.74 (2H, m), 1.74-1.86 (1H, m), 2.41-2.52 (2H, m), 2.89-2.98 (2H, m), 3.76 (3H, s), 3.79 (2H, d, J=6.3 Hz), 5.39 (2H, s), 7.11 (1H, dd, J=9.0, 3.2 Hz), 7.21 (1H, d, J=9.0 Hz), 7.25-7.35 (3H, m), 7.43-7.51 (4H, m), 7.52-7.59 (3H, m), 7.70-7.76 (2H, m), 8.07 (1H, d, J=8.3 Hz), 9.04 (1H, d, J=1.5 Hz).

Example 188a

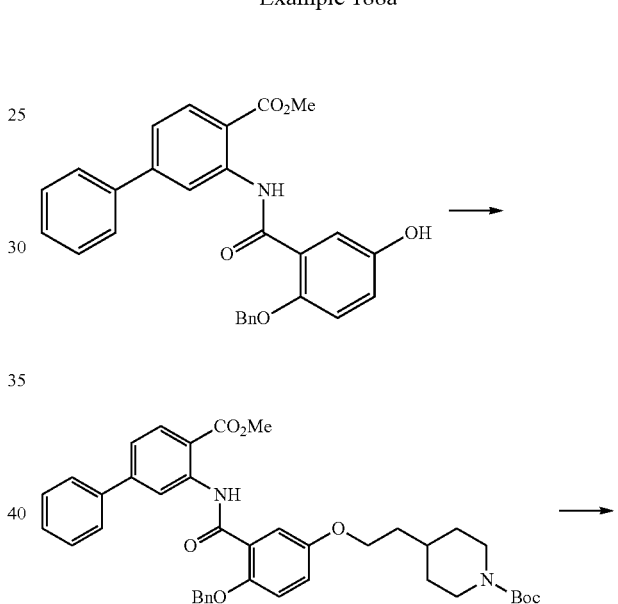

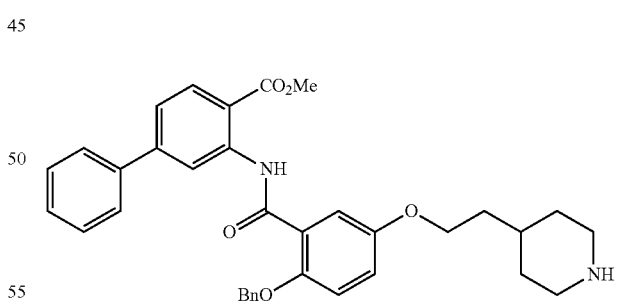

As in Example 187a, the following compound was prepared.

Methyl 2-(2-(benzyloxy)-5-(2-(piperidin-4-yl)ethoxy)benzamido)-4-phenylbenzoate $^1$H-NMR (DMSO-d$_6$) δ: 1.10-1.28 (2H, m), 1.57-1.77 (5H, m), 2.56-2.67 (2H, m), 3.00-3.10 (2H, m), 3.76 (3H, s), 3.96-4.06 (2H, m), 5.41 (2H, s), 7.10 (1H, dd, J=9.2, 3.2 Hz), 7.20

(1H, d, J=9.2 Hz), 7.24-7.36 (3H, m), 7.43-7.59 (7H, m), 7.70-7.77 (2H, m), 8.07 (1H, d, J=8.3 Hz), 9.04-9.09 (1H, m), 12.03 (1H, s).

Example 189a

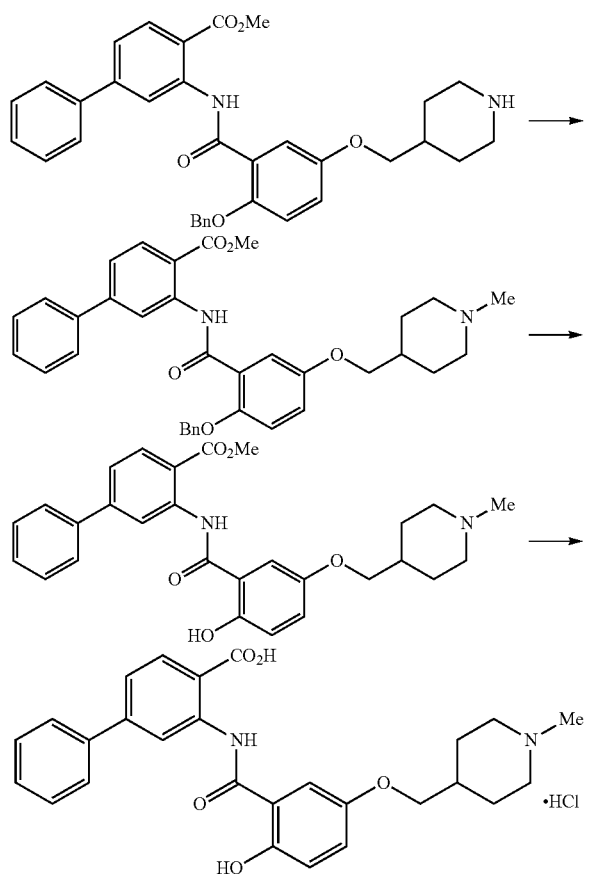

A 37% aqueous solution of formaldehyde (0.17 mL) and sodium triacetoxyborohydride (0.073 g) were sequentially added to a chloroform (1.9 mL) solution of methyl 2-(2-(benzyloxy)-5-(piperidin-4-ylmethoxy)benzamido)-4-phenylbenzoate (0.13 g), followed by stirring at room temperature for 1 hour and 30 minutes. A saturated aqueous solution of sodium bicarbonate and chloroform were added to the reaction mixture. The organic layer was separated and dried over anhydrous sodium sulfate, and the solvent was evaporated under reduced pressure. The obtained residue was purified by silica gel column chromatography [Kanto Chemical Co., Inc., silica gel 60 (spherical), eluent: 100-90% chloroform/methanol] to obtain 0.11 g of methyl 2-(2-(benzyloxy)-5-(1-methylpiperidin-4-yl)methoxy)benzamido)-4-phenylbenzoate as a colorless oily substance.

To a solution mixture of the obtained methyl 2-(2-(benzyloxy)-5-((1-methylpiperidin-4-yl)methoxy)benzamido)-4-phenylbenzoate (0.11 g) in ethyl acetate (1.5 mL) and methanol (1.5 mL), 10% palladium-carbon (0.11 g) was added, followed by stirring under a hydrogen atmosphere at room temperature for 1 hour and 30 minutes. Chloroform was added to the reaction mixture. The insoluble substance was removed by filtration, and the solvent was evaporated under reduced pressure. Diisopropyl ether was added to the obtained residue, and the solid substance was collected by filtration to obtain 0.070 g of methyl 2-(2-hydroxy-5-((1-methylpiperidin-4-yl)methoxy)benzamido)-4-phenylbenzoate as a light yellow solid.

A 2.0 mol/L aqueous solution of sodium hydroxide (0.37 mL) was added to a 2-propanol (1.0 mL) suspension of the obtained methyl 2-(2-hydroxy-5-((1-methylpiperidin-4-yl)methoxy)benzamido)-4-phenylbenzoate (0.070 g), followed by stirring at 50° C. for 1 hour and 30 minutes. The reaction mixture was cooled to room temperature, and then water was added thereto. After adjusting the pH to 6.0 with 1 mol/L hydrochloric acid, the solid substance was collected by filtration. Ethyl acetate (2.0 mL) and a 4 mol/L hydrogen chloride dioxane solution (0.20 mL) were added to the obtained solid substance, followed by stirring at room temperature for 2 hours. The solid substance was collected from the reaction mixture by filtration to obtain 0.058 g of 2-(2-hydroxy-5-(1-methylpiperidin-4-ylmethoxy)benzamido)-4-phenylbenzoic acid hydrochloride as a light yellow solid.

$^1$H-NMR (DMSO-$d_6$) δ: 1.47-1.63 (2H, m), 1.82-2.04 (3H, m), 2.70-2.79 (3H, m), 2.88-3.03 (2H, m), 3.40-3.49 (2H, m), 3.82-3.89 (2H, m), 6.97 (1H, d, J=9.0 Hz), 7.08 (1H, dd, J=9.0, 3.1 Hz), 7.43-7.58 (5H, m), 7.69-7.76 (2H, m), 8.09 (1H, d, J=8.3 Hz), 9.02 (1H, d, J=1.7 Hz), 9.66-9.80 (1H, broad), 11.03 (1H, s), 12.28-12.38 (1H, broad), 13.38-13.52 (1H, broad).

Example 190a

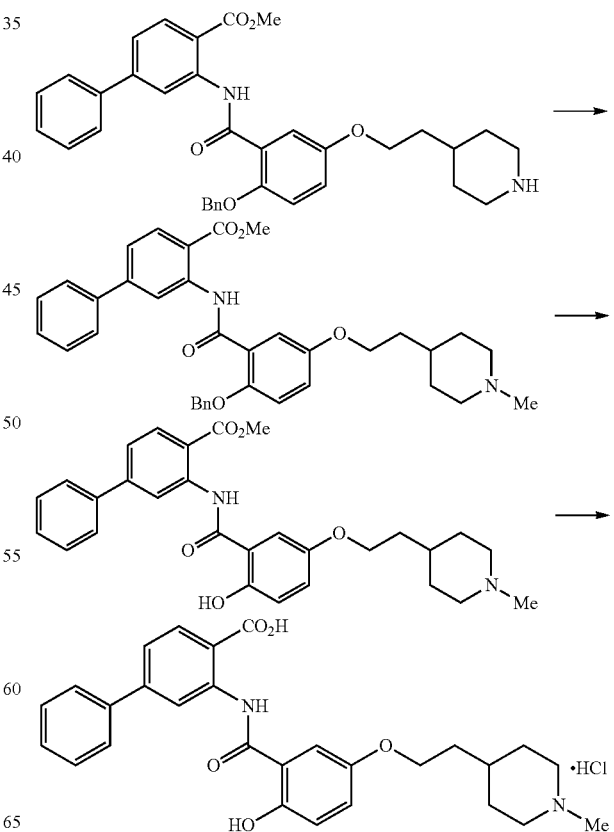

As in Example 189a, the following compound was prepared.

2-(2-Hydroxy-5-(2-(1-methylpiperidin-4-yl)ethoxy)benzamido)-4-phenylbenzoic acid hydrochloride $^1$H-NMR (DMSO-$d_6$-$D_2O$) δ: 1.33-1.48 (2H, m), 1.64-1.88 (3H, m), 1.88-1.98 (2H, m), 2.74 (3H, s), 2.87-2.98 (2H, m), 3.36-3.45 (2H, m), 3.97-4.06 (2H, m), 6.97 (1H, d, J=8.8 Hz), 7.08 (1H, dd, J=8.8, 3.2 Hz), 7.42-7.50 (2H, m), 7.51-7.59 (3H, m), 7.70-7.76 (2H, m), 8.11 (1H, d, J=8.3 Hz), 9.01 (1H, d, J=1.7 Hz).

Examples 191a to 194a

As in Example 164a, the compounds shown in Table 22a were prepared.

TABLE 22a

| Example No. | R$^7$ |
|---|---|
| 191a | (2,6-dimethylmorpholin-4-yl, N-Me) |
| 192a | (4-methyl-1,4-oxazepan-4-yl) |
| 193a | (4-methyl-3-oxopiperazin-1-yl, N-Me) |
| 194a | (4-ethyl-3-oxopiperazin-1-yl, N-Me) |

2-(5-((2S,6R)-2,6-Dimethylmorpholin-4-yl)-2-hydroxybenzamido)-4-phenylbenzoic acid $^1$H-NMR (DMSO-$d_6$) δ: 1.16 (6H, d, J=6.1 Hz), 2.22 (2H, dd, J=11.0, 10.6 Hz), 3.44 (2H, d, J=10.6 Hz), 3.67-3.78 (2H, m), 6.92 (1H, d, J=8.8 Hz), 7.16 (1H, dd, J=8.8, 3.0 Hz), 7.42-7.58 (5H, m), 7.70-7.76 (2H, m), 8.09 (1H, d, J=8.3 Hz), 9.03 (1H, d, J=1.7 Hz), 10.89 (1H, s), 12.24-12.36 (1H, broad).

2-(2-Hydroxy-5-(1,4-oxazepane-4-yl)benzamido)-4-phenylbenzoic acid $^1$H-NMR (DMSO-$d_6$) δ: 1.88-1.98 (2H, m), 3.51-3.62 (6H, m), 3.71-3.77 (2H, m), 6.88 (1H, d, J=9.0 Hz), 6.98 (1H, dd, J=9.0, 2.9 Hz), 7.21 (1H, d, J=2.9 Hz), 7.42-7.58 (4H, m), 7.70-7.77 (2H, m), 8.10 (1H, d, J=8.3 Hz), 9.03 (1H, d, J=1.7 Hz), 10.68 (1H, s), 12.30-12.42 (1H, broad).

2-(2-Hydroxy-5-(4-methyl-3-oxopiperazin-1-yl)benzamido)-4-phenylbenzoic acid $^1$H-NMR (DMSO-$d_6$+$D_2O$) δ: 2.91 (3H, s), 3.36-3.48 (4H, m), 3.69 (2H, s), 6.98 (1H, d, J=9.0 Hz), 7.21 (1H, dd, J=9.0, 2.9 Hz), 7.43 (1H, d, J=2.9 Hz), 7.44-7.60 (4H, m), 7.70-7.78 (2H, m), 8.12 (1H, d, J=8.3 Hz), 8.97 (1H, d, J=1.7 Hz).

2-(5-(4-Ethyl-3-oxopiperazin-1-yl)-2-hydroxybenzamido)-4-phenylbenzoic acid $^1$H-NMR (DMSO-$d_6$) δ: 1.07 (3H, t, J=7.1 Hz), 3.15-3.48 (6H, m), 3.68 (2H, s), 6.94 (1H, d, J=8.9 Hz), 7.21 (1H, dd, J=8.9, 2.9 Hz), 7.40-7.57 (5H, m), 7.68-7.76 (2H, m), 8.10 (1H, d, J=8.3 Hz), 8.99 (1H, d, J=1.9 Hz), 11.02-11.22 (1H, broad).

$^1$H-NMR (DMSO-$d_6$-$D_2O$) δ: 1.08 (3H, t, J=7.2 Hz), 3.34-3.50 (6H, m), 3.69 (2H, s), 6.97 (1H, d, J=9.0 Hz), 7.21 (1H, dd, J=9.0, 3.0 Hz), 7.42-7.59 (4H, m), 7.43 (1H, d, J=3.0 Hz), 7.70-7.77 (2H, m), 8.12 (1H, d, J=8.3 Hz), 8.97 (1H, d, J=1.7 Hz).

Example 195a

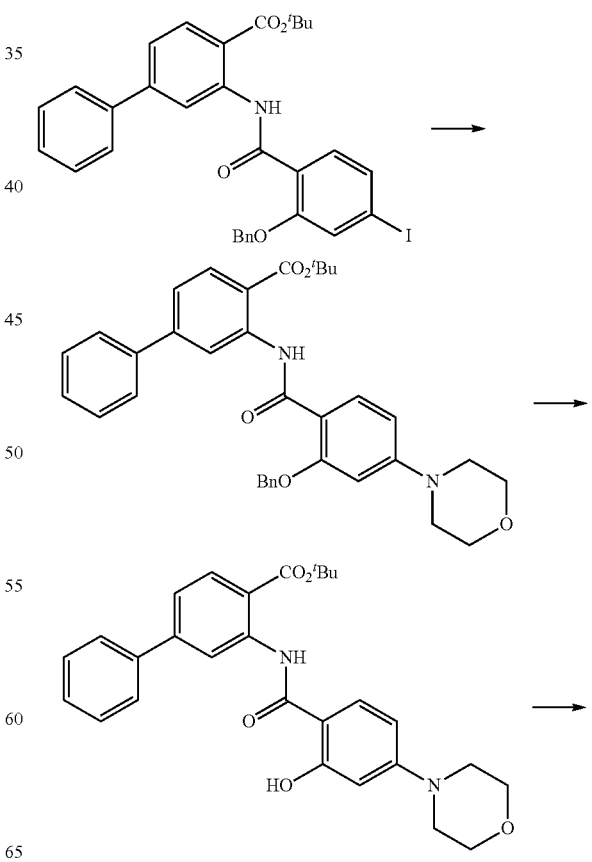

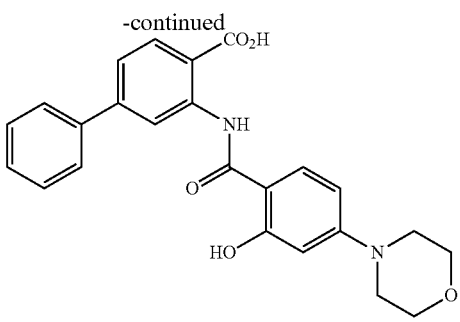

As in Example 164a, the following compound was prepared.

2-(2-Hydroxy-4-(morpholin-4-yl)benzamido)-4-phenylbenzoic acid $^1$H-NMR (DMSO-$d_6$) δ: 3.22-3.29 (4H, m), 3.69-3.77 (4H, m), 6.40 (1H, d, J=2.4 Hz), 6.64 (1H, dd, J=9.3, 2.4 Hz), 7.42-7.57 (4H, m), 7.69-7.76 (3H, m), 8.10 (1H, d, J=8.3 Hz), 8.95 (1H, d, J=2.0 Hz), 11.85 (1H, s), 12.19-12.28 (1H, broad).

Example 196a

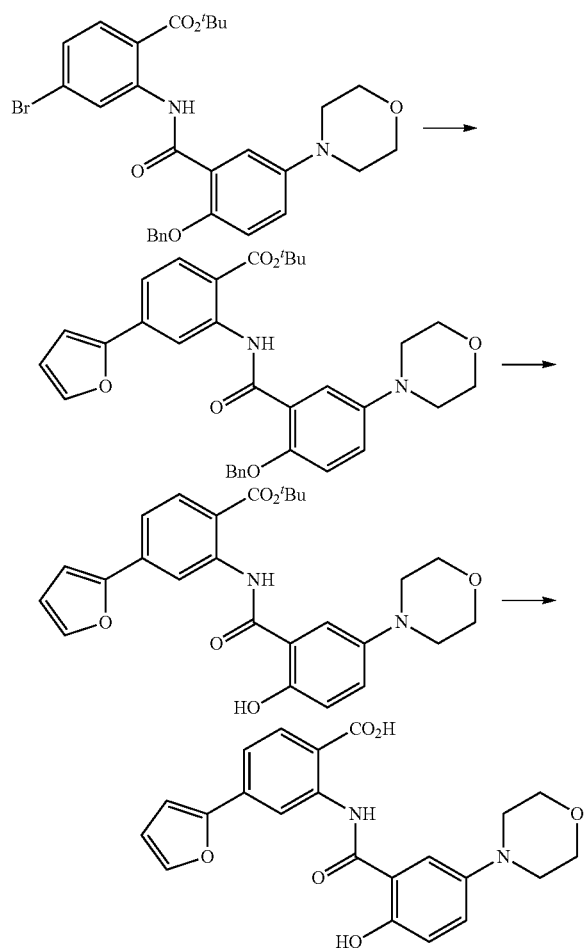

Ethylene glycol dimethyl ether (2.0 mL), water (0.60 mL), furan-2-boronic acid (0.047 g), sodium carbonate (0.093 g), and bis(triphenylphosphine)palladium(II) dichloride (4.9 mg) were added to tert-butyl 2-(2-(benzyloxy)-5-(morpholin-4-yl)benzamido)-4-bromobenzoate (0.20 g), followed by stirring at 75° C. for 2 hours. The reaction mixture was cooled to room temperature, and bis(triphenylphosphine)palladium (II) dichloride (4.9 mg) was added thereto, followed by stirring at 75° C. for 2 hours. The reaction mixture was cooled to room temperature, and water and ethyl acetate were added thereto. The organic layer was separated and dried over anhydrous magnesium sulfate, and the solvent was evaporated under reduced pressure. The obtained residue was purified by silica gel column chromatography [eluent: 85-70% hexane/ethyl acetate] to obtain 0.14 g of tert-butyl 2-(2-(benzyloxy)-5-(morpholin-4-yl)benzamido)-4-(furan-2-yl)benzoate as a light yellow solid.

To a solution mixture of the obtained tert-butyl 2-(2-(benzyloxy)-5-(morpholin-4-yl)benzamido)-4-(furan-2-yl)benzoate (0.14 g) in methanol (2.0 mL) and ethyl acetate (2.0 mL), 10% palladium-carbon (0.029 g) was added, followed by stirring under a hydrogen atmosphere at room temperature for 1 hour. Chloroform was added to the reaction mixture. The insoluble substance was removed by filtration, and the solvent was evaporated under reduced pressure. The obtained residue was purified by silica gel column chromatography [Kanto Chemical Co., Inc., silica gel 60 (spherical), eluent: 85-75% hexane/ethyl acetate] to obtain 0.085 g of tert-butyl 4-(furan-2-yl)-2-(2-hydroxy-5-(morpholin-4-yl)benzamido)benzoate as a yellow solid.

Trifluoroacetic acid (2.0 mL) was added to the obtained tert-butyl 4-(furan-2-yl)-2-(2-hydroxy-5-(morpholin-4-yl)benzamido)benzoate (0.085 g), followed by stirring at room temperature for 30 minutes. The solvent was evaporated under reduced pressure, and water and 2-propanol were added to the residue. After adjusting the pH to 6.0 with a saturated aqueous solution of sodium bicarbonate, the solid substance was collected by filtration to obtain 0.064 g of 4-(furan-2-yl)-2-(2-hydroxy-5-(morpholin-4-yl)benzamido)benzoic acid as a yellow solid.

$^1$H-NMR (DMSO-$d_6$) δ: 2.99-3.08 (4H, m), 3.71-3.79 (4H, m), 6.68 (1H, dd, J=3.4, 1.5 Hz), 6.94 (1H, d, J=9.0 Hz), 7.12 (1H, d, J=3.4 Hz), 7.18 (1H, dd, J=9.0, 3.0 Hz), 7.42 (1H, d, J=3.0 Hz), 7.54 (1H, dd, J=8.3, 1.7 Hz), 7.88 (1H, d, J=1.5 Hz), 8.05 (1H, d, J=8.3 Hz), 9.06 (1H, d, J=1.7 Hz), 10.99 (1H, s), 12.38 (1H, s).

Examples 197a to 210a

As in Example 196a, the compounds shown in Table 23a were prepared.

TABLE 23a

| Example No. | R³ |
|---|---|
| 197a | 2-F-phenyl |

TABLE 23a-continued

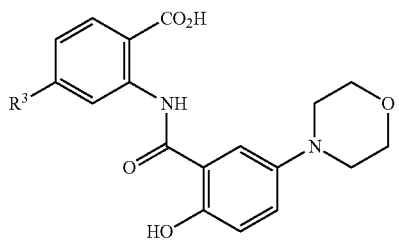

| Example No. | R³ |
|---|---|
| 198a | 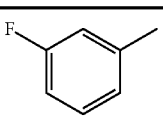 |
| 199a | 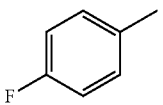 |
| 200a | 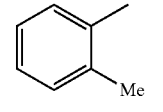 |
| 201a | 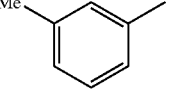 |
| 202a | 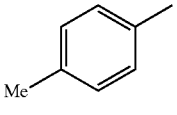 |
| 203a | 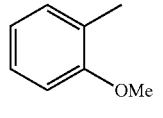 |
| 204a | 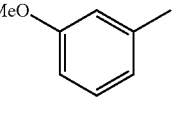 |
| 205a | 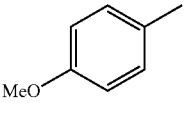 |
| 206a | 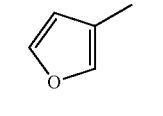 |
| 207a | 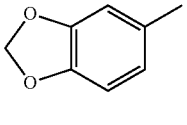 |
| 208a | 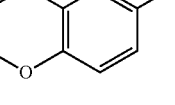 |

TABLE 23a-continued

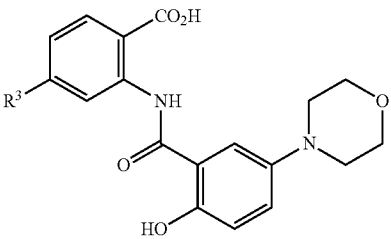

| Example No. | R³ |
|---|---|
| 209a | 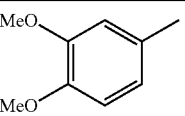 |
| 210a | 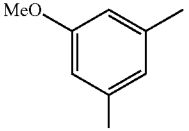 |

4-(2-Fluorophenyl)-2-(2-hydroxy-5-(morpholin-4-yl)benzamido)benzoic acid

¹H-NMR (DMSO-$d_6$) δ: 2.98-3.09 (4H, m), 3.70-3.81 (4H, m), 6.94 (1H, d, J=9.0 Hz), 7.18 (1H, dd, J=9.0, 2.9 Hz), 7.32-7.45 (4H, m), 7.46-7.55 (1H, m), 7.56-7.64 (1H, m), 8.11 (1H, d, J=8.3 Hz), 8.91 (1H, s), 10.97 (1H, s), 12.29 (1H, s), 13.20-14.00 (1H, broad).

4-(3-Fluorophenyl)-2-(2-hydroxy-5-(morpholin-4-yl)benzamido)benzoic acid

¹H-NMR (DMSO-$d_6$) δ: 2.99-3.08 (4H, m), 3.72-3.80 (4H, m), 6.94 (1H, d, J=8.9 Hz), 7.18 (1H, dd, J=8.9, 3.0 Hz), 7.26-7.35 (1H, m), 7.43 (1H, d, J=3.0 Hz), 7.52-7.63 (4H, m), 8.10 (1H, d, J=8.3 Hz), 9.02 (1H, d, J=2.0 Hz), 10.99 (1H, s), 12.32 (1H, s).

4-(4-Fluorophenyl)-2-(2-hydroxy-5-(morpholin-4-yl)benzamido)benzoic acid

¹H-NMR (DMSO-$d_6$) δ: 2.98-3.08 (4H, m), 3.72-3.80 (4H, m), 6.94 (1H, d, J=9.0 Hz), 7.18 (1H, dd, J=9.0, 2.9 Hz), 7.33-7.41 (2H, m), 7.42 (1H, d, J=2.9 Hz), 7.47-7.53 (1H, m), 7.73-7.82 (2H, m), 8.09 (1H, d, J=8.3 Hz), 8.99 (1H, d, J=1.7 Hz), 10.99 (1H, s), 12.33 (1H, s).

2-(2-Hydroxy-5-(morpholin-4-yl)benzamido)-4-(2-methylphenyl)benzoic acid

¹H-NMR (DMSO-$d_6$) δ: 2.29 (3H, s), 2.97-3.06 (4H, m), 3.70-3.79 (4H, m), 6.93 (1H, d, J=9.0 Hz), 7.13-7.22 (2H, m), 7.23-7.41 (5H, m), 8.07 (1H, d, J=8.1 Hz), 8.66 (1H, d, J=1.5 Hz), 10.95 (1H, s), 12.30 (1H, s), 13.25-13.85 (1H, broad).

2-(2-Hydroxy-5-(morpholin-4-yl)benzamido)-4-(3-methylphenyl)benzoic acid

¹H-NMR (DMSO-$d_6$) δ: 2.41 (3H, s), 2.98-3.08 (4H, m), 3.70-3.80 (4H, m), 6.94 (1H, d, J=8.9 Hz), 7.18 (1H, dd,

J=8.9, 2.9 Hz), 7.27 (1H, d, J=7.3 Hz), 7.37-7.58 (5H, m), 8.09 (1H, d, J=8.3 Hz), 8.99 (1H, d, J=1.7 Hz), 10.99 (1H, s), 12.33 (1H, s), 13.10-13.95 (1H, broad).

2-(2-Hydroxy-5-(morpholin-4-yl)benzamido)-4-(4-methylphenyl)benzoic acid $^1$H-NMR (DMSO-d$_6$) δ: 2.38 (3H, s), 2.97-3.08 (4H, m), 3.68-3.80 (4H, m), 6.94 (1H, d, J=8.9 Hz), 7.18 (1H, dd, J=8.9, 2.9 Hz), 7.34 (2H, d, J=8.0 Hz), 7.42 (1H, d, J=2.9 Hz), 7.49 (1H, dd, J=8.3, 1.8 Hz), 7.63 (2H, d, J=8.0 Hz), 8.08 (1H, d, J=8.3 Hz), 9.00 (1H, d, J=1.8 Hz), 11.00 (1H, s), 12.35 (1H, s).

2-(2-Hydroxy-5-(morpholin-4-yl)benzamido)-4-(2-methoxyphenyl)benzoic acid $^1$H-NMR (DMSO-d$_6$) δ: 2.99-3.07 (4H, m), 3.71-3.78 (4H, m), 3.80 (3H, s), 6.93 (1H, d, J=8.8 Hz), 7.04-7.12 (1H, m), 7.13-7.20 (2H, m), 7.32 (1H, dd, J=8.2, 1.8 Hz), 7.35 (1H, dd, J=7.6, 1.7 Hz), 7.38-7.46 (2H, m), 8.03 (1H, d, J=8.2 Hz), 8.78 (1H, d, J=1.7 Hz), 11.05 (1H, s), 12.30-12.54 (1H, broad), 13.10-13.90 (1H, broad).

2-(2-Hydroxy-5-(morpholin-4-yl)benzamido)-4-(3-methoxyphenyl)benzoic acid $^1$H-NMR (DMSO-d$_6$) δ: 3.00-3.07 (4H, m), 3.70-3.79 (4H, m), 3.85 (3H, s), 6.94 (1H, d, J=8.9 Hz), 7.01-7.07 (1H, m), 7.18 (1H, dd, J=8.9, 3.1 Hz), 7.21-7.26 (1H, m), 7.26-7.32 (1H, m), 7.43 (1H, d, J=3.1 Hz), 7.45 (1H, dd, J=7.9, 7.9 Hz), 7.52 (1H, dd, J=8.3, 1.8 Hz), 8.09 (1H, d, J=8.3 Hz), 8.99 (1H, d, J=1.8 Hz), 10.99 (1H, s), 12.31 (1H, s), 13.20-13.90 (1H, broad).

2-(2-Hydroxy-5-(morpholin-4-yl)benzamido)-4-(4-methoxyphenyl)benzoic acid $^1$H-NMR (DMSO-d$_6$) δ: 2.99-3.08 (4H, m), 3.71-3.80 (4H, m), 3.83 (3H, s), 6.94 (1H, d, J=8.8 Hz), 7.06-7.13 (2H, m), 7.18 (1H, dd, J=8.8, 3.0 Hz), 7.42 (1H, d, J=3.0 Hz), 7.47 (1H, dd, J=8.3, 1.8 Hz), 7.65-7.72 (2H, m), 8.06 (1H, d, J=8.3 Hz), 8.98 (1H, d, J=1.8 Hz), 11.00 (1H, s), 12.33 (1H, s).

4-(Furan-3-yl)-2-(2-hydroxy-5-(morpholin-4-yl)benzamido)benzoic acid $^1$H-NMR (DMSO-d$_6$) δ: 2.98-3.09 (4H, m), 3.70-3.81 (4H, m), 6.93 (1H, d, J=8.9 Hz), 6.94-7.00 (1H, m), 7.18 (1H, dd, J=8.9, 2.9 Hz), 7.42 (1H, d, J=2.9 Hz), 7.46 (1H, dd, J=8.3, 1.5 Hz), 7.80-7.85 (1H, m), 8.02 (1H, d, J=8.3 Hz), 8.30 (1H, s), 8.86 (1H, d, J=1.5 Hz), 11.02 (1H, s), 12.28 (1H, s).

4-(Benzo-[1,3]-dioxazol-5-yl)-2-(2-hydroxy-5-(morpholin-4-yl)benzamido)benzoic acid $^1$H-NMR (DMSO-d$_6$) δ: 2.99-3.08 (4H, m), 3.71-3.80 (4H, m), 6.11 (2H, s), 6.93 (1H, d, J=9.0 Hz), 7.07 (1H, d, J=8.1 Hz), 7.18 (1H, dd, J=9.0, 3.0 Hz), 7.23 (1H, dd, J=8.1, 1.8 Hz), 7.29 (1H, d, J=1.8 Hz), 7.42 (1H, d, J=3.0 Hz), 7.45 (1H, dd, J=8.3, 1.7 Hz), 8.05 (1H, d, J=8.3 Hz), 8.94 (1H, d, J=1.7 Hz), 10.99 (1H, s), 12.27-12.40 (1H, broad).

4-(2,3-Dihydrobenzo[1,4]dioxin-6-yl)-2-(2-hydroxy-5-(morpholin-4-yl)benzamido)benzoic acid $^1$H-NMR (DMSO-d$_6$) δ: 3.00-3.07 (4H, m), 3.72-3.79 (4H, m), 4.31 (41H, s), 6.93 (1H, d, J=9.0 Hz), 6.98-7.04 (1H, m), 7.18 (1H, dd, J=8.9, 3.0 Hz), 7.18-7.24 (2H, m), 7.42 (1H, d, J=3.0 Hz), 7.45 (1H, dd, J=8.4, 1.8 Hz), 8.04 (1H, d, J=8.4 Hz), 8.94 (1H, d, J=1.8 Hz), 10.97 (1H, s), 12.30 (1H, s).

4-(3,4-Dimethoxyphenyl)-2-(2-hydroxy-5-(morpholin-4-yl)benzamido)benzoic acid $^1$H-NMR (DMSO-d$_6$) δ: 2.99-3.06 (4H, m), 3.70-3.77 (4H, m), 3.80 (3H, s), 3.84 (3H, s), 6.89 (1H, d, J=9.0 Hz), 7.04-7.12 (1H, m), 7.16 (1H, dd, J=9.0, 2.7 Hz), 7.20-7.26 (2H, m), 7.41 (1H, dd, J=8.3, 1.7 Hz), 7.47 (1H, d, J=2.7 Hz), 8.06 (1H, d, J=8.3 Hz), 8.89 (1H, d, J=1.7 Hz), 11.30-11.90 (1H, broad), 13.90-14.45 (1H, broad).

4-(3,5-Dimethoxyphenyl)-2-(2-hydroxy-5-(morpholin-4-yl)benzamido)benzoic acid $^1$H-NMR (DMSO-d$_6$) δ: 2.99-3.07 (4H, m), 3.71-3.79 (4H, m), 3.83 (6H, s), 6.60 (1H, dd, J=2.2, 2.2 Hz), 6.82 (2H, d, J=2.2 Hz), 6.94 (1H, d, J=9.0 Hz), 7.17 (1H, dd, J=9.0, 3.1 Hz), 7.42 (1H, d, J=3.1 Hz), 7.51 (1H, dd, J=8.3, 1.9 Hz), 8.07 (1H, d, J=8.3 Hz), 8.95 (1H, d, J=1.9 Hz), 10.98 (1H, s), 12.28 (1H, s), 13.30-13.80 (1H, broad).

Example 211a

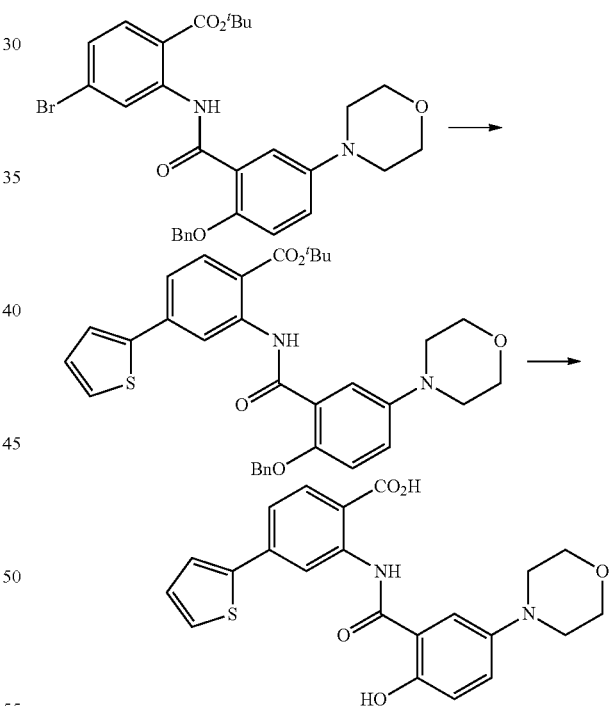

Ethylene glycol dimethyl ether (2.0 mL), water (0.60 mL), thiophene-2-boronic acid (0.054 g), sodium carbonate (0.093 g), and bis(triphenylphosphine)palladium(II) dichloride (4.9 mg) were added to tert-butyl 2-(2-(benzyloxy)-5-(morpholin-4-yl)benzamido)-4-bromobenzoate (0.20 g), followed by heating to reflux under a nitrogen atmosphere for 2 hours. The reaction mixture was cooled to room temperature, and water and ethyl acetate were added thereto. The organic layer was separated and dried over anhydrous magnesium sulfate, and the solvent was evaporated under reduced pressure. The obtained residue was purified by silica gel column chromatography [eluent: 85-70% hexane/ethyl acetate] to obtain 0.19 g of tert-butyl 2-(2-(benzyloxy)-5-(morpholin-4-yl)benzamido)-4-(thiophen-2-yl)benzoate as a light yellow solid.

Thioanisole (2.0 mL) and trifluoroacetic acid (6.8 mL) were added to the obtained tert-butyl 2-(2-(benzyloxy)-5-(morpholin-4-yl)benzamido)-4-(thiophen-2-yl)benzoate (0.19 g), followed by stirring at room temperature for 24 hours. The solvent was evaporated under reduced pressure, and ethyl acetate was added to the residue. The solid substance was collected by filtration, and water and 2-propanol were added to the obtained solid substance. After adjusting the pH to 6.0 with a saturated aqueous solution of sodium bicarbonate, the solid substance was collected by filtration to obtain 0.11 g of 2-(2-hydroxy-5-(morpholin-4-yl)benzamido)-4-(thiophen-2-yl)benzoic acid as a yellow solid.

$^1$H-NMR (DMSO-$d_6$) δ: 2.98-3.09 (4H, m), 3.70-3.80 (4H, m), 6.94 (1H, d, J=9.0 Hz), 7.18 (1H, dd, J=9.0, 2.9 Hz), 7.21 (1H, dd, J=5.1, 3.7 Hz), 7.42 (1H, d, J=2.9 Hz), 7.53 (1H, dd, J=8.3, 1.7 Hz), 7.61-7.67 (1H, m), 7.67-7.73 (1H, m), 8.04 (1H, d, J=8.3 Hz), 9.06 (1H, d, J=1.7 Hz), 10.96 (1H, s), 12.36 (1H, s), 13.26-13.80 (1H, broad).

Example 212a

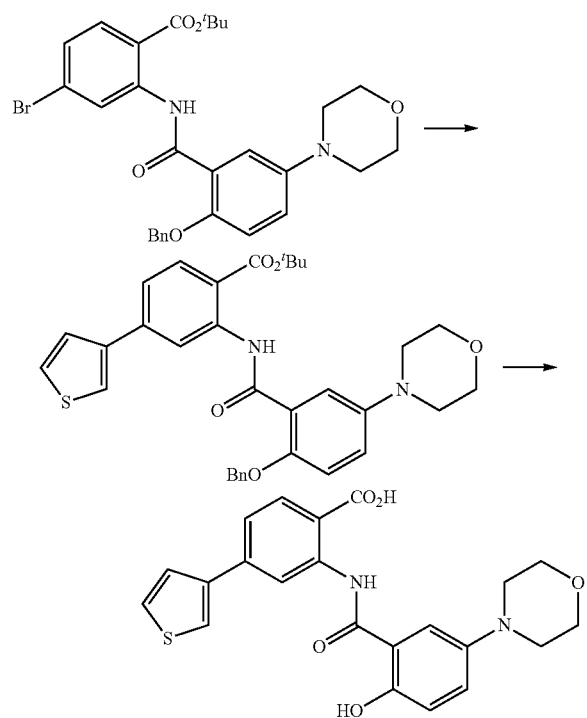

As in Example 211a, the following compound was prepared.

2-(2-Hydroxy-5-(morpholin-4-yl)benzamido)-4-(thiophen-3-yl)benzoic acid $^1$H-NMR (DMSO-$d_6$) δ: 2.98-3.08 (4H, m), 3.70-3.81 (4H, m), 6.94 (1H, d, J=8.9 Hz), 7.18 (1H, dd, J=8.9, 3.0 Hz), 7.42 (1H, d, J=3.0 Hz), 7.53-7.62 (2H, m), 7.72 (1H, dd, J=5.1, 2.9 Hz), 7.98-8.03 (1H, m), 8.05 (1H, d, J=8.3 Hz), 9.01 (1H, d, J=1.7 Hz), 11.01 (1H, s), 12.27 (1H, s), 13.20-13.80 (1H, broad).

Example 213a

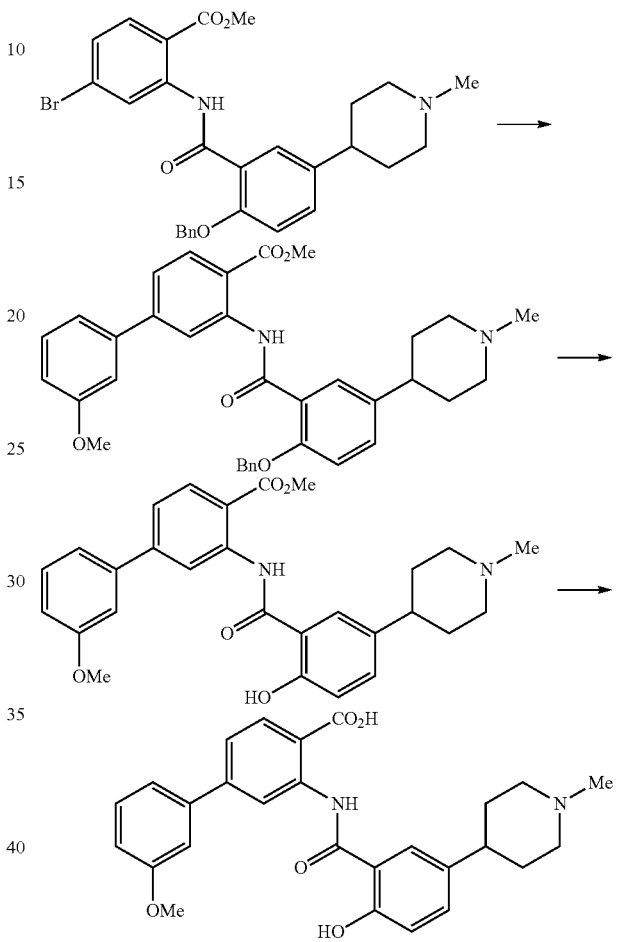

Ethylene glycol dimethyl ether (0.90 mL), water (0.27 mL), 3-methoxyphenylboronic acid (0.030 g), sodium carbonate (0.044 g), and bis(triphenylphosphine)palladium(II) dichloride (2.3 mg) were added to methyl 2-(2-(benzyloxy)-5-(1-methylpiperidin-4-yl)benzamido)-4-bromobenzoate (0.090 g), followed by heating to reflux under a nitrogen atmosphere for 2 hours. The reaction mixture was cooled to room temperature, and water and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 100-92% chloroform/methanol] to obtain 0.093 g of methyl 2-(2-(benzyloxy)-5-(1-methylpiperidin-4-yl)benzamido)-4-(3-methoxyphenyl)benzoate as a light brown solid.

To a solution mixture of the obtained methyl 2-(2-(benzyloxy)-5-(1-methylpiperidin-4-yl)benzamido)-4-(3-methoxyphenyl)benzoate (0.093 g) in methanol (2.0 mL) and ethyl acetate (2.0 mL), 10% palladium-carbon (0.050 g) was added, followed by stirring under a hydrogen atmosphere at room temperature for 2 hours. Chloroform was added to the reaction mixture. The insoluble substance was removed by filtration, and the solvent was evaporated under reduced pressure. The obtained residue was purified by silica gel column chromatography [eluent: 100-92% chloroform/methanol] to obtain 0.026 g of methyl 2-(2-hydroxy-5-(1-methylpiperidin-4-yl)benzamido)-4-(3-methoxyphenyl)benzoate as a white solid.

A 2.0 mol/L aqueous solution of sodium hydroxide (0.27 mL) was added to a methanol (1.0 mL) suspension of the obtained methyl 2-(2-hydroxy-5-(1-methylpiperidin-4-yl)benzamido)-4-(3-methoxyphenyl)benzoate (0.026 g), followed by stirring at 50° C. for 3 hours. After cooling the reaction mixture to room temperature and adjusting the pH to 6.0 with 2.0 mol/L hydrochloric acid, the solid substance was collected by filtration to obtain 0.025 g of 2-(2-hydroxy-5-(1-methylpiperidin-4-yl)benzamido)-4-(3-methoxyphenyl)benzoic acid as a light yellow solid.

$^1$H-NMR (DMSO-d$_6$+D$_2$O) δ: 1.85-2.12 (4H, m), 2.80-2.94 (1H, m), 2.83 (3H, s), 3.04-3.16 (2H, m), 3.47-3.59 (2H, m), 3.84 (3H, s), 6.96 (1H, d, J=8.3 Hz), 7.01 (1H, dd, J=8.3, 2.0 Hz), 7.16-7.22 (1H, m), 7.27 (1H, d, J=8.0 Hz), 7.38-7.50 (3H, m), 7.92 (1H, d, J=2.2 Hz), 8.15 (1H, d, J=8.1 Hz), 8.90 (1H, d, J=1.7 Hz).

Examples 214a and 215a

As in Example 213a, the compounds shown in Table 24a were prepared.

TABLE 24a

| Example No. | R$^3$ |
|---|---|
| 214a | 3-fluorophenyl |
| 215a | 4-fluorophenyl |

4-(3-Fluorophenyl)-2-(2-hydroxy-5-(1-methylpiperidin-4-yl)benzamido)benzoic acid $^1$H-NMR (DMSO-d$_6$+D$_2$O) δ: 1.84-2.12 (4H, m), 2.80-2.94 (1H, m), 2.83 (3H, s), 3.04-3.18 (2H, m), 3.48-3.60 (2H, m), 6.96 (1H, d, J=8.6 Hz), 7.21-7.30 (1H, m), 7.37-7.62 (5H, m), 7.92 (1H, d, J=1.9 Hz), 8.17 (1H, d, J=8.3 Hz), 8.92 (1H, d, J=1.7 Hz).

4-(4-Fluorophenyl)-2-(2-hydroxy-5-(1-methylpiperidin-4-yl)benzamido)benzoic acid $^1$H-NMR (DMSO-d$_6$+D$_2$O) δ: 1.83-2.12 (4H, m), 2.80-2.95 (1H, m), 2.83 (3H, s), 3.02-3.20 (2H, m), 3.46-3.60 (2H, m), 6.96 (1H, d, J=8.6 Hz), 7.31-7.44 (4H, m), 7.70-7.78 (2H, m), 7.93 (1H, d, J=1.9 Hz), 8.15 (1H, d, J=8.3 Hz), 8.89 (1H, d, J=1.9 Hz).

Example 216a

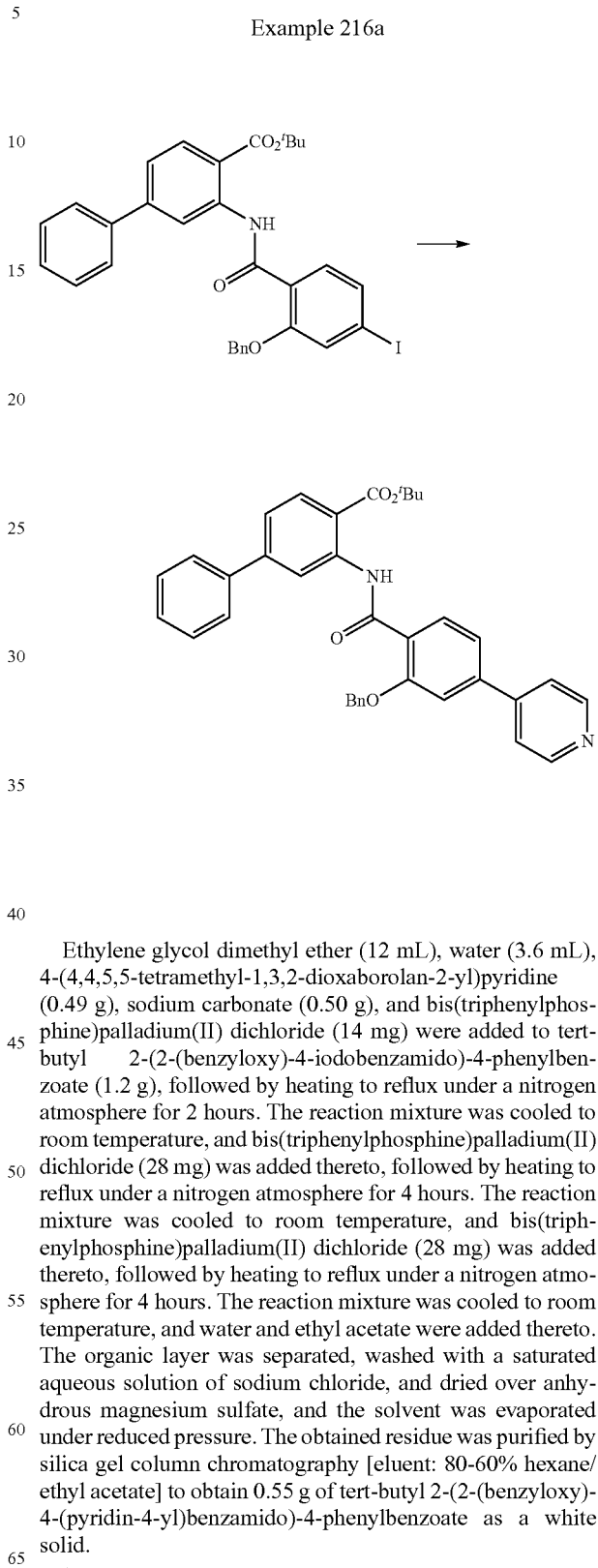

Ethylene glycol dimethyl ether (12 mL), water (3.6 mL), 4-(4,4,5,5-tetramethyl-1,3,2-dioxaborolan-2-yl)pyridine (0.49 g), sodium carbonate (0.50 g), and bis(triphenylphosphine)palladium(II) dichloride (14 mg) were added to tert-butyl 2-(2-(benzyloxy)-4-iodobenzamido)-4-phenylbenzoate (1.2 g), followed by heating to reflux under a nitrogen atmosphere for 2 hours. The reaction mixture was cooled to room temperature, and bis(triphenylphosphine)palladium(II) dichloride (28 mg) was added thereto, followed by heating to reflux under a nitrogen atmosphere for 4 hours. The reaction mixture was cooled to room temperature, and bis(triphenylphosphine)palladium(II) dichloride (28 mg) was added thereto, followed by heating to reflux under a nitrogen atmosphere for 4 hours. The reaction mixture was cooled to room temperature, and water and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 80-60% hexane/ethyl acetate] to obtain 0.55 g of tert-butyl 2-(2-(benzyloxy)-4-(pyridin-4-yl)benzamido)-4-phenylbenzoate as a white solid.

$^1$H-NMR (DMSO-d$_6$) δ: 1.51 (9H, s), 5.66 (2H, s), 7.25-7.37 (3H, m), 7.44-7.49 (1H, m), 7.51-7.59 (6H, m), 7.62-

7.66 (1H, m), 7.71-7.78 (4H, m), 8.04-8.11 (2H, m), 8.66-8.73 (2H, m), 9.07-9.12 (1H, m), 12.21 (1H, s).

Example 217a

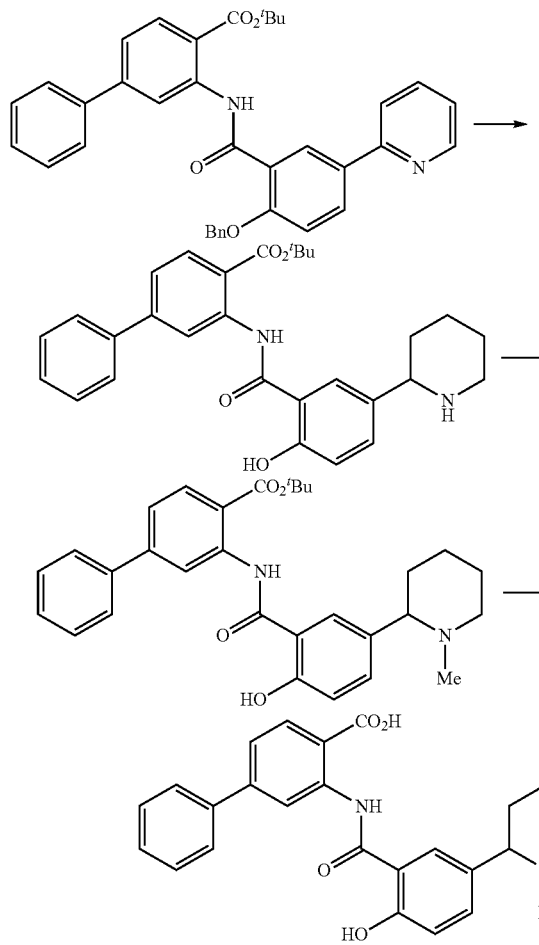

To an acetic acid (5 mL) solution of tert-butyl 2-(2-(benzyloxy)-5-(pyridin-2-yl)benzamido)-4-phenylbenzoate (0.12 g), 10% palladium-carbon (0.060 g) was added, followed by stirring under hydrogen pressure (5 kg/cm²) at 80° C. for 2 hours and 30 minutes. The reaction mixture was cooled to room temperature, and methanol and acetic acid were added thereto. The insoluble substance was removed by filtration, and the solvent was removed under reduced pressure. Chloroform and a saturated aqueous solution of sodium bicarbonate were added to the residue. The organic layer was separated, washed with a saturated aqueous solution of sodium chloride, and dried over anhydrous magnesium sulfate, and the solvent was evaporated under reduced pressure. Diisopropyl ether was added to the obtained residue, and the solid substance was collected by filtration to obtain 0.062 g of tert-butyl 2-(2-hydroxy-5-(piperidin-2-yl)benzamido)-4-phenylbenzoate as a white solid.

$^1$H-NMR (CDCl$_3$) δ: 1.46-1.75 (4H, m), 1.67 (9H, s), 1.81-1.98 (2H, m), 2.77-2.89 (1H, m), 3.14-3.25 (1H, m), 3.64 (1H, dd, J=10.8, 2.1 Hz), 6.97 (1H, d, J=8.4 Hz), 7.36 (1H, dd, J=8.4, 1.7 Hz), 7.38-7.44 (1H, m), 7.44-7.52 (3H, m), 7.66-7.73 (2H, m), 7.91 (1H, d, J=1.7 Hz), 8.08 (1H, d, J=8.3 Hz), 9.05 (1H, d, J=1.7 Hz), 12.55 (1H, s).

A 37% aqueous solution of formaldehyde (8.2 μL), acetic acid (9.7 μL), and sodium triacetoxyborohydride (0.045 g) were sequentially added to a methylene chloride (1.5 mL) solution of the obtained tert-butyl 2-(2-hydroxy-5-(piperidin-2-yl)benzamido)-4-phenylbenzoate (0.040 g), followed by stirring at room temperature for 3 hours. The solvent was evaporated under reduced pressure, and chloroform was added thereto. The insoluble substance was removed by filtration, and then a saturated aqueous solution of sodium bicarbonate was added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 100-92% chloroform/methanol] to obtain 0.040 g of tert-butyl 2-(2-hydroxy-5-(1-methylpiperidin-2-yl)benzamido)-4-phenylbenzoate as a white solid.

Trifluoroacetic acid (2.0 mL) was added to the obtained tert-butyl 2-(2-hydroxy-5-(1-methylpiperidin-2-yl)benzamido)-4-phenylbenzoate (0.040 g), followed by stirring at room temperature for 1 hour. The solvent was evaporated under reduced pressure, and methanol and water were added to the residue. After adjusting the pH to 6.0 with a saturated aqueous solution of sodium bicarbonate, the solid substance was collected from the reaction mixture by filtration to obtain 0.034 g of 2-(2-hydroxy-5-(1-methylpiperidin-2-yl)benzamido)-4-phenylbenzoic acid as a white solid.

$^1$H-NMR (DMSO-d$_6$+D$_2$O) δ: 1.56-1.73 (1H, m), 1.80-2.12 (5H, m), 2.48 (3H, s), 3.01-3.19 (1H, m), 3.45-3.59 (1H, m), 4.12-4.29 (1H, m), 7.09 (1H, d, J=8.6 Hz), 7.39-7.47 (2H, m), 7.48-7.62 (3H, m), 7.65-7.74 (2H, m), 8.00 (1H, d, J=1.7 Hz), 8.14 (1H, d, J=8.0 Hz), 8.89 (1H, d, J=1.5 Hz).

Example 218a

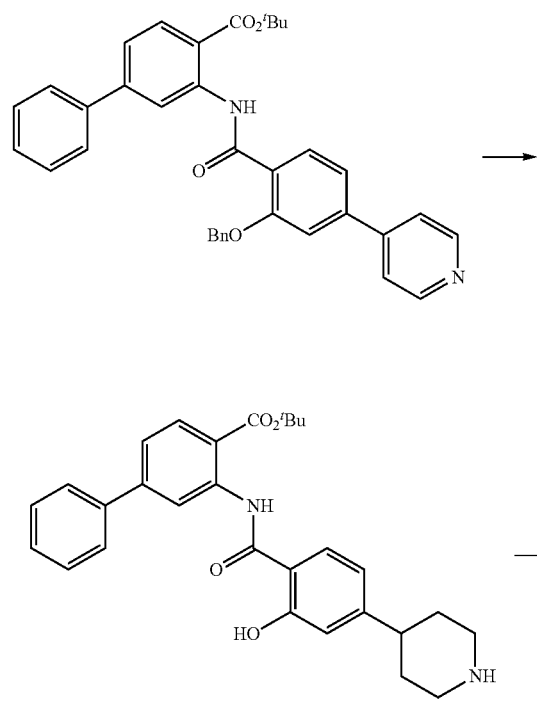

-continued

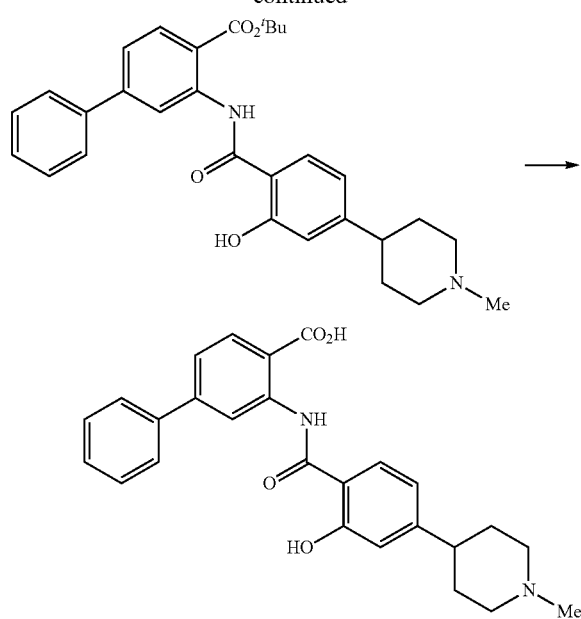

As in Example 217a, the following compound was prepared.

2-(2-Hydroxy-4-(1-methylpiperidin-4-yl)benzamido)-4-phenylbenzoic acid $^1$H-NMR (DMSO-$d_6$) δ: 1.76-2.08 (4H, m), 2.72-2.84 (1H, m), 2.76 (3H, s), 2.87-3.02 (2H, m), 3.40-3.53 (2H, m), 6.74-6.84 (2H, m), 7.35-7.43 (2H, m), 7.46-7.54 (2H, m), 7.64-7.71 (2H, m), 7.88 (1H, d, J=8.1 Hz), 8.12 (1H, d, J=8.0 Hz), 8.87 (1H, d, J=1.7 Hz).

Example 219a

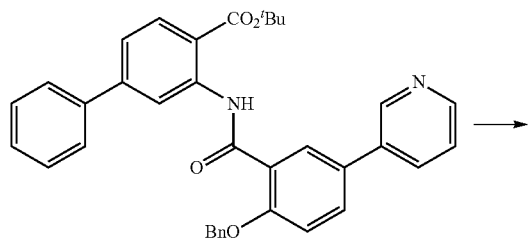

-continued

To an acetic acid (15 mL) solution of tert-butyl 2-(2-(benzyloxy)-5-(pyridin-3-yl)benzamido)-4-phenylbenzoate (0.88 g), 10% palladium-carbon (0.44 g) was added, followed by stirring under hydrogen pressure (5 kg/cm$^2$) at 80° C. for 3 hours. The reaction mixture was cooled to room temperature, and methanol and acetic acid were added thereto. The insoluble substance was removed by filtration. The solvent was removed under reduced pressure, and chloroform and a saturated aqueous solution of sodium bicarbonate were added to the residue. The organic layer was separated, washed with a saturated aqueous solution of sodium chloride, and dried over anhydrous magnesium sulfate, and the solvent was evaporated under reduced pressure. Diisopropyl ether was added to the obtained residue, and the solid substance was collected by filtration to obtain 0.51 g of tert-butyl 2-(2-hydroxy-5-(piperidin-3-yl)benzamido)-4-phenylbenzoate as a white solid.

Trifluoroacetic acid (2.0 mL) was added to the obtained tert-butyl 2-(2-hydroxy-5-(piperidin-3-yl)benzamido)-4-phenylbenzoate (0.10 g), followed by stirring at room temperature for 3 hours. The solvent was evaporated under reduced pressure, and methanol and water were added the residue. After adjusting the pH to 6.0 with a saturated aqueous solution of sodium bicarbonate, the solid substance was collected from the reaction mixture by filtration to obtain 0.088 g of 2-(2-hydroxy-5-(piperidin-3-yl)benzamido)-4-phenylbenzoic acid as a white solid.

$^1$H-NMR (DMSO-$d_6$+$D_2O$) δ: 1.68-2.04 (4H, m), 2.92-3.09 (3H, m), 3.26-3.41 (2H, m), 7.01 (1H, d, J=8.6 Hz), 7.40-7.50 (3H, m), 7.50-7.59 (2H, m), 7.67-7.74 (2H, m), 7.82 (1H, d, J=2.0 Hz), 8.15 (1H, d, J=8.1 Hz), 8.90 (1H, d, J=1.7 Hz).

Example 220a

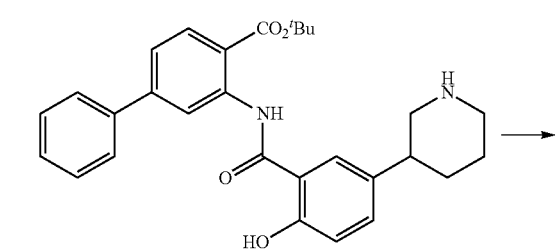

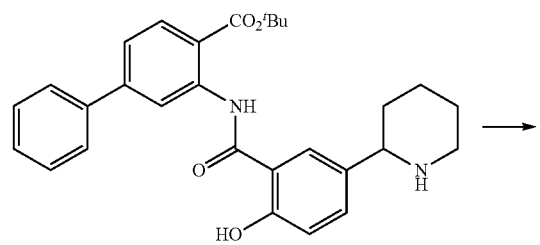

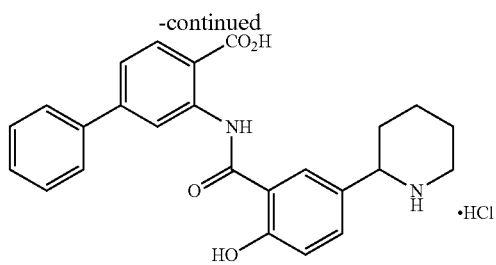

Trifluoroacetic acid (1.0 mL) was added to tert-butyl 2-(2-hydroxy-5-(piperidin-2-yl)benzamido)-4-phenylbenzoate (0.015 g), followed by stirring at room temperature for 1 hour. The solvent was evaporated under reduced pressure, and methanol and water were added to the residue. After adjusting the pH to 6.0 with a saturated aqueous solution of sodium bicarbonate, the solid substance was collected from the reaction mixture by filtration. Ethyl acetate (1.0 mL) and a 2.5 mol/L hydrogen chloride-ethyl acetate solution (1.0 mL) were added to the solid substance, followed by stirring at room temperature for 30 minutes. The solid substance was collected from the reaction mixture by filtration to obtain 0.010 g of 2-(2-hydroxy-5-(piperidin-2-yl)benzamido)-4-phenylbenzoic acid hydrochloride as a white solid.

$^1$H-NMR (DMSO-$d_6$+$D_2O$) δ: 1.56-1.78 (2H, m), 1.79-2.01 (4H, m), 2.98-3.12 (1H, m), 3.27-3.37 (1H, m), 4.20 (1H, dd, J=11.2, 3.2 Hz), 7.10 (1H, d, J=8.5 Hz), 7.44-7.60 (5H, m), 7.70-7.76 (2H, m), 8.09 (1H, d, J=2.4 Hz), 8.12 (1H, d, J=8.3 Hz), 9.03 (1H, d, J=2.0 Hz).

Example 221a

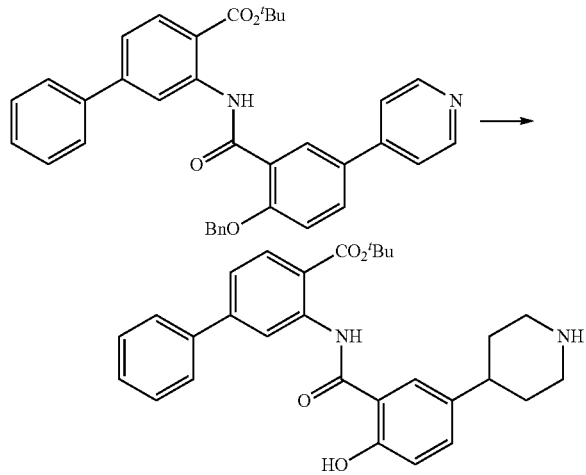

To an acetic acid (20 mL) solution of tert-butyl 2-(2-(benzyloxy)-5-(pyridin-4-yl)benzamido)-4-phenylbenzoate (0.77 g), 10% palladium-carbon (0.35 g) was added, followed by stirring under hydrogen pressure (5 kg/cm$^2$) at 70 to 80° C. for 7 hours. The reaction mixture was cooled to room temperature, and acetic acid, methanol, and chloroform were added thereto. The insoluble substance was removed by filtration. The solvent was removed under reduced pressure, and then chloroform and a saturated aqueous solution of sodium bicarbonate were added to the residue. The organic layer was separated, washed with a saturated aqueous solution of sodium chloride, and dried over anhydrous magnesium sulfate, and the solvent was evaporated under reduced pressure. Diisopropyl ether was added to the obtained residue, and the solid substance was collected by filtration to obtain 0.36 g of tert-butyl 2-(2-hydroxy-5-(piperidin-4-yl)benzamido)-4-phenylbenzoate as a white solid.

$^1$H-NMR (CDCl$_3$) δ: 1.59-1.78 (2H, m), 1.67 (9H, s), 1.91-2.03 (2H, m), 2.60-2.74 (1H, m), 2.76-2.88 (2H, m), 3.19-3.32 (2H, m), 6.98 (1H, d, J=8.5 Hz), 7.33 (1H, dd, J=8.5, 2.2 Hz), 7.37 (1H, dd, J=8.4, 1.9 Hz), 7.38-7.53 (3H, m), 7.66-7.77 (3H, m), 8.09 (1H, d, J=8.4 Hz), 9.08 (1H, d, J=1.9 Hz), 12.57 (1H, s).

Example 222a

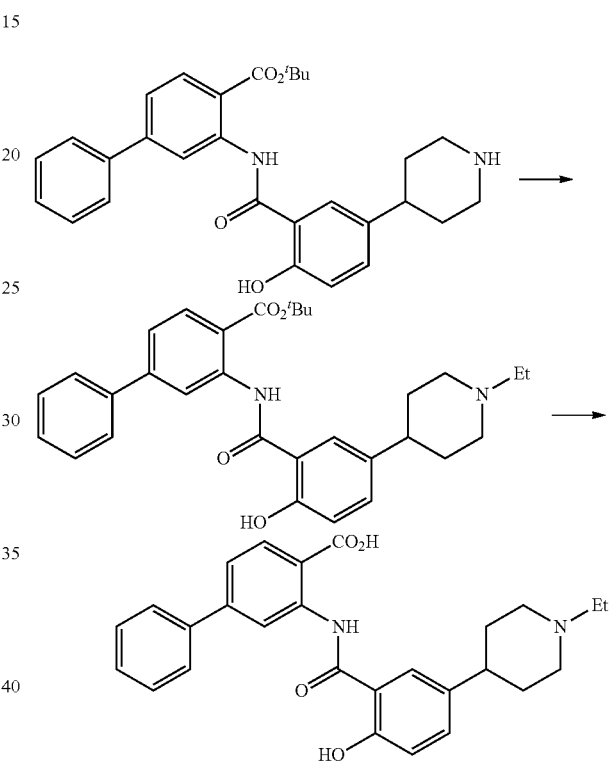

Acetaldehyde (0.016 mL), acetic acid (0.024 mL), and sodium triacetoxyborohydride (0.11 g) were sequentially added to a methylene chloride (1.0 mL) suspension of tert-butyl 2-(2-hydroxy-5-(piperidin-4-yl)benzamido)-4-phenylbenzoate (0.10 g), followed by stirring at room temperature for 1 hour. Acetaldehyde (0.016 mL) and sodium triacetoxyborohydride (0.11 g) were sequentially added to the reaction mixture, followed by stirring at room temperature for 2 hours. The solvent was evaporated under reduced pressure, and ethyl acetate was added to the residue. After removal of the insoluble substance by filtration, a saturated aqueous solution of sodium bicarbonate was added thereto. The organic layer was separated, washed with a saturated aqueous solution of sodium chloride, and dried over anhydrous sodium sulfate, and the solvent was evaporated under reduced pressure. The obtained residue was purified by silica gel column chromatography [eluent: 100-90% chloroform/methanol] to obtain 0.045 g of tert-butyl 2-(5-(1-ethylpiperidin-4-yl)-2-hydroxybenzamido)-4-phenylbenzoate as a light yellow solid.

Trifluoroacetic acid (2.0 mL) was added to the obtained tert-butyl 2-(5-(1-ethylpiperidin-4-yl)-2-hydroxybenzamido)-4-phenylbenzoate (0.040 g), followed by stirring at room temperature for 3 hours. The solvent was evaporated under reduced pressure, and methanol and water were added to the residue. After adjusting the pH to 6.0 with a saturated aqueous solution of sodium bicarbonate, the solid substance was collected from the reaction mixture by filtration to obtain 5.0 mg of 2-(5-(1-ethylpiperidin-4-yl)-2-hydroxybenzamido)-4-phenylbenzoic acid as a white solid.

$^1$H-NMR (DMSO-$d_6$+$D_2O$) δ: 1.29 (3H, t, J=7.3 Hz), 1.85-2.15 (4H, m), 2.83-3.10 (3H, m), 3.10-3.23 (2H, m), 3.54-3.66 (2H, m), 6.96 (1H, d, J=8.3 Hz), 7.38-7.48 (3H, m), 7.50-7.57 (2H, m), 7.66-7.74 (2H, m), 7.94 (1H, d, J=1.2 Hz), 8.16 (1H, d, J=8.3 Hz), 8.92 (1H, d, J=1.7 Hz).

Example 223a

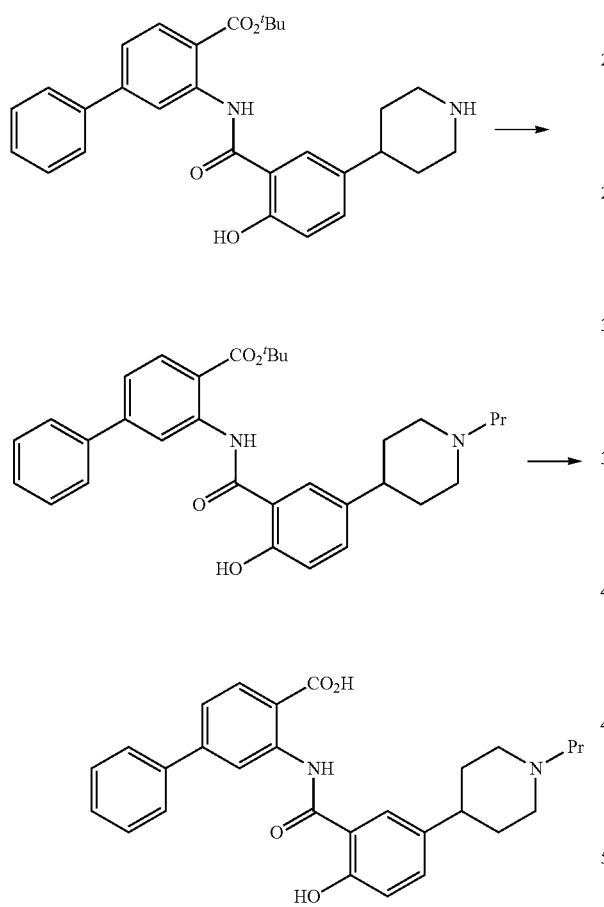

As in Example 222a, the following compound was prepared.

2-(2-Hydroxy-5-(1-propylpiperidin-4-yl)benzamido)-4-phenylbenzoic acid $^1$H-NMR (DMSO-$d_6$+$D_2O$) δ: 0.95 (3H, t, J=7.5 Hz), 1.64-1.79 (2H, m), 1.88-2.12 (4H, m), 2.81-3.15 (5H, m), 3.49-3.67 (2H, m), 6.96 (1H, d, J=8.3 Hz), 7.37-7.47 (3H, m), 7.49-7.57 (2H, m), 7.66-7.74 (2H, m), 7.95 (1H, d, J=1.7 Hz), 8.16 (1H, d, J=8.1 Hz), 8.92 (1H, d, J=1.7 Hz).

Example 224a

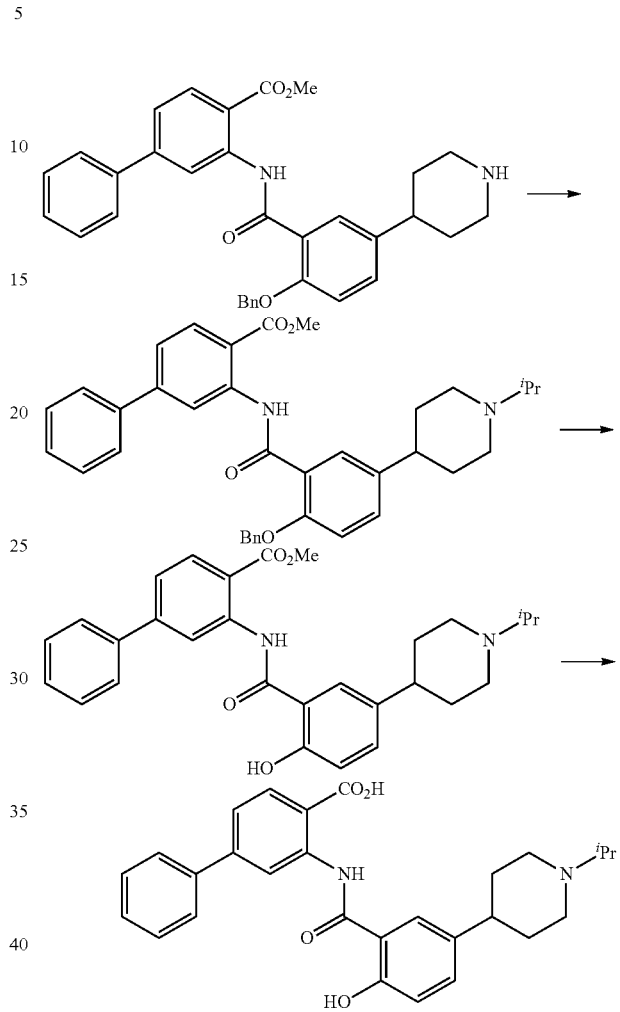

Potassium carbonate (0.033 mg) and isopropyl iodide (0.024 mL) were sequentially added to an acetonitrile (1.9 mL) suspension of methyl 2-(2-(benzyloxy)-5-(piperidin-4-yl)benzamido)-4-phenylbenzoate (0.13 g), followed by heating to reflux for 1 hour. The reaction mixture was cooled to room temperature, and potassium carbonate (6.7 mg) and isopropyl iodide (4.8 μL) were sequentially added thereto, followed by heating to reflux for 2 hours. After cooling the reaction mixture to room temperature, the solvent was evaporated under reduced pressure, and ethyl acetate and a saturated aqueous solution of sodium bicarbonate were added to the residue. The organic layer was separated, washed with a saturated aqueous solution of sodium chloride, and dried over anhydrous sodium sulfate, and the solvent was evaporated under reduced pressure. The obtained residue was purified by silica gel column chromatography [eluent: 100-95% chloroform/methanol] to obtain 0.12 g of methyl 2-(2-(benzyloxy)-5-(1-isopropylpiperidin-4-yl)benzamido)-4-phenylbenzoate as an orange oily sub stance.

To a solution mixture of the obtained methyl 2-(2-(benzyloxy)-5-(1-isopropylpiperidin-4-yl)benzamido)-4-phenylbenzoate (0.12 g) in ethyl acetate (1.5 mL) and methanol (1.5 mL), 10% palladium-carbon (0.12 g) was added, followed by stirring under a hydrogen atmosphere at room temperature for 1 hour. Chloroform was added to the reaction mixture, and the insoluble substance was removed by filtration. The solvent was evaporated under reduced pressure to obtain 0.086 g of methyl 2-(2-hydroxy-5-(1-isopropylpiperidin-4-yl)benzamido)-4-phenylbenzoate as an orange solid.

A 2.0 mol/L aqueous solution of sodium hydroxide (0.27 mL) was added to a 2-propanol (1.5 mL) suspension of the obtained methyl 2-(2-hydroxy-5-(1-isopropylpiperidin-4-yl)benzamido)-4-phenylbenzoate (0.086 g), followed by stirring at 50° C. for 1 hour. A 2.0 mol/L aqueous solution of sodium hydroxide (0.091 mL) was added to the reaction mixture, followed by stirring at 50° C. for 30 minutes. The reaction mixture was cooled to room temperature, and water was added thereto. After adjusting the pH to 6.0 with 1.0 mol/L hydrochloric acid, the solid substance was collected by filtration to obtain 0.062 g of 2-(2-hydroxy-5-(1-isopropylpiperidin-4-yl)benzamido)-4-phenylbenzoic acid as a light yellow solid.

$^1$H-NMR (DMSO-d$_6$-D$_2$O) δ: 1.31 (6H, d, J=6.6 Hz), 1.91-2.13 (4H, m), 2.83-2.98 (1H, m), 3.03-3.19 (2H, m), 3.43-3.54 (3H, m), 6.95 (1H, d, J=8.6 Hz), 7.37-7.46 (3H, m), 7.49-7.57 (2H, m), 7.66-7.74 (2H, m), 7.98 (1H, d, J=2.0 Hz), 8.17 (1H, d, J=8.0 Hz), 8.92 (1H, d, J=1.7 Hz).

Example 225a

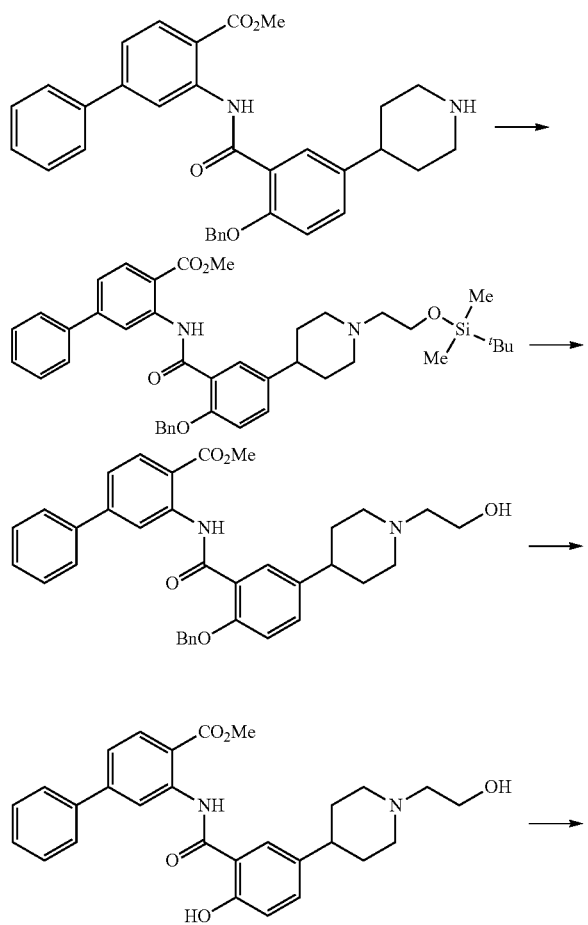

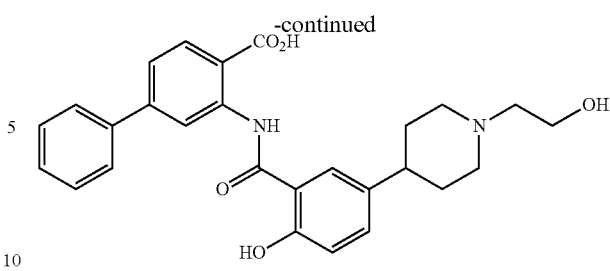

Acetic acid (0.023 mL), 2-(tert-butyldimethylsilyloxy)acetaldehyde (0.046 mL), and sodium triacetoxyborohydride (0.11 g) were sequentially added to a tetrahydrofuran (1.0 mL) solution of methyl 2-(2-(benzyloxy)-5-(piperidin-4-yl)benzamido)-4-phenylbenzoate (0.11 g), followed by stirring at room temperature for 13 hours. The solvent was evaporated under reduced pressure, and ethyl acetate was added to the residue. After removal of the insoluble substance by filtration, a saturated aqueous solution of sodium bicarbonate was added thereto. The organic layer was separated, washed with a saturated aqueous solution of sodium chloride, dried over anhydrous magnesium sulfate, and the solvent was evaporated under reduced pressure. The obtained residue was purified by silica gel column chromatography [eluent: 100-92% chloroform/methanol] to obtain 0.13 g of methyl 2-(2-(benzyloxy)-5-(1-(2-(tert-butyldimethylsilyloxy)ethyl)piperidin-4-yl)benzamido)-4-phenylbenzoate as a white solid.

A 1.0 mol/L tetrabutylammonium fluoride-tetrahydrofuran solution (0.38 mL) was added to a tetrahydrofuran (1.3 mL) solution of the obtained methyl 2-(2-(benzyloxy)-5-(1-(2-(tert-butyldimethylsilyloxy)ethyl)piperidin-4-yl)benzamido)-4-phenylbenzoate (0.13 g), followed by stirring at room temperature for 4 hours. Under ice-cooling, water and ethyl acetate were added to the reaction mixture. The organic layer was separated, washed with a saturated aqueous solution of sodium chloride, dried over anhydrous magnesium sulfate, and the solvent was evaporated under reduced pressure. The obtained residue was purified by silica gel column chromatography [eluent: 100-92% chloroform/methanol] to obtain 0.085 g of methyl 2-(2-(benzyloxy)-5-(1-(2-hydroxyethyl)piperidin-4-yl)benzamido)-4-phenylbenzoate as a white solid.

To a solution mixture of the obtained methyl 2-(2-(benzyloxy)-5-(1-(2-hydroxyethyl)piperidin-4-yl)benzamido)-4-phenylbenzoate (0.085 g) in ethyl acetate (1.0 mL) and methanol (1.0 mL), 10% palladium-carbon (0.040 g) was added, followed by stirring under a hydrogen atmosphere at room temperature for 2 hours. To the reaction mixture, 10% palladium-carbon (0.040 g) was added, followed by stirring under a hydrogen atmosphere at room temperature for 4 hours. The insoluble substance was removed from the reaction mixture by filtration, and the solvent was evaporated under reduced pressure. The obtained residue was purified by silica gel column chromatography [eluent: 100-92% chloroform/methanol] to obtain 0.035 g of methyl 2-(2-hydroxy-5-(1-(2-hydroxyethyl)piperidin-4-yl)benzamido)-4-phenylbenzoate as a white solid.

Methanol (1.0 mL) and a 2.0 mol/L aqueous solution of sodium hydroxide (0.37 mL) were added to the obtained methyl 2-(2-hydroxy-5-(1-(2-hydroxyethyl)piperidin-4-yl)benzamido)-4-phenylbenzoate (0.035 g), followed by stirring at 50° C. for 2 hours. After cooling the reaction mixture to room temperature and adjusting the pH to 6.0 with 2.0 mol/L hydrochloric acid, the solid substance was collected by filtration to obtain 0.030 g of 2-(2-hydroxy-5-(1-(2-hydroxyethyl)piperidin-4-yl)benzamido)-4-phenylbenzoic acid as a white solid.

$^1$H-NMR (DMSO-d$_6$+D$_2$O) δ: 1.92-2.13 (4H, m), 2.86-3.00 (1H, m), 3.05-3.27 (4H, m), 3.58-3.73 (2H, m), 3.77-3.87 (2H, m), 6.98 (1H, d, J=8.6 Hz), 7.40-7.49 (3H, m), 7.50-7.58 (2H, m), 7.67-7.75 (2H, m), 7.90 (1H, d, J=1.7 Hz), 8.16 (1H, d, J=8.0 Hz), 8.92 (1H, d, J=1.5 Hz).

Example 1b

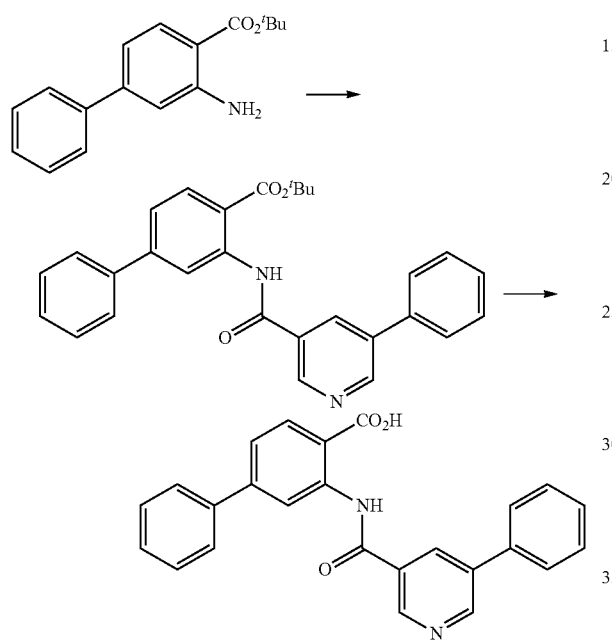

N,N-Dimethylformamide (0.9 µL) and oxalyl chloride (0.023 mL) were added to a methylene chloride (0.5 mL) suspension of 5-phenylpyridine-3-carboxylic acid (44 mg) at room temperature, followed by stirring at the same temperature for 1 hour. The reaction mixture was added to a solution mixture of tert-butyl 2-amino-4-phenylbenzoate (40 mg) in methylene chloride (1 mL) and triethylamine (0.17 mL) at room temperature, followed by stirring at the same temperature for 1 hour. The solvent was evaporated under reduced pressure, and ethyl acetate and a 10% aqueous solution of citric acid were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [Trikonex AB, FlashTube 2008, eluent: hexane/ethyl acetate=2:1] to obtain tert-butyl 4-phenyl-2-(5-phenylpyridine-3-carboxamido)benzoate.

Trifluoroacetic acid (5 mL) was added to the obtained tert-butyl 4-phenyl-2-(5-phenylpyridine-3-carboxamido)benzoate, followed by stirring at room temperature for 3 hours. The solvent was evaporated under reduced pressure, and ethyl acetate was added to the obtained residue. The solid substance was collected by filtration to obtain 40 mg of 4-phenyl-2-(5-phenylpyridine-3-carboxamido)benzoic acid as a white solid.

$^1$H-NMR (DMSO-d$_6$) δ: 7.45-7.61 (7H, m), 7.72-7.78 (2H, m), 7.81-7.87 (2H, m), 8.15 (1H, d, J=8.3 Hz), 8.56 (1H, dd, J=2.2, 2.2 Hz), 9.02 (1H, d, J=1.7 Hz), 9.14 (1H, d, J=2.0 Hz), 9.15 (1H, d, J=2.0 Hz), 12.33 (1H, s).

Example 2b

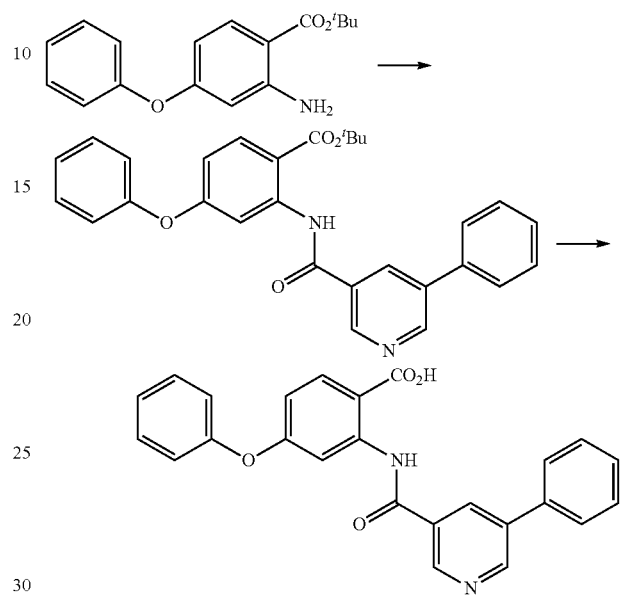

As in Example 1b, the following compound was prepared.

4-Phenoxy-2-(5-phenylpyridine-3-carboxamido)benzoic acid $^1$H-NMR (DMSO-d$_6$) δ: 6.83 (1H, dd, J=8.8, 2.5 Hz), 7.17-7.22 (2H, m), 7.27-7.33 (1H, m), 7.46-7.59 (5H, m), 7.79-7.85 (2H, m), 8.09 (1H, d, J=8.8 Hz), 8.36 (1H, d, J=2.5 Hz), 8.49 (1H, dd, J=2.2, 2.1 Hz), 9.07 (1H, d, J=2.1 Hz), 9.13 (1H, d, J=2.2 Hz), 12.54 (1H, s).

Example 3b

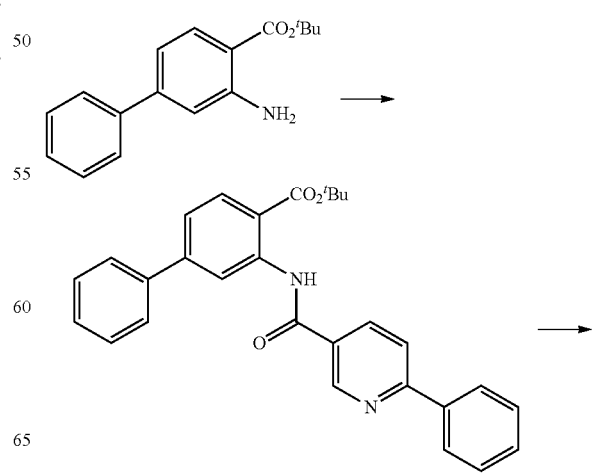

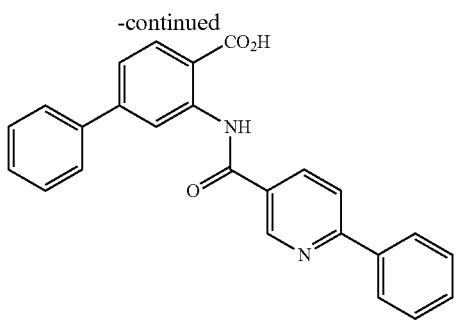

N,N-Dimethylformamide (0.9 μl) and oxalyl chloride (0.023 mL) were added to a methylene chloride (0.5 mL) suspension of 6-phenylpyridine-3-carboxylic acid (44 mg) at room temperature, followed by stirring at the same temperature for 1 hour. The reaction mixture was added to a solution mixture of tert-butyl 2-amino-4-phenylbenzoate (40 mg) in methylene chloride (1 mL) and triethylamine (0.17 mL) at room temperature, followed by stirring at same temperature for 1 hour. The solvent was evaporated under reduced pressure, and ethyl acetate and a 10% aqueous solution of citric acid were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [Trikonex AB, FlashTube 2008, eluent: hexane/ethyl acetate=2:1] to obtain tert-butyl 4-phenyl-2-(6-phenylpyridine-3-carboxamido)benzoate.

Trifluoroacetic acid (5 mL) was added to the obtained tert-butyl 4-phenyl-2-(6-phenylpyridine-3-carboxamido)benzoate, followed by stirring at room temperature for 3 hours. The solvent was evaporated under reduced pressure, and methanol was added to the obtained residue. The solid substance was collected by filtration to obtain 53 mg of 4-phenyl-2-(6-phenylpyridine-3-carboxamido)benzoic acid as a light yellow solid.

$^1$H-NMR (DMSO-$d_6$) δ: 7.44-7.60 (7H, m), 7.72-7.79 (2H, m), 8.16 (1H, d, J=8.3 Hz), 8.18-8.26 (3H, m), 8.39 (1H, dd, J=8.3, 2.4 Hz), 9.02-9.06 (1H, m), 9.24 (1H, d, J=1.7 Hz), 12.30 (1H, s).

Examples 4b and 5b

As in Example 3b, the compounds shown in Table 7b were prepared.

TABLE 7b

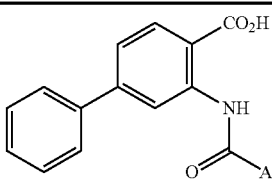

| Example No. | A |
|---|---|
| 4b | 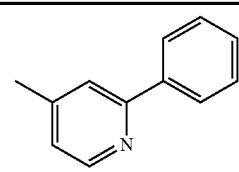 |

TABLE 7b-continued

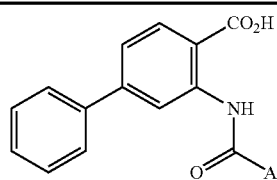

| Example No. | A |
|---|---|
| 5b | 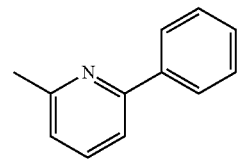 |

4-Phenyl-2-(2-phenylpyridine-4-carboxamido)benzoic acid $^1$H-NMR (DMSO-$d_6$) δ: 7.45-7.62 (7H, m), 7.72-7.78 (2H, m), 7.84 (1H, dd, J=4.9, 1.6 Hz), 8.13-8.20 (3H, m), 8.41 (1H, s), 8.94 (1H, d, J=4.9 Hz), 9.02 (1H, d, J=1.7 Hz), 12.39 (1H, s).

4-Phenyl-2-(6-phenylpyridine-2-carboxamido)benzoic acid $^1$H-NMR (DMSO-$d_6$) δ: 7.45-7.61 (7H, m), 7.73-7.80 (2H, m), 8.16-8.22 (3H, m), 8.29-8.36 (1H, m), 8.43-8.50 (2H, m), 9.28 (1H, d, J=1.7 Hz), 13.33 (1H, s), 13.60-13.80 (1H, broad).

Example 6b

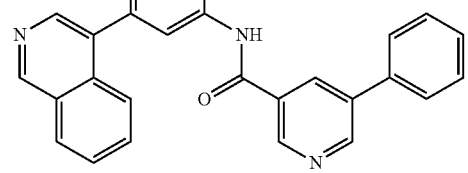

N,N-Dimethylformamide (2.3 μL) and oxalyl chloride (0.039 mL) were added to a methylene chloride (2 mL) suspension of 5-phenylpyridine-3-carboxylic acid (60 mg) at room temperature, followed by stirring at the same temperature for 1 hour. The solvent was evaporated under reduced pressure, and methylene chloride (1.5 mL) was added to the residue. The reaction mixture was added to a solution mixture of tert-butyl 2-amino-4-(isoquinolin-4-yl)benzoate (80 mg) in methylene chloride (2 mL) and pyridine (0.050 mL) at room temperature, followed by stirring at the same temperature for 1 hour. A saturated aqueous solution of sodium bicarbonate was added to the reaction mixture. The organic layer was separated, and the solvent was evaporated under reduced pressure. The obtained residue was purified by silica gel column chromatography [Fuji Silysia Chemical Ltd., PSQ100B (spherical), eluent: 90-50% hexane/ethyl acetate] to obtain 0.10 g of tert-butyl 4-(isoquinolin-4-yl)-2-(5-phenylpyridine-3-carboxamido)benzoate as a white solid.

Trifluoroacetic acid (5 mL) was added to the obtained tert-butyl 4-(isoquinolin-4-yl)-2-(5-phenylpyridine-3-carboxamido)benzoate (0.10 g), followed by stirring at room temperature for 4 hours. The solvent was evaporated under reduced pressure, and ethyl acetate and water were added to the residue. After adjusting the pH to 6.5 with a 2 mol/L aqueous solution of sodium hydroxide, the solid substance was collected by filtration to obtain 81 mg of 4-(isoquinolin-4-yl)-2-(5-phenylpyridine-3-carboxamido)benzoic acid as a light yellow solid.

Methanol (5 mL), dioxane (5 mL), and a 2 mol/L aqueous solution of sodium hydroxide (0.091 mL) were added to the obtained 4-(isoquinolin-4-yl)-2-(5-phenylpyridine-3-carboxamido)benzoic acid (81 mg), and the solvent was evaporated under reduced pressure. Diisopropyl ether was added to the obtained residue, and the solid substance was collected by filtration to obtain 83 mg of sodium 4-(isoquinolin-4-yl)-2-(5-phenylpyridine-3-carboxamido)benzoate as a light yellow solid.

$^1$H-NMR (DMSO-$d_6$) δ: 7.21 (1H, dd, J=7.9, 1.8 Hz), 7.46-7.53 (1H, m), 7.54-7.61 (2H, m), 7.73-7.79 (1H, m), 7.80-7.87 (3H, m), 7.96-8.01 (1H, m), 8.20-8.28 (2H, m), 8.49 (1H, s), 8.60 (1H, dd, J=2.2, 2.2 Hz), 8.88 (1H, d, J=1.8 Hz), 9.09 (1H, d, J=2.2 Hz), 9.17 (1H, d, J=2.0 Hz), 9.37 (1H, s).

Example 7b

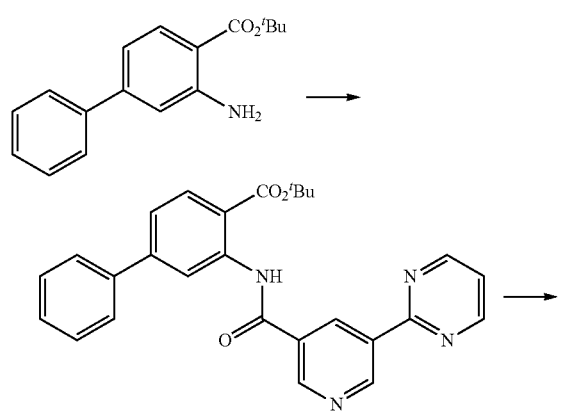

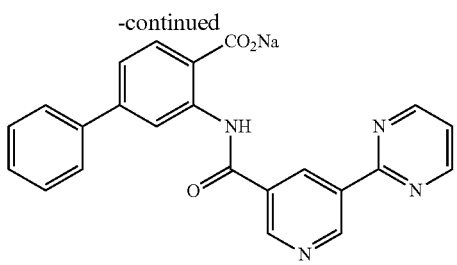

As in Example 6b, the following compound was prepared.

Sodium 4-phenyl-2-(5-(pyrimidin-2-yl)pyridine-3-carboxamido)benzoate $^1$H-NMR (DMSO-$d_6$) δ: 7.33 (1H, dd, J=8.1, 1.9 Hz), 7.37-7.43 (1H, m), 7.47-7.54 (2H, m), 7.60 (1H, t, J=4.9 Hz), 7.66-7.72 (2H, m), 8.12 (1H, d, J=8.1 Hz), 9.01-9.06 (3H, m), 9.28 (1H, dd, J=2.1, 2.0 Hz), 9.35 (1H, d, J=2.1 Hz), 9.67 (1H, d, J=2.0 Hz).

Example 8b

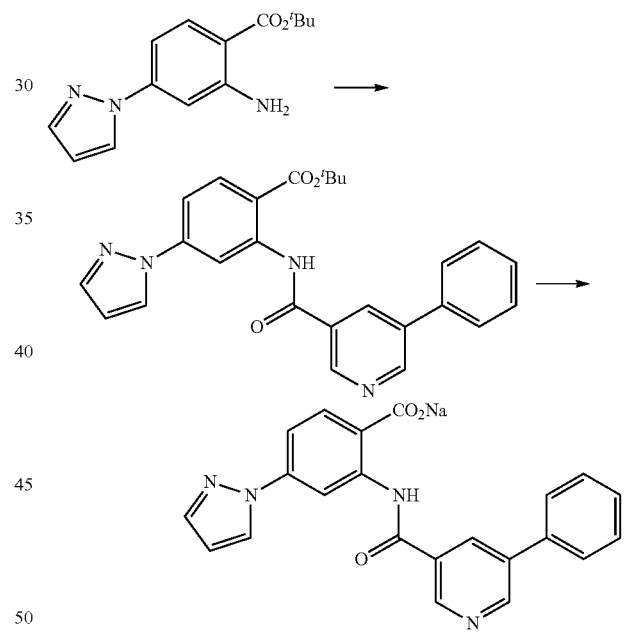

N,N-Dimethylformamide (2.2 μL) and oxalyl chloride (0.037 mL) were added to a methylene chloride (1.2 mL) suspension of 5-phenylpyridine-3-carboxylic acid (57 mg) at room temperature, followed by stirring at the same temperature for 1 hour and 30 minutes. The solvent was evaporated under reduced pressure, and methylene chloride (1.2 mL) was added to the residue. The reaction mixture was added to a solution mixture of tert-butyl 2-amino-4-(1H-pyrazol-1-yl)benzoate (62 mg) in methylene chloride (1.2 mL) and pyridine (0.048 mL) at room temperature, followed by stirring at the same temperature for 2 hours. Methylene chloride and a 1 mol/L aqueous solution of sodium hydroxide were added to the reaction mixture. The organic layer was separated, washed with a 1 mol/L aqueous solution of sodium hydroxide and a saturated aqueous solution of sodium chloride sequentially, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 90-70% hexane/ethyl acetate] to obtain 68 mg of tert-butyl 2-(5-phenylpyridine-3-carboxamido)-4-(1H-pyrazol-1-yl)benzoate as a white solid.

Trifluoroacetic acid (5 mL) was added to the obtained tert-butyl 2-(5-phenylpyridine-3-carboxamido)-4-(1H-pyrazol-1-yl)benzoate (68 mg), followed by stirring at room temperature for 4 hours. The solvent was evaporated under reduced pressure, and methanol was added to the obtained residue. The solid substance was collected by filtration to obtain 53 mg of 2-(5-phenylpyridine-3-carboxamido)-4-(1H-pyrazol-1-yl)benzoic acid.

Methanol (2 mL), dioxane (2 mL), and a 2 mol/L aqueous solution of sodium hydroxide (0.083 mL) were added to the obtained 2-(5-phenylpyridine-3-carboxamido)-4-(1H-pyrazol-1-yl)-benzoic acid (53 mg), and the solvent was evaporated under reduced pressure. Water and acetone were added to the obtained residue, and the solid substance was collected by filtration to obtain 23 mg of sodium 2-(5-phenylpyridine-3-carboxamido)-4-(1H-pyrazol-1-yl)benzoate as a white solid.

$^1$H-NMR (DMSO-$d_6$) δ: 6.56 (1H, dd, J=1.9, 1.9 Hz), 7.44-7.54 (2H, m), 7.55-7.62 (2H, m), 7.77 (1H, d, J=1.5 Hz), 7.81-7.87 (2H, m), 8.12 (1H, d, J=8.3 Hz), 8.45 (1H, d, J=2.4 Hz), 8.59-8.64 (1H, m), 9.10 (1H, d, J=2.2 Hz), 9.17-9.22 (2H, m).

Example 9b

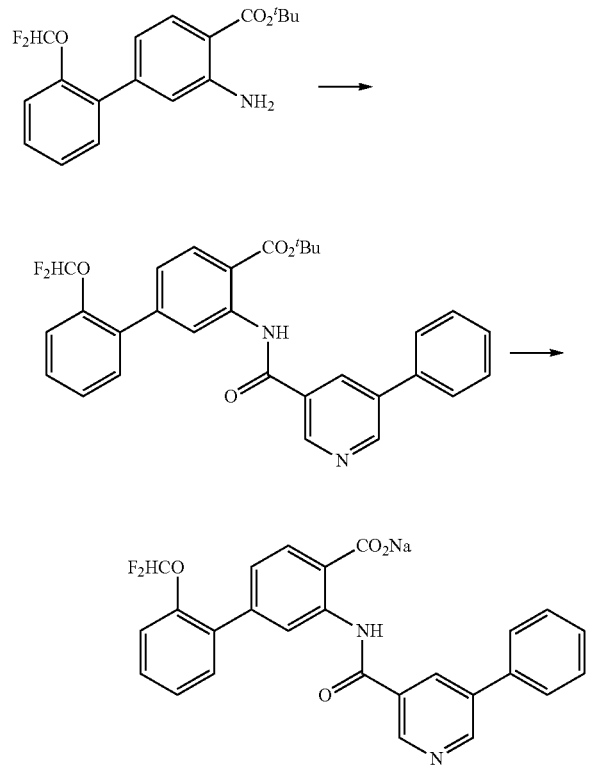

As in Example 8b, the following compound was prepared.

Sodium 4-(2-difluoromethoxy)phenyl)-2-(5-phenylpyridine-3-carboxamido)benzoate $^1$H-NMR (DMSO-$d_6$) δ: 6.96-7.42 (4H, m), 7.45-7.53 (3H, m), 7.53-7.61 (2H, m), 7.80-7.87 (2H, m), 8.11 (1H, d, J=7.8 Hz), 8.59 (1H, s), 8.82 (1H, s), 9.10 (1H, s), 9.17 (1H, s).

Example 10b

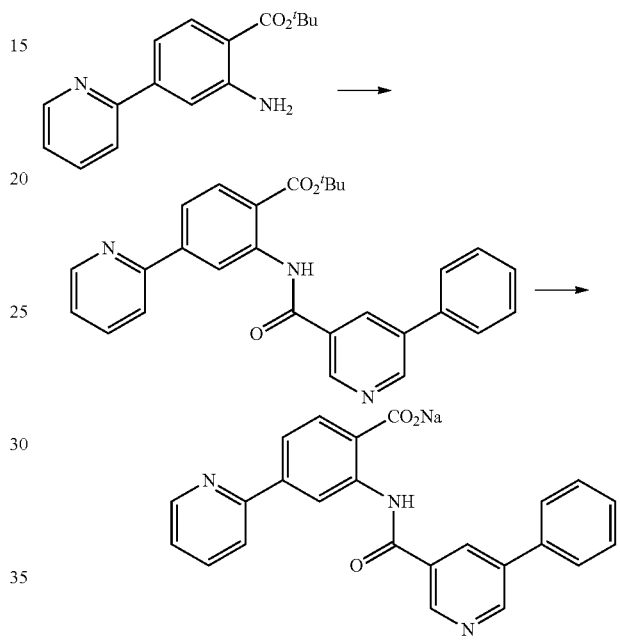

Under ice-cooling, N,N-dimethylformamide (0.010 mL) and oxalyl chloride (0.059 mL) were added to a tetrahydrofuran (3.0 mL) suspension of 5-phenylpyridine-3-carboxylic acid (0.11 g), followed by stirring at room temperature for 1 hour. The solvent was evaporated under reduced pressure, and tetrahydrofuran (5.5 mL) was added to the residue. Under ice-cooling, the reaction mixture was added to a solution mixture of tert-butyl 2-amino-4-(pyridin-2-yl)benzoate (0.12 g) in tetrahydrofuran (2.0 mL) and pyridine (0.073 mL), followed by stirring at room temperature for 4 hours and 30 minutes. A 10% aqueous solution of citric acid and ethyl acetate were added to the reaction mixture. The organic layer was separated, washed with a saturated aqueous solution of sodium chloride, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 80-55% hexane/ethyl acetate] to obtain a solid substance. Ethyl acetate and a saturated aqueous solution of sodium bicarbonate were added to the obtained solid substance. The organic layer was separated, washed with a saturated aqueous solution of sodium chloride, and dried over anhydrous magnesium sulfate, and the solvent was evaporated under reduced pressure. Diisopropyl ether was added to the obtained residue, and the solid substance was collected by filtration to obtain 0.13 g of tert-butyl 2-(5-phenylpyridine-3-carboxamido)-4-(pyridin-2-yl)benzoate as a light yellow solid.

Trifluoroacetic acid (4.0 mL) was added to the obtained tert-butyl 2-(5-phenylpyridine-3-carboxamido)-4-(pyridin-2-yl)benzoate (0.13 g), followed by stirring at room temperature for 1 hour. The solvent was evaporated under reduced pressure, and diisopropyl ether was added to the obtained residue. The solid substance was collected by filtration. Dioxane (3.0 mL) and a 2 mol/L aqueous solution of sodium hydroxide (0.19 mL) were added to the obtained solid, followed by stirring at room temperature for 1 hour. A 10% aqueous solution of citric acid and ethyl acetate were added to the reaction mixture, and the solid substance was collected by filtration to obtain 74 mg of 2-(5-phenylpyridine-3-carboxamido)-4-(pyridin-2-yl)benzoic acid as a white solid.

Ethanol (2.0 mL) and a 2 mol/L aqueous solution of sodium hydroxide (0.094 mL) were sequentially added to the obtained 2-(5-phenylpyridine-3-carboxamido)-4-(pyridin-2-yl)benzoic acid (74 mg), followed by stirring at room temperature for 1 hour and 30 minutes. The solid substance was collected by filtration to obtain 59 mg of sodium 2-(5-phenylpyridine-3-carboxamido)-4-(pyridin-2-yl)benzoate as a white solid.

$^1$H-NMR (DMSO-$d_6$) δ: 7.36-7.42 (1H, m), 7.47-7.54 (1H, m), 7.55-7.62 (2H, m), 7.74 (1H, dd, J=8.2, 1.7 Hz), 7.82-7.88 (2H, m), 7.89-7.97 (2H, m), 8.16 (1H, d, J=8.2 Hz), 8.63 (1H, dd, J=2.1, 2.0 Hz), 8.72 (1H, d, J=4.6 Hz), 9.11 (1H, d, J=2.1 Hz), 9.21 (1H, d, J=2.0 Hz), 9.45 (1H, d, J=1.7 Hz).

Example 11b

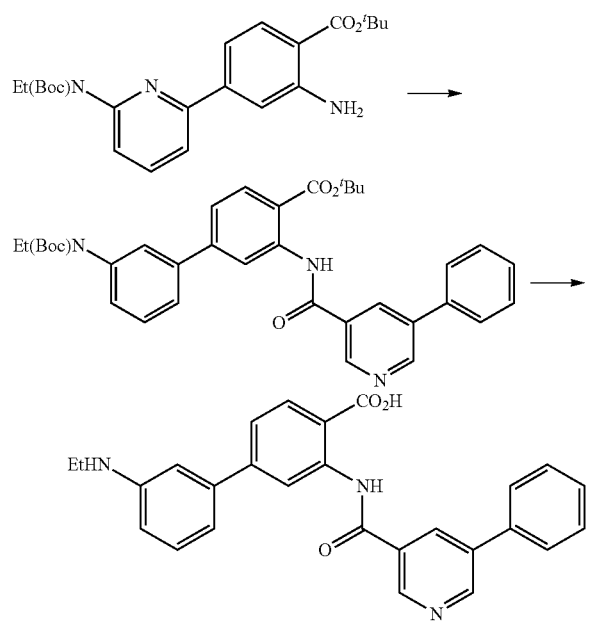

N,N-Dimethylformamide (3 μL) and oxalyl chloride (0.047 mL) were added to methylene chloride (2 mL) suspension of 5-phenylpyridine-3-carboxylic acid (73 mg) at room temperature, followed by stirring at the same temperature for 40 minutes. The solvent was evaporated under reduced pressure, and methylene chloride (2 mL) was added to the residue. The reaction mixture was added to a solution mixture of tert-butyl 2-amino-4-(3-((tert-butoxycarbonyl)(ethyl)amino)phenyl)benzoate (0.13 g) in methylene chloride (2 mL) and pyridine (0.062 mL) at room temperature, followed by stirring at the same temperature for 20 minutes. The solvent was evaporated under reduced pressure, and the obtained residue was purified by silica gel column chromatography [eluent: 90-60% hexane/ethyl acetate] to obtain 0.15 g of tert-butyl 4-(3-((tert-butoxycarbonyl)(ethyl)amino)phenyl)-2-(5-phenylpyridine-3-carboxamido)benzoate as a white solid.

Trifluoroacetic acid (2.0 mL) was added to a methylene chloride (2.0 mL) solution of the obtained tert-butyl 4-(3-((tert-butoxycarbonyl)(ethyl)amino)phenyl)-2-(5-phenylpyridine-3-carboxamido)benzoate (0.15 g) at room temperature, followed by stirring at the same temperature for 7 hours and 30 minutes. The solvent was evaporated under reduced pressure, and methanol (3 mL) and dioxane (1 mL) were added to the obtained residue. The pH was adjusted to 13.0 with a 2 mol/L aqueous solution of sodium hydroxide, then to a pH of 4.6 with a 10% aqueous solution of citric acid. The solid substance was collected by filtration to obtain 0.10 g of 4-(3-(ethylamino)phenyl)-2-(5-phenylpyridine-3-carboxamido)benzoic acid as a light yellow solid.

$^1$H-NMR (DMSO-$d_6$) δ: 1.21 (3H, t, J=7.1 Hz), 3.11 (2H, q, J=7.1 Hz), 6.61-6.69 (1H, m), 6.84-6.93 (2H, m), 7.23 (1H, dd, J=7.8, 7.8 Hz), 7.45-7.62 (4H, m), 7.80-7.88 (2H, m), 8.12 (1H, d, J=8.3 Hz), 8.55 (1H, dd, J=2.1, 2.1 Hz), 8.98 (1H, d, J=1.7 Hz), 9.11-9.18 (2H, m), 12.37 (1H, s).

Examples 12b and 13b

As in Example 11b, the compounds shown in Table 8b were prepared.

TABLE 8b

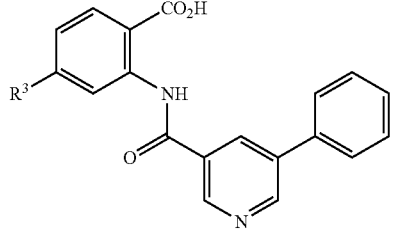

| Example No. | R³ |
|---|---|
| 12b | MeHN—（2-methylphenyl） |
| 13b | MeHN—（3-methylphenyl） |

4-(2-(Methylamino)phenyl)-2-(5-phenylpyridine-3-carboxamido)benzoic acid $^1$H-NMR (DMSO-$d_6$) δ: 2.70 (3H, s), 6.64-6.75 (2H, m), 7.02-7.09 (1H, m), 7.22-7.32 (2H, m), 7.46-7.53 (1H, m), 7.54-7.61 (2H, m), 7.80-7.87 (2H, m), 8.12 (1H, d, J=8.0 Hz), 8.50-8.55 (1H, m), 8.74 (1H, d, J=1.4 Hz), 9.11 (1H, d, J=2.2 Hz), 9.14 (1H, d, J=2.2 Hz), 12.38 (1H, s).

4-(3-(Methylamino)phenyl)-2-(5-phenylpyridine-3-carboxamido)benzoic acid $^1$H-NMR (DMSO-$d_6$) δ: 2.75 (3H, s), 6.63 (1H, dd, J=8.2, 1.8 Hz), 6.85-6.92 (2H, m), 7.25 (1H, dd, J=7.8, 7.8 Hz), 7.46-7.54 (2H, m), 7.54-7.61 (2H, m), 7.81-7.87 (2H, m), 8.12 (1H, d, J=8.2 Hz), 8.56 (1H, dd, J=2.1, 2.1 Hz), 8.98 (1H, d, J=1.8 Hz), 9.14 (1H, d, J=2.1 Hz), 9.15 (1H, d, J=2.1 Hz), 12.36 (1H, s).

Example 14b

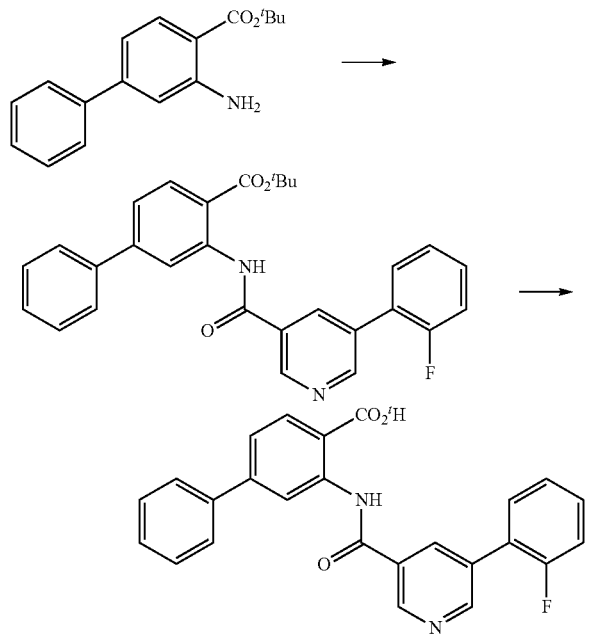

As in Example 11b, the following compound was prepared.

2-(5-(2-Fluorophenyl)pyridine-3-carboxamido)-4-phenylbenzoic acid $^1$H-NMR (DMSO-d$_6$) δ: 7.38-7.51 (3H, m), 7.52-7.60 (4H, m), 7.70-7.78 (3H, m), 8.15 (1H, d, J=8.3 Hz), 8.47-8.52 (1H, m), 9.00-9.05 (2H, m), 9.18 (1H, d, J=2.2 Hz), 12.37 (1H, s).

Example 15b

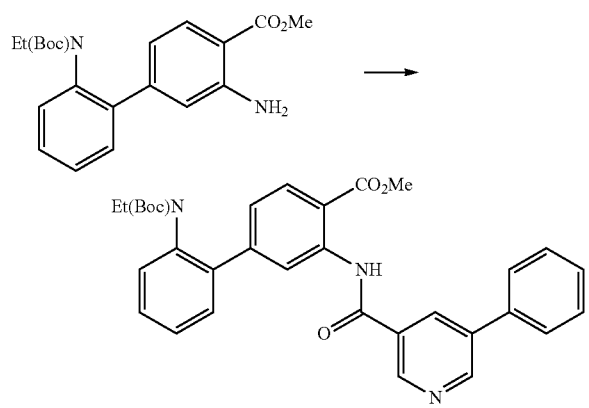

Under ice-cooling, oxalyl chloride (0.23 mL) was added to a solution mixture of 5-phenylpyridine-3-carboxylic acid (0.48 g) in tetrahydrofuran (4.8 mL) and N,N-dimethylformamide (0.010 mL), followed by stirring at room temperature for 40 minutes. The reaction mixture was added to a solution mixture of methyl 2-amino-4-(2-((tert-butoxycarbonyl)(ethyl)amino)phenyl)benzoate (0.80 g) in tetrahydrofuran (8.0 mL) and pyridine (0.44 mL) under ice-cooling, followed by stirring at room temperature for 1 hour and 10 minutes. Ethyl acetate and water were added to the reaction mixture. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 85-70% hexane/ethyl acetate] to obtain 0.86 g of methyl 4-(2-((tert-butoxycarbonyl)(ethyl)amino)phenyl)-2-(5-phenylpyridine-3-carboxamido)benzoate as a white solid.

$^1$H-NMR (CD$_3$OD) δ: 1.02-1.16 (3H, m), 1.18-1.46 (9H, m), 2.83-3.02 (1H, m), 3.52-3.84 (1H, m), 4.00 (3H, s), 7.18-7.35 (2H, m), 7.39-7.59 (6H, m), 7.72-7.78 (2H, m), 8.09-8.20 (1H, m), 8.56-8.61 (1H, m), 8.77-8.90 (1H, m), 9.02 (1H, d, J=2.2 Hz), 9.12 (1H, d, J=2.2 Hz).

Example 16b

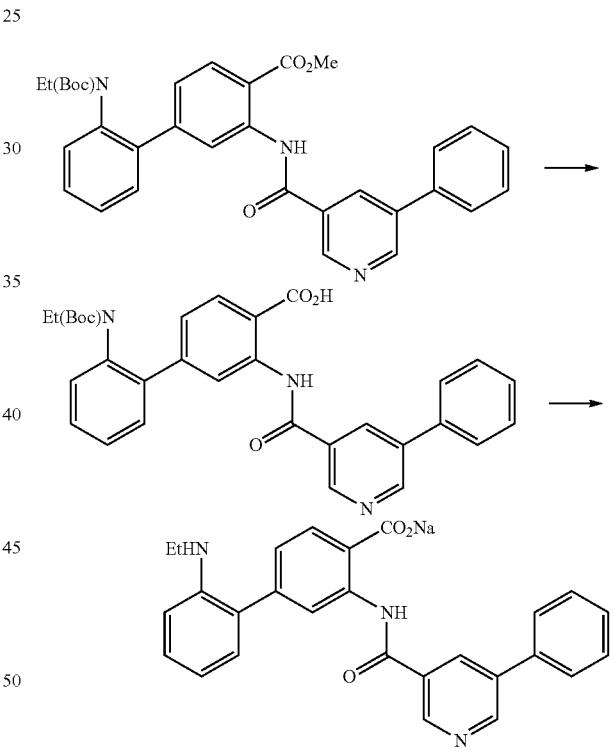

A 2 mol/L aqueous solution of sodium hydroxide (3.8 mL) was added to a solution mixture of methyl 4-(2-((tert-butoxycarbonyl)(ethyl)amino)phenyl)-2-(5-phenylpyridine-3-carboxamido)benzoate (0.84 g) in methanol (4.2 mL) and dioxane (4.2 mL) at room temperature, followed by stirring at the same temperature for 3 hours and 10 minutes. After adjusting the pH to 4.9 with a 10% aqueous solution of citric acid, chloroform was added thereto. The organic layer was separated, washed with water and a saturated aqueous solution of sodium chloride sequentially, and dried over anhydrous magnesium sulfate, and the solvent was evaporated under reduced pressure. Diisopropyl ether was added to the obtained residue, and the solid substance was collected by filtration to obtain 0.80 g of 4-(2-((tert-butoxycarbonyl)(ethyl)amino)phenyl)-2-(5-phenylpyridine-3-carboxamido)benzoic acid as a white solid.

Trifluoroacetic acid (7.9 mL) was added to the obtained 4-(2-((tert-butoxycarbonyl)(ethyl)amino)phenyl)-2-(5-phenylpyridine-3-carboxamido)benzoic acid (0.79 g), followed by stirring at room temperature for 1 hour. The solvent was evaporated under reduced pressure, and a 30% aqueous solution of ethanol was added to the obtained residue. After adjusting the pH to 5.0 with a 4.0 mol/L aqueous solution of sodium hydroxide, the solid substance was collected by filtration to obtain 0.61 g of 4-(2-(ethylamino)phenyl)-2-(5-phenylpyridine-3-carboxamido)benzoic acid as a yellow solid.

Ethanol (18 mL) and a 1.0 mol/L aqueous solution of sodium hydroxide (1.3 mL) were sequentially added to the obtained 4-(2-(ethylamino)phenyl)-2-(5-phenylpyridine-3-carboxamido)benzoic acid (0.60 g), followed by stirring at room temperature for 1 hour. The solvent was evaporated under reduced pressure, and a 10% aqueous solution of ethanol was added to the obtained residue. The solid substance was collected by filtration to obtain 0.57 g of sodium 4-(2-(ethylamino)phenyl)-2-(5-phenylpyridine-3-carboxamido)benzoate as a light yellow solid.

$^1$H-NMR (DMSO-$d_6$) δ: 1.12 (3H, t, J=7.1 Hz), 3.03-3.17 (2H, m), 4.41-4.52 (1H, m), 6.65-6.73 (2H, m), 7.00-7.08 (2H, m), 7.14-7.23 (1H, m), 7.45-7.62 (3H, m), 7.78-7.87 (2H, m), 8.11 (1H, d, J=7.8 Hz), 8.56-8.62 (1H, m), 8.68-8.73 (1H, m), 9.06-9.11 (1H, m), 9.14-9.19 (1H, m).

Example 17b

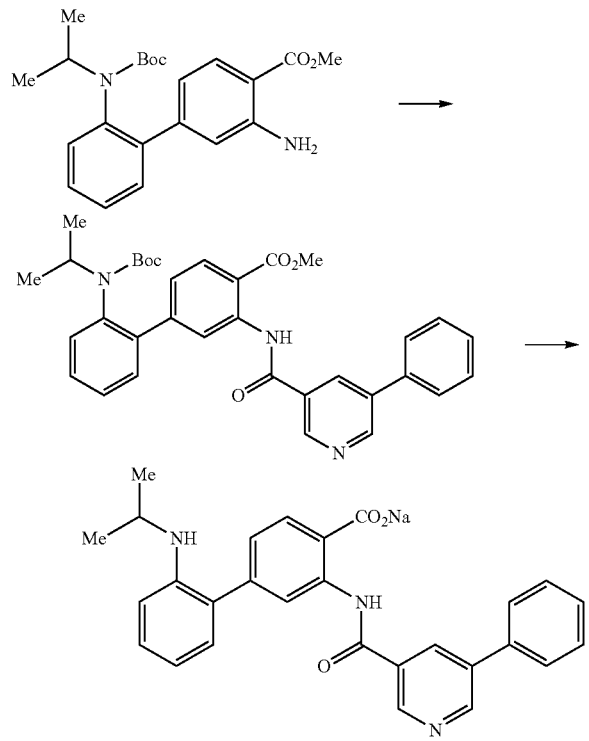

Oxalyl chloride (0.014 mL) was added to a solution mixture of 5-phenylpyridine-3-carboxylic acid (26 mg) in methylene chloride (1.5 mL) and N,N-dimethylformamide (0.010 mL) at room temperature, followed by stirring at the same temperature for 30 minutes. The solvent was evaporated under reduced pressure, and methylene chloride (2.0 mL) was added to the residue. The reaction mixture was added to a solution mixture of methyl 2-amino-4-(2-((tert-butoxycarbonyl)(isopropyl)amino)phenyl)benzoate (42 mg) in methylene chloride (1.0 mL) and pyridine (0.013 mL) at room temperature, followed by stirring at the same temperature for 3 hours. The solvent was evaporated under reduced pressure, and ethyl acetate and a saturated aqueous solution of sodium bicarbonate were added to the residue. The organic layer was separated, washed with a 10% aqueous solution of citric acid and a saturated aqueous solution of sodium chloride sequentially, and dried over anhydrous magnesium sulfate, and the solvent was evaporated under reduced pressure. The obtained residue was purified by silica gel column chromatography [eluent: 80-70% hexane/ethyl acetate] to obtain methyl 4-(2-((tert-butoxycarbonyl)(isopropyl)amino)phenyl)-2-(5-phenylpyridine-3-carboxamido)benzoate.

Trifluoroacetic acid (3.0 mL) was added to the obtained methyl 4-(2-((tert-butoxycarbonyl)(isopropyl)amino)phenyl)-2-(5-phenylpyridine-3-carboxamido)benzoate, followed by stirring at room temperature for 1 hour. The solvent was evaporated under reduced pressure, and dioxane (3.0 mL) and a 1 mol/L aqueous solution of sodium hydroxide (0.33 mL) were sequentially added to the obtained residue, followed by stirring at room temperature for 30 minutes and then at 50° C. for 1 hour. The reaction mixture was cooled to room temperature, and then a 1 mol/L aqueous solution of sodium hydroxide (0.33 mL) was added thereto, followed by stirring at 50° C. for 40 minutes. After cooling the reaction mixture to room temperature, the solvent was evaporated under reduced pressure. Water was added to the obtained residue, and the solid substance was collected by filtration to obtain 24 mg of sodium 4-(2-(isopropylamino)phenyl)-2-(5-phenylpyridine-3-carboxamido)benzoate as a yellow solid.

$^1$H-NMR (DMSO-$d_6$) 1.12 (6H, d, J=6.3 Hz), 3.59-3.70 (1H, m), 4.13 (1H, d, J=8.5 Hz), 6.68 (1H, dd, J=7.3, 7.3 Hz), 6.74 (1H, d, J=8.0 Hz), 7.00-7.08 (2H, m), 7.19 (1H, dd, J=7.6, 7.6 Hz), 7.50 (1H, dd, J=7.3, 7.3 Hz), 7.54-7.62 (2H, m), 7.80-7.87 (2H, m), 8.11 (1H, d, J=8.0 Hz), 8.59 (1H, s), 8.68-8.74 (1H, m), 9.09 (1H, d, J=1.9 Hz), 9.17 (1H, d, J=1.7 Hz).

Example 18b

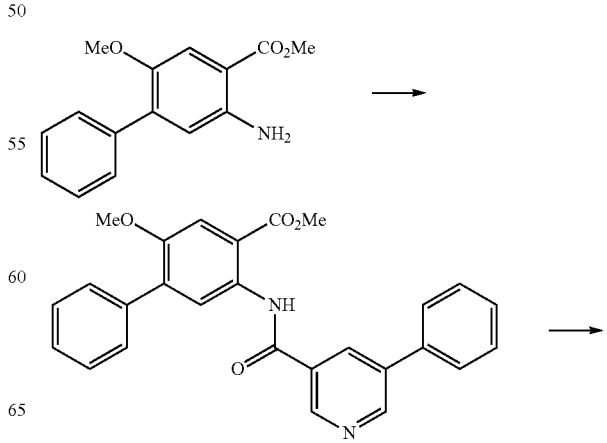

309

-continued

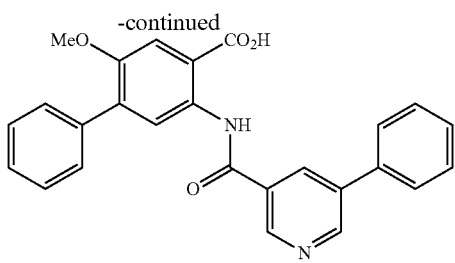

310

-continued

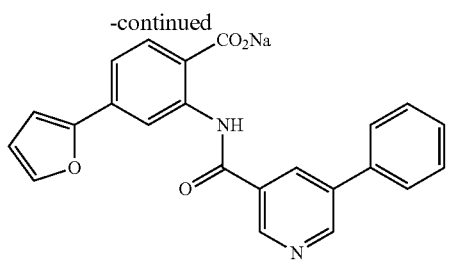

Oxalyl chloride (0.054 mL) was added to a solution mixture of 5-phenylpyridine-3-carboxylic acid (84 mg) in methylene chloride (2 mL) and N,N-dimethylformamide (3.2 µL) at room temperature, followed by stirring at the same temperature for 1 hour and 20 minutes. The solvent was evaporated under reduced pressure, and methylene chloride (2 mL) was added to the residue. The reaction mixture was added to a solution mixture of methyl 2-amino-5-methoxy-4-phenyl) benzoate (90 mg) in methylene chloride (2 mL) and pyridine (0.071 mL) at room temperature, followed by stirring at the same temperature for 50 minutes. The solvent was evaporated under reduced pressure, and the obtained residue was purified by silica gel column chromatography [Fuji Silysia Chemical Ltd., PSQ100B (spherical), eluent: 75-30% hexane/ethyl acetate] to obtain 0.12 g of methyl 5-methoxy-4-phenyl-2-(5-phenylpyridine-3-carboxamido)benzoate as a brown solid.

A 2 mol/L aqueous solution of sodium hydroxide (1.3 mL) was added to a methanol (2.2 mL) suspension of the obtained methyl 5-methoxy-4-phenyl-2-(5-phenylpyridine-3-carboxamido)-benzoate (0.11 g) at room temperature, followed by stirring at the same temperature for 30 minutes. Chloroform (3 mL) and methanol (2 mL) were added to the reaction mixture, followed by stirring at room temperature for 4 hours. The solvent was evaporated under reduced pressure, and ethanol and water were added to the obtained residue. After adjusting the pH to 1 with 6 mol/L hydrochloric acid, the solid substance was collected by filtration to obtain 88 mg of 5-methoxy-4-phenyl-2-(5-phenylpyridine-3-carboxamido) benzoic acid as a white solid.

$^1$H-NMR (DMSO-$d_6$) δ: 3.83 (3H, s), 7.38-7.62 (8H, m), 7.67 (1H, s), 7.80-7.89 (2H, m), 8.49-8.55 (1H, m), 8.58 (1H, s), 9.10 (1H, d, J=2.0 Hz), 9.13 (1H, d, J=2.2 Hz), 11.96 (1H, s).

Example 19b

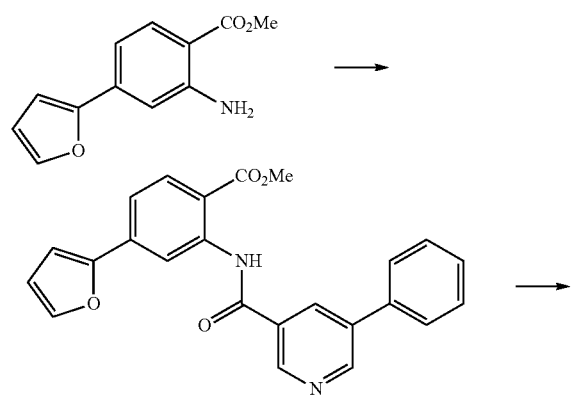

Oxalyl chloride (0.047 mL) was added to a solution mixture of 5-phenylpyridine-3-carboxylic acid (86 mg) in methylene chloride (1.5 mL) and N,N-dimethylformamide (0.010 mL) at room temperature, followed by stirring at the same temperature for 30 minutes. The solvent was evaporated under reduced pressure, and methylene chloride (2.0 mL) was added to the residue. The reaction mixture was added to a solution mixture of methyl 2-amino-4-(furan-2-yl)benzoate (78 mg) in methylene chloride (1.5 mL) and pyridine (0.044 mL) at room temperature, followed by stirring at the same temperature for 1 hour and 20 minutes. The solvent was evaporated under reduced pressure, and ethyl acetate and a saturated aqueous solution of sodium bicarbonate were added to the residue. The organic layer was separated, washed with a 10% aqueous solution of citric acid and a saturated aqueous solution of sodium chloride sequentially, and dried over anhydrous magnesium sulfate, and the solvent was evaporated under reduced pressure. The obtained residue was purified by silica gel column chromatography [Kanto Chemical Co., Inc., silica gel 60 (spherical), eluent: 80-20% hexane/ethyl acetate] to obtain 76 mg of methyl 4-(furan-2-yl)-2-(5-phenylpyridine-3-carboxamido)benzoate as a light yellow solid.

A 2 mol/L aqueous solution of sodium hydroxide (0.19 mL) was added to a dioxane (3.0 mL) suspension of the obtained methyl 4-(furan-2-yl)-2-(5-phenylpyridine-3-carboxamido)benzoate (76 mg) at room temperature, followed by stirring at the same temperature for 3 hours and 20 minutes. A 2 mol/L aqueous solution of sodium hydroxide (0.19 mL) was added to the reaction mixture at room temperature, followed by stirring at 50 to 55° C. for 4 hours. After cooling the reaction mixture to room temperature, the solvent was evaporated under reduced pressure. To the obtained residue, 1 mol/L hydrochloric acid (1.5 mL) was added. The solid substance was collected by filtration to obtain 69 mg of 4-(furan-2-yl)-2-(5-phenylpyridine-3-carboxamido)benzoic acid as a white solid.

Ethanol (4.5 mL) and a 2 mol/L aqueous solution of sodium hydroxide (0.085 mL) were added to the obtained 4-(furan-2-yl)-2-(5-phenylpyridine-3-carboxamido)benzoic acid (69 mg), followed by stirring at room temperature for 1 hour and 20 minutes. The solid substance was collected by filtration to obtain 31 mg of sodium 4-(furan-2-yl)-2-(5-phenylpyridine-3-carboxamido)benzoate as a white solid.

$^1$H-NMR (DMSO-$d_6$) δ: 6.63 (1H, dd, J=3.3, 1.7 Hz), 6.94 (1H, d, J=3.3 Hz), 7.39 (1H, dd, J=8.1, 1.7 Hz), 7.50 (1H, dd, J=7.3, 7.3 Hz), 7.54-7.62 (2H, m), 7.78-7.87 (3H, m), 8.08

(1H, d, J=8.1 Hz), 8.61 (1H, dd, J=2.1, 2.1 Hz), 9.06 (1H, d, J=1.5 Hz), 9.10 (1H, d, J=2.0 Hz), 9.18 (1H, d, J=1.7 Hz).

Example 20b

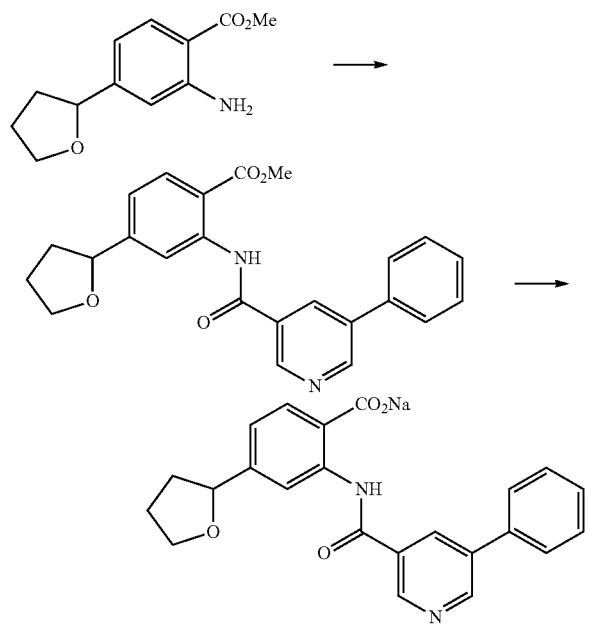

As in Example 19b, the following compound was prepared.

Sodium 2-(5-phenylpyridine-3-carboxamido)-4-(tetrahydrofuran-2-yl)benzoate

¹H-NMR (DMSO-d₆) δ: 1.64-1.75 (1H, m), 1.91-2.01 (2H, m), 2.27-2.38 (1H, m), 3.83 (1H, ddd, J=7.4, 7.4, 7.4 Hz), 4.01 (1H, ddd, J=7.1, 7.1, 7.1 Hz), 4.82 (1H, dd, J=7.2, 7.2 Hz), 6.97 (1H, d, J=8.1 Hz), 7.50 (1H, dd, J=7.2, 7.2 Hz), 7.54-7.61 (2H, m), 7.80-7.86 (2H, m), 8.00 (1H, d, J=7.8 Hz), 8.57-8.62 (1H, m), 8.67 (1H, s), 9.07-9.11 (1H, m), 9.15-9.19 (1H, m).

Example 21b

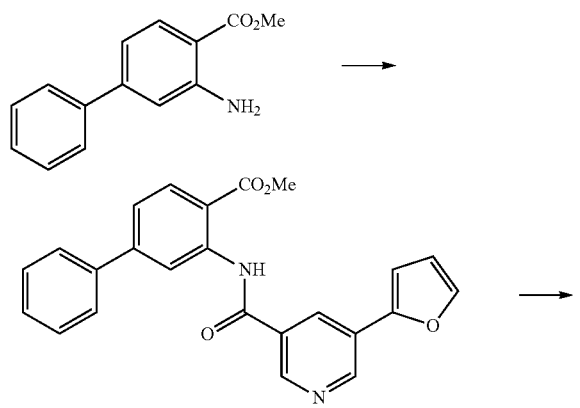

-continued

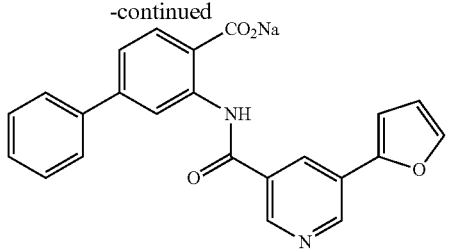

As in Example 19b, the following compound was prepared.

Sodium 2-(5-(furan-2-yl)pyridine-3-carboxamido)-4-phenylbenzoate

¹H-NMR (DMSO-d₆) δ: 6.71 (1H, dd, J=3.4, 1.7 Hz), 7.25 (1H, d, J=3.4 Hz), 7.34 (1H, dd, J=8.1, 2.0 Hz), 7.40 (1H, dd, J=7.3, 7.3 Hz), 7.47-7.54 (2H, m), 7.66-7.72 (2H, m), 7.92 (1H, d, J=1.7 Hz), 8.12 (1H, d, J=8.1 Hz), 8.61 (1H, dd, J=2.0, 2.0 Hz), 9.02 (1H, d, J=2.0 Hz), 9.11 (1H, d, J=2.0 Hz), 9.14 (1H, d, J=2.0 Hz).

Example 22b

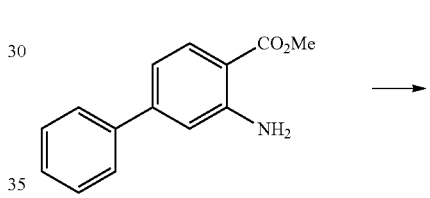

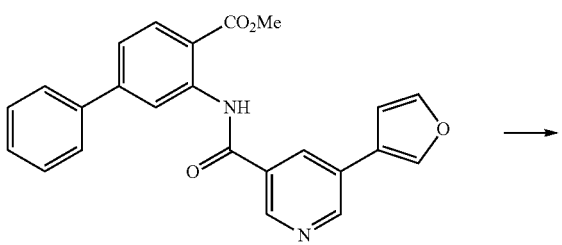

As in Example 19b, the following compound was prepared.

Sodium 2-(5-(furan-3-yl)pyridine-3-carboxamido)-4-phenylbenzoate

¹H-NMR (DMSO-d₆) δ: 7.14 (1H, s), 7.31-7.37 (1H, m), 7.40 (1H, dd, J=7.1, 7.1 Hz), 7.47-7.55 (2H, m), 7.65-7.73

(2H, m), 7.87 (1H, d, J=1.5 Hz), 8.13 (1H, d, J=8.0 Hz), 8.42 (1H, s), 8.55 (1H, d, J=2.0 Hz), 9.01-9.05 (1H, m), 9.06-9.12 (2H, m).

Example 23b

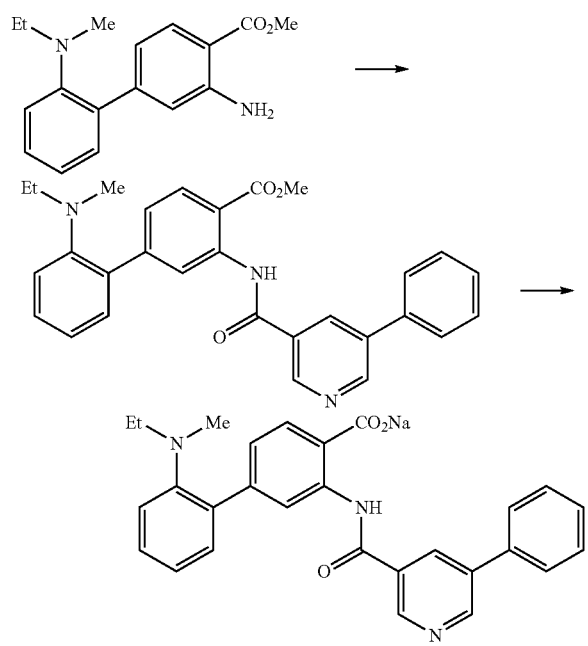

Oxalyl chloride (0.046 mL) was added to a solution mixture of 5-phenylpyridine-3-carboxylic acid (83 mg) in methylene chloride (3.0 mL) and N,N-dimethylformamide (0.010 mL) at room temperature, followed by stirring at the same temperature for 30 minutes. The solvent was evaporated under reduced pressure, and methylene chloride (2.5 mL) was added to the residue. The reaction mixture was added to a solution mixture of methyl 2-amino-4-(2-((ethyl)(methyl) amino)phenyl)benzoate (99 mg) in methylene chloride (1.5 mL) and pyridine (0.042 mL) under ice-cooling, followed by stirring at room temperature for 1 hour. The solvent was evaporated under reduced pressure, and ethyl acetate and a saturated aqueous solution of sodium bicarbonate were added to the residue. The organic layer was separated, washed with a 10% aqueous solution of citric acid and a saturated aqueous solution of sodium chloride sequentially, and dried over anhydrous magnesium sulfate, and the solvent was evaporated under reduced pressure. The obtained residue was purified by silica gel column chromatography [eluent: 95-85% hexane/ethyl acetate] to obtain 0.10 g of methyl 4-(2-((ethyl) (methyl)amino)phenyl)-2-(5-phenylpyridine-3-carboxamido)benzoate as a yellow solid.

A 1 mol/L aqueous solution of sodium hydroxide (0.67 mL) was added to a dioxane (3.0 mL) solution of the obtained methyl 4-(2-((ethyl)(methyl)amino)phenyl)-2-(5-phenylpyridine-3-carboxamido)benzoate (0.10 g) at room temperature, followed by stirring at the same temperature for 1 hour and then at 55° C. for 1 hour and 30 minutes. After cooling the reaction mixture to room temperature and adjusting the pH to 7.3 with 1 mol/L hydrochloric acid, the solvent was evaporated under reduced pressure. Water was added to the obtained residue, and the solid substance was collected by filtration. Ethanol (1.5 mL) and a 1 mol/L aqueous solution of sodium hydroxide (0.091 mL) were sequentially added to the obtained solid substance, followed by stirring at room temperature for 1 hour. Then, the solvent was evaporated under reduced pressure, and water was added to the obtained residue. The solid substance was collected by filtration to obtain 2.5 mg of sodium 4-(2-((ethyl)(methyl)amino)phenyl)-2-(5-phenylpyridine-3-carboxamido)benzoate as a yellow solid.

$^1$H-NMR (DMSO-$d_6$) δ: 0.86 (3H, t, J=7.0 Hz), 2.57 (3H, s), 2.81 (2H, q, J=7.0 Hz), 7.04-7.11 (1H, m), 7.15 (1H, d, J=8.1 Hz), 7.24 (1H, dd, J=7.4, 1.6 Hz), 7.31-7.38 (1H, m), 7.44 (1H, dd, J=8.3, 1.7 Hz), 7.47-7.53 (1H, m), 7.54-7.61 (2H, m), 7.81-7.87 (2H, m), 8.09 (1H, d, J=8.3 Hz), 8.54 (1H, dd, J=2.1, 2.1 Hz), 8.87 (1H, d, J=1.7 Hz), 9.12 (1H, d, J=2.1 Hz), 9.14 (1H, d, J=2.1 Hz).

Example 24b

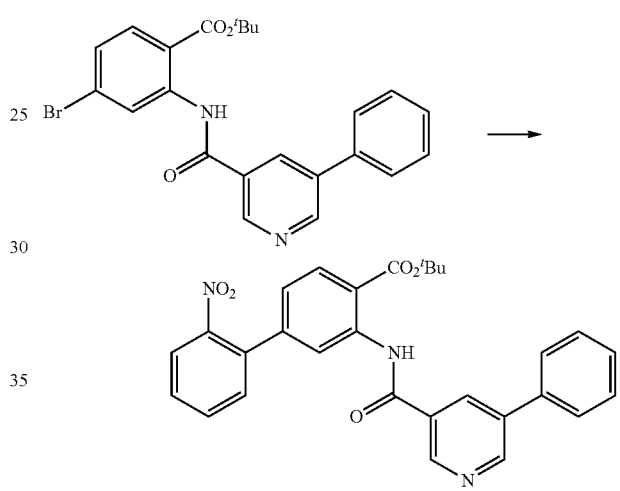

Water (0.6 mL), sodium carbonate (70 mg), 2-nitrophenylboronic acid (44 mg), and tetrakis(triphenylphosphine)palladium(0) (13 mg) were added to an ethylene glycol dimethyl ether (2.0 mL) solution of tert-butyl 4-bromo-2-(5-phenylpyridine-3-carboxamido)benzoate (0.10 g), followed by heating to reflux under a nitrogen atmosphere for 2 hours and 30 minutes. The reaction mixture was cooled to room temperature, and then sodium carbonate (23 mg), 2-nitrophenylboronic acid (37 mg), and tetrakis(triphenylphosphine)palladium(0) (13 mg) were added thereto, followed by heating to reflux under a nitrogen atmosphere for 2 hours and 50 minutes. The reaction mixture was cooled to room temperature, and a 10% aqueous solution of citric acid and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 91-80% hexane/ethyl acetate] to obtain 68 mg of tert-butyl 4-(2-nitrophenyl)-2-(5-phenylpyridine-3-carboxamido)benzoate as a light green solid.

$^1$H-NMR (CDCl$_3$) δ: 1.66 (9H, s), 7.06 (1H, dd, J=8.2, 1.8 Hz), 7.43-7.49 (1H, m), 7.50-7.59 (4H, m), 7.64-7.73 (3H, m), 7.93-7.99 (1H, m), 8.09 (1H, d, J=8.2 Hz), 8.56 (1H, dd,

J=2.2, 2.1 Hz), 8.99 (1H, d, J=1.7 Hz), 9.04 (1H, d, J=2.2 Hz), 9.26 (1H, d, J=2.1 Hz), 12.60 (1H, s).

Example 25b

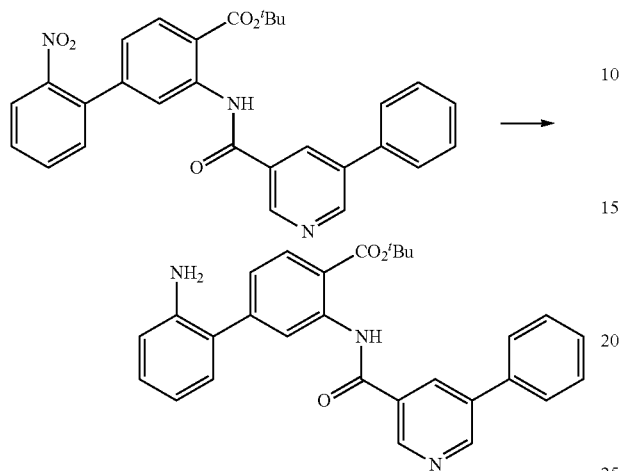

To a solution mixture of tert-butyl 4-(2-nitrophenyl)-2-(5-phenylpyridine-3-carboxamido)benzoate (0.28 g) in chloroform (3.0 mL) and methanol (2.0 mL), 10% palladium-carbon (0.13 g) was added, followed by stirring under a hydrogen atmosphere at room temperature for 5 hours and 40 minutes. The insoluble substance was removed by filtration, and the solvent was evaporated under reduced pressure. The obtained residue was purified by silica gel column chromatography [eluent: 100-90% chloroform/methanol] to obtain 0.22 g of tert-butyl 4-(2-aminophenyl)-2-(5-phenylpyridine-3-carboxamido)benzoate as a light yellow solid.

$^1$H-NMR (DMSO-$d_6$) δ: 1.55 (9H, s), 7.00-7.19 (2H, m), 7.21-7.36 (2H, m), 7.44 (1H, dd, J=8.2, 1.6 Hz), 7.47-7.62 (3H, m), 7.82-7.90 (2H, m), 8.00 (1H, d, J=8.2 Hz), 8.35 (1H, d, J=1.6 Hz), 8.62 (1H, dd, J=2.0, 2.0 Hz), 9.10-9.22 (2H, m), 11.62 (1H, s).

Example 26b

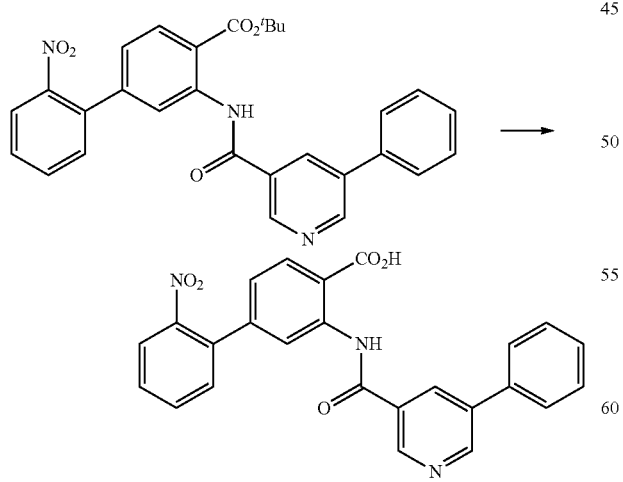

Trifluoroacetic acid (3.0 mL) was added to tert-butyl 4-(2-nitrophenyl)-2-(5-phenylpyridine-3-carboxamido)benzoate (68 mg), followed by stirring at room temperature for 1 hour. The solvent was evaporated under reduced pressure, and diisopropyl ether was added to the obtained residue. The solid substance was collected by filtration, and dioxane (3.0 mL) and a 2 mol/L aqueous solution of sodium hydroxide (0.053 mL) were sequentially added to the obtained solid substance, followed by stirring at room temperature for 1 hour and 50 minutes. Water was added to the reaction mixture. After adjusting the pH to 6.3 with 1 mol/L hydrochloric acid, the solid substance was collected by filtration to obtain 47 mg of 4-(2-nitrophenyl)-2-(5-phenylpyridine-3-carboxamido)benzoic acid as a white solid.

$^1$H-NMR (DMSO-$d_6$) δ: 7.20-7.27 (1H, m), 7.50 (1H, dd, J=7.4, 7.4 Hz), 7.53-7.61 (2H, m), 7.64 (1H, d, J=7.8 Hz), 7.72 (1H, dd, J=7.8, 7.8 Hz), 7.80-7.89 (3H, m), 8.08 (1H, d, J=8.0 Hz), 8.14 (1H, d, J=8.1 Hz), 8.50-8.57 (1H, m), 8.66-8.72 (1H, m), 9.11 (1H, d, J=1.7 Hz), 9.14 (1H, d, J=1.7 Hz), 12.49-12.64 (1H, broad).

Example 27b

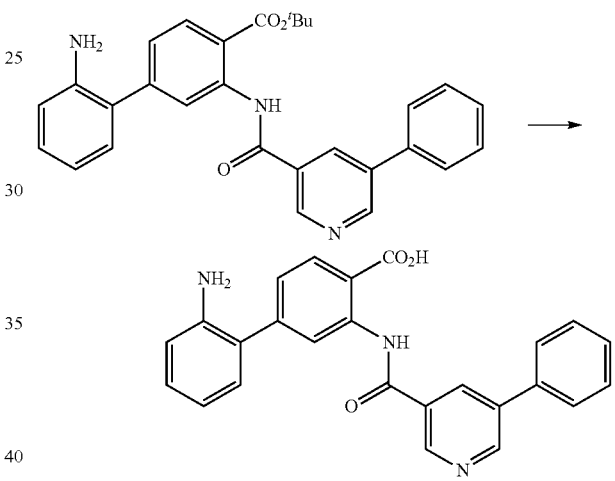

As in Example 26b, the following compound was prepared.

4-(2-Aminophenyl)-2-(5-phenylpyridine-3-carboxamido)benzoic acid $^1$H-NMR (DMSO-$d_6$) δ: 6.69 (1H, dd, J=7.3, 7.3 Hz), 6.81 (1H, d, J=7.8 Hz), 7.05-7.16 (2H, m), 7.33 (1H, d, J=8.1 Hz), 7.46-7.62 (3H, m), 7.80-7.87 (2H, m), 8.12 (1H, d, J=8.3 Hz), 8.53 (1H, s), 8.78 (1H, s), 9.09-9.17 (2H, m), 12.33 (1H, s).

Example 28b

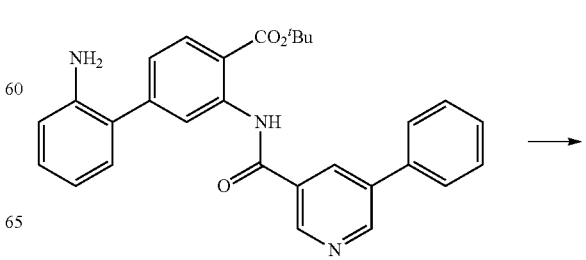

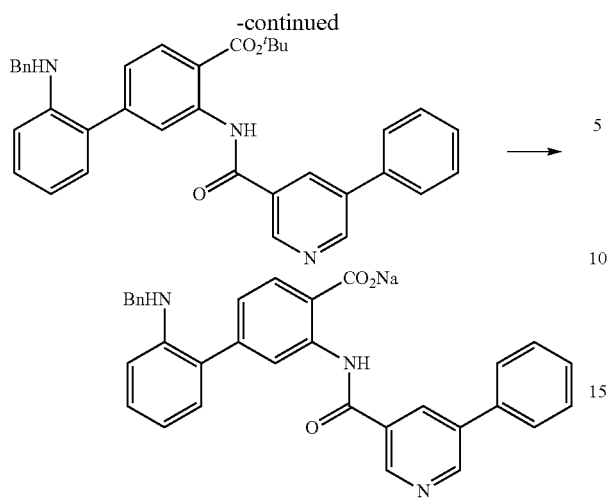

Benzaldehyde (0.027 mL) and sodium triacetoxyborohydride (70 mg) were added to a methylene chloride (1 mL) suspension of tert-butyl 4-(2-aminophenyl)-2-(5-phenylpyridine-3-carboxamido)benzoate (0.10 g) at room temperature, followed by stirring at the same temperature for 3 hours and 30 minutes. Methylene chloride (2 mL) was added to the reaction mixture at room temperature, followed by stirring at the same temperature for 1 hour and 50 minutes. Acetic acid (0.013 mL) and sodium triacetoxyborohydride (47 mg) were added to the reaction mixture at room temperature, followed by stirring at the same temperature for 2 hours and 50 minutes. Sodium triacetoxyborohydride (47 mg), methylene chloride (3 mL), and benzaldehyde (0.027 mL) were added to the reaction mixture at room temperature, followed by heating to reflux for 1 hour and 30 minutes. The reaction mixture was cooled to room temperature, and then sodium triacetoxyborohydride (47 mg) was added thereto, followed by heating to reflux for 4 hours and 40 minutes. The reaction mixture was cooled to room temperature, and then chloroform and water were added thereto. The organic layer was separated and dried over anhydrous magnesium sulfate, and the solvent was evaporated under reduced pressure. The obtained residue was purified by silica gel column chromatography [eluent:85-60% hexane/ethyl acetate] to obtain 78 mg of tert-butyl 4-(2-(benzylamino)phenyl)-2-(5-phenylpyridine-3-carboxamido)benzoate as a light yellow solid.

Trifluoroacetic acid (1.0 mL) was added to the obtained tert-butyl 4-(2-(benzylamino)phenyl)-2-(5-phenylpyridine-3-carboxamido)benzoate (75 mg), followed by stirring at room temperature for 6 hours and 30 minutes. The solvent was evaporated under reduced pressure, and methanol (2 mL) was added to the obtained residue. After adjusting the pH to 12.0 with a 2 mol/L aqueous solution of sodium hydroxide, the solvent was evaporated under reduced pressure. Water was added to the obtained residue, and the solid substance was collected by filtration to obtain 68 mg of sodium 4-(2-(benzylamino)phenyl)-2-(5-phenylpyridine-3-carboxamido)benzoate as a light green solid.

$^1$H-NMR (DMSO-d$_6$) δ: 4.28-4.36 (2H, m), 5.36 (1H, t, J=5.5 Hz), 6.54 (1H, d, J=8.0 Hz), 6.61-6.69 (1H, m), 7.01-7.15 (3H, m), 7.17-7.24 (1H, m), 7.27-7.42 (4H, m), 7.45-7.62 (3H, m), 7.80-7.87 (2H, m), 8.14 (1H, d, J=8.0 Hz), 8.60 (1H, dd, J=2.1, 2.1 Hz), 8.81 (1H, d, J=1.7 Hz), 9.09 (1H, d, J=2.1 Hz), 9.18 (1H, d, J=2.1 Hz).

Example 29b

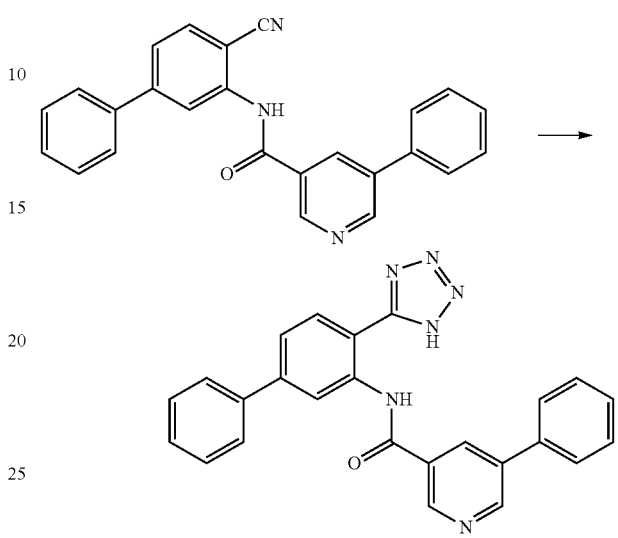

Sodium azide (38 mg) and ammonium chloride (31 mg) were added to a N,N-dimethylformamide (1.1 mL) solution of N-(2-cyano-5-phenylphenyl)-5-phenylpyridine-3-carboxamide (0.11 g) at room temperature, followed by stirring at 110° C. for 2 hours and 30 minutes. The reaction mixture was cooled to room temperature, and then ethyl acetate and 1.0 mol/L hydrochloric acid (6.0 mL) were added thereto. The solid substance was collected by filtration to obtain 84 mg of 5-phenyl-N-(5-phenyl-2-(1H-tetrazol-5-yl)phenyl)pyridine-3-carboxamide as a yellow solid.

$^1$H-NMR (DMSO-d$_6$) δ: 7.44-7.63 (6H, m), 7.75-7.83 (3H, m), 7.87-7.93 (2H, m), 8.13 (1H, d, J=8.0 Hz), 8.70-8.75 (1H, m), 8.78 (1H, d, J=1.5 Hz), 9.18 (1H, d, J=2.2 Hz), 9.20 (1H, d, J=2.0 Hz), 11.60 (1H, s).

Example 30b

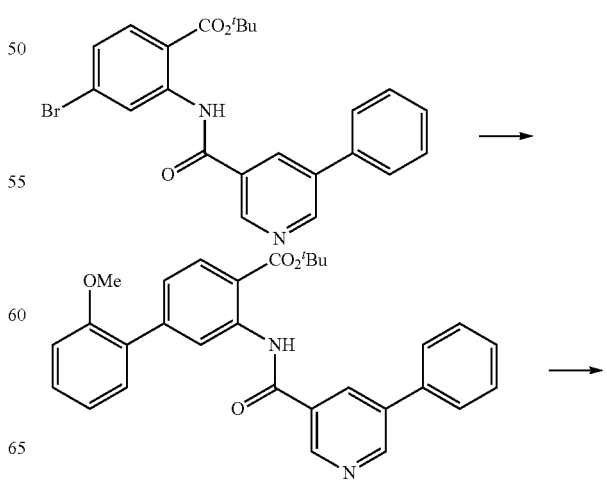

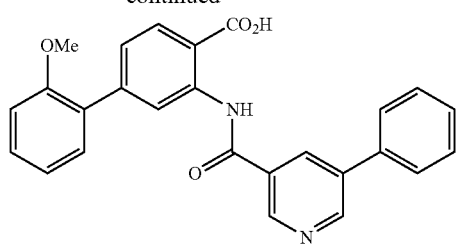

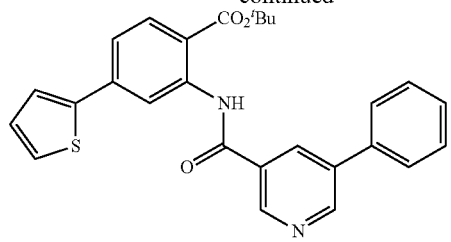

Water (0.6 mL), sodium carbonate (70 mg), 2-methoxyphenylboronic acid (40 mg), and tetrakis(triphenylphosphine)palladium(0) (13 mg) were added to an ethylene glycol dimethyl ether (2.0 mL) suspension of tert-butyl 4-bromo-2-(5-phenylpyridine-3-carboxamido)benzoate (0.10 g), followed by heating to reflux under a nitrogen atmosphere for 1 hour. After cooling the reaction mixture to room temperature, the insoluble substance was removed by filtration, and a 10% aqueous solution of citric acid and ethyl acetate were added to the residue. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 91-80% hexane/ethyl acetate] to obtain 61 mg of tert-butyl 4-(2-methoxyphenyl)-2-(5-phenylpyridine-3-carboxamido)benzoate as a white solid.

Trifluoroacetic acid (4.0 mL) was added to the obtained tert-butyl 4-(2-methoxyphenyl)-2-(5-phenylpyridine-3-carboxamido)benzoate (61 mg), followed by stirring at room temperature for 1 hour. The solvent was evaporated under reduced pressure, and diisopropyl ether was added to the obtained residue. The solid substance was collected by filtration, and dioxane (3.0 mL), water, and a 2 mol/L aqueous solution of sodium hydroxide (0.080 mL) were added to the obtained residue. After adjusting the pH to 7.6 with 1 mol/L hydrochloric acid, the solid substance was collected by filtration to obtain 32 mg of 4-(2-methoxyphenyl)-2-(5-phenylpyridine-3-carboxamido)benzoic acid as a white solid.

$^1$H-NMR (DMSO-$d_6$) δ: 3.81 (3H, s), 7.09 (1H, dd, J=7.4, 7.4 Hz), 7.18 (1H, d, J=8.3 Hz), 7.33-7.40 (2H, m), 7.40-7.47 (1H, m), 7.50 (1H, dd, J=7.3, 7.3 Hz), 7.53-7.61 (2H, m), 7.80-7.87 (2H, m), 8.09 (1H, d, J=8.3 Hz), 8.52-8.56 (1H, m), 8.80-8.85 (1H, m), 9.12 (1H, d, J=2.0 Hz), 9.14 (1H, d, J=2.2 Hz), 12.35-12.49 (1H, broad).

Example 31b

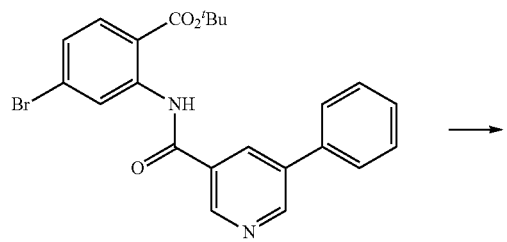

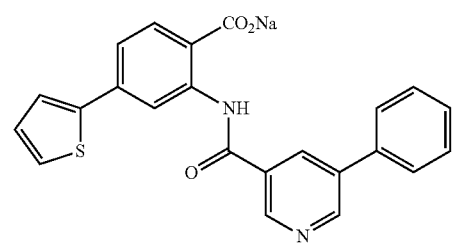

Water (0.60 mL), 2-thiopheneboronic acid (34 mg), sodium carbonate (70 mg), and tetrakis(triphenylphosphine)palladium(0) (13 mg) were added to an ethylene glycol dimethyl ether (2.0 mL) suspension of tert-butyl 4-bromo-2-(5-phenylpyridine-3-carboxamido)benzoate (0.10 g), followed by heating to reflux under a nitrogen atmosphere for 2 hours. The reaction mixture was cooled to room temperature, and then ethyl acetate and a 10% aqueous solution of citric acid were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [Kanto Chemical Co., Inc., silica gel 60 (spherical), eluent: 95-85% hexane/ethyl acetate] to obtain tert-butyl 2-(5-phenylpyridine-3-carboxamido)-4-(thiophen-2-yl)benzoate.

Trifluoroacetic acid (4.0 mL) was added to the obtained tert-butyl 2-(5-phenylpyridine-3-carboxamido)-4-(thiophen-2-yl)benzoate, followed by stirring at room temperature for 2 hours. The solvent was evaporated under reduced pressure, and diisopropyl ether was added to the obtained residue. The solid substance was collected by filtration to obtain 54 mg of 2-(5-phenylpyridine-3-carboxamido)-4-(thiophen-2-yl)benzoic acid as a white solid.

A 1 mol/L aqueous solution of sodium hydroxide (0.13 mL) was added to an ethanol (4.0 mL) suspension of the obtained 2-(5-phenylpyridine-3-carboxamido)-4-(thiophen-2-yl)benzoic acid (54 mg) at room temperature, followed by stirring at the same temperature for 2 hours and 30 minutes. The solvent was evaporated under reduced pressure, and water was added to the obtained residue. The solid substance was collected by filtration to obtain 35 mg of sodium 2-(5-phenylpyridine-3-carboxamido)-4-(thiophen-2-yl)benzoate as a white solid.

$^1$H-NMR (DMSO-$d_6$) δ: 7.15-7.21 (1H, m), 7.40 (1H, dd, J=8.1, 1.7 Hz), 7.46-7.63 (5H, m), 7.81-7.88 (2H, m), 8.08 (1H, d, J=8.1 Hz), 8.58-8.64 (1H, m), 9.06 (1H, d, J=1.7 Hz), 9.11 (1H, d, J=1.9 Hz), 9.19 (1H, d, J=1.7 Hz).

Examples 32b to 43b

As in Example 31b, the compounds shown in Table 9b were prepared.

TABLE 9b

| Example No. | R³ |
|---|---|
| 32b | Me (2-methylphenyl) |
| 33b | CF₃ (2-trifluoromethylphenyl) |
| 34b | F₃C (3-trifluoromethylphenyl) |
| 35b | MeO (3-methoxyphenyl) |
| 36b | MeO (4-methoxyphenyl) |
| 37b | MeO, OMe (2,3-dimethoxyphenyl) |
| 38b | OEt (2-ethoxyphenyl) |
| 39b | EtO (3-ethoxyphenyl) |

TABLE 9b-continued

| Example No. | R³ |
|---|---|
| 40b | OCF₃ (2-trifluoromethoxyphenyl) |
| 41b | F₃CO (3-trifluoromethoxyphenyl) |
| 42b | F₂HCO (3-difluoromethoxyphenyl) |
| 43b | Me-CH(Me)-O- (2-isopropoxyphenyl) |

Sodium 4-(2-methylphenyl)-2-(5-phenylpyridine-3-carboxamido)benzoate $^1$H-NMR (DMSO-d$_6$) δ: 2.29 (3H, s), 7.00 (1H, dd, J=8.1, 1.7 Hz), 7.22-7.35 (4H, m), 7.46-7.53 (1H, m), 7.54-7.61 (2H, m), 7.80-7.86 (2H, m), 8.10 (1H, d, J=8.1 Hz), 8.59 (1H, dd, J=2.1, 2.1 Hz), 8.67 (1H, d, J=1.7 Hz), 9.09 (1H, d, J=2.1 Hz), 9.17 (1H, d, J=2.1 Hz).

Sodium 2-(5-phenylpyridine-3-carboxamido)-4-(2-(trifluoromethyl)phenyl)benzoate $^1$H-NMR (DMSO-d$_6$) δ: 6.98 (1H, d, J=7.8 Hz), 7.44-7.53 (2H, m), 7.54-7.61 (2H, m), 7.64 (1H, dd, J=7.7, 7.7 Hz), 7.75 (1H, dd, J=7.4, 7.4 Hz), 7.80-7.90 (3H, m), 8.09 (1H, d, J=7.8 Hz), 8.56-8.62 (1H, m), 8.70 (1H, s), 9.09 (1H, d, J=1.5 Hz), 9.16 (1H, d, J=1.5 Hz).

Sodium 2-(5-phenylpyridine-3-carboxamido)-4-(3-(trifluoromethyl)phenyl)benzoate $^1$H-NMR (DMSO-d$_6$) δ: 7.44 (1H, d, J=8.3 Hz), 7.47-7.54 (1H, m), 7.55-7.63 (2H, m), 7.73-7.81 (2H, m), 7.82-7.89 (2H, m), 7.96 (1H, s), 7.99-8.06 (1H, m), 8.18 (1H, d, J=8.0 Hz), 8.61-8.67 (1H, m), 9.07-9.15 (2H, m), 9.21 (1H, s).

Sodium 4-(3-methoxyphenyl)-2-(5-phenylpyridine-3-carboxamido)benzoate $^1$H-NMR (DMSO-d$_6$) δ: 3.85 (3H, s), 6.94-7.03 (1H, m), 7.20 (1H, s), 7.26 (1H, d, J=7.6 Hz), 7.31-7.37 (1H, m), 7.42

(1H, dd, J=7.9, 7.9 Hz), 7.50 (1H, dd, J=7.3, 7.3 Hz), 7.54-7.63 (2H, m), 7.81-7.89 (2H, m), 8.12 (1H, d, J=8.0 Hz), 8.62 (1H, s), 9.02 (1H, s), 9.10 (1H, d, J=1.7 Hz), 9.17-9.24 (1H, m).

Sodium 4-(4-methoxyphenyl)-2-(5-phenylpyridine-3-carboxamido)benzoate

¹H-NMR (DMSO-d₆) δ: 3.82 (3H, s), 7.04-7.11 (2H, m), 7.35 (1H, dd, J=8.2, 1.8 Hz), 7.46-7.53 (1H, m), 7.54-7.61 (2H, m), 7.62-7.69 (2H, m), 7.80-7.87 (2H, m), 8.10 (1H, d, J=8.2 Hz), 8.60 (1H, dd, J=2.1, 2.0 Hz), 9.00 (1H, d, J=1.8 Hz), 9.11 (1H, d, J=2.1 Hz), 9.18 (1H, d, J=2.0 Hz).

Sodium 4-(2,3-dimethoxyphenyl)-2-(5-phenylpyridine-3-carboxamido)benzoate

¹H-NMR (DMSO-d₆) δ: 3.61 (3H, s), 3.86 (3H, s), 6.91-6.97 (1H, m), 7.06-7.19 (3H, m), 7.46-7.53 (1H, m), 7.54-7.62 (2H, m), 7.80-7.87 (2H, m), 8.07 (1H, d, J=8.0 Hz), 8.60 (1H, s), 8.82 (1H, s), 9.06-9.12 (1H, m), 9.15-9.20 (1H, m).

Sodium 4-(2-ethoxyphenyl)-2-(5-phenylpyridine-3-carboxamido)benzoate

¹H-NMR (DMSO-d₆) δ: 1.31 (3H, t, J=7.0 Hz), 4.07 (2H, q, J=7.0 Hz), 7.05 (1H, dd, J=7.3, 7.3 Hz), 7.12 (1H, d, J=8.6 Hz), 7.20 (1H, d, J=8.0 Hz), 7.30-7.40 (2H, m), 7.50 (1H, dd, J=7.2, 7.2 Hz), 7.54-7.63 (2H, m), 7.80-7.89 (2H, m), 8.07 (1H, d, J=8.0 Hz), 8.60 (1H, s), 8.89 (1H, s), 9.09 (1H, d, J=1.7 Hz), 9.16-9.23 (1H, m).

Sodium 4-(3-ethoxyphenyl)-2-(5-phenylpyridine-3-carboxamido)benzoate

¹H-NMR (DMSO-d₆) δ: 1.38 (3H, t, J=7.0 Hz), 4.12 (2H, q, J=7.0 Hz), 6.96 (1H, dd, J=8.1, 2.4 Hz), 7.16-7.20 (1H, m), 7.24 (1H, d, J=7.6 Hz), 7.33 (1H, dd, J=7.9, 1.4 Hz), 7.40 (1H, dd, J=7.9, 7.9 Hz), 7.46-7.53 (1H, m), 7.54-7.62 (2H, m), 7.81-7.87 (2H, m), 8.11 (1H, d, J=8.0 Hz), 8.62 (1H, dd, J=1.9, 1.8 Hz), 9.02 (1H, d, J=1.5 Hz), 9.10 (1H, d, J=1.9 Hz), 9.19 (1H, d, J=1.8 Hz).

Sodium 2-(5-phenylpyridine-3-carboxamido)-4-(2-(trifluoromethoxy)phenyl)benzoate ¹H-NMR (DMSO-d₆) δ: 7.09-7.16 (1H, m), 7.46-7.62 (7H, m), 7.80-7.87 (2H, m), 8.11 (1H, d, J=8.0 Hz), 8.57-8.63 (1H, m), 8.81-8.86 (1H, m), 9.09 (1H, d, J=2.0 Hz), 9.17 (1H, d, J=2.0 Hz).

Sodium 2-(5-phenylpyridine-3-carboxamido)-4-(3-(trifluoromethoxy)phenyl)benzoate ¹H-NMR (DMSO-d₆) δ: 7.36-7.45 (2H, m), 7.47-7.54 (1H, m), 7.55-7.69 (4H, m), 7.72-7.78 (1H, m), 7.82-7.88 (2H, m), 8.15 (1H, d, J=8.0 Hz), 8.60-8.65 (1H, m), 9.06 (1H, d, J=1.7 Hz), 9.11 (1H, d, J=2.2 Hz), 9.20 (1H, d, J=1.9 Hz).

Sodium 4-(3-(difluoromethoxy)phenyl)-2-(5-phenylpyridine-3-carboxamido)benzoate

¹H-NMR (DMSO-d₆) δ: 7.16-7.63 (9H, m), 7.81-7.88 (2H, m), 8.14 (1H, d, J=8.0 Hz), 8.60-8.65 (1H, m), 9.04 (1H, d, J=1.7 Hz), 9.10 (1H, d, J=2.2 Hz), 9.20 (1H, d, J=1.7 Hz).

Sodium 4-(2-isopropoxyphenyl)-2-(5-phenylpyridine-3-carboxamido)benzoate

¹H-NMR (DMSO-d₆) δ: 1.24 (6H, d, J=6.1 Hz), 4.58 (1H, heptet, J=6.1 Hz), 7.03 (1H, dd, J=7.4, 7.4 Hz), 7.12 (1H, d, J=8.3 Hz), 7.18 (1H, dd, J=8.0, 1.6 Hz), 7.29-7.37 (2H, m), 7.46-7.53 (1H, m), 7.54-7.61 (2H, m), 7.80-7.87 (2H, m), 8.05 (1H, d, J=8.0 Hz), 8.59 (1H, dd, J=2.2, 2.2 Hz), 8.88 (1H, d, J=1.6 Hz), 9.09 (1H, d, J=2.2 Hz), 9.17 (1H, d, J=2.2 Hz).

Example 44b

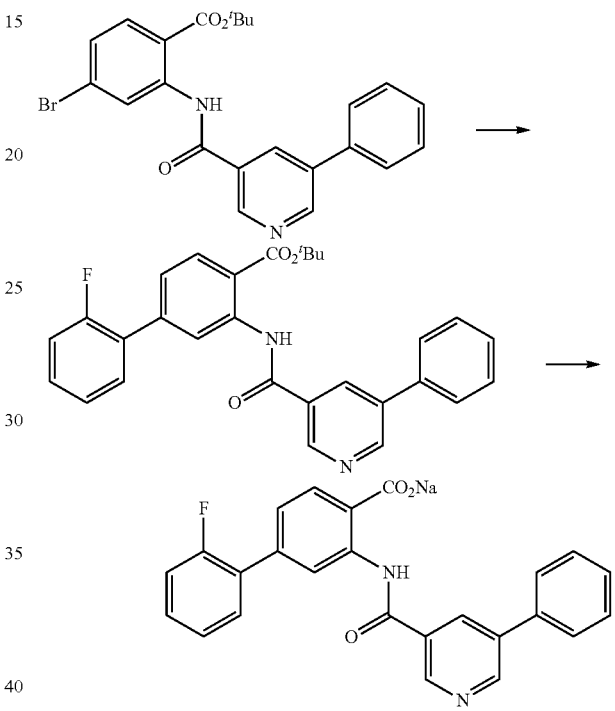

Ethanol (0.62 mL), water (0.31 mL), sodium carbonate (70 mg), 2-fluorophenylboronic acid (37 mg), and tetrakis(triphenylphosphine)palladium(0) (13 mg) were added to a toluene (2.1 mL) suspension of tert-butyl 4-bromo-2-(5-phenylpyridine-3-carboxamido)benzoate (0.10 g), followed by heating to reflux under a nitrogen atmosphere for 2 hours and 30 minutes. The reaction mixture was cooled to room temperature, and then a 10% aqueous solution of citric acid and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 91-85% hexane/ethyl acetate] to obtain tert-butyl 4-(2-fluorophenyl)-2-(5-phenylpyridine-3-carboxamido)benzoate.

Trifluoroacetic acid (3.0 mL) was added to the obtained tert-butyl 4-(2-fluorophenyl)-2-(5-phenylpyridine-3-carboxamido)benzoate, followed by stirring at room temperature for 1 hour and 30 minutes. The solvent was evaporated under reduced pressure, and diisopropyl ether was added to the obtained residue. The solid substance was collected by filtration. Dioxane (3.0 mL) and a 2 mol/L aqueous solution of sodium hydroxide (0.041 mL) were added to the obtained solid substance, followed by stirring at room temperature for 1 hour. A 10% aqueous solution of citric acid was added to the reaction mixture, and the solid substance was collected by filtration to obtain 36 mg of 4-(2-fluorophenyl)-2-(5-phenylpyridine-3-carboxamido)benzoic acid as a white solid.

Ethanol (1.5 mL) and a 1 mol/L aqueous solution of sodium hydroxide (0.087 mL) were sequentially added to the obtained 4-(2-fluorophenyl)-2-(5-phenylpyridine-3-carboxamido)benzoic acid (36 mg), followed by stirring at room temperature for 3 hours. The solid substance was collected by filtration to obtain 22 mg of sodium 4-(2-fluorophenyl)-2-(5-phenylpyridine-3-carboxamido)-benzoate as a white solid.

$^1$H-NMR (DMSO-$d_6$) δ: 7.21 (1H, ddd, J=8.0, 1.8, 1.8 Hz), 7.30-7.38 (2H, m), 7.41-7.53 (2H, m), 7.53-7.61 (3H, m), 7.81-7.87 (2H, m), 8.13 (1H, d, J=8.0 Hz), 8.61 (1H, dd, J=2.2, 2.1 Hz), 8.90-8.94 (1H, m), 9.09 (1H, d, J=2.2 Hz), 9.18 (1H, d, J=2.1 Hz).

Example 45b

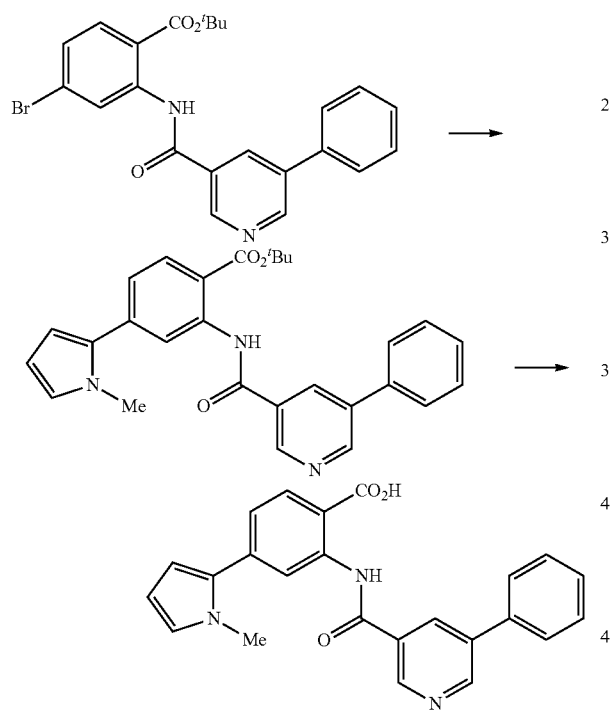

Ethanol (0.62 mL), water (0.31 mL), sodium carbonate (70 mg), 1-methyl-2-(4,4,5,5-tetramethyl-1,3,2-dioxaborolan-2-yl)-1H-pyrrole (55 mg), and tetrakis(triphenylphosphine)palladium(0) (13 mg) were added to a toluene (2.1 mL) solution of tert-butyl 4-bromo-2-(5-phenylpyridine-3-carboxamido)benzoate (0.10 g), followed by heating to reflux under a nitrogen atmosphere for 2 hours. The reaction mixture was cooled to room temperature, and then sodium carbonate (23 mg), 1-methyl-2-(4,4,5,5-tetramethyl-1,3,2-dioxaborolan-2-yl)-1H-pyrrole (46 mg), and tetrakis(triphenylphosphine)palladium(0) (13 mg) were added thereto, followed by heating to reflux under a nitrogen atmosphere for 3 hours and 30 minutes. The reaction mixture was cooled to room temperature, and then toluene (1.0 mL), ethanol (0.31 mL), and water (0.16 mL) were added thereto, followed by heating to reflux under a nitrogen atmosphere for 2 hours. The reaction mixture was cooled to room temperature, and then a 10% aqueous solution of citric acid and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 95-85% hexane/ethyl acetate] to obtain 71 mg of tert-butyl 4-(1-methyl-1H-pyrrol-2-yl)-2-(5-phenylpyridine-3-carboxamido)benzoate as a light yellow solid.

Methanol (1.5 mL), dioxane (1.5 mL), and a 2 mol/L aqueous solution of sodium hydroxide (0.24 mL) were added the obtained tert-butyl 4-(1-methyl-1H-pyrrol-2-yl)-2-(5-phenylpyridine-3-carboxamido)benzoate (71 mg), followed by stirring at 50 to 55° C. for 2 hours. The reaction mixture was cooled to room temperature, and then a 10% aqueous solution of citric acid was added thereto. The solid substance was collected by filtration to obtain 50 mg of 4-(1-methyl-1H-pyrrol-2-yl)-2-(5-phenylpyridine-3-carboxamido)benzoic acid as a white solid.

$^1$H-NMR (DMSO-$d_6$) S13.79 (3H, s), 6.15 (1H, dd, J=3.0, 3.0 Hz), 6.38-6.43 (1H, m), 6.97 (1H, dd, J=2.1, 2.1 Hz), 7.36 (1H, dd, J=8.3, 1.6 Hz), 7.47-7.53 (1H, m), 7.54-7.61 (2H, m), 7.81-7.87 (2H, m), 8.07 (1H, d, J=8.3 Hz), 8.54 (1H, dd, J=2.1, 2.1 Hz), 8.84 (1H, d, J=1.6 Hz), 9.13 (1H, d, J=2.1 Hz), 9.15 (1H, d, J=2.1 Hz), 12.37 (1H, s).

Example 46b

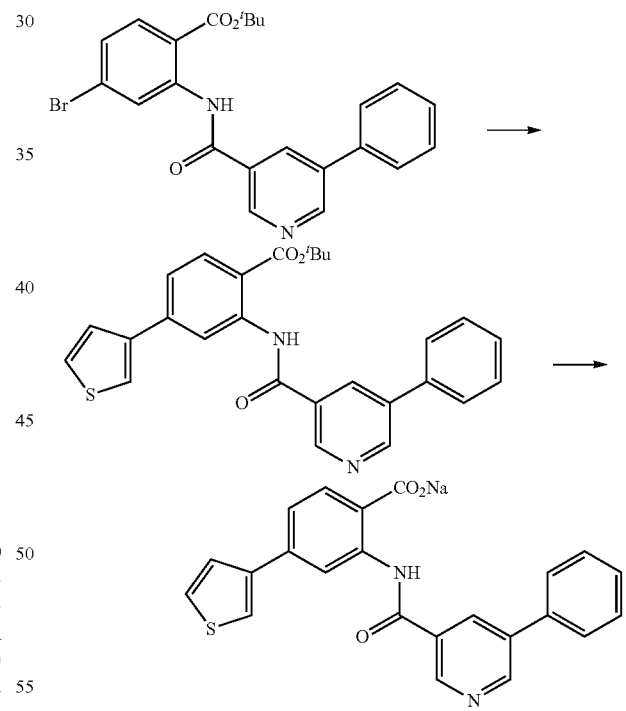

Water (0.6 mL), sodium carbonate (47 mg), 3-thiopheneboronic acid (27 mg), and bis(triphenylphosphine)palladium(II) dichloride (2.5 mg) were added to an ethylene glycol dimethyl ether (2.0 mL) solution of tert-butyl 4-bromo-2-(5-phenylpyridine-3-carboxamido)benzoate (80 mg), followed by heating to reflux under a nitrogen atmosphere for 2 hours and 10 minutes. The reaction mixture was cooled to room temperature, and then ethyl acetate and a 10% aqueous solution of citric acid was added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 95-85% hexane/ethyl acetate] to obtain tert-butyl 2-(5-phenylpyridine-3-carboxamido)-4-(thiophen-3-yl)benzoate.

Trifluoroacetic acid (4.0 mL) was added to the obtained tert-butyl 2-(5-phenylpyridine-3-carboxamido)-4-(thiophen-3-yl)benzoate, followed by stirring at room temperature for 1 hour and 30 minutes. The solvent was evaporated under reduced pressure, and diisopropyl ether was added to the obtained residue. The solid substance was collected by filtration to obtain 47 mg of 2-(5-phenylpyridine-3-carboxamido)-4-(thiophen-3-yl)benzoic acid as a white solid.

A 1 mol/L aqueous solution of sodium hydroxide (0.10 mL) was added to an ethanol (4.0 mL) suspension of the obtained 2-(5-phenylpyridine-3-carboxamido)-4-(thiophen-3-yl)benzoic acid (47 mg) at room temperature, followed by stirring at the same temperature for 1 hour and 10 minutes. The solvent was evaporated under reduced pressure, and ethanol and water were added to the obtained residue. The solid substance was collected by filtration to obtain 40 mg of sodium 2-(5-phenylpyridine-3-carboxamido)-4-(thiophen-3-yl)benzoate as a white solid.

$^1$H-NMR (DMSO-$d_6$) δ: 7.36-7.42 (1H, m), 7.46-7.54 (2H, m), 7.54-7.61 (2H, m), 7.65-7.70 (1H, m), 7.81-7.87 (3H, m), 8.04-8.10 (1H, m), 8.59-8.64 (1H, m), 9.01-9.05 (1H, m), 9.08-9.12 (1H, m), 9.17-9.21 (1H, m).

Example 47b

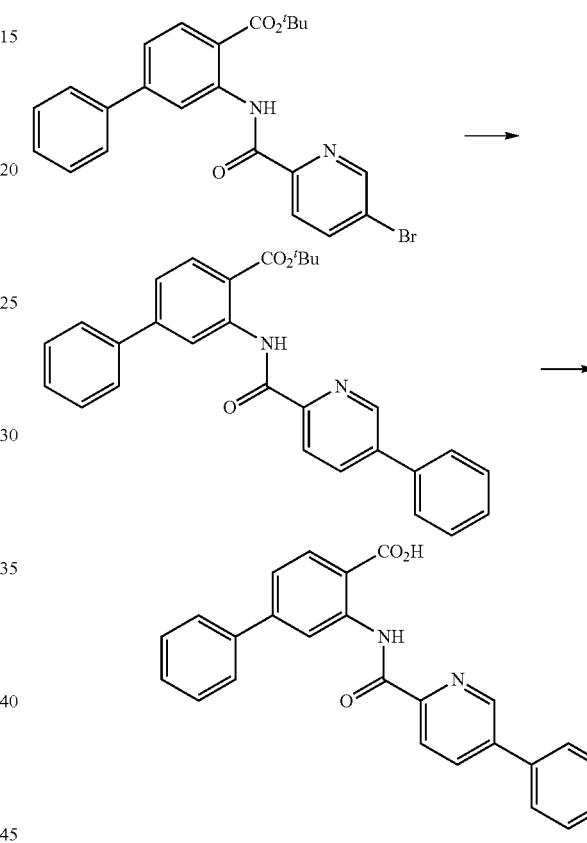

As in Example 46b, the following compound was prepared.

Sodium 4-(4-(difluoromethoxy)phenyl)-2-(5-phenylpyridine-3-carboxamido)benzoate $^1$H-NMR (DMSO-$d_6$) δ: 7.12-7.53 (5H, m), 7.54-7.62 (2H, m), 7.72-7.78 (2H, m), 7.81-7.87 (2H, m), 8.13 (1H, d, J=7.8 Hz), 8.59-8.65 (1H, m), 9.01-9.05 (1H, m), 9.11 (1H, d, J=1.5 Hz), 9.20 (1H, d, J=1.5 Hz).

Example 48b

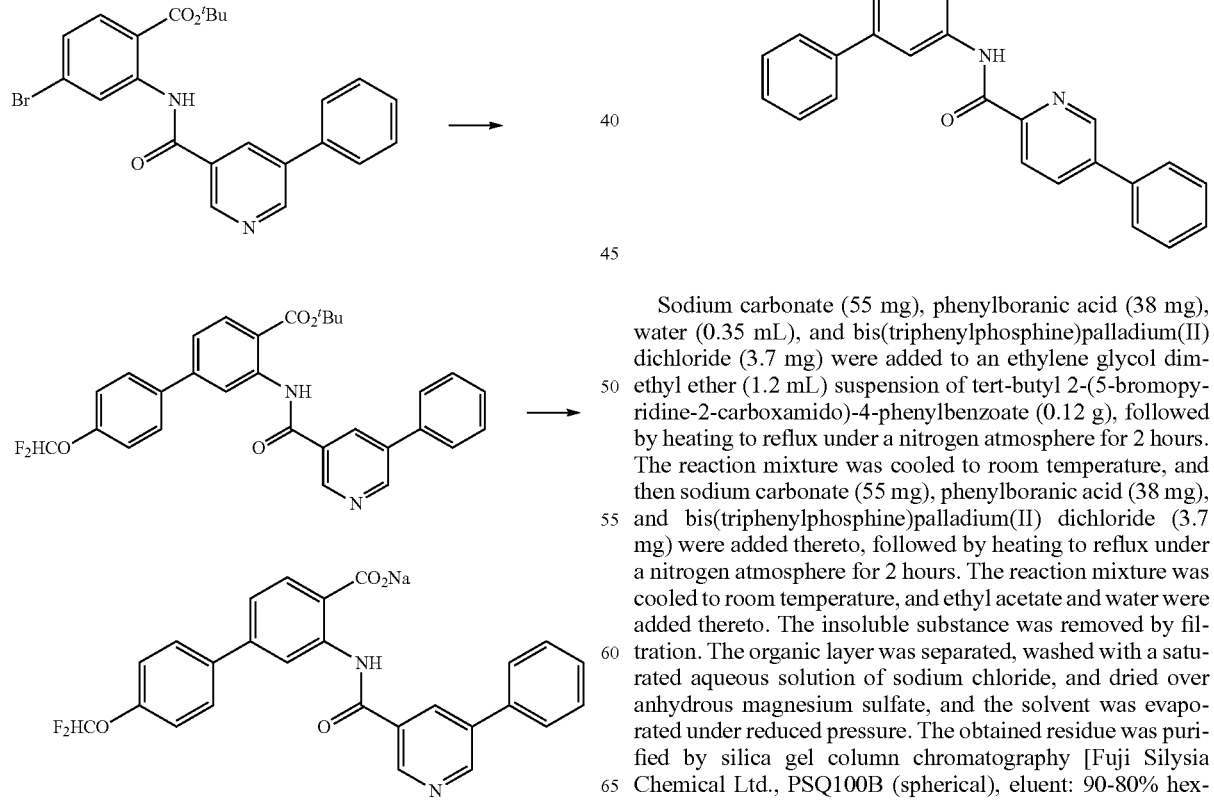

Sodium carbonate (55 mg), phenylboranic acid (38 mg), water (0.35 mL), and bis(triphenylphosphine)palladium(II) dichloride (3.7 mg) were added to an ethylene glycol dimethyl ether (1.2 mL) suspension of tert-butyl 2-(5-bromopyridine-2-carboxamido)-4-phenylbenzoate (0.12 g), followed by heating to reflux under a nitrogen atmosphere for 2 hours. The reaction mixture was cooled to room temperature, and then sodium carbonate (55 mg), phenylboranic acid (38 mg), and bis(triphenylphosphine)palladium(II) dichloride (3.7 mg) were added thereto, followed by heating to reflux under a nitrogen atmosphere for 2 hours. The reaction mixture was cooled to room temperature, and ethyl acetate and water were added thereto. The insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 90-80% hexane/ethyl acetate] to obtain 0.11 g of tert-butyl 4-phenyl-2-(5-phenylpyridine-2-carboxamido)benzoate as a white solid.

Trifluoroacetic acid (5 mL) was added to the obtained tert-butyl 4-phenyl-2-(5-phenylpyridine-2-carboxamido)benzoate (0.11 g), followed by stirring at room temperature for 4 hours. The solvent was evaporated under reduced pressure, and ethyl acetate and water were added to the obtained residue. After adjusting the pH to 6.5 with a saturated aqueous solution of sodium bicarbonate, the organic layer was separated, washed with water and a saturated aqueous solution of sodium chloride sequentially, and dried over anhydrous magnesium sulfate, and the solvent was evaporated under reduced pressure. Diisopropyl ether was added to the obtained residue, and the solid substance was collected by filtration to obtain 90 mg of 4-phenyl-2-(5-phenylpyridine-2-carboxamido)benzoic acid as a white solid.

$^1$H-NMR (DMSO-d$_6$) δ: 7.44-7.60 (7H, m), 7.73-7.79 (2H, m), 7.85-7.91 (2H, m), 8.15 (1H, d, J=8.1 Hz), 8.29 (1H, d, J=8.3 Hz), 8.40 (1H, dd, J=8.2, 2.3 Hz), 9.08 (1H, d, J=2.0 Hz), 9.26 (1H, d, J=1.7 Hz), 13.23 (1H, s).

Example 49b

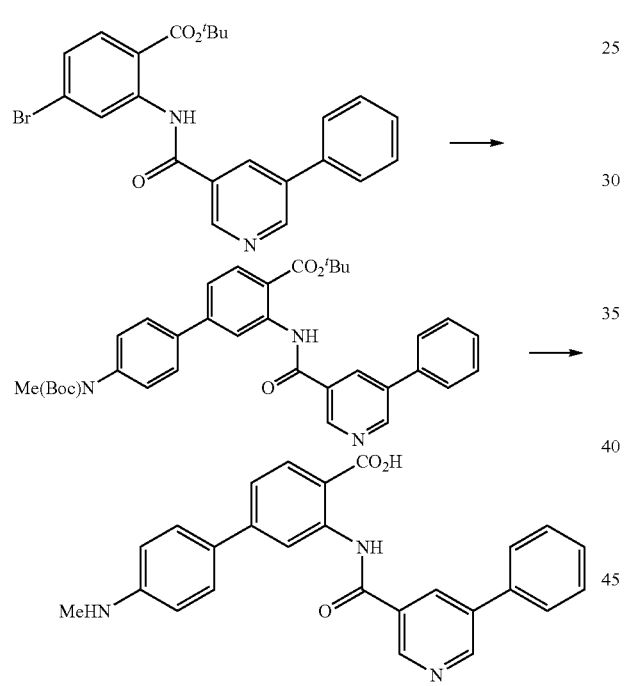

Water (0.60 mL), sodium carbonate (88 mg), tert-butyl methyl(4-(4,4,5,5-tetramethyl-1,3,2-dioxaborolan-2-yl)phenyl)carbamate (0.13 g), and bis(triphenylphosphine)palladium(II) dichloride (5.0 mg) were added to an ethylene glycol dimethyl ether (2.0 mL) solution of tert-butyl 4-bromo-2-(5-phenylpyridine-3-carboxamido)benzoate (0.15 g), followed by heating to reflux under a nitrogen atmosphere for 1 hour. The reaction mixture was cooled to room temperature, and then a 10% aqueous solution of citric acid and ethyl acetate were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 95-85% hexane/ethyl acetate] to obtain 0.16 g of tert-butyl 4-(4-((tert-butoxycarbonyl)(methyl)amino)phenyl)-2-(5-phenylpyridine-3-carboxamido)benzoate as a white solid.

Trifluoroacetic acid (4.0 mL) was added to the obtained tert-butyl 4-(4-((tert-butoxycarbonyl)(methyl)amino)phenyl)-2-(5-phenylpyridine-3-carboxamido)benzoate (0.16 g), followed by stirring at room temperature for 1 hour. The solvent was evaporated under reduced pressure, and diisopropyl ether was added to the obtained residue. The solid substance was collected by filtration, and ethanol and water were added to the obtained solid substance. After adjusting the pH to 5.5 with a 1 mol/L aqueous solution of sodium hydroxide, the solid substance was collected by filtration to obtain 0.11 g of 4-(4-(methylamino)phenyl)-2-(5-phenylpyridine-3-carboxamido)benzoic acid as a light yellow solid.

$^1$H-NMR (DMSO-d$_6$) δ: 2.74 (3H, s), 6.65-6.71 (2H, m), 7.43-7.61 (6H, m), 7.81-7.87 (2H, m), 8.05 (1H, d, J=8.3 Hz), 8.53-8.58 (1H, m), 8.97 (1H, d, J=1.5 Hz), 9.11-9.18 (2H, m), 12.39 (1H, s).

Example 50b

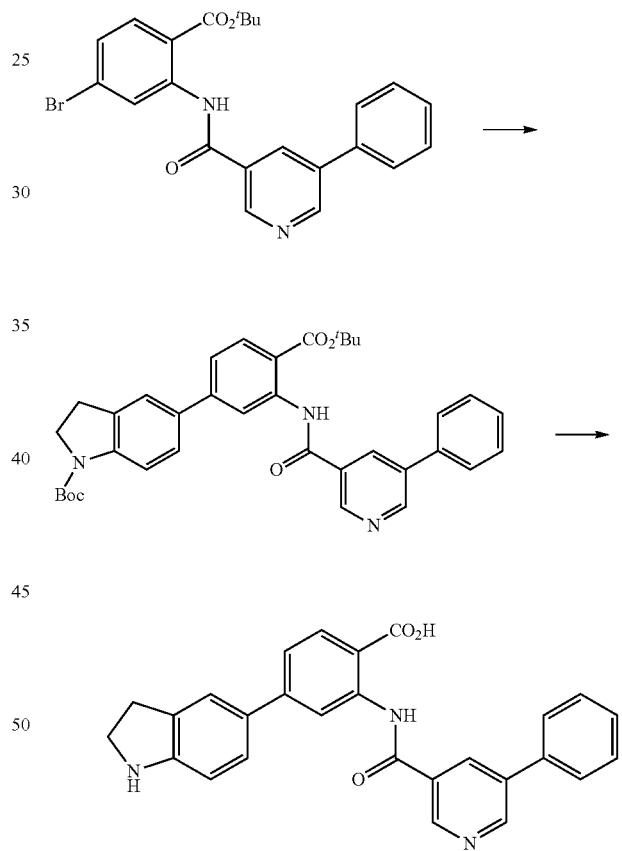

As in Example 49b, the following compound was prepared.

4-(Indolin-5-yl)-2-(5-phenylpyridine-3-carboxamido)benzoic acid $^1$H-NMR (DMSO-d$_6$) δ: 3.02 (2H, t, J=8.4 Hz), 3.51 (2H, t, J=8.4 Hz), 6.61 (1H, d, J=8.3 Hz), 7.37 (1H, d, J=8.3 Hz), 7.40-7.48 (2H, m), 7.50 (1H, dd, J=7.3, 7.3 Hz), 7.54-7.62

(2H, m), 7.80-7.89 (2H, m), 8.05 (1H, d, J=8.3 Hz), 8.56 (1H, s), 8.97 (1H, s), 9.07-9.23 (2H, m), 12.46 (1H, s).

Example 51b

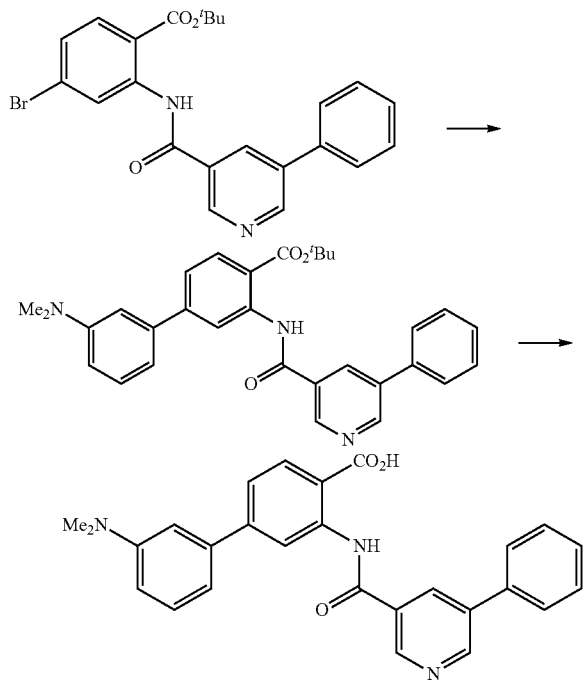

As in Example 49b, the following compound was prepared.

4-(3-(Dimethylamino)phenyl)-2-(5-phenylpyridine-3-carboxamido)benzoic acid $^1$H-NMR (DMSO-d$_6$) δ: 2.99 (6H, s), 6.79-6.87 (1H, m), 6.95-7.04 (2H, m), 7.34 (1H, dd, J=8.2, 8.2 Hz), 7.47-7.63 (4H, m), 7.81-7.89 (2H, m), 8.12 (1H, d, J=8.3 Hz), 8.56 (1H, dd, J=2.1, 2.1 Hz), 8.98 (1H, d, J=1.7 Hz), 9.11-9.19 (2H, m), 12.35 (1H, s).

Example 52b

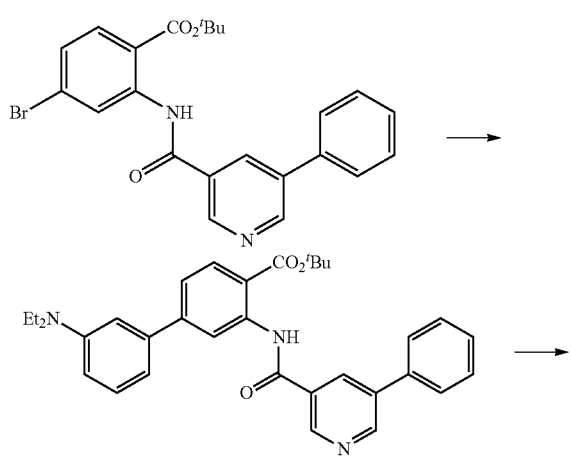

-continued

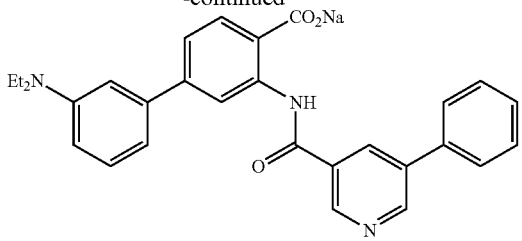

Tert-butyl 4-bromo-2-(5-phenylpyridine-3-carboxamido)benzoate (0.11 g), sodium carbonate (64 mg), water (0.30 mL), and bis(triphenylphosphine)palladium(II) dichloride (3.5 mg) were added to an ethylene glycol dimethyl ether (1.0 mL) solution of N,N-diethyl-3-(4,4,5,5-tetramethyl-1,3,2-dioxaborolan-2-yl)aniline (83 mg), followed by heating to reflux under a nitrogen atmosphere for 2 hours and 40 minutes. The reaction mixture was cooled to room temperature, and then water and chloroform were added thereto. The organic layer was separated and dried over anhydrous magnesium sulfate, and the solvent was evaporated under reduced pressure. The obtained residue was purified by silica gel column chromatography [eluent: 90-70% hexane/ethyl acetate] to obtain 0.12 g of tert-butyl 4-(3-(diethylamino)phenyl)-2-(5-phenylpyridine-3-carboxamido)benzoate as a yellow solid.

Trifluoroacetic acid (1.0 mL) was added to the obtained tert-butyl 4-(3-(diethylamino)phenyl)-2-(5-phenylpyridine-3-carboxamido)benzoate (0.12 g), followed by stirring at room temperature for 1 hour and 10 minutes. The solvent was evaporated under reduced pressure, and methanol (2.0 mL) was added to the obtained residue. After adjusting the pH to 12.7 with a 2 mol/L aqueous solution of sodium hydroxide, the solid substance was collected by filtration to obtain 99 mg of sodium 4-(3-(diethylamino)phenyl)-2-(5-phenylpyridine-3-carboxamido)benzoate as a white solid.

$^1$H-NMR (DMSO-d$_6$) δ: 1.15 (6H, t, J=7.0 Hz), 3.41 (4H, q, J=7.0 Hz), 6.70 (1H, dd, J=8.4, 2.3 Hz), 6.81-6.92 (2H, m), 7.21-7.31 (2H, m), 7.46-7.62 (3H, m), 7.81-7.89 (2H, m), 8.09 (1H, d, J=7.8 Hz), 8.59-8.65 (1H, m), 8.98 (1H, d, J=1.7 Hz), 9.09 (1H, d, J=2.0 Hz), 9.19 (1H, d, J=2.0 Hz).

Example 53b

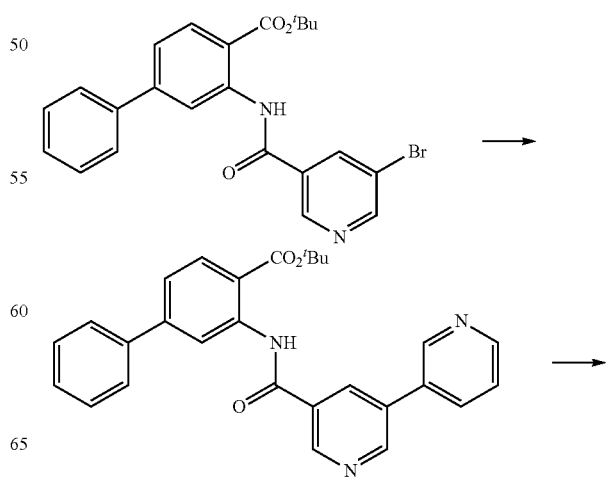

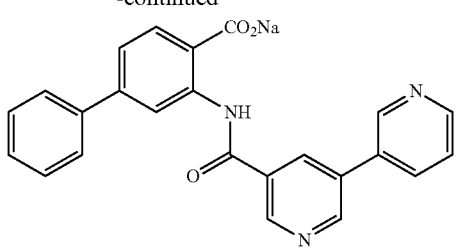

As in Example 52b, the following compound was prepared.

Sodium 4-phenyl-2-(5-(pyridin-3-yl)pyridine-3-carboxamido)benzoate $^1$H-NMR (DMSO-$d_6$) δ: 7.34 (1H, dd, J=8.0, 1.8 Hz), 7.37-7.43 (1H, m), 7.47-7.54 (2H, m), 7.60 (1H, dd, J=8.0, 4.9 Hz), 7.66-7.72 (2H, m), 8.12 (1H, d, J=8.0 Hz), 8.26 (1H, ddd, J=8.0, 2.0, 2.0 Hz), 8.67 (1H, dd, J=2.2, 2.2 Hz), 8.70 (1H, dd, J=4.9, 1.4 Hz), 9.03 (1H, d, J=1.7 Hz), 9.05 (1H, d, J=1.9 Hz), 9.17 (1H, d, J=2.2 Hz), 9.24 (1H, d, J=2.0 Hz).

Example 54b

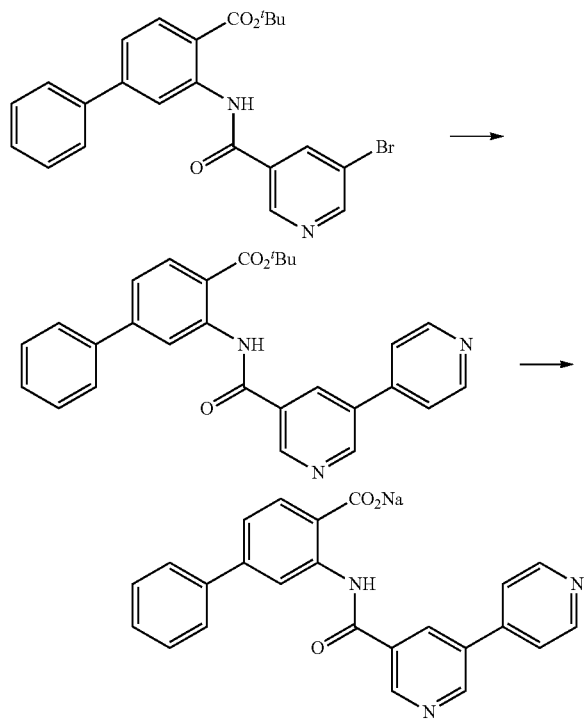

As in Example 52b, the following compound was prepared.

Sodium 4-phenyl-2-(5-(pyridin-4-yl)pyridine-3-carboxamido)benzoate $^1$H-NMR (DMSO-$d_6$) δ: 7.31-7.36 (1H, m), 7.36-7.43 (1H, m), 7.47-7.54 (2H, m), 7.66-7.72 (2H, m), 7.87-7.92 (2H, m), 8.12 (1H, d, J=8.1 Hz), 8.71-8.78 (3H, m), 9.00-9.04 (1H, m), 9.21-9.24 (1H, m), 9.26-9.30 (1H, m).

Example 55b

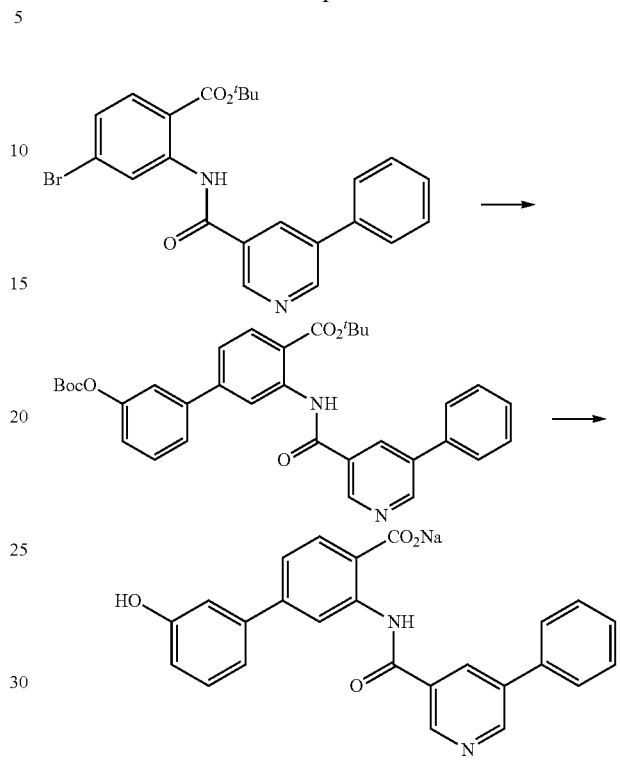

Water (0.6 mL), sodium carbonate (58 mg), tert-butyl 3-(4,4,5,5-tetramethyl-1,3,2-dioxaborolan-2-yl)phenylcarbonate (85 mg), and bis(triphenylphosphine)palladium(II) dichloride (3.0 mg) were added to an ethylene glycol dimethyl ether (2.0 mL) suspension of tert-butyl 4-bromo-2-(5-phenylpyridine-3-carboxamido)benzoate (0.10 g), followed by heating to reflux under a nitrogen atmosphere for 1 hour. The reaction mixture was cooled to room temperature, and then ethyl acetate and a 10% aqueous solution of citric acid were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 95-80% hexane/ethyl acetate] to obtain tert-butyl 4-(3-(tert-butoxycarbonyl)oxyphenyl)-2-(5-phenylpyridine-3-carboxamido)benzoate.

Trifluoroacetic acid (4.0 mL) was added to the obtained tert-butyl 4-(3-(tert-butoxycarbonyl)oxyphenyl)-2-(5-phenylpyridine-3-carboxamido)benzoate, followed by stirring at room temperature for 1 hour and 15 minutes. The solvent was evaporated under reduced pressure, and diisopropyl ether was added to the obtained residue. The solid substance was collected by filtration to obtain 70 mg of 4-(3-hydroxyphenyl)-2-(5-phenylpyridine-3-carboxamido)benzoic acid as a light yellow solid.

Ethanol (4.0 mL) and a 1 mol/L aqueous solution of sodium hydroxide (0.17 mL) were sequentially added to the obtained 4-(3-hydroxyphenyl)-2-(5-phenylpyridine-3-carboxamido)benzoic acid (70 mg), followed by stirring at room temperature for 1 hour. The solvent was evaporated under reduced pressure, and ethanol and water were added to the obtained residue. The solid substance was collected by filtration to obtain 26 mg of sodium 4-(3-hydroxyphenyl)-2-(5-phenylpyridine-3-carboxamido)benzoate as a white solid.

$^1$H-NMR (DMSO-$d_6$) δ: 6.76-6.83 (1H, m), 7.08-7.14 (2H, m), 7.25-7.33 (2H, m), 7.46-7.53 (1H, m), 7.54-7.62 (2H, m), 7.81-7.87 (2H, m), 8.10 (1H, d, J=8.1 Hz), 8.61 (1H, dd, J=2.2, 2.1 Hz), 9.00 (1H, d, J=1.7 Hz), 9.10 (1H, d, J=2.2 Hz), 9.18 (1H, d, J=2.1 Hz), 9.59 (1H, s).

Example 56b

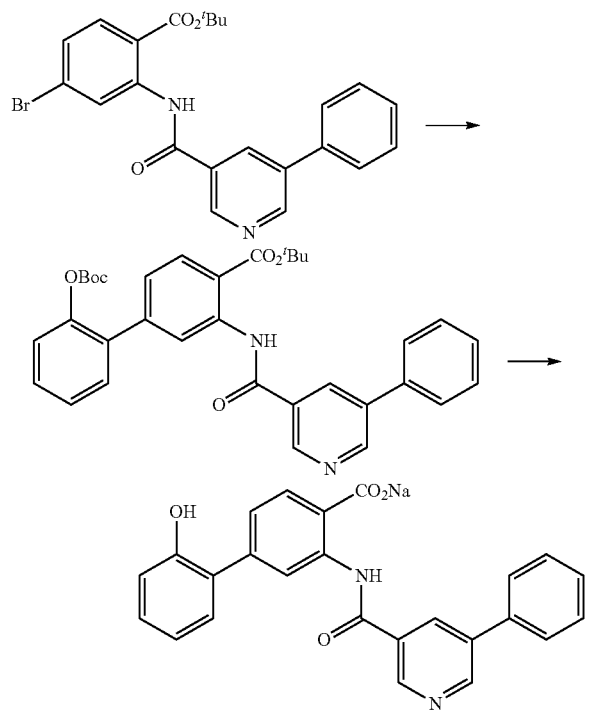

As in Example 31b, the following compound was prepared.

Sodium 4-(2-hydroxyphenyl)-2-(5-phenylpyridine-3-carboxamido)benzoate $^1$H-NMR (DMSO-$d_6$) δ: 6.90 (1H, dd, J=7.4, 7.4 Hz), 6.96 (1H, d, J=8.0 Hz), 7.14-7.26 (2H, m), 7.26-7.32 (1H, m), 7.49 (1H, dd, J=7.3, 7.3 Hz), 7.54-7.61 (2H, m), 7.80-7.87 (2H, m), 8.05 (1H, d, J=8.0 Hz), 8.60 (1H, dd, J=2.1, 2.1 Hz), 8.88 (1H, d, J=1.4 Hz), 9.09 (1H, d, J=2.0 Hz), 9.17 (1H, d, J=1.7 Hz), 9.54 (1H, s).

Example 57b

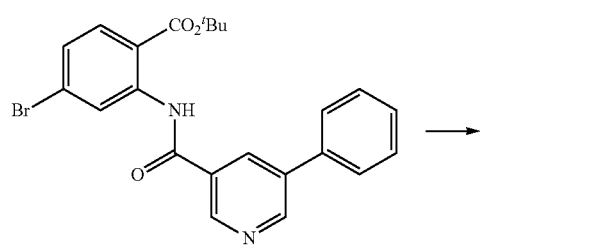

As in Example 55b, the following compound was prepared.

Sodium 4-(furan-3-yl)-2-(5-phenylpyridine-3-carboxamido)benzoate $^1$H-NMR (DMSO-$d_6$) δ: 6.91 (1H, s), 7.31 (1H, d, J=8.0 Hz), 7.45-7.63 (3H, m), 7.76-7.89 (3H, m), 8.06 (1H, d, J=7.8 Hz), 8.17 (1H, s), 8.61 (1H, s), 8.91 (1H, s), 9.10 (1H, s), 9.19 (1H, s).

Example 58b

Tripotassium phosphate (0.12 g), 1-(tert-butoxycarbonyl)-1H-pyrrole-2-boronic acid (56 mg), 2-dicyclohexylphosphino-2',6'-dimethoxybiphenyl (1 mg), and palladium(II) acetate (1 mg) were added to a toluene (3.0 mL) solution of tert-butyl 4-bromo-2-(5-phenylpyridine-3-carboxamido)

benzoate (0.10 g), followed by heating to reflux under a nitrogen atmosphere for 3 hours. The reaction mixture was cooled to room temperature, and tripotassium phosphate (47 mg), 1-(tert-butoxycarbonyl)-1H-pyrrole-2-boronic acid (47 mg), 2-dicyclohexylphosphino-2',6'-dimethoxybiphenyl (1 mg), and palladium(II) acetate (1 mg) were added thereto, followed by heating to reflux under a nitrogen atmosphere for 1 hour and 30 minutes. The reaction mixture was cooled to room temperature, and ethyl acetate and a 10% aqueous solution of citric acid were added thereto. The organic layer was separated, washed with a saturated aqueous solution of sodium chloride, and dried over anhydrous magnesium sulfate, and the solvent was evaporated under reduced pressure. Dioxane (1.5 mL), methanol (1.5 mL), and a 2 mol/L aqueous solution of sodium hydroxide (0.29 mL) were sequentially added to the obtained residue, followed by stiffing at 50° C. for 1 hour and 30 minutes. The reaction mixture was cooled to room temperature, and then a 10% aqueous solution of citric acid and ethyl acetate were sequentially added thereto. The solid substance was collected by filtration to obtain 39 mg of 2-(5-phenylpyridine-3-carboxamido)-4-(1H-pyrrol-2-yl) benzoic acid as a white solid.

$^1$H-NMR (DMSO-$d_6$) δ: 6.18-6.24 (1H, m), 6.63-6.69 (1H, m), 6.95-7.01 (1H, m), 7.46-7.54 (2H, m), 7.54-7.62 (2H, m), 7.81-7.88 (2H, m), 8.03 (1H, d, J=8.3 Hz), 8.56 (1H, dd, J=2.1, 2.1 Hz), 8.90 (1H, d, J=1.7 Hz), 9.12-9.17 (2H, m), 11.61 (1H, s), 12.38 (1H, s), 13.50-13.82 (1H, broad).

Example 59b

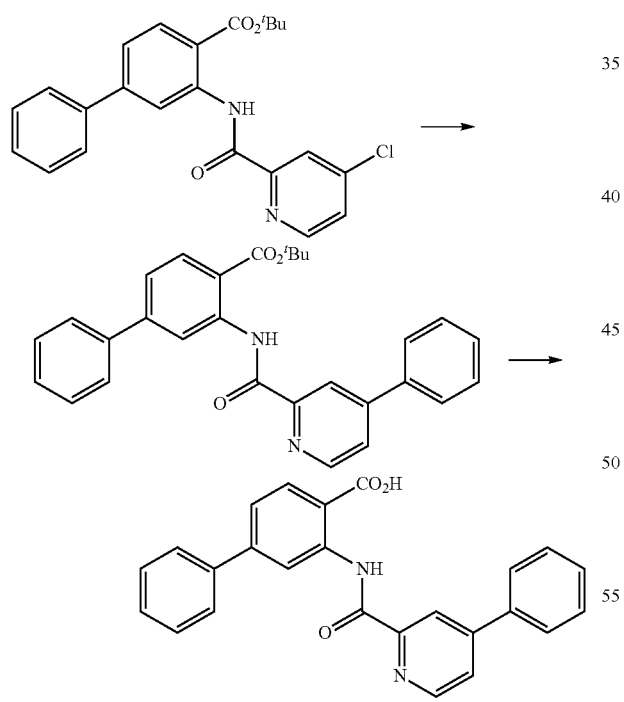

Phenylboranic acid (21 mg), tripotassium phosphate (69 mg), 2-dicyclohexylphosphino-2',6'-dimethoxybiphenyl (1.2 mg), and palladium(II) acetate (1.3 mg) were added to a toluene (1.2 mL) solution of tert-butyl 2-(4-chloropyridine-2-carboxamido)-4-phenylbenzoate (60 mg), followed by heating to reflux under a nitrogen atmosphere for 3 hours. The reaction mixture was cooled to room temperature, and then phenylboranic acid (5.4 mg), tripotassium phosphate (16 mg), 2-dicyclohexylphosphino-2',6'-dimethoxybiphenyl (1.2 mg), and palladium(II) acetate (1.3 mg) were added thereto, followed by heating to reflux under a nitrogen atmosphere for 2 hours. The reaction mixture was cooled to room temperature, and then ethyl acetate and a 10% aqueous solution of citric acid were added thereto. The insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 100-85% hexane/ethyl acetate] to obtain 65 mg of tert-butyl 4-phenyl-2-(4-phenylpyridine-2-carboxamido)benzoate as a colorless oily substance.

Trifluoroacetic acid (5 mL) was added to the obtained tert-butyl 4-phenyl-2-(4-phenylpyridine-2-carboxamido) benzoate (64 mg), followed by stirring at room temperature for 3 hours. The solvent was evaporated under reduced pressure, and ethyl acetate and water were added to the obtained residue. After adjusting the pH to 6.5 with a saturated aqueous solution of sodium bicarbonate, the organic layer was separated, washed with water and a saturated aqueous solution of sodium chloride sequentially, and dried over anhydrous magnesium sulfate, and the solvent was evaporated under reduced pressure. Diisopropyl ether was added to the obtained residue, and the solid substance was collected by filtration to obtain 50 mg of 4-phenyl-2-(4-phenylpyridine-2-carboxamido)benzoic acid as a white solid.

$^1$H-NMR (DMSO-$d_6$) δ: 7.44-7.51 (1H, m), 7.51-7.62 (6H, m), 7.73-7.78 (2H, m), 7.89-7.94 (2H, m), 8.04 (1H, dd, J=5.1, 1.9 Hz), 8.15 (1H, d, J=8.3 Hz), 8.48 (1H, d, J=1.2 Hz), 8.82 (1H, d, J=5.1 Hz), 9.27 (1H, d, J=1.7 Hz), 13.20 (1H, s).

Example 60b

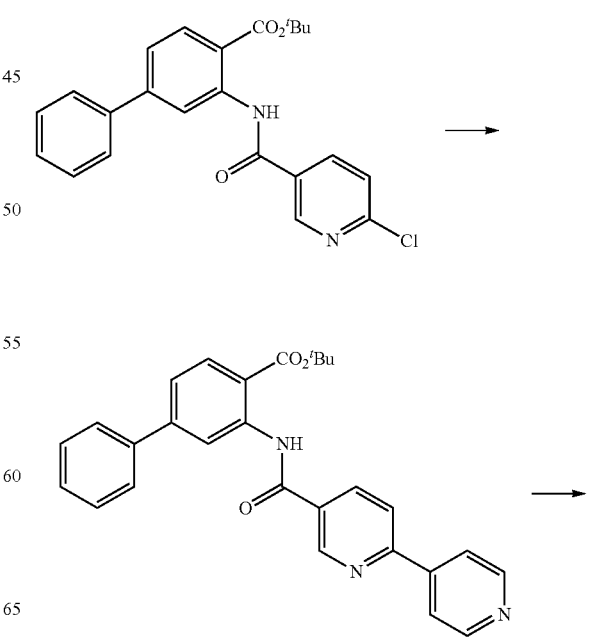

-continued

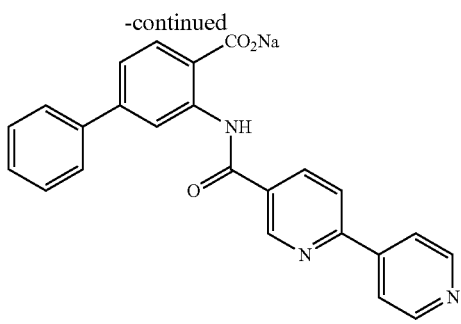

4-(4,4,5,5-Tetramethyl-1,3,2-dioxaborolan-2-yl)-pyridine (48 mg), tripotassium phosphate (91 mg), 2-dicyclohexylphosphino-2',6'-dimethoxybiphenyl (1.6 mg), and palladium (II) acetate (1.8 mg) were added to a toluene (1.6 mL) suspension of tert-butyl 2-(6-chloropyridine-3-carboxamido)-4-phenylbenzoate (80 mg), followed by heating to reflux under a nitrogen atmosphere for 2 hours and 30 minutes. The reaction mixture was cooled to room temperature, and then 4-(4,4,5,5-tetramethyl-1,3,2-dioxaborolan-2-yl)pyridine (48 mg), tripotassium phosphate (91 mg), 2-dicyclohexylphosphino-2',6'-dimethoxybiphenyl (1.6 mg), and palladium(II) acetate (1.8 mg) were added thereto, followed by heating to reflux under a nitrogen atmosphere for 3 hours. The reaction mixture was cooled to room temperature, and then 2-dicyclohexylphosphino-2',6'-dimethoxybiphenyl (1.6 mg) and palladium(II) acetate (1.8 mg) were added thereto, followed by heating to reflux under a nitrogen atmosphere for 2 hours. After cooling the reaction mixture to room temperature, the solvent was evaporated under reduced pressure, and chloroform and water were added to the residue. The insoluble substance was removed by filtration. The organic layer was separated, washed with a saturated aqueous solution of sodium chloride, and dried over anhydrous magnesium sulfate, and the solvent was evaporated under reduced pressure. The obtained residue was purified by silica gel column chromatography [Fuji Silysia Chemical Ltd., PSQ100B (spherical), eluent: 90-15% hexane/ethyl acetate] to obtain 25 mg of tert-butyl 4-phenyl-2-(6-(pyridin-4-yl)pyridine-3-carboxamido)benzoate as a light yellow solid.

Trifluoroacetic acid (5 mL) was added to the obtained tert-butyl 4-phenyl-2-(6-(pyridin-4-yl)pyridine-3-carboxamido)benzoate (25 mg), followed by stirring at room temperature for 3 hours. The solvent was evaporated under reduced pressure, and water was added to the obtained residue. After adjusting the pH to 5.5 with a saturated aqueous solution of sodium bicarbonate, the solid substance was collected by filtration to obtain 20 mg of 4-phenyl-2-(6-(pyridin-4-yl)pyridine-3-carboxamido)benzoic acid as a yellow solid.

Dioxane (2 mL), methanol (2 mL), and a 2 mol/L aqueous solution of sodium hydroxide (0.025 mL) were added to the obtained 4-phenyl-2-(6-(pyridin-4-yl)pyridine-3-carboxamido)benzoic acid (20 mg), and the solvent was evaporated under reduced pressure. Acetone was added to the obtained residue. The solid substance was collected by filtration to obtain 17 mg of sodium 4-phenyl-2-(6-(pyridin-4-yl)pyridine-3-carboxamido)benzoate as a yellow solid.

$^1$H-NMR (DMSO-$d_6$) δ: 7.30-7.43 (2H, m), 7.46-7.54 (2H, m), 7.66-7.72 (2H, m), 8.08-8.20 (3H, m), 8.32-8.38 (1H, m), 8.49-8.55 (1H, m), 8.73-8.80 (2H, m), 9.00-9.04 (1H, m), 9.35 (1H, s).

Example 61b

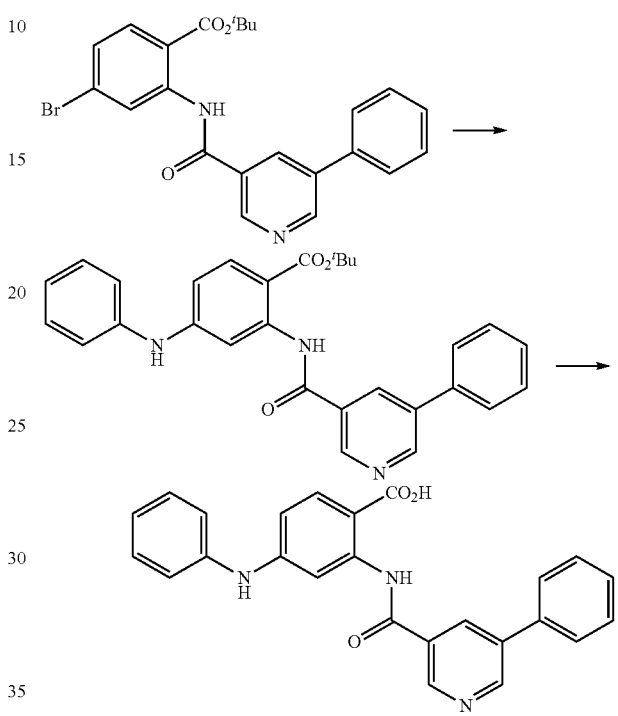

Cesium carbonate (0.14 g), aniline (0.030 mL), tris(dibenzylideneacetone)dipalladium(0) (2 mg), palladium(II) acetate (1 mg), and 2-dicyclohexylphosphino-2',4',6'-triisopropylbiphenyl (5 mg) were added to a toluene (2.5 mL) solution of tert-butyl 4-bromo-2-(5-phenylpyridine-3-carboxamido)benzoate (0.10 g), followed by heating to reflux under a nitrogen atmosphere for 1 hour and 10 minutes. The reaction mixture was cooled to room temperature, and then ethyl acetate and a 10% aqueous solution of citric acid were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 91-80% hexane/ethyl acetate] to obtain tert-butyl 4-anilino-2-(5-phenylpyridine-3-carboxamido)benzoate.

Trifluoroacetic acid (3.0 mL) was added to the obtained tert-butyl 4-anilino-2-(5-phenylpyridine-3-carboxamido)benzoate, followed by stirring at room temperature for 1 hour and 30 minutes. The solvent was evaporated under reduced pressure, and diisopropyl ether was added to the obtained residue. The solid substance was collected by filtration. Dioxane (3.0 mL) and a 2 mol/L aqueous solution of sodium hydroxide (0.068 mL) were sequentially added to the obtained solid substance, followed by stirring at room temperature for 1 hour and 30 minutes. A 10% aqueous solution of citric acid was added to the reaction mixture, and the solid substance was collected by filtration to obtain 73 mg of 4-anilino-2-(5-phenylpyridine-3-carboxamido)benzoic acid as a yellow solid.

¹H-NMR (DMSO-d₆) δ: 6.80 (1H, dd, J=8.8, 2.2 Hz), 7.00-7.07 (1H, m), 7.22-7.28 (2H, m), 7.33-7.40 (2H, m), 7.46-7.52 (1H, m), 7.53-7.60 (2H, m), 7.80-7.86 (2H, m), 7.91 (1H, d, J=8.8 Hz), 8.48-8.52 (1H, m), 8.55 (1H, d, J=2.2 Hz), 9.00 (1H, s), 9.10 (1H, d, J=1.7 Hz), 9.13 (1H, d, J=2.0 Hz), 12.67 (1H, s), 13.14-13.27 (1H, broad).

Example 62b

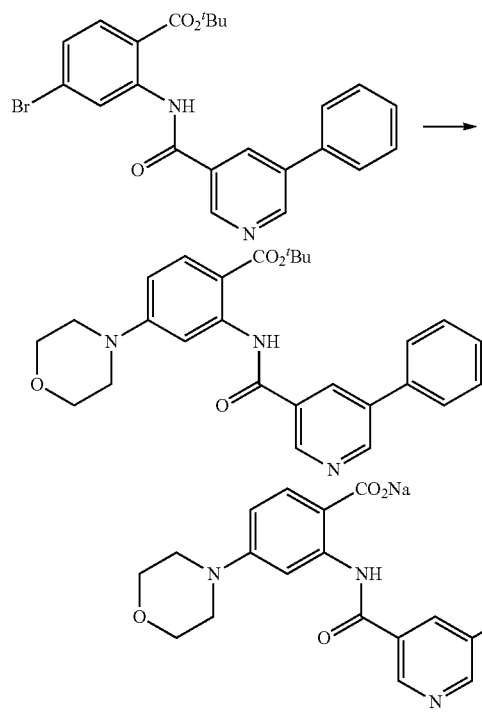

Cesium carbonate (0.14 g), morpholine (0.029 mL), 2-dicyclohexylphosphino-2',4',6'-triisopropylbiphenyl (5 mg), tris(dibenzylideneacetone)dipalladium(0) (2 mg), and palladium(II) acetate (1 mg) were added to a toluene (3.0 mL) solution of tert-butyl 4-bromo-2-(5-phenylpyridine-3-carboxamido)benzoate (0.10 g), followed by heating to reflux under a nitrogen atmosphere for 1 hour. The reaction mixture was cooled to room temperature, and then morpholine (0.029 mL) was added thereto, followed by heating to reflux under a nitrogen atmosphere for 2 hours. The reaction mixture was cooled to room temperature, and then cesium carbonate (72 mg), morpholine (0.029 mL), 2-dicyclohexylphosphino-2',4',6'-triisopropylbiphenyl (5 mg), tris(dibenzylideneacetone)dipalladium(0) (2 mg), and palladium(II) acetate (1 mg) were added thereto, followed by heating to reflux under a nitrogen atmosphere for 4 hours. The reaction mixture was cooled to room temperature, and then ethyl acetate and a 10% aqueous solution of citric acid were added thereto. The organic layer was separated, washed with a saturated aqueous solution of sodium chloride, and dried over anhydrous magnesium sulfate, and the solvent was evaporated under reduced pressure. The obtained residue was purified by silica gel column chromatography [eluent: 85-70% hexane/ethyl acetate] to obtain tert-butyl 4-morpholino-2-(5-phenylpyridine-3-carboxamido)benzoate.

Trifluoroacetic acid (3.0 mL) was added to the obtained tert-butyl 4-morpholino-2-(5-phenylpyridine-3-carboxamido)benzoate, followed by stirring at room temperature for 3 hours. The solvent was evaporated under reduced pressure, and diisopropyl ether was added to the obtained residue. The solid substance was collected by filtration, and ethanol (2.5 mL) and a 1 mol/L aqueous solution of sodium hydroxide (0.44 mL) were sequentially added to the obtained solid substance, followed by stirring at room temperature for 1 hour. The solvent was evaporated under reduced pressure, and water was added to the obtained residue. The solid substance was collected by filtration to obtain 35 mg of sodium 4-morpholino-2-(5-phenylpyridine-3-carboxamido)benzoate as a white solid. ¹H-NMR (DMSO-d₆) δ: 3.13-3.21 (4H, m), 3.73-3.81 (4H, m), 6.62 (1H, dd, J=8.8, 2.6 Hz), 7.46-7.52 (1H, m), 7.54-7.61 (2H, m), 7.80-7.86 (2H, m), 7.90 (1H, d, J=8.8 Hz), 8.37 (1H, d, J=2.6 Hz), 8.59 (1H, dd, J=2.1, 2.2 Hz), 9.08 (1H, d, J=2.2 Hz), 9.17 (1H, d, J=2.1 Hz).

Example 63b

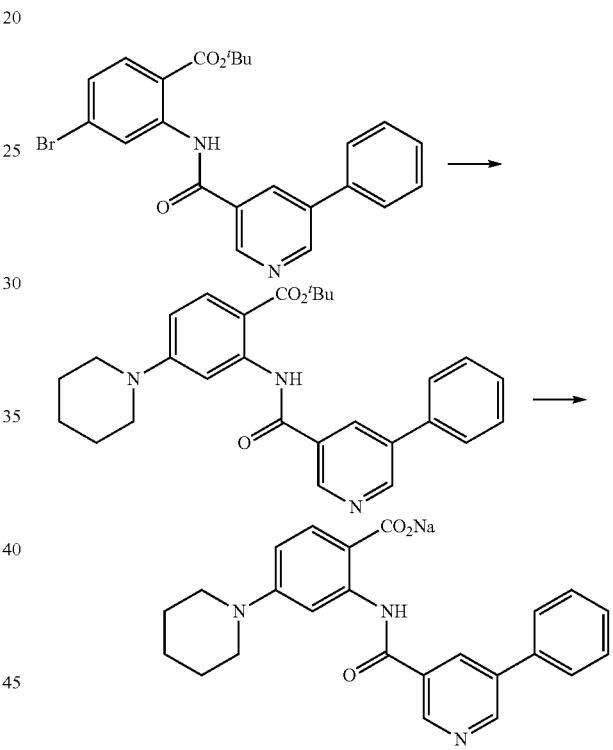

As in Example 62b, the following compound was prepared.

Sodium 2-(5-phenylpyridine-3-carboxamido)-4-(piperidin-1-yl)benzoate

¹H-NMR (DMSO-d₆) δ: 1.53-1.67 (6H, m), 3.18-3.25 (4H, m), 6.57 (1H, dd, J=8.9, 2.1 Hz), 7.46-7.53 (1H, m), 7.53-7.61 (2H, m), 7.79-7.87 (3H, m), 8.34 (1H, d, J=2.4 Hz), 8.58-8.63 (1H, m), 9.07 (1H, d, J=2.2 Hz), 9.16 (1H, d, J=2.0 Hz).

INDUSTRIAL APPLICABILITY

Since the N-acyl anthranilic acid derivative of the present invention or a salt thereof has collagen production inhibitory action, it is useful for the prevention, treatment and the like of diseases associated with excessive production of collagen, such as pulmonary fibrosis, scleroderma, nephrosclerosis and hepatocirrhosis.

The invention claimed is:
1. An N-acyl anthranilic acid derivative of formula (I) or a salt thereof:

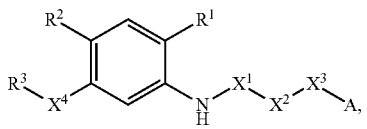

wherein
- $R^1$ represents an optionally protected carboxyl group or an optionally protected 1H-tetrazol-5-yl group;
- $R^2$ represents a hydrogen atom, a halogen atom, a cyano group, a nitro group, an optionally protected hydroxyl group, an optionally protected amino group, an optionally protected or substituted alkylamino group, an optionally substituted dialkylamino group, an optionally substituted alkyl group or an optionally substituted alkoxy group;
- $R^3$ represents an optionally substituted aryl group or an optionally substituted heterocyclic group;
- $X^1$ represents a carbonyl group;
- $X^2$ represents a bond;
- $X^3$ represents a bond;
- $X^4$ represents an oxygen atom, an optionally protected imino group, an optionally substituted alkylene group or a bond; and
- A represents a group of formula (II):

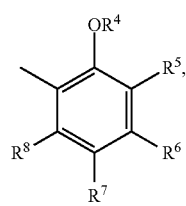

wherein
- $R^4$ represents a hydrogen atom or a phenolic hydroxyl protecting group;
- one of $R^5$, $R^6$, $R^7$, and $R^8$ represents a group of formula —Y—$R^9$:

wherein
- $R^9$ represents a cyano group, a nitro group, an optionally protected hydroxyl group, an optionally protected amino group, an optionally protected or substituted alkylamino group, an optionally substituted dialkylamino group, an optionally substituted alkyl group, an optionally substituted alkoxy group, an optionally substituted aryl group, an optionally substituted aryloxy group, an optionally substituted heterocyclic group, an optionally substituted heterocyclic oxy group, an optionally substituted acyl group, or an optionally substituted acyloxy group;
- Y represents an optionally substituted alkylene group, an optionally substituted alkenylene group, an optionally substituted alkynylene group, a bond, a group of formula —$(CH_2)_m$—O—$(CH_2)_n$—, or a group of formula —$(CH_2)_m$—$NR^{10}$—$(CH_2)_n$—,
wherein m represents an integer of 0 to 4, and n represents an integer of 1 to 4, wherein $R^{10}$ represents a hydrogen atom, an optionally substituted lower alkyl group or an imino protecting group, and m represents an integer of 0 to 4, and n represents an integer of 1 to 4, and
remaining moieties identically or differently each represent a hydrogen atom, a halogen atom, an optionally protected hydroxyl group, an optionally protected amino group, an optionally protected or substituted alkylamino group, or an optionally substituted dialkylamino group; or
- $R^5$ and $R^8$ identically or differently each represent a hydrogen atom, a halogen atom, an optionally protected hydroxyl group, or an optionally protected amino group, and
- $R^6$ and $R^7$ each represent, together with carbon atoms to which they bind, an optionally substituted 5- to 7-membered heterocyclic group, or
- A represents a group of formula (III):

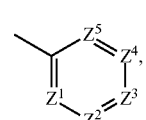

wherein
- one of $Z^1$, $Z^2$, $Z^3$, $Z^4$, and $Z^5$ represents a nitrogen atom,
- one of the remaining four represents a group of formula C—$R^{11}$,
  wherein $R^{11}$ represents an optionally substituted aryl group, an optionally substituted nitrogen-comprising 6-membered aromatic heterocyclic group, an optionally substituted oxygen-comprising 5-membered aromatic heterocyclic group, an optionally substituted nitrogen-comprising oxygen-comprising 5-membered aromatic heterocyclic group or an optionally substituted nitrogen-comprising sulfur-comprising 5-membered aromatic heterocyclic group,
- the remaining three identically or differently each represent a group of formula C—$R^{12}$,
  wherein $R^{12}$ represents a hydrogen atom or a halogen atom.

2. The derivative or salt of claim 1, wherein A represents a group of formula (IV):

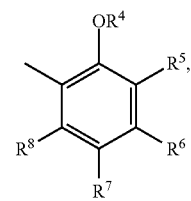

wherein
- $R^4$ represents a hydrogen atom or a phenolic hydroxyl protecting group;
- one of $R^5$, $R^6$, $R^7$, and $R^8$ represents a group of formula —Y—$R^9$:

wherein
- $R^9$ represents a cyano group, a nitro group, an optionally protected hydroxyl group, an optionally protected amino group, an optionally protected or substituted alkylamino group, an optionally substituted dialkylamino group, an optionally substituted alkyl group, an optionally substituted alkoxy group, an optionally substituted aryl group, an optionally substituted aryloxy group, an optionally substituted heterocyclic group, an optionally substituted heterocyclic oxy group, an optionally substituted acyl group, or an optionally substituted acyloxy group;

Y represents an optionally substituted alkylene group, an optionally substituted alkenylene group, an optionally substituted alkynylene group, a bond, a group of formula —$(CH_2)_m$—O—$(CH_2)_n$—, or a group of formula —$(CH_2)_m$—$NR^{10}$—$(CH_2)_n$—, wherein m represents an integer of 0 to 4, and n represents an integer of 1 to 4, wherein $R^{10}$ represents a hydrogen atom, an optionally substituted lower alkyl group or an imino protecting group; and m represents an integer of 0 to 4, and n represents an integer of 1 to 4, and the remaining moieties identically or differently each represent a hydrogen atom, a halogen atom, an optionally protected hydroxyl group, an optionally protected amino group, an optionally protected or substituted alkylamino group, or an optionally substituted dialkylamino group; or $R^5$ and $R^8$ identically or differently each represent a hydrogen atom, a halogen atom, an optionally protected hydroxyl group, or an optionally protected amino group, and $R^6$ and $R^7$ each represent, together with carbon atoms to which they bind, an optionally substituted 5- to 7-membered heterocyclic group.

3. The derivative or salt of claim 2, wherein $X^4$ represents an oxygen atom, an optionally protected imino group, or a bond.

4. The derivative or salt of claim 2, wherein $R^1$ represents an optionally protected carboxyl group.

5. The derivative or salt of claim 2, wherein $R^2$ represents a hydrogen atom or a halogen atom.

6. The derivative or salt of claim 2, wherein $R^3$ represents an optionally substituted phenyl group or an optionally substituted furanyl group.

7. The derivative or salt of claim 2, wherein $R^4$ represents a hydrogen atom.

8. The derivative or salt of claim 2, wherein $X^4$ represents a bond.

9. The derivative or salt of claim 2, wherein one of $R^5$, $R^6$, $R^7$, and $R^8$ represents a group of formula —$Y^a$—$R^{9a}$:

wherein $R^{9a}$ represents a nitro group, an optionally protected hydroxyl group, an optionally protected amino group, an optionally protected or substituted alkylamino group, an optionally substituted dialkylamino group, an optionally substituted alkyl group, an optionally substituted alkoxy group, an optionally substituted aryl group, an optionally substituted aryloxy group, an optionally substituted heterocyclic group, an optionally substituted heterocyclic oxy group, an optionally substituted acyl group, or an optionally substituted acyloxy group; and $Y^a$ represents an optionally substituted alkylene group, a bond, a group of formula —O—$(CH_2)_n$—, or a group of formula —$NR^{10a}$—$(CH_2)_n$—, wherein n represents an integer of 1 to 4, wherein $R^{10a}$ represents a lower alkyl group, and n represents an integer of 1 to 4, and remaining moieties each represent a hydrogen atom.

10. The derivative or salt of claim 2, wherein $R^5$, $R^6$ and $R^8$ each represent a hydrogen atom, and $R^7$ represents a group of formula —$Y^b$—$R^{9b}$:

wherein $R^{9b}$ represents an optionally substituted heterocyclic group; and $Y^b$ represents an alkylene group, a bond, or a group of formula —O—$(CH_2)_n$—, wherein n represents an integer of 1 to 4.

11. The derivative or salt of claim 2, wherein $R^5$, $R^6$ and $R^8$ each represent a hydrogen atom, and $R^7$ represents a group of formula —$Y^c$—$R^{9c}$:

wherein $R^{9c}$ represents a heterocyclic group that is optionally substituted with a lower alkyl group; and $Y^c$ represents a methylene group, a bond, or a group of formula —O—$(CH_2)_2$—.

12. The derivative or salt of claim 1, wherein A represents a group of formula (V):

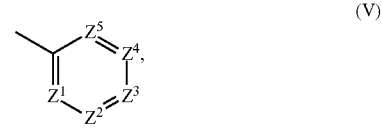

wherein one of $Z^1$, $Z^2$, $Z^3$, $Z^4$, and $Z^5$ represents a nitrogen atom, one of the remaining four represents a group of formula C—$R^{11}$:

wherein $R^{11}$ represents an optionally substituted aryl group, an optionally substituted nitrogen-comprising 6-membered aromatic heterocyclic group, an optionally substituted oxygen-comprising 5-membered aromatic heterocyclic group, an optionally substituted nitrogen-comprising oxygen-comprising 5-membered aromatic heterocyclic group or an optionally substituted nitrogen-comprising sulfur-comprising 5-membered aromatic heterocyclic group, and the remaining three identically or differently each represent a group of formula C—$R^{12}$:

wherein $R^{12}$ represents a hydrogen atom or a halogen atom.

13. The derivative or salt of claim 12, wherein $X^4$ represents an oxygen atom, an optionally protected imino group or a bond.

14. The derivative or salt of claim 12, wherein $R^1$ represents an optionally protected carboxyl group.

15. The derivative or salt of claim 12, wherein $R^2$ represents a hydrogen atom or a halogen atom.

16. The derivative or salt of claim 12, wherein $X^4$ represents a bond.

17. The derivative or salt of claim 12, wherein $R^3$ represents an optionally substituted phenyl group or an optionally substituted furanyl group.

18. The derivative or salt of claim 12, wherein $Z^1$ represents CH, $Z^2$ represents a nitrogen atom, $Z^3$ represents CH, $Z^4$ represents a group of formula C—$R^{11a}$:

wherein $R^{11a}$ represents an optionally substituted aryl group, an optionally substituted nitrogen-comprising 6-membered aromatic heterocyclic group, or an optionally substituted oxygen-comprising 5-membered aromatic heterocyclic group, and $Z^5$ represents CH.

19. The derivative or salt of claim 12, wherein
$Z^1$ represents CH,
$Z^2$ represents a nitrogen atom,
$Z^3$ represents CH,
$Z^4$ represents C—$C_6H_5$, and
$Z^5$ represents CH.

\* \* \* \* \*